US007220557B2

(12) United States Patent
Hastings et al.

(10) Patent No.: US 7,220,557 B2
(45) Date of Patent: May 22, 2007

(54) METH1 POLYNUCLEOTIDES

(75) Inventors: Gregg A. Hastings, Westlake Village, CA (US); Zdenka L. Jonak, Devon, PA (US); Stephen H. Trulli, Havertown, PA (US); James A. Fornwald, Norristown, PA (US); Jonathan A. Terrett, Oxon (GB)

(73) Assignees: Human Genome Sciences, Inc., Rockville, MD (US); Beth Israel-Deaconess Medical Center, Boston, MA (US); SmithKline Beecham Corporation, King of Prussia, PA (US)

( * ) Notice: Subject to any disclaimer, the term of this patent is extended or adjusted under 35 U.S.C. 154(b) by 0 days.

(21) Appl. No.: 09/373,658

(22) Filed: Aug. 13, 1999

(65) Prior Publication Data
US 2003/0092900 A1     May 15, 2003

Related U.S. Application Data

(63) Continuation-in-part of application No. 09/318,208, filed on May 25, 1999, now abandoned, which is a continuation-in-part of application No. 09/235,810, filed on Jan. 22, 1999, now abandoned, and a continuation-in-part of application No. 08/845,496, filed on Apr. 24, 1997, now abandoned.

(60) Provisional application No. 60/147,823, filed on Aug. 10, 1999, provisional application No. 60/144,882, filed on Jul. 20, 1999, provisional application No. 60/098,539, filed on Aug. 28, 1998.

(51) Int. Cl.
*C12N 15/00* (2006.01)
*C12N 15/12* (2006.01)
*C12N 15/63* (2006.01)
*C07N 21/04* (2006.01)

(52) U.S. Cl. ............. 435/69.1; 435/252.3; 435/254.11; 435/320.1; 435/325; 435/455; 435/471; 536/23.5; 536/24.31

(58) Field of Classification Search ............... 536/23.4, 536/24.5, 24.31, 23.1, 23.5; 435/69.1, 252.3, 435/254.11, 320.1, 325, 455, 471
See application file for complete search history.

(56) References Cited

U.S. PATENT DOCUMENTS

| 5,194,596 A | 3/1993 | Tischer et al. |
| 5,350,836 A | 9/1994 | Kopchick et al. |
| 5,639,725 A | 6/1997 | O'Reilly et al |
| 5,837,680 A | 11/1998 | Moses et al. |
| 6,416,974 B1 * | 7/2002 | Holtzman et al. ......... 435/69.1 |
| 6,649,377 B1 | 11/2003 | Allard et al. |

FOREIGN PATENT DOCUMENTS

| AU | 766767 | 8/1999 |
| AU | 36226/00 | 9/2000 |
| EP | 0 742 012 | 11/1996 |
| EP | 0 874 050 A2 | 10/1998 |
| WO | WO-93/16716 | 9/1993 |
| WO | WO 98/55643 | 12/1998 |
| WO | WO-98/56804 | 12/1998 |
| WO | WO 99/07850 | 2/1999 |
| WO | WO-99/14234 | 3/1999 |
| WO | 1 004 674 A1 | 5/2000 |

OTHER PUBLICATIONS

Burgess et al "Possible Dissociation of the Heparin-binding and Mitogenic Acivities of Heparin-binding Growth Factor-1 from Its Receptor-binding Activities by Site-directed Mutagenesis of a single Lysine Residue", Journal of Cellular Biology, vol. 111, pp., 1990.*
Lazar et al, "Transforming Growth Factor Alpha: Mutation of Aspartic Acid 47 and Leuine 48 Results in Different Biological Activities", Molecular and Cellular Biology, vol. 8, pp. 1247-1252, 1988.*
Verma et al (Nature, 1997, vol. 389, pp. 239-242).*
Eck et al (Gene-Based Therapy, In: The Pharmacological Basis of Therapeutics, Goodman and Gilman, Ed.s, 1996, pp. 77-10.*
Orkin et al ("Report and Recommendation of the Panel to Assess the NIH Investment in Research on Gene Therapy", NIH, 1995).*
The abstract of Trikha et al, Cancer Research, 1994, vol. 54, pp. 4993-4998.*
U.S. Appl. No. 60/058,108.*
U.S. Appl. No. 60/054,966.*
Adams, J.C., "Molecules in Focus: Thrombospondin-1," *Int. J. Biochem. Cell Biol.* 29:861-865 (Jun. 1997).
Asch, A.S. et al., "Analysis of CD36 Binding Domains: Ligand Specificity Controlled by Dephosphorylation of an Ectodomain," *Science* 262:1436-1440 (1993).
Bjarnason, J.B. and J.W. Fox, "Snake Venom Metalloendopeptidases: Reprolysins," *Meth. Enzymol.* 248:345-369 (1995).
Bornstein, P., "Thrombospondins: structure and regulation of expression," *FASEB J.* 6:3290-3299 (1992).

(Continued)

*Primary Examiner*—Karen A. Canella

(57) ABSTRACT

The present invention relates to novel anti-angiogenic proteins, related to thrombospondin. More specifically, isolated nucleic acid molecules are provided encoding human METH1 and METH2. METH1 and METH2 polypeptides are also provided, as are vectors, host cells and recombinant methods for producing the same. Also provided are diagnostic methods for the prognosis of cancer and therapeutic methods for treating individuals in need of an increased amount of METH1 or METH2. Also provided are methods for inhibiting angiogenesis using METH1 or METH2.

17 Claims, 12 Drawing Sheets

OTHER PUBLICATIONS

Catimel, B. et al., "Human platelet glycoprotein IIIb binds to thrombospondin fragments bearing the C-terminal region, and/or the type I repeats (CSVTCG motif), but not the N-terminal heparin-binding region," *Biochem. J.* 284:231-236 (1992).

Colige, A. et al., "cDNA cloning and expression of bovine procollagen I N-proteinase: A new member of the superfamily of zinc-metalloproteinases with binding sites for cells and other matrix components," *Proc. Natl. Acad. Sci. USA* 94:2374-2379 (Mar. 1997).

Dameron, K.M. et al., "Control of Angiogenesis in Fibroblasts by p53 Regulation of Thrombospondin-1," *Science* 265:1582-1584 (1994).

Dawson, D.W. et al., "CD36 Mediates the In-Vitro Inhibitory Effects of Thrombospondin-1 on Endothelial Cells," *J. Cell Biol.* 138:707-717 (Aug. 1997).

Guo, N.-H. et al., "Heparin-binding Peptides from the Type I Repeats of Thrombospondin," *J. Biol. Chem.* 267:19349-19355 (1992).

Guo, N.-H. et al., "Antiproliferative and antitumor activities of D-reverse peptides derived from the second type-1 repeat of thrombospondin-1," *J. Peptide Res.* 50:210-221 (Sep. 1997).

Iruela-Arispe, M.L. et al., "Differential Expression of Thrombospondin 1, 2, and 3 During Murine Development," *Develop. Dynamics* 197:40-56 (1993).

Iruela-Arispe, M.L. and H.F. Dvorak, "Angiogenesis: a Dynamic Balance of Stimulators and Inhibitors," *Thrombosis & Haemostasis* 78:672-677 (Jul. 1997).

Kuno, K. et al., "Molecular Cloning of a Gene Encoding a New Type of Metalloproteinase-disintegrin Family Protein with Thrombospondin Motifs as an Inflammation Associated Gene," *J. Biol. Chem.* 272:556-562 (Jan. 1997).

Kyriakides, T.R. et al., "Mice That Lack Thrombospondin 2 Display Connective Tissue Abnormalities That Are Associated with Disordered Collagen Fibrillogenesis, an Increased Vascular Density, and a Bleeding Diathesis," *J. Cell Biol.* 140:419-430 (Jan. 1998).

Lawler, J. et al., "Thrombospondin-1 Is Required for Normal Murine Pulmonary Homeostasis and Its Absence Causes Pneumonia," *J. Clin. Invest.* 101:982-992 (Mar. 1998).

Nishimori, H. et al., "A novel brain-specific p53-target gene, BAI1, containing thrombospondin type 1 repeats inhibits experimental angiogenesis," *Oncogene* 15:2145-2150 (Oct. 1997).

Pfaff, M. et al., "Comparison of Disintegrins with Limited Variation in the RGD Loop in Their Binding to Purified Integrins αIIbβ3, αVβ3 and α5β1 and in Cell Adhesion Inhibition," *Cell Adhesion & Comm.* 2:491-501 (1994).

Rawlings, N.D, and A.J. Barrett, "Evolutionary Families of Metallopeptidases," *Meth. Enzymol.* 248:183-229 (1995).

Tolsma, S.S. et al., "Peptides Derived from Two Seperate Domains of the Matrix Protein Thrombospondin-1 Have Anti-Angiogenic Activity," *J. Cell Biol.* 122:497-511 (1993).

Usami, Y. et al., "A 28 kDa-protein with disintegrin-like structure (jarahagin-C) purified from *Bothrops jararaca* venom inhibits collagen- and ADP-induced platelet aggregation," *Biochem. & Biophys. Res. Comm.* 201:331-339 (1994).

Vogel, T. et al., "Modulation of Endothelial Cell Proliferation, Adhesion, and Motility by Recombinant Heparin-Binding Domain and Synthetic Peptides From the Type I Repeats of Thrombospondin," *J. Cell. Biochem.* 53:74-84 (1993).

Wolfsberg, T.G. and J.M. White, "Review: ADAMs in Fertilization and Development," *Develop. Biol.* 180:389-401 (1996).

GenBank Accession No. D67076, Kuno, K. (Feb. 1999).
GenBank Accession No. AB001735, Kuno, K. (Jan. 1998).
GenBank Accession No. X14787, Hennessy, S.W. et al. (1995).
GenBank Accession No. U64857, Wilson, R. et al. (Nov. 1998).
GenBank Accession No. X04665, Lawler, J. and R.O. Hynes (1995).
GenBank Accession No. M64866, Bornstein, P. et al. (1993).
GenBank Accession No. L07803, Laherty, C.D. et al. (1994).
GenBank Accession No. U08006, Michelotti, G.A. et al. (1995).
GenBank Accession No. M16974, Rao, A.G. et al. (1994).
GenBank Accession No. L13855, Dean, H.J. and A.K. Cheung (1994).
GenBank Accession No. AL021529, Murphy, L. and D. Harris (Jan. 1998).
GenBank Accession No. D86074, Sudo, S. (Feb. 1999).
GenBank Accession No. L05390, Blanco, G. et al. (1993).
GenBank Accession No. Z69361, Gajadsty, S. et al. (Nov. 1998).
GenBank Accession No. X99599, Borghese, R. et al. (Feb. 1998).
GenBank Accession No. AF018073, Schneider, K.H. et al. (Oct. 1997).
GenBank Accession No. L23760, Lin, Q. et al. (1994).
GenBank Accession No. Z46970, Wiese, M. (1995).
GenBank Accession No. AC004449, Lamerdin, J.E. et al. (Sep. 1998).
GenBank Accession No. Z69589, Dreusch, A. et al. (1996).
GenBank Accession No. Z22279, Zabarovsky, E. et al. (1994).
GenBank Accession No. X17524, Ohama, T. et al. (1992).
GenBank Accession No. AB005287, Ueno, A. et al. (Mar. 1998).
GenBank Accession No. X87619, Zafar, R.S. (1995).
GenBank Accession No. M87276, Laherty, C.D. et al. (1994).
GenBank Accession No. M62458, Lawler, J. et al. (1994).
GenBank Accession No. AB002364, Nagase, T. et al. (Feb. 1999).
GenBank Accession No. AB005297, Nakamura, Y. et al. (Nov. 1997).
GenBank Accession No. X69161, Akam, M.E. et al. (1995).
GenBank Accession No. X16619, Debuchy, R. et al. (Feb. 1999).
GenBank Accession No. I36448, Goodearl, A. et al. (Mar. 1997).
GenBank Accession No. L12260, Marchionni, M.A. et al. (Sep. 1997).
GenBank Accession No. I36352, Goodearl, A. et al. (Mar. 1997).
GenBank Accession No. X15898, Liberator, P.A. et al. (1995).
GenBank Accession No. I07789, Liberator, P.A. et al. (1994).
GenBank Accession No. I08144, Altenburger, W. et al. (1994).
GenBank Accession No. U31814, Yang, W.M. et al. (1996).
GenBank Accession No. AF001444, Mundlos, S. et al. (Aug. 1997).

English language translation of WO 98/55643 (Document AM1).

Vazquez, F. et al., "Meth-1 and Meth-2 are Novel Proteins that Contain the Anti-Angiogenic Domain of Thrombospondin 1," *FASEB J.* 11:A336, Abstract No. 1947 (Feb. 1997).

Adams, M.D., et al., "3,400 new expressed sequence tags identify diversity of transcripts in human brain," *Nat. Genet.* 4:256-267, Nature Publishing Company, (1993).

Bowie, J.U., et al., "Deciphering the Message in Protein Sequences: Tolerance to Amino Acid Substitutions," *Science* 247:1306-1310, American Association for the Advancement of Science (1990).

Hsu, S.C., et al., "Inhibition of Angiogenesis in Human Glioblastomas by Chromosome 10 Induction of Thrombospondin-1," *Cancer Res.* 56:5684-5691, American Association for Cancer Research (1996).

Kuno, K., et al., "The Exon/Intron Organization and Chromosomal Mapping of the Mouse ADAMTS-1 Gene Encoding an ADAM Family Protein with TSP Motifs," *Genomics* 46:466-471, Academic Press, Inc. (Dec. 1997).

Kuno, K., "Mouse mRNA for secretory protein containing thrombospondin motifs, complete cds," Database EMBL 'Online!, Database Accession No. D67076 (Feb. 1997).

Lawler, J., et al., "Characterization of the murine thrombospondin gene," *Genomics* 11:587-600, Academic Press, Inc. (1991).

NCI-CGAP, "National Cancer Institute, Cancer Genome Anatomy Project (CGAP), Tumor Gene Index http://www.ncbi.nim.nih.gov/ncicgap," Database EMBL 'Online!, Database Accession No. AA635657 (Oct. 1997).

Skolnick, J., and Fetrow, J.S., "From genes to protein structure and function: novel applications of computational approaches in the genomic era," *Trends Biotechnol.* 18:34-39, Elsevier Science, Ltd. (Jan. 2000).

Vázquez, F., et al., "METH-1, a Human Ortholog of ADAMTS-1, and METH-2 Are Members of a New Family of Proteins with Angio-inhibitory Activity," *J. Biol. Chem.* 274:23349-23357, American Society for Biochemistry and Molecular Biology, Inc. (Aug. 1999).

"Molecular Biology/ Reagent Systems," 1994-1995 Promega Catalog, p. 167, Promega (1994-1995).

Human Genome Sciences, Corp. EST #1039649.

Co-pending U.S. Appl. No. 09/989,687, Hastings et al., filed Nov. 21, 2001.

Co-pending U.S. Appl. No. 10/115,286, Jonak et al., filed Apr. 4, 2002.

Pending Non-Provisional U.S. Appl. No. 09/912,293, Rosen et al., Not Published: pp. 1-75 ( pp. 1 +2 partially redacted ); portion of Table 2; and Seq ID Nos:177073, 84851, 25609, and 99884.

Pending Non-Provisional U.S. Appl. No. 09/912,292, Rosen et al., Not Published: pp. 1-75 ( pp. 1 +2 partially redacted ); portion of Table 2; and Seq ID Nos:37915, 35520, 28946, and 23336.

Supplementary Partial European Search Report for European Application No. EP 99 90 4190 completed Jul. 8, 2002.

Good et al. "A tumor suppressor-dependent inhibitor of angiogenesis is immunologically and functionally indistinguishable from a fragment of thrombospondin" , PNAS USA 87:6624-6628 (1990).

Dameron et al. "Control of angiogenesis in fibroblasts by p53 regulation of thrombospondin-1", Science 265:1582-1584 (1994).

GenBank Accession No. R19976, Hillier et al., "yg38e05.r1 Soares infant brain 1NIB Homo sapiens cDNA clone Image:34684 5', mRNA sequence" (Apr. 17, 1995).

GenBank Accession No. W47316, Hillier et al., "zc40g02.r1 Soares_senescent_fibroblasts_NbHSF Homo sapiens cDNA clone Image:324818 5', mRNA sequence" (Oct. 11, 1996).

GenBank Accession No. R13547, Hillier et al., yf59g08.r1 Soares infant brain 1NIB Homo sapiens cDNA clone Image:26419 5', mRNA sequence (Apr. 12, 1995).

Johnson and Tracey, "Peptide and Protein Drug Delivery", In: Encyclopedia of Controlled Drug Delivery, vol. 2 1999, pp. 816-833.

* cited by examiner

```
ATGGGGAACGCGGAGCGGGCTCCGGGGTCTCGGAGCTTTGGGCCCGTACCCACGCTGCTGCTGCTCGCCGCGGCGCTA
 M  G  N  A  E  R  A  P  G  S  R  S  F  G  P  V  P  T  L  L  L  A  A  A  L

CTGGCCGTGTCGGACGCACTCGGGCGCCCCTCCGAGGAGGACGAGGAGCTAGTGGTGCCGGAGCTGGAGCGCGCCCCG
 L  A  V  S  D  A  L  G  R  P  S  E  E  D  E  E  L  V  V  P  E  L  E  R  A  P

GGACACGGGACCACGCGCCTCCGCCTGCACGCCTTTGACCAGCAGCTGGATCTGGAGCTGCGGCCCGACAGCAGCTTT
 G  H  G  T  T  R  L  R  L  H  A  F  D  Q  Q  L  D  L  E  L  R  P  D  S  S  F

TTGGCGCCCGGCTTCACGCTCCAGAACGTGGGGCGCAAATCCGGGTCCGAGACGCCGCTTCCGGAAACCGACCTGGCG
 L  A  P  G  F  T  L  Q  N  V  G  R  K  S  G  S  E  T  P  L  P  E  T  D  L  A

CACTGCTTCTACTCCGGCACCGTGAATGGCGATCCCAGCTCGGCTGCCGCCCTCAGCCTCTGCGAGGGCGTGCGCGGC
 H  C  F  Y  S  G  T  V  N  G  D  P  S  S  A  A  A  L  S  L  C  E  G  V  R  G

GCCTTCTACCTGCTGGGGGAGGCGTATTTCATCCAGCCGCTGCCCGCCGCCAGCGAGCGCCTCGCCACCGCCGCCCCA
 A  F  Y  L  L  G  E  A  Y  F  I  Q  P  L  P  A  A  S  E  R  L  A  T  A  A  P

GGGGAGAAGCCGCCGGCACCACTACAGTTCCACCTCCTGCGGCGGAATCGGCAGGGCGACGTAGGCGGCACGTGCGGG
 G  E  K  P  P  A  P  L  Q  F  H  L  L  R  R  N  R  Q  G  D  V  G  G  T  C  G

GTCGTGGACGACGAGCCCCGGCCGACTGGGAAAGCGGAGACCGAAGACGAGGACGAAGGGACTGAGGGCGAGGACGAA
 V  V  D  D  E  P  R  P  T  G  K  A  E  T  E  D  E  D  E  G  T  E  G  E  D  E

GGGCCTCAGTGGTCGCCGCAGGACCCGGCACTGCAAGGCGTAGGACAGCCCACAGGAACTGGAAGCATAAGAAAGAAG
 G  P  Q  W  S  P  Q  D  P  A  L  Q  G  V  G  Q  P  T  G  T  G  S  I  R  K  K

CGATTTGTGTCCAGTCACCGCTATGTGGAAACCATGCTTGTGGCAGACCAGTCGATGGCAGAATTCCACGGCAGTGGT
 R  F  V  S  S  H  R  Y  V  E  T  M  L  V  A  D  Q  S  M  A  E  F  H  G  S  G

CTAAAGCATTACCTTCTCACGTTGTTTTCGGTGGCAGCCAGATTGTACAAACACCCCAGCATTCGTAATTCAGTTAGC
 L  K  H  Y  L  L  T  L  F  S  V  A  A  R  L  Y  K  H  P  S  I  R  N  S  V  S

CTGGTGGTGGTGAAGATCTTGGTCATCCACGATGAACAGAAGGGGCCGGAAGTGACCTCCAATGCTGCCCTCACTCTG
 L  V  V  V  K  I  L  V  I  H  D  E  Q  K  G  P  E  V  T  S  N  A  A  L  T  L

CGGAACTTTTGCAACTGGCAGAAGCAGCACAACCCACCCAGTGACCGGGATGCAGAGCACTATGACACAGCAATTCTT
 R  N  F  C  N  W  Q  K  Q  H  N  P  P  S  D  R  D  A  E  H  Y  D  T  A  I  L

TTCACCAGACAGGACTTGTGTGGGTCCCAGACATGTGATACTCTTGGGATGGCTGATGTTGGAACTGTGTGTGATCCG
 F  T  R  Q  D  L  C  G  S  Q  T  C  D  T  L  G  M  A  D  V  G  T  V  C  D  P

AGCAGAAGCTGCTCCGTCATAGAAGATGATGGTTTACAAGCTGCCTTCACCACAGCCCATGAATTAGGCCACGTGTTT
 S  R  S  C  S  V  I  E  D  D  G  L  Q  A  A  F  T  T  A  H  E  L  G  H  V  F

AACATGCCACATGATGATGCAAAGCAGTGTGCCAGCCTTAATGGTGTGAACCAGGATTCCCACATGATGGCGTCAATG
 N  M  P  H  D  D  A  K  Q  C  A  S  L  N  G  V  N  Q  D  S  H  M  M  A  S  M

CTTTCCAACCTGGACCACAGCCAGCCTTGGTCTCCTTGCAGTGCCTACATGATTACATCATTTCTGGATAATGGTCAT
 L  S  N  L  D  H  S  Q  P  W  S  P  C  S  A  Y  M  I  T  S  F  L  D  N  G  H

GGGGAATGTTTGATGGACAAGCCTCAGAATCCCATACAGCTCCCAGGCGATCTCCCTGGCACCTCGTACGATGCCAAC
 G  E  C  L  M  D  K  P  Q  N  P  I  Q  L  P  G  D  L  P  G  T  S  Y  D  A  N

CGGCAGTGCCAGTTTACATTTGGGGAGGACTCCAAACACTGCCCTGATGCAGCCAGCACATGTAGCACCTTGTGGTGT
 R  Q  C  Q  F  T  F  G  E  D  S  K  H  C  P  D  A  A  S  T  C  S  T  L  W  C

ACCGGCACCTCTGGTGGGGTGCTGGTGTGTCAAACCAAACACTTCCCGTGGGCGGATGGCACCAGCTGTGGAGAAGGG
 T  G  T  S  G  G  V  L  V  C  Q  T  K  H  F  P  W  A  D  G  T  S  C  G  E  G

AAATGGTGTATCAACGGCAAGTGTGTGAACAAAACCGACAGAAAGCATTTTGATACGCCTTTTCATGGAAGCTGGGGA
 K  W  C  I  N  G  K  C  V  N  K  T  D  R  K  H  F  D  T  P  F  H  G  S  W  G
```

FIGURE 1

```
ATGTGGGGGCCTTGGGGAGACTGTTCGAGAACGTGCGGTGGAGGAGTCCAGTACACGATGAGGGAATGTGACAACCCA
 M  W  G  P  W  G  D  C  S  R  T  C  G  G  G  V  Q  Y  T  M  R  E  C  D  N  P

GTCCCAAAGAATGGAGGGAAGTACTGTGAAGGCAAACGAGTGCGCTACAGATCCTGTAACCTTGAGGACTGTCCAGAC
 V  P  K  N  G  G  K  Y  C  E  G  K  R  V  R  Y  R  S  C  N  L  E  D  C  P  D

AATAATGGAAAAACCTTTAGAGAGGAACAATGTGAAGCACACAACGAGTTTTCAAAAGCTTCCTTTGGGAGTGGGCCT
 N  N  G  K  T  F  R  E  E  Q  C  E  A  H  N  E  F  S  K  A  S  F  G  S  G  P

GCGGTGGAATGGATTCCCAAGTACGCTGGCGTCTCACCAAAGGACAGGTGCAAGCTCATCTGCCAAGCCAAAGGCATT
 A  V  E  W  I  P  K  Y  A  G  V  S  P  K  D  R  C  K  L  I  C  Q  A  K  G  I

GGCTACTTCTTCGTTTTGCAGCCCAAGGTTGTAGATGGTACTCCATGTAGCCCAGATTCCACCTCTGTCTGTGTGCAA
 G  Y  F  F  V  L  Q  P  K  V  V  D  G  T  P  C  S  P  D  S  T  S  V  C  V  Q

GGACAGTGTGTAAAAGCTGGTTGTGATCGCATCATAGACTCCAAAAAGAAGTTTGATAAATGTGGTGTTTGCGGGGGA
 G  Q  C  V  K  A  G  C  D  R  I  I  D  S  K  K  K  F  D  K  C  G  V  C  G  G

AATGGATCTACTTGTAAAAAAATATCAGGATCAGTTACTAGTGCAAAACCTGGATATCATGATATCATCACAATTCCA
 N  G  S  T  C  K  K  I  S  G  S  V  T  S  A  K  P  G  Y  H  D  I  I  T  I  P

ACTGGAGCCACCAACATCGAAGTGAAACAGCGGAACCAGAGGGGATCCAGGAACAATGGCAGCTTTCTTGCCATCAAA
 T  G  A  T  N  I  E  V  K  Q  R  N  Q  R  G  S  R  N  N  G  S  F  L  A  I  K

GCTGCTGATGGCACATATATTCTTAATGGTGACTACACTTTGTCCACCTTAGAGCAAGACATTATGTACAAAGGTGTT
 A  A  D  G  T  Y  I  L  N  G  D  Y  T  L  S  T  L  E  Q  D  I  M  Y  K  G  V

GTCTTGAGGTACAGCGGCTCCTCTGCGGCATTGGAAAGAATTCGCAGCTTTAGCCCTCTCAAAGAGCCCTTGACCATC
 V  L  R  Y  S  G  S  S  A  A  L  E  R  I  R  S  F  S  P  L  K  E  P  L  T  I

CAGGTTCTTACTGTGGGCAATGCCCTTCGACCTAAAATTAAATACACCTACTTCGTAAAGAAGAAGAAGGAATCTTTC
 Q  V  L  T  V  G  N  A  L  R  P  K  I  K  Y  T  Y  F  V  K  K  K  K  E  S  F

AATGCTATCCCCACTTTTTCAGCATGGGTCATTGAAGAGTGGGGCGAATGTTCTAAGTCATGTGAATTGGGTTGGCAG
 N  A  I  P  T  F  S  A  W  V  I  E  E  W  G  E  C  S  K  S  C  E  L  G  W  Q

AGAAGACTGGTAGAATGCCGAGACATTAATGGACAGCCTGCTTCCGAGTGTGCAAAGGAAGTGAAGCCAGCCAGCACC
 R  R  L  V  E  C  R  D  I  N  G  Q  P  A  S  E  C  A  K  E  V  K  P  A  S  T

AGACCTTGTGCAGACCATCCCTGCCCCCAGTGGCAGCTGGGGGAGTGGTCATCATGTTCTAAGACCTGTGGGAAGGGT
 R  P  C  A  D  H  P  C  P  Q  W  Q  L  G  E  W  S  S  C  S  K  T  C  G  K  G

TACAAAAAAAGAAGCTTGAAGTGTCTGTCCCATGATGGAGGGGTGTTATCTCATGAGAGCTGTGATCCTTTAAAGAAA
 Y  K  K  R  S  L  K  C  L  S  H  D  G  G  V  L  S  H  E  S  C  D  P  L  K  K

CCTAAACATTTCATAGACTTTTGCACAATGGCAGAATGCAGTTAAGTGGTTTAAGTGGTGTTAGCTTTGAGGCAAGGC
 P  K  H  F  I  D  F  C  T  M  A  E  C  S

AAAGTGAGGAAGGGCTGGTGCAGGGAAAGCAAGAAGGCTGGAGGGATCCAGCGTATCTTGCCAGTAACCAGTGAGGTG
TATCAGTAAGGTGGGATTATGGGGGTAGATAGAAAGGAGTTGAATCATCAGAGTAAACTGCCAGTTGCAAATTTGAT
AGGATAGTTAGTGAGGATTATTAACCTCTGAGCAGTGATATAGCATAATAAANCCCCGGGCATTATTATTATTATTTC
TTTTGTTACATCTATTACAAGTTTAGAAAAAACAAAGCAATTGTCAAAAAAAAAAAAAAAAAAAAAAAAAAAAAAAGG
GCGGCCGCTCTAGAGGATCCCTCGAGGGGCCCAAGCTTACGCGTGCATGNTGTCATNAGTCTN
```

FIGURE 1

```
ATGTTCCCCGCCCCCGCCGCCCCCGGTGGCTTCCGTTCCTGCTGCTGCTGCTGCTGCTGCTGCCGCTGGCCCGC
 M  F  P  A  P  A  A  P  R  W  L  P  F  L  L  L  L  L  L  L  P  L  A  R

GGCGCCCCGGCCCGGCCCGCAGCCGGGGGGCAGGCCTCGGAGCTGGTGGTGCCCACGCGGTTGCCCGGCAGCGCGGGC
 G  A  P  A  R  P  A  A  G  G  Q  A  S  E  L  V  V  P  T  R  L  P  G  S  A  G

GAGCTCGCGCTCCACCTGTCCGCCTTCGGCAAGGGCTTCGTGTTGCGCCTGGCGCCCGACGACAGCTTCCTGGCGCCC
 E  L  A  L  H  L  S  A  F  G  K  G  F  V  L  R  L  A  P  D  D  S  F  L  A  P

GAGTTCAAGATCGAGCGCCTCGGGGGCTCCGGCCGGGCGACCGGGGGCGAGCGGGGGCTGCGCGGCTGTTTTTTTTCC
 E  F  K  I  E  R  L  G  G  S  G  R  A  T  G  G  E  R  G  L  R  G  C  F  F  S

GGCACCGTGAATGGGGAGCCCGAGTCGCTGGCGGCGGTCAGCCTGTGCCGCGGGCTGAGCGGCTCCTTCCTGCTGGAC
 G  T  V  N  G  E  P  E  S  L  A  A  V  S  L  C  R  G  L  S  G  S  F  L  L  D

GGCGAGGAGTTCACCATCCAGCCGCAGGGCGCGGGGGGCTCCCTGGCTCAGCCGCACCGCCTGCAGCGCTGGGGTCCC
 G  E  E  F  T  I  Q  P  Q  G  A  G  G  S  L  A  Q  P  H  R  L  Q  R  W  G  P

GCCGGAGCCCGCCCCCTCCCGCGAGGACCCGAGTGGGAGGTGGAGACGGGAGAGGGTCAGAGGCAGGAGAGAGGAGAC
 A  G  A  R  P  L  P  R  G  P  E  W  E  V  E  T  G  E  G  Q  R  Q  E  R  G  D

CACCAGGAGGACAGCGAGGAGGAGAGCCAAGAAGAGGAGGCAGAAGGCGCTAGCGAGCCGCCACCGCCCCTGGGGGCC
 H  Q  E  D  S  E  E  E  S  Q  E  E  E  A  E  G  A  S  E  P  P  P  P  L  G  A

ACGAGTAGGACCAAGCGGTTTGTGTCTGAGGCGCGCTTCGTGGAGACGCTGCTGGTGGCCGATGCGTCCATGGCTGCC
 T  S  R  T  K  R  F  V  S  E  A  R  F  V  E  T  L  L  V  A  D  A  S  M  A  A

TTCTACGGGGCCGACCTGCAGAACCACATCCTGACGTTAATGTCTGTGGCAGCCCGAATCTACAAGCACCCCAGCATC
 F  Y  G  A  D  L  Q  N  H  I  L  T  L  M  S  V  A  A  R  I  Y  K  H  P  S  I

AAGAATTCCATCAACCTGATGGTGGTAAAAGTGCTGATCGTAGAAGATGAAAAATGGGGCCCAGAGGTGTCCGACAAT
 K  N  S  I  N  L  M  V  V  K  V  L  I  V  E  D  E  K  W  G  P  E  V  S  D  N

GGGGGGCTTACACTGCGTAACTTCTGCAACTGGCAGCGGCGTTTCAACCAGCCCAGCGACCGCCACCCAGAGCACTAC
 G  G  L  T  L  R  N  F  C  N  W  Q  R  R  F  N  Q  P  S  D  R  H  P  E  H  Y

GACACGGCCATCCTGCTCACCAGACAGAACTTCTGTGGGCAGGAGGGGCTGTGTGACACCCTGGGTGTGGCAGACATC
 D  T  A  I  L  L  T  R  Q  N  F  C  G  Q  E  G  L  C  D  T  L  G  V  A  D  I

GGGACCATTTGTGACCCCAACAAAAGCTGCTCCGTGATCGAGGATGAGGGGCTCCAGGCGGCCCACACCCTGGCCCAT
 G  T  I  C  D  P  N  K  S  C  S  V  I  E  D  E  G  L  Q  A  A  H  T  L  A  H

GAACTAGGGCACGTCCTCAGCATGCCCCACGACGACTCCAAGCCCTGCACACGGCTCTTCGGGCCCATGGGCAAGCAC
 E  L  G  H  V  L  S  M  P  H  D  D  S  K  P  C  T  R  L  F  G  P  M  G  K  H

CACGTGATGGCACCGCTGTTCGTCCACCTGAACCAGACGCTGCCCTGGTCCCCCTGCAGCGCCATGTATCTCACAGAG
 H  V  M  A  P  L  F  V  H  L  N  Q  T  L  P  W  S  P  C  S  A  M  Y  L  T  E

CTTCTGGACGGCGGGCACGGAGACTGTCTCCTGGATGCCCCTGGTGCGGCCCTGCCCCTCCCCACAGGCCTCCCGGGC
 L  L  D  G  G  H  G  D  C  L  L  D  A  P  G  A  A  L  P  L  P  T  G  L  P  G

CGCATGGCCCTGTACCAGCTGGACCAGCAGTGCAGGCAGATCTTTGGGCCGGATTTCCGCCACTGCCCCAACACCTCT
 R  M  A  L  Y  Q  L  D  Q  Q  C  R  Q  I  F  G  P  D  F  R  H  C  P  N  T  S

GCTCAGGACGTCTGCGCCCAGCTTTGGTGCCACACTGATGGGGCTGAGCCCCTGTGCCACACGAAGAATGGCAGCCTG
 A  Q  D  V  C  A  Q  L  W  C  H  T  D  G  A  E  P  L  C  H  T  K  N  G  S  L

CCCTGGGCTGACGGCACGCCGTGCGGGCCTGGGCACCTCTGCTCAGAAGGCAGCTGTCTACCTGAGGAGGAAGTGGAG
 P  W  A  D  G  T  P  C  G  P  G  H  L  C  S  E  G  S  C  L  P  E  E  E  V  E

AGGCCCAAGCCCGTGGTAGATGGAGGCTGGGCACCGTGGGGACCCTGGGGAGAATGTTCTCGGACCTGTGGAGGAGGA
 R  P  K  P  V  V  D  G  G  W  A  P  W  G  P  W  G  E  C  S  R  T  C  G  G
```

FIGURE 2

```
GTACAGTTTTCACACCGTGAGTGCAAGGACCCCGAGCCTCAGAATGGAGGAAGATACTGCCTGGGTCGGAGAGCCAAG
 V  Q  F  S  H  R  E  C  K  D  P  E  P  Q  N  G  G  R  Y  C  L  G  R  R  A  K

TACCAGTCATGCCACACGGAGGAATGCCCCCCTGACGGGAAAAGCTTCAGGGAGCAGCAGTGTGAGAAGTATAATGCC
 Y  Q  S  C  H  T  E  E  C  P  P  D  G  K  S  F  R  E  Q  Q  C  E  K  Y  N  A

TACAATTACACTGACATGGACGGGAATCTCCTGCAGTGGGTCCCCAAGTATGCTGGGGTGTCCCCCCGGGACCGCTGC
 Y  N  Y  T  D  M  D  G  N  L  L  Q  W  V  P  K  Y  A  G  V  S  P  R  D  R  C

AAGTTGTTCTGCCGAGCCCGGGGGAGGAGCGAGTTCAAAGTGTTCGAGGCCAAGGTGATTGATGGCACCCTGTGTGGG
 K  L  F  C  R  A  R  G  R  S  E  F  K  V  F  E  A  K  V  I  D  G  T  L  C  G

CCAGAAACACTGGCCATCTGTGTCCGTGGCCAGTGTGTCAAGGCCGGCTGTGACCATGTGGTGGACTCGCCTCGGAAG
 P  E  T  L  A  I  C  V  R  G  Q  C  V  K  A  G  C  D  H  V  V  D  S  P  R  K

CTGGACAAATGCGGGGTGTGTGGGGCAAAGGCAACTCCTGCAGGAAGGTCTCCGGGTCCCTCACCCCCACCAATTAT
 L  D  K  C  G  V  C  G  G  K  G  N  S  C  R  K  V  S  G  S  L  T  P  T  N  Y

GGCTACAATGACATTGTCACCATCCCAGCTGGTGCCACTAATATTGACGTGAAGCAGCGGAGCCACCCGGGTGTGCAG
 G  Y  N  D  I  V  T  I  P  A  G  A  T  N  I  D  V  K  Q  R  S  H  P  G  V  Q

AACGATGGGAACTACCTGGCGCTGAAGACGGCTGATGGGCAGTACCTGCTCAACGGCAACCTGGCCATCTCTGCCATA
 N  D  G  N  Y  L  A  L  K  T  A  D  G  Q  Y  L  L  N  G  N  L  A  I  S  A  I

GAGCAGGACATCTTGGTGAAGGGGACCATCCTGAAGTACAGCGGCTCCATCGCCACCCTGGAGCGCCTGCAGAGCTTC
 E  Q  D  I  L  V  K  G  T  I  L  K  Y  S  G  S  I  A  T  L  E  R  L  Q  S  F

CGGCCCTTGCCAGAGCCTCTGACAGTGCAGCTCCTGACAGTCCCTGGCGAGGTCTTCCCCCCAAAAGTCAAATACACC
 R  P  L  P  E  P  L  T  V  Q  L  L  T  V  P  G  E  V  F  P  P  K  V  K  Y  T

TTCTTTGTTCCTAATGACGTGGACTTTAGCATGCAGAGCAGCAAAGAGAGAGCAACCACCAACATCATCCAGCCGCTG
 F  F  V  P  N  D  V  D  F  S  M  Q  S  S  K  E  R  A  T  T  N  I  I  Q  P  L

CTCCACGCACAGTGGGTGCTGGGGGACTGGTCTGAGTGCTCTAGCACCTGCGGGGCCGGCTGGCAGAGGCGAACTGTA
 L  H  A  Q  W  V  L  G  D  W  S  E  C  S  S  T  C  G  A  G  W  Q  R  R  T  V

GAGTGCAGGGACCCCTCCGGCCAGGCCTCTGCCACCTGCAACAAGGCTCTGAAACCCGAGGATGCCAAGCCCTGCGAA
 E  C  R  D  P  S  G  Q  A  S  A  T  C  N  K  A  L  K  P  E  D  A  K  P  C  E

AGCCAGCTGTGCCCCCTGTGATTCAGGGGGGCAGGGGCCAGTCTTGTGCTCCTGGACATGCGGTACTGAGGTGCAGAC
 S  Q  L  C  P  L

AAGGTCTCCACTGTGGTGACTGGGTCCCTTGGCCATATCAAGGCAGCACGGCCCACCCAGGCCTCCCATTGCCGCAAC
CCCTCCAGTACTGCACAAATTCCTAAGGGGGAAGAGAAAAGGTATGGGGCGGCAAAACCTATCATCAACTGTCCAWTG
NAATGGAACTTGCTCGGGTTCAATTAAAGGCATAAGTTAAAGTAAATTCATTATGATCAACAGACCTCACNTCATCTG
TTGCANGATACAACTANTAAAAAAAAAAAAAAAAAAAAAAAAAAAA
```

```
1   AAGCTT AAAAAATAGT TTGACT[Operator 1]TAAGA
                      -35
50  TAAGAT GTACCCA[Operator 2]TTCACACATTAA
    -10
94  AGAGGAG AAATTA CATATG
    S/D
```

METH1 POLYNUCLEOTIDES

CROSS-REFERENCE TO RELATED APPLICATIONS

This application is a continuation-in-part of U.S. application Ser. No. 09/318,208, filed May 25, 1999 (now abandoned), the disclosure of which is incorporated by reference herein; said Ser. No. 09/318,208 is a continuation-in-part of U.S. application Ser. No. 09/235,810, filed Jan. 22, 1999 (now abandoned), the disclosure of which is incorporated by reference herein; said Ser. No. 09/235,810 claims benefit of U.S. Provisional Application Ser. No. 60/098,539, filed Aug. 28, 1998, and U.S. Provisional Application Ser. No. 60/072,298, filed Jan. 23, 1998, the disclosures of both of which are incorporated by reference herein. This application is also a continuation-in-part of U.S. application Ser. No. 08/845,496, filed Apr. 24, 1997(now abandoned), the disclosure of which is incorporated by reference herein. This application also claims benefit of U.S. Provisional Application Ser. No. 60/147,823, filed Aug. 10, 1999 and U.S. Provisional Application Ser. No. 60/144,882, filed Jul. 20, 1999, the disclosures of both of which are incorporated by reference herein.

BACKGROUND OF THE INVENTION

FEDERALLY-SPONSORED RESEARCH AND DEVELOPMENT

Part of the work performed during development of this invention utilized U.S. Government funds. The U.S. Government has certain rights in this invention.

1. Field of the Invention

The present invention relates to novel anti-angiogenic proteins, related to thrombospondin. More specifically, isolated nucleic acid molecules are provided encoding human METH1 and METH2 (ME, for metalloprotease, and TH, for thrombospondin). METH1 and METH2 polypeptides are also provided, as are vectors, host cells and recombinant methods for producing the same. Also provided are diagnostic methods for the prognosis of cancer and therapeutic methods for treating individuals in need of an increased amount of METH1 or METH2. Also provided are methods for inhibiting angiogenesis using METH1 or METH2.

2. Related Art

Angiogenesis, the formation of new blood vessels from pre-existing vasculature, is a tightly regulated process in normal adults. Under physiological circumstances, growth of new capillaries is tightly controlled by an interplay of growth regulatory proteins which act either to stimulate or to inhibit blood vessel growth. Normally, the balance between these forces is tipped in favor of inhibition and consequently blood vessel growth is restrained. Under certain pathological circumstances, however, local inhibitory controls are unable to restrain the increased activity of angiogenic inducers. Angiogenesis is a key step in the metastasis of cancer (Folkman, *Nature Med.* 1:27–31 (1995)) and in abnormal wound healing, inflammation, rheumatoid arthritis, psoriasis, and diabetic retinopathy, it is integral to the pathology (Folkman et al., *Science* 235:442–447 (1987)), engendering the hope that these pathological entities could be regulated by pharmacological and/or genetic suppression of blood vessel growth (Iruela-Arispe et al., *Thromb. Haem.* 78:672–677 1997)).

Thrombospondin-1 (TSP-1) is a 450 kDa, anti-angiogenic adhesive glycoprotein released from activated platelets and secreted by growing cells (reviewed in Adams, *Int. J. Biochem. Cell. Biol.* 29:861–865 (1997)). TSP-1 is a homotrimer, with each subunit comprised of a 1152 amino acid residue polypeptide, post-translationally modified by N-linked glycosylation and beta-hydroxylation of asparagine residues.

TSP-1 protein and mRNA levels are regulated by a variety of factors. TSP-1 protein levels are downregulated by IL-1 alpha and TNF alpha. TSP-1 mRNA and protein levels are upregulated by polypeptide growth factors including PDGF, TGF-beta, and bFGF (Bornstein, *Faseb J.* 6: 3290–3299 (1992)) and are also regulated by the level of expression of the p53 tumor suppressor gene product (Dameron et al., *Science* 265:1582–1584 (1994)). At least four other members of the thrombospondin family have been identified: TSP-2, TSP-3, TSP-4, and TSP-5 (also called COMP). There is a need in the art to identify other molecules involved in the regulation of angiogenesis.

SUMMARY OF THE INVENTION

The present invention provides isolated nucleic acid molecules comprising a polynucleotide encoding the METH1 polypeptide having the amino acid sequence shown in SEQ ID NO:2 or the amino acid sequence encoded by the cDNA clone deposited in a bacterial host as ATCC Deposit Number 209581 on Jan. 15, 1998.

The present invention also provides isolated nucleic acid molecules comprising a polynucleotide encoding the METH2 polypeptide having the amino acid sequence shown in SEQ ID NO:4 or the amino acid sequence encoded by the cDNA clone deposited in a bacterial host as ATCC Deposit Number 209582 on Jan. 15, 1998.

The present invention also relates to recombinant vectors, which include the isolated nucleic acid molecules of the present invention, and to host cells containing the recombinant vectors, as well as to methods of making such vectors and host cells and for using them for production of METH1 or METH2 polypeptides or peptides by recombinant techniques.

The invention further provides an isolated METH1 or METH2 polypeptide having an amino acid sequence encoded by a polynucleotide described herein.

The invention further provides a diagnostic method useful during diagnosis or prognosis of cancer.

An additional aspect of the invention is related to a method for treating an individual in need of an increased level of METH1 or METH2 activity in the body comprising administering to such an individual a composition comprising a therapeutically effective amount of an isolated METH1 or METH2 polypeptide of the invention or an agonist thereof.

BRIEF DESCRIPTION OF THE FIGURES

FIG. 1 shows the nucleotide (SEQ ID NO:1) and deduced amino acid (SEQ ID NO:2) sequences of METH1. The protein has a predicted leader sequence of about 28 amino acid residues (underlined).

FIG. 2 shows the nucleotide (SEQ ID NO:3) and deduced amino acid (SEQ ID NO:4) sequences of METH2. The protein has a predicted leader sequence of about 23 amino acid residues (underlined).

FIG. 3 shows a comparison of the amino acid sequence of METH1 (SEQ ID NO:2) and METH2 (SEQ ID NO:4) with that of their closest homologue, a bovine metalloprotease (pNPI) (SEQ ID NO:5). Identical amino acids are boxed. Functional domains predicted by sequence and structural homology are labeled, including the signal peptide (single line), the potential cleavage site for mammalian subtilisin (double underlined), the zinc-binding-site (dotted line; amino acids 383–395 in METH1 and 363–375 in METH2) in the metalloprotease domain, and the putative disintegrin loops (arrows).

FIG. 9 shows the nucleotide sequence of the regulatory elements of the pHE promoter (SEQ ID NO:13). The two lac operator sequences, the Shine-Delgarno sequence (S/D), and the terminal HindIII and NdeI restriction sites (italicized) are indicated.

TABLE 1

Figures 4, 5:
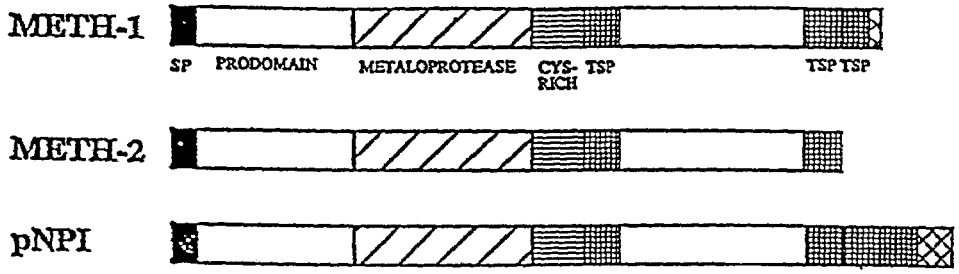
FIG. 4 shows the primary structure of METH1, METH2 and pNPI which includes a prodomain, a catalytic metalloprotease domain, a cysteine rich disintegrin domain, a TSP-like domain, a spacer region and a different number of TSP-like domains, three for METH1, two for METH2, and four for pNPI.
FIG. 5 shows a comparison of the TSP-like domain of METH1 (SEQ ID NO:2) and METH2 (SEQ ID NO:4) with those of TSP1 (SEQ ID NOs:6, 7, and 8) and TSP2 (SEQ ID NOs:9, 10, and 11), cysteines are numbered 1 to 6, tryptophans are marked by asterisks.

| Res | Pos. | Garni...Alpha | Chou...Alpha | Garni...Beta | Chou...Beta | Garni...Turn | Chou...Turn | Garni...Coil | Kyte...Hydro. | Eisen...Alpha | Eisen...Beta | Karpl...Flexi. | James...Antig. | Emini Surfa. |
|---|---|---|---|---|---|---|---|---|---|---|---|---|---|---|
| Met | 1 | | A | | | | | | 0.41 | | | | −0.30 | 0.60 |
| Gly | 2 | A | A | | | | | | 0.91 | | | | 0.50 | 0.81 |
| Asn | 3 | A | A | | | | | | 0.71 | | | | 0.75 | 1.24 |
| Ala | 4 | A | A | | | | | | 0.89 | | | | 1.09 | 1.26 |
| Glu | 5 | A | A | | | | | | 0.93 | | | F | 1.58 | 1.97 |
| Arg | 6 | | | B | | | | | 1.23 | | | F | 1.92 | 1.21 |
| Ala | 7 | | A | B | | | | | 1.69 | | | F | 2.66 | 1.61 |
| Pro | 8 | | | | | T | T | | 1.39 | | | F | 3.40 | 1.82 |
| Gly | 9 | | | | | T | T | | 1.28 | | | F | 3.06 | 1.25 |
| Ser | 10 | | | | | T | T | | 0.93 | | | F | 2.42 | 1.07 |
| Arg | 11 | | | | | T | T | | 0.61 | | * | F | 1.93 | 1.07 |
| Ser | 12 | | | | | T | T | | 0.34 | | | F | 1.74 | 0.68 |
| Phe | 13 | | | | | | T | | 0.34 | | | F | 0.25 | 0.59 |
| Gly | 14 | | | B | | | | | 0.38 | | | F | 0.25 | 0.47 |
| Pro | 15 | | | B | B | | | | −0.13 | | | | −0.45 | 0.50 |
| Val | 16 | | | B | B | | | | −1.06 | | | | −0.45 | 0.48 |
| Pro | 17 | | | B | B | | | | −1.57 | | | | −0.45 | 0.40 |
| Thr | 18 | | A | B | | | | | −1.68 | | | | −0.45 | 0.21 |
| Leu | 19 | A | A | B | | | | | −1.92 | | | | −0.60 | 0.24 |
| Leu | 20 | A | A | | | | | | −2.30 | | | | −0.60 | 0.15 |
| Leu | 21 | A | A | | | | | | −2.03 | | | | −0.60 | 0.11 |
| Leu | 22 | A | A | | | | | | −2.63 | * | | | −0.60 | 0.13 |
| Ala | 23 | A | A | | | | | | −3.13 | * | | | −0.60 | 0.13 |
| Ala | 24 | A | A | | | | | | −2.91 | * | | | −0.60 | 0.13 |
| Leu | 25 | A | A | | | | | | −2.96 | * | | | −0.60 | 0.16 |
| Leu | 26 | A | A | | B | | | | −2.44 | | | | −0.60 | 0.12 |
| Ala | 27 | A | A | | B | | | | −1.63 | | | | −0.60 | 0.16 |
| Ala | 28 | A | A | | B | | | | −1.63 | | | | −0.30 | 0.26 |
| Val | 29 | A | A | | B | | | | −1.86 | | | | −0.30 | 0.32 |
| Ser | 30 | A | A | | | | | | −1.61 | | * | | −0.30 | 0.32 |
| Asp | 31 | A | A | | | | | | −0.69 | | * | F | −0.15 | 0.31 |
| Ala | 32 | A | A | | | | | | −0.09 | | * | F | 0.75 | 0.83 |
| Leu | 33 | | | | | | | C | 0.20 | * | * | F | 1.55 | 0.96 |
| Gly | 34 | | | | | | | C | 1.06 | * | * | F | 1.85 | 0.77 |
| Arg | 35 | | | | | | | C | 1.36 | * | * | F | 2.70 | 1.32 |
| Pro | 36 | | | | | T | T | C | 1.36 | * | * | F | 3.00 | 2.76 |
| Ser | 37 | | | | | T | T | C | 1.94 | | * | F | 2.70 | 4.66 |
| Glu | 38 | A | A | | | | | | 2.76 | * | | F | 2.20 | 4.12 |
| Glu | 39 | A | A | | | | | | 2.29 | * | | F | 1.50 | 4.61 |
| Asp | 40 | A | A | | | | | | 1.32 | * | | F | 1.20 | 2.84 |
| Glu | 41 | A | A | | | | | | 0.68 | | | F | 0.90 | 1.22 |
| Glu | 42 | A | A | | | | | | 0.77 | | | F | 0.75 | 0.52 |
| Leu | 43 | A | A | | | | | | 0.77 | | | F | 0.60 | 0.48 |
| Val | 44 | A | A | | | | | | −0.04 | * | | | 0.60 | 0.48 |
| Val | 45 | A | A | | | | | | −0.04 | * | | | −0.30 | 0.23 |
| Pro | 46 | A | | | | | | | 0.07 | | | | −0.30 | 0.48 |
| Glu | 47 | A | A | | | | | | −0.52 | | | F | 1.10 | 1.27 |
| Leu | 48 | A | | | | | | | 0.08 | * | | F | 1.41 | 1.73 |

TABLE 1-continued

| Res | Pos. | Garni...Alpha | Chou...Alpha | Garni...Beta | Chou...Beta | Garni...Turn | Chou...Turn | Garni...Coil | Kyte...Hydro. | Eisen...Alpha | Eisen...Beta | Karpl...Flexi. | James...Antig. | Emini Surfa... |
|---|---|---|---|---|---|---|---|---|---|---|---|---|---|---|
| Glu | 49 | A | . | . | . | . | . | . | 0.59 | . | . | . | 1.72 | 1.73 |
| Arg | 50 | A | . | . | . | . | . | . | 1.41 | . | . | F | 1.88 | 0.99 |
| Ala | 51 | A | . | . | . | . | . | . | 1.28 | . | . | F | 2.24 | 1.64 |
| Pro | 52 | . | . | . | . | . | . | . | 0.97 | . | . | F | 3.10 | 0.93 |
| Gly | 53 | . | . | . | . | T | T | . | 1.47 | * | * | F | 2.49 | 0.69 |
| His | 54 | . | . | . | . | T | T | C | 1.58 | * | * | F | 1.38 | 0.98 |
| Gly | 55 | . | . | . | . | T | T | C | 0.66 | * | * | F | 1.62 | 1.25 |
| Thr | 56 | . | . | . | . | . | . | C | 1.36 | * | * | F | 0.71 | 1.04 |
| Thr | 57 | . | A | . | . | . | . | . | 0.76 | . | * | F | 0.60 | 1.49 |
| Arg | 58 | . | A | B | . | . | . | . | 1.07 | . | * | F | 0.60 | 1.25 |
| Leu | 59 | . | A | B | . | . | . | . | 0.51 | . | * | F | 0.45 | 1.17 |
| Arg | 60 | . | A | B | . | . | . | . | 0.16 | . | * | . | 0.30 | 0.82 |
| Leu | 61 | . | A | B | . | . | . | . | 0.47 | . | * | . | −0.30 | 0.36 |
| His | 62 | A | A | . | . | . | . | . | 0.78 | . | * | . | −0.30 | 0.74 |
| Ala | 63 | A | A | . | . | . | . | . | 0.67 | . | * | . | 0.30 | 0.65 |
| Phe | 64 | A | A | . | . | . | . | . | 0.37 | . | * | . | −0.15 | 1.37 |
| Asp | 65 | A | A | . | . | . | . | . | 0.56 | . | * | . | −0.15 | 0.83 |
| Gln | 66 | A | A | . | . | . | . | . | 0.56 | . | * | F | 0.60 | 1.37 |
| Gln | 67 | A | A | . | . | . | . | . | 0.59 | * | * | F | 0.60 | 1.30 |
| Leu | 68 | A | A | B | . | . | . | . | 1.18 | * | * | F | 0.90 | 1.35 |
| Asp | 69 | A | A | B | . | . | . | . | 0.97 | . | * | . | 0.30 | 0.64 |
| Leu | 70 | A | A | . | . | . | . | . | 0.97 | . | * | . | 0.94 | 0.73 |
| Glu | 71 | . | A | B | . | . | . | . | 0.67 | . | * | . | 1.43 | 1.37 |
| Leu | 72 | . | A | B | . | . | . | C | 1.18 | * | . | . | 1.77 | 1.37 |
| Arg | 73 | . | . | . | . | T | T | . | 0.48 | * | . | F | 2.86 | 2.22 |
| Pro | 74 | . | . | . | . | T | T | . | 0.48 | . | . | F | 3.40 | 1.72 |
| Asp | 75 | . | . | . | . | . | T | C | −0.11 | . | . | F | 2.76 | 1.80 |
| Ser | 76 | . | . | B | . | T | . | . | 0.49 | * | . | F | 2.07 | 0.76 |
| Ser | 77 | . | . | B | B | . | . | . | 0.03 | * | . | . | 0.73 | 0.50 |
| Phe | 78 | . | . | B | B | . | . | . | −0.46 | * | . | . | 0.24 | 0.46 |
| Leu | 79 | . | . | B | B | . | . | . | −0.77 | * | . | . | −0.40 | 0.34 |
| Ala | 80 | . | . | B | . | T | . | . | −1.28 | * | . | . | −0.20 | 0.22 |
| Pro | 81 | . | . | B | . | . | . | . | −0.98 | * | . | . | −0.20 | 0.37 |
| Gly | 82 | . | . | . | . | . | T | . | −0.28 | . | . | . | 0.20 | 0.37 |
| Phe | 83 | . | . | B | . | . | T | . | −0.32 | * | . | . | −0.20 | 0.63 |
| Thr | 84 | . | . | B | B | T | T | . | −0.08 | * | . | . | −0.60 | 0.65 |
| Leu | 85 | . | . | B | B | . | T | . | 0.24 | * | * | . | −0.60 | 0.49 |
| Gln | 86 | . | . | B | . | . | T | . | 0.63 | . | * | . | −0.29 | 0.56 |
| Asn | 87 | . | . | . | . | . | . | . | 1.03 | . | * | F | 0.87 | 0.76 |
| Val | 88 | . | . | . | . | . | . | . | 1.00 | . | * | F | 1.93 | 1.84 |
| Gly | 89 | . | . | . | . | . | . | C | 1.51 | . | . | F | 2.74 | 1.42 |
| Arg | 90 | . | . | . | . | . | T | . | 1.51 | . | . | F | 3.10 | 0.87 |
| Lys | 91 | . | . | . | . | . | T | C | 1.20 | . | . | F | 2.74 | 1.58 |
| Ser | 92 | . | . | . | . | . | T | C | 1.84 | . | . | F | 2.43 | 2.76 |
| Gly | 93 | . | . | . | . | . | T | C | 1.38 | . | . | F | 2.38 | 2.04 |
| Ser | 94 | . | . | . | . | . | T | C | 1.06 | . | . | F | 2.33 | 1.57 |
| Glu | 95 | . | . | . | . | . | . | C | 1.01 | . | . | F | 1.63 | 0.97 |
| Thr | 96 | . | . | . | . | . | . | C | 1.01 | . | . | F | 2.04 | 1.51 |
| Pro | 97 | . | . | . | . | . | . | C | 1.00 | . | . | F | 2.60 | 1.96 |

TABLE 1-continued

| Res | Pos. | Garni...Alpha | Chou...Alpha | Garni...Beta | Chou...Beta | Garni...Turn | Chou...Turn | Garni...Coil | Kyte...Hydro. | Eisen. | Eisen...Alpha | Eisen...Beta | Kapl. | Flexi. | James...Antig. | Emini Surfa. |
|---|---|---|---|---|---|---|---|---|---|---|---|---|---|---|---|---|
| Leu | 98 | . | . | . | . | . | . | . | 1.34 | . | . | . | . | . | 2.04 | 1.63 |
| Pro | 99 | A | . | . | . | . | . | . | 0.83 | . | . | . | . | . | 1.58 | 1.89 |
| Glu | 100 | A | A | . | . | . | . | . | 0.24 | . | . | . | . | F | 1.12 | 1.01 |
| Thr | 101 | A | A | . | . | . | . | . | 0.52 | . | . | . | . | F | 0.86 | 1.23 |
| Asp | 102 | A | A | . | . | . | . | . | 0.07 | . | . | . | . | F | 0.60 | 1.08 |
| Leu | 103 | A | A | . | . | . | . | . | 0.18 | . | . | . | . | F | 0.30 | 0.34 |
| Ala | 104 | A | A | . | . | . | . | . | 0.14 | . | . | . | . | . | -0.60 | 0.20 |
| His | 105 | . | A | B | . | . | . | . | -0.16 | . | . | . | . | . | -0.60 | 0.19 |
| Cys | 106 | . | A | B | . | . | . | . | -0.19 | . | . | . | . | . | -0.60 | 0.31 |
| Phe | 107 | . | A | B | . | . | . | . | -0.50 | . | . | . | . | . | -0.60 | 0.30 |
| Tyr | 108 | . | . | B | . | . | T | . | -0.54 | . | . | . | . | . | -0.20 | 0.32 |
| Ser | 109 | . | . | . | . | T | T | . | 0.04 | . | . | . | . | . | 0.35 | 0.44 |
| Gly | 110 | . | . | . | . | T | T | . | -0.27 | . | . | * | . | F | 0.35 | 0.82 |
| Thr | 111 | . | . | . | . | T | T | . | 0.40 | . | . | * | . | F | 0.59 | 0.52 |
| Val | 112 | . | . | B | B | . | . | . | 0.89 | . | . | * | . | F | 0.93 | 0.65 |
| Asn | 113 | . | . | . | . | T | . | . | 0.83 | . | . | * | . | F | 1.72 | 1.01 |
| Gly | 114 | . | . | . | . | . | . | C | 0.59 | . | . | * | . | F | 1.61 | 0.94 |
| Asp | 115 | . | . | B | B | T | T | C | 0.31 | . | . | . | . | F | 2.40 | 1.69 |
| Pro | 116 | . | . | . | B | . | T | C | 0.58 | . | . | * | . | F | 2.16 | 1.06 |
| Ser | 117 | . | . | . | . | . | T | C | -0.23 | . | . | . | . | F | 1.92 | 1.08 |
| Ser | 118 | A | A | . | . | . | . | . | -0.19 | . | . | * | . | F | 1.33 | 0.66 |
| Ala | 119 | A | A | . | . | . | . | . | -1.00 | . | . | * | . | F | -0.06 | 0.35 |
| Ala | 120 | A | A | . | . | . | . | . | -1.46 | . | . | * | . | . | -0.30 | 0.35 |
| Leu | 121 | A | A | . | . | . | . | . | -1.16 | . | * | . | . | . | -0.60 | 0.22 |
| Ser | 122 | A | A | . | . | . | . | . | -1.20 | . | * | . | . | . | -0.60 | 0.11 |
| Ser | 123 | A | A | B | . | . | . | . | -1.47 | . | * | . | . | . | -0.30 | 0.20 |
| Leu | 124 | A | A | B | . | . | . | . | -0.77 | . | * | . | . | . | -0.30 | 0.19 |
| Cys | 125 | . | . | . | . | . | . | . | -0.52 | . | * | . | . | . | -0.30 | 0.17 |
| Glu | 126 | . | . | . | B | . | . | . | -0.30 | . | * | . | . | . | 0.30 | 0.25 |
| Gly | 127 | A | . | . | B | . | . | . | -0.70 | . | * | . | . | F | 0.65 | 0.30 |
| Val | 128 | A | . | B | B | . | . | . | -0.13 | . | . | * | . | F | 0.65 | 0.57 |
| Arg | 129 | . | . | B | B | . | . | . | -0.28 | . | . | * | . | F | 0.65 | 0.29 |
| Gly | 130 | . | . | B | B | . | . | . | -1.09 | . | . | * | . | F | -0.60 | 0.45 |
| Ala | 131 | . | A | B | B | . | . | . | -1.09 | . | . | * | . | . | -0.60 | 0.50 |
| Phe | 132 | . | A | B | B | . | . | . | -0.23 | . | . | * | . | . | -0.60 | 0.21 |
| Tyr | 133 | . | A | B | B | . | . | . | -0.93 | . | . | * | . | . | -0.60 | 0.21 |
| Leu | 134 | A | A | . | . | . | . | . | -0.83 | . | . | * | . | . | -0.60 | 0.36 |
| Gly | 135 | A | A | . | . | . | . | . | -0.94 | . | . | . | . | . | -0.60 | 0.42 |
| Glu | 136 | A | A | . | B | . | . | . | -1.13 | . | . | . | . | . | -0.60 | 0.42 |
| Ala | 137 | . | A | B | . | . | . | . | -0.89 | . | . | . | . | . | -0.60 | 0.44 |
| Tyr | 138 | A | A | B | B | . | . | . | -0.29 | . | . | . | . | . | -0.60 | 0.38 |
| Phe | 139 | A | A | B | B | . | . | . | -0.29 | . | . | . | . | . | -0.60 | 0.66 |
| Ile | 140 | . | . | B | B | . | . | . | -0.16 | . | . | . | . | . | -0.60 | 0.59 |
| Gln | 141 | . | . | B | B | . | . | . | -0.74 | . | . | . | . | . | -0.60 | 0.48 |
| Pro | 142 | . | . | B | B | . | . | . | -0.94 | . | . | * | . | . | -0.60 | 0.48 |
| Leu | 143 | . | . | B | . | . | . | C | -0.80 | . | * | . | . | . | -0.40 | 0.55 |
| Pro | 144 | A | A | . | . | . | . | C | -0.10 | . | * | . | . | . | -0.10 | 0.80 |
| Ala | 145 | A | A | . | . | . | . | C | 0.90 | . | * | * | . | . | 0.30 | 0.62 |
| Ala | 146 | A | A | . | . | . | . | . | 0.69 | . | . | * | . | . | . | 0.69 |

TABLE 1-continued

| Res | Pos. | Garni...Alpha | Chou...Alpha | Garni...Beta | Chou...Beta | Garni...Turn | Chou...Turn | Garni...Coil | Kyte-...Hydro. | Eisen... | Eisen...Alpha | Eisen...Beta | Kapl...Flexi. | James...Antig. | Emini Surfa... |
|---|---|---|---|---|---|---|---|---|---|---|---|---|---|---|---|
| Ala | 147 | A | A | . | . | . | . | . | 0.09 | . | . | . | . | 0.75 | 1.64 |
| Ser | 148 | A | A | . | . | . | . | . | -0.29 | . | * | . | F | 0.75 | 0.88 |
| Glu | 149 | A | A | . | . | . | . | . | 0.21 | . | * | . | F | 0.45 | 0.88 |
| Arg | 150 | A | A | . | . | . | . | . | -0.17 | . | * | . | F | 0.60 | 1.25 |
| Leu | 151 | A | A | . | . | . | . | . | -0.17 | . | . | . | . | 0.30 | 0.94 |
| Ala | 152 | A | A | . | . | . | . | . | 0.21 | . | * | * | . | 0.30 | 0.55 |
| Thr | 153 | A | A | . | . | . | . | . | 0.17 | . | . | * | . | 0.04 | 0.43 |
| Ala | 154 | A | A | . | . | . | . | . | 0.17 | . | . | . | . | 0.08 | 0.52 |
| Ala | 155 | . | . | . | . | . | T | C | 0.10 | . | . | . | . | 2.07 | 0.89 |
| Pro | 156 | . | . | . | . | . | T | C | 0.70 | . | . | * | F | 2.86 | 1.24 |
| Gly | 157 | . | . | . | . | T | T | . | 1.08 | . | . | . | F | 3.40 | 1.90 |
| Glu | 158 | . | . | . | . | . | T | C | 0.80 | . | . | * | F | 2.86 | 2.90 |
| Lys | 159 | . | . | . | . | . | . | C | 1.18 | . | . | * | F | 2.32 | 1.90 |
| Pro | 160 | . | . | . | . | . | . | C | 0.96 | . | . | * | F | 1.98 | 2.97 |
| Pro | 161 | . | . | . | . | . | . | C | 1.17 | . | . | . | F | 1.64 | 1.41 |
| Ala | 162 | A | A | . | . | . | . | . | 0.81 | . | . | . | . | 0.60 | 1.22 |
| Pro | 163 | A | A | . | . | . | . | . | 0.78 | . | . | * | . | -0.60 | 0.68 |
| Leu | 164 | A | A | . | . | . | . | . | -0.08 | . | * | . | . | -0.60 | 0.60 |
| Gln | 165 | A | A | . | . | . | . | . | -0.68 | . | * | . | . | -0.60 | 0.49 |
| Phe | 166 | . | . | B | . | . | . | . | -0.36 | . | * | . | . | -0.60 | 0.26 |
| His | 167 | . | A | B | . | . | . | . | 0.34 | . | * | . | . | -0.26 | 0.62 |
| Leu | 168 | A | A | B | . | . | . | . | 0.56 | . | * | . | . | 0.38 | 0.70 |
| Leu | 169 | . | A | B | . | . | . | . | 1.48 | . | * | * | . | 0.87 | 1.31 |
| Arg | 170 | . | . | . | . | T | T | . | 1.48 | . | . | * | F | 3.06 | 1.88 |
| Arg | 171 | . | . | . | . | T | T | . | 1.83 | . | . | . | F | 3.40 | 3.96 |
| Asn | 172 | . | . | . | . | T | T | . | 1.87 | . | . | . | F | 3.06 | 4.75 |
| Arg | 173 | . | . | . | . | T | T | . | 1.82 | . | . | * | F | 2.72 | 4.05 |
| Gln | 174 | . | . | . | . | T | . | . | 2.29 | . | . | * | F | 2.43 | 1.53 |
| Gly | 175 | . | . | . | . | T | T | . | 1.83 | . | . | * | F | 2.19 | 0.94 |
| Asp | 176 | . | . | . | . | . | T | . | 1.41 | . | . | * | F | 2.30 | 0.48 |
| Val | 177 | . | . | B | . | . | . | . | 0.74 | . | . | . | F | 1.85 | 0.40 |
| Gly | 178 | . | . | . | . | T | T | . | 0.29 | . | . | . | F | 2.50 | 0.22 |
| Gly | 179 | . | . | B | . | . | . | . | -0.57 | . | * | . | F | 1.85 | 0.13 |
| Thr | 180 | . | . | B | B | . | . | . | -1.08 | . | . | * | . | 0.30 | 0.13 |
| Cys | 181 | . | . | B | B | . | . | . | -1.08 | . | . | * | . | -0.10 | 0.10 |
| Gly | 182 | . | . | B | B | . | . | . | -0.22 | . | * | * | . | -0.05 | 0.16 |
| Val | 183 | . | . | B | B | . | . | . | 0.12 | . | * | * | . | 0.30 | 0.19 |
| Val | 184 | . | . | B | . | . | . | . | 0.26 | . | * | * | . | 0.90 | 0.60 |
| Asp | 185 | . | . | B | . | . | . | . | 0.68 | . | . | * | F | 1.75 | 0.94 |
| Asp | 186 | . | . | B | . | . | . | . | 1.13 | . | . | * | F | 2.20 | 2.49 |
| Glu | 187 | . | . | B | . | . | . | . | 1.17 | . | . | * | F | 2.50 | 5.18 |
| Pro | 188 | . | . | . | . | . | T | C | 1.68 | . | * | * | F | 3.00 | 4.48 |
| Arg | 189 | . | . | . | . | . | T | C | 2.58 | . | * | * | F | 2.70 | 2.66 |
| Pro | 190 | . | . | . | . | . | T | C | 1.99 | . | * | * | F | 2.40 | 3.07 |
| Thr | 191 | . | . | . | . | . | T | C | 1.99 | . | * | * | F | 2.10 | 2.00 |
| Gly | 192 | . | . | . | . | . | T | . | 1.68 | . | * | * | F | 1.80 | 1.77 |
| Lys | 193 | A | A | . | . | . | . | . | 1.89 | . | * | * | F | 0.90 | 1.65 |
| Ala | 194 | A | A | . | . | . | . | . | 1.78 | . | * | * | F | 0.90 | 1.98 |
| Glu | 195 | A | A | . | . | . | . | . | 1.99 | . | * | * | F | 0.90 | 3.35 |

TABLE 1-continued

| Res | Pos. | Garni...Alpha | Chou...Alpha | Garni...Beta | Chou...Beta | Garni...Turn | Chou...Turn | Garni...Coil | Kyte-...Hydro. | Eisen...Alpha | Eisen...Beta | Kapl...Flexi. | James...Antig. | Emini Surfa. |
|---|---|---|---|---|---|---|---|---|---|---|---|---|---|---|
| Thr | 196 | A | A | . | . | . | . | . | 2.30 | . | . | F | 0.90 | 2.90 |
| Glu | 197 | A | A | . | . | . | . | . | 2.64 | . | * | F | 0.90 | 4.79 |
| Asp | 198 | A | A | . | . | . | . | . | 2.26 | . | * | F | 0.90 | 4.79 |
| Glu | 199 | A | A | . | . | . | . | . | 2.53 | . | . | F | 0.90 | 3.29 |
| Asp | 200 | A | . | . | . | . | T | . | 2.53 | . | . | F | 1.30 | 2.74 |
| Glu | 201 | A | A | . | . | . | T | . | 2.50 | . | . | F | 1.30 | 2.84 |
| Gly | 202 | A | A | . | . | . | T | . | 2.50 | . | . | F | 1.30 | 1.62 |
| Thr | 203 | A | . | . | . | . | T | . | 2.50 | . | . | F | 1.30 | 1.68 |
| Glu | 204 | A | A | . | . | . | . | . | 2.50 | . | . | F | 0.90 | 1.62 |
| Gly | 205 | A | A | . | . | . | . | . | 2.16 | . | . | F | 1.20 | 2.84 |
| Glu | 206 | A | A | . | . | . | . | . | 1.94 | . | . | F | 1.50 | 1.95 |
| Asp | 207 | . | A | . | . | T | . | . | 2.29 | . | . | F | 2.20 | 1.74 |
| Glu | 208 | . | A | . | . | . | T | C | 2.31 | * | . | F | 2.30 | 3.04 |
| Gly | 209 | . | . | . | . | T | T | C | 2.01 | * | . | F | 3.00 | 1.85 |
| Pro | 210 | . | . | . | . | T | T | . | 2.14 | * | . | F | 2.60 | 1.48 |
| Gln | 211 | . | . | . | . | T | T | . | 2.14 | . | . | F | 2.30 | 1.32 |
| Trp | 212 | . | . | . | . | . | . | C | 2.14 | . | . | F | 1.44 | 2.32 |
| Ser | 213 | . | . | . | . | . | T | C | 1.93 | . | . | F | 1.78 | 2.50 |
| Pro | 214 | . | . | . | . | T | T | . | 1.69 | . | . | F | 2.12 | 2.23 |
| Gln | 215 | . | . | . | . | . | . | C | 1.56 | * | . | F | 1.56 | 2.15 |
| Asp | 216 | . | . | . | . | . | T | C | 1.09 | * | . | F | 2.40 | 1.32 |
| Pro | 217 | . | . | . | . | T | T | . | 1.03 | * | . | F | 2.16 | 1.48 |
| Ala | 218 | . | . | . | . | . | . | . | 0.48 | . | . | F | 1.77 | 0.85 |
| Leu | 219 | . | . | B | . | . | . | . | 0.34 | * | . | F | 0.53 | 0.38 |
| Gln | 220 | . | . | B | . | . | . | . | 0.13 | . | . | F | -0.01 | 0.24 |
| Gly | 221 | . | . | B | . | . | T | . | 0.03 | * | . | F | -0.05 | 0.41 |
| Val | 222 | . | . | B | . | . | . | . | 0.28 | * | . | F | -0.05 | 0.77 |
| Gly | 223 | . | . | B | . | . | . | . | 0.78 | * | . | F | 0.25 | 0.64 |
| Gln | 224 | . | . | B | B | . | . | . | 0.43 | * | . | F | 0.25 | 0.64 |
| Pro | 225 | . | . | . | . | . | . | . | 0.48 | . | . | . | 0.20 | 1.25 |
| Thr | 226 | . | . | . | . | T | T | C | 0.44 | * | . | F | 0.60 | 1.25 |
| Gly | 227 | . | . | B | B | . | . | . | 0.90 | * | . | F | 0.45 | 0.97 |
| Thr | 228 | . | . | B | B | . | T | . | 0.94 | * | . | F | 0.25 | 0.44 |
| Gly | 229 | . | . | B | . | . | T | . | 1.20 | * | . | F | 0.85 | 0.60 |
| Ser | 230 | . | . | B | . | . | . | . | 1.62 | * | . | F | 1.30 | 1.20 |
| Ile | 231 | A | A | B | . | . | . | . | 1.27 | . | . | F | 0.90 | 1.67 |
| Arg | 232 | A | A | B | . | . | . | . | 0.72 | . | . | F | 0.90 | 3.30 |
| Lys | 233 | A | A | B | . | . | . | . | 0.77 | . | . | F | 0.90 | 2.13 |
| Lys | 234 | A | A | B | B | . | . | . | 0.77 | . | . | F | 0.90 | 2.26 |
| Arg | 235 | A | A | B | B | . | . | . | 0.28 | . | . | F | 0.90 | 1.55 |
| Phe | 236 | . | . | B | B | . | . | . | 1.62 | . | . | . | 0.75 | 1.04 |
| Val | 237 | . | . | B | . | . | . | . | 1.33 | . | . | . | 0.30 | 0.71 |
| Ser | 238 | . | . | . | . | . | T | . | 0.43 | * | . | . | 0.70 | 0.71 |
| Ser | 229 | . | . | . | . | . | T | C | 0.32 | * | . | . | 0.15 | 1.28 |
| His | 240 | . | . | . | . | . | T | C | 0.71 | * | . | . | 0.45 | 1.28 |
| Arg | 241 | . | . | . | . | . | . | C | 0.97 | * | . | . | 1.05 | 1.65 |
| Tyr | 242 | A | . | . | B | . | . | . | 0.46 | . | . | . | 0.45 | 1.78 |
| Val | 243 | A | . | . | B | . | . | . | 0.46 | . | . | . | 0.45 | 1.29 |
| Glu | 244 | . | . | B | B | . | . | . | -0.10 | * | . | . | -0.30 | 0.54 |

TABLE 1-continued

| Res | Pos. | Garni...Alpha | Chou...Alpha | Garni...Beta | Chou...Beta | Garni...Turn | Chou...Turn | Garni...Coil | Kyte-...Hydro. | Eisen... | Eisen...Alpha | Eisen...Beta | Kapl...Flexi. | James...Antig. | Emini Surfa... |
|---|---|---|---|---|---|---|---|---|---|---|---|---|---|---|---|
| Thr | 245 | . | . | . | B | . | . | . | -0.66 | . | . | . | . | -0.60 | 0.26 |
| Met | 246 | A | . | B | B | . | . | . | -0.77 | . | . | . | . | -0.60 | 0.35 |
| Leu | 247 | A | . | B | B | . | . | . | -0.52 | . | . | . | . | 0.30 | 0.34 |
| Val | 248 | A | . | . | B | . | . | . | 0.03 | . | . | . | . | 0.30 | 0.41 |
| Ala | 249 | A | . | . | B | . | . | . | -0.57 | . | . | . | . | -0.30 | 0.55 |
| Asp | 250 | A | . | . | . | . | T | . | -0.84 | . | . | . | . | -0.30 | 0.66 |
| Gln | 251 | A | . | . | . | . | T | . | -0.24 | . | . | . | . | 0.25 | 0.90 |
| Ser | 252 | A | . | . | . | . | T | . | -0.13 | . | . | . | . | 0.25 | 0.25 |
| Met | 253 | A | . | . | . | . | T | . | 0.69 | . | . | . | . | 1.30 | 1.54 |
| Ala | 254 | A | . | . | . | . | . | . | 0.93 | . | * | * | . | 0.70 | 0.80 |
| Glu | 255 | A | . | . | . | . | . | . | 0.63 | . | * | * | . | -0.10 | 0.63 |
| Phe | 256 | A | . | . | . | . | . | . | 0.29 | . | . | * | . | -0.10 | 0.46 |
| His | 257 | A | . | . | . | . | T | . | -0.22 | . | . | . | . | -0.10 | 0.63 |
| Gly | 258 | A | . | . | . | . | T | . | 0.42 | . | . | . | F | 0.10 | 0.61 |
| Ser | 259 | A | . | . | . | . | T | . | 0.98 | . | . | . | F | 0.25 | 0.29 |
| Gly | 260 | A | . | . | . | . | T | . | 0.63 | . | . | . | F | 0.25 | 0.68 |
| Leu | 261 | A | . | . | . | . | . | . | 0.73 | . | . | . | . | 0.85 | 0.68 |
| Lys | 262 | A | A | . | . | . | . | . | 0.62 | . | . | . | . | 0.00 | 1.07 |
| His | 263 | . | A | B | . | . | . | . | -0.16 | . | . | . | F | -0.60 | 0.66 |
| Tyr | 264 | . | A | B | . | . | . | . | -0.12 | . | . | * | F | -0.60 | 0.55 |
| Leu | 265 | . | A | B | . | . | . | . | -0.63 | . | . | * | F | -0.60 | 0.96 |
| Leu | 266 | . | A | B | . | . | . | . | -0.99 | . | . | * | . | -0.60 | 0.40 |
| Thr | 267 | . | A | B | . | . | . | . | -0.48 | . | * | * | . | -0.60 | 0.25 |
| Leu | 268 | . | A | B | . | . | . | . | -1.38 | . | * | * | . | -0.60 | 0.22 |
| Phe | 269 | A | A | . | . | . | . | . | -1.93 | . | * | * | . | -0.60 | 0.19 |
| Ser | 270 | A | A | . | . | . | . | . | -2.28 | . | * | * | . | -0.60 | 0.24 |
| Val | 271 | A | A | . | . | . | . | . | -1.36 | . | * | * | . | -0.60 | 0.17 |
| Ala | 272 | A | A | . | . | . | . | . | -1.36 | . | * | * | . | -0.60 | 0.39 |
| Ala | 273 | A | A | . | . | . | . | . | -1.29 | . | * | * | . | -0.60 | 0.38 |
| Arg | 274 | A | A | . | . | . | . | . | -0.43 | . | * | * | . | -0.60 | 0.44 |
| Leu | 275 | A | . | . | . | . | . | . | 0.23 | . | * | * | . | -0.15 | 1.18 |
| Tyr | 276 | . | . | . | . | T | . | . | 0.32 | . | * | * | . | 0.45 | 1.59 |
| Lys | 277 | . | . | B | . | . | T | . | 0.88 | . | * | * | F | 1.39 | 2.44 |
| His | 278 | . | . | B | B | . | T | . | 0.58 | . | * | * | F | 1.48 | 1.67 |
| Pro | 279 | . | . | B | B | . | T | . | 1.28 | . | * | * | F | 1.12 | 1.42 |
| Ser | 280 | . | . | . | . | T | . | . | 1.17 | . | * | * | F | 2.36 | 1.77 |
| Ile | 281 | . | . | B | B | . | . | . | 1.68 | . | * | * | F | 3.40 | 1.43 |
| Arg | 282 | . | . | B | B | . | . | . | 1.07 | . | * | * | F | 2.36 | 1.41 |
| Asn | 283 | . | . | B | B | . | . | . | 0.72 | . | . | * | F | 1.47 | 0.67 |
| Ser | 284 | . | . | B | B | . | . | . | -0.06 | . | . | . | . | 1.13 | 0.67 |
| Val | 285 | . | . | B | B | . | . | . | -0.70 | . | . | . | . | 0.19 | 0.79 |
| Ser | 286 | . | . | B | B | . | . | . | -1.26 | . | . | . | . | -0.30 | 0.30 |
| Ser | 287 | . | . | B | B | . | . | . | -1.22 | . | . | . | . | -0.60 | 0.14 |
| Leu | 288 | . | . | B | B | . | . | . | -1.29 | . | . | * | . | -0.60 | 0.08 |
| Val | 289 | . | . | B | B | . | . | . | -2.18 | . | . | . | . | -0.60 | 0.21 |
| Val | 290 | . | . | B | B | . | . | . | -2.69 | . | . | * | . | -0.60 | 0.11 |
| Val | 291 | . | . | B | B | . | . | . | -2.69 | . | . | . | . | -0.60 | 0.11 |
| Lys | 292 | . | . | B | B | . | . | . | -3.28 | . | . | . | . | -0.60 | 0.10 |
| Ile | 293 | . | . | B | B | . | . | . | -2.50 | . | . | . | . | -0.60 | 0.10 |
| Leu | . | . | . | B | B | . | . | . | -1.64 | . | . | * | . | -0.60 | 0.19 |

TABLE 1-continued

| Res | Pos. | Garni...Alpha | Chou...Alpha | Garni...Beta | Chou...Beta | Garni...Turn | Chou...Turn | Garni...Coil | Kyte-...Hydro. | Eisen... | Eisen...Alpha | Eisen...Beta | Kapl...Flexi. | James...Antig. | Emini Surfa. |
|---|---|---|---|---|---|---|---|---|---|---|---|---|---|---|---|
| Val | 294 | . | . | . | B | . | . | . | −0.79 | . | . | . | . | −0.30 | 0.16 |
| Ile | 295 | . | . | B | B | . | . | . | 0.07 | . | . | * | . | 0.00 | 0.39 |
| His | 296 | A | . | . | B | . | . | . | 0.07 | . | . | * | . | 0.90 | 0.81 |
| Asp | 297 | A | . | B | B | . | . | . | 0.61 | . | . | . | F | 1.80 | 2.19 |
| Glu | 298 | A | . | . | . | . | . | . | 1.21 | . | . | . | F | 2.30 | 3.09 |
| Gln | 299 | . | . | . | . | T | . | . | 2.07 | * | * | . | F | 3.00 | 3.51 |
| Lys | 300 | . | . | . | . | . | . | C | 2.10 | . | . | . | F | 2.50 | 3.64 |
| Gly | 301 | . | . | . | . | . | . | C | 1.82 | . | . | . | F | 2.40 | 1.56 |
| Pro | 302 | . | . | . | . | . | . | C | 1.52 | . | . | . | F | 2.10 | 1.30 |
| Glu | 303 | A | . | B | . | . | . | . | 1.52 | . | * | . | F | 1.45 | 0.87 |
| Val | 304 | A | . | . | . | . | . | . | 0.93 | . | . | . | F | 1.00 | 1.42 |
| Thr | 305 | A | . | . | . | . | T | . | 0.30 | . | . | * | F | 0.85 | 0.93 |
| Ser | 306 | A | . | . | . | . | T | . | −0.17 | . | . | . | F | 0.85 | 0.54 |
| Asn | 307 | A | . | . | . | . | T | . | −0.27 | . | . | . | F | −0.05 | 0.60 |
| Ala | 308 | A | . | . | . | . | T | . | −1.08 | . | . | * | F | −0.20 | 0.60 |
| Ala | 309 | A | . | . | . | . | T | . | −0.11 | . | . | * | . | −0.40 | 0.37 |
| Leu | 310 | . | . | . | . | . | . | . | 0.20 | . | . | * | . | −0.10 | 0.45 |
| Thr | 311 | . | . | B | . | T | . | . | −0.20 | . | . | * | . | −0.10 | 0.72 |
| Leu | 312 | . | . | B | . | T | . | . | −0.87 | . | . | * | . | −0.40 | 0.61 |
| Arg | 313 | . | . | B | . | T | . | . | −0.28 | . | . | * | . | −0.40 | 0.40 |
| Asn | 314 | . | . | . | . | T | T | . | 0.02 | . | * | * | . | 0.30 | 0.44 |
| Phe | 315 | . | . | . | . | T | T | . | 0.83 | . | * | . | . | 0.20 | 0.57 |
| Cys | 316 | . | . | . | . | T | T | . | 1.19 | . | * | . | . | 0.20 | 0.50 |
| Asn | 317 | . | . | . | . | T | T | . | 2.00 | . | * | . | . | 0.20 | 0.62 |
| Trp | 318 | . | . | . | . | T | . | . | 1.86 | . | * | . | . | 0.35 | 1.25 |
| Gln | 319 | . | . | . | . | . | . | . | 1.86 | . | * | . | . | 0.45 | 3.16 |
| Lys | 320 | . | . | . | . | . | . | . | 2.34 | . | * | . | F | 0.60 | 3.16 |
| Gln | 321 | . | . | . | . | . | . | . | 2.80 | . | * | . | F | 0.94 | 4.65 |
| His | 322 | . | . | . | . | . | . | C | 2.50 | . | . | . | F | 1.68 | 4.15 |
| Asn | 323 | . | . | . | . | . | . | C | 2.79 | . | . | . | F | 2.02 | 2.78 |
| Pro | 324 | . | . | . | . | T | . | C | 2.90 | . | * | . | F | 2.56 | 2.68 |
| Ser | 325 | . | . | . | . | . | T | . | 2.86 | . | * | . | F | 3.40 | 3.86 |
| Asp | 326 | . | . | . | . | . | T | C | 2.27 | . | . | . | F | 2.86 | 4.01 |
| Arg | 327 | . | A | . | . | . | T | . | 2.30 | . | * | . | F | 2.52 | 2.62 |
| Arg | 328 | A | A | . | . | . | T | . | 2.27 | . | * | . | F | 1.58 | 2.94 |
| Asp | 329 | A | A | . | . | . | T | . | 2.23 | . | * | . | F | 1.24 | 2.98 |
| Ala | 330 | A | A | . | . | . | . | . | 2.44 | . | * | . | F | 0.90 | 2.80 |
| Glu | 331 | A | . | . | . | . | . | . | 2.43 | . | * | . | . | 0.75 | 2.38 |
| His | 332 | . | . | . | . | . | T | . | 1.84 | . | * | . | . | 1.15 | 2.06 |
| Tyr | 333 | . | . | . | . | . | T | . | 0.84 | . | . | . | . | 0.85 | 2.06 |
| Asp | 334 | A | A | . | . | . | T | . | 0.03 | . | . | . | . | 0.70 | 0.83 |
| Thr | 335 | A | A | . | . | . | T | . | −0.08 | . | . | . | . | −0.20 | 0.51 |
| Ala | 336 | A | A | . | . | . | . | . | −0.39 | . | . | . | . | −0.60 | 0.28 |
| Ile | 337 | A | A | B | . | . | . | . | −0.24 | . | . | * | . | −0.60 | 0.24 |
| Leu | 338 | . | . | B | . | . | . | . | 0.00 | . | . | * | . | −0.60 | 0.33 |
| Phe | 339 | . | . | B | . | . | . | . | −0.50 | . | . | * | . | −0.60 | 0.56 |
| Thr | 340 | . | A | B | . | . | . | . | −0.58 | . | . | * | F | 0.00 | 1.34 |
| Arg | 341 | . | A | . | . | T | . | . | 0.00 | . | . | * | F | 0.25 | 1.34 |
| Gln | 342 | . | A | . | . | . | . | . | −0.03 | . | . | * | F | 1.35 | 0.83 |

TABLE 1-continued

| Res | Pos. | Garni...Alpha | Chou...Alpha | Garni...Beta | Chou...Beta | Garni...Turn | Chou...Turn | Garni...Coil | Kyte-...Hydro. | Eisen...Alpha | Eisen...Beta | Kapl...Flexi. | James...Antig. | Emini Surfa. |
|---|---|---|---|---|---|---|---|---|---|---|---|---|---|---|
| Asp | 343 | . | . | . | . | . | . | . | 0.48 | . | . | . | 1.60 | 0.57 |
| Leu | 344 | . | A | . | . | . | . | . | 1.18 | . | * | F | 2.15 | 0.39 |
| Cys | 345 | . | A | . | . | . | . | . | 1.18 | . | . | F | 2.50 | 0.39 |
| Gly | 346 | . | . | . | . | T | . | . | 0.40 | . | * | F | 2.25 | 0.34 |
| Ser | 347 | . | . | . | . | T | T | . | 0.40 | . | . | F | 1.10 | 0.22 |
| Gln | 348 | . | . | B | . | T | T | . | 0.09 | . | . | F | 1.35 | 0.68 |
| Thr | 349 | . | . | B | . | T | T | . | 0.09 | . | . | F | 0.90 | 0.99 |
| Cys | 350 | . | . | B | . | . | . | . | 0.41 | . | . | F | 0.05 | 0.61 |
| Asp | 351 | . | . | B | . | . | T | . | 0.16 | * | . | F | 0.25 | 0.35 |
| Thr | 352 | . | . | B | . | . | T | . | -0.13 | . | . | F | 0.25 | 0.24 |
| Leu | 353 | . | . | B | . | . | T | . | -0.13 | . | . | . | 0.10 | 0.45 |
| Gly | 354 | . | . | B | . | . | T | . | -0.68 | . | . | . | 0.70 | 0.45 |
| Met | 355 | . | . | B | . | . | . | . | -0.36 | . | . | . | -0.10 | 0.23 |
| Ala | 356 | . | . | B | . | . | . | . | -0.67 | . | . | . | -0.10 | 0.28 |
| Asp | 357 | . | . | B | . | . | T | . | -1.21 | . | . | . | 0.10 | 0.41 |
| Val | 358 | . | . | B | . | . | T | . | -1.07 | . | . | . | 0.10 | 0.30 |
| Gly | 359 | . | . | B | . | . | T | . | -0.72 | . | . | . | 0.10 | 0.16 |
| Thr | 360 | . | . | B | . | . | . | . | -0.33 | . | . | . | 0.70 | 0.16 |
| Val | 361 | . | . | B | . | . | . | . | -0.04 | * | . | . | 0.24 | 0.34 |
| Cys | 362 | . | . | B | . | . | . | . | 0.07 | . | . | . | 1.18 | 0.46 |
| Asp | 363 | . | . | . | . | T | T | . | 0.62 | * | . | F | 1.87 | 0.62 |
| Pro | 364 | . | . | . | . | T | T | . | 0.30 | * | . | F | 3.06 | 1.12 |
| Ser | 365 | . | . | . | . | T | T | . | 0.31 | * | . | F | 3.40 | 1.12 |
| Arg | 366 | . | . | . | . | . | . | . | 0.31 | * | . | F | 2.91 | 0.90 |
| Ser | 367 | . | . | B | B | . | . | . | 0.09 | * | . | . | 1.87 | 0.43 |
| Cys | 368 | . | . | B | B | . | . | . | 0.09 | * | . | . | 0.38 | 0.22 |
| Ser | 369 | . | . | B | B | . | . | . | 0.30 | * | . | . | 0.64 | 0.20 |
| Val | 370 | . | . | B | B | . | . | . | 0.60 | * | . | . | 0.30 | 0.25 |
| Ile | 371 | . | . | B | B | . | . | . | 0.14 | * | . | . | 0.30 | 0.25 |
| Glu | 372 | . | . | . | . | . | . | . | -0.37 | . | . | . | 0.60 | 0.77 |
| Asp | 373 | A | . | . | . | . | T | . | 0.30 | * | . | F | 0.60 | 0.57 |
| Asp | 374 | A | . | . | . | . | T | . | 0.01 | . | . | . | 1.15 | 0.63 |
| Gly | 375 | A | . | . | . | . | T | . | 0.28 | * | . | . | 1.30 | 1.56 |
| Leu | 376 | A | . | . | . | . | T | . | 0.47 | . | . | . | 1.00 | 0.91 |
| Gln | 377 | A | . | . | . | . | . | . | 0.16 | * | . | . | 0.70 | 0.55 |
| Ala | 378 | A | A | . | . | . | . | . | -0.16 | . | . | . | -0.30 | 0.29 |
| Ala | 379 | A | A | . | . | . | . | . | -0.74 | * | . | . | -0.60 | 0.42 |
| Phe | 380 | A | A | . | . | . | . | . | -0.43 | * | . | . | -0.60 | 0.73 |
| Thr | 381 | A | A | . | . | . | . | . | 0.38 | * | . | . | -0.60 | 0.43 |
| Thr | 382 | A | A | . | . | . | . | . | -0.43 | * | * | . | -0.60 | 0.57 |
| Ala | 383 | A | A | . | . | . | . | . | -0.19 | * | . | . | -0.60 | 0.98 |
| His | 384 | A | A | . | . | . | . | . | 0.37 | * | . | . | -0.30 | 0.94 |
| Glu | 385 | A | A | . | . | . | . | . | 0.21 | * | . | . | -0.30 | 0.64 |
| Leu | 386 | A | . | . | . | . | . | . | -0.18 | * | . | . | -0.30 | 0.61 |
| Gly | 387 | A | . | . | B | . | . | . | 0.13 | * | . | . | -0.30 | 0.45 |
| His | 388 | A | . | . | B | . | . | . | 0.12 | * | . | . | -0.60 | 0.28 |
| Val | 389 | . | . | . | B | . | . | . | -0.06 | * | . | . | -0.60 | 0.26 |
| Phe | 390 | . | . | . | B | . | . | . | -0.09 | * | . | . | -0.60 | 0.32 |
| Asn | 391 | . | . | B | B | . | . | . | 0.72 | . | . | . | -0.60 | 0.49 |

TABLE 1-continued

| Res | Pos. | Garni...Alpha | Chou...Alpha | Garni...Beta | Chou...Beta | Garni...Turn | Chou...Turn | Garni...Coil | Kyte-...Hydro... | Eisen...Alpha | Eisen...Beta | Kapl...Flexi. | James...Antig... | Emini Surfa... |
|---|---|---|---|---|---|---|---|---|---|---|---|---|---|---|
| Met | 392 | . | . | B | . | . | . | . | 1.07 | . | . | . | 0.25 | 1.11 |
| Pro | 393 | A | . | . | . | . | T | . | 0.51 | . | . | . | 0.85 | 2.14 |
| His | 394 | . | . | . | . | T | T | . | 1.41 | . | . | F | 1.70 | 1.34 |
| Asp | 395 | A | . | . | . | . | T | . | 2.11 | . | . | F | 1.30 | 2.72 |
| Ala | 396 | A | A | . | . | . | . | . | 1.44 | * | . | F | 0.90 | 3.04 |
| Ala | 397 | A | A | . | . | . | . | . | 1.46 | * | . | F | 0.90 | 1.20 |
| Lys | 398 | A | A | . | . | . | . | . | 1.37 | * | * | F | 0.75 | 0.73 |
| Gln | 399 | A | A | . | . | . | . | . | 0.59 | . | * | . | 0.60 | 0.58 |
| Cys | 400 | . | A | B | . | . | . | . | 0.59 | . | * | . | -0.30 | 0.48 |
| Ala | 401 | . | A | . | . | . | . | . | 0.24 | . | . | . | 0.30 | 0.38 |
| Ser | 402 | . | . | B | . | . | T | . | -0.02 | . | . | . | 0.10 | 0.22 |
| Leu | 403 | . | . | B | . | . | T | . | -0.07 | . | . | . | 0.04 | 0.30 |
| Asn | 404 | . | . | . | . | . | T | . | -0.07 | . | . | . | 0.68 | 0.48 |
| Gly | 405 | . | . | . | . | . | . | C | 0.60 | . | . | F | 1.37 | 0.62 |
| Val | 406 | . | . | . | . | . | . | C | 0.89 | . | . | F | 1.96 | 1.26 |
| Asn | 407 | . | . | . | . | T | T | C | 1.16 | . | . | F | 2.40 | 1.05 |
| Gln | 408 | A | . | . | . | T | T | . | 1.37 | . | . | F | 1.96 | 1.44 |
| Asp | 409 | A | A | . | . | . | T | . | 0.77 | . | . | F | 1.72 | 1.92 |
| Ser | 410 | A | A | . | . | . | T | . | 0.52 | * | * | . | 1.33 | 1.18 |
| His | 411 | A | A | . | . | . | . | . | 1.08 | * | . | . | -0.06 | 0.69 |
| Met | 412 | A | A | . | . | . | . | . | 0.48 | . | . | . | 0.30 | 0.55 |
| Met | 413 | A | A | . | . | . | . | . | -0.33 | * | . | . | -0.60 | 0.41 |
| Ala | 414 | A | A | . | . | . | . | . | -0.63 | * | . | . | -0.60 | 0.25 |
| Ser | 415 | A | A | . | . | . | . | . | -0.33 | * | . | . | -0.60 | 0.34 |
| Met | 416 | A | . | . | . | . | T | . | -1.11 | * | * | . | -0.60 | 0.55 |
| Leu | 417 | . | . | . | . | . | T | . | -0.51 | * | . | . | -0.20 | 0.45 |
| Ser | 418 | . | . | . | . | . | T | . | 0.06 | . | . | . | 0.38 | 0.56 |
| Asn | 419 | . | . | . | . | . | T | . | 0.34 | . | . | . | 0.66 | 0.76 |
| Leu | 420 | . | . | . | . | . | T | C | 0.64 | . | . | . | 1.29 | 1.24 |
| Asp | 421 | . | . | . | . | T | T | . | 1.03 | . | . | F | 2.37 | 1.60 |
| His | 422 | . | . | . | . | T | T | . | 1.56 | . | . | F | 2.80 | 1.54 |
| Ser | 423 | . | . | . | . | . | T | C | 1.56 | . | . | F | 1.72 | 1.97 |
| Gln | 424 | . | . | . | . | . | T | C | 1.34 | . | . | F | 1.44 | 1.58 |
| Pro | 425 | . | . | . | . | T | . | . | 1.49 | . | . | . | 0.86 | 1.79 |
| Trp | 426 | . | . | . | . | T | . | . | 1.19 | . | . | . | 0.43 | 0.72 |
| Ser | 427 | . | . | . | . | . | T | C | 0.63 | . | . | . | 0.15 | 0.55 |
| Pro | 428 | . | . | . | . | T | T | . | 0.69 | . | . | . | 0.35 | 0.36 |
| Cys | 429 | . | . | . | . | T | T | . | 0.09 | . | . | . | 0.20 | 0.54 |
| Ser | 430 | . | . | . | B | . | . | . | -0.59 | . | . | . | -0.20 | 0.40 |
| Ala | 431 | . | . | B | B | . | . | . | -0.61 | . | . | . | -0.60 | 0.18 |
| Tyr | 432 | . | . | B | B | . | . | . | -1.10 | . | . | . | -0.60 | 0.49 |
| Met | 433 | . | . | B | B | . | . | . | -1.24 | . | . | . | -0.60 | 0.42 |
| Ile | 434 | . | . | B | B | . | . | . | -0.94 | * | . | . | -0.60 | 0.22 |
| Thr | 435 | . | . | B | B | . | . | . | -0.36 | * | . | . | -0.60 | 0.37 |
| Ser | 436 | . | . | B | B | . | . | . | -0.46 | * | . | . | -0.60 | 0.85 |
| Pro | 437 | . | . | . | . | . | . | . | 0.11 | * | . | . | 0.56 | 0.58 |
| Leu | 438 | . | . | B | . | T | T | . | 0.66 | . | . | F | 1.27 | 0.59 |
| Asp | 439 | . | . | . | . | . | T | . | 0.97 | . | . | F | 1.38 | 0.68 |
| Asn | 440 | . | . | . | . | . | T | C | | | | | | |

TABLE 1-continued

| Res | Pos. | Garni..Alpha | Chou..Alpha | Garni..Beta | Chou..Beta | Garni..Turn | Chou..Turn | Garni..Coil | Kyte..Hydro. | Eisen..Alpha | Eisen..Beta | Kapl..Flexi. | James..Antig. | Emini..Surfa. |
|---|---|---|---|---|---|---|---|---|---|---|---|---|---|---|
| Gly | 441 | . | . | . | . | . | T | . | 0.60 | . | . | . | 2.94 | 1.42 |
| His | 442 | . | . | . | . | T | T | . | 0.49 | . | . | F | 3.10 | 0.46 |
| Gly | 443 | A | . | . | . | T | T | . | 0.70 | . | . | F | 1.49 | 0.23 |
| Glu | 444 | A | . | . | . | T | T | . | 0.70 | . | . | F | 1.03 | 0.23 |
| Cys | 445 | . | . | B | . | . | T | . | 0.74 | . | * | . | 1.32 | 0.29 |
| Leu | 446 | . | A | B | . | . | . | . | 0.88 | . | . | . | 1.25 | 0.58 |
| Met | 447 | . | A | B | . | . | . | . | 0.91 | . | . | . | 1.28 | 0.52 |
| Asp | 448 | . | A | . | . | T | . | . | 1.26 | . | . | . | 2.02 | 1.67 |
| Lys | 449 | . | A | . | . | . | . | C | 1.04 | * | . | . | 2.16 | 3.26 |
| Pro | 450 | . | . | . | . | T | T | . | 0.82 | . | * | F | 3.40 | 5.10 |
| Gln | 451 | . | . | . | . | T | T | . | 1.63 | . | * | F | 3.06 | 2.14 |
| Asn | 452 | . | . | B | . | . | T | . | 1.42 | . | * | F | 2.02 | 1.85 |
| Pro | 453 | . | . | B | . | . | . | . | 1.21 | . | . | F | 0.63 | 0.99 |
| Ile | 454 | . | . | B | . | . | . | . | 0.82 | . | * | F | 0.09 | 0.88 |
| Gln | 455 | . | . | B | . | . | . | . | 1.03 | . | * | F | -0.25 | 0.54 |
| Leu | 456 | . | . | B | . | . | T | . | 0.22 | . | * | F | -0.25 | 0.59 |
| Pro | 457 | . | . | . | . | . | T | C | 0.01 | . | . | F | 1.05 | 0.69 |
| Gly | 458 | . | . | B | . | . | T | . | -0.12 | . | * | F | 0.25 | 0.62 |
| Asp | 459 | . | . | B | . | . | T | . | 0.46 | . | * | F | 0.25 | 0.74 |
| Leu | 460 | . | . | B | . | . | T | C | 0.16 | . | * | F | 1.05 | 0.69 |
| Pro | 461 | . | . | . | . | . | . | . | 0.72 | . | . | . | 0.85 | 0.93 |
| Gly | 462 | . | . | B | . | T | T | . | 0.93 | . | * | F | 0.25 | 0.88 |
| Thr | 463 | . | . | B | . | T | T | . | 0.69 | . | * | F | 0.74 | 1.78 |
| Ser | 464 | . | . | B | . | T | T | . | 0.69 | . | . | F | 1.48 | 1.16 |
| Tyr | 465 | . | . | . | . | T | T | . | 1.61 | . | . | F | 2.22 | 1.88 |
| Asp | 466 | . | . | B | B | T | T | . | 1.82 | . | * | F | 2.61 | 2.56 |
| Ala | 467 | . | . | B | B | T | T | . | 1.50 | . | . | F | 3.40 | 3.31 |
| Asn | 468 | . | . | B | B | T | T | . | 1.81 | . | * | F | 2.76 | 1.13 |
| Arg | 469 | . | . | . | B | . | . | . | 1.41 | * | . | F | 2.32 | 1.13 |
| Gln | 470 | . | . | B | B | . | T | . | 1.34 | * | . | F | 0.53 | 1.17 |
| Gln | 471 | . | . | B | B | . | T | . | 0.64 | . | . | . | 0.04 | 1.01 |
| Phe | 472 | . | . | B | B | . | . | . | 0.89 | * | . | . | -0.60 | 0.90 |
| Thr | 473 | . | . | B | B | . | T | . | 0.89 | * | . | . | -0.26 | 0.40 |
| Phe | 474 | . | . | . | . | . | T | . | 0.78 | . | . | . | 0.08 | 0.23 |
| Gly | 475 | . | . | . | . | T | T | . | 0.48 | . | . | F | 1.72 | 0.74 |
| Glu | 476 | . | . | . | . | T | T | . | 1.19 | * | . | F | 2.76 | 0.71 |
| Asp | 477 | . | . | . | . | T | . | . | 1.16 | * | . | F | 3.40 | 1.10 |
| Ser | 478 | . | . | . | . | T | . | . | 1.19 | * | . | F | 3.06 | 1.52 |
| Lys | 479 | . | . | . | . | T | . | . | 1.29 | * | . | F | 2.72 | 2.39 |
| His | 480 | . | . | . | . | . | . | . | 1.99 | * | . | F | 2.43 | 1.30 |
| Cys | 481 | . | . | . | . | . | T | C | 1.74 | * | . | F | 2.34 | 1.16 |
| Pro | 482 | A | . | . | . | . | T | . | 1.16 | * | . | F | 2.10 | 1.16 |
| Asp | 483 | . | . | . | . | . | T | . | 0.86 | * | . | F | 2.15 | 0.87 |
| Ala | 484 | A | . | B | . | . | . | . | 0.84 | . | . | F | 2.50 | 0.44 |
| Ala | 485 | A | . | B | . | T | . | . | 0.13 | . | . | F | 2.00 | 0.43 |
| Ser | 486 | . | . | . | . | . | . | . | -0.13 | . | . | F | 1.40 | 1.17 |
| Thr | 487 | . | . | B | . | T | . | . | 0.22 | . | * | F | 1.75 | 0.41 |
| Cys | 488 | . | . | B | . | . | T | . | -0.38 | . | * | F | 0.50 | 0.33 |
| | 489 | . | . | . | . | . | T | . | -0.67 | . | * | F | -0.05 | 0.38 |

TABLE 1-continued

| Res | Pos. | Garni...Alpha | Chou...Alpha | Garni...Beta | Chou...Beta | Garni...Turn | Chou...Turn | Garni...Coil | Kyte-...Hydro. | Eisen...Alpha | Eisen...Beta | Karpl...Flexi. | James...Antig. | Emini Surfa... |
|---|---|---|---|---|---|---|---|---|---|---|---|---|---|---|
| Ser | 490 | . | . | . | . | . | . | . | −0.74 | . | . | . | −0.05 | 0.30 |
| Thr | 491 | . | . | B | B | . | T | . | −0.47 | . | . | . | −0.60 | 0.11 |
| Leu | 492 | . | . | B | B | . | . | . | −0.51 | . | . | . | −0.60 | 0.30 |
| Trp | 493 | . | . | B | B | . | . | . | −0.51 | . | . | . | −0.60 | 0.22 |
| Cys | 494 | . | . | B | B | . | . | . | −0.14 | . | . | . | −0.60 | 0.22 |
| Thr | 495 | . | . | B | B | . | . | . | −0.19 | . | . | F | −0.60 | 0.36 |
| Gly | 496 | . | . | B | B | . | . | . | −0.22 | . | . | . | −0.05 | 0.34 |
| Thr | 497 | . | . | . | . | T | T | . | −0.27 | . | . | . | 0.65 | 0.62 |
| Ser | 498 | . | . | . | . | T | T | . | −0.79 | . | . | F | 0.65 | 0.32 |
| Gly | 499 | . | . | . | . | T | T | . | −0.98 | . | . | F | 0.35 | 0.27 |
| Gly | 500 | . | . | . | . | T | T | . | −1.33 | . | . | F | 0.35 | 0.14 |
| Val | 501 | . | . | B | B | . | . | . | −0.99 | . | . | F | −0.60 | 0.05 |
| Leu | 502 | . | . | B | B | . | T | . | −0.64 | . | . | . | −0.60 | 0.10 |
| Val | 503 | . | . | B | B | . | T | . | −0.33 | . | . | . | −0.60 | 0.14 |
| Cys | 504 | . | . | B | . | . | T | . | −0.69 | . | . | . | −0.20 | 0.38 |
| Gln | 505 | . | . | B | . | . | . | . | −0.04 | . | . | F | 0.10 | 0.62 |
| Thr | 506 | . | . | B | B | T | T | . | 0.48 | . | . | F | 0.25 | 0.72 |
| Lys | 507 | . | . | B | . | T | T | . | 0.74 | . | . | . | 0.40 | 2.09 |
| His | 508 | . | . | . | . | . | . | C | 1.41 | . | . | . | −0.05 | 1.27 |
| Phe | 509 | . | . | B | . | . | . | . | 1.07 | . | . | . | −0.40 | 0.89 |
| Pro | 510 | . | . | . | . | T | T | . | 1.07 | . | . | F | 0.30 | 0.74 |
| Trp | 511 | . | . | . | . | T | T | . | 0.72 | . | . | F | 0.20 | 0.54 |
| Ala | 512 | . | . | . | . | T | T | . | 0.09 | . | . | F | 0.51 | 0.90 |
| Asp | 513 | . | . | . | . | T | T | . | 0.44 | . | . | F | 1.27 | 0.78 |
| Gly | 514 | . | . | . | . | T | T | . | 0.66 | . | . | F | 1.58 | 0.40 |
| Thr | 515 | . | . | . | . | T | T | . | 0.60 | . | * | F | 2.49 | 0.39 |
| Ser | 516 | . | . | . | . | . | T | . | 1.23 | . | * | F | 3.10 | 0.40 |
| Cys | 517 | . | . | . | . | . | . | . | 0.94 | . | * | F | 2.49 | 0.40 |
| Gly | 518 | . | . | . | . | T | T | . | 0.62 | . | * | F | 2.48 | 0.56 |
| Glu | 519 | . | . | . | . | T | T | . | 0.04 | . | * | F | 1.67 | 0.44 |
| Gly | 520 | . | . | . | . | T | T | . | 0.34 | . | * | F | 1.36 | 0.44 |
| Lys | 521 | . | . | B | . | . | . | . | 0.67 | . | * | . | 0.45 | 0.31 |
| Trp | 522 | . | . | B | . | . | . | . | 1.06 | . | * | . | 0.90 | 0.29 |
| Cys | 523 | . | . | . | . | T | T | . | 0.39 | . | . | . | −0.20 | 0.29 |
| Ile | 524 | . | . | . | . | T | T | . | −0.12 | . | . | . | 0.70 | 0.15 |
| Asn | 525 | . | . | . | . | . | . | . | −0.17 | * | * | F | 0.20 | 0.20 |
| Gly | 526 | . | . | . | . | . | . | . | 0.17 | . | . | . | 0.65 | 0.47 |
| Lys | 527 | . | . | . | . | . | . | . | 0.52 | . | . | . | 0.45 | 0.58 |
| Cys | 528 | . | . | B | B | . | . | . | 1.41 | * | * | . | 1.40 | 0.85 |
| Val | 529 | . | . | B | B | . | . | . | 1.52 | * | * | . | 1.04 | 0.71 |
| Asn | 530 | . | . | B | B | . | . | . | 1.91 | * | * | F | 1.83 | 2.58 |
| Lys | 531 | . | . | B | . | . | T | . | 1.83 | * | * | F | 2.32 | 6.96 |
| Thr | 532 | . | . | . | . | T | T | . | 1.80 | * | * | F | 2.66 | 5.89 |
| Asp | 533 | . | . | . | . | T | T | . | 2.66 | * | * | F | 3.40 | 2.55 |
| Arg | 534 | . | . | . | B | . | . | . | 2.34 | * | . | F | 3.06 | 2.95 |
| Lys | 535 | . | . | B | B | . | . | . | 2.09 | * | . | F | 2.32 | 2.55 |
| His | 536 | . | . | B | B | . | . | . | 1.78 | . | . | F | 1.78 | 2.01 |
| Phe | 537 | . | . | B | B | . | . | . | 1.70 | . | . | F | 1.44 | 2.01 |
| Asp | 538 | . | . | B | B | . | . | . | 1.67 | . | . | F | 0.65 | 0.87 |

TABLE 1-continued

| Res | Pos. | Garni...Alpha | Chou...Alpha | Garni...Beta | Chou...Beta | Garni...Turn | Chou...Turn | Garni...Coil | Kyte-...Hydro. | Eisen... | Eisen...Alpha | Eisen...Beta | Karpl...Flexi. | James...Antig. | Emini Surfa. |
|---|---|---|---|---|---|---|---|---|---|---|---|---|---|---|---|
| Thr | 539 | . | . | B | . | . | . | . | 1.21 | . | . | . | . | −0.25 | 0.87 |
| Pro | 540 | . | . | . | . | . | . | C | 0.87 | . | * | . | F | −0.05 | 1.00 |
| Phe | 541 | . | . | . | . | . | . | . | 0.61 | . | * | * | F | 0.45 | 0.80 |
| His | 542 | . | . | . | . | T | T | . | 0.97 | . | . | * | F | 0.20 | 0.58 |
| Gly | 543 | . | . | . | . | T | T | . | 0.37 | . | . | . | . | 0.20 | 0.37 |
| Ser | 544 | . | . | . | . | T | T | . | 0.39 | . | . | * | . | 0.20 | 0.43 |
| Trp | 545 | . | . | . | . | T | . | . | 0.26 | . | . | * | . | 0.20 | 0.33 |
| Gly | 546 | . | . | . | . | . | . | C | 0.74 | . | . | . | . | −0.20 | 0.33 |
| Met | 547 | . | . | . | . | . | T | . | 0.49 | . | . | * | . | 0.00 | 0.38 |
| Trp | 548 | . | . | . | . | T | T | . | 0.49 | . | . | . | . | 0.00 | 0.38 |
| Gly | 549 | . | . | . | . | T | T | C | 0.79 | . | . | . | . | 0.00 | 0.38 |
| Pro | 550 | . | . | . | . | T | T | . | 0.41 | . | . | . | . | 0.35 | 0.64 |
| Trp | 551 | . | . | . | . | T | T | . | 0.46 | . | . | . | F | 0.66 | 0.33 |
| Gly | 552 | . | . | . | . | T | T | . | 1.17 | . | . | . | F | 1.27 | 0.44 |
| Asp | 553 | . | . | . | . | T | T | . | 1.14 | . | . | . | F | 1.98 | 0.56 |
| Cys | 554 | . | . | . | . | T | T | . | 0.82 | . | . | . | F | 2.49 | 0.77 |
| Ser | 555 | . | . | . | . | T | T | . | 0.69 | . | . | . | F | 3.10 | 0.42 |
| Arg | 556 | . | . | B | . | . | T | . | 0.63 | . | * | . | F | 2.79 | 0.25 |
| Thr | 557 | . | . | B | . | . | T | . | 0.63 | . | * | * | F | 2.18 | 0.46 |
| Cys | 558 | . | . | B | . | . | T | . | −0.22 | . | * | * | F | 1.87 | 0.34 |
| Gly | 559 | . | . | B | . | . | T | . | 0.44 | . | * | * | F | 1.56 | 0.13 |
| Gly | 560 | . | . | B | . | . | T | . | 0.50 | . | * | * | F | 0.65 | 0.15 |
| Gly | 561 | . | . | . | . | . | T | . | 0.08 | . | * | . | F | 0.35 | 0.45 |
| Val | 562 | . | . | B | B | T | . | . | −0.21 | . | * | * | . | −0.60 | 0.65 |
| Gln | 563 | . | . | B | B | T | . | . | 0.57 | . | * | * | . | −0.60 | 0.65 |
| Tyr | 564 | . | . | B | B | . | . | . | 0.91 | . | * | . | . | −0.15 | 1.29 |
| Thr | 565 | . | . | B | B | . | T | . | 0.59 | . | * | . | F | 0.79 | 3.01 |
| Met | 566 | . | . | B | B | T | T | . | 0.93 | . | * | * | F | 0.38 | 0.93 |
| Arg | 567 | . | . | . | . | . | . | . | 1.79 | . | * | . | F | 1.62 | 0.99 |
| Glu | 568 | . | . | . | . | T | . | . | 1.58 | . | * | . | F | 2.86 | 1.11 |
| Cys | 569 | . | . | . | . | T | T | . | 0.97 | . | * | . | F | 3.40 | 1.73 |
| Asp | 570 | . | . | . | . | . | T | . | 1.07 | . | . | . | F | 2.91 | 0.66 |
| Asn | 571 | . | . | . | . | . | . | C | 1.71 | . | . | . | F | 2.37 | 0.59 |
| Pro | 572 | . | . | . | . | . | T | C | 1.60 | . | * | . | F | 2.52 | 2.18 |
| Val | 573 | . | . | . | . | T | T | . | 1.26 | . | * | . | F | 2.32 | 2.10 |
| Pro | 574 | . | . | . | . | T | T | . | 1.58 | . | * | . | F | 2.42 | 1.29 |
| Lys | 575 | . | . | . | . | T | T | . | 1.62 | . | * | . | F | 2.61 | 0.83 |
| Asn | 576 | . | . | . | . | . | . | . | 1.38 | . | * | . | F | 3.40 | 2.23 |
| Gly | 577 | . | . | . | . | . | . | . | 0.92 | . | * | . | F | 3.06 | 2.26 |
| Lys | 578 | . | . | B | . | . | T | . | 1.78 | . | * | . | F | 2.27 | 0.61 |
| Tyr | 579 | . | . | B | B | . | T | . | 1.64 | . | . | . | F | 1.53 | 0.66 |
| Glu | 580 | . | . | B | B | . | T | . | 1.76 | . | . | . | F | 1.19 | 0.65 |
| Gly | 581 | . | . | B | B | . | T | . | 1.24 | . | . | * | F | 1.30 | 1.32 |
| Lys | 582 | . | . | B | B | . | T | . | 1.70 | . | . | * | F | 1.10 | 1.29 |
| Cys | 583 | . | . | B | B | . | T | . | 1.41 | . | . | . | F | 0.75 | 0.61 |
| Gly | 584 | . | . | B | B | . | . | . | 1.77 | . | . | * | F | 0.90 | 0.65 |
| Lys | 585 | . | . | B | B | . | . | . | 2.13 | . | * | * | . | 1.15 | 2.24 |
| Arg | 586 | . | . | B | B | . | . | . | 1.47 | . | . | * | . | 1.25 | 4.01 |
| Tyr | 587 | . | . | B | B | . | . | . | . | . | * | * | . | 1.50 | 2.68 |

TABLE 1-continued

| Res | Pos. | Garni...Alpha | Chou...Alpha | Garni...Beta | Chou...Beta | Garni...Turn | Chou...Turn | Garni...Coil | Kyte...Hydro. | Eisen...Alpha | Eisen...Beta | Kapl...Flexi. | James...Antig. | Emini Surfa. |
|---|---|---|---|---|---|---|---|---|---|---|---|---|---|---|
| Tyr | 588 | . | . | . | . | . | . | . | 1.81 | . | * | . | 2.00 | 0.73 |
| Arg | 589 | . | . | B | . | . | T | . | 0.96 | . | * | . | 2.50 | 1.59 |
| Ser | 590 | . | . | . | . | . | T | . | 0.84 | * | * | . | 2.10 | 0.67 |
| Cys | 591 | . | . | . | . | . | T | . | 1.70 | * | * | . | 1.85 | 0.74 |
| Asn | 592 | . | A | . | . | T | . | . | 0.92 | * | . | . | 1.50 | 0.63 |
| Leu | 593 | . | A | B | . | T | . | . | 0.96 | * | . | . | 0.89 | 0.25 |
| Glu | 594 | . | A | B | . | T | . | . | 0.84 | . | . | . | 1.13 | 0.73 |
| Asp | 595 | . | A | . | . | . | . | . | 1.17 | . | . | . | 2.17 | 0.76 |
| Cys | 596 | . | . | B | . | . | T | . | 1.81 | . | . | . | 2.66 | 1.48 |
| Pro | 597 | . | . | . | . | T | T | . | 1.47 | . | * | . | 3.40 | 1.37 |
| Asp | 598 | . | . | . | . | T | T | . | 2.32 | . | * | . | 2.91 | 0.81 |
| Asn | 599 | . | . | . | . | T | T | . | 2.01 | * | . | . | 3.02 | 3.03 |
| Gly | 600 | . | . | . | . | T | T | . | 1.31 | * | . | . | 2.98 | 2.83 |
| Lys | 601 | . | . | . | . | T | T | C | 2.09 | * | . | . | 2.94 | 1.47 |
| Thr | 602 | . | . | . | . | T | T | C | 2.30 | * | . | F | 2.70 | 1.79 |
| Phe | 603 | . | A | . | . | . | T | . | 2.30 | * | . | F | 3.00 | 1.92 |
| Arg | 604 | A | A | . | . | . | . | . | 2.30 | * | . | F | 2.10 | 3.37 |
| Glu | 605 | A | A | . | . | . | . | . | 1.63 | * | . | F | 1.80 | 2.91 |
| Glu | 606 | A | A | . | . | . | . | . | 1.98 | * | . | F | 1.50 | 1.08 |
| Gln | 607 | A | A | . | . | . | . | . | 1.34 | * | . | F | 1.20 | 2.17 |
| Gln | 608 | A | A | . | . | . | . | . | 1.62 | * | . | F | 0.90 | 1.12 |
| Cys | 609 | A | A | . | . | . | . | . | 2.32 | * | * | F | 0.60 | 0.88 |
| Glu | 610 | A | A | . | . | . | . | . | 2.21 | * | * | F | 0.60 | 0.81 |
| Ala | 611 | A | A | . | . | . | . | . | 1.51 | . | . | . | 0.60 | 0.81 |
| His | 612 | A | A | . | . | . | . | . | 1.21 | * | . | . | 0.45 | 1.32 |
| Asn | 613 | A | A | . | . | . | . | . | 1.26 | * | . | . | 0.45 | 1.02 |
| Glu | 614 | A | A | . | . | . | . | . | 1.33 | * | . | F | 0.45 | 2.02 |
| Phe | 615 | A | A | . | . | . | . | . | 1.03 | * | . | F | 0.60 | 1.50 |
| Ser | 616 | . | A | . | . | . | . | . | 0.92 | . | . | F | 0.90 | 1.25 |
| Lys | 617 | A | A | . | . | . | . | . | 0.61 | . | . | F | 0.45 | 0.62 |
| Ala | 618 | A | A | . | . | T | . | . | 0.31 | . | . | F | 0.25 | 0.71 |
| Ser | 619 | A | . | . | . | T | . | . | -0.03 | . | . | F | 0.85 | 0.71 |
| Phe | 620 | . | . | . | . | . | T | . | 0.46 | . | . | . | 1.26 | 0.35 |
| Gly | 621 | . | . | . | . | . | T | C | 0.17 | . | . | F | 1.07 | 0.54 |
| Ser | 622 | . | . | . | . | . | T | C | -0.73 | . | . | F | 1.08 | 0.41 |
| Gly | 623 | . | . | . | . | . | T | C | -0.14 | * | . | F | 0.99 | 0.35 |
| Pro | 624 | . | . | . | . | . | . | C | -0.13 | * | . | F | 2.10 | 0.61 |
| Ala | 625 | . | A | . | . | T | . | . | -0.32 | * | . | . | 0.89 | 0.48 |
| Val | 626 | . | A | B | . | T | . | . | -0.19 | * | . | . | 0.03 | 0.34 |
| Glu | 627 | . | A | B | . | T | . | . | 0.16 | * | . | F | -0.18 | 0.34 |
| Trp | 628 | . | A | B | . | T | . | . | 0.26 | * | . | F | -0.09 | 0.67 |
| Ile | 629 | . | . | B | . | . | T | . | -0.12 | * | . | F | -0.25 | 1.42 |
| Pro | 630 | . | . | . | . | . | T | . | 0.12 | * | . | F | 0.10 | 0.83 |
| Lys | 631 | . | . | . | . | . | T | . | 0.12 | * | . | F | 0.20 | 0.78 |
| Tyr | 632 | . | . | . | . | . | T | . | -0.18 | * | . | F | 0.20 | 0.82 |
| Ala | 633 | . | . | . | . | . | . | . | -0.10 | . | . | . | 0.84 | 0.71 |
| Gly | 634 | . | . | B | . | . | . | . | 0.83 | . | . | . | 0.98 | 0.55 |
| Val | 635 | . | . | B | . | . | . | . | 1.04 | . | * | . | 0.92 | 0.70 |
| Ser | 626 | . | . | . | . | . | T | . | 1.11 | . | * | F | 2.66 | 1.17 |

TABLE 1-continued

| Res | Pos. | Garni...Alpha | Chou...Alpha | Garni...Beta | Chou...Beta | Garni...Turn | Chou...Turn | Garni...Coil | Kyte...Hydro. | Eisen...Alpha | Eisen...Beta | Kapl...Flexi. | James...Antig. | Emini Surfa. |
|---|---|---|---|---|---|---|---|---|---|---|---|---|---|---|
| Pro | 637 | . | . | . | . | . | . | . | 0.69 | . | . | . | 3.40 | 2.31 |
| Lys | 638 | a | a | a | a | T | T | . | 1.32 | . | * | F | 3.06 | 1.67 |
| Asp | 639 | . | . | . | . | T | T | . | 0.86 | . | * | F | 2.72 | 2.49 |
| Arg | 640 | A | A | . | . | . | . | . | 0.82 | . | * | F | 1.58 | 1.33 |
| Cys | 641 | A | A | . | . | . | . | . | 0.46 | * | * | F | 1.09 | 0.46 |
| Lys | 642 | . | A | B | . | . | . | . | 0.67 | . | * | F | 0.30 | 0.15 |
| Leu | 643 | . | A | B | . | . | . | . | 0.03 | . | * | . | 0.30 | 0.13 |
| Ile | 644 | . | A | B | . | . | . | . | 0.08 | . | * | . | -0.60 | 0.25 |
| Cys | 645 | . | A | B | a | . | . | . | -0.38 | * | . | . | 0.30 | 0.25 |
| Gln | 646 | . | A | B | . | . | . | . | -0.60 | * | . | . | -0.30 | 0.30 |
| Ala | 647 | . | A | B | . | . | . | . | -0.99 | * | . | . | -0.30 | 0.30 |
| Lys | 648 | . | A | . | . | . | . | . | -0.42 | * | . | . | -0.15 | 0.55 |
| Gly | 649 | . | . | . | . | . | . | . | -0.23 | . | * | F | 0.65 | 0.50 |
| Ile | 650 | . | . | B | . | T | T | . | -0.27 | . | * | . | 0.20 | 0.43 |
| Gly | 651 | . | . | B | . | T | T | . | -1.12 | . | * | . | -0.20 | 0.18 |
| Tyr | 652 | . | . | B | . | . | T | . | -1.34 | . | . | . | -0.20 | 0.14 |
| Phe | 653 | . | . | B | B | . | . | . | -1.39 | . | * | . | -0.60 | 0.16 |
| Phe | 654 | . | . | B | B | . | . | . | -1.26 | * | . | . | -0.60 | 0.29 |
| Val | 655 | . | . | B | B | . | . | . | -0.32 | * | . | . | -0.60 | 0.28 |
| Leu | 656 | . | . | B | . | . | . | . | -0.83 | * | . | . | -0.60 | 0.65 |
| Gln | 657 | . | . | . | . | T | T | . | -1.44 | . | * | . | -0.20 | 0.56 |
| Pro | 658 | . | . | B | . | . | T | . | -0.74 | . | . | . | -0.05 | 0.56 |
| Lys | 659 | . | . | B | . | T | T | . | -0.39 | * | . | F | 1.40 | 1.13 |
| Val | 660 | . | . | . | . | . | . | . | 0.16 | . | . | F | 0.85 | 0.65 |
| Val | 661 | . | . | B | . | . | T | . | 0.76 | . | * | F | 0.85 | 0.60 |
| Asp | 662 | . | . | B | . | . | . | . | 0.09 | . | . | F | 1.06 | 0.47 |
| Gly | 663 | . | . | B | . | . | . | . | 0.00 | * | . | F | 0.67 | 0.34 |
| Thr | 664 | . | . | B | . | . | . | . | -0.26 | * | . | F | 1.48 | 0.61 |
| Pro | 665 | . | . | B | . | . | . | . | 0.60 | . | . | F | 1.49 | 0.56 |
| Cys | 666 | . | . | . | . | . | . | . | 1.16 | . | . | F | 2.10 | 0.95 |
| Ser | 667 | . | . | . | . | T | T | C | 0.84 | . | . | F | 1.89 | 0.88 |
| Pro | 668 | . | . | . | . | T | T | . | 0.89 | . | . | F | 1.88 | 0.82 |
| Asp | 669 | . | . | . | . | T | T | . | 0.34 | . | . | F | 1.82 | 2.06 |
| Ser | 670 | . | . | . | . | T | T | . | -0.11 | . | . | F | 1.61 | 1.14 |
| Thr | 671 | . | . | B | B | . | . | . | -0.30 | . | * | F | 0.85 | 0.39 |
| Ser | 672 | . | . | B | B | . | . | . | 0.00 | . | * | . | -0.15 | 0.18 |
| Val | 673 | . | . | B | B | . | . | . | -0.13 | . | * | . | -0.60 | 0.23 |
| Cys | 674 | . | . | B | B | . | . | . | -0.13 | . | * | . | -0.60 | 0.16 |
| Val | 675 | . | . | B | B | . | . | . | -0.50 | . | * | . | -0.60 | 0.20 |
| Gln | 676 | . | . | B | B | . | . | . | -1.04 | . | * | . | -0.45 | 0.15 |
| Gly | 677 | . | . | B | B | . | . | . | -0.70 | . | * | . | -0.15 | 0.20 |
| Gln | 678 | . | . | B | B | . | . | . | -0.43 | . | * | . | -0.15 | 0.54 |
| Cys | 679 | . | . | . | . | T | T | . | -0.11 | * | . | F | 0.30 | 0.32 |
| Val | 680 | . | . | B | B | . | . | . | 0.08 | * | . | F | 0.10 | 0.32 |
| Lys | 681 | . | . | B | . | T | T | . | 0.08 | * | . | F | 0.10 | 0.10 |
| Ala | 682 | . | . | . | . | . | . | . | 0.53 | * | . | F | 0.70 | 0.30 |
| Gly | 683 | . | . | . | . | . | T | . | -0.36 | * | . | F | 1.00 | 0.80 |
| Cys | 684 | . | . | B | . | . | T | . | -0.58 | . | * | F | 1.00 | 0.28 |
| Asp | 685 | A | . | . | B | . | . | . | 0.28 | . | . | . | 0.30 | 0.20 |

TABLE 1-continued

| Res | Pos. | Garni...Alpha | Chou...Alpha | Garni...Beta | Chou...Beta | Garni...Turn | Chou...Turn | Garni...Coil | Kyte...Hydro. | Eisen... | Eisen...Alpha | Eisen...Beta | Karpl...Flexi. | James...Antig. | Emini Surfa. |
|---|---|---|---|---|---|---|---|---|---|---|---|---|---|---|---|
| Arg | 686 | A | | | B | | | | −0.07 | | | | | 0.60 | 0.33 |
| Ile | 687 | A | | | B | | | | 0.57 | | * | | | 0.60 | 0.82 |
| Ile | 688 | A | | | B | | | | 0.96 | | * | | | 0.75 | 0.99 |
| Asp | 689 | A | | | | | T | | 1.67 | | * | * | F | 1.30 | 1.01 |
| Ser | 690 | A | | | | | T | | 0.97 | | * | | F | 1.30 | 2.88 |
| Lys | 691 | A | | | | T | T | | 0.86 | | * | * | F | 1.61 | 3.55 |
| Lys | 692 | | | | | T | T | | 1.79 | | * | | F | 2.32 | 3.55 |
| Lys | 693 | | | | | T | T | | 2.01 | | * | * | F | 2.43 | 5.30 |
| Phe | 694 | | | | | | | | 1.67 | | * | | F | 2.74 | 1.42 |
| Asp | 695 | | | | | | T | | 1.11 | | * | * | F | 3.10 | 0.70 |
| Lys | 696 | | | B | | | T | | 0.40 | | * | | F | 2.39 | 0.26 |
| Cys | 697 | | | B | | | T | | 0.01 | | * | | F | 1.63 | 0.16 |
| Gly | 698 | | | B | | | T | | −0.38 | | * | | | 1.32 | 0.10 |
| Val | 699 | | | | | | | | 0.32 | | * | | | 0.21 | 0.05 |
| Cys | 700 | | | | | | T | | −0.02 | | * | | F | 0.00 | 0.14 |
| Gly | 701 | | | | | T | T | | −0.37 | | | | F | 0.65 | 0.14 |
| Gly | 702 | | | B | | T | T | | −0.01 | | | | F | 0.65 | 0.26 |
| Asn | 703 | | | B | | T | T | | −0.33 | | | | F | 0.65 | 0.69 |
| Gly | 704 | | | B | | T | T | | 0.57 | | | * | F | 0.65 | 0.37 |
| Ser | 705 | | | B | | | | | 1.28 | | | | F | 1.25 | 0.76 |
| Thr | 706 | | | B | B | | | | 0.73 | | | | F | 1.41 | 0.94 |
| Cys | 707 | | | B | B | | T | | 0.78 | | | * | F | 1.37 | 0.67 |
| Lys | 708 | | | B | B | | T | | 0.43 | | | * | F | 1.63 | 0.67 |
| Lys | 709 | | | B | B | | T | | 0.48 | | | * | F | 1.69 | 0.46 |
| Ile | 710 | | | B | B | | T | | −0.08 | | * | * | F | 2.60 | 1.14 |
| Ser | 711 | | | B | | | T | | −0.08 | | * | | F | 1.89 | 0.42 |
| Gly | 712 | | | B | | | T | | 0.29 | | * | | F | 1.03 | 0.31 |
| Ser | 713 | | | B | B | | T | | −0.34 | | * | * | F | 0.77 | 0.58 |
| Val | 714 | | | B | B | | T | | 0.33 | | * | | F | 0.11 | 0.44 |
| Thr | 715 | | | B | B | | | | 0.29 | | * | | F | 0.73 | 0.89 |
| Ser | 716 | | | B | | | T | | 0.39 | | * | | F | 1.16 | 1.03 |
| Ala | 717 | | | B | | | T | | 0.62 | | * | | F | 1.64 | 1.37 |
| Lys | 718 | | | | | | T | C | 0.66 | | * | | F | 2.32 | 1.49 |
| Pro | 719 | | | | | | T | | 1.51 | | * | | | 2.80 | 1.51 |
| Gly | 720 | | | | | | T | | 0.93 | | * | | | 2.52 | 2.50 |
| Tyr | 721 | | | | | | | | 0.34 | | * | | | 1.54 | 0.88 |
| His | 722 | | | | | | | C | 0.62 | | | | | −0.04 | 0.40 |
| Asp | 723 | | | B | B | | | | −0.31 | | | | | −0.32 | 0.58 |
| Ile | 724 | | | B | B | | | | −0.31 | | | | | −0.60 | 0.26 |
| Ile | 725 | | | B | B | | | | −0.28 | | | | | −0.60 | 0.29 |
| Thr | 726 | | | B | B | | | | −0.38 | | | | | −0.60 | 0.25 |
| Ile | 727 | | | B | | | | | −0.93 | | | | | −0.20 | 0.36 |
| Pro | 728 | | | | | | | C | −1.24 | | | | | −0.05 | 0.52 |
| Thr | 729 | | | | | | | C | −0.36 | | | | F | 0.15 | 0.52 |
| Gly | 730 | | | | | | | C | −0.36 | | | * | F | 0.30 | 1.19 |
| Ala | 731 | | | B | B | | | | −0.04 | | | | F | −0.25 | 0.54 |
| Thr | 732 | | | B | B | | | | −0.01 | | | * | F | 0.65 | 0.65 |
| Asn | 733 | | | B | B | | | | 0.24 | | | * | F | −0.15 | 0.48 |
| Ile | 734 | | | B | B | | | | 0.56 | | | * | F | 0.45 | 0.96 |

TABLE 1-continued

| Res | Pos. | Garni...Alpha | Chou...Alpha | Garni...Beta | Chou...Beta | Garni...Turn | Chou...Turn | Garni...Coil | Kyte-...Hydro. | Eisen... | Eisen...Alpha | Eisen...Beta | Kapl...Flexi. | James...Antig. | Emini Surfa. |
|---|---|---|---|---|---|---|---|---|---|---|---|---|---|---|---|
| Glu | 735 | . | . | B | B | . | . | . | 1.01 | . | . | . | . | 0.60 | 1.15 |
| Val | 736 | . | . | B | B | . | . | . | 1.60 | . | . | * | F | 0.90 | 1.40 |
| Lys | 737 | . | . | B | B | . | . | . | 1.91 | . | . | * | F | 1.24 | 3.21 |
| Gln | 738 | . | . | B | B | . | . | . | 2.02 | . | . | * | F | 1.78 | 3.21 |
| Arg | 739 | . | . | B | B | . | . | . | 2.57 | . | * | * | F | 2.12 | 8.48 |
| Asn | 740 | . | . | B | B | . | . | . | 2.27 | . | * | * | F | 2.66 | 4.20 |
| Gln | 741 | . | . | . | . | T | T | . | 3.23 | . | * | * | F | 3.40 | 3.25 |
| Arg | 742 | . | . | . | . | T | T | . | 3.19 | . | * | * | F | 3.06 | 3.40 |
| Gly | 743 | . | . | . | . | T | T | . | 3.19 | . | * | * | F | 3.00 | 3.25 |
| Ser | 744 | . | . | . | . | . | . | . | 2.73 | . | * | * | F | 2.74 | 3.25 |
| Arg | 745 | . | . | . | . | . | . | C | 2.43 | . | * | * | F | 2.48 | 3.02 |
| Asn | 746 | . | . | . | . | T | T | . | 1.73 | . | * | * | F | 2.82 | 1.52 |
| Gly | 747 | . | . | . | . | T | T | . | 0.81 | . | * | . | F | 2.80 | 2.06 |
| Ser | 748 | . | . | B | B | . | T | C | 0.57 | . | * | . | F | 1.57 | 1.33 |
| Phe | 749 | . | A | B | B | . | . | . | -0.02 | * | . | . | F | 0.79 | 0.56 |
| Leu | 750 | . | A | B | B | . | . | . | -0.09 | * | . | . | . | -0.04 | 0.35 |
| Ala | 751 | . | A | B | . | . | . | . | -0.68 | * | . | . | . | -0.32 | 0.15 |
| Ile | 752 | . | A | . | . | . | . | . | -1.27 | * | . | . | . | -0.60 | 0.31 |
| Lys | 753 | A | A | . | . | . | . | . | -0.92 | * | . | . | . | -0.60 | 0.23 |
| Ala | 754 | A | . | . | . | . | . | . | -0.97 | * | . | . | . | -0.60 | 0.27 |
| Ala | 755 | A | . | . | . | . | . | . | -0.58 | * | . | . | . | 0.30 | 0.55 |
| Asp | 756 | A | . | B | . | . | . | . | -0.01 | . | . | * | F | 0.60 | 0.54 |
| Gly | 757 | . | . | B | . | . | T | . | -0.31 | . | . | * | F | 0.85 | 1.12 |
| Thr | 758 | . | . | B | . | . | T | . | -0.23 | . | . | . | F | 0.25 | 0.87 |
| Tyr | 759 | . | . | B | . | . | T | . | -0.28 | . | . | * | F | -0.05 | 0.61 |
| Ile | 760 | . | . | B | . | . | . | . | -0.03 | . | . | * | F | -0.20 | 0.50 |
| Leu | 761 | . | . | B | . | . | . | . | 0.56 | . | . | * | . | -0.40 | 0.48 |
| Asn | 762 | A | . | B | . | . | . | . | 0.31 | . | . | * | F | -0.40 | 0.48 |
| Gly | 763 | A | . | B | . | T | T | . | 0.34 | . | . | * | F | -0.50 | 0.55 |
| Asp | 764 | A | . | . | . | T | T | . | -0.16 | . | . | * | F | 0.50 | 0.55 |
| Tyr | 765 | A | . | . | . | . | T | . | -0.21 | . | . | * | F | 0.50 | 1.14 |
| Thr | 766 | . | . | . | . | . | . | C | 0.37 | . | . | * | F | 0.45 | 1.14 |
| Leu | 767 | . | . | B | B | . | . | . | 0.37 | . | * | * | . | -0.15 | 0.95 |
| Ser | 768 | . | . | B | B | . | . | . | 0.37 | . | * | . | F | -0.60 | 1.38 |
| Thr | 769 | . | . | B | B | . | . | . | 0.71 | . | * | . | F | -0.45 | 0.68 |
| Leu | 770 | . | . | B | B | . | . | . | 0.71 | . | * | . | F | -0.15 | 0.75 |
| Glu | 771 | A | . | . | B | . | . | . | 0.07 | . | . | * | . | 0.60 | 0.90 |
| Gln | 772 | A | . | . | B | . | . | . | -0.22 | . | . | * | . | 0.45 | 1.83 |
| Asp | 773 | A | . | . | B | . | . | . | 0.34 | . | . | * | . | 0.45 | 0.96 |
| Ile | 774 | A | . | . | B | . | . | . | 0.69 | . | . | * | F | 0.00 | 0.66 |
| Met | 775 | A | . | . | B | . | . | . | 0.66 | . | . | * | F | 0.75 | 1.25 |
| Tyr | 776 | . | . | . | B | . | . | . | 0.61 | . | . | * | F | 0.30 | 1.44 |
| Leu | 777 | . | . | . | B | . | . | . | -0.24 | . | . | * | . | -0.30 | 0.82 |
| Glu | 778 | . | . | B | B | . | . | . | -1.06 | . | . | * | . | -0.60 | 0.37 |
| Gln | 779 | . | . | B | B | . | . | . | -0.94 | . | . | * | . | -0.45 | 0.39 |
| Gly | 780 | . | . | B | B | . | . | . | -0.30 | . | . | * | . | -0.15 | 0.32 |
| Val | 781 | . | . | B | B | . | . | . | 0.00 | . | . | * | . | -0.30 | 0.40 |
| Leu | 782 | . | . | B | B | . | . | . | -0.10 | . | . | * | . | -0.30 | 0.32 |
| Arg | 783 | . | . | B | B | . | . | . | -0.44 | . | . | * | . | -0.60 | 0.43 |
| | | | | | | | | | | | | | | | 0.57 |

TABLE 1-continued

| Res | Pos. | Garni...Alpha | Chou...Alpha | Garni...Beta | Chou...Beta | Garni...Turn | Chou...Turn | Garni...Coil | Kyte-...Hydro... | Eisen... | Eisen...Alpha | Eisen...Beta | Kapl... | Flexi... | James...Antig... | Emini Surfa... |
|---|---|---|---|---|---|---|---|---|---|---|---|---|---|---|---|---|
| Tyr | 784 | . | . | . | . | . | . | . | -0.40 | . | . | . | . | . | 0.25 | 1.03 |
| Ser | 785 | . | . | B | . | . | T | . | -0.13 | . | * | * | . | F | 0.80 | 1.68 |
| Gly | 786 | . | . | . | . | T | T | . | 0.13 | . | . | * | . | F | 1.05 | 0.86 |
| Ser | 787 | . | . | . | . | . | T | C | 0.13 | . | * | . | . | F | 0.45 | 0.56 |
| Ser | 788 | . | A | . | . | . | T | C | 0.02 | . | . | * | . | F | 0.05 | 0.34 |
| Ala | 789 | A | A | . | . | . | . | C | 0.38 | . | * | . | . | F | 0.45 | 0.60 |
| Ala | 790 | A | A | . | . | . | . | . | -0.21 | . | . | * | . | . | 0.60 | 0.88 |
| Leu | 791 | A | A | . | . | . | . | . | 0.24 | . | * | . | . | . | 0.30 | 0.88 |
| Glu | 792 | . | A | B | . | . | . | . | 0.24 | . | * | * | . | . | 0.60 | 0.46 |
| Arg | 793 | . | A | B | B | . | . | . | -0.16 | . | * | . | . | . | 0.60 | 0.89 |
| Ile | 794 | A | A | . | B | . | . | . | 0.13 | . | * | * | . | . | 0.90 | 1.18 |
| Arg | 795 | A | A | . | B | T | . | . | 0.13 | . | * | . | . | . | 0.60 | 1.24 |
| Ser | 796 | . | . | . | . | . | . | . | 0.51 | . | * | . | . | . | 0.75 | 0.96 |
| Phe | 797 | . | . | . | . | . | . | . | 0.51 | . | * | * | . | F | 1.13 | 0.76 |
| Ser | 798 | . | . | . | . | . | T | C | 0.56 | . | * | . | . | F | 0.81 | 0.89 |
| Pro | 799 | . | . | . | . | T | T | C | 0.44 | . | . | * | . | F | 1.89 | 0.91 |
| Leu | 800 | . | . | . | . | . | T | C | 1.12 | . | . | * | . | F | 2.32 | 1.17 |
| Lys | 801 | . | . | B | B | . | . | . | 0.20 | . | * | * | . | F | 2.80 | 2.10 |
| Glu | 802 | A | . | B | B | . | . | . | 0.19 | . | . | * | . | F | 2.32 | 1.29 |
| Pro | 803 | A | . | B | B | . | . | . | 0.00 | . | * | * | . | F | 1.84 | 1.20 |
| Leu | 804 | . | . | B | B | . | . | . | 0.30 | . | * | * | . | F | 1.16 | 1.02 |
| Thr | 805 | . | . | B | B | . | . | . | -0.34 | . | * | * | . | F | 0.73 | 0.89 |
| Ile | 806 | . | . | B | B | . | . | . | -0.34 | . | . | * | . | F | -0.30 | 0.38 |
| Gln | 807 | . | . | B | B | . | . | . | -0.70 | . | . | * | . | F | -0.60 | 0.20 |
| Val | 808 | . | . | B | B | . | . | . | -1.56 | . | * | * | . | F | -0.60 | 0.35 |
| Leu | 809 | . | . | B | B | . | . | . | -1.69 | . | * | * | . | . | -0.60 | 0.18 |
| Thr | 810 | . | . | B | B | . | . | . | -0.88 | . | . | * | . | . | -0.60 | 0.26 |
| Val | 811 | . | . | B | B | . | . | . | -1.16 | . | . | * | . | . | -0.60 | 0.24 |
| Gly | 812 | . | . | B | B | . | . | . | -1.08 | . | . | * | . | . | -0.60 | 0.33 |
| Asn | 813 | A | . | . | . | . | . | . | -0.97 | . | * | . | . | . | -0.60 | 0.33 |
| Ala | 814 | A | . | . | . | . | . | . | -0.32 | . | * | . | . | . | 0.12 | 0.44 |
| Leu | 815 | A | . | . | . | . | . | . | 0.53 | . | * | . | . | F | 0.34 | 0.92 |
| Arg | 816 | . | . | B | . | . | . | . | -0.04 | . | . | * | . | F | 1.76 | 1.86 |
| Pro | 817 | . | . | B | B | . | . | . | 0.86 | . | . | . | . | F | 1.53 | 0.81 |
| Lys | 818 | . | . | B | B | . | . | . | 0.96 | . | . | . | . | F | 2.20 | 1.61 |
| Ile | 819 | . | A | B | B | . | . | . | 0.64 | . | . | . | . | F | 1.48 | 3.05 |
| Leu | 820 | . | . | B | B | . | . | . | 0.99 | . | . | . | . | F | 1.56 | 2.25 |
| Lys | 821 | . | . | B | B | . | . | . | 1.10 | . | . | . | . | F | 0.44 | 2.28 |
| Tyr | 822 | . | . | B | B | . | . | . | 0.13 | . | . | . | . | . | -0.38 | 0.99 |
| Thr | 823 | A | . | . | . | . | . | . | 0.39 | . | * | . | . | . | -0.45 | 1.04 |
| Tyr | 824 | A | . | . | . | . | . | . | 0.39 | . | * | . | . | . | -0.45 | 1.04 |
| Phe | 825 | A | . | . | . | . | . | . | 1.32 | . | * | . | . | . | -0.45 | 1.33 |
| Val | 826 | A | A | . | . | . | . | . | 1.57 | . | * | . | . | . | 0.45 | 1.85 |
| Lys | 827 | A | . | . | . | . | . | . | 1.58 | . | * | * | . | F | 0.90 | 2.36 |
| Lys | 828 | A | A | . | . | . | . | . | 1.12 | . | * | * | . | F | 0.90 | 4.71 |
| Lys | 829 | A | A | . | . | . | . | . | 1.82 | . | * | * | . | F | 0.90 | 8.51 |
| Glu | 830 | A | A | . | . | . | . | . | 2.09 | . | * | . | . | F | 0.90 | 3.68 |
| Ser | 831 | A | A | . | . | . | . | . | 1.16 | . | . | . | . | F | 0.90 | 2.96 |
| Phe | 832 | A | A | . | . | . | . | . | 0.90 | . | . | . | . | F | 0.30 | 0.52 |

TABLE 1-continued

| Res | Pos. | Garni...Alpha | Chou-..Alpha | Garni...Beta | Chou-..Beta | Garni...Turn | Chou-..Turn | Garni...Coil | Kyte-..Hydro. | Eisen...Alpha | Eisen...Beta | Kapl...Flexi. | James...Antig. | Emini Surfa. |
|---|---|---|---|---|---|---|---|---|---|---|---|---|---|---|
| Asn | 833 | . | . | . | . | . | . | . | 0.54 | . | . | . | −0.30 | 0.47 |
| Ala | 834 | . | A | B | . | . | . | . | −0.20 | . | * | . | −0.40 | 0.50 |
| Ile | 835 | . | . | B | . | . | . | . | −0.50 | * | . | . | −0.20 | 0.50 |
| Pro | 836 | . | . | . | . | . | . | C | −0.79 | . | . | . | 0.00 | 0.42 |
| The | 837 | . | . | . | . | T | T | . | −0.38 | . | . | . | 0.20 | 0.42 |
| Phe | 838 | A | . | . | . | . | T | C | −1.23 | * | * | . | −0.20 | 0.63 |
| Ser | 839 | . | . | . | . | . | T | . | −1.53 | . | . | . | 0.00 | 0.30 |
| Ala | 840 | . | A | . | B | . | . | C | −0.64 | * | . | . | −0.60 | 0.15 |
| Trp | 841 | A | A | B | B | . | . | . | −0.43 | . | . | . | −0.60 | 0.29 |
| Val | 842 | A | A | . | B | . | . | . | −0.41 | * | . | . | −0.30 | 0.38 |
| Ile | 843 | A | A | . | B | . | . | . | −0.06 | * | . | . | −0.60 | 0.40 |
| Glu | 844 | A | A | . | B | . | . | . | 0.24 | . | . | . | −0.60 | 0.37 |
| Glu | 845 | A | A | . | . | . | . | . | 0.17 | * | . | . | 0.30 | 0.87 |
| Trp | 846 | A | . | . | . | . | . | . | 0.16 | * | . | F | 0.61 | 0.66 |
| Gly | 847 | A | . | . | . | . | . | . | 1.06 | * | . | . | 1.37 | 0.51 |
| Glu | 848 | . | A | . | . | T | . | . | 1.64 | . | * | . | 2.08 | 0.59 |
| Cys | 849 | . | . | . | . | T | . | . | 0.98 | * | . | . | 2.09 | 0.76 |
| Ser | 850 | . | . | . | . | T | T | . | 0.98 | * | . | . | 3.10 | 0.41 |
| Lys | 851 | . | . | . | . | T | T | . | 0.46 | . | . | . | 2.79 | 0.41 |
| Ser | 852 | . | . | . | . | T | T | . | 0.46 | . | . | . | 2.18 | 0.63 |
| Cys | 853 | . | . | . | . | . | . | . | 0.17 | . | * | . | 2.02 | 0.47 |
| Glu | 854 | A | A | . | . | . | . | . | 0.83 | . | . | . | 0.61 | 0.24 |
| Leu | 855 | A | A | . | . | . | . | . | 1.24 | . | . | . | −0.30 | 0.32 |
| Glu | 856 | . | A | . | . | . | . | . | 1.31 | * | * | . | 0.85 | 1.16 |
| Trp | 857 | A | A | . | . | . | . | . | 0.80 | . | . | . | −0.30 | 0.31 |
| Gln | 858 | A | A | . | . | . | . | . | 0.61 | . | * | . | 0.75 | 1.31 |
| Arg | 859 | A | A | . | . | . | . | . | 0.61 | . | * | . | −0.15 | 0.98 |
| Arg | 860 | . | . | B | . | . | . | . | 0.76 | * | * | . | −0.30 | 1.61 |
| Leu | 861 | . | A | B | . | . | . | . | 1.21 | . | . | . | 0.45 | 0.50 |
| Val | 862 | . | A | B | . | . | . | . | 1.50 | . | * | . | 0.60 | 0.50 |
| Glu | 863 | . | A | B | . | . | . | . | 0.61 | . | . | . | 0.60 | 0.43 |
| Cys | 864 | . | A | B | . | . | . | . | 0.50 | . | . | . | 0.94 | 0.36 |
| Arg | 865 | . | . | . | . | . | . | . | 0.04 | . | . | . | 0.98 | 0.78 |
| Asp | 866 | . | . | . | . | T | T | . | 0.86 | . | . | F | 2.17 | 0.45 |
| Ile | 867 | . | . | . | . | T | T | . | 1.50 | . | . | F | 2.91 | 1.45 |
| Asn | 868 | . | . | . | . | T | T | . | 0.91 | . | . | F | 3.40 | 1.14 |
| Glu | 869 | . | . | . | . | . | T | C | 1.28 | * | . | F | 3.06 | 0.69 |
| Gln | 870 | . | . | . | . | . | T | C | 1.17 | * | . | F | 2.07 | 1.32 |
| Pro | 871 | . | . | . | . | . | T | C | 0.50 | . | . | F | 1.28 | 1.42 |
| Ala | 872 | . | . | . | . | . | T | C | 0.80 | * | . | . | 1.54 | 0.77 |
| Ser | 873 | . | A | . | . | . | . | . | 0.84 | . | * | . | 1.05 | 0.45 |
| Glu | 874 | A | A | . | . | . | . | . | 1.19 | * | . | F | 0.85 | 0.58 |
| Cys | 875 | A | A | . | . | . | . | . | 0.33 | . | . | F | 0.75 | 1.00 |
| Ala | 876 | . | A | . | . | . | . | . | 0.59 | * | . | . | 0.60 | 0.55 |
| Lys | 877 | A | A | . | . | . | . | . | 0.97 | * | . | F | 0.75 | 0.64 |
| Glu | 878 | A | A | . | . | . | . | . | 0.68 | * | . | F | 0.90 | 1.84 |
| Val | 879 | A | A | . | . | . | . | . | 0.38 | * | . | F | 0.90 | 1.84 |
| Lys | 880 | A | A | . | . | . | . | . | 0.73 | * | . | . | 0.90 | 1.23 |
| Pro | 881 | A | . | . | . | . | T | . | 1.43 | * | . | F | 1.30 | 1.03 |

TABLE 1-continued

| Res | Pos. | Garni...Alpha | Chou-...Alpha | Garni...Beta | Chou-...Beta | Garni...Turn | Chou-...Turn | Garni...Coil | Kyte-...Hydro. | Eisen...Alpha | Eisen...Beta | Karpl...Flexi. | James...Antig. | Emini Surfa. |
|---|---|---|---|---|---|---|---|---|---|---|---|---|---|---|
| Ala | 882 | . | . | . | . | . | T | . | 1.18 | . | . | . | 2.01 | 2.71 |
| Ser | 883 | . | . | . | . | T | T | . | 0.51 | . | . | F | 2.32 | 2.10 |
| Thr | 884 | . | . | . | . | T | T | . | 0.78 | . | * | F | 2.18 | 0.73 |
| Arg | 885 | . | . | B | . | T | T | . | 0.73 | . | * | F | 2.09 | 0.73 |
| Pro | 886 | . | . | . | . | . | T | . | 0.91 | . | * | F | 3.10 | 0.91 |
| Cys | 887 | . | . | . | . | T | T | . | 1.29 | . | * | F | 2.64 | 0.85 |
| Ala | 888 | . | . | . | . | T | T | . | 0.92 | . | * | . | 2.43 | 0.67 |
| Asp | 889 | . | . | . | . | T | T | . | 1.02 | . | * | . | 1.72 | 0.23 |
| His | 890 | . | . | . | . | . | . | C | 0.91 | . | . | . | 1.51 | 0.67 |
| Pro | 891 | . | . | . | . | T | T | . | 0.83 | . | * | . | 1.65 | 1.16 |
| Cys | 892 | . | . | . | . | T | T | . | 1.50 | . | * | . | 1.00 | 0.73 |
| Pro | 893 | . | . | . | . | T | T | . | 1.28 | . | * | . | 0.60 | 0.93 |
| Gln | 894 | . | . | . | . | . | . | . | 0.93 | . | . | . | 0.10 | 0.49 |
| Trp | 895 | . | A | B | . | . | . | . | 0.97 | . | . | . | -0.40 | 0.91 |
| Gln | 896 | . | A | B | . | . | . | . | 0.89 | . | . | . | -0.05 | 1.02 |
| Leu | 897 | . | A | B | . | . | . | . | 1.26 | . | . | . | -0.60 | 0.62 |
| Hly | 898 | . | . | . | . | . | . | . | 1.17 | . | . | . | 0.00 | 0.79 |
| Glu | 899 | . | . | . | . | T | . | . | 0.50 | . | . | F | 0.45 | 0.61 |
| Trp | 900 | . | . | . | . | . | . | . | 0.49 | . | . | F | 0.45 | 0.40 |
| Ser | 901 | . | . | . | . | T | T | . | 0.53 | . | . | F | 0.65 | 0.54 |
| Ser | 902 | . | . | B | . | T | T | . | 1.03 | . | * | F | 1.25 | 0.62 |
| Cys | 903 | . | . | B | . | T | T | . | 0.71 | . | * | F | 0.65 | 0.85 |
| Ser | 904 | . | . | B | . | T | T | . | 0.37 | . | * | F | 1.25 | 0.34 |
| Lys | 905 | . | . | . | . | T | . | . | 0.70 | * | . | F | 1.05 | 0.25 |
| Thr | 906 | . | . | . | . | T | . | . | 0.66 | * | . | F | 1.69 | 0.94 |
| Cys | 907 | . | . | . | . | T | . | . | 0.71 | * | . | F | 2.03 | 0.69 |
| Glu | 908 | . | . | . | . | . | . | . | 1.42 | * | . | F | 2.27 | 0.54 |
| Lys | 909 | . | . | . | . | . | . | . | 1.77 | * | . | F | 2.61 | 0.75 |
| Gly | 910 | . | . | . | . | . | . | . | 1.83 | * | . | F | 3.40 | 2.81 |
| Tyr | 911 | . | . | . | . | . | . | . | 1.84 | . | . | F | 3.06 | 5.57 |
| Lys | 912 | . | A | B | . | T | T | . | 1.70 | * | . | F | 1.92 | 3.73 |
| Lys | 913 | . | A | B | . | T | T | . | 2.09 | * | . | F | 1.58 | 3.11 |
| Arg | 914 | . | A | B | . | . | . | . | 1.38 | * | . | F | 1.24 | 3.97 |
| Ser | 915 | . | A | B | . | . | . | . | 0.91 | * | . | F | 0.90 | 1.06 |
| Leu | 916 | . | A | B | . | . | . | . | 0.86 | * | . | F | 0.75 | 0.44 |
| Lys | 917 | . | A | B | . | . | . | . | 0.78 | * | . | F | 0.30 | 0.30 |
| Cys | 918 | . | A | B | . | . | . | . | 0.73 | * | . | F | -0.30 | 0.30 |
| Leu | 919 | . | A | B | . | . | . | . | 0.28 | * | . | F | 0.30 | 0.62 |
| Ser | 920 | . | . | . | . | . | . | . | 0.23 | * | . | . | 0.50 | 0.31 |
| His | 921 | . | . | B | . | T | T | . | 0.19 | . | . | F | 0.85 | 0.56 |
| Asp | 922 | . | . | . | . | T | T | . | -0.67 | . | . | T | 0.65 | 0.51 |
| Gly | 923 | . | . | . | . | T | T | . | -0.30 | . | . | F | 0.65 | 0.31 |
| Gly | 924 | . | . | . | . | . | . | . | 0.48 | . | . | . | -0.10 | 0.31 |
| Val | 925 | . | . | B | . | . | . | . | 0.78 | . | . | . | 0.25 | 0.25 |
| Leu | 926 | . | . | B | . | . | . | . | 0.51 | . | . | . | -0.10 | 0.44 |
| Ser | 927 | . | . | B | . | . | . | . | -0.16 | . | . | . | -0.10 | 0.59 |
| His | 928 | . | . | B | . | . | . | . | 0.19 | . | . | F | 0.10 | 0.43 |
| Glu | 929 | . | . | B | . | . | T | . | 0.32 | . | . | . | 0.85 | 0.87 |
| Ser | 930 | A | . | . | . | . | T | . | 0.37 | * | . | F | 1.30 | 1.00 |

TABLE 1-continued

| Res | Pos. | Garni...Alpha | Chou-...Alpha | Garni...Beta | Chou-...Beta | Garni...Turn | Chou-...Turn | Garni...Coil | Kyte-...Hydro... | Eisen...Alpha | Eisen...Beta | Karpl...Flexi... | James...Antig... | Emini Surfa... |
|---|---|---|---|---|---|---|---|---|---|---|---|---|---|---|
| Cys | 931 | A | . | . | . | . | . | . | 1.22 | . | . | . | 0.85 | 0.61 |
| Asp | 932 | A | . | . | . | . | T | . | 1.57 | . | . | F | 1.15 | 0.70 |
| Pro | 933 | A | . | . | . | . | T | . | 1.39 | . | . | F | 1.30 | 1.05 |
| Leu | 934 | A | . | . | . | . | T | . | 1.43 | . | . | F | 1.30 | 3.02 |
| Lys | 935 | A | A | . | . | . | T | . | 1.70 | * | . | F | 1.30 | 3.62 |
| Lys | 936 | A | A | . | . | . | . | . | 1.67 | * | . | F | 0.90 | 3.18 |
| Pro | 937 | A | A | . | . | . | . | . | 0.78 | * | . | F | 0.90 | 3.34 |
| Lys | 938 | A | A | . | . | . | . | . | 0.99 | * | . | F | 0.90 | 1.17 |
| His | 939 | A | A | . | . | . | . | . | 1.10 | * | * | . | 0.60 | 0.98 |
| Phe | 940 | . | A | B | . | . | . | . | 0.39 | * | * | . | -0.30 | 0.55 |
| Ile | 941 | A | A | B | . | . | . | . | 0.03 | * | * | . | -0.30 | 0.15 |
| Asp | 942 | A | A | . | . | . | . | . | -0.36 | * | * | . | -0.60 | 0.16 |
| Phe | 943 | A | A | . | . | . | . | . | -0.99 | * | . | . | -0.60 | 0.18 |
| Cys | 944 | A | A | . | . | . | . | . | -0.96 | * | * | . | -0.60 | 0.26 |
| Thr | 945 | A | A | . | . | . | . | . | -0.92 | . | . | . | 0.30 | 0.27 |
| Met | 946 | A | A | . | . | . | . | . | -0.33 | . | . | . | -0.60 | 0.16 |
| Ala | 947 | A | A | . | . | . | . | . | -0.72 | . | . | . | -0.30 | 0.41 |
| Glu | 948 | A | A | . | . | . | . | . | -0.41 | . | . | . | 0.30 | 0.36 |
| Cys | 949 | A | A | . | . | . | . | . | -0.13 | . | . | . | 0.30 | 0.47 |
| Ser | 950 | A | A | . | . | . | . | . | -0.21 | . | . | . | 0.30 | 0.60 |

TABLE 2

| Res | Pos. | Garni... Alpha | Chou-... Alpha | Garni... Beta | Chou-... Beta | Garni... Turn | Chou-... Turn | Garni... Coil | Kyte-... Hydro... | Eisen... Alpha | Eisen... Beta | Karpi... Flexi... | James... Antig... | Emini Surfa... |
|---|---|---|---|---|---|---|---|---|---|---|---|---|---|---|
| Met | 1 | . | . | B | . | . | . | . | −0.37 | . | . | . | −0.40 | 0.50 |
| Phe | 2 | . | . | B | . | . | . | . | −0.57 | . | . | . | 0.40 | 0.61 |
| Pro | 3 | . | . | B | . | . | . | . | −0.77 | . | . | . | −0.40 | 0.48 |
| Ala | 4 | . | . | . | . | . | . | C | −0.59 | . | * | . | −0.20 | 0.49 |
| Pro | 5 | . | . | . | . | . | . | C | −0.09 | . | * | . | −0.20 | 0.87 |
| Ala | 6 | . | . | . | . | . | . | C | 0.22 | * | * | . | 0.85 | 1.11 |
| Ala | 7 | . | . | . | . | . | T | C | 0.11 | * | * | . | 0.45 | 1.15 |
| Pro | 8 | A | . | . | . | . | T | . | 0.11 | * | . | . | −0.20 | 0.61 |
| Arg | 9 | . | . | . | . | T | T | . | 0.00 | * | . | . | 0.20 | 0.94 |
| Trp | 10 | . | . | B | . | . | T | . | −0.60 | * | . | . | −0.20 | 0.81 |
| Leu | 11 | . | A | B | . | . | . | . | −0.82 | * | . | . | −0.60 | 0.43 |
| Pro | 12 | . | A | B | . | . | . | . | −1.04 | * | . | . | −0.60 | 0.18 |
| Phe | 13 | . | A | B | . | . | . | . | −1.64 | * | . | . | −0.60 | 0.14 |
| Leu | 14 | A | A | . | . | . | . | . | −2.57 | * | . | . | −0.60 | 0.14 |
| Leu | 15 | A | A | . | . | . | . | . | −3.09 | . | . | . | −0.60 | 0.08 |
| Leu | 16 | A | A | . | . | . | . | . | −3.09 | . | . | . | −0.60 | 0.07 |
| Leu | 17 | A | A | . | . | . | . | . | −3.69 | . | . | . | −0.60 | 0.07 |
| Leu | 18 | A | A | . | . | . | . | . | −3.80 | . | . | . | −0.60 | 0.07 |
| Leu | 19 | A | A | . | . | . | . | . | −3.20 | . | . | . | −0.60 | 0.07 |
| Leu | 20 | A | A | . | . | . | . | . | −3.20 | . | . | . | −0.60 | 0.14 |
| Leu | 21 | A | A | . | . | . | . | . | −2.98 | * | . | . | −0.60 | 0.14 |
| Leu | 22 | . | A | B | . | . | . | . | −2.06 | * | . | . | −0.60 | 0.17 |
| Pro | 23 | . | A | B | . | . | . | . | −1.59 | * | . | . | −0.60 | 0.39 |
| Leu | 24 | A | A | . | . | . | . | . | −1.37 | * | . | . | −0.60 | 0.47 |
| Ala | 25 | A | A | . | . | . | . | . | −0.77 | * | . | . | −0.04 | 0.58 |
| Arg | 26 | . | A | B | . | . | . | . | −0.54 | * | . | . | 0.82 | 0.58 |
| Gly | 27 | . | A | B | . | . | . | . | 0.38 | . | . | F | 0.63 | 0.71 |
| Ala | 28 | . | . | B | . | . | . | . | 0.38 | . | . | F | 2.14 | 1.37 |
| Pro | 29 | . | . | . | . | . | . | C | 0.60 | . | . | F | 2.60 | 1.08 |
| Ala | 30 | . | . | B | . | . | . | . | 0.60 | . | . | F | 1.84 | 1.11 |
| Arg | 31 | . | . | B | . | . | . | . | 0.14 | . | . | F | 1.58 | 1.11 |
| Pro | 32 | . | . | B | . | . | . | . | 0.14 | . | * | F | 1.17 | 0.71 |
| Ala | 33 | . | . | B | . | . | T | . | 0.73 | . | * | F | 1.11 | 0.69 |
| Ala | 34 | A | . | . | . | . | T | . | 0.36 | . | * | F | 0.85 | 0.61 |
| Gly | 35 | . | . | . | . | . | T | C | 0.64 | . | * | F | 0.45 | 0.40 |
| Gly | 36 | . | . | . | . | . | T | C | 0.53 | . | * | F | 0.45 | 0.53 |
| Gln | 37 | A | . | . | . | . | . | . | −0.07 | . | . | F | 0.65 | 0.91 |
| Ala | 38 | . | . | B | . | . | . | . | −0.33 | . | . | F | 0.65 | 0.76 |
| Ser | 39 | . | . | B | B | B | . | . | −0.60 | . | . | F | −0.15 | 0.57 |
| Glu | 40 | . | . | B | B | B | . | . | −0.47 | . | . | F | −0.15 | 0.24 |
| Leu | 41 | . | . | B | B | B | . | . | −0.43 | . | * | . | −0.30 | 0.37 |
| Val | 42 | . | . | B | B | B | . | . | −0.32 | . | * | . | 0.30 | 0.40 |
| Val | 43 | . | . | B | B | B | . | . | −0.54 | . | * | . | 0.30 | 0.46 |
| Pro | 44 | . | . | B | B | B | . | . | −0.46 | . | * | F | −0.24 | 0.46 |
| Thr | 45 | . | . | B | B | B | . | . | −0.80 | . | * | F | 0.27 | 0.95 |
| Arg | 46 | . | . | B | B | B | . | . | −0.29 | . | * | F | 0.63 | 1.26 |
| Leu | 47 | . | . | . | . | . | T | C | −0.02 | . | * | F | 2.04 | 1.10 |
| Pro | 48 | . | . | . | . | . | T | C | 0.49 | * | * | F | 2.10 | 0.77 |
| Gly | 49 | . | . | . | . | . | T | C | 0.70 | * | * | F | 1.89 | 0.39 |
| Ser | 50 | . | . | . | . | . | T | C | 0.20 | * | * | F | 1.68 | 0.81 |
| Ala | 51 | A | A | . | . | . | . | . | −0.50 | * | * | F | 0.87 | 0.43 |
| Gly | 52 | A | A | . | . | . | . | . | −0.50 | * | . | F | 0.66 | 0.44 |
| Glu | 53 | A | A | . | . | . | . | . | −0.32 | . | * | . | −0.30 | 0.27 |
| Leu | 54 | A | A | . | . | . | . | . | −0.79 | . | * | . | −0.30 | 0.37 |
| Ala | 55 | A | A | . | . | . | . | . | −0.79 | . | * | . | −0.60 | 0.31 |
| Leu | 56 | A | A | . | . | . | . | . | −0.79 | . | * | . | −0.60 | 0.24 |
| His | 57 | A | A | . | . | . | . | . | −1.14 | . | * | . | −0.60 | 0.29 |
| Leu | 58 | A | A | . | . | . | . | . | −1.49 | * | * | . | −0.60 | 0.25 |
| Ser | 59 | A | A | . | . | . | . | . | −0.63 | * | * | . | −0.60 | 0.30 |
| Ala | 60 | A | A | . | . | . | . | . | −0.39 | * | * | . | −0.30 | 0.44 |
| Phe | 61 | A | A | . | . | . | . | . | −0.28 | * | * | . | −0.30 | 0.53 |
| Gly | 62 | . | . | . | . | . | T | T | −1.10 | * | . | . | 0.50 | 0.34 |
| Lys | 63 | A | . | . | . | . | T | . | −1.10 | . | * | F | −0.05 | 0.25 |
| Gly | 64 | . | . | B | . | . | T | . | −0.69 | . | * | . | −0.20 | 0.24 |
| Phe | 65 | . | . | B | . | . | T | . | −0.91 | . | * | . | 0.70 | 0.47 |
| Val | 66 | . | . | B | B | . | . | . | −0.80 | * | * | . | −0.30 | 0.19 |
| Leu | 67 | . | . | B | B | . | . | . | −0.67 | * | * | . | −0.30 | 0.20 |
| Arg | 68 | . | . | B | B | . | . | . | −0.71 | . | * | . | 0.00 | 0.35 |
| Leu | 69 | . | . | B | B | . | . | . | −0.37 | . | * | . | 1.20 | 0.80 |
| Ala | 70 | . | . | . | . | . | T | C | 0.03 | . | * | . | 2.55 | 1.61 |
| Pro | 71 | . | . | . | . | . | T | C | 0.19 | * | * | F | 3.00 | 1.10 |
| Asp | 72 | . | . | . | . | T | T | . | 0.19 | . | * | F | 2.60 | 1.16 |
| Asp | 73 | A | . | . | . | . | T | . | −0.51 | . | * | F | 1.75 | 0.95 |
| Ser | 74 | A | A | . | . | . | . | . | 0.09 | . | . | . | 0.90 | 0.62 |
| Phe | 75 | A | A | . | . | . | . | . | 0.68 | . | . | . | 0.60 | 0.57 |
| Leu | 76 | A | A | . | . | . | . | . | 0.19 | . | * | . | 0.30 | 0.59 |

TABLE 2-continued

| Res | Pos. | Garni... Alpha | Chou-... Alpha | Garni... Beta | Chou-... Beta | Garni... Turn | Chou-... Turn | Garni... Coil | Kyte-... Hydro... | Eisen... Alpha | Eisen... Beta | Karpi... Flexi... | James... Antig... | Emini Surfa... |
|---|---|---|---|---|---|---|---|---|---|---|---|---|---|---|
| Ala | 77 | A | A | . | . | . | . | . | 0.23 | . | * | . | 0.60 | 0.38 |
| Pro | 78 | A | A | . | . | . | . | . | −0.66 | . | * | . | 0.30 | 0.89 |
| Glu | 79 | A | A | . | . | . | . | . | −0.36 | * | * | F | −0.15 | 0.75 |
| Phe | 80 | A | A | . | . | . | . | . | 0.46 | * | . | F | 0.90 | 1.29 |
| Lys | 81 | A | A | . | . | . | . | . | 0.46 | * | * | F | 0.90 | 1.63 |
| Ile | 82 | A | A | . | . | . | . | . | 0.70 | * | . | F | 0.75 | 0.78 |
| Glu | 83 | A | A | . | . | . | . | . | 0.57 | * | * | F | 0.45 | 0.89 |
| Arg | 84 | A | A | . | . | . | . | . | 0.27 | * | * | F | 0.75 | 0.44 |
| Leu | 85 | . | A | . | . | T | . | . | 0.62 | * | * | F | 0.85 | 0.84 |
| Gly | 86 | . | A | . | . | T | . | . | 0.69 | * | * | F | 1.15 | 0.48 |
| Gly | 87 | . | . | . | . | . | T | C | 0.99 | * | * | F | 1.35 | 0.48 |
| Ser | 88 | . | . | . | . | . | T | C | 0.68 | * | * | F | 1.05 | 0.59 |
| Gly | 89 | . | . | . | . | . | T | C | 0.22 | * | * | F | 1.05 | 0.86 |
| Arg | 90 | . | . | B | . | . | T | . | 0.69 | . | * | F | 1.19 | 0.86 |
| Ala | 91 | . | . | . | . | . | T | C | 1.03 | . | * | F | 1.73 | 0.63 |
| Thr | 92 | . | . | B | . | . | T | . | 1.49 | . | * | F | 2.32 | 1.11 |
| Gly | 93 | . | . | B | . | . | T | . | 1.44 | . | * | F | 2.66 | 1.11 |
| Gly | 94 | . | . | . | . | T | T | . | 0.98 | * | * | F | 3.40 | 1.09 |
| Glu | 95 | . | . | B | . | . | . | . | 0.98 | * | * | F | 2.31 | 0.62 |
| Arg | 96 | . | . | B | . | . | . | . | 1.22 | * | . | F | 2.12 | 1.23 |
| Gly | 97 | . | . | . | . | T | . | . | 0.87 | * | * | F | 2.18 | 1.23 |
| Leu | 98 | . | . | B | . | . | T | . | 0.51 | * | . | F | 1.49 | 0.38 |
| Arg | 99 | . | . | B | . | . | T | . | 0.16 | * | . | . | 0.70 | 0.17 |
| Gly | 100 | . | . | B | . | . | T | . | −0.14 | * | . | . | −0.20 | 0.15 |
| Cys | 101 | . | . | B | . | . | T | . | −0.60 | * | . | . | −0.20 | 0.24 |
| Phe | 102 | . | . | B | . | . | . | . | −0.57 | . | * | . | 0.10 | 0.12 |
| Phe | 103 | . | . | B | . | . | T | . | −0.61 | . | * | . | 0.20 | 0.18 |
| Ser | 104 | . | . | B | . | . | T | . | −0.72 | . | * | F | −0.05 | 0.24 |
| Gly | 105 | . | . | . | . | . | T | C | −0.72 | . | * | F | 0.15 | 0.45 |
| Thr | 106 | . | . | . | . | . | T | C | −0.06 | * | * | F | 0.45 | 0.52 |
| Val | 107 | . | . | . | B | . | . | C | 0.43 | . | * | F | 1.25 | 0.67 |
| Asn | 108 | . | . | . | B | . | . | C | 1.13 | . | * | F | 1.70 | 1.05 |
| Gly | 109 | . | . | . | B | . | . | C | 1.13 | . | * | F | 2.30 | 1.26 |
| Glu | 110 | . | . | . | . | . | T | C | 0.67 | . | * | F | 3.00 | 2.27 |
| Pro | 111 | A | . | . | . | . | T | . | 0.39 | . | * | F | 2.50 | 1.16 |
| Glu | 112 | A | . | . | . | . | T | . | 0.66 | . | * | F | 2.20 | 1.19 |
| Ser | 113 | A | . | . | . | . | T | . | −0.20 | . | . | F | 1.75 | 0.69 |
| Leu | 114 | A | A | . | B | . | . | . | −0.16 | . | . | . | 0.00 | 0.33 |
| Ala | 115 | A | A | . | B | . | . | . | −0.97 | . | . | . | −0.30 | 0.26 |
| Ala | 116 | A | A | . | B | . | . | . | −1.42 | . | . | . | −0.60 | 0.16 |
| Val | 117 | A | A | . | B | . | . | . | −1.31 | . | . | . | −0.60 | 0.10 |
| Ser | 118 | . | A | B | B | . | . | . | −1.36 | * | . | . | −0.30 | 0.20 |
| Leu | 119 | . | . | B | B | . | . | . | −1.36 | * | . | . | −0.30 | 0.20 |
| Cys | 120 | . | . | B | . | . | T | . | −1.07 | * | . | . | 0.10 | 0.22 |
| Arg | 121 | . | . | B | . | . | T | . | −0.82 | * | . | . | 0.10 | 0.22 |
| Gly | 122 | . | . | . | . | T | T | . | −0.27 | * | . | F | 0.65 | 0.26 |
| Leu | 123 | . | . | . | . | T | T | . | −0.67 | * | . | F | 1.25 | 0.65 |
| Ser | 124 | . | . | . | . | . | T | C | −0.67 | * | . | F | 0.45 | 0.29 |
| Gly | 125 | . | . | B | . | . | T | . | −0.81 | . | * | F | −0.05 | 0.24 |
| Ser | 126 | . | . | B | . | . | T | . | −0.92 | . | * | F | −0.05 | 0.24 |
| Phe | 127 | . | . | B | . | . | T | . | −0.92 | . | * | . | 0.10 | 0.30 |
| Leu | 128 | . | A | B | . | . | . | C | −0.11 | . | * | . | −0.30 | 0.30 |
| Leu | 129 | . | A | . | . | . | . | . | 0.19 | . | * | F | 0.65 | 0.39 |
| Asp | 130 | A | A | . | . | . | . | . | −0.17 | . | . | F | 0.45 | 0.77 |
| Gly | 131 | A | A | . | . | . | . | . | −0.18 | . | . | F | 0.45 | 0.81 |
| Glu | 132 | A | A | . | . | . | . | . | −0.37 | . | * | F | 0.90 | 1.42 |
| Glu | 133 | A | A | . | . | . | . | . | 0.44 | . | * | F | 0.75 | 0.60 |
| Phe | 134 | A | A | . | . | . | . | . | 1.04 | . | * | . | 0.45 | 1.04 |
| Thr | 135 | . | A | B | . | . | . | . | 1.04 | . | * | . | 0.30 | 0.93 |
| Ile | 136 | . | . | B | . | . | . | . | 1.04 | . | * | F | 0.05 | 0.93 |
| Gln | 137 | . | . | B | . | . | . | . | 0.46 | . | * | F | −0.10 | 1.06 |
| Pro | 138 | . | . | . | . | . | . | C | 0.11 | . | * | F | 0.25 | 0.75 |
| Gln | 139 | . | . | . | . | T | . | . | 0.47 | . | * | F | 0.60 | 1.05 |
| Gly | 140 | . | . | . | . | . | T | C | 0.48 | . | * | F | 0.45 | 0.60 |
| Ala | 141 | . | . | . | . | T | T | . | 0.56 | . | * | F | 1.25 | 0.52 |
| Gly | 142 | . | . | . | . | T | T | C | −0.03 | . | . | F | 0.45 | 0.25 |
| Gly | 143 | . | . | . | . | T | T | C | 0.18 | . | . | F | 0.65 | 0.25 |
| Ser | 144 | . | . | . | . | . | . | C | −0.03 | . | . | F | 0.65 | 0.43 |
| Leu | 145 | . | . | B | . | . | . | . | 0.28 | * | . | F | 0.65 | 0.68 |
| Ala | 146 | . | . | B | . | . | . | . | 0.98 | * | . | F | 0.85 | 0.93 |
| Gln | 147 | . | . | B | . | . | T | . | 0.51 | . | * | F | 2.00 | 1.36 |
| Pro | 148 | . | . | B | . | . | T | . | 0.86 | * | . | . | 1.05 | 1.36 |
| His | 149 | . | . | B | . | . | T | . | 1.27 | * | . | . | 1.45 | 2.34 |
| Arg | 150 | . | . | B | . | . | T | . | 1.79 | * | . | . | 1.55 | 2.64 |
| Leu | 151 | . | . | B | . | . | . | . | 2.03 | * | . | . | 0.85 | 1.80 |
| Gln | 152 | . | . | B | . | . | . | . | 1.82 | * | . | . | 0.65 | 1.31 |

TABLE 2-continued

| Res | Pos. | Garni... Alpha | Chou-... Alpha | Garni... Beta | Chou-... Beta | Garni... Turn | Chou-... Turn | Garni... Coil | Kyte-... Hydro... | Eisen... Alpha | Eisen... Beta | Karpi... Flexi... | James... Antig... | Emini Surfa... |
|---|---|---|---|---|---|---|---|---|---|---|---|---|---|---|
| Arg | 153 | . | . | . | . | T | . | . | 1.44 | * | . | . | 1.05 | 1.03 |
| Trp | 154 | . | . | . | . | T | . | . | 1.13 | * | . | F | 0.84 | 1.26 |
| Gly | 155 | . | . | . | . | . | T | C | 0.43 | * | . | F | 0.93 | 0.72 |
| Pro | 156 | . | . | . | . | . | T | C | 1.36 | * | . | F | 1.17 | 0.37 |
| Ala | 157 | . | . | . | . | T | T | . | 1.14 | * | . | F | 1.61 | 0.69 |
| Gly | 158 | . | . | . | . | . | T | C | 0.22 | * | . | F | 2.40 | 1.08 |
| Ala | 159 | . | . | . | . | . | . | C | 0.30 | * | * | F | 1.81 | 0.58 |
| Arg | 160 | . | . | B | . | . | . | . | 0.76 | * | * | F | 1.37 | 0.89 |
| Pro | 161 | . | . | B | . | . | . | . | 0.62 | * | * | F | 1.58 | 1.75 |
| Leu | 162 | . | . | . | . | . | . | C | 1.00 | * | * | F | 1.84 | 1.72 |
| Pro | 163 | . | . | . | . | . | . | C | 1.34 | * | * | F | 1.90 | 1.35 |
| Arg | 164 | . | . | . | . | . | . | C | 1.64 | * | * | F | 2.20 | 1.52 |
| Gly | 165 | . | . | . | . | . | T | C | 1.53 | * | * | F | 2.40 | 1.93 |
| Pro | 166 | . | . | . | . | . | T | C | 0.89 | * | . | F | 3.00 | 2.17 |
| Glu | 167 | . | . | . | . | . | T | C | 1.70 | * | . | F | 2.55 | 0.82 |
| Trp | 168 | A | . | . | . | . | T | . | 1.60 | * | . | . | 2.05 | 1.44 |
| Glu | 169 | A | . | . | . | . | . | . | 1.14 | * | . | . | 1.85 | 1.34 |
| Val | 170 | A | . | . | . | . | . | . | 1.49 | . | . | F | 1.85 | 0.77 |
| Glu | 171 | A | . | . | . | . | . | . | 1.36 | . | * | F | 2.00 | 1.26 |
| Thr | 172 | A | . | . | . | . | . | . | 1.36 | . | * | F | 2.15 | 0.72 |
| Gly | 173 | . | . | . | . | . | T | C | 1.76 | . | . | F | 3.00 | 1.68 |
| Glu | 174 | A | . | . | . | . | T | . | 1.76 | . | . | F | 2.50 | 1.90 |
| Gly | 175 | A | . | . | . | . | T | . | 2.61 | . | . | F | 2.20 | 2.28 |
| Gln | 176 | A | . | . | . | . | T | . | 2.72 | . | . | F | 1.90 | 4.00 |
| Arg | 177 | A | A | . | . | . | . | . | 2.69 | . | * | F | 1.54 | 4.52 |
| Gln | 178 | A | A | . | . | . | . | . | 3.03 | . | * | F | 1.58 | 4.52 |
| Glu | 179 | . | A | . | . | T | . | . | 3.00 | * | * | F | 2.32 | 4.36 |
| Arg | 180 | . | A | . | . | T | . | . | 3.34 | * | . | F | 2.66 | 3.03 |
| Gly | 181 | . | . | . | . | T | T | . | 3.34 | . | * | F | 3.40 | 3.03 |
| Asp | 182 | . | . | . | . | . | T | C | 3.23 | . | . | F | 2.86 | 3.03 |
| His | 183 | . | . | . | . | . | T | C | 2.93 | . | * | F | 2.52 | 2.58 |
| Gln | 184 | . | . | . | . | . | T | C | 2.93 | . | * | F | 2.18 | 3.50 |
| Glu | 185 | . | A | . | . | . | . | C | 2.82 | . | * | F | 1.44 | 3.63 |
| Asp | 186 | A | A | . | . | . | . | . | 3.17 | . | . | F | 0.90 | 4.61 |
| Ser | 187 | A | A | . | . | . | . | . | 2.87 | . | . | F | 0.90 | 4.61 |
| Glu | 188 | A | A | . | . | . | . | . | 2.90 | . | . | F | 0.90 | 3.57 |
| Glu | 189 | A | A | . | . | . | . | . | 2.90 | . | . | F | 0.90 | 3.70 |
| Glu | 190 | A | A | . | . | . | . | . | 2.90 | . | . | F | 0.90 | 4.79 |
| Ser | 191 | A | A | . | . | . | . | . | 2.90 | . | . | F | 0.90 | 4.79 |
| Gln | 192 | A | A | . | . | . | . | . | 2.61 | . | . | F | 0.90 | 4.79 |
| Glu | 193 | A | A | . | . | . | . | . | 2.61 | . | . | F | 0.90 | 2.79 |
| Glu | 194 | A | A | . | . | . | . | . | 2.27 | . | . | F | 0.90 | 3.61 |
| Glu | 195 | A | A | . | . | . | . | . | 1.68 | . | . | F | 0.90 | 2.06 |
| Ala | 196 | A | A | . | . | . | . | . | 1.68 | . | . | F | 1.16 | 1.20 |
| Glu | 197 | A | A | . | . | . | . | . | 1.68 | . | . | F | 1.27 | 0.93 |
| Gly | 198 | A | A | . | . | . | . | . | 1.47 | . | . | F | 1.53 | 0.93 |
| Ala | 199 | . | A | . | . | T | . | . | 1.26 | . | . | F | 2.34 | 1.42 |
| Ser | 200 | . | . | . | . | . | . | C | 1.04 | . | . | F | 2.60 | 1.27 |
| Glu | 201 | . | . | . | . | . | . | C | 1.42 | * | . | F | 2.04 | 1.99 |
| Pro | 202 | . | . | . | . | . | . | C | 0.61 | * | . | F | 1.78 | 3.04 |
| Pro | 203 | . | . | . | . | . | . | C | 0.61 | . | . | F | 1.52 | 1.87 |
| Pro | 204 | . | . | . | . | . | T | C | 0.61 | . | . | F | 1.46 | 1.07 |
| Pro | 205 | . | . | . | . | . | T | C | 0.60 | . | . | F | 0.45 | 0.70 |
| Leu | 206 | . | . | . | . | . | T | C | 0.30 | * | * | F | 0.45 | 0.65 |
| Gly | 207 | . | . | B | . | . | T | . | 0.62 | . | * | F | 0.51 | 0.57 |
| Ala | 208 | . | . | B | . | . | . | . | 0.52 | . | * | F | 1.17 | 0.72 |
| Thr | 209 | . | . | B | . | . | . | . | 0.78 | * | * | F | 1.58 | 1.25 |
| Ser | 210 | . | . | B | . | . | T | . | 1.10 | * | . | F | 2.34 | 2.53 |
| Arg | 211 | . | . | B | . | . | T | . | 1.21 | * | . | F | 2.60 | 4.91 |
| Thr | 212 | . | . | B | . | . | T | . | 0.70 | * | . | F | 2.34 | 2.95 |
| Lys | 213 | . | . | B | . | . | T | . | 0.99 | * | . | F | 2.08 | 1.63 |
| Arg | 214 | . | . | B | B | . | . | . | 1.30 | * | . | F | 1.42 | 1.12 |
| Phe | 215 | . | . | B | B | . | . | . | 1.01 | * | * | . | 1.01 | 1.34 |
| Val | 216 | . | . | B | B | . | . | . | 1.01 | * | * | . | 0.60 | 0.68 |
| Ser | 217 | A | . | . | B | . | . | . | 0.62 | * | * | . | 0.60 | 0.68 |
| Glu | 218 | A | A | . | . | . | . | . | −0.28 | * | * | . | −0.30 | 0.68 |
| Ala | 219 | A | A | . | B | . | . | . | −0.39 | * | * | . | 0.30 | 0.68 |
| Arg | 220 | A | A | . | B | . | . | . | 0.00 | * | * | . | 0.60 | 0.87 |
| Phe | 221 | A | A | . | B | . | . | . | 0.04 | * | . | . | 0.60 | 0.73 |
| Val | 222 | A | A | . | B | . | . | . | −0.47 | * | * | . | −0.30 | 0.59 |
| Glu | 223 | A | A | . | B | . | . | . | −1.32 | * | * | . | −0.30 | 0.25 |
| Thr | 224 | A | A | . | B | . | . | . | −1.32 | * | . | . | −0.60 | 0.21 |
| Leu | 225 | A | A | . | B | . | . | . | −1.43 | * | * | . | −0.60 | 0.29 |
| Leu | 226 | A | A | . | B | . | . | . | −1.32 | . | . | . | 0.30 | 0.28 |
| Val | 227 | A | A | . | B | . | . | . | −0.77 | . | . | . | −0.60 | 0.20 |
| Ala | 228 | A | A | . | B | . | . | . | −1.37 | . | . | . | −0.30 | 0.32 |

TABLE 2-continued

| Res | Pos. | Garni... Alpha | Chou-... Alpha | Garni... Beta | Chou-... Beta | Garni... Turn | Chou-... Turn | Garni... Coil | Kyte-... Hydro... | Eisen... Alpha | Eisen... Beta | Karpi... Flexi... | James... Antig... | Emini Surfa... |
|---|---|---|---|---|---|---|---|---|---|---|---|---|---|---|
| Asp | 229 | A | A | . | B | . | . | . | −1.64 | . | . | . | −0.30 | 0.38 |
| Ala | 230 | A | A | . | . | . | . | . | −1.42 | . | . | . | −0.30 | 0.52 |
| Ser | 231 | A | A | . | . | . | . | . | −1.31 | . | . | . | 0.30 | 0.52 |
| Met | 232 | A | A | . | . | . | . | . | −0.70 | . | . | . | −0.30 | 0.27 |
| Ala | 233 | A | A | . | . | . | . | . | −0.46 | . | . | . | −0.60 | 0.42 |
| Ala | 234 | A | A | . | . | . | . | . | −1.04 | . | . | . | −0.60 | 0.31 |
| Phe | 235 | A | A | . | . | . | . | . | −0.46 | . | . | . | −0.60 | 0.32 |
| Tyr | 236 | A | A | . | . | . | . | . | −0.97 | . | . | . | −0.60 | 0.52 |
| Gly | 237 | A | A | . | . | . | . | . | −0.37 | . | . | . | −0.60 | 0.43 |
| Ala | 238 | A | A | . | . | . | . | . | 0.22 | . | . | . | −0.60 | 0.86 |
| Asp | 239 | A | A | . | . | . | . | . | 0.78 | * | * | . | −0.30 | 0.88 |
| Leu | 240 | A | A | . | . | . | . | . | 0.59 | * | . | . | 0.45 | 1.21 |
| Gln | 241 | A | A | . | B | . | . | . | 0.02 | * | * | . | −0.30 | 0.84 |
| Asn | 242 | A | A | . | B | . | . | . | 0.06 | * | . | . | −0.30 | 0.41 |
| His | 243 | . | A | B | B | . | . | . | −0.17 | * | * | . | −0.60 | 0.72 |
| Ile | 244 | . | A | B | B | . | . | . | −0.77 | * | . | . | −0.60 | 0.35 |
| Leu | 245 | . | A | B | B | . | . | . | −0.26 | * | . | . | −0.60 | 0.21 |
| Thr | 246 | . | A | B | B | . | . | . | −1.11 | * | . | . | −0.60 | 0.21 |
| Leu | 247 | . | A | B | B | . | . | . | −1.70 | * | . | . | −0.60 | 0.22 |
| Met | 248 | A | A | . | B | . | . | . | −2.26 | * | * | . | −0.60 | 0.27 |
| Ser | 249 | A | A | . | B | . | . | . | −1.26 | * | * | . | −0.60 | 0.19 |
| Val | 250 | A | A | . | B | . | . | . | −1.33 | * | * | . | −0.30 | 0.45 |
| Ala | 251 | A | A | . | B | . | . | . | −1.27 | * | * | . | −0.30 | 0.32 |
| Ala | 252 | A | A | . | B | . | . | . | −0.41 | * | * | . | −0.60 | 0.37 |
| Arg | 253 | A | A | . | B | . | . | . | 0.16 | * | * | . | −0.15 | 1.01 |
| Ile | 254 | A | A | . | B | . | . | . | 0.24 | * | * | . | 0.45 | 1.36 |
| Tyr | 255 | A | . | . | . | . | . | . | 0.80 | * | * | . | 0.99 | 2.08 |
| Lys | 256 | . | . | B | . | . | . | . | 0.50 | * | * | . | 1.33 | 1.42 |
| His | 257 | . | . | B | . | . | T | . | 1.13 | . | * | F | 1.12 | 1.42 |
| Pro | 258 | . | . | . | . | . | T | C | 1.02 | . | * | F | 2.56 | 1.81 |
| Ser | 259 | . | . | . | . | T | T | . | 1.61 | . | * | F | 3.40 | 1.46 |
| Ile | 260 | . | . | . | . | T | T | . | 0.97 | . | * | F | 2.76 | 1.44 |
| Lys | 261 | . | . | B | . | . | . | . | 0.92 | . | * | F | 1.67 | 0.65 |
| Asn | 262 | . | . | . | . | T | . | . | 0.14 | * | * | F | 1.73 | 0.78 |
| Ser | 263 | . | . | B | B | . | . | . | −0.24 | * | * | F | 0.19 | 0.92 |
| Ile | 264 | . | . | B | B | . | . | . | −0.80 | * | * | . | −0.30 | 0.45 |
| Asp | 265 | . | . | B | B | . | . | . | −0.77 | * | . | . | −0.60 | 0.21 |
| Leu | 266 | . | . | B | B | . | . | . | −0.77 | * | . | . | −0.60 | 0.12 |
| Met | 267 | A | . | . | B | . | . | . | −1.62 | * | . | . | −0.60 | 0.33 |
| Val | 268 | . | . | B | B | . | . | . | −2.13 | . | * | . | −0.60 | 0.15 |
| Val | 269 | . | . | B | B | . | . | . | −2.13 | . | . | . | −0.60 | 0.15 |
| Lys | 270 | A | . | . | B | . | . | . | −2.99 | . | . | . | −0.60 | 0.11 |
| Val | 271 | . | . | B | B | . | . | . | −2.18 | . | . | . | −0.60 | 0.11 |
| Leu | 272 | . | . | B | B | . | . | . | −1.58 | . | . | . | −0.30 | 0.25 |
| Ile | 273 | A | . | . | B | . | . | . | −0.72 | . | * | . | 0.30 | 0.21 |
| Val | 274 | A | . | . | B | . | . | . | 0.18 | . | * | . | 0.30 | 0.49 |
| Glu | 275 | A | . | . | B | . | . | . | −0.16 | . | . | . | 0.75 | 1.19 |
| Asp | 276 | A | A | . | . | . | . | . | 0.36 | . | . | F | 0.90 | 1.79 |
| Glu | 277 | A | A | . | . | . | . | . | 0.96 | * | . | F | 0.90 | 2.39 |
| Lys | 278 | . | A | . | . | T | . | . | 1.84 | * | * | F | 1.30 | 2.13 |
| Trp | 279 | . | A | . | . | . | . | C | 1.84 | . | * | F | 1.10 | 2.21 |
| Gly | 280 | . | . | . | . | T | . | C | 1.54 | * | . | F | 1.35 | 0.95 |
| Pro | 281 | . | . | . | . | T | . | C | 1.54 | * | * | F | 1.36 | 0.64 |
| Glu | 282 | . | . | B | . | T | . | . | 1.54 | * | * | F | 1.62 | 1.01 |
| Val | 283 | . | . | B | . | T | . | . | 1.16 | * | * | F | 2.23 | 1.64 |
| Ser | 284 | . | . | . | . | T | . | C | 1.10 | * | * | F | 2.74 | 1.05 |
| Asp | 285 | . | . | . | . | T | T | . | 0.63 | . | . | F | 3.10 | 0.60 |
| Asn | 286 | . | . | . | . | T | T | . | 0.53 | . | * | F | 2.49 | 0.67 |
| Gly | 287 | . | . | . | . | T | T | . | −0.28 | * | * | F | 2.18 | 0.72 |
| Gly | 288 | . | . | . | . | T | . | . | 0.69 | * | * | F | 1.07 | 0.35 |
| Leu | 289 | . | . | B | . | . | . | . | 0.99 | * | * | F | 0.36 | 0.43 |
| Thr | 290 | . | . | B | . | . | . | . | 0.29 | * | * | . | −0.10 | 0.70 |
| Leu | 291 | . | . | B | . | . | . | . | −0.38 | * | * | . | −0.40 | 0.61 |
| Arg | 292 | . | . | B | . | . | . | . | −0.03 | * | * | . | −0.40 | 0.40 |
| Asn | 293 | . | . | B | . | . | . | . | 0.02 | * | * | . | −0.10 | 0.44 |
| Phe | 294 | . | . | . | . | T | T | . | 0.83 | * | * | . | 0.20 | 0.57 |
| Cys | 295 | . | . | . | . | T | T | . | 1.26 | * | * | . | 0.20 | 0.50 |
| Asn | 296 | . | . | . | . | T | T | . | 2.18 | * | * | . | 0.20 | 0.61 |
| Trp | 297 | . | . | . | . | T | T | . | 1.37 | * | * | . | 0.65 | 1.38 |
| Gln | 298 | . | . | . | . | T | . | . | 1.37 | * | . | . | 0.45 | 2.23 |
| Arg | 299 | . | . | . | . | T | . | . | 2.07 | * | . | . | 1.05 | 2.23 |
| Arg | 300 | . | . | . | . | T | . | . | 2.52 | * | * | F | 1.20 | 3.67 |
| Phe | 301 | . | . | . | . | T | . | . | 2.22 | * | * | F | 1.84 | 3.28 |
| Asn | 302 | . | . | . | . | T | . | . | 2.51 | * | * | F | 2.18 | 2.24 |
| Gln | 303 | . | . | . | . | . | T | C | 2.62 | * | . | F | 2.52 | 1.91 |
| Pro | 304 | . | . | . | . | . | T | C | 2.48 | * | . | F | 2.86 | 4.33 |

TABLE 2-continued

| Res | Pos. | Garni... Alpha | Chou-... Alpha | Garni... Beta | Chou-... Beta | Garni... Turn | Chou-... Turn | Garni... Coil | Kyte-... Hydro... | Eisen... Alpha | Eisen... Beta | Karpi... Flexi... | James... Antig... | Emini Surfa... |
|---|---|---|---|---|---|---|---|---|---|---|---|---|---|---|
| Ser | 305 | . | . | . | . | T | T | . | 2.16 | * | * | F | 3.40 | 3.66 |
| Asp | 306 | . | — | . | . | T | T | . | 2.86 | * | . | F | 3.06 | 3.27 |
| Arg | 307 | . | . | . | . | . | . | C | 2.82 | * | . | F | 2.32 | 3.66 |
| His | 308 | . | . | . | . | . | . | C | 2.58 | * | . | F | 1.98 | 3.72 |
| Pro | 309 | . | . | . | . | . | . | C | 2.79 | * | . | F | 1.64 | 3.49 |
| Glu | 310 | . | . | . | . | T | . | . | 2.78 | * | . | F | 1.50 | 2.97 |
| His | 311 | A | . | . | . | . | T | . | 2.19 | * | . | F | 1.00 | 3.15 |
| Tyr | 312 | A | . | . | . | . | T | . | 1.19 | * | . | F | 1.00 | 2.06 |
| Asp | 313 | A | . | . | . | . | T | . | 0.41 | . | . | F | 0.85 | 0.83 |
| Thr | 314 | A | . | . | . | . | T | . | −0.19 | . | . | . | −0.20 | 0.51 |
| Ala | 315 | A | . | . | B | . | . | . | −0.50 | * | . | . | −0.60 | 0.27 |
| Ile | 316 | . | . | B | B | . | . | . | −0.36 | * | . | . | −0.60 | 0.23 |
| Leu | 317 | . | . | B | B | . | . | . | −0.11 | . | . | . | −0.60 | 0.31 |
| Leu | 318 | . | . | B | B | . | . | . | −0.11 | . | * | . | −0.60 | 0.53 |
| Thr | 319 | . | . | B | B | . | . | . | −0.50 | . | . | F | 0.00 | 1.23 |
| Arg | 320 | . | . | B | B | . | . | . | −0.58 | . | * | F | −0.08 | 1.29 |
| Gln | 321 | . | . | . | B | T | . | . | −0.03 | . | * | F | 0.69 | 0.84 |
| Asn | 322 | . | . | . | . | T | T | . | 0.78 | . | * | F | 1.31 | 0.57 |
| Phe | 323 | . | . | . | . | T | T | . | 1.59 | . | . | . | 1.98 | 0.51 |
| Cys | 324 | . | . | . | . | T | T | . | 1.56 | . | * | . | 2.20 | 0.51 |
| Gly | 325 | . | . | . | . | T | T | . | 0.63 | . | * | F | 1.53 | 0.31 |
| Gln | 326 | . | . | . | . | T | . | . | −0.03 | . | . | F | 1.11 | 0.30 |
| Glu | 327 | . | . | . | . | T | . | . | −0.03 | . | . | F | 0.89 | 0.30 |
| Gly | 328 | . | . | . | . | T | . | . | 0.36 | . | . | F | 1.27 | 0.50 |
| Leu | 329 | . | . | B | . | . | . | . | 0.21 | . | . | F | 0.65 | 0.42 |
| Cys | 330 | . | . | B | . | . | . | . | 0.21 | . | . | . | 0.50 | 0.20 |
| Asp | 331 | . | . | B | . | . | T | . | −0.64 | . | . | . | 0.10 | 0.20 |
| Thr | 332 | . | . | B | . | . | T | . | −1.23 | * | . | . | −0.20 | 0.18 |
| Leu | 333 | . | . | B | . | . | T | . | −0.89 | . | . | . | 0.10 | 0.34 |
| Gly | 334 | . | . | B | . | . | T | . | −0.97 | . | . | . | 0.70 | 0.34 |
| Val | 335 | . | . | B | . | . | . | . | −0.64 | . | . | . | −0.40 | 0.16 |
| Ala | 336 | . | . | B | . | . | . | . | −0.96 | . | . | . | −0.10 | 0.20 |
| Asp | 337 | . | . | B | . | . | T | . | −1.53 | . | . | . | 0.10 | 0.29 |
| Ile | 338 | . | . | B | . | . | T | . | −1.39 | . | . | . | −0.20 | 0.27 |
| Gly | 339 | . | . | B | . | . | T | . | −1.04 | * | . | . | 0.10 | 0.14 |
| Thr | 340 | . | . | B | . | . | T | . | −0.40 | . | . | . | 0.70 | 0.14 |
| Ile | 341 | . | . | B | . | . | . | . | 0.19 | . | . | . | 0.24 | 0.32 |
| Cys | 342 | . | . | B | . | . | . | . | 0.23 | . | . | . | 1.18 | 0.52 |
| Asp | 343 | . | . | B | . | . | T | . | 0.82 | * | . | F | 1.87 | 0.72 |
| Pro | 344 | . | . | . | . | T | T | . | 0.50 | . | . | F | 3.06 | 1.37 |
| Asn | 345 | . | . | . | . | T | T | . | 0.51 | . | . | F | 3.40 | 1.37 |
| Lys | 346 | . | . | . | . | T | T | . | 0.54 | * | . | F | 3.06 | 1.10 |
| Ser | 347 | . | . | . | B | T | . | . | 0.32 | . | . | F | 1.87 | 0.53 |
| Cys | 348 | . | . | B | B | . | . | . | 0.32 | * | . | . | 0.38 | 0.23 |
| Ser | 349 | . | . | B | B | . | . | . | 0.53 | * | . | . | 0.64 | 0.20 |
| Val | 350 | . | . | B | B | . | . | . | 0.53 | * | . | . | 0.30 | 0.25 |
| Ile | 351 | . | . | B | B | . | . | . | 0.14 | * | . | . | 0.60 | 0.80 |
| Glu | 352 | A | . | . | B | . | . | . | −0.37 | . | . | . | 0.60 | 0.59 |
| Asp | 353 | A | A | . | . | . | . | . | 0.30 | . | . | F | 0.75 | 0.66 |
| Glu | 354 | A | A | . | . | . | . | . | 0.01 | * | . | F | 0.90 | 1.62 |
| Gly | 355 | A | A | . | . | . | . | . | 0.28 | * | . | F | 0.75 | 0.95 |
| Leu | 356 | A | A | . | . | . | . | . | 1.13 | * | . | . | 0.30 | 0.57 |
| Gln | 357 | A | A | . | . | . | . | . | 0.82 | * | . | . | −0.30 | 0.45 |
| Ala | 358 | A | A | . | . | . | . | . | 0.01 | * | . | . | −0.60 | 0.66 |
| Ala | 359 | A | A | . | . | . | . | . | −0.58 | * | . | . | −0.60 | 0.66 |
| His | 360 | A | A | . | . | . | . | . | −0.27 | * | . | . | −0.60 | 0.38 |
| Thr | 361 | A | A | . | . | . | . | . | 0.54 | * | . | . | −0.60 | 0.52 |
| Leu | 362 | A | A | . | . | . | . | . | −0.27 | * | . | . | −0.30 | 0.88 |
| Ala | 363 | A | A | . | . | . | . | . | −0.02 | * | . | . | −0.30 | 0.54 |
| His | 364 | A | A | . | . | . | . | . | 0.53 | * | . | . | −0.30 | 0.37 |
| Glu | 365 | A | A | . | . | . | . | . | −0.29 | * | . | . | −0.30 | 0.61 |
| Leu | 366 | A | A | . | B | . | . | . | −0.79 | * | . | . | −0.30 | 0.45 |
| Gly | 367 | A | A | . | B | . | . | . | −0.28 | * | . | . | −0.60 | 0.27 |
| His | 368 | A | A | . | B | . | . | . | −0.29 | * | . | . | −0.30 | 0.21 |
| Val | 369 | A | A | . | B | . | . | . | −0.47 | * | . | . | −0.60 | 0.25 |
| Leu | 370 | . | A | B | B | . | . | . | −0.50 | * | . | . | −0.26 | 0.39 |
| Ser | 371 | . | A | B | B | . | . | . | 0.31 | * | . | . | 0.08 | 0.39 |
| Met | 372 | . | . | B | . | . | . | . | 0.66 | . | . | . | 0.92 | 0.88 |
| Pro | 373 | . | . | . | . | T | . | . | 0.39 | * | . | . | 2.41 | 1.78 |
| His | 374 | . | . | . | . | T | T | . | 1.29 | * | . | F | 3.40 | 1.78 |
| Asp | 375 | . | . | . | . | T | T | . | 1.89 | . | . | F | 3.06 | 3.61 |
| Asp | 376 | . | . | . | . | T | T | . | 1.52 | . | . | F | 2.89 | 3.61 |
| Ser | 377 | . | . | . | . | T | T | . | 1.81 | * | * | F | 2.72 | 1.42 |
| Lys | 378 | . | . | B | . | . | T | . | 2.13 | * | * | F | 2.15 | 1.23 |
| Pro | 379 | . | . | . | . | T | T | . | 1.36 | * | * | F | 2.38 | 1.44 |
| Cys | 380 | . | . | B | . | . | T | . | 0.66 | * | * | F | 1.70 | 0.89 |

TABLE 2-continued

| Res | Pos. | Garni... Alpha | Chou-... Alpha | Garni... Beta | Chou-... Beta | Garni... Turn | Chou-... Turn | Garni... Coil | Kyte-... Hydro... | Eisen... Alpha | Eisen... Beta | Karpi... Flexi... | James... Antig... | Emini Surfa... |
|---|---|---|---|---|---|---|---|---|---|---|---|---|---|---|
| Thr | 381 | . | . | B | . | . | T | . | 0.31 | * | * | F | 1.53 | 0.38 |
| Arg | 382 | . | . | B | B | . | . | . | 0.40 | * | * | F | 0.36 | 0.25 |
| Leu | 383 | . | . | B | B | . | . | . | −0.24 | * | * | . | 0.04 | 0.71 |
| Phe | 384 | . | . | B | B | . | . | . | −0.38 | * | . | . | −0.43 | 0.49 |
| Gly | 385 | . | . | . | B | . | . | C | 0.33 | * | . | F | 0.05 | 0.25 |
| Pro | 386 | . | . | . | . | . | T | C | 0.61 | * | * | F | 0.45 | 0.59 |
| Met | 387 | . | . | . | . | T | T | . | 0.47 | * | * | F | 0.65 | 0.93 |
| Gly | 388 | A | . | . | . | . | T | . | 0.42 | . | . | F | 1.00 | 1.29 |
| Lys | 389 | A | . | . | . | . | T | . | 0.52 | . | . | . | 0.10 | 0.62 |
| His | 390 | A | A | . | . | . | . | . | 0.28 | . | . | . | −0.30 | 0.62 |
| His | 391 | A | A | . | . | . | . | . | 0.28 | . | * | . | 0.30 | 0.63 |
| Val | 392 | . | A | B | . | . | . | . | 0.07 | . | . | . | −0.30 | 0.49 |
| Met | 393 | A | A | . | . | . | . | . | −0.29 | . | * | . | −0.60 | 0.30 |
| Ala | 394 | A | A | . | . | . | . | . | −1.19 | . | * | . | −0.60 | 0.19 |
| Pro | 395 | A | A | . | . | . | . | . | −1.19 | . | * | . | −0.60 | 0.19 |
| Leu | 396 | A | A | . | . | . | . | . | −1.97 | . | * | . | −0.60 | 0.26 |
| Phe | 397 | A | A | . | . | . | . | . | −1.11 | * | * | . | −0.60 | 0.21 |
| Val | 398 | A | A | . | . | . | . | . | −0.51 | * | . | . | −0.60 | 0.22 |
| His | 399 | . | A | B | . | . | . | . | −0.23 | * | * | . | −0.60 | 0.46 |
| Leu | 400 | . | A | B | . | . | . | . | −0.83 | * | * | . | −0.60 | 0.77 |
| Asn | 401 | . | A | . | . | T | . | . | −0.23 | * | * | F | −0.05 | 0.85 |
| Gln | 402 | . | A | . | . | T | . | . | 0.18 | . | * | F | −0.05 | 0.97 |
| Thr | 403 | . | A | . | . | T | . | . | 0.73 | . | * | F | 0.10 | 1.24 |
| Leu | 404 | . | A | . | . | . | . | C | 0.56 | . | * | F | −0.10 | 1.03 |
| Pro | 405 | . | . | . | . | T | . | . | 0.70 | . | . | . | 0.00 | 0.92 |
| Trp | 406 | . | . | . | . | T | . | . | 0.40 | . | . | . | 0.00 | 0.34 |
| Ser | 407 | . | . | . | . | . | T | C | −0.19 | . | . | . | 0.00 | 0.55 |
| Pro | 408 | . | . | . | . | T | T | . | −0.48 | . | . | . | 0.20 | 0.36 |
| Cys | 409 | . | . | . | . | T | T | . | 0.09 | . | . | . | 0.20 | 0.34 |
| Ser | 410 | . | . | B | . | . | T | . | −0.51 | . | . | . | −0.20 | 0.40 |
| Ala | 411 | . | A | B | . | . | . | . | −0.53 | . | . | . | −0.60 | 0.21 |
| Met | 412 | . | A | B | . | . | . | . | −0.23 | . | . | . | −0.60 | 0.57 |
| Tyr | 413 | . | A | B | . | . | . | . | −0.83 | . | . | . | −0.60 | 0.74 |
| Leu | 414 | . | A | B | . | . | . | . | −0.98 | * | . | . | −0.60 | 0.60 |
| Thr | 415 | . | A | B | . | . | . | . | −0.68 | * | . | . | −0.60 | 0.50 |
| Glu | 416 | A | A | . | . | . | . | . | −0.43 | * | . | . | −0.30 | 0.54 |
| Leu | 417 | A | A | . | . | . | . | . | −0.18 | * | . | F | 0.76 | 0.64 |
| Leu | 418 | A | . | . | . | . | T | . | 0.03 | * | . | F | 1.47 | 0.44 |
| Asp | 419 | . | . | . | . | T | T | . | 0.50 | * | . | F | 2.18 | 0.35 |
| Gly | 420 | . | . | . | . | T | T | . | 0.81 | . | . | F | 1.89 | 0.42 |
| Gly | 421 | . | . | . | . | T | T | . | 0.14 | . | . | F | 3.10 | 0.84 |
| His | 422 | . | . | . | . | T | T | . | 0.14 | . | . | F | 2.79 | 0.27 |
| Gly | 423 | . | . | . | . | T | T | . | 0.14 | . | . | F | 1.58 | 0.23 |
| Asp | 424 | . | . | B | . | . | T | . | 0.14 | . | * | . | 0.72 | 0.19 |
| Cys | 425 | . | . | B | . | . | T | . | −0.10 | . | * | . | 1.01 | 0.23 |
| Leu | 426 | . | . | B | . | . | . | . | 0.03 | . | * | . | 0.50 | 0.24 |
| Leu | 427 | . | . | B | . | . | . | . | −0.28 | . | * | . | 0.50 | 0.22 |
| Asp | 428 | . | . | B | . | . | . | . | −0.52 | * | * | . | −0.10 | 0.40 |
| Ala | 429 | . | . | B | . | . | T | . | −1.11 | * | . | F | 0.25 | 0.49 |
| Pro | 430 | A | . | . | . | . | T | . | −1.26 | . | . | F | 0.25 | 0.60 |
| Gly | 431 | . | . | . | . | T | T | . | −0.66 | . | . | F | 0.65 | 0.30 |
| Ala | 432 | . | . | B | . | . | T | . | −0.66 | . | . | . | −0.20 | 0.46 |
| Ala | 433 | . | . | B | . | . | . | . | −0.87 | . | . | . | −0.40 | 0.24 |
| Leu | 434 | . | . | B | . | . | . | . | −0.59 | . | . | . | −0.40 | 0.38 |
| Pro | 435 | . | . | B | . | . | . | . | −0.72 | . | . | . | −0.40 | 0.54 |
| Leu | 436 | . | . | B | . | . | T | . | −1.19 | . | . | . | −0.20 | 0.53 |
| Pro | 437 | . | . | B | . | . | T | . | −0.81 | . | . | F | 0.00 | 0.53 |
| Thr | 438 | . | . | . | . | T | T | . | −0.57 | . | * | F | 0.45 | 0.53 |
| Gly | 439 | . | . | . | . | T | T | C | 0.36 | . | * | F | 0.30 | 0.64 |
| Leu | 440 | . | . | . | . | T | T | C | −0.03 | . | * | F | 1.25 | 0.81 |
| Pro | 441 | . | . | B | . | . | T | . | 0.19 | . | * | F | 0.50 | 0.55 |
| Gly | 442 | . | . | B | . | . | T | . | −0.41 | . | * | F | 0.45 | 0.57 |
| Arg | 443 | . | . | B | . | . | T | . | −0.34 | . | * | . | 0.25 | 0.57 |
| Met | 444 | . | A | B | . | . | . | . | 0.00 | . | * | . | −0.50 | 0.57 |
| Ala | 445 | . | A | B | . | . | . | . | 0.00 | * | * | . | −0.10 | 1.00 |
| Leu | 446 | . | A | B | . | . | . | . | 0.21 | * | . | . | −0.60 | 0.42 |
| Tyr | 447 | . | A | B | . | . | . | . | 0.56 | * | * | . | −0.60 | 0.71 |
| Gln | 448 | . | A | B | . | . | . | . | 0.44 | * | * | . | −0.45 | 1.22 |
| Leu | 449 | A | A | . | . | . | . | . | 0.38 | * | * | . | −0.15 | 2.57 |
| Asp | 450 | A | A | . | . | . | . | . | 1.08 | * | * | F | −0.15 | 0.88 |
| Gln | 451 | . | A | B | . | . | . | . | 1.89 | * | * | F | 0.75 | 0.99 |
| Gln | 452 | . | A | B | . | . | . | . | 1.24 | * | * | F | 0.90 | 2.09 |
| Cys | 453 | . | A | B | . | . | . | . | 0.54 | * | * | F | 0.75 | 0.88 |
| Arg | 454 | . | A | B | . | . | . | . | 1.01 | * | * | . | −0.30 | 0.44 |
| Gln | 455 | . | A | B | . | . | . | . | 0.80 | * | * | . | −0.30 | 0.25 |
| Ile | 456 | . | A | B | . | . | . | . | 0.80 | * | * | . | −0.30 | 0.72 |

TABLE 2-continued

| Res | Pos. | Garni... Alpha | Chou-... Alpha | Garni... Beta | Chou-... Beta | Garni... Turn | Chou-... Turn | Garni... Coil | Kyte-... Hydro... | Eisen... Alpha | Eisen... Beta | Karpi... Flexi... | James... Antig... | Emini Surfa... |
|---|---|---|---|---|---|---|---|---|---|---|---|---|---|---|
| Phe | 457 | . | A | . | . | T | . | . | 0.10 | * | * | . | 0.70 | 0.62 |
| Gly | 458 | . | . | . | . | . | T | C | 0.88 | * | * | . | 0.00 | 0.31 |
| Pro | 459 | . | . | . | . | T | T | . | 0.73 | * | * | F | 0.65 | 0.86 |
| Asp | 460 | . | . | . | . | T | T | . | 0.07 | * | * | F | 1.40 | 1.35 |
| Phe | 461 | . | . | . | . | T | T | . | 0.74 | * | * | . | 1.35 | 0.73 |
| Arg | 462 | . | . | . | . | T | . | . | 1.44 | * | * | . | 1.40 | 0.73 |
| His | 463 | . | . | . | . | T | . | . | 1.48 | * | * | . | 1.65 | 0.71 |
| Cys | 464 | . | . | . | . | . | T | C | 1.39 | * | * | . | 1.45 | 1.18 |
| Pro | 465 | . | . | . | . | T | T | . | 0.80 | * | . | F | 2.50 | 0.80 |
| Asn | 466 | . | . | . | . | T | T | . | 1.50 | * | * | F | 1.65 | 0.60 |
| Thr | 467 | . | . | . | . | T | T | . | 1.39 | * | * | F | 1.55 | 1.93 |
| Ser | 468 | . | A | . | . | T | . | . | 0.57 | * | . | F | 1.50 | 2.08 |
| Ala | 469 | . | A | . | . | T | . | . | 0.57 | . | . | F | 1.10 | 0.96 |
| Gln | 470 | . | A | B | . | . | . | . | 0.19 | . | . | F | 0.45 | 0.36 |
| Asp | 471 | . | A | B | . | . | . | . | 0.19 | * | * | F | 0.45 | 0.27 |
| Val | 472 | . | A | B | . | . | . | . | −0.31 | * | . | . | −0.30 | 0.46 |
| Cys | 473 | . | A | B | . | . | . | . | −0.30 | * | . | . | −0.30 | 0.22 |
| Ala | 474 | . | A | B | . | . | . | . | −0.38 | * | * | . | 0.60 | 0.14 |
| Gln | 475 | . | A | B | . | . | . | . | −0.41 | . | * | . | −0.60 | 0.10 |
| Leu | 476 | . | A | B | . | . | . | . | −0.72 | * | * | . | −0.60 | 0.25 |
| Trp | 477 | . | A | B | . | . | . | . | 0.13 | . | * | . | −0.60 | 0.36 |
| Cys | 478 | . | A | B | . | . | . | . | 0.46 | . | . | . | −0.26 | 0.35 |
| His | 479 | . | . | . | . | T | T | . | 0.46 | . | . | . | 0.88 | 0.42 |
| Thr | 480 | . | . | . | . | T | T | . | 0.46 | . | * | . | 1.52 | 0.40 |
| Asp | 481 | . | . | . | . | T | T | . | 1.06 | . | . | F | 3.06 | 1.30 |
| Gly | 482 | . | . | . | . | T | T | . | 0.53 | . | . | F | 3.40 | 1.48 |
| Ala | 483 | . | . | . | . | T | . | C | 0.53 | * | . | F | 2.41 | 0.85 |
| Glu | 484 | A | . | . | . | . | . | . | 0.53 | * | . | F | 1.67 | 0.27 |
| Pro | 485 | A | . | . | . | . | . | . | 0.53 | . | . | F | 0.73 | 0.37 |
| Leu | 486 | A | . | . | . | . | . | . | 0.58 | * | . | . | 0.24 | 0.53 |
| Cys | 487 | A | . | . | . | . | . | . | 0.92 | . | . | . | 0.78 | 0.62 |
| His | 488 | . | . | B | . | . | . | . | 1.17 | . | . | F | 0.61 | 0.64 |
| Thr | 489 | . | . | . | . | T | T | . | 0.87 | . | . | F | 1.49 | 0.77 |
| Lys | 490 | . | . | . | . | T | T | . | 0.27 | . | . | F | 2.52 | 1.92 |
| Asn | 491 | . | . | . | . | T | T | . | 0.87 | . | . | F | 2.80 | 1.16 |
| Gly | 492 | . | . | . | . | T | T | . | 1.24 | . | . | F | 2.52 | 1.25 |
| Ser | 493 | . | . | . | . | . | . | C | 0.69 | . | . | F | 1.09 | 0.66 |
| Leu | 494 | . | . | . | . | . | . | C | 1.00 | . | . | . | 0.36 | 0.41 |
| Pro | 495 | . | . | B | . | . | . | . | 0.61 | . | . | . | 0.18 | 0.69 |
| Trp | 496 | . | . | . | . | T | T | . | 0.30 | . | . | . | 0.50 | 0.51 |
| Ala | 497 | . | . | B | . | . | T | . | 0.43 | . | . | . | 0.05 | 0.90 |
| Asp | 498 | . | . | . | . | T | T | . | 0.07 | . | . | F | 1.15 | 0.90 |
| Gly | 499 | . | . | . | . | T | T | . | 0.53 | . | . | F | 1.40 | 0.46 |
| Thr | 500 | . | . | . | . | . | T | C | 0.53 | . | . | F | 2.05 | 0.45 |
| Pro | 501 | . | . | . | . | T | T | . | 0.48 | . | . | F | 2.50 | 0.42 |
| Cys | 502 | . | . | . | . | T | T | . | 1.03 | . | * | F | 1.65 | 0.42 |
| Gly | 503 | . | . | . | . | . | T | C | 0.22 | . | . | F | 1.20 | 0.39 |
| Pro | 504 | . | . | . | . | T | . | . | −0.10 | . | . | F | 0.65 | 0.21 |
| Gly | 505 | . | . | . | . | T | . | . | −0.09 | . | . | . | 0.25 | 0.21 |
| His | 506 | . | . | B | . | . | . | . | 0.12 | . | . | . | −0.40 | 0.28 |
| Leu | 507 | . | . | B | . | . | . | . | 0.44 | . | . | . | 0.50 | 0.32 |
| Cys | 508 | . | . | B | . | . | T | . | 0.49 | . | * | . | 0.91 | 0.32 |
| Ser | 509 | . | . | . | . | T | T | . | 0.03 | . | . | F | 1.67 | 0.31 |
| Glu | 510 | . | . | . | . | T | T | . | −0.43 | . | . | F | 1.28 | 0.20 |
| Gly | 511 | . | . | . | . | T | T | . | −0.61 | * | . | F | 1.49 | 0.31 |
| Ser | 512 | . | . | . | . | T | . | . | 0.20 | * | . | F | 2.10 | 0.36 |
| Cys | 513 | . | A | . | . | . | . | C | 0.87 | . | . | F | 1.79 | 0.36 |
| Leu | 514 | . | A | . | . | . | . | C | 1.17 | . | . | F | 1.58 | 0.63 |
| Pro | 515 | A | A | . | . | . | . | . | 0.31 | . | . | F | 1.17 | 0.81 |
| Glu | 516 | A | A | . | . | . | . | . | 0.66 | * | . | F | 1.11 | 1.13 |
| Glu | 517 | A | A | . | . | . | . | . | 1.07 | * | . | F | 0.90 | 2.37 |
| Glu | 518 | A | A | . | . | . | . | . | 1.52 | . | . | F | 0.90 | 3.00 |
| Val | 519 | A | A | . | . | . | . | . | 2.38 | . | . | F | 0.90 | 2.68 |
| Glu | 520 | A | A | . | . | . | . | . | 2.38 | * | . | F | 0.90 | 3.09 |
| Arg | 521 | A | . | . | . | T | . | . | 1.52 | * | . | F | 1.30 | 2.76 |
| Pro | 522 | A | . | . | . | T | . | . | 0.67 | * | * | F | 1.30 | 2.76 |
| Lys | 523 | A | . | . | . | T | . | . | 0.67 | * | * | F | 1.30 | 1.18 |
| Pro | 524 | . | . | B | . | T | . | . | 1.18 | * | * | F | 1.30 | 1.01 |
| Val | 525 | . | . | B | . | . | . | . | 0.83 | * | . | F | 0.65 | 0.65 |
| Val | 526 | . | . | B | . | . | . | . | 0.43 | . | * | F | 0.65 | 0.32 |
| Asp | 527 | . | . | B | . | T | . | . | 0.06 | * | . | F | −0.05 | 0.22 |
| Gly | 528 | . | . | B | . | T | . | . | −0.20 | . | . | F | −0.05 | 0.30 |
| Gly | 529 | . | . | . | . | T | T | . | −0.28 | . | . | F | 0.65 | 0.62 |
| Trp | 530 | . | . | . | . | T | T | C | 0.23 | . | . | . | 0.00 | 0.39 |
| Ala | 531 | . | . | . | . | . | . | C | 0.88 | . | . | . | −0.20 | 0.39 |
| Pro | 532 | . | . | . | . | T | . | . | 0.59 | . | . | . | 0.00 | 0.61 |

TABLE 2-continued

| Res | Pos. | Garni... Alpha | Chou-... Alpha | Garni... Beta | Chou-... Beta | Garni... Turn | Chou-... Turn | Garni... Coil | Kyte-... Hydro... | Eisen... Alpha | Eisen... Beta | Karpi... Flexi... | James... Antig... | Emini Surfa... |
|---|---|---|---|---|---|---|---|---|---|---|---|---|---|---|
| Trp | 533 | . | . | . | . | T | . | . | 0.59 | . | . | . | 0.00 | 0.61 |
| Gly | 534 | . | . | . | . | . | T | C | 0.93 | . | . | . | 0.00 | 0.59 |
| Pro | 535 | . | . | . | . | T | T | . | 0.56 | . | . | F | 0.35 | 0.66 |
| Trp | 536 | . | . | . | . | T | T | . | 0.84 | * | . | F | 0.66 | 0.34 |
| Gly | 537 | . | . | . | . | . | T | C | 1.17 | * | . | F | 1.07 | 0.46 |
| Glu | 538 | . | . | . | . | T | . | . | 1.14 | * | . | F | 1.98 | 0.58 |
| Cys | 539 | . | . | . | . | T | T | . | 0.82 | * | . | F | 2.49 | 0.80 |
| Ser | 540 | . | . | . | . | T | T | . | 0.69 | * | . | F | 3.10 | 0.43 |
| Arg | 541 | . | . | . | . | T | T | . | 0.63 | * | . | F | 2.79 | 0.25 |
| Thr | 542 | . | . | . | . | T | T | . | 0.63 | * | . | F | 2.18 | 0.46 |
| Cys | 543 | . | . | . | . | T | T | . | −0.22 | * | . | F | 1.87 | 0.34 |
| Gly | 544 | . | . | . | . | T | T | . | 0.44 | * | . | F | 1.56 | 0.13 |
| Gly | 545 | . | . | . | . | T | T | . | 0.04 | * | * | F | 0.65 | 0.15 |
| Gly | 546 | . | . | . | . | T | T | . | −0.37 | * | * | F | 0.35 | 0.25 |
| Val | 547 | . | . | B | B | . | . | . | −0.09 | * | * | . | −0.60 | 0.33 |
| Gln | 548 | . | . | B | B | . | . | . | 0.69 | * | * | . | −0.60 | 0.46 |
| Phe | 549 | . | . | B | B | . | . | . | 1.03 | * | * | . | −0.30 | 0.91 |
| Ser | 550 | . | . | B | B | . | . | . | 0.71 | * | * | . | 0.79 | 2.13 |
| His | 551 | . | . | B | . | . | . | . | 1.10 | * | * | . | 1.18 | 0.66 |
| Arg | 552 | . | . | . | . | T | . | . | 1.96 | * | * | . | 2.37 | 1.52 |
| Glu | 553 | . | . | . | . | T | . | . | 1.74 | * | * | F | 2.86 | 1.89 |
| Cys | 554 | . | . | . | . | T | T | . | 2.44 | * | . | F | 3.40 | 2.15 |
| Lys | 555 | . | . | . | . | T | T | . | 2.53 | * | . | F | 3.06 | 1.90 |
| Asp | 556 | . | . | . | . | . | T | C | 2.57 | * | . | F | 2.52 | 1.70 |
| Pro | 557 | . | . | . | . | . | T | C | 2.46 | * | . | F | 2.52 | 5.49 |
| Glu | 558 | . | . | . | . | . | . | C | 2.11 | . | . | F | 2.32 | 4.41 |
| Pro | 559 | . | . | . | . | T | T | . | 2.43 | . | * | F | 2.72 | 2.62 |
| Gln | 560 | . | . | . | . | T | T | . | 2.50 | . | * | F | 2.76 | 1.67 |
| Asn | 561 | . | . | . | . | T | T | . | 2.26 | * | * | F | 3.40 | 1.89 |
| Gly | 562 | . | . | . | . | T | T | . | 1.80 | * | * | F | 2.76 | 1.92 |
| Gly | 563 | . | . | . | . | T | T | . | 0.99 | * | * | F | 2.27 | 0.59 |
| Arg | 564 | . | . | B | . | . | T | . | 0.86 | * | . | F | 0.93 | 0.30 |
| Tyr | 565 | . | . | B | . | . | T | . | 0.97 | . | . | . | 0.44 | 0.30 |
| Cys | 566 | . | . | B | . | . | T | . | 1.08 | . | . | . | 1.00 | 0.60 |
| Leu | 567 | . | . | B | . | . | . | . | 0.83 | . | * | . | 1.40 | 0.60 |
| Gly | 568 | . | . | B | . | . | . | . | 1.22 | . | * | F | 1.55 | 0.39 |
| Arg | 569 | . | . | B | . | . | . | . | 0.87 | . | * | F | 2.30 | 1.45 |
| Arg | 570 | . | . | . | . | T | . | . | 1.11 | * | * | F | 3.00 | 2.75 |
| Ala | 571 | . | . | . | . | T | . | . | 1.48 | * | * | F | 2.70 | 4.82 |
| Lys | 572 | . | . | . | . | T | . | . | 1.62 | * | * | F | 2.40 | 3.30 |
| Tyr | 573 | . | . | . | . | T | T | . | 1.93 | * | . | F | 1.85 | 0.90 |
| Gln | 574 | . | . | . | . | T | T | . | 1.51 | . | . | F | 1.10 | 1.22 |
| Ser | 575 | . | . | . | . | T | T | . | 1.40 | . | * | . | 0.50 | 0.88 |
| Cys | 576 | . | . | . | . | T | T | . | 1.99 | . | . | . | 0.50 | 0.97 |
| His | 577 | . | A | B | . | . | . | . | 1.28 | . | . | . | 0.60 | 0.97 |
| Thr | 578 | . | A | . | . | T | . | . | 1.31 | . | . | F | 0.85 | 0.39 |
| Glu | 579 | . | A | . | . | T | . | . | 1.10 | . | . | F | 1.00 | 1.12 |
| Glu | 580 | . | A | . | . | T | . | . | 1.40 | . | . | F | 1.64 | 1.27 |
| Cys | 581 | . | A | B | . | . | . | . | 1.72 | . | * | F | 1.58 | 1.47 |
| Pro | 582 | . | . | . | . | . | T | C | 1.80 | . | * | F | 2.37 | 0.84 |
| Pro | 583 | . | . | . | . | T | T | . | 1.81 | * | . | F | 2.91 | 0.97 |
| Asp | 584 | . | . | . | . | T | T | . | 1.11 | * | . | F | 3.40 | 2.43 |
| Gly | 585 | . | . | . | . | T | T | . | 1.22 | * | . | F | 3.06 | 1.36 |
| Lys | 586 | . | A | . | . | T | . | . | 1.89 | * | . | F | 2.32 | 1.72 |
| Ser | 587 | A | A | . | . | . | . | . | 2.10 | . | . | F | 1.58 | 1.79 |
| Phe | 588 | A | A | . | . | . | . | . | 2.31 | . | . | F | 1.24 | 3.13 |
| Arg | 589 | A | A | . | . | . | . | . | 1.64 | . | . | F | 0.90 | 2.71 |
| Glu | 590 | A | A | . | . | . | . | . | 1.99 | . | . | F | 0.60 | 1.08 |
| Gln | 591 | A | A | . | . | . | . | . | 1.99 | . | . | F | 0.90 | 2.17 |
| Gln | 592 | A | A | . | . | . | . | . | 2.04 | . | * | F | 0.90 | 2.21 |
| Cys | 593 | A | A | . | . | . | . | . | 2.74 | . | * | F | 1.15 | 2.00 |
| Glu | 594 | . | A | . | . | T | . | . | 2.04 | . | . | F | 1.50 | 1.86 |
| Lys | 595 | . | A | . | . | T | . | . | 1.80 | . | . | F | 1.75 | 1.08 |
| Tyr | 596 | . | . | . | . | T | . | . | 1.80 | . | . | . | 2.05 | 3.17 |
| Asn | 597 | . | . | . | . | T | T | . | 1.56 | . | . | . | 2.50 | 2.94 |
| Ala | 598 | . | . | . | . | T | T | . | 1.91 | . | . | . | 1.35 | 2.30 |
| Tyr | 599 | . | . | B | . | . | T | . | 1.91 | . | . | . | 0.70 | 2.12 |
| Asn | 600 | . | . | B | . | . | T | . | 1.27 | . | * | . | 0.75 | 2.20 |
| Tyr | 601 | . | . | B | . | . | . | . | 1.51 | . | . | . | 0.25 | 2.16 |
| Thr | 602 | . | . | B | . | . | . | . | 1.17 | . | * | F | 0.70 | 2.30 |
| Asp | 603 | . | . | B | . | . | T | . | 1.76 | . | * | F | 1.75 | 1.42 |
| Met | 604 | . | . | B | . | . | . | . | 1.19 | . | * | F | 2.00 | 1.45 |
| Asp | 605 | . | . | . | . | T | T | . | 0.38 | * | . | F | 2.50 | 0.83 |
| Gly | 606 | . | . | B | . | . | T | . | 0.62 | * | * | F | 1.85 | 0.41 |
| Asn | 607 | . | . | B | B | . | . | . | 0.64 | * | * | F | 0.60 | 0.72 |
| Leu | 608 | A | . | . | B | . | . | . | −0.21 | * | * | . | 0.10 | 0.45 |

TABLE 2-continued

| Res | Pos. | Garni... Alpha | Chou-... Alpha | Garni... Beta | Chou-... Beta | Garni... Turn | Chou-... Turn | Garni... Coil | Kyte-... Hydro... | Eisen... Alpha | Eisen... Beta | Karpi... Flexi... | James... Antig... | Emini Surfa... |
|---|---|---|---|---|---|---|---|---|---|---|---|---|---|---|
| Leu | 609 | . | . | B | B | . | . | . | 0.18 | * | * | . | −0.35 | 0.34 |
| Gln | 610 | . | . | B | B | . | . | . | 0.22 | * | . | . | −0.60 | 0.33 |
| Trp | 611 | . | . | B | B | . | . | . | 0.32 | * | . | . | −0.60 | 0.79 |
| Val | 612 | . | . | B | B | . | . | . | −0.27 | * | . | . | −0.45 | 1.50 |
| Pro | 613 | . | . | B | . | . | T | . | 0.20 | * | . | . | −0.20 | 0.88 |
| Lys | 614 | . | . | B | . | . | T | . | 0.16 | * | * | . | −0.20 | 0.82 |
| Tyr | 615 | . | . | B | . | . | T | . | −0.14 | . | . | . | 0.10 | 0.82 |
| Ala | 616 | . | . | . | . | T | T | . | −0.07 | * | * | . | 0.50 | 0.71 |
| Gly | 617 | . | . | . | . | T | . | . | 0.90 | * | . | . | 0.64 | 0.55 |
| Val | 618 | . | . | B | . | . | . | . | 1.11 | . | * | . | 0.58 | 0.69 |
| Ser | 619 | . | . | B | . | . | T | . | 1.18 | . | * | F | 2.32 | 1.14 |
| Pro | 620 | . | . | B | . | . | T | . | 0.76 | . | * | F | 2.66 | 2.26 |
| Arg | 621 | . | . | . | . | T | T | . | 1.39 | . | * | F | 3.40 | 1.63 |
| Asp | 622 | . | . | . | . | T | T | . | 0.92 | . | * | F | 3.06 | 2.43 |
| Arg | 623 | . | A | . | . | T | . | . | 1.08 | . | * | F | 2.32 | 1.30 |
| Cys | 624 | . | A | B | . | . | . | . | 0.71 | * | * | F | 1.43 | 0.57 |
| Lys | 625 | . | A | B | . | . | . | . | 1.03 | * | * | . | 0.64 | 0.18 |
| Leu | 626 | . | A | B | . | . | . | . | 0.33 | * | * | . | 0.30 | 0.18 |
| Phe | 627 | . | A | B | . | . | . | . | 0.44 | . | * | . | 0.04 | 0.35 |
| Cys | 628 | . | A | B | . | . | . | . | −0.01 | . | * | . | 0.98 | 0.34 |
| Arg | 629 | . | A | B | . | . | . | . | 0.77 | * | * | . | 1.32 | 0.41 |
| Ala | 630 | A | . | . | . | . | T | . | 0.42 | * | * | . | 2.36 | 0.92 |
| Arg | 631 | . | . | . | . | T | T | . | 1.23 | . | * | F | 3.40 | 2.31 |
| Gly | 632 | . | . | . | . | T | T | . | 1.23 | . | * | F | 3.06 | 2.04 |
| Arg | 633 | . | . | . | . | T | T | . | 1.94 | . | * | F | 2.72 | 1.75 |
| Ser | 634 | A | A | . | . | . | . | . | 0.98 | * | * | F | 1.58 | 1.79 |
| Glu | 635 | A | A | . | . | . | . | . | 0.87 | * | * | F | 1.24 | 1.34 |
| Phe | 636 | A | A | . | . | . | . | . | 0.76 | * | * | F | 0.45 | 0.59 |
| Lys | 637 | A | A | . | . | . | . | . | 0.51 | * | * | . | 0.30 | 0.77 |
| Val | 638 | A | A | . | . | . | . | . | 0.44 | * | * | . | 0.30 | 0.45 |
| Phe | 639 | A | A | . | . | . | . | . | −0.11 | . | . | . | 0.45 | 1.03 |
| Glu | 640 | A | A | . | . | . | . | . | −1.00 | * | . | . | 0.30 | 0.38 |
| Ala | 641 | A | . | . | B | . | . | . | −0.30 | * | . | . | −0.30 | 0.36 |
| Lys | 642 | A | . | . | B | . | . | . | −0.69 | . | . | . | 0.30 | 0.70 |
| Val | 643 | A | . | . | B | . | . | . | −0.14 | . | . | . | 0.60 | 0.40 |
| Ile | 644 | A | . | . | B | . | . | . | −0.26 | . | * | F | 0.45 | 0.57 |
| Asp | 645 | . | . | B | B | . | . | . | −0.92 | . | . | F | 0.45 | 0.23 |
| Gly | 646 | . | . | B | B | . | . | . | −0.68 | * | . | F | −0.45 | 0.17 |
| Thr | 647 | . | . | B | B | . | . | . | −0.93 | . | . | F | −0.15 | 0.24 |
| Leu | 648 | . | . | . | B | . | . | C | −0.08 | . | . | F | 0.05 | 0.22 |
| Cys | 649 | . | . | . | B | T | . | . | 0.50 | * | * | . | 0.10 | 0.39 |
| Gly | 650 | . | . | . | . | . | T | C | −0.31 | . | . | F | 0.45 | 0.39 |
| Pro | 651 | . | . | . | . | T | T | . | −0.56 | . | . | F | 0.65 | 0.39 |
| Glu | 652 | A | . | . | . | . | T | . | −1.13 | . | . | F | 0.25 | 0.73 |
| Thr | 653 | A | . | . | . | . | T | . | −0.99 | . | . | F | 0.25 | 0.52 |
| Leu | 654 | A | . | . | B | . | . | . | −1.18 | * | * | . | −0.30 | 0.18 |
| Ala | 655 | . | . | B | B | . | . | . | −0.72 | * | * | . | −0.60 | 0.08 |
| Ile | 656 | . | . | B | B | . | . | . | −0.86 | . | * | . | −0.60 | 0.10 |
| Cys | 657 | . | . | B | B | . | . | . | −0.86 | . | * | . | −0.60 | 0.13 |
| Val | 658 | A | . | . | B | . | . | . | −1.21 | . | * | . | −0.30 | 0.21 |
| Arg | 659 | . | . | B | B | . | . | . | −1.26 | . | * | . | −0.30 | 0.16 |
| Gly | 660 | . | . | . | B | T | T | . | −0.62 | . | * | F | 0.25 | 0.23 |
| Gln | 661 | . | . | B | B | . | . | . | −0.32 | . | * | F | 0.45 | 0.61 |
| Cys | 662 | . | . | B | B | . | . | . | 0.00 | . | * | . | 0.30 | 0.32 |
| Val | 663 | . | . | B | B | . | . | . | 0.19 | . | * | . | 0.30 | 0.32 |
| Lys | 664 | . | . | B | . | . | T | . | 0.08 | . | * | . | 0.10 | 0.10 |
| Ala | 665 | . | . | B | . | . | T | . | 0.39 | * | . | . | 0.70 | 0.30 |
| Gly | 666 | . | . | B | . | . | T | . | −0.47 | * | . | . | 0.70 | 0.56 |
| Cys | 667 | . | . | B | . | . | T | . | −0.66 | * | * | . | 0.70 | 0.21 |
| Asp | 668 | . | . | B | B | . | . | . | 0.20 | * | * | . | −0.30 | 0.15 |
| His | 669 | . | . | B | B | . | . | . | −0.14 | * | . | . | 0.30 | 0.26 |
| Val | 670 | . | . | B | B | . | . | . | 0.23 | * | . | . | 0.30 | 0.64 |
| Val | 671 | . | . | B | B | . | . | . | 0.69 | * | . | . | 0.64 | 0.59 |
| Asp | 672 | . | . | B | B | . | . | . | 1.40 | * | . | F | 1.13 | 0.86 |
| Ser | 673 | . | . | . | B | . | . | . | 0.59 | * | . | F | 2.32 | 2.31 |
| Pro | 674 | A | . | . | . | . | T | . | 0.62 | * | . | F | 2.66 | 2.56 |
| Arg | 675 | . | . | . | . | T | T | . | 1.52 | * | . | F | 3.40 | 2.56 |
| Lys | 676 | . | . | . | . | T | T | . | 1.71 | * | . | F | 3.06 | 3.82 |
| Leu | 677 | . | . | . | . | T | . | . | 1.37 | * | . | F | 2.52 | 1.33 |
| Asp | 678 | . | . | . | . | T | T | . | 0.81 | * | . | F | 2.23 | 0.67 |
| Lys | 679 | . | . | B | . | . | T | . | 0.36 | * | . | F | 1.49 | 0.25 |
| Cys | 680 | . | . | B | . | . | T | . | −0.10 | * | . | . | 0.70 | 0.16 |
| Gly | 681 | . | . | B | . | . | T | . | −0.49 | * | . | . | 0.70 | 0.10 |
| Val | 682 | . | . | B | . | . | . | . | 0.37 | * | . | . | −0.10 | 0.05 |
| Cys | 683 | . | . | B | . | . | T | . | 0.02 | . | . | . | 0.10 | 0.18 |
| Gly | 684 | . | . | . | . | T | T | . | −0.02 | . | . | F | 1.59 | 0.18 |

TABLE 2-continued

| Res | Pos. | Garni... Alpha | Chou-... Alpha | Garni... Beta | Chou-... Beta | Garni... Turn | Chou-... Turn | Garni... Coil | Kyte-... Hydro... | Eisen... Alpha | Eisen... Beta | Karpi... Flexi... | James... Antig... | Emini Surfa... |
|---|---|---|---|---|---|---|---|---|---|---|---|---|---|---|
| Gly | 685 | . | . | . | . | T | T | . | 0.34 | . | . | F | 1.93 | 0.38 |
| Lys | 686 | . | . | . | . | T | T | . | 0.02 | . | . | F | 2.27 | 0.96 |
| Gly | 687 | . | . | . | . | T | . | . | 0.99 | . | . | F | 2.41 | 0.52 |
| Asn | 688 | . | . | . | . | T | T | . | 1.70 | . | . | F | 3.40 | 1.03 |
| Ser | 689 | . | . | B | . | . | T | . | 1.19 | . | . | F | 2.66 | 1.03 |
| Cys | 690 | . | . | B | . | . | T | . | 1.23 | . | . | F | 2.34 | 0.77 |
| Arg | 691 | . | . | B | . | . | T | . | 0.84 | . | . | F | 2.17 | 0.64 |
| Lys | 692 | . | . | B | . | . | . | . | 0.89 | * | . | F | 1.80 | 0.47 |
| Val | 693 | . | . | B | . | . | T | . | 0.08 | * | . | F | 1.98 | 1.18 |
| Ser | 694 | . | . | B | . | . | T | . | 0.07 | * | . | F | 1.70 | 0.50 |
| Gly | 695 | . | . | B | . | . | T | . | 0.52 | * | . | F | 0.93 | 0.36 |
| Ser | 696 | . | . | B | . | . | T | . | 0.10 | * | . | F | 0.46 | 0.75 |
| Leu | 697 | . | . | B | . | . | . | . | 0.06 | . | * | F | 0.39 | 0.81 |
| Thr | 698 | . | . | B | . | . | . | . | 0.67 | . | . | F | 0.37 | 1.31 |
| Pro | 699 | . | . | B | . | . | T | . | 0.62 | . | . | F | 0.10 | 1.53 |
| Thr | 700 | . | . | . | . | T | T | . | 0.72 | . | . | F | 0.50 | 1.84 |
| Asn | 701 | . | . | B | . | . | T | . | 1.02 | . | . | F | 0.10 | 2.00 |
| Tyr | 702 | . | . | . | . | T | T | . | 1.83 | * | . | . | 0.35 | 2.08 |
| Gly | 703 | . | . | . | . | T | T | . | 1.26 | * | . | . | 0.65 | 2.41 |
| Tyr | 704 | . | . | . | . | T | T | . | 0.61 | * | . | . | 0.35 | 1.05 |
| Asn | 705 | . | . | B | . | . | T | . | 0.61 | * | . | . | -0.20 | 0.50 |
| Asp | 706 | . | . | B | . | . | T | . | -0.28 | * | . | . | 0.10 | 0.72 |
| Ile | 707 | . | . | B | B | . | . | . | -0.24 | * | . | . | -0.60 | 0.32 |
| Val | 708 | . | . | B | B | . | . | . | -0.49 | . | . | . | -0.30 | 0.31 |
| Thr | 709 | . | . | B | B | . | . | . | -0.59 | * | . | . | -0.60 | 0.19 |
| Ile | 710 | . | . | B | B | . | . | . | -1.18 | . | . | . | -0.60 | 0.27 |
| Pro | 711 | . | . | B | . | . | T | . | -1.49 | * | . | . | -0.20 | 0.36 |
| Ala | 712 | . | . | B | . | . | T | . | -0.60 | * | . | . | -0.20 | 0.36 |
| Gly | 713 | . | . | . | . | . | T | C | -0.63 | . | * | . | 0.00 | 0.83 |
| Ala | 714 | . | . | . | . | . | T | C | -0.32 | . | * | F | 0.15 | 0.38 |
| Thr | 715 | . | . | B | B | . | . | . | -0.29 | . | * | F | 0.45 | 0.62 |
| Asn | 716 | . | . | B | B | . | . | . | -0.03 | . | * | F | -0.15 | 0.47 |
| Ile | 717 | . | . | B | B | . | . | . | 0.56 | . | * | F | 0.45 | 0.92 |
| Asp | 718 | . | . | B | B | . | . | . | 1.01 | . | * | F | 0.60 | 1.11 |
| Val | 719 | . | . | B | B | . | . | . | 1.30 | . | * | F | 0.90 | 1.35 |
| Lys | 720 | . | . | B | B | . | . | . | 1.58 | . | * | F | 0.90 | 2.58 |
| Gln | 721 | . | . | B | . | . | . | . | 1.37 | . | * | F | 1.10 | 2.10 |
| Arg | 722 | . | . | B | . | . | . | . | 1.91 | . | * | F | 1.10 | 4.38 |
| Ser | 723 | . | . | . | . | . | . | C | 1.06 | * | * | F | 1.30 | 2.17 |
| His | 724 | . | . | . | . | . | T | C | 1.91 | * | * | F | 1.05 | 0.93 |
| Pro | 725 | . | . | . | . | . | T | C | 1.87 | . | * | F | 1.33 | 0.82 |
| Gly | 726 | . | . | . | . | T | T | . | 1.87 | * | * | F | 1.21 | 0.99 |
| Val | 727 | . | . | B | . | . | T | . | 1.41 | * | * | F | 1.84 | 1.21 |
| Gln | 728 | . | . | B | . | . | . | . | 1.71 | . | * | F | 1.77 | 0.77 |
| Asn | 729 | . | . | B | . | T | T | . | 1.50 | * | . | F | 2.80 | 1.26 |
| Asp | 730 | . | . | . | . | T | T | . | 0.90 | * | . | F | 1.92 | 2.66 |
| Gly | 731 | . | . | . | . | T | T | . | 0.66 | . | . | F | 1.64 | 1.27 |
| Asn | 732 | . | . | B | . | . | T | . | 0.70 | . | * | F | 0.81 | 0.80 |
| Tyr | 733 | . | A | B | . | . | . | . | 0.74 | . | . | . | -0.32 | 0.39 |
| Leu | 734 | . | A | B | . | . | . | . | 0.43 | * | . | . | -0.60 | 0.79 |
| Ala | 735 | . | A | B | . | . | . | . | -0.16 | * | . | . | -0.60 | 0.71 |
| Leu | 736 | . | A | B | . | . | . | . | 0.19 | . | . | . | -0.40 | 0.46 |
| Lys | 737 | . | A | B | . | . | . | . | -0.16 | . | . | F | 0.85 | 0.93 |
| Thr | 738 | . | . | B | . | . | T | . | 0.09 | . | . | F | 1.45 | 0.91 |
| Ala | 739 | A | . | . | . | . | T | . | 0.66 | . | . | F | 2.10 | 1.91 |
| Asp | 740 | . | . | B | . | . | T | . | 0.43 | . | . | F | 2.00 | 1.50 |
| Gly | 741 | . | . | B | . | . | T | . | 0.43 | . | * | F | 1.05 | 0.86 |
| Gln | 742 | . | . | B | . | . | . | . | 0.39 | . | * | F | 0.35 | 0.70 |
| Tyr | 743 | . | . | B | . | . | . | . | 0.36 | . | * | . | 0.30 | 0.67 |
| Leu | 744 | . | . | B | . | . | . | . | 0.94 | . | * | . | -0.20 | 0.67 |
| Leu | 745 | . | . | B | . | . | . | . | 0.13 | . | * | . | -0.40 | 0.63 |
| Asn | 746 | . | . | B | . | . | T | . | -0.11 | . | * | F | -0.05 | 0.33 |
| Gly | 747 | . | . | . | . | T | T | . | -1.00 | . | * | F | 0.35 | 0.40 |
| Asn | 748 | . | . | . | . | . | T | C | -1.06 | . | * | . | 0.00 | 0.34 |
| Leu | 749 | . | . | . | . | . | T | C | -0.83 | . | * | . | 0.00 | 0.29 |
| Ala | 750 | A | A | B | . | . | . | . | -0.91 | . | * | . | -0.60 | 0.29 |
| Ile | 751 | . | A | B | . | . | . | . | -0.91 | * | * | . | -0.60 | 0.13 |
| Ser | 752 | . | A | B | . | . | . | . | -0.57 | . | * | . | -0.60 | 0.27 |
| Ala | 753 | A | A | . | . | . | . | . | -0.57 | * | * | . | -0.30 | 0.46 |
| Ile | 754 | A | A | . | . | . | . | . | -0.64 | * | . | . | 0.45 | 1.09 |
| Glu | 755 | A | A | . | . | . | . | . | -0.87 | * | . | F | 0.45 | 0.57 |
| Gln | 756 | A | . | . | . | . | B | . | -0.83 | . | * | F | 0.45 | 0.47 |
| Asp | 757 | A | . | . | . | . | B | . | -0.49 | . | * | . | -0.15 | 0.49 |
| Ile | 758 | A | . | . | . | . | B | . | -0.24 | . | * | . | 0.60 | 0.57 |
| Leu | 759 | A | . | . | . | . | B | . | 0.33 | . | * | . | 0.30 | 0.33 |
| Val | 760 | A | . | . | . | . | B | . | -0.56 | . | * | . | 0.30 | 0.28 |

TABLE 2-continued

| Res | Pos. | Garni... Alpha | Chou-... Alpha | Garni... Beta | Chou-... Beta | Garni... Turn | Chou-... Turn | Garni... Coil | Kyte-... Hydro... | Eisen... Alpha | Eisen... Beta | Karpi... Flexi... | James... Antig... | Emini Surfa... |
|---|---|---|---|---|---|---|---|---|---|---|---|---|---|---|
| Lys | 761 | A | . | . | B | . | . | . | −1.37 | . | * | F | −0.45 | 0.28 |
| Gly | 762 | . | . | B | B | . | . | . | −1.32 | . | * | F | −0.45 | 0.28 |
| Thr | 763 | . | . | B | B | . | . | . | −0.68 | . | * | F | 0.45 | 0.76 |
| Ile | 764 | . | . | B | B | . | . | . | −0.17 | . | . | F | −0.15 | 0.59 |
| Leu | 765 | . | . | B | B | . | . | . | 0.34 | . | * | . | −0.60 | 0.80 |
| Lys | 766 | . | . | B | B | . | . | . | 0.00 | . | * | F | −0.45 | 0.55 |
| Tyr | 767 | . | . | B | . | . | T | . | −0.54 | * | * | F | 0.40 | 1.05 |
| Ser | 768 | . | . | . | . | . | T | C | −0.82 | * | * | F | 0.45 | 0.89 |
| Gly | 769 | . | . | . | . | . | T | C | −0.24 | * | . | F | 0.45 | 0.45 |
| Ser | 770 | . | . | . | . | . | T | C | −0.24 | . | * | F | 0.15 | 0.42 |
| Ile | 771 | . | A | B | . | . | . | . | −0.29 | * | * | . | −0.60 | 0.26 |
| Ala | 772 | . | A | B | . | . | . | . | 0.07 | * | . | . | −0.30 | 0.45 |
| Thr | 773 | . | A | B | . | . | . | . | −0.44 | * | * | . | 0.30 | 0.66 |
| Leu | 774 | . | A | B | . | . | . | . | −0.10 | * | . | . | −0.30 | 0.77 |
| Glu | 775 | A | A | . | . | . | . | . | −0.10 | * | . | . | 0.45 | 1.32 |
| Arg | 776 | . | A | B | . | . | . | . | 0.09 | . | . | F | 0.60 | 1.23 |
| Leu | 777 | . | A | . | . | . | T | . | 0.79 | . | . | F | 1.00 | 1.29 |
| Gln | 778 | . | A | . | . | . | T | . | 0.89 | . | . | F | 1.30 | 1.46 |
| Ser | 779 | . | A | . | . | . | T | . | 0.89 | . | . | F | 1.00 | 1.15 |
| Phe | 780 | . | . | B | . | . | . | . | 0.68 | * | . | F | 0.41 | 1.15 |
| Arg | 781 | . | . | . | . | . | . | C | 0.57 | . | * | F | 0.82 | 1.03 |
| Pro | 782 | . | . | . | . | . | . | C | 1.17 | * | . | F | 1.63 | 1.33 |
| Leu | 783 | . | . | . | . | . | T | C | 0.36 | * | . | F | 2.04 | 2.37 |
| Pro | 784 | . | . | . | . | . | T | C | 0.34 | * | * | F | 2.10 | 1.00 |
| Glu | 785 | . | . | . | . | . | T | C | 0.19 | * | * | F | 1.29 | 0.93 |
| Pro | 786 | . | . | . | . | . | T | . | 0.08 | * | * | F | 0.88 | 0.84 |
| Leu | 787 | . | . | B | B | . | . | . | −0.52 | . | * | F | 0.27 | 0.94 |
| Thr | 788 | . | . | B | B | . | . | . | −0.52 | . | * | . | −0.09 | 0.45 |
| Val | 789 | . | . | B | B | . | . | . | −0.62 | . | . | . | −0.60 | 0.24 |
| Gln | 790 | . | . | B | B | . | . | . | −1.48 | . | . | . | −0.60 | 0.42 |
| Leu | 791 | . | . | B | B | . | . | . | −1.48 | . | . | . | −0.60 | 0.21 |
| Leu | 792 | . | . | B | B | . | . | . | −1.01 | . | * | . | −0.60 | 0.45 |
| Thr | 793 | . | . | B | B | . | . | . | −0.70 | . | * | . | −0.60 | 0.26 |
| Val | 794 | . | . | B | . | . | T | . | −0.70 | * | . | F | 0.25 | 0.54 |
| Pro | 795 | . | . | B | . | . | T | . | −1.40 | * | . | F | 0.25 | 0.48 |
| Gly | 796 | . | . | B | . | . | T | . | −0.80 | * | . | F | −0.05 | 0.29 |
| Glu | 797 | . | . | B | . | . | T | . | −0.20 | . | * | F | 0.25 | 0.60 |
| Val | 798 | . | . | B | . | . | . | . | 0.16 | . | * | F | 0.05 | 0.60 |
| Phe | 799 | . | . | B | . | . | . | . | 0.16 | . | * | F | 1.00 | 1.22 |
| Pro | 800 | . | . | B | . | . | T | . | 0.41 | * | * | F | 1.25 | 0.52 |
| Pro | 801 | . | . | . | . | T | T | . | 0.51 | * | * | F | 2.00 | 1.41 |
| Lys | 802 | . | . | . | . | T | T | . | 0.20 | * | * | F | 1.60 | 2.55 |
| Val | 803 | . | . | B | . | . | T | . | 0.36 | . | * | F | 2.00 | 2.38 |
| Lys | 804 | . | . | B | B | . | . | . | 0.36 | . | * | F | 0.80 | 1.33 |
| Tyr | 805 | . | . | B | B | . | . | . | −0.29 | . | * | . | 0.00 | 0.58 |
| Thr | 806 | . | . | B | B | . | . | . | −0.29 | . | * | . | −0.20 | 0.58 |
| Phe | 807 | . | . | B | B | . | . | . | −0.33 | . | * | . | −0.40 | 0.45 |
| Phe | 808 | . | . | B | B | . | . | . | 0.52 | * | * | . | −0.60 | 0.46 |
| Val | 809 | . | . | B | . | . | T | . | −0.38 | * | * | . | −0.20 | 0.53 |
| Pro | 810 | . | . | B | . | . | T | . | −0.13 | . | * | F | −0.05 | 0.45 |
| Asn | 811 | . | . | . | . | T | T | . | −0.52 | . | * | F | 1.25 | 0.88 |
| Asp | 812 | . | . | . | . | T | T | . | −0.12 | . | * | F | 1.40 | 1.02 |
| Val | 813 | A | . | . | . | . | . | . | −0.02 | * | * | F | 0.65 | 0.89 |
| Asp | 814 | A | . | . | . | . | . | . | 0.83 | * | * | . | 0.50 | 0.54 |
| Phe | 815 | A | . | . | . | . | . | . | 0.74 | . | * | . | 0.80 | 0.57 |
| Ser | 816 | A | . | . | . | . | . | . | 0.44 | . | * | . | 0.65 | 1.02 |
| Met | 817 | A | . | . | . | . | . | . | 0.49 | . | * | . | 1.40 | 0.82 |
| Gln | 818 | A | . | . | . | . | T | . | 1.34 | . | * | F | 2.20 | 1.89 |
| Ser | 819 | . | . | . | . | . | T | C | 1.46 | . | * | F | 3.00 | 2.44 |
| Ser | 820 | . | . | . | . | . | T | C | 1.57 | . | * | F | 2.70 | 4.84 |
| Lys | 821 | A | . | . | . | . | T | . | 1.56 | . | * | F | 2.20 | 2.82 |
| Glu | 822 | A | . | . | . | . | . | . | 1.84 | . | * | F | 1.70 | 3.04 |
| Arg | 823 | A | . | . | B | . | . | . | 1.84 | * | * | F | 1.20 | 3.27 |
| Ala | 824 | A | . | . | . | . | . | . | 1.26 | * | * | F | 0.90 | 2.63 |
| Thr | 825 | . | . | B | B | . | . | . | 0.67 | * | * | F | 0.60 | 1.06 |
| Thr | 826 | . | . | B | B | . | . | . | 0.62 | * | * | F | −0.15 | 0.38 |
| Asn | 827 | . | . | B | B | . | . | . | 0.41 | * | * | . | −0.60 | 0.65 |
| Ile | 828 | . | . | B | B | . | . | . | −0.51 | * | . | . | −0.60 | 0.70 |
| Ile | 829 | . | . | B | B | . | . | . | −0.73 | * | . | . | −0.60 | 0.40 |
| Gln | 830 | . | A | B | . | . | . | . | −0.46 | * | . | . | −0.60 | 0.21 |
| Pro | 831 | . | A | B | . | . | . | . | −0.73 | * | . | . | −0.60 | 0.40 |
| Leu | 832 | . | A | B | . | . | . | . | −0.73 | * | * | . | −0.60 | 0.57 |
| Leu | 833 | . | A | B | . | . | . | . | −0.13 | . | . | . | −0.60 | 0.57 |
| His | 834 | . | A | B | . | . | . | . | −0.10 | . | * | . | −0.60 | 0.39 |
| Ala | 835 | . | A | B | B | . | . | . | −0.91 | . | * | . | −0.60 | 0.35 |
| Gln | 836 | . | A | B | B | . | . | . | −1.04 | . | . | . | −0.60 | 0.35 |

TABLE 2-continued

| Res | Pos. | Garni... Alpha | Chou-... Alpha | Garni... Beta | Chou-... Beta | Garni... Turn | Chou-... Turn | Garni... Coil | Kyte-... Hydro... | Eisen... Alpha | Eisen... Beta | Karpi... Flexi... | James... Antig... | Emini Surfa... |
|---|---|---|---|---|---|---|---|---|---|---|---|---|---|---|
| Trp | 837 | . | A | B | B | . | . | . | −0.23 | . | . | . | −0.60 | 0.26 |
| Val | 838 | . | A | B | B | . | . | . | 0.29 | . | * | . | −0.60 | 0.42 |
| Leu | 839 | . | . | B | . | . | T | . | 0.02 | * | . | . | −0.20 | 0.26 |
| Gly | 840 | . | . | . | . | T | T | . | 0.61 | * | . | . | 0.45 | 0.33 |
| Asp | 841 | . | . | . | . | T | T | . | −0.06 | . | . | F | 1.15 | 0.76 |
| Trp | 842 | . | . | . | . | T | T | . | −0.07 | . | . | F | 2.00 | 0.50 |
| Ser | 843 | . | . | . | . | . | T | C | 0.49 | * | . | F | 2.05 | 0.67 |
| Glu | 844 | . | . | . | . | T | T | . | 0.99 | . | . | F | 2.50 | 0.54 |
| Cys | 845 | . | . | . | . | T | T | . | 0.67 | . | . | F | 1.65 | 0.74 |
| Ser | 846 | . | . | . | . | T | T | . | 0.32 | . | . | F | 2.00 | 0.30 |
| Ser | 847 | . | . | . | . | T | . | . | 0.02 | . | . | F | 1.55 | 0.17 |
| Thr | 848 | . | . | . | . | T | . | . | −0.02 | . | . | F | 0.70 | 0.32 |
| Cys | 849 | . | . | . | . | T | . | . | −0.31 | . | . | F | 0.45 | 0.24 |
| Gly | 850 | . | . | . | . | T | T | . | 0.36 | * | . | . | 0.20 | 0.18 |
| Ala | 851 | . | . | . | . | T | T | . | 0.77 | . | . | . | 0.20 | 0.22 |
| Gly | 852 | . | . | . | . | T | T | . | 1.18 | . | . | . | 0.50 | 0.81 |
| Trp | 853 | . | . | . | . | T | T | . | 1.18 | * | . | . | 1.25 | 1.60 |
| Gln | 854 | . | . | B | B | . | . | . | 0.99 | * | . | F | 0.60 | 2.29 |
| Arg | 855 | . | . | B | B | . | . | . | 1.33 | * | . | F | 0.60 | 1.72 |
| Arg | 856 | . | . | B | B | . | . | . | 1.26 | . | * | F | 0.90 | 2.83 |
| Thr | 857 | . | . | B | B | . | . | . | 1.71 | . | . | F | 1.05 | 0.87 |
| Val | 858 | . | . | B | B | . | . | . | 2.00 | . | . | . | 1.20 | 0.87 |
| Glu | 859 | . | . | B | B | . | . | . | 1.79 | . | . | . | 1.50 | 0.75 |
| Cys | 860 | . | . | . | . | T | . | . | 1.38 | . | * | . | 2.40 | 0.80 |
| Arg | 861 | . | . | . | . | T | . | . | 0.92 | . | . | F | 3.00 | 1.44 |
| Asp | 862 | . | . | . | . | . | T | C | 1.23 | . | * | F | 2.55 | 0.82 |
| Pro | 863 | . | . | . | . | T | T | . | 1.50 | . | * | F | 2.60 | 2.66 |
| Ser | 864 | . | . | . | . | T | T | . | 1.20 | . | * | F | 2.30 | 1.37 |
| Gly | 865 | . | . | . | . | T | T | . | 1.28 | . | . | F | 1.70 | 1.10 |
| Gln | 866 | A | . | . | . | . | . | . | 0.86 | . | * | F | 0.05 | 0.72 |
| Ala | 867 | . | . | B | . | . | . | . | 0.19 | . | * | F | 0.05 | 0.78 |
| Ser | 868 | . | . | B | . | . | . | . | 0.40 | . | * | . | −0.10 | 0.42 |
| Ala | 869 | A | . | . | . | . | . | . | 0.74 | . | * | . | −0.10 | 0.39 |
| Thr | 870 | A | . | . | . | . | T | . | 0.50 | * | . | . | 0.70 | 0.77 |
| Cys | 871 | A | . | . | . | . | T | . | −0.31 | * | . | . | 0.70 | 0.58 |
| Asn | 872 | A | . | . | . | . | T | . | 0.32 | * | . | . | 0.10 | 0.48 |
| Lys | 873 | A | . | . | . | . | T | . | 0.41 | . | . | F | 0.85 | 0.66 |
| Ala | 874 | A | . | . | . | . | . | . | 1.00 | * | . | F | 0.80 | 1.90 |
| Leu | 875 | A | . | . | . | . | . | . | 1.31 | * | . | F | 1.10 | 2.05 |
| Lys | 876 | A | . | . | . | . | T | . | 1.39 | . | . | F | 1.30 | 1.71 |
| Pro | 877 | A | . | . | . | . | T | . | 1.43 | . | . | F | 1.30 | 1.71 |
| Glu | 878 | A | . | . | . | . | T | . | 1.18 | . | . | F | 1.30 | 4.14 |
| Asp | 879 | A | . | . | . | . | T | . | 1.10 | . | . | F | 1.30 | 3.20 |
| Ala | 880 | A | . | . | . | . | . | . | 1.91 | . | . | F | 1.10 | 1.11 |
| Lys | 881 | A | . | . | . | . | T | . | 1.57 | . | . | F | 1.30 | 1.11 |
| Pro | 882 | A | . | . | . | . | T | . | 1.78 | * | . | F | 1.15 | 0.89 |
| Cys | 883 | A | . | . | . | . | T | . | 0.97 | * | . | F | 1.30 | 1.53 |
| Glu | 884 | A | . | . | . | . | T | . | 0.30 | . | . | F | 1.15 | 0.63 |
| Ser | 885 | A | A | . | . | . | . | . | 0.68 | * | . | F | −0.15 | 0.22 |
| Gln | 886 | . | A | B | . | . | . | . | −0.18 | * | . | F | −0.15 | 0.63 |
| Leu | 887 | . | A | B | . | . | . | . | −0.36 | . | . | . | −0.30 | 0.30 |
| Cys | 888 | . | A | B | . | . | . | . | −0.08 | . | . | . | −0.60 | 0.29 |
| Pro | 889 | . | A | B | . | . | . | . | −0.47 | . | . | . | −0.60 | 0.21 |
| Leu | 890 | . | . | B | . | . | . | . | −0.56 | . | . | . | −0.40 | 0.33 |

DETAILED DESCRIPTION OF THE PREFERRED EMBODIMENTS

By screening cDNA libraries with cDNA encoding the anti-angiogenic domain of TSP-1, the present inventors have identified two novel proteins, METH1 and METH2 (also called VEGA-1 and VEGA-2, respectively, for vascular endothelial growth antagonist) which contain the anti-angiogenic domain of TSP-1, a metalloproteinase domain, and a disintegrin-like domain. The present inventors have demonstrated that both METH1 and METH2 have anti-angiogenic activity.

Thus, the present invention provides isolated nucleic acid molecules comprising a polynucleotide encoding a METH1 polypeptide having the amino acid sequence shown in SEQ ID NO:2, which was determined by sequencing a cloned cDNA. The METH1 protein of the present invention shares sequence homology with thrombospondin-1 and pNPI. The nucleotide sequence shown in SEQ ID NO:1 was obtained by sequencing a cDNA clone, which was deposited on Jan. 15, 1998 at the American Type Culture Collection, 10801 University Boulevard, Manassas, Va. 20110-2209, and given accession number 209581. The cDNA clone contained in ATCC Deposit No. 209581 contains a METH1 sequence, encoding amino acids 1 to 950 of SEQ ID NO:2.

The present invention also provides isolated nucleic acid molecules comprising a polynucleotide encoding a METH2 polypeptide having the amino acid sequence shown in SEQ ID NO:4, which was partially determined by sequencing a cloned cDNA. The METH2 protein of the present invention shares sequence homology with thrombospondin-1 and pNPI. The nucleotide sequence shown in SEQ ID NO:3 was partially obtained by sequencing a cDNA clone, which was deposited on Jan. 15, 1998 at the American Type Culture Collection, 10801 University Boulevard, Manassas, Va. 20110-2209, and given accession number 209582. The cDNA clone contained in ATCC Deposit No. 209582 contains a partial METH2 sequence, encoding amino acids 112–890 of SEQ ID NO:4.

Nucleic Acid Molecules

Some of the nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in SEQ ID NO: 1 or SEQ ID NO:3, a nucleic acid molecule of the present invention encoding a METH1 or METH2 polypeptide may be obtained using standard cloning and screening procedures, such as those for cloning cDNAs using mRNA as starting material. Illustrative of the invention, the nucleic acid molecule described in SEQ ID NO:1 was discovered in a cDNA library derived from human heart and the nucleic acid molecule described in SEQ ID NO:3 was discovered in a cDNA library derived from human lung. The determined nucleotide sequence of the METH1 cDNA of SEQ ID NO:1 contains an open reading frame encoding a protein of about 950 amino acid residues, including a predicted leader sequence of about 28 amino acid residues. The present inventors have determined that the nucleotide sequence of the METH2 cDNA of SEQ ID NO:3 contains an open reading frame encoding a protein of about 890 amino acid residues, including a predicted leader sequence of about 23 amino acid residues.

The present invention also provides the mature form(s) of the METH1 and METH2 proteins of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature METH1 polypeptide having the amino acid sequence encoded by the cDNA clone contained in the host identified as ATCC Deposit No. 209581 and as shown in SEQ ID NO:2. The present invention also provides a nucleotide sequence encoding the mature METH2 polypeptide having the amino acid sequence as shown in SEQ ID NO:4. By the mature METH1 protein having the amino acid sequence encoded by the cDNA clone contained in the host identified as ATCC Deposit No. 209581 is meant the mature form(s) of the METH1 protein produced by expression in a mammalian cell (e.g., COS cells, as described below) of the complete open reading frame encoded by the human DNA sequence of the clone contained in the vector in the deposited host. As indicated below, the mature METH1 having the amino acid sequence encoded by the cDNA clone contained in ATCC Deposit No. 209581 may or may not differ from the predicted "mature" METH1 protein shown in SEQ ID NO:2 (amino acids from about 29 to about 950) depending on the accuracy of the predicted cleavage site based on computer analysis; and the mature METH2 may or may not differ from the predicted "mature" METH2 protein shown in SEQ ID NO:4 (amino acids from about 24 to about 890) depending on the accuracy of the predicted cleavage site based on computer analysis. Additionally, the mature form of the protein may then undergo even more processing after the prodomain has been cleaved (e.g., a second cleavage distal to the prodomain, located in the metalloprotease domain/cysteine-rich region). Thus, "mature" forms of the proteins encompass not only those forms produced by cleavage of the prodomain, but also other processed forms of the protein.

Methods for predicting whether a protein has a secretory leader as well as the cleavage point for that leader sequence are available. For instance, the methods of McGeoch (*Virus Res*. 3:271–286 (1985)) and von Heinje (*Nucleic Acids Res*. 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete METH1 and METH2 polypeptides of the present invention were analyzed by a computer program ("PSORT") (K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage site between amino acids 28 and 29 in SEQ ID NO:2 and amino acids 23 and 24 in SEQ ID NO:4. Thereafter, the complete amino acid sequences were further analyzed by visual inspection, applying a simple form of the (−1,−3) rule of von Heinje. von Heinje, supra. Thus, the leader sequence for the METH1 protein is predicted to consist of amino acid residues from about 1 to about 28 in SEQ ID NO:2, while the mature METH1 protein is predicted to consist of residues from about 29 to about 950; and the leader sequence for the METH2 protein is predicted to consist of amino acid residues from about 1 to about 23 in SEQ ID NO:4, while the mature METH2 protein is predicted to consist of residues from about 24 to about 890. An alternative predicted mature METH1 protein consists of residues 30 to 950 in SEQ ID NO:2. Another alternative predicted mature METH1 protein consists of residues 35 to 950 of SEQ ID NO:2. An alternative predicted mature METH2 protein consists of residues 31 to 890 of SEQ ID NO:4.

As one of ordinary skill would appreciate, due to the possibilities of sequencing errors, as well as the variability of cleavage sites for leaders in different known proteins, the predicted METH1 polypeptide encoded by the deposited cDNA comprises about 950 amino acids, but may be anywhere in the range of 910–990 amino acids; and the predicted leader sequence of this protein is about 28 amino acids, but may be anywhere in the range of about 18 to about 38 amino acids. An alternative predicted METH1 polypeptide is shown in SEQ ID NO:126, encoded by SEQ ID NO:125, and comprises an additional 18 amino acid residues on the N-terminus. Also, the predicted METH2 polypeptide comprises about 890 amino acids, but may be anywhere in the range of 850 to about 930 amino acids; and the predicted leader sequence of this protein is about 23 amino acids, but may be anywhere in the range of about 13 to about 33 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in SEQ ID NO:1; DNA molecules comprising the coding sequence for the mature METH1 protein; and DNA molecules which comprise a sequence substantially different from those described above but which, due to the degeneracy of the genetic code, still encode the METH1 protein. Also included are DNA molecules comprising an open reading frame (ORF) shown in SEQ ID NO:3; DNA molecules comprising the coding sequence for the mature METH2 protein; and DNA molecules which comprise a sequence substantially different from those described above but which, due to the degeneracy of the genetic code, still encode the METH2 protein. Of course, the genetic code is well known in the art. Thus, it would be routine for one skilled in the art to generate such degenerate variants.

Polynucleotides of the present invention encompass not only polynucleotides encoding the full length sequence, but polynucleotides encoding the mature, proprotein, processed forms of the protein, deletion mutants, substitution variants, allelic variants, analogs, derivatives, etc.

In another aspect, the invention provides isolated nucleic acid molecules encoding the METH1 or METH2 polypeptides having an amino acid sequence as encoded by the cDNA clones contained in the plasmids deposited as ATCC Deposit No. 209581 on Jan. 15, 1998 or ATCC Deposit No. 209582 on Jan. 15, 1998, respectively. In a further embodiment, nucleic acid molecules are provided encoding the mature METH1 or METH2 polypeptide or the full-length METH1 or METH2 polypeptide lacking the N-terminal methionine. The invention also provides an isolated nucleic acid molecule having the nucleotide sequence shown in SEQ ID NO:1 or SEQ ID NO:3 or the nucleotide sequence of the METH1 or METH2 cDNA contained in the above-described deposited clones, or a nucleic acid molecule having a sequence complementary to one of the above sequences. Such isolated molecules, particularly DNA molecules, are useful as probes for gene mapping, by in situ hybridization with chromosomes, and for detecting expression of the METH1 or METH2 gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in SEQ ID NO:1 or SEQ ID NO:3 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 100, 150, 200, 250, 300, 350, 400, 450, 500, 550, 600, 650, 700, 750, 800, 850, 900, 950, 1000, 1050, 1100, 1200, 1300, 1400, 1500, 1600, 1700, 1800, 1900, 2000, 2100, 2200, 2300, 2400, 2500, 2600, 2700, 2800, 2900, or 3000 nt in length are also useful according to the present invention as are fragments corresponding to most, if not all, of the nucleotide sequence of the deposited cDNA or as shown in SEQ ID NO:1 or SEQ ID NO:3. By a fragment at least 20 nt in length, for example, is intended fragments which include 20 or more contiguous bases from the nucleotide sequence of the deposited cDNA or the nucleotide sequence as shown in SEQ ID NO:1 or SEQ ID NO:3.

Preferred nucleic acid fragments of the present invention include nucleic acid molecules encoding epitope-bearing portions of the METH1 or METH2 protein. Methods for determining epitope-bearing portions of the METH1 and METH2 proteins are described in detail below.

Other preferred nucleic acid fragments of the present invention include nucleic acid molecules encoding: the metalloprotease domain of METH1, amino acids 235 to 459 in SEQ ID NO:2; the disintegrin domain of METH1, amino acids 460 to 544 in SEQ ID NO:2; the first TSP-like domain of METH1, amino acids 545 to 598 in SEQ ID NO:2; the second TSP-like domain of METH1, amino acids 841 to 894 in SEQ ID NO:2; the third TSP-like domain of METH1, amino acids 895 to 934 in SEQ ID NO:2; amino acids 536 to 613 in SEQ ID NO:2; amino acids 549 to 563 in SEQ ID NO:2; the metalloprotease domain of METH2, amino acids 214 to 439 in SEQ ID NO:4; the disintegrin domain of METH2, amino acids 440 to 529 in SEQ ID NO:4; the first TSP-like domain of METH2, amino acids 530 to 583 in SEQ ID NO:4; the second TSP-like domain of METH2, amino acids 837 to 890 in SEQ ID NO:4; amino acids 280 to 606 in SEQ ID NO:4; and amino acids 529 to 548 in SEQ ID NO:4; and nucleic acid molecules encoding combinations of these domains.

Thus, preferred embodiments include a nucleic acid molecule encoding a METH1 or METH2 protein lacking the signal sequence (cleavage occurs for METH1 somewhere about 1–24 to about 1–34 and about 1–23 to about 1–30 for METH2); a METH1 or METH2 protein lacking the signal sequence and the prodomain (cleavage for the prodomain can occur in METH1 between amino acids about 232 to 236 and in METH2 between amino acids about 211 to 215); a METH1 or METH2 protein lacking the signal sequence, the prodomain, and the metalloprotease domain; a METH1 or METH2 protein lacking the signal sequence, the prodomain, the metalloprotease domain, and the cysteine rich domain; a METH1 or METH2 protein lacking the signal sequence, the prodomain, the metalloprotease domain, cysteine rich domain and TSP1; a METH1 or METH2 protein lacking the signal sequence, the prodomain, the metalloprotease domain, cysteine rich domain, TSP1 and TSP2. Also preferred are polypeptides encoded by such nucleic acids.

Similarly, preferred embodiments include a nucleic acid encoding a METH1 protein lacking TSP3; a METH1 protein lacking TSP2 and TSP3; a METH1 protein lacking TSP3, TSP2, and TSP1; a METH1 protein lacking the cysteine-rich domain, TSP1, TSP2, and TSP3; a METH1 protein lacking the metalloprotease domain, the cysteine-rich domain, TSP1, TSP2 and TSP3; and a METH1 protein lacking the prodomain, the metalloprotease domain, the cysteine-rich domain, TSP1, TSP2, and TSP3; a METH2 protein lacking TSP2; a METH2 protein lacking TSP1 and TSP2; a METH2 protein lacking the cysteine-rich domain, TSP1 and TSP2; a METH2 protein lacking the metalloprotease domain, the cysteine-rich domain, TSP1 and TSP2; and a METH2 protein lacking the prodomain, the metalloprotease domain, the cysteine-rich domain, TSP1 and TSP2. Also preferred are polypeptide encoded by such nucleic acids.

Also preferred are nucleic acids encoding any combination of METH1 domains. For example, nucleic acid molecule encoding polypeptides comprising the following domains of METH1 are preferred: signal sequence and prodomain; signal sequence, prodomain and metalloprotease domain; signal sequence and metalloprotease domain; signal sequence, prodomain, metalloprotease domain, and cysteine rich domain; signal sequence and cysteine rich domain; signal sequence, metalloprotease domain and cysteine rich domain; signal sequence, prodomain, and cysteine rich domain; signal sequence, prodomain, metalloprotease domain, cysteine rich domain, and TSP1; signal sequence and TSP1; signal sequence, prodomain and TSP1; signal sequence, prodomain, metalloprotease domain and TSP1; signal sequence, metalloprotease domain, and TSP1; signal sequence, prodomain, cysteine rich domain and TSP1; signal sequence, cysteine rich domain and TSP1; signal sequence, metalloprotease domain, cysteine rich domain and TSP1; signal sequence, prodomain, metalloprotease domain, cysteine rich domain, TSP1 and TSP2; signal sequence and TSP2; signal sequence, prodomain and TSP2; signal sequence, metalloprotease domain and TSP2; signal sequence, cysteine rich domain and TSP2; signal sequence, TSP1 and TSP2; signal sequence, prodomain, metalloprotease domain and TSP2; signal sequence, prodomain, cysteine rich domain and TSP2; signal sequence, prodomain, TSP1 and TSP2; signal sequence, metalloprotease domain, cysteine rich domain and TSP2; signal sequence, metalloprotease domain, TSP1 and TSP2; signal sequence, metalloprotease domain, cysteine rich domain, TSP1 and TSP2; signal sequence, prodomain, cysteine rich domain, TSP1 and TSP2; signal sequence and TSP3; signal sequence, prodomain and TSP3; signal sequence, prodomain, metalloprotease domain and TSP3; signal sequence, metalloprotease domain and TSP3; signal sequence, prodomain, metalloprotease domain, cysteine rich domain and TSP3; signal sequence, cysteine rich domain and TSP3; signal sequence, prodomain, cysteine rich domain and TSP3; signal sequence, prodomain, metalloprotease domain, cysteine rich domain, TSP1 and TSP3; signal sequence, TSP1 and TSP3; signal sequence, prodomain, TSP1 and TSP3; signal sequence, prodomain, metalloprotease domain, TSP1 and TSP3; signal sequence, prodomain, cysteine rich domain, TSP1 and TSP3; signal sequence, TSP2 and TSP3; signal sequence, prodomain, cysteine rich domain, TSP1, TSP2 and TSP3; signal sequence, prodomain, metalloprotease domain, TSP1, TSP2 and TSP3; signal sequence, metalloprotease domain, TSP1, TSP2 and TSP3; signal sequence, TSP1, TSP2 and TSP3; signal sequence, metalloprotease domain, cysteine rich domain, TSP1, TSP2 and TSP3; signal sequence, prodomain, metalloprotease domain, TSP1 and TSP2; signal sequence, prodomain, metalloprotease domain, cysteine rich domain, and TSP2; signal sequence, prodomain, metalloprotease domain, cysteine rich domain, TSP2 and TSP3; signal sequence, TSP1, TSP2 and TSP3; signal sequence, cysteine rich domain, TSP1 and TSP2; signal sequence, cysteine rich domain, TSP1 and TSP3; signal sequence, cysteine rich domain, TSP2 and TSP3; signal sequence, cysteine rich domain, TSP1, TSP2, and TSP3; signal sequence, metalloprotease domain, cysteine rich domain, and TSP3; signal sequence, metalloprotease domain, cysteine rich domain, TSP1 and TSP3; signal sequence, metalloprotease domain, cysteine rich domain, TSP2 and TSP3; signal sequence, metalloprotease domain, TSP1 and TSP3; signal sequence, metalloprotease domain, TSP2 and TSP3; signal sequence, prodomain, metalloprotease domain, TSP1 and TSP3; signal sequence, prodomain, metalloprotease domain, TSP2 and TSP3; prodomain and metalloprotease domain; prodomain and cysteine rich domain; prodomain and TSP1; prodomain and TSP2; prodomain and TSP3; prodomain, metalloprotease domain and cysteine rich domain; prodomain, metalloprotease domain and TSP1; prodomain, metalloprotease domain and TSP2; prodomain, metalloprotease domain and TSP3; prodomain, metalloprotease domain, cysteine rich domain and TSP1; prodomain, metalloprotease domain, cysteine rich domain and TSP2; prodomain, metalloprotease domain, cysteine rich domain and TSP3; prodomain, cysteine rich domain and TSP1; prodomain, cysteine rich domain and TSP2; prodomain, cysteine rich domain and TSP3; prodomain, metalloprotease domain, cysteine rich domain, TSP1 and TSP2; prodomain, metalloprotease domain, cysteine rich domain, TSP1, TSP2 and TSP3; prodomain, cysteine rich domain, TSP1 and TSP2; prodomain, metalloprotease domain, TSP1 and TSP2; prodomain, metalloprotease domain, cysteine rich domain, TSP2 and TSP3; prodomain, cysteine rich domain, TSP1 and TSP3; prodomain, cysteine rich domain, TSP2 and TSP3; prodomain, TSP1 and TSP2; prodomain, TSP1 and TSP3; prodomain, TSP2 and TSP3; prodomain, metalloprotease domain, TSP1 and TSP2; prodomain, metalloprotease domain, TSP1 and TSP3; prodomain, metalloprotease domain, TSP2 and TSP3; prodomain, metalloprotease domain, cysteine rich domain, TSP2 and TSP3; prodomain, TSP1 and TSP2; prodomain, TSP1 and TSP3; prodomain, TSP2 and TSP3; prodomain, metalloprotease domain, TSP1 and TSP2; prodomain, metalloprotease domain, TSP1 and TSP3; prodomain, metalloprotease domain, TSP2 and TSP3; prodomain, metalloprotease domain, cysteine domain, TSP1 and TSP3; prodomain, cysteine rich domain, TSP1, TSP2 and TSP3; prodomain, metalloprotease domain, TSP1, TSP2, and TSP3; metalloprotease domain and cysteine rich domain; metalloprotease domain and TSP1; metalloprotease domain and TSP2; metalloprotease domain and TSP3; metalloprotease domain, cysteine rich domain and TSP1; metalloprotease domain, cysteine rich domain and TSP2; metalloprotease domain, cysteine rich domain and TSP3; metalloprotease domain, cysteine rich domain, TSP1 and TSP2; metalloprotease domain, cysteine rich domain, TSP1, TSP2 and TSP3; metalloprotease domain, cysteine rich domain, TSP1 and TSP3; metalloprotease domain, cysteine rich domain, TSP2 and TSP3; metalloprotease domain, TSP1 and TSP2; metalloprotease domain, TSP1 and TSP3; metalloprotease domain, TSP2 and TSP3; metalloprotease domain, TSP1, TSP2 and TSP3; cysteine rich domain and TSP1; cysteine rich domain and TSP2; cysteine rich domain and TSP3; cysteine rich domain, TSP1 and TSP2; cysteine rich domain, TSP1 and TSP3; cysteine rich domain, TSP2 and TSP3; cysteine rich domain, TSP1, TSP2 and TSP3; TSP1 and TSP2; TSP1 and TSP3; TSP2 and TSP3; and/or TSP1, TSP2 and TSP3. These domains may be present in the METH1 molecule in the same order or a different order than in the naturally occurring molecule. Also preferred are polypeptides encoded by such nucleic acids.

Also preferred are nucleic acids encoding any combination of METH2 domains. For example, nucleic acid molecule encoding polypeptides comprising the following domains of METH2 are preferred: signal sequence and prodomain; signal sequence, prodomain and metalloprotease domain; signal sequence and metalloprotease domain; signal sequence, prodomain, metalloprotease domain, and cysteine rich domain; signal sequence and cysteine rich domain; signal sequence, metalloprotease domain and cysteine rich domain; signal sequence, prodomain, and cysteine rich domain; signal sequence, prodomain, metalloprotease domain, cysteine rich domain, and TSP1; signal sequence and TSP1; signal sequence, prodomain and TSP1; signal sequence, prodomain, metalloprotease domain and TSP1; signal sequence, metalloprotease domain, and TSP1; signal sequence, prodomain, cysteine rich domain and TSP1; signal sequence, cysteine rich domain and TSP1; signal sequence, metalloprotease domain, cysteine rich domain and TSP1; signal sequence, prodomain, metalloprotease domain, cysteine rich domain, TSP1 and TSP2; signal sequence and TSP2; signal sequence, prodomain and TSP2; signal sequence, metalloprotease domain and TSP2; signal sequence, cysteine rich domain and TSP2; signal sequence, TSP1 and TSP2; signal sequence, prodomain, metalloprotease domain and TSP2; signal sequence, prodomain, cysteine rich domain and TSP2; signal sequence, prodomain, TSP1 and TSP2; signal sequence, metalloprotease domain, cysteine rich domain and TSP2; signal sequence, metalloprotease domain, TSP1 and TSP2; signal sequence, metalloprotease domain, cysteine rich domain, TSP1 and TSP2; signal sequence, prodomain, cysteine rich domain, TSP1 and TSP2; signal sequence, prodomain, metalloprotease domain, TSP1 and TSP2; signal sequence, metalloprotease domain, cysteine rich domain, and TSP2; signal sequence, cysteine rich domain, TSP1 and TSP2; prodomain and metalloprotease domain; prodomain and cysteine rich domain; prodomain and TSP1; prodomain and TSP2; prodomain, metalloprotease domain and cysteine rich domain; prodomain, metalloprotease domain and TSP1; prodomain, metalloprotease domain and TSP2; prodomain, metalloprotease domain, cysteine rich domain and TSP1; prodomain, metalloprotease domain, cysteine rich domain and TSP2; prodomain, cysteine rich domain and TSP1; prodomain, cysteine rich domain and TSP2; prodomain, metalloprotease domain, cysteine rich domain, TSP1 and TSP2; prodomain, cysteine rich domain, TSP1 and TSP2; prodomain, metalloprotease domain, TSP1 and TSP2; prodomain, TSP1 and TSP2; prodomain, metalloprotease domain, TSP1 and TSP2; metalloprotease domain and cysteine rich domain; metalloprotease domain and TSP1; metalloprotease domain and TSP2; metalloprotease domain, cysteine rich domain and TSP1; metalloprotease domain, cysteine rich domain and TSP2; metalloprotease domain, cysteine rich domain, TSP1 and TSP2; metalloprotease domain, TSP1 and TSP2; cysteine rich domain and TSP1; cysteine rich domain and TSP2; cysteine rich domain, TSP1 and TSP2. These domains may be present in the METH2 molecule in the same order or a different order than in the naturally occurring molecule. Also preferred are polypeptides encoded by such nucleic acids.

Additionally, METH1 and METH2 domains may be combined to form hybrid molecules. Any domain of METH1 may be combined with any domain of METH2 to form a hybrid molecule. For example, the TSP1 domain of METH1 may be replaced with the TSP1 domain of METH2 to form a hybrid molecule, leaving the remainder of the METH1 molecule intact. Also, the TSP1 domain of meth1 may be replaced with the TSP2 domain of METH2 to form a hybrid molecule, leaving the remainder of the METH1 molecule intact. Additionally, the TSP1 domain of METH1 may be combined with the TSP2 domain of METH2 to form a hybrid molecule, without any additional METH1 and/or METH2 sequences. These domains may be present in the same or a different order as occurs in the naturally occurring molecules. Also preferred are polypeptides encoded by such nucleic acids.

Further embodiments include nucleic acids encoding a METH1 or METH2 polypeptide in which: one or more TSP domains have been replaced with other known TSP domains; the metalloprotease domain has been replaced with another known metalloprotease domain; the disintegrin domain has been replaced with another known disintegrin domain. One or more domains may be replaced in this manner. For example, the both the metalloprotease and disintegrin domains may be replaced. Alternatively, all three TSP domains may be replaced. Also preferred are polypeptides encoded by such nucleic acids.

Preferred embodiments are polynucleotides encoding the amino acid sequence of SEQ ID NO:2 or SEQ ID NO:4 except for several, 5–10, 1–5, 1–3, 1–2 or 1 amino acid residues are substituted, deleted or added, in any combination.

In addition, the present inventors have identified the following cDNA clones related to portions of the sequence shown in SEQ ID NO:1: HOUCQ17RA (SEQ ID NO:14), HPLBM11R (SEQ ID NO:15), HGBI07R (SEQ ID NO:16), HNTMA49R (SEQ ID NO:17), HNALE27R (SEQ ID NO:18), and HIBDB45R (SEQ ID NO:19).

The following public ESTs, which relate to portions of SEQ ID NO:1, have also been identified: D67076 (SEQ ID NO:20), AB001735 (SEQ ID NO:21), X14787 (SEQ ID NO:22), U64857 (SEQ ID NO:23), X04665 (SEQ ID NO:24), M64866 (SEQ ID NO:25), L07803 (SEQ ID NO:26), U08006 (SEQ ID NO:27), M16974 (SEQ ID NO:28), L13855 (SEQ ID NO:29), AL021529 (SEQ ID NO:30), D86074 (SEQ ID NO:31), L05390 (SEQ ID NO:32), Z69361 (SEQ ID NO:33), X99599 (SEQ ID NO:34), AF018073 (SEQ ID NO:35), L23760 (SEQ ID NO:36), Z46970 (SEQ ID NO:37), AC004449 (SEQ ID NO:38), Z69589 (SEQ ID NO:39), Z22279 (SEQ ID NO:40), X17524 (SEQ ID NO:41), AI126019 (SEQ ID NO:103), AI571069 (SEQ ID NO:104), AI148739 (SEQ ID NO:105), AI335849 (SEQ ID NO:106), AA677116 (SEQ ID NO:107), H27128 (SEQ ID NO:108), AA368429 (SEQ ID NO:109), AA345812 (SEQ ID NO:110), AA373718 (SEQ ID NO:111), AI537518 (SEQ ID NO:112), N88341 (SEQ ID NO:113), C03600 (SEQ ID NO:114), AA066142 (SEQ ID NO:115), AI40095 (SEQ ID NO:94), AA288689 (SEQ ID NO:116), AI464076 (SEQ ID NO:97), R13547 (SEQ ID NO:117), R19976 (SEQ ID NO:118), Z43925 (SEQ ID NO:119), AA670987 (SEQ ID NO:120), AA635657 (SEQ ID NO:96), W24878 (SEQ ID NO:121), W47316 (SEQ ID NO:122), W35345 (SEQ ID NO:123), and N27243 (SEQ ID NO:124).

The present inventors have also identified the following cDNA clones related to portions of SEQ ID NO:3: HCE4D69FP02 (SEQ ID NO:42), HIBDB45F (SEQ ID NO:43), HKIXH64R (SEQ ID NO:44), HIBDB45R (SEQ ID NO:19), HCE3Z95R (SEQ ID NO:45), HTLEQ90R (SEQ ID NO:46), HMWEF45R (SEQ ID NO:47), HTOFC34RA (SEQ ID NO:48), HHFDI20R (SEQ ID NO:49), HMSHY47R (SEQ ID NO:50), HCESF90R (SEQ ID NO:51), HMCAO46R (SEQ ID NO:52), HTTAQ67R (SEQ ID NO:53), HFKCF19F (SEQ ID NO:54), HMCAS31R (SEQ ID NO:55), HMWGP26R (SEQ ID NO:56), HLHTP36R (SEQ ID NO:57), HE8AN11R (SEQ ID NO:58), HEONN73R (SEQ ID NO:59), HBNBG53R (SEQ ID NO:60), and HMSCH94R (SEQ ID NO:61).

The following public ESTs, which relate to portions of the sequence shown in SEQ ID NO:3, have also been identified: D67076 (SEQ ID NO:20), AB001735 (SEQ ID NO:21), AB005287 (SEQ ID NO:62), X87619 (SEQ ID NO:63), X14787 (SEQ ID NO:22), X04665 (SEQ ID NO:24), M87276 (SEQ ID NO:64), M62458 (SEQ ID NO:65), AB002364 (SEQ ID NO:66), AB005297 (SEQ ID NO:67), X69161 (SEQ ID NO:68), X16619 (SEQ ID NO:69), I36448 (SEQ ID NO:70), L12260 (SEQ ID NO:71), I36352 (SEQ ID NO:72), X15898 (SEQ ID NO:73), I07789 (SEQ ID NO:74), I08144 (SEQ ID NO:75), U31814 (SEQ ID NO:76), AF001444 (SEQ ID NO:77), AI400905 (SEQ ID NO:94), AI378857 (SEQ ID NO:95), AA635657 (SEQ ID NO:96), AI464076 (SEQ ID NO:97), CO6578 (SEQ ID NO:98), AA855532 (SEQ ID NO:99), H11881 (SEQ ID NO:100), AA350801 (SEQ ID NO:101), and AA350802 (SEQ ID NO:102).

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of METH1 or METH2 coding sequence, but do not comprise all or a portion of any METH1 or METH2 intron. In another embodiment, the nucleic acid comprising METH1 or METH2 coding sequence does not contain coding sequences of a genomic flanking gene (i.e., 5' or 3' to the METH1 or METH2 gene in the genome).

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clones contained in ATCC Deposit No. 209581 or ATCC Deposit No. 209582. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30, 40, 50, 60 or 70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNAs or the nucleotide sequence as shown in SEQ ID NO:1 or SEQ ID NO:3). Of course, a polynucleotide which hybridizes only to a poly A sequence (such as the 3' terminal poly(A) tract of the METH1 or METH2 cDNA shown in SEQ ID NO:1 and SEQ ID NO:3, respectively) or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

Also contemplated are nucleic acid molecules that hybridize to the METH1 or METH2 polynucleotides at moderately high stringency hybridization conditions. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 3° C. in a solution comprising 6×SSPE (20×SSPE=3M NaCl; 0.2M NaH$_2$PO$_4$; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The METH1 or METH2 polynucleotide can be composed of any polyribonucleotide or polydeoxribonucleotide, which may be unmodified RNA or DNA or modified RNA or DNA. For example, METH1 or METH2 polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the METH1 or METH2 polynucleotides can be composed of triple-stranded regions comprising RNA or DNA or both RNA and DNA. METH1 or METH2 polynucleotides may also contain one or more modified bases or DNA or RNA backbones modified for stability or for other reasons. "Modified" bases include, for example, tritylated bases and unusual bases such as inosine.

A variety of modifications can be made to DNA and RNA; thus, "polynucleotide" embraces chemically, enzymatically, or metabolically modified forms.

"SEQ ID NO:1" refers to a METH1 polynucleotide sequence while "SEQ ID NO:2" refers to a METH1 polypeptide sequence. "SEQ ID NO:3" refers to a METH2 polynucleotide sequence while "SEQ ID NO:4" refers to a METH2 polypeptide sequence.

As indicated, nucleic acid molecules of the present invention which encode a METH1 or METH2 polypeptide may include, but are not limited to, those encoding the amino acid sequence of the mature polypeptide, by itself; the coding sequence for the mature polypeptide and additional sequences, such as those encoding the leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778 (1984). As discussed below, other such fusion proteins include the METH1 or METH2 fused to Fc at the N- or C-terminus. Other fusion proteins include METH1 or METH2 fused to Flag at the N- or C-terminus. Other fusion proteins include METH1 fragments or METH2 fragments fused to Flag or Fc at the N- or C-terminus. Particularly preferred are fragments of METH1 or METH2, such as H541-Q894, M1-P799, F236-E614, or K801-Q950 of SEQ ID NO:2, fused to Fc or Flag at the N- or C-terminus.

As stated above, METH1 or METH2 may be fused with the FLAG polypeptide sequence (see U.S. Pat. No. 4,851,341; see also Hopp et al., *Bio/Technology* 6:1204, 1988). The FLAG polypeptide sequence is highly antigenic and provides an epitope for binding by a specific monoclonal antibody, enabling rapid purification of the expressed recombinant protein. This sequence is also specifically cleaved by bovine mucosal enterokinase at the residue immediately following the Asp-Lys pairing.

The present invention further relates to variants of the nucleic acid molecules of the present invention, which encode portions, analogs or derivatives of the METH1 or METH2 protein. Variants may occur naturally, such as a natural allelic variant. By an "allelic variant" is intended one of several alternate forms of a gene occupying a given locus on a chromosome of an organism. Lewin, B., ed., *Genes II*, John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the METH1 or METH2 protein or portions thereof. Also especially preferred in this regard are conservative substitutions.

Further embodiments of the invention include isolated nucleic acid molecules comprising a polynucleotide having a nucleotide sequence at least 95% identical, and more preferably at least 96%, 97%, 98% or 99% identical to: a nucleotide sequence encoding the polypeptide having the amino acid sequence in SEQ ID NO:2; a nucleotide sequence encoding the polypeptide having the amino acid sequence in SEQ ID NO:2, but lacking the N-terminal methionine; a nucleotide sequence encoding the polypeptide having the amino acid sequence at positions from about 29 to about 950 in SEQ ID NO:2; a nucleotide sequence encoding the polypeptide having the amino acid sequence at position from about 30 to about 950 in SEQ ID NO:2; a nucleotide sequence encoding the polypeptide having the amino acid sequence encoded by the cDNA clone contained in ATCC Deposit No. 209581; a nucleotide sequence encoding the mature METH1 polypeptide having the amino acid sequence encoded by the cDNA clone contained in ATCC Deposit No. 209581; a nucleotide sequence encoding amino acids 235 to 459 in SEQ ID NO:2 (the metalloprotease domain of METH1); a nucleotide sequence encoding amino acids 460 to 544 in SEQ ID NO:2 (the disintegrin domain of METH1); a nucleotide sequence encoding amino acids 545 to 598 in SEQ ID NO:2 (the first TSP-like domain of METH1); a nucleotide sequence encoding amino acids 841 to 894 in SEQ ID NO:2 (the second TSP-like domain of METH1); a nucleotide sequence encoding amino acids 895 to 934 in SEQ ID NO:2 (the third TSP-like domain of METH1); a nucleotide sequence encoding amino acids 536 to 613 in SEQ ID NO:2; a nucleotide sequence encoding amino acids 549 to 563 in SEQ ID NO:2; a nucleotide sequence encoding the polypeptide having the amino acid sequence in SEQ ID NO:4; a nucleotide sequence encoding the polypeptide having the amino acid sequence in SEQ ID NO:4, but lacking the N-terminal methionine; a nucleotide sequence encoding the polypeptide having the amino acid sequence at positions from about 24 to about 890 in SEQ ID NO:4; a nucleotide sequence encoding the polypeptide having the amino acid sequence at positions from about 112 to about 890 in SEQ ID NO:4; a nucleotide sequence encoding the polypeptide having the amino acid sequence encoded by the cDNA clone contained in ATCC Deposit No. 209582; a nucleotide sequence encoding the mature METH2 polypeptide having the amino acid sequence encoded by the cDNA clone contained in ATCC Deposit No. 209582; a nucleotide sequence encoding amino acids 214 to 439 in SEQ ID NO:4 (the metalloprotease domain of METH2); a nucleotide sequence encoding amino acids 440 to 529 in SEQ ID NO:4 (the disintegrin domain of METH2); a nucleotide sequence encoding amino acids 530 to 583 in SEQ ID NO:4 (the first TSP-like domain of METH2); a nucleotide sequence encoding amino acids 837 to 890 in SEQ ID NO:4 (the second TSP-like domain of METH2); a nucleotide sequence encoding amino acids 280 to 606 in SEQ ID NO:4; a nucleotide sequence encoding amino acids 529 to 548 in SEQ ID NO:4; or a nucleotide sequence complementary to any of the above nucleotide sequences.

By a polynucleotide having a nucleotide sequence at least, for example, 95% "identical" to a reference nucleotide sequence encoding a METH1 or METH2 polypeptide is intended that the nucleotide sequence of the polynucleotide is identical to the reference sequence except that the polynucleotide sequence may include up to five point mutations per each 100 nucleotides of the reference nucleotide sequence encoding the METH1 or METH2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NO:1 or SEQ ID NO:3 or to the nucleotide sequence of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

A preferred method for determining the best overall match between a query sequence (a sequence of the present invention) and a subject sequence, also referred to as a global sequence alignment, can be determined using the FASTDB computer program based on the algorithm of Brutlag et al., *Comp. Appl. Biosci.* 6:237–245 (1990). In a sequence alignment, the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by the results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and, therefore, the FASTDB alignment does not show a match/alignment of the first 10 bases at the 5' end. The 10 unpaired bases represent 10% of the sequence (number of bases at the 5' and 3' ends not matched/total number of bases in the query sequence), so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal, so that there are no bases on the 5' or 3' ends of the subject sequence which are not matched/aligned with the query. In this case, the percent identity calculated by FASTDB is not manually corrected. Once again, only bases 5' and 3' of the subject sequence which are not matched/aligned with the query sequence are manually corrected for. No other manual corrections are to be made for the purposes of the present invention.

The present application is directed to nucleic acid molecules at least 95%, 96%, 97%, 98% or 99% identical to the nucleic acid sequence shown in SEQ ID NO:1 or SEQ ID NO:3 or to the nucleic acid sequence of the deposited cDNAs, irrespective of whether they encode a polypeptide having METH1 or METH2 activity. This is because even where a particular nucleic acid molecule does not encode a polypeptide having METH1 or METH2 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having METH1 or METH2 activity include, inter alia, (1) isolating the METH1 or METH2 gene or allelic variants thereof in a cDNA library; (2) in situ hybridization (e.g., "FISH") to metaphase chromosomal spreads to provide precise chromosomal location of the METH1 or METH2 gene, as described in Verma et al., *Human Chromosomes: A Manual of Basic Techniques*, Pergamon Press, New York (1988); and (3) Northern Blot analysis for detecting METH1 or METH2 mRNA expression in specific tissues.

Preferred, however, are nucleic acid molecules having sequences at least 95%, 96%, 97%, 98% or 99% identical to the nucleic acid sequence shown in SEQ ID NO:1 or SEQ ID NO:3 or to a nucleic acid sequence of the deposited cDNAs which do, in fact, encode a polypeptide having METH1 or METH2 protein activity. By "a polypeptide having METH1 activity" is intended polypeptides exhibiting METH1 activity in a particular biological assay. For example, METH1 protein activity can be measured using the chorioallantoic membrane assay (Iruela-Arispe et al., *Thrombosis and Haemostasis* 78(1):672–677 (1997)) or the cornea pocket assay (Tolsma et al., *J. Cell. Biol.* 122:

497–511(1993)), both described in Example 4, below. By "a polypeptide having METH2 activity" is intended polypeptides exhibiting METH2 activity in a particular biological assay. For example, METH2 protein activity can also be measured using the chorioallantoic membrane assay (Iruela-Arispe et al., *Thrombosis and Haemostasis* 78(1):672–677 (1997)) or the cornea pocket assay (Tolsma et al., *J. Cell. Biol.* 122:497–511 (1993)), both described in Example 4, below.

Briefly, in the chorioallantoic assay, the potentially anti-angiogenic compound of interest is added to type I collagen pellets (Vitrogen), along with an angiogenic growth factor, such as bFGF. The samples are mixed and placed onto nylon meshes, and allowed to polymerize. After polymerization is complete, the meshes are placed onto the chorioallantoic membrane of 12 day old chick embryos and placed at 37° C. for 24 hours. The embryos are then injected with a fluorescent agent, such as FITC-dextran, and the meshes are fixed and mounted for observation under a fluorescent microscope.

In the cornea pocket assay, hydron pellets containing the compound of interest and an angiogenic growth factor, such as bFGF, are implanted 1 to 2 mm from the limbus of the cornea of rats or mice. Response is examined after a period of time, for example 5 days. The extent of angiogenesis is evaluated by measuring the capillaries migrating from the limb of the cornea.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence of the deposited cDNAs or a nucleic acid sequence shown in SEQ ID NO:1 or SEQ ID NO:3 will encode a polypeptide "having METH1 or METH2 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having METH1 or METH2 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of METH1 or METH2 polypeptides or fragments thereof by recombinant techniques. Cell-free translation systems can also be employed to produce such proteins using RNAs derived from the DNA constructs of the present invention.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

In addition to the use of expression vectors in the practice of the present invention, the present invention further includes novel expression vectors comprising operator and promoter elements operatively linked to nucleotide sequences encoding a protein of interest. One example of such a vector is pHE4-5 which is described in detail below.

Figure 8:
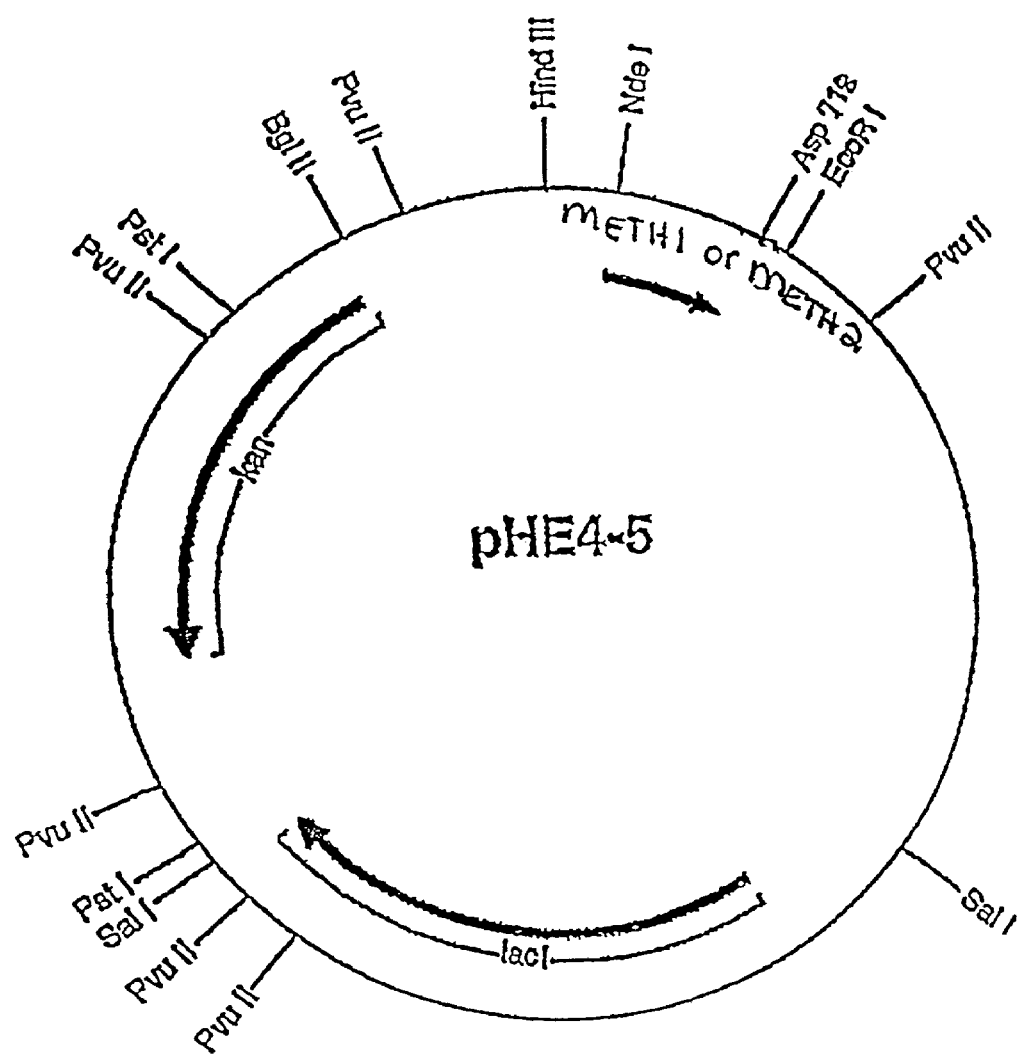
FIG. 8 shows a schematic representation of the pHE4-5 expression vector (SEQ ID NO:12) and the subcloned METH1 or METH2 cDNA coding sequence. The locations of the kanamycin resistance marker gene, the METH1 or METH2 coding sequence, the oriC sequence, and the lacIq coding sequence are indicated.

As summarized in FIGS. 8 and 9, components of the pHE4-5 vector (SEQ ID NO:12) include: 1) a neomycin-phosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq). The origin of replication (oriC) is derived from pUC19 (LTI, Gaithersburg, Md.). The promoter sequence and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303. A nucleotide sequence encoding METH1 (SEQ ID NO:2) or METH2 (SEQ ID NO:4), is operatively linked to the promoter and operator by inserting the nucleotide sequence between the NdeI and Asp718 sites of the pHE4-5 vector.

As noted above, the pHE4-5 vector contains a lacIq gene. LacIq is an allele of the lacI gene which confers tight regulation of the lac operator. Amann, E. et al., *Gene* 69:301–315 (1988); Stark, M., *Gene* 51:255–267 (1987). The lacIq gene encodes a repressor protein which binds to lac operator sequences and blocks transcription of downstream (i.e., 3') sequences. However, the lacIq gene product dissociates from the lac operator in the presence of either lactose or certain lactose analogs, e.g., isopropyl B-D-thiogalactopyranoside (IPTG). METH1 or METH2 thus is not produced in appreciable quantities in uninduced host cells containing the pHE4-5 vector. Induction of these host cells by the addition of an agent such as IPTG, however, results in the expression of the METH1 or METH2 coding sequence.

The promoter/operator sequences of the pHE4-5 vector (SEQ ID NO:13) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802–807.

The pHE4 series of vectors contain all of the components of the pHE4-5 vector except for the METH1 or METH2 coding sequence. Features of the pHE4 vectors include optimized synthetic T5 phage promoter, lac operator, and Shine-Delgarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4-5 vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vectors useful for the production of the proteins of the present invention. This aspect of the invention is exemplified by the pHE4-5 vector (SEQ ID NO:12).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when the Fc portion proves to be a hindrance to use in therapy and diagnosis, for example when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., *J. Mol. Recognition* 8:52–58 (1995) and K. Johanson et al., *J. of Biol. Chem.* 270(16):9459–9471 (1995).

The METH1 or METH2 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

In addition, polypeptides of the invention can be chemically synthesized using techniques known in the art (e.g., see Creighton, 1983, Proteins: Structures and Molecular Principles, W.H. Freeman & Co., N.Y., and Hunkapiller, M., et al., 1984, *Nature* 310:105–111). For example, a peptide corresponding to a fragment of the METH1 and/or METH2 polypeptides of the invention can be synthesized by use of a peptide synthesizer. Furthermore, if desired, nonclassical amino acids or chemical amino acid analogs can be introduced as a substitution or addition into the METH1 and/or METH2 polynucleotide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses METH1 and/or METH2 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of METH1 and/or METH2 which may provide additional advantages such as increased solubility, stability and circulating time of the polypeptide, or decreased immunogenicity (see U.S. Pat. No. 4,179,337). The chemical moieties for derivitization maybe selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The METH1 and/or METH2 polypeptides of the invention may be in monomers or multimers (i.e., dimers, trimers, tetramers and higher multimers). Accordingly, the present invention relates to monomers and multimers of the METH1 and/or METH2 polypeptides of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only METH1 and/or METH2 polypeptides of the invention (including METH1 and/or METH2 fragments, variants, splice variants, and fusion proteins, as described herein). These homomers may contain METH1 and/or METH2 polypeptides having identical or different amino acid sequences. In a specific embodiment, a homomer of the invention is a multimer containing only METH1 and/or METH2 polypeptides having an identical amino acid sequence. In another specific embodiment, a homomer of the invention is a multimer containing METH1 and/or METH2 polypeptides having different amino acid sequences. In specific embodiments, the multimer of the invention is a homodimer (e.g., containing METH1 and/or METH2 polypeptides having identical or different amino acid sequences) or a homotrimer (e.g., containing METH1 and/or METH2 polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the METH1 and/or METH2 polypeptides of the invention. In a specific embodiment, the multimer of the invention is a heterodimer, a heterotrimer, or a heterotetramer. In additional embodiments, the homomeric multimer of the invention is at least a homodimer, at least a homotrimer, or at least a homotetramer.

Multimers of the invention may be the result of hydrophobic, hydrophilic, ionic and/or covalent associations and/or may be indirectly linked by, for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the METH1 and/or METH2 polypeptides of the invention. Such covalent associations may involve one or more amino acid residues contained in the polypeptide sequence (e.g., that recited in SEQ ID NO:2 or 4, or contained in the polypeptide encoded by the clone HATCK89). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a METH1 and/or METH2 fusion protein. In one example, covalent associations are between the heterologous sequence contained in a fusion protein of the invention (see, e.g., U.S. Pat. No. 5,478,925). In a specific example, the covalent associations are between the heterologous sequence contained in a METH1 and/or METH2-Fc fusion protein of the invention (as described herein). In another specific example, covalent associations of fusion proteins of the invention are between heterologous polypeptide sequence from another Fibroblast Growth Factor family member that is capable of forming covalently associated multimers, such as for example, oseteoprotegerin (see, e.g., International Publication No. WO 98/49305, the contents of which are herein incorporated by reference in its entirety).

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

METH1 and METH2 Polypeptides and Fragments

The invention further provides an isolated METH1 polypeptide having the amino acid sequence encoded by the deposited cDNA, or the amino acid sequence in SEQ ID NO:2, or a peptide or polypeptide comprising a portion of the above polypeptides. The invention also provides an isolated METH2 polypeptide having the amino acid sequence encoded by the deposited cDNA, or the amino acid sequence in SEQ ID NO:4, or a peptide or polypeptide comprising a portion of the above polypeptides.

Polypeptides of the present invention encompass not only full length polypeptides, but the mature, proprotein, processed forms of the protein, deletion mutants, substitution variants, allelic variants, analogs, derivatives, etc.

METH1 or METH2 polypeptides can be composed of amino acids joined to each other by peptide bonds or modified peptide bonds, i.e., peptide isosteres, and may contain amino acids other than the 20 gene-encoded amino acids. The METH1 or METH2 polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in the METH1 or METH2 polypeptide, including the peptide backbone, the amino acid side-chains and the amino or carboxyl termini. It will be appreciated that the same type of modification may be present in the same or varying degrees at several sites in a given METH1 or METH2 polypeptide. Also, a given METH1 or METH2 polypeptide may contain many types of modifications. METH1 or METH2 polypeptides may be branched, for example, as a result of ubiquitination, and they may be cyclic, with or without branching. Cyclic, branched, and branched cyclic METH1 or METH2 polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W.H. Freeman and Company, New York (1993); POST-TRANSLATIONAL COVALENT MODIFICATION OF PROTEINS, B. C. Johnson, Ed., Academic Press, New York, pgs. 1–12 (1983); Seifter et al., *Meth Enzymol* 182: 626–646 (1990); Rattan et al., *Ann NY Acad Sci* 663:48–62 (1992).)

It will be recognized in the art that some amino acid sequences of the METH1 and METH2 polypeptides can be varied without significant effect of the structure or function of the protein. If such differences in sequence are contemplated, it should be remembered that there will be critical areas on the protein which determine activity.

The present inventors have shown that METH1 and METH2 inhibit angiogenesis in vitro and in vivo. METH1 and METH2 each contain a metalloprotease domain, a disintegrin domain, and TSP-like domains. The metalloprotease domain may be catalytically active. The disintegrin domain may play a role in inhibiting angiogenesis by interacting with integrins, since integrins are essential for the mediation of both proliferative and migratory signals. The present inventors have shown that peptides derived from the TSP-like domains of METH1 and METH2 inhibit angiogenesis in vitro and in vivo.

Thus, the invention further includes variations of the METH1 polypeptide which show substantial METH1 polypeptide activity or which include regions of METH1 protein such as the protein portions discussed below; and variations of the METH2 polypeptide which show substantial METH2 polypeptide activity or which include regions of METH2 protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2 or SEQ ID NO:4, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the METH1 or METH2 proteins. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331–340 (1967); Robbins et al., *Diabetes* 36:838–845 (1987); Cleland et al., *Crit. Rev. Therapeutic Drug Carrier Systems* 10:307–377 (1993)).

As indicated, changes are preferably of a minor nature, such as conservative amino acid substitutions that do not significantly affect the folding or activity of the protein (see Table 3).

TABLE 3

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of amino acid substitutions for any given METH1 or METH2 polypeptide will not be more than 50, 40, 30, 20, 10, 9, 8, 7, 6, 5, 4, 3, 2 or 1.

In particular, preferred METH1 molecules contain one or more of the following conservative substitutions: M1 replaced with A, G, I, L, S, T, or V; G2 replaced with A, I, L, S, T, M, or V; N3 replaced with Q; A4 replaced with G, I, L, S, T, M, or V; E5 replaced with D; R6 replaced with H, or K; A7 replaced with G, I, L, S, T, M, or V; G9 replaced with A, I, L, S, T, M, or V; S10 replaced with A, G, I, L, T, M, or V; R11 replaced with H, or K; S12 replaced with A, G, I, L, T, M, or V; F13 replaced with W, or Y; G14 replaced with A, I, L, S, T, M, or V; V16 replaced with A, G, I, L, S, T, or M; T18 replaced with A, G, I, L, S, M, or V; L19 replaced with A, G, I, S, T, M, or V; L20 replaced with A, G, I, S, T, M, or V; L21 replaced with A, G, I, S, T, M, or V; L22 replaced with A, G, I, S, T, M, or V; A23 replaced with G, I, L, S, T, M, or V; A24 replaced with G, I, L, S, T, M, or V; A25 replaced with G, I, L, S, T, M, or V; L26 replaced with A, G, I, S, T, M, or V; L27 replaced with A, G, I, S, T, M, or V; A28 replaced with G, I, L, S, T, M, or V; V29 replaced with A, G, I, L, S, T, or M; S30 replaced with A, G, I, L, T, M, or V; D31 replaced with E; A32 replaced with G, I, L, S, T, M, or V; L33 replaced with A, G, I, S, T, M, or V; G34 replaced with A, I, L, S, T, M, or V; R35 replaced with H, or K; S37 replaced with A, G, I, L, T, M, or V; E38 replaced with D; E39 replaced with D; D40 replaced with E; E41 replaced with D; E42 replaced with D; L43 replaced with A, G, I, S, T, M, or V; V44 replaced with A, G, I, L, S, T, or M; V45 replaced with A, G, I, L, S, T, or M; E47 replaced with D; LA8 replaced with A, G, I, S, T, M, or V; E49 replaced with D; R50 replaced with H, or K; A51 replaced with G, I, L, S, T, M, or V; G53 replaced with A, I, L, S, T, M, or V; H54 replaced with K, or R; G55 replaced with A, I, L, S, T, M, or V; T56 replaced with A, G, I, L, S, M, or V; T57 replaced with A, G, I, L, S, M, or V; R58 replaced with H, or K; L59 replaced with A, G, I, S, T, M, or V; R60 replaced with H, or K; L61 replaced with A, G, I, S, T, M, or V; H62 replaced with K, or R; A63 replaced with G, I, L, S, T, M, or V; F64 replaced with W, or Y; D65 replaced with E; Q66 replaced with N; Q67 replaced with N; L68 replaced with A, G, I, S, T, M, or V; D69 replaced with E; L70 replaced with A, G, I, S, T, M, or V; E71 replaced with D; L72 replaced with A, G, I, S, T, M, or V; R73 replaced with H, or K; D75 replaced with E; S76 replaced with A, G, I, L, T, M, or V; S77 replaced with A, G, I, L, T, M, or V; F78 replaced with W, or Y; L79 replaced with A, G, I, S, T, M, or V; A80 replaced with G, I, L, S, T, M, or V; G82 replaced with A, I, L, S, T, M, or V; F83 replaced with W, or Y; T84 replaced with A, G, I, L, S, M, or V; L85 replaced with A, G, I, S, T, M, or V; Q86 replaced with N; N87 replaced with Q; V88 replaced with A, G, I, L, S, T, or M; G89 replaced with A, I, L, S, T, M, or V; R90 replaced with H, or K; K91 replaced with H, or R; S92 replaced with A, G, I, L, T, M, or V; G93 replaced with A, I, L, S, T, M, or V; S94 replaced with A, G, I, L, T, M, or V; E95 replaced with D; T96 replaced with A, G, I, L, S, M, or V; L98 replaced with A, G, I, S, T, M, or V; E100 replaced with D; T101 replaced with A, G, I, L, S, M, or V; D102 replaced with E; L103 replaced with A, G, I, S, T, M, or V; A104 replaced with G, I, L, S, T, M, or V; H105 replaced with K, or R; F107 replaced with W, or Y; Y108 replaced with F, or W; S109 replaced with A, G, I, L, T, M, or V; G110 replaced with A, I, L, S, T, M, or V; T111 replaced with A, G, I, L, S, M, or V; V112 replaced with A, G, I, L, S, T, or M; N113 replaced with Q; G114 replaced with A, I, L, S, T, M, or V; D115 replaced with E; S117 replaced with A, G, I, L, T, M, or V; S118 replaced with A, G, I, L, T, M, or V; A119 replaced with G, I, L, S, T, M, or V; A120 replaced with G, I, L, S, T, M, or V; A121 replaced with G, I, L, S, T, M, or V; L122 replaced with A, G, I, S, T, M, or V; S123 replaced with A, G, I, L, T, M, or V; L124 replaced with A, G, I, S, T, M, or V; E126 replaced with D; G127 replaced with A, I, L, S, T, M, or V; V128 replaced with A, G, I, L, S, T, or M; R129 replaced with H, or K; G130 replaced with A, I, L, S, T, M, or V; A131 replaced with G, I, L, S, T, M, or V; F132 replaced with W, or Y; Y133 replaced with F, or W; L134 replaced with A, G, I, S, T, M, or V; L135 replaced with A, G, I, S, T, M, or V; G136 replaced with A, I, L, S, T, M, or V; E137 replaced with D; A138 replaced with G, I, L, S, T, M, or V; Y139 replaced with F, or W; F140 replaced with W, or Y; I141 replaced with A, G, L, S, T, M, or V; Q142 replaced with N; L144 replaced with A, G, I, S, T, M, or V; A146 replaced with G, I, L, S, T, M, or V; A147 replaced with G, I, L, S, T, M, or V; S148 replaced with A, G, I, L, T, M, or V; E149 replaced with D; R150 replaced with H, or K; L151 replaced with A, G, I, S, T, M, or V; A152 replaced with G, I, L, S, T, M, or V; T153 replaced with A, G, I, L, S, M, or V; A154 replaced with G, I, L, S, T, M, or V; A155 replaced with G, I, L, S, T, M, or V; G157 replaced with A, I, L, S, T, M, or V; E158 replaced with D; K159 replaced with H, or R; A162 replaced with G, I, L, S, T, M, or V; L164 replaced with A, G, I, S, T, M, or V; Q165 replaced with N; F166 replaced with W, or Y; H167 replaced with K, or R; L168 replaced with A, G, I, S, T, M, or V; L169 replaced with A, G, I, S, T, M, or V; R170 replaced with H, or K; R171 replaced with H, or K; N172 replaced with Q; R173 replaced with H, or K; Q174 replaced with N; G175 replaced with A, I, L, S, T, M, or V; D176 replaced with E; V177 replaced with A, G, I, L, S, T, or M; G178 replaced with A, I, L, S, T, M, or V; G179 replaced with A, I, L, S, T, M, or V; T180 replaced with A, G, I, L, S, M, or V; G182 replaced with A, I, L, S, T, M, or V; V183 replaced with A, G, I, L, S, T, or M; V184 replaced with A, G, I, L, S, T, or M; D185 replaced with E; D186 replaced with E; E187 replaced with D; R189 replaced with H, or K; T191 replaced with A, G, I, L, S, M, or V; G192 replaced with A, I, L, S, T, M, or V; K193 replaced with H, or R; A194 replaced with G, I, L, S, T, M, or V; E195 replaced with D; T196 replaced with A, G, I, L, S, M, or V; E197 replaced with D; D198 replaced with E; E199 replaced with D; D200 replaced with E; E201 replaced with D; G202 replaced with A, I, L, S, T, M, or V; T203 replaced with A, G, I, L, S, M, or V; E204 replaced with D; G205 replaced with A, I, L, S, T, M, or V; E206 replaced with D; D207 replaced with E; E208 replaced with D; G209 replaced with A, I, L, S, T, M, or V; Q211 replaced with N; W212 replaced with F, or Y; S213 replaced with A, G, I, L, T, M, or V; Q215 replaced with N; D216 replaced with E; A218 replaced with G, I, L, S, T, M, or V; L219 replaced with A, G, I, S, T, M, or V; Q220 replaced with N; G221 replaced with A, I, L, S, T, M, or V; V222 replaced with A, G, I, L, S, T, or M; G223 replaced with A, I, L, S, T, M, or V; Q224 replaced with N; T226 replaced with A, G, I, L, S, M, or V; G227 replaced with A, I, L, S, T, M, or V; T228 replaced with A, G, I, L, S, M, or V; G229 replaced with A, I, L, S, T, M, or V; S230 replaced with A, G, I, L, T, M, or V; I231 replaced with A, G, L, S, T, M, or V; R232 replaced with H, or K; K233 replaced with H, or R; K234 replaced with H, or R; R235 replaced with H, or K; F236 replaced with W, or Y; V237 replaced with A, G, I, L, S, T, or M; S238 replaced with A, G, I, L, T, M, or V; S239 replaced with A, G, I, L, T, M, or V; H240 replaced with K, or R; R241 replaced with H, or K; Y242 replaced with F, or W; V243 replaced with A, G, I, L, S, T, or M; E244 replaced with D; T245 replaced with A, G, I, L, S, M, or V; M246 replaced with A, G, I, L, S, T, or V; L247 replaced with A, G, I, S, T, M, or V; V248 replaced with A, G, I, L, S, T, or M; A249 replaced with G, I, L, S, T, M, or V; D250 replaced with E; Q251 replaced with N; S252 replaced with A, G, I, L, T, M, or V; M253 replaced with A, G, I, L, S, T, or V; A254 replaced with G, I, L, S, T, M, or V; E255 replaced with D; F256 replaced with W, or Y; H257 replaced with K, or R; G258 replaced with A, I, L, S, T, M, or V; S259 replaced with A, G, I, L, T, M, or V; G260 replaced with A, I, L, S, T, M, or V; L261 replaced with A, G, I, S, T, M, or V; K262 replaced with H, or R; H263 replaced with K, or R; Y264 replaced with F, or W; L265 replaced with A, G, I, S, T, M, or V; L266 replaced with A, G, I, S, T, M, or V; T267 replaced with A, G, I, L, S, M, or V; L268 replaced with A, G, I, S, T, M, or V; F269 replaced with W, or Y; S270 replaced with A, G, I, L, T, M, or V; V271 replaced with A, G, I, L, S, T, or M; A272 replaced with G, I, L, S, T, M, or V; A273 replaced with G, I, L, S, T, M or V; R274 replaced with H, or K; L275 replaced with A, G, I, S, T, M, or V; Y276 replaced with F, or W; K277 replaced with H, or R; H278 replaced with K, or R; S280 replaced with A, G, I, L, T, M, or V; I281 replaced with A, G, L, S, T, M, or V; R282 replaced with H, or K; N283 replaced with Q; S284 replaced with A, G, I, L, T, M, or V; V285 replaced with A, G, I, L, S, T, or M; S286 replaced with A, G, I, L, T, M, or V; L287 replaced with A, G, I, S, T, M, or V; V288 replaced with A, G, I, L, S, T, or M; V289 replaced with A, G, I, L, S, T, or M; V290 replaced with A, G, I, L, S, T, or M; K291 replaced with H, or R; I292 replaced with A, G, L, S, T, M, or V; L293 replaced with A, G, I, S, T, M, or V; V294 replaced with A, G, I, L, S, T, or M; I295 replaced with A, G, L, S, T, M, or V; H296 replaced with K, or R; D297 replaced with E; E298 replaced with D; Q299 replaced with N; K300 replaced with H, or R; G301 replaced with A, I, L, S, T, M, or V; E303 replaced with D; V304 replaced with A, G, I, L, S, T, or M; T305 replaced with A, G, I, L, S, M, or V; S306 replaced with A, G, I, L, T, M, or V; N307 replaced with Q; A308 replaced with G, I, L, S, T, M, or V; A309 replaced with G, I, L, S, T, M, or V; L310 replaced with A, G, I, S, T, M, or V; T311 replaced with A, G, I, L, S, M, or V; L312 replaced with A, G, I, S, T, M, or V; R313 replaced with H, or K; N314 replaced with Q; F315 replaced with W, or Y; N317 replaced with Q; W318 replaced with F, or Y; Q319 replaced with N; K320 replaced with H, or R; Q321 replaced with N; H322 replaced with K, or R; N323 replaced with Q; S326 replaced with A, G, I, L, T, M, or V; D327 replaced with E; R328 replaced with H, or K; D329 replaced with E; A330 replaced with G, I, L, S, T, M, or V; E331 replaced with D; H332 replaced with K, or R; Y333 replaced with F, or W; D334 replaced with E; T335 replaced with A, G, I, L, S, M, or V; A336 replaced with G, I, L, S, T, M, or V; I337 replaced with A, G, L, S, T, M, or V; L338 replaced with A, G, I, S, T, M, or V; F339 replaced with W, or Y; T340 replaced with A, G, I, L, S, M, or V; R341 replaced with H, or K; Q342 replaced with N; D343 replaced with E; L344 replaced with A, G, I, S, T, M, or V; G346 replaced with A, I, L, S, T, M, or V; S347 replaced with A, G, I, L, T, M, or V; Q348 replaced with N; T349 replaced with A, G, I, L, S, M, or V; D351 replaced with E; T352 replaced with A, G, I, L, S, M, or V; L353 replaced with A, G, I, S, T, M, or V; G354 replaced with A, I, L, S, T, M, or V; M355 replaced with A, G, I, L, S, T, or V; A356 replaced with G, I, L, S, T, M, or V; D357 replaced with E; V358 replaced with A, G, I, L, S, T, or M; G359 replaced with A, I, L, S, T, M, or V; T360 replaced with A, G, I, L, S, M, or V; V361 replaced with A, G, I, L, S, T, or M; D363 replaced with E; S365 replaced with A, G, I, L, T, M, or V; R366 replaced with H, or K; S367 replaced with A, G, I, L, T, M, or V; S369 replaced with A, G, I, L, T, M, or V; V370 replaced with A, G, I, L, S, T, or M; I371 replaced with A, G, L, S, T, M, or V; E372 replaced with D; D373 replaced with E; D374 replaced with E; G375 replaced with A, I, L, S, T, M, or V; L376 replaced with A, G, I, S, T, M, or V; Q377 replaced with N; A378 replaced with G, I, L, S, T, M, or V; A379 replaced with G, I, L, S, T, M, or V; F380 replaced with W, or Y; T381 replaced with A, G, I, L, S, M, or V; T382 replaced with A, G, I, L, S, M, or V; A383 replaced with G, I, L, S, T, M, or V; H384 replaced with K, or R; E385 replaced with D; L386 replaced with A, G, I, S, T, M, or V; G387 replaced with A, I, L, S, T, M, or V; H388 replaced with K, or R; V389 replaced with A, G, I, L, S, T, or M; F390 replaced with W, or Y; N391 replaced with Q; M392 replaced with A, G, I, L, S, T, or V; H394 replaced with K, or R; D395 replaced with E; D396 replaced with E; A397 replaced with G, I, L, S, T, M, or V; K398 replaced with H, or R; Q399 replaced with N; A401 replaced with G, I, L, S, T, M, or V; S402 replaced with A, G, I, L, T, M, or V; L403 replaced with A, G, I, S, T, M, or V; N404 replaced with Q; G405 replaced with A, I, L, S, T, M, or V; V406 replaced with A, G, I, L, S, T, or M; N407 replaced with Q; Q408 replaced with N; D409 replaced with E; S410 replaced with A, G, I, L, T, M, or V; H411 replaced with K, or R; M412 replaced with A, G, I, L, S, T, or V; M413 replaced with A, G, I, L, S, T, or V; A414 replaced with G, I, L, S, T, M, or V; S415 replaced with A, G, I, L, T, M, or V; M416 replaced with A, G, I, L, S, T, or V; L417 replaced with A, G, I, S, T, M, or V; S418 replaced with A, G, I, L, T, M, or V; N419 replaced with Q; L420 replaced with A, G, I, S, T, M, or V; D421 replaced with E; 422 replaced with K, or R; S423 replaced with A, G, I, L, T, M, or V; Q424 replaced with N; W426 replaced with F, or Y; S427 replaced with A, G, I, L, T, M, or V; S430 replaced with A, G, I, L, T, M, or V; A431 replaced with G, I, L, S, T, M, or V; Y432 replaced with F, or W; M433 replaced with A, G, I, L, S, T, or V; I434 replaced with A, G, L, S, T, M, or V; T435 replaced with A, G, I, L, S, M, or V; S436 replaced with A, G, I, L, T, M, or V; F437 replaced with W, or Y; L438 replaced with A, G, I, S, T, M, or V; D439 replaced with E; N440 replaced with Q; G441 replaced with A, I, L, S, T, M, or V; H442 replaced with K, or R; G443 replaced with A, I, L, S, T, M, or V; E444 replaced with D; L446 replaced with A, G, I, S, T, M, or V; M447 replaced with A, G, I, L, S, T, or V; D448 replaced with E; K449 replaced with H, or R; Q451 replaced with N; N452 replaced with Q; I454 replaced with A, G, L, S, T, M, or V; Q455 replaced with N; L456 replaced with A, G, I, S, T, M, or V; G458 replaced with A, I, L, S, T, M, or V; D459 replaced with E; L460 replaced with A, G, I, S, T, M, or V; G462 replaced with A, I, L, S, T, M, or V; T463 replaced with A, G, I, L, S, M, or V; S464 replaced with A, G, I, L, T, M, or V; Y465 replaced with F, or W; D466 replaced with E; A467 replaced with G, I, L, S, T, M, or V; N468 replaced with Q; R469 replaced with H, or K; Q470 replaced with N; Q472 replaced with N; F473 replaced with W, or Y; T474 replaced with A, G, I, L, S, M, or V; F475 replaced with W, or Y; G476 replaced with A, I, L, S, T, M, or V; E477 replaced with D; D478 replaced with E; S479 replaced with A, G, I, L, T, M, or V; K480 replaced with H, or R; H481 replaced with K, or R; D484 replaced with E; A485 replaced with G, I, L, S, T, M, or V; A486 replaced with G, I, L, S, T, M, or V; S487 replaced with A, G, I, L, T, M, or V; T488 replaced with A, G, I, L, S, M, or V; S490 replaced with A, G, I, L, T, M, or V; T491 replaced with A, G, I, L, S, M, or V; L492 replaced with A, G, I, S, T, M, or V; W493 replaced with F, or Y; T495 replaced with A, G, I, L, S, M, or V; G496 replaced with A, I, L, S, T, M, or V; T497 replaced with A, G, I, L, S, M, or V; S498 replaced with A, G, I, L, T, M, or V; G499 replaced with A, I, L, S, T, M, or V; G500 replaced with A, I, L, S, T, M, or V; V501 replaced with A, G, I, L, S, T, or M; L502 replaced with A, G, I, S, T, M, or V; V503 replaced with A, G, I, L, S, T, or M; Q505 replaced with N; T506 replaced with A, G, I, L, S, M, or V; K507 replaced with H, or R; H508 replaced with K, or R; F509 replaced with W, or Y; W511 replaced with F, or Y; A512 replaced with G, I, L, S, T, M, or V; D513 replaced with E; G514 replaced with A, I, L, S, T, M, or V; T515 replaced with A, G, I, L, S, M, or V; S516 replaced with A, G, I, L, T, M, or V; G518 replaced with A, I, L, S, T, M, or V; E519 replaced with D; G520 replaced with A, I, L, S, T, M, or V; K521 replaced with H, or R; W522 replaced with F, or Y; I524 replaced with A, G, L, S, T, M, or V; N525 replaced with Q; G526 replaced with A, I, L, S, T, M, or V; K527 replaced with H, or R; V529 replaced with A, G, I, L, S, T, or M; N530 replaced with Q; K531 replaced with H, or R; T532 replaced with A, G, I, L, S, M, or V; D533 replaced with E; R534 replaced with H, or K; K535 replaced with H, or R; H536 replaced with K, or R; F537 replaced with W, or Y; D538 replaced with E; T539 replaced with A, G, I, L, S, M, or V; F541 replaced with W, or Y; H542 replaced with K, or R; G543 replaced with A, I, L, S, T, M, or V; S544 replaced with A, G, I, L, T, M, or V; W545 replaced with F, or Y; G546 replaced with A, I, L, S, T, M, or V; M547 replaced with A, G, I, L, S, T, or V; W548 replaced with F, or Y; G549 replaced with A, I, L, S, T, M, or V; W551 replaced with F, or Y; G552 replaced with A, I, L, S, T, M, or V; D553 replaced with E; S555 replaced with A, G, I, L, T, M, or V; R556 replaced with H, or K; T557 replaced with A, G, I, L, S, M, or V; G559 replaced with A, I, L, S, T, M, or V; G560 replaced with A, I, L, S, T, M, or V; G561 replaced with A, I, L, S, T, M, or V; V562 replaced with A, G, I, L, S, T, or M; Q563 replaced with N; Y564 replaced with F, or W; T565 replaced with A, G, I, L, S, M, or V; M566 replaced with A, G, I, L, S, T, or V; R567 replaced with H, or K; E568 replaced with D; D570 replaced with E; N571 replaced with Q; V573 replaced with A, G, I, L, S, T, or M; K575 replaced with H, or R; N576 replaced with Q; G577 replaced with A, I, L, S, T, M, or V; G578 replaced with A, I, L, S, T, M, or V; K579 replaced with H, or R; Y580 replaced with F, or W; E582 replaced with D; G583 replaced with A, I, L, S, T, M, or V; K584 replaced with H, or R; R585 replaced with H, or K; V586 replaced with A, G, I, L, S, T, or M; R587 replaced with H, or K; Y588 replaced with F, or W; R589 replaced with H, or K; S590 replaced with A, G, I, L, T, M, or V; N592 replaced with Q; L593 replaced with A, G, I, S, T, M, or V; E594 replaced with D; D595 replaced with E; D598 replaced with E; N599 replaced with Q; N600 replaced with Q; G601 replaced with A, I, L, S, T, M, or V; K602 replaced with H, or R; T603 replaced with A, G, I, L, S, M, or V; F604 replaced with W, or Y; R605 replaced with H, or K; E606 replaced with D; E607 replaced with D; Q608 replaced with N; E610 replaced with D; A611 replaced with G, I, L, S, T, M, or V; H612 replaced with K, or R; N613 replaced with Q; E614 replaced with D; F615 replaced with W, or Y; S616 replaced with A, G, I, L, T, M, or V; K617 replaced with H, or R; A618 replaced with G, I, L, S, T, M, or V; S619 replaced with A, G, I, L, T, M, or V; F620 replaced with W, or Y; G621 replaced with A, I, L, S, T, M, or V; S622 replaced with A, G, I, L, T, M, or V; G623 replaced with A, I, L, S, T, M, or V; A625 replaced with G, I, L, S, T, M, or V; V626 replaced with A, G, I, L, S, T, or M; E627 replaced with D; W628 replaced with F, or Y; I629 replaced with A, G, L, S, T, M, or V; K631 replaced with H, or R; Y632 replaced with F, or W; A633 replaced with G, I, L, S, T, M, or V; G634 replaced with A, I, L, S, T, M, or V; V635 replaced with A, G, I, L, S, T, or M; S636 replaced with A, G, I, L, T, M, or V; K638 replaced with H, or R; D639 replaced with E; R640 replaced with H, or K; K642 replaced with H, or R; L643 replaced with A, G, I, S, T, M, or V; I644 replaced with A, G, L, S, T, M, or V; Q646 replaced with N; A647 replaced with G, I, L, S, T, M, or V; K648 replaced with H, or R; G649 replaced with A, I, L, S, T, M, or V; I650 replaced with A, G, L, S, T, M, or V; G651 replaced with A, I, L, S, T, M, or V; Y652 replaced with F, or W; F653 replaced with W, or Y; F654 replaced with W, or Y; V655 replaced with A, G, I, L, S, T, or M; L656 replaced with A, G, I, S, T, M, or V; Q657 replaced with N; K659 replaced with H, or R; V660 replaced with A, G, I, L, S, T, or M; V661 replaced with A, G, I, L, S, T, or M; D662 replaced with E; G663 replaced with A, I, L, S, T, M, or V; T664 replaced with A, G, I, L, S, M, or V; S667 replaced with A, G, I, L, T, M, or V; D669 replaced with E; S670 replaced with A, G, I, L, T, M, or V; T671 replaced with A, G, I, L, S, M, or V; S672 replaced with A, G, I, L, T, M, or V; V673 replaced with A, G, I, L, S, T, or M; V675 replaced with A, G, I, L, S, T, or M; Q676 replaced with N; G677 replaced with A, I, L, S, T, M, or V; Q678 replaced with N; V680 replaced with A, G, I, L, S, T, or M; K681 replaced with H, or R; A682 replaced with G, I, L, S, T, M, or V; G683 replaced with A, I, L, S, T, M, or V; D685 replaced with E; R686 replaced with H, or K; I687 replaced with A, G, L, S, T, M, or V; I688 replaced with A, G, L, S, T, M, or V; D689 replaced with E; S690 replaced with A, G, I, L, T, M, or V; K691 replaced with H, or R; K692 replaced with H, or R; K693 replaced with H, or R; F694 replaced with W, or Y; D695 replaced with E; K696 replaced with H, or R; G698 replaced with A, I, L, S, T, M, or V; V699 replaced with A, G, I, L, S, T, or M; G701 replaced with A, I, L, S, T, M, or V; G702 replaced with A, I, L, S, T, M, or V; N703 replaced with Q; G704 replaced with A, I, L, S, T, M, or V; S705 replaced with A, G, I, L, T, M, or V; T706 replaced with A, G, I, L, S, M, or V; K708 replaced with H, or R; K709 replaced with H, or R; I710 replaced with A, G, L, S, T, M, or V; S711 replaced with A, G, I, L, T, M, or V; G712 replaced with A, G, L, S, T, M, or V; S713 replaced with A, G, I, L, T, M, or V; V714 replaced with A, G, I, L, S, T, or M; T715 replaced with A, G, I, L, S, M, or V; S716 replaced with A, G, I, L, T, M, or V; A717 replaced with G, I, L, S, T, M, or V; K718 replaced with H, or R; G720 replaced with A, I, L, S, T, M, or V; Y721 replaced with F, or W; H722 replaced with K, or R; D723 replaced with E; I724 replaced with A, G, L, S, T, M, or V; I725 replaced with A, G, L, S, T, M, or V; T726 replaced with A, G, I, L, S, M, or V; I727 replaced with A, G, L, S, T, M, or V; T729 replaced with A, G, I, L, S, M, or V; G730 replaced with A, G, L, S, T, M, or V; A731 replaced with G, I, L, S, T, M, or V; T732 replaced with A, G, I, L, S, M, or V; N733 replaced with Q; I734 replaced with A, G, L, S, T, M, or V; E735 replaced with D; V736 replaced with A, G, I, L, S, T, or M; K737 replaced with H, or R; Q738 replaced with N; R739 replaced with H, or K; N740 replaced with Q; Q741 replaced with N; R742 replaced with H, or K; G743 replaced with A, I, L, S, T, M, or V; S744 replaced with A, G, I, L, T, M, or V; R745 replaced with H, or K; N746 replaced with Q; N747 replaced with Q; G748 replaced with A, I, L, S, T, M, or V; S749 replaced with A, G, I, L, T, M, or V; F750 replaced with W, or Y; L751 replaced with A, G, I, S, T, M, or V; A752 replaced with G, I, L, S, T, M, or V; I753 replaced with A, G, L, S, T, M, or V; K754 replaced with H, or R; A755 replaced with G, I, L, S, T, M, or V; A756 replaced with G, I, L, S, T, M, or V; D757 replaced with E; G758 replaced with A, I, L, S, T, M, or V; T759 replaced with A, G, I, L, S, M, or V; Y760 replaced with F, or W; I761 replaced with A, G, L, S, T, M, or V; L762 replaced with A, G, I, S, T, M, or V; N763 replaced with Q; G764 replaced with A, I, L, S, T, M, or V; D765 replaced with E; Y766 replaced with F, or W; T767 replaced with A, G, I, L, S, M, or V; L768 replaced with A, G, I, S, T, M, or V; S769 replaced with A, G, I, L, T, M, or V; T770 replaced with A, G, I, L, S, M, or V; L771 replaced with A, G, I, S, T, M, or V; E772 replaced with D; Q773 replaced with N; D774 replaced with E; I775 replaced with A, G, L, S, T, M, or V; M776 replaced with A, G, I, L, S, T, or V; Y777 replaced with F, or W; K778 replaced with H, or R; G779 replaced with A, I, L, S, T, M, or V; V780 replaced with A, G, I, L, S, T, or M; V781 replaced with A, G, I, L, S, T, or M; L782 replaced with A, G, I, S, T, M, or V; R783 replaced with H, or K; Y784 replaced with F, or W; S785 replaced with A, G, I, L, T, M, or V; G786 replaced with A, I, L, S, T, M, or V; S787 replaced with A, G, I, L, T, M, or V; S788 replaced with A, G, I, L, T, M, or V; A789 replaced with G, I, L, S, T, M, or V; A790 replaced with G, I, L, S, T, M, or V; L791 replaced with A, G, I, S, T, M, or V; E792 replaced with D; R793 replaced with H, or K; I794 replaced with A, G, L, S, T, M, or V; R795 replaced with H, or K; S796 replaced with A, G, I, L, T, M, or V; F797 replaced with W, or Y; S798 replaced with A, G, I, L, T, M, or V; L800 replaced with A, G, I, S, T, M, or V; K801 replaced with H, or R; E802 replaced with D; L804 replaced with A, G, I, S, T, M, or V; T805 replaced with A, G, I, L, S, M, or V; I806 replaced with A, G, L, S, T, M, or V; Q807 replaced with N; V808 replaced with A, G, I, L, S, T, or M; L809 replaced with A, G, I, S, T, M, or V; T810 replaced with A, G, I, L, S, M, or V; V811 replaced with A, G, I, L, S, T, or M; G812 replaced with A, I, L, S, T, M, or V; N813 replaced with Q; A814 replaced with G, I, L, S, T, M, or V; L815 replaced with A, G, I, S, T, M, or V; R816 replaced with H, or K; K818 replaced with H, or R; I819 replaced with A, G, L, S, T, M, or V; K820 replaced with H, or R; Y821 replaced with F, or W; T822 replaced with A, G, I, L, S, M, or V; Y823 replaced with F, or W; F824 replaced with W, or Y; V825 replaced with A, G, I, L, S, T, or M; K826 replaced with H, or R; K827 replaced with H, or R; K828 replaced with H, or R; K829 replaced with H, or R; E830 replaced with D; S831 replaced with A, G, I, L, T, M, or V; F832 replaced with W, or Y; N833 replaced with Q; A834 replaced with G, I, L, S, T, M, or V; I835 replaced with A, G, L, S, T, M, or V; T837 replaced with A, G, I, L, S, M, or V; F838 replaced with W, or Y; S839 replaced with A, G, I, L, T, M, or V; A840 replaced with G, I, L, S, T, M, or V; W841 replaced with F, or Y; V842 replaced with A, G, I, L, S, T, or M; I843 replaced with A, G, L, S, T, M, or V; E844 replaced with D; E845 replaced with D; W846 replaced with F, or Y; G847 replaced with A, I, L, S, T, M, or V; E848 replaced with D; S850 replaced with A, G, I, L, T, M, or V; K851 replaced with H, or R; S852 replaced with A, G, I, L, T, M, or V; E854 replaced with D; L855 replaced with A, G, I, S, T, M, or V; G856 replaced with A, I, L, S, T, M, or V; W857 replaced with F, or Y; Q858 replaced with N; R859 replaced with H, or K; R860 replaced with H, or K; L861 replaced with A, G, I, S, T, M, or V; V862 replaced with A, G, I, L, S, T, or M; E863 replaced with D; R865 replaced with H, or K; D866 replaced with E; I867 replaced with A, G, L, S, T, M, or V; N868 replaced with Q; G869 replaced with A, I, L, S, T, M, or V; Q870 replaced with N; A872 replaced with G, I, L, S, T, M, or V; S873 replaced with A, G, I, L, T, M, or V; E874 replaced with D; A876 replaced with G, I, L, S, T, M, or V; K877 replaced with H, or R; E878 replaced with D; V879 replaced with A, G, I, L, S, T, or M; K880 replaced with H, or R; A882 replaced with G, I, L, S, T, M, or V; S883 replaced with A, G, I, L, T, M, or V; T884 replaced with A, G, I, L, S, M, or V; R885 replaced with H, or K; A888 replaced with G, I, L, S, T, M, or V; D889 replaced with E; H890 replaced with K, or R; Q894 replaced with N; W895 replaced with F, or Y; Q896 replaced with N; L897 replaced with A, G, I, S, T, M, or V; G898 replaced with A, I, L, S, T, M, or V; E899 replaced with D; W900 replaced with F, or Y; S901 replaced with A, G, I, L, T, M, or V; S902 replaced with A, G, I, L, T, M, or V; S904 replaced with A, G, I, L, T, M, or V; K905 replaced with H, or R; T906 replaced with A, G, I, L, S, M, or V; G908 replaced with A, I, L, S, T, M, or V; K909 replaced with H, or R; G910 replaced with A, I, L, S, T, M, or V; Y911 replaced with F, or W; K912 replaced with H, or R; K913 replaced with H, or R; R914 replaced with H, or K; S915 replaced with A, G, I, L, T, M, or V; L916 replaced with A, G, I, S, T, M, or V; K917 replaced with H, or R; L919 replaced with A, G, I, S, T, M, or V; S920 replaced with A, G, I, L, T, M, or V; H921 replaced with K, or R; D922 replaced with E; G923 replaced with A, I, L, S, T, M, or V; G924 replaced with A, I, L, S, T, M, or V; V925 replaced with A, G, I, L, S, T, or M; L926 replaced with A, G, I, S, T, M, or V; S927 replaced with A, G, I, L, T, M, or V; H928 replaced with K, or R; E929 replaced with D; S930 replaced with A, G, I, L, T, M, or V; D932 replaced with E; L934 replaced with A, G, I, S, T, M, or V; K935 replaced with H, or R; K936 replaced with H, or R; K938 replaced with H, or R; H939 replaced with K, or R; F940 replaced with W, or Y; I941 replaced with A, G, L, S, T, M, or V; D942 replaced with E; F943 replaced with W, or Y; T945 replaced with A, G, I, L, S, M, or V; M946 replaced with A, G, I, L, S, T, or V; A947 replaced with G, I, L, S, T, M, or V; E948 replaced with D; S950 replaced with A, G, I, L, T, M, or V.

Also preferred are METH1 polypeptides with one or more of the following non-conservative substitutions: M1 replaced with D, E, H, K, R, N, Q, F, W, Y, P, or C; G2 replaced with D, E, H, K, R, N, Q, F, W, Y, P, or C; N3 replaced with D, E, H, K, R, A, G, I, L, S, T, M, V, F, W, Y, P, or C; A4 replaced with D, E, H, K, R, N, Q, F, W, Y, P, or C; E5 replaced with H, K, R, A, G, I, L, S, T, M, V, N, Q, F, W, Y, P, or C; R6 replaced with D, E, A, G, I, L, S, T, M, V, N, Q, F, W, Y, P, or C; A7 replaced with D, E, H, K, R, N, Q, F, W, Y, P, or C; P8 replaced with D, E, H, K, R, A, G, I, L, S, T, M, V, N, Q, F, W, Y, or C; G9 replaced with D, E, H, K, R, N, Q, F, W, Y, P, or C; S10 replaced with D, E, H, K, R, N, Q, F, W, Y, P, or C; R11 replaced with D, E, A, G, I, L, S, T, M, V, N, Q, F, W, Y, P, or C; S12 replaced with D, E, H, K, R, N, Q, F, W, Y, P, or C; F13 replaced with D, E, H, K, R, N, Q, A, G, I, L, S, T, M, V, P, or C; G14 replaced with D, E, H, K, R, N, Q, F, W, Y, P, or C; P15 replaced with D, E, H, K, R, A, G, I, L, S, T, M, V, N, Q, F, W, Y, or C; V16 replaced with D, E, H, K, R, N, Q, F, W, Y, P, or C; P17 replaced with D, E, H, K, R, A, G, I, L, S, T, M, V, N, Q, F, W, Y, or C; T18 replaced with D, E, H, K, R, N, Q, F, W, Y, P, or C; L19 replaced with D, E, H, K, R, N, Q, F, W, Y, P, or C; L20 replaced with D, E, H, K, R, N, Q, F, W, Y, P, or C; L21 replaced with D, E, H, K, R, N, Q, F, W, Y, P, or C; L22 replaced with D, E, H, K, R, N, Q, F, W, Y, P, or C; A23 replaced with D, E, H, K, R, N, Q, F, W, Y, P, or C; A24 replaced with D, E, H, K, R, N, Q, F, W, Y, P, or C; A25 replaced with D, E, H, K, R, N, Q, F, W, Y, P, or C; L26 replaced with D, E, H, K, R, N, Q, F, W, Y, P, or C; L27 replaced with D, E, H, K, R, N, Q, F, W, Y, P, or C; A28 replaced with D, E, H, K, R, N, Q, F, W, Y, P, or C; V29 replaced with D, E, H, K, R, N, Q, F, W, Y, P, or C; S30 replaced with D, E, H, K, R, N, Q, F, W, Y, P, or C; D31 replaced with H, K, R, A, G, I, L, S, T, M, V, N, Q, F, W, Y, P, or C; A32 replaced with D, E, H, K, R, N, Q, F, W, Y, P, or C; L33 replaced with D, E, H, K, R, N, Q, F, W, Y, P, or C; G34 replaced with D, E, H, K, R, N, Q, F, W, Y, P, or C; R35 replaced with D, E, A, G, I, L, S, T, M, V, N, Q, F, W, Y, P, or C; P36 replaced with D, E, H, K, R, A, G, I, L, S, T, M, V, N, Q, F, W, Y, or C; S37 replaced with D, E, H, K, R, N, Q, F, W, Y, P, or C; E38 replaced with H, K, R, A, G, I, L, S, T, M, V, N, Q, F, W, Y, P, or C; E39 replaced with H, K, R, A, G, I, L, S, T, M, V, N, Q, F, W, Y, P, or C; D40 replaced with H, K, R, A, G, I, L, S, T, M, V, N, Q, F, W, Y, P, or C; E41 replaced with H, K, R, A, G, I, L, S, T, M, V, N, Q, F, W, Y, P, or C; E42 replaced with H, K, R, A, G, I, L, S, T, M, V, N, Q, F, W, Y, P, or C; L43 replaced with D, E, H, K, R, N, Q, F, W, Y, P, or C; V44 replaced with D, E, H, K, R, N, Q, F, W, Y, P, or C; V45 replaced with D, E, H, K, R, N, Q, F, W, Y, P, or C; P46 replaced with D, E, H, K, R, A, G, I, L, S, T, M, V, N, Q, F, W, Y, or C; E47 replaced with H, K, R, A, G, I, L, S, T, M, V, N, Q, F, W, Y, P, or C; L48 replaced with D, E, H, K, R, N, Q, F, W, Y, P, or C; E49 replaced with H, K, R, A, G, I, L, S, T, M, V, N, Q, F, W, Y, P, or C; R50 replaced with D, E, A, G, I, L, S, T, M, V, N, Q, F, W, Y, P, or C; A51 replaced with D, E, H, K, R, N, Q, F, W, Y, P, or C; P52 replaced with D, E, H, K, R, A, G, I, L, S, T, M, V, N, Q, F, W, Y, or C; G53 replaced with D, E, H, K, R, N, Q, F, W, Y, P, or C; H54 replaced with D, E, A, G, I, L, S, T, M, V, N, Q, F, W, Y, P, or C; G55 replaced with D, E, H, K, R, N, Q, F, W, Y, P, or C; T56 replaced with D, E, H, K, R, N, Q, F, W, Y, P, or C; T57 replaced with D, E, H, K, R, N, Q, F, W, Y, P, or C; R58 replaced with D, E, A, G, I, L, S, T, M, V, N, Q, F, W, Y, P, or C; L59 replaced with D, E, H, K, R, N, Q, F, W, Y, P, or C; R60 replaced with D, E, A, G, I, L, S, T, M, V, N, Q, F, W, Y, P, or C; L61 replaced with D, E, H, K, R, N, Q, F, W, Y, P, or C; H62 replaced with D, E, A, G, I, L, S, T, M, V, N, Q, F, W, Y, P, or C; A63 replaced with D, E, H, K, R, N, Q, F, W, Y, P, or C; F64 replaced with D, E, H, K, R, N, Q, A, G, I, L, S, T, M, V, P, or C; D65 replaced with H, K, R, A, G, I, L, S, T, M, V, N, Q, F, W, Y, P, or C; Q66 replaced with D, E, H, K, R, A, G, I, L, S, T, M, V, F, W, Y, P, or C; Q67 replaced with D, E, H, K, R, A, G, I, L, S, T, M, V, F, W, Y, P, or C; L68 replaced with D, E, H, K, R, N, Q, F, W, Y, P, or C; D69 replaced with H, K, R, A, G, I, L, S, T, M, V, N, Q, F, W, Y, P, or C; L70 replaced with D, E, H, K, R, N, Q, F, W, Y, P, or C; E71 replaced with H, K, R, A, G, I, L, S, T, M, V, N, Q, F, W, Y, P, or C; L72 replaced with D, E, H, K, R, N, Q, F, W, Y, P, or C; R73 replaced with D, E, A, G, I, L, S, T, M, V, N, Q, F, W, Y, P, or C; P74 replaced with D, E, H, K, R, A, G, I, L, S, T, M, V, N, Q, F, W, Y, or C; D75 replaced with H, K, R, A, G, I, L, S, T, M, V, N, Q, F, W, Y, P, or C; S76 replaced with D, E, H, K, R, N, Q, F, W, Y, P, or C; S77 replaced with D, E, H, K, R, N, Q, F, W, Y, P, or C; F78 replaced with D, E, H, K, R, N, Q, A, G, I, L, S, T, M, V, P, or C; L79 replaced with D, E, H, K, R, N, Q, F, W, Y, P, or C; A80 replaced with D, E, H, K, R, N, Q, F, W, Y, P, or C; P81 replaced with D, E, H, K, R, A, G, I, L, S, T, M, V, N, Q, F, W, Y, or C; G82 replaced with D, E, H, K, R, N, Q, F, W, Y, P, or C; F83 replaced with D, E, H, K, R, N, Q, A, G, I, L, S, T, M, V, P, or C; T84 replaced with D, E, H, K, R, N, Q, F, W, Y, P, or C; L85 replaced with D, E, H, K, R, N, Q, F, W, Y, P, or C; Q86 replaced with D, E, H, K, R, A, G, I, L, S, T, M, V, F, W, Y, P, or C; N87 replaced with D, E, H, K, R, A, G, I, L, S, T, M, V, F, W, Y, P, or C; V88 replaced with D, E, H, K, R, N, Q, F, W, Y, P, or C; G89 replaced with D, E, H, K, R, N, Q, F, W, Y, P, or C; R90 replaced with D, E, A, G, I, L, S, T, M, V, N, Q, F, W, Y, P, or C; K91 replaced with D, E, A, G, I, L, S, T, M, V, N, Q, F, W, Y, P, or C; S92 replaced with D, E, H, K, R, N, Q, F, W, Y, P, or C; G93 replaced with D, E, H, K, R, N, Q, F, W, Y, P, or C; S94 replaced with D, E, H, K, R, N, Q, F, W, Y, P, or C; E95 replaced with H, K, R, A, G, I, L, S, T, M, V, N, Q, F, W, Y, P, or C; T96 replaced with D, E, H, K, R, N, Q, F, W, Y, P, or C; P97 replaced with D, E, H, K, R, A, G, I, L, S, T, M, V, N, Q, F, W, Y, or C; L98 replaced with D, E, H, K, R, N, Q, F, W, Y, P, or C; P99 replaced with D, E, H, K, R, A, G, I, L, S, T, M, V, N, Q, F, W, Y, or C; E100 replaced with H, K, R, A, G, I, L, S, T, M, V, N, Q, F, W, Y, P, or C; T101 replaced with D, E, H, K, R, N, Q, F, W, Y, P, or C; D102 replaced with H, K, R, A, G, I, L, S, T, M, V, N, Q, F, W, Y, P, or C; L103 replaced with D, E, H, K, R, N, Q, F, W, Y, P, or C; A104 replaced with D, E, H, K, R, N, Q, F, W, Y, P, or C; H105 replaced with D, E, A, G, I, L, S, T, M, V, N, Q, F, W, Y, P, or C; C106 replaced with D, E, H, K, R, A, G, I, L, S, T, M, V, N, Q, F, W, Y, or P; F107 replaced with D, E, H, K, R, N, Q, A, G, I, L, S, T, M, V, P, or C; Y108 replaced with D, E, H, K, R, N, Q, A, G, I, L, S, T, M, V, P, or C; S109 replaced with D, E, H, K, R, N, Q, F, W, Y, P, or C; G110 replaced with D, E, H, K, R, N, Q, F, W, Y, P, or C; T111 replaced with D, E, H, K, R, N, Q, F, W, Y, P, or C; V112 replaced with D, E, H, K, R, N, Q, F, W, Y, P, or C; N113 replaced with D, E, H, K, R, A, G, I, L, S, T, M, V, F, W, Y, P, or C; G114 replaced with D, E, H, K, R, N, Q, F, W, Y, P, or C; D115 replaced with H, K, R, A, G, I, L, S, T, M, V, N, Q, F, W, Y, P, or C; P116 replaced with D, E, H, K, R, A, G, I, L, S, T, M, V, N, Q, F, W, Y, or C; S117 replaced with D, E, H, K, R, N, Q, F, W, Y, P, or C; S118 replaced with D, E, H, K, R, N, Q, F, W, Y, P, or C; A119 replaced with D, E, H, K, R, N, Q, F, W, Y, P, or C; A120 replaced with D, E, H, K, R, N, Q, F, W, Y, P, or C; A121 replaced with D, E, H, K, R, N, Q, F, W, Y, P, or C; L122 replaced with D, E, H, K, R, N, Q, F, W, Y, P, or C; S123 replaced with D, E, H, K, R, N, Q, F, W, Y, P, or C; L124 replaced with D, E, H, K, R, N, Q, F, W, Y, P, or C; C125 replaced with D, E, H, K, R, A, G, I, L, S, T, M, V, N, Q, F, W, Y, or P; E126 replaced with H, K, R, A, G, I, L, S, T, M, V, N, Q, F, W, Y, P, or C; G127 replaced with D, E, H, K, R, N, Q, F, W, Y, P, or C; V128 replaced with D, E, H, K, R, N, Q, F, W, Y, P, or C; R129 replaced with D, E, A, G, I, L, S, T, M, V, N, Q, F, W, Y, P, or C; G130 replaced with D, E, H, K, R, N, Q, F, W, Y, P, or C; A131 replaced with D, E, H, K, R, N, Q, F, W, Y, P, or C; F132 replaced with D, E, H, K, R, N, Q, A, G, I, L, S, T, M, V, P, or C; Y133 replaced with D, E, H, K, R, N, Q, A, G, I, L, S, T, M, V, P, or C; L134 replaced with D, E, H, K, R, N, Q, F, W, Y, P, or C; L135 replaced with D, E, H, K, R, N, Q, F, W, Y, P, or C; G136 replaced with D, E, H, K, R, N, Q, F, W, Y, P, or C; E137 replaced with H, K, R, A, G, I, L, S, T, M, V, N, Q, F, W, Y, P, or C; A138 replaced with D, E, H, K, R, N, Q, F, W, Y, P, or C; Y139 replaced with D, E, H, K, R, N, Q, A, G, I, L, S, T, M, V, P, or C; F140 replaced with D, E, H, K, R, N, Q, A, G, I, L, S, T, M, V, P, or C; I141 replaced with D, E, H, K, R, N, Q, F, W, Y, P, or C; Q142 replaced with D, E, H, K, R, A, G, I, L, S, T, M, V, F, W, Y, P, or C; P143 replaced with D, E, H, K, R, A, G, I, L, S, T, M, V, N, Q, F, W, Y, or C; L144 replaced with D, E, H, K, R, N, Q, F, W, Y, P, or C; P145 replaced with D, E, H, K, R, A, G, I, L, S, T, M, V, N, Q, F, W, Y, or C; A146 replaced with D, E, H, K, R, N, Q, F, W, Y, P, or C; A147 replaced with D, E, H, K, R, N, Q, F, W, Y, P, or C; S148 replaced with D, E, H, K, R, N, Q, F, W, Y, P, or C; E149 replaced with H, K, R, A, G, I, L, S, T, M, V, N, Q, F, W, Y, P, or C; R150 replaced with D, E, A, G, I, L, S, T, M, V, N, Q, F, W, Y, P, or C; L151 replaced with D, E, H, K, R, N, Q, F, W, Y, P, or C; A152 replaced with D, E, H, K, R, N, Q, F, W, Y, P, or C; T153 replaced with D, E, H, K, R, N, Q, F, W, Y, P, or C; A154 replaced with D, E, H, K, R, N, Q, F, W, Y, P, or C; A155 replaced with D, E, H, K, R, N, Q, F, W, Y, P, or C; P156 replaced with D, E, H, K, R, A, G, I, L, S, T, M, V, N, Q, F, W, Y, or C; G157 replaced with D, E, H, K, R, N, Q, F, W, Y, P, or C; E158 replaced with H, K, R, A, G, I, L, S, T, M, V, N, Q, F, W, Y, P, or C; K159 replaced with D, E, A, G, I, L, S, T, M, V, N, Q, F, W, Y, P, or C; P160 replaced with D, E, H, K, R, A, G, I, L, S, T, M, V, N, Q, F, W, Y, or C; P161 replaced with D, E, H, K, R, A, G, I, L, S, T, M, V, N, Q, F, W, Y, or C; A162 replaced with D, E, H, K, R, N, Q, F, W, Y, P, or C; P163 replaced with D, E, H, K, R, A, G, I, L, S, T, M, V, N, Q, F, W, Y, or C; L164 replaced with D, E, H, K, R, N, Q, F, W, Y, P, or C; Q165 replaced with D, E, H, K, R, A, G, I, L, S, T, M, V, F, W, Y, P, or C; F166 replaced with D, E, H, K, R, N, Q, A, G, I, L, S, T, M, V, P, or C; H167 replaced with D, E, A, G, I, L, S, T, M, V, N, Q, F, W, Y, P, or C; L168 replaced with D, E, H, K, R, N, Q, F, W, Y, P, or C; L169 replaced with D, E, H, K, R, N, Q, F, W, Y, P, or C; R170 replaced with D, E, A, G, I, L, S, T, M, V, N, Q, F, W, Y, P, or C; R171 replaced with D, E, A, G, I, L, S, T, M, V, N, Q, F, W, Y, P, or C; N172 replaced with D, E, H, K, R, A, G, I, L, S, T, M, V, F, W, Y, P, or C; R173 replaced with D, E, A, G, I, L, S, T, M, V, N, Q, F, W, Y, P, or C; Q174 replaced with D, E, H, K, R, A, G, I, L, S, T, M, V, F, W, Y, P, or C; G175 replaced with D, E, H, K, R, N, Q, F, W, Y, P, or C; D176 replaced with H, K, R, A, G, I, L, S, T, M, V, N, Q, F, W, Y, P, or C; V177 replaced with D, E, H, K, R, N, Q, F, W, Y, P, or C; G178 replaced with D, E, H, K, R, N, Q, F, W, Y, P, or C; G179 replaced with D, E, H, K, R, N, Q, F, W, Y, P, or C; T180 replaced with D, E, H, K, R, N, Q, F, W, Y, P, or C; C181 replaced with D, E, H, K, R, A, G, I, L, S, T, M, V, N, Q, F, W, Y, or P; G182 replaced with D, E, H, K, R, N, Q, F, W, Y, P, or C; V183 replaced with D, E, H, K, R, N, Q, F, W, Y, P, or C; V184 replaced with D, E, H, K, R, N, Q, F, W, Y, P, or C; D185 replaced with H, K, R, A, G, I, L, S, T, M, V, N, Q, F, W, Y, P, or C; D186 replaced with H, K, R, A, G, I, L, S, T, M, V, N, Q, F, W, Y, P, or C; E187 replaced with H, K, R, A, G, I, L, S, T, M, V, N, Q, F, W, Y, P, or C; P188 replaced with D, E, H, K, R, A, G, I, L, S, T, M, V, N, Q, F, W, Y, or C; R189 replaced with D, E, A, G, I, L, S, T, M, V, N, Q, F, W, Y, P, or C; P190 replaced with D, E, H, K, R, A, G, I, L, S, T, M, V, N, Q, F, W, Y, or C; T191 replaced with D, E, H, K, R, N, Q, F, W, Y, P, or C; G192 replaced with D, E, H, K, R, N, Q, F, W, Y, P, or C; K193 replaced with D, E, A, G, I, L, S, T, M, V, N, Q, F, W, Y, P, or C; A194 replaced with D, E, H, K, R, N, Q, F, W, Y, P, or C; E195 replaced with H, K, R, A, G, I, L, S, T, M, V, N, Q, F, W, Y, P, or C; T196 replaced with D, E, H, K, R, N, Q, F, W, Y, P, or C; E197 replaced with H, K, R, A, G, I, L, S, T, M, V, N, Q, F, W, Y, P, or C; D198 replaced with H, K, R, A, G, I, L, S, T, M, V, N, Q, F, W, Y, P, or C; E199 replaced with H, K, R, A, G, I, L, S, T, M, V, N, Q, F, W, Y, P, or C; D200 replaced with H, K, R, A, G, I, L, S, T, M, V, N, Q, F, W, Y, P, or C; E201 replaced with H, K, R, A, G, I, L, S, T, M, V, N, Q, F, W, Y, P, or C; G202 replaced with D, E, H, K, R, N, Q, F, W, Y, P, or C; T203 replaced with D, E, H, K, R, N, Q, F, W, Y, P, or C; E204 replaced with H, K, R, A, G, I, L, S, T, M, V, N, Q, F, W, Y, P, or C; G205 replaced with D, E, H, K, R, N, Q, F, W, Y, P, or C; E206 replaced with H, K, R, A, G, I, L, S, T, M, V, N, Q, F, W, Y, P, or C; D207 replaced with H, K, R, A, G, I, L, S, T, M, V, N, Q, F, W, Y, P, or C; E208 replaced with H, K, R, A, G, I, L, S, T, M, V, N, Q, F, W, Y, P, or C; G209 replaced with D, E, H, K, R, N, Q, F, W, Y, P, or C; P210 replaced with D, E, H, K, R, A, G, I, L, S, T, M, V, N, Q, F, W, Y, or C; Q211 replaced with D, E, H, K, R, A, G, I, L, S, T, M, V, F, W, Y, P, or C; W212 replaced with D, E, H, K, R, N, Q, A, G, I, L, S, T, M, V, P, or C; S213 replaced with D, E, H, K, R, N, Q, F, W, Y, P, or C; P214 replaced with D, E, H, K, R, A, G, I, L, S, T, M, V, N, Q, F, W, Y, or C; Q215 replaced with D, E, H, K, R, A, G, I, L, S, T, M, V, F, W, Y, P, or C; D216 replaced with H, K, R, A, G, I, L, S, T, M, V, N, Q, F, W, Y, P, or C; P217 replaced with D, E, H, K, R, A, G, I, L, S, T, M, V, N, Q, F, W, Y, or C; A218 replaced with D, E, H, K, R, N, Q, F, W, Y, P, or C; L219 replaced with D, E, H, K, R, N, Q, F, W, Y, P, or C; Q220 replaced with D, E, H, K, R, A, G, I, L, S, T, M, V, F, W, Y, P, or C; G221 replaced with D, E, H, K, R, N, Q, F, W, Y, P, or C; V222 replaced with D, E, H, K, R, N, Q, F, W, Y, P, or C; G223 replaced with D, E, H, K, R, N, Q, F, W, Y, P, or C; Q224 replaced with D, E, H, K, R, A, G, I, L, S, T, M, V, F, W, Y, P, or C; P225 replaced with D, E, H, K, R, A, G, I, L, S, T, M, V, N, Q, F, W, Y, or C; T226 replaced with D, E, H, K, R, N, Q, F, W, Y, P, or C; G227 replaced with D, E, H, K, R, N, Q, F, W, Y, P, or C; T228 replaced with D, E, H, K, R, N, Q, F, W, Y, P, or C; G229 replaced with D, E, H, K, R, N, Q, F, W, Y, P, or C; S230 replaced with D, E, H, K, R, N, Q, F, W, Y, P, or C; I231 replaced with D, E, H, K, R, N, Q, F, W, Y, P, or C; R232 replaced with D, E, A, G, I, L, S, T, M, V, N, Q, F, W, Y, P, or C; K233 replaced with D, E, A, G, I, L, S, T, M, V, N, Q, F, W, Y, P, or C; K234 replaced with D, E, A, G, I, L, S, T, M, V, N, Q, F, W, Y, P, or C; R235 replaced with D, E, A, G, I, L, S, T, M, V, N, Q, F, W, Y, P, or C; F236 replaced with D, E, H, K, R, N, Q, A, G, I, L, S, T, M, V, P, or C; V237 replaced with D, E, H, K, R, N, Q, F, W, Y, P, or C; S238 replaced with D, E, H, K, R, N, Q, F, W, Y, P, or C; S239 replaced with D, E, H, K, R, N, Q, F, W, Y, P, or C; H240 replaced with D, E, A, G, I, L, S, T, M, V, N, Q, F, W, Y, P, or C; R241 replaced with D, E, A, G, I, L, S, T, M, V, N, Q, F, W, Y, P, or C; Y242 replaced with D, E, H, K, R, N, Q, A, G, I, L, S, T, M, V, P, or C; V243 replaced with D, E, H, K, R, N, Q, F, W, Y, P, or C; E244 replaced with H, K, R, A, G, I, L, S, T, M, V, N, Q, F, W, Y, P, or C; T245 replaced with D, E, H, K, R, N, Q, F, W, Y, P, or C; M246 replaced with D, E, H, K, R, N, Q, F, W, Y, P, or C; L247 replaced with D, E, H, K, R, N, Q, F, W, Y, P, or C; V248 replaced with D, E, H, K, R, N, Q, F, W, Y, P, or C; A249 replaced with D, E, H, K, R, N, Q, F, W, Y, P, or C; D250 replaced with H, K, R, A, G, I, L, S, T, M, V, N, Q, F, W, Y, P, or C; Q251 replaced with D, E, H, K, R, A, G, I, L, S, T, M, V, F, W, Y, P, or C; S252 replaced with D, E, H, K, R, N, Q, F, W, Y, P, or C; M253 replaced with D, E, H, K, R, N, Q, F, W, Y, P, or C; A254 replaced with D, E, H, K, R, N, Q, F, W, Y, P, or C; E255 replaced with H, K, R, A, G, I, L, S, T, M, V, N, Q, F, W, Y, P, or C; F256 replaced with D, E, H, K, R, N, Q, A, G, I, L, S, T, M, V, P, or C; H257 replaced with D, E, A, G, I, L, S, T, M, V, N, Q, F, W, Y, P, or C; G258 replaced with D, E, H, K, R, N, Q, F, W, Y, P, or C; S259 replaced with D, E, H, K, R, N, Q, F, W, Y, P, or C; G260 replaced with D, E, H, K, R, N, Q, F, W, Y, P, or C; L261 replaced with D, E, H, K, R, N, Q, F, W, Y, P, or C; K262 replaced with D, E, A, G, I, L, S, T, M, V, N, Q, F, W, Y, P, or C; H263 replaced with D, E, A, G, I, L, S, T, M, V, N, Q, F, W, Y, P, or C; Y264 replaced with D, E, H, K, R, N, Q, A, G, I, L, S, T, M, V, P, or C; L265 replaced with D, E, H, K, R, N, Q, F, W, Y, P, or C; L266 replaced with D, E, H, K, R, N, Q, F, W, Y, P, or C; T267 replaced with D, E, H, K, R, N, Q, F, W, Y, P, or C; L268 replaced with D, E, H, K, R, N, Q, F, W, Y, P, or C; F269 replaced with D, E, H, K, R, N, Q, A, G, I, L, S, T, M, V, P, or C; S270 replaced with D, E, H, K, R, N, Q, F, W, Y, P, or C; V271 replaced with D, E, H, K, R, N, Q, F, W, Y, P, or C; A272 replaced with D, E, H, K, R, N, Q, F, W, Y, P, or C; A273 replaced with D, E, H, K, R, N, Q, F, W, Y, P, or C; R274 replaced with D, E, A, G, I, L, S, T, M, V, N, Q, F, W, Y, P, or C; L275 replaced with D, E, H, K, R, N, Q, F, W, Y, P, or C; Y276 replaced with D, E, H, K, R, N, Q, A, G, I, L, S, T, M, V, P, or C; K277 replaced with D, E, A, G, I, L, S, T, M, V, N, Q, F, W, Y, P, or C; H278 replaced with D, E, A, G, I, L, S, T, M, V, N, Q, F, W, Y, P, or C; P279 replaced with D, E, H, K, R, A, G, I, L, S, T, M, V, N, Q, F, W, Y, or C; S280 replaced with D, E, H, K, R, N, Q, F, W, Y, P, or C; I281 replaced with D, E, H, K, R, N, Q, F, W, Y, P, or C; R282 replaced with D, E, A, G, I, L, S, T, M, V, N, Q, F, W, Y, P, or C; N283 replaced with D, E, H, K, R, A, G, I, L, S, T, M, V, F, W, Y, P, or C; S284 replaced with D, E, H, K, R, N, Q, F, W, Y, P, or C; V285 replaced with D, E, H, K, R, N, Q, F, W, Y, P, or C; S286 replaced with D, E, H, K, R, N, Q, F, W, Y, P, or C; L287 replaced with D, E, H, K, R, N, Q, F, W, Y, P, or C; V288 replaced with D, E, H, K, R, N, Q, F, W, Y, P, or C; V289 replaced with D, E, H, K, R, N, Q, F, W, Y, P, or C; V290 replaced with D, E, H, K, R, N, Q, F, W, Y, P, or C; K291 replaced with D, E, A, G, I, L, S, T, M, V, N, Q, F, W, Y, P, or C; I292 replaced with D, E, H, K, R, N, Q, F, W, Y, P, or C; L293 replaced with D, E, H, K, R, N, Q, F, W, Y, P, or C; V294 replaced with D, E, H, K, R, N, Q, F, W, Y, P, or C; I295 replaced with D, E, H, K, R, N, Q, F, W, Y, P, or C; H296 replaced with D, E, A, G, I, L, S, T, M, V, N, Q, F, W, Y, P, or C; D297 replaced with H, K, R, A, G, I, L, S, T, M, V, N, Q, F, W, Y, P, or C; E298 replaced with H, K, R, A, G, I, L, S, T, M, V, N, Q, F, W, Y, P, or C; Q299 replaced with D, E, H, K, R, A, G, I, L, S, T, M, V, F, W, Y, P, or C; K300 replaced with D, E, A, G, I, L, S, T, M, V, N, Q, F, W, Y, P, or C; G301 replaced with D, E, H, K, R, N, Q, F, W, Y, P, or C; P302 replaced with D, E, H, K, R, A, G, I, L, S, T, M, V, N, Q, F, W, Y, or C; E303 replaced with H, K, R, A, G, I, L, S, T, M, V, N, Q, F, W, Y, P, or C; V304 replaced with D, E, H, K, R, N, Q, F, W, Y, P, or C; T305 replaced with D, E, H, K, R, N, Q, F, W, Y, P, or C; S306 replaced with D, E, H, K, R, N, Q, F, W, Y, P, or C; N307 replaced with D, E, H, K, R, A, G, I, L, S, T, M, V, F, W, Y, P, or C; A308 replaced with D, E, H, K, R, N, Q, F, W, Y, P, or C; A309 replaced with D, E, H, K, R, N, Q, F, W, Y, P, or C; L310 replaced with D, E, H, K, R, N, Q, F, W, Y, P, or C; T311 replaced with D, E, H, K, R, N, Q, F, W, Y, P, or C; L312 replaced with D, E, H, K, R, N, Q, F, W, Y, P, or C; R313 replaced with D, E, A, G, I, L, S, T, M, V, N, Q, F, W, Y, P, or C; N314 replaced with D, E, H, K, R, A, G, I, L, S, T, M, V, F, W, Y, P, or C; F315 replaced with D, E, H, K, R, N, Q, A, G, I, L, S, T, M, V, P, or C; C316 replaced with D, E, H, K, R, A, G, I, L, S, T, M, V, N, Q, F, W, Y, or P; N317 replaced with D, E, H, K, R, A, G, I, L, S, T, M, V, F, W, Y, P, or C; W318 replaced with D, E, H, K, R, N, Q, A, G, I, L, S, T, M, V, P, or C; Q319 replaced with D, E, H, K, R, A, G, I, L, S, T, M, V, F, W, Y, P, or C; K320 replaced with D, E, A, G, I, L, S, T, M, V, N, Q, F, W, Y, P, or C; Q321 replaced with D, E, H, K, R, A, G, I, L, S, T, M, V, F, W, Y, P, or C; H322 replaced with D, E, A, G, I, L, S, T, M, V, N, Q, F, W, Y, P, or C; N323 replaced with D, E, H, K, R, A, G, I, L, S, T, M, V, F, W, Y, P, or C; P324 replaced with D, E, H, K, R, A, G, I, L, S, T, M, V, N, Q, F, W, Y, or C; P325 replaced with D, E, H, K, R, A, G, I, L, S, T, M, V, N, Q, F, W, Y, or C; S326 replaced with D, E, H, K, R, N, Q, F, W, Y, P, or C; D327 replaced with H, K, R, A, G, I, L, S, T, M, V, N, Q, F, W, Y, P, or C; R328 replaced with D, E, A, G, I, L, S, T, M, V, N, Q, F, W, Y, P, or C; D329 replaced with H, K, R, A, G, I, L, S, T, M, V, N, Q, F, W, Y, P, or C; A330 replaced with D, E, H, K, R, N, Q, F, W, Y, P, or C; E331 replaced with H, K, R, A, G, I, L, S, T, M, V, N, Q, F, W, Y, P, or C; H332 replaced with D, E, A, G, I, L, S, T, M, V, N, Q, F, W, Y, P, or C; Y333 replaced with D, E, H, K, R, N, Q, A, G, I, L, S, T, M, V, P, or C; D334 replaced with H, K, R, A, G, I, L, S, T, M, V, N, Q, F, W, Y, P, or C; T335 replaced with D, E, H, K, R, N, Q, F, W, Y, P, or C; A336 replaced with D, E, H, K, R, N, Q, F, W, Y, P, or C; I337 replaced with D, E, H, K, R, N, Q, F, W, Y, P, or C; L338 replaced with D, E, H, K, R, N, Q, F, W, Y, P, or C; F339 replaced with D, E, H, K, R, N, Q, A, G, I, L, S, T, M, V, P, or C; T340 replaced with D, E, H, K, R, N, Q, F, W, Y, P, or C; R341 replaced with D, E, A, G, I, L, S, T, M, V, N, Q, F, W, Y, P, or C; Q342 replaced with D, E, H, K, R, A, G, I, L, S, T, M, V, F, W, Y, P, or C; D343 replaced with H, K, R, A, G, I, L, S, T, M, V, N, Q, F, W, Y, P, or C; L344 replaced with D, E, H, K, R, N, Q, F, W, Y, P, or C; C345 replaced with D, E, H, K, R, A, G, I, L, S, T, M, V, N, Q, F, W, Y, or P; G346 replaced with D, E, H, K, R, N, Q, F, W, Y, P, or C; S347 replaced with D, E, H, K, R, N, Q, F, W, Y, P, or C; Q348 replaced with D, E, H, K, R, A, G, I, L, S, T, M, V, F, W, Y, P, or C; T349 replaced with D, E, H, K, R, N, Q, F, W, Y, P, or C; C350 replaced with D, E, H, K, R, A, G, I, L, S, T, M, V, N, Q, F, W, Y, or P; D351 replaced with H, K, R, A, G, I, L, S, T, M, V, N, Q, F, W, Y, P, or C; T352 replaced with D, E, H, K, R, N, Q, F, W, Y, P, or C; L353 replaced with D, E, H, K, R, N, Q, F, W, Y, P, or C; G354 replaced with D, E, H, K, R, N, Q, F, W, Y, P, or C; M355 replaced with D, E, H, K, R, N, Q, F, W, Y, P, or C; A356 replaced with D, E, H, K, R, N, Q, F, W, Y, P, or C; D357 replaced with H, K, R, A, G, I, L, S, T, M, V, N, Q, F, W, Y, P, or C; V358 replaced with D, E, H, K, R, N, Q, F, W, Y, P, or C; G359 replaced with D, E, H, K, R, N, Q, F, W, Y, P, or C; T360 replaced with D, E, H, K, R, N, Q, F, W, Y, P, or C; V361 replaced with D, E, H, K, R, N, Q, F, W, Y, P, or C; C362 replaced with D, E, H, K, R, A, G, I, L, S, T, M, V, N, Q, F, W, Y, or P; D363 replaced with H, K, R, A, G, I, L, S, T, M, V, N, Q, F, W, Y, P, or C; P364 replaced with D, E, H, K, R, A, G, I, L, S, T, M, V, N, Q, F, W, Y, or C; S365 replaced with D, E, H, K, R, N, Q, F, W, Y, P, or C; R366 replaced with D, E, A, G, I, L, S, T, M, V, N, Q, F, W, Y, P, or C; S367 replaced with D, E, H, K, R, N, Q, F, W, Y, P, or C; C368 replaced with D, E, H, K, R, A, G, I, L, S, T, M, V, N, Q, F, W, Y, or P; S369 replaced with D, E, H, K, R, N, Q, F, W, Y, P, or C; V370 replaced with D, E, H, K, R, N, Q, F, W, Y, P, or C; I371 replaced with D, E, H, K, R, N, Q, F, W, Y, P, or C; E372 replaced with H, K, R, A, G, I, L, S, T, M, V, N, Q, F, W, Y, P, or C; D373 replaced with H, K, R, A, G, I, L, S, T, M, V, N, Q, F, W, Y, P, or C; D374 replaced with H, K, R, A, G, I, L, S, T, M, V, N, Q, F, W, Y, P, or C; G375 replaced with D, E, H, K, R, N, Q, F, W, Y, P, or C; L376 replaced with D, E, H, K, R, N, Q, F, W, Y, P, or C; Q377 replaced with D, E, H, K, R, A, G, I, L, S, T, M, V, F, W, Y, P, or C; A378 replaced with D, E, H, K, R, N, Q, F, W, Y, P, or C; A379 replaced with D, E, H, K, R, N, Q, F, W, Y, P, or C; F380 replaced with D, E, H, K, R, N, Q, A, G, I, L, S, T, M, V, P, or C; T381 replaced with D, E, H, K, R, N, Q, F, W, Y, P, or C; T382 replaced with D, E, H, K, R, N, Q, F, W, Y, P, or C; A383 replaced with D, E, H, K, R, N, Q, F, W, Y, P, or C; H384 replaced with D, E, A, G, I, L, S, T, M, V, N, Q, F, W, Y, P, or C; E385 replaced with H, K, R, A, G, I, L, S, T, M, V, N, Q, F, W, Y, P, or C; L386 replaced with D, E, H, K, R, N, Q, F, W, Y, P, or C; G387 replaced with D, E, H, K, R, N, Q, F, W, Y, P, or C; H388 replaced with D, E, A, G, I, L, S, T, M, V, N, Q, F, W, Y, P, or C; V389 replaced with D, E, H, K, R, N, Q, F, W, Y, P, or C; F390 replaced with D, E, H, K, R, N, Q, A, G, I, L, S, T, M, V, P, or C; N391 replaced with D, E, H, K, R, A, G, I, L, S, T, M, V, F, W, Y, P, or C; M392 replaced with D, E, H, K, R, N, Q, F, W, Y, P, or C; P393 replaced with D, E, H, K, R, A, G, I, L, S, T, M, V, N, Q, F, W, Y, or C; H394 replaced with D, E, A, G, I, L, S, T, M, V, N, Q, F, W, Y, P, or C; D395 replaced with H, K, R, A, G, I, L, S, T, M, V, N, Q, F, W, Y, P, or C; D396 replaced with H, K, R, A, G, I, L, S, T, M, V, N, Q, F, W, Y, P, or C; A397 replaced with D, E, H, K, R, N, Q, F, W, Y, P, or C; K398 replaced with D, E, A, G, I, L, S, T, M, V, N, Q, F, W, Y, P, or C; Q399 replaced with D, E, H, K, R, A, G, I, L, S, T, M, V, F, W, Y, P, or C; C400 replaced with D, E, H, K, R, A, G, I, L, S, T, M, V, N, Q, F, W, Y, or P; A401 replaced with D, E, H, K, R, N, Q, F, W, Y, P, or C; S402 replaced with D, E, H, K, R, N, Q, F, W, Y, P, or C; L403 replaced with D, E, H, K, R, N, Q, F, W, Y, P, or C; N404 replaced with D, E, H, K, R, A, G, I, L, S, T, M, V, F, W, Y, P, or C; G405 replaced with D, E, H, K, R, N, Q, F, W, Y, P, or C; V406 replaced with D, E, H, K, R, N, Q, F, W, Y, P, or C; N407 replaced with D, E, H, K, R, A, G, I, L, S, T, M, V, F, W, Y, P, or C; Q408 replaced with D, E, H, K, R, A, G, I, L, S, T, M, V, F, W, Y, P, or C; D409 replaced with H, K, R, A, G, I, L, S, T, M, V, N, Q, F, W, Y, P, or C; S410 replaced with D, E, H, K, R, N, Q, F, W, Y, P, or C; H411 replaced with D, E, A, G, I, L, S, T, M, V, N, Q, F, W, Y, P, or C; M412 replaced with D, E, H, K, R, N, Q, F, W, Y, P, or C; M413 replaced with D, E, H, K, R, N, Q, F, W, Y, P, or C; A414 replaced with D, E, H, K, R, N, Q, F, W, Y, P, or C; S415 replaced with D, E, H, K, R, N, Q, F, W, Y, P, or C; M416 replaced with D, E, H, K, R, N, Q, F, W, Y, P, or C; L417 replaced with D, E, H, K, R, N, Q, F, W, Y, P, or C; S418 replaced with D, E, H, K, R, N, Q, F, W, Y, P, or C;

N419 replaced with D, E, H, K, R, A, G, I, L, S, T, M, V, F, W, Y, P, or C; L420 replaced with D, E, H, K, R, N, Q, F, W, Y, P, or C; D421 replaced with H, K, R, A, G, I, L, S, T, M, V, N, Q, F, W, Y, P, or C; H422 replaced with D, E, A, G, I, L, S, T, M, V, N, Q, F, W, Y, P, or C; S423 replaced with D, E, H, K, R, N, Q, F, W, Y, P, or C; Q424 replaced with D, E, H, K, R, A, G, I, L, S, T, M, V, F, W, Y, P, or C; P425 replaced with D, E, H, K, R, A, G, I, L, S, T, M, V, N, Q, F, W, Y, or C; W426 replaced with D, E, H, K, R, N, Q, A, G, I, L, S, T, M, V, P, or C; S427 replaced with D, E, H, K, R, N, Q, F, W, Y, P, or C; P428 replaced with D, E, H, K, R, A, G, I, L, S, T, M, V, N, Q, F, W, Y, or C; C429 replaced with D, E, H, K, R, A, G, I, L, S, T, M, V, N, Q, F, W, Y, or P; S430 replaced with D, E, H, K, R, N, Q, F, W, Y, P, or C; A431 replaced with D, E, H, K, R, N, Q, F, W, Y, P, or C; Y432 replaced with D, E, H, K, R, N, Q, A, G, I, L, S, T, M, V, P, or C; M433 replaced with D, E, H, K, R, N, Q, F, W, Y, P, or C; I434 replaced with D, E, H, K, R, N, Q, F, W, Y, P, or C; T435 replaced with D, E, H, K, R, N, Q, F, W, Y, P, or C; S436 replaced with D, E, H, K, R, N, Q, F, W, Y, P, or C; F437 replaced with D, E, H, K, R, N, Q, A, G, I, L, S, T, M, V, P, or C; L438 replaced with D, E, H, K, R, N, Q, F, W, Y, P, or C; D439 replaced with H, K, R, A, G, I, L, S, T, M, V, N, Q, F, W, Y, P, or C; N440 replaced with D, E, H, K, R, A, G, I, L, S, T, M, V, F, W, Y, P, or C; G441 replaced with D, E, H, K, R, N, Q, F, W, Y, P, or C; H442 replaced with D, E, A, G, I, L, S, T, M, V, N, Q, F, W, Y, P, or C; G443 replaced with D, E, H, K, R, N, Q, F, W, Y, P, or C; E444 replaced with H, K, R, A, G, I, L, S, T, M, V, N, Q, F, W, Y, P, or C; C445 replaced with D, E, H, K, R, A, G, I, L, S, T, M, V, N, Q, F, W, Y, or P; L446 replaced with D, E, H, K, R, N, Q, F, W, Y, P, or C; M447 replaced with D, E, H, K, R, N, Q, F, W, Y, P, or C; D448 replaced with H, K, R, A, G, I, L, S, T, M, V, N, Q, F, W, Y, P, or C; K449 replaced with D, E, A, G, I, L, S, T, M, V, N, Q, F, W, Y, P, or C; P450 replaced with D, E, H, K, R, A, G, I, L, S, T, M, V, N, Q, F, W, Y, or C; Q451 replaced with D, E, H, K, R, A, G, I, L, S, T, M, V, F, W, Y, P, or C; N452 replaced with D, E, H, K, R, A, G, I, L, S, T, M, V, F, W, Y, P, or C; P453 replaced with D, E, H, K, R, A, G, I, L, S, T, M, V, N, Q, F, W, Y, or C; I454 replaced with D, E, H, K, R, N, Q, F, W, Y, P, or C; Q455 replaced with D, E, H, K, R, A, G, I, L, S, T, M, V, F, W, Y, P, or C; L456 replaced with D, E, H, K, R, N, Q, F, W, Y, P, or C; P457 replaced with D, E, H, K, R, A, G, I, L, S, T, M, V, N, Q, F, W, Y, or C; G458 replaced with D, E, H, K, R, N, Q, F, W, Y, P, or C; D459 replaced with H, K, R, A, G, I, L, S, T, M, V, N, Q, F, W, Y, P, or C; L460 replaced with D, E, H, K, R, N, Q, F, W, Y, P, or C; P461 replaced with D, E, H, K, R, A, G, I, L, S, T, M, V, N, Q, F, W, Y, or C; G462 replaced with D, E, H, K, R, N, Q, F, W, Y, P, or C; T463 replaced with D, E, H, K, R, N, Q, F, W, Y, P, or C; S464 replaced with D, E, H, K, R, N, Q, F, W, Y, P, or C; Y465 replaced with D, E, H, K, R, N, Q, A, G, I, L, S, T, M, V, P, or C; D466 replaced with H, K, R, A, G, I, L, S, T, M, V, N, Q, F, W, Y, P, or C; A467 replaced with D, E, H, K, R, N, Q, F, W, Y, P, or C; N468 replaced with D, E, H, K, R, A, G, I, L, S, T, M, V, F, W, Y, P, or C; R469 replaced with D, E, A, G, I, L, S, T, M, V, N, Q, F, W, Y, P, or C; Q470 replaced with D, E, H, K, R, A, G, I, L, S, T, M, V, F, W, Y, P, or C; C471 replaced with D, E, H, K, R, A, G, I, L, S, T, M, V, N, Q, F, W, Y, or P; Q472 replaced with D, E, H, K, R, A, G, I, L, S, T, M, V, F, W, Y, P, or C; F473 replaced with D, E, H, K, R, N, Q, A, G, I, L, S, T, M, V, P, or C; T474 replaced with D, E, H, K, R, N, Q, F, W, Y, P, or C; F475 replaced with D, E, H, K, R, N, Q, A, G, I, L, S, T, M, V, P, or C; G476 replaced with D, E, H, K, R, N, Q, F, W, Y, P, or C; E477 replaced with H, K, R, A, G, I, L, S, T, M, V, N, Q, F, W, Y, P, or C; D478 replaced with H, K, R, A, G, I, L, S, T, M, V, N, Q, F, W, Y, P, or C; S479 replaced with D, E, H, K, R, N, Q, F, W, Y, P, or C; K480 replaced with D, E, A, G, I, L, S, T, M, V, N, Q, F, W, Y, P, or C; H481 replaced with D, E, A, G, I, L, S, T, M, V, N, Q, F, W, Y, P, or C; C482 replaced with D, E, H, K, R, A, G, I, L, S, T, M, V, N, Q, F, W, Y, or P; P483 replaced with D, E, H, K, R, A, G, I, L, S, T, M, V, N, Q, F, W, Y, or C; D484 replaced with H, K, R, A, G, I, L, S, T, M, V, N, Q, F, W, Y, P, or C; A485 replaced with D, E, H, K, R, N, Q, F, W, Y, P, or C; A486 replaced with D, E, H, K, R, N, Q, F, W, Y, P, or C; S487 replaced with D, E, H, K, R, N, Q, F, W, Y, P, or C; T488 replaced with D, E, H, K, R, N, Q, F, W, Y, P, or C; C489 replaced with D, E, H, K, R, A, G, I, L, S, T, M, V, N, Q, F, W, Y, or P; S490 replaced with D, E, H, K, R, N, Q, F, W, Y, P, or C; T491 replaced with D, E, H, K, R, N, Q, F, W, Y, P, or C; L492 replaced with D, E, H, K, R, N, Q, F, W, Y, P, or C; W493 replaced with D, E, H, K, R, N, Q, A, G, I, L, S, T, M, V, P, or C; C494 replaced with D, E, H, K, R, A, G, I, L, S, T, M, V, N, Q, F, W, Y, or P; T495 replaced with D, E, H, K, R, N, Q, F, W, Y, P, or C; G496 replaced with D, E, H, K, R, N, Q, F, W, Y, P, or C; T497 replaced with D, E, H, K, R, N, Q, F, W, Y, P, or C; S498 replaced with D, E, H, K, R, N, Q, F, W, Y, P, or C; G499 replaced with D, E, H, K, R, N, Q, F, W, Y, P, or C; G500 replaced with D, E, H, K, R, N, Q, F, W, Y, P, or C; V501 replaced with D, E, H, K, R, N, Q, F, W, Y, P, or C; L502 replaced with D, E, H, K, R, N, Q, F, W, Y, P, or C; V503 replaced with D, E, H, K, R, N, Q, F, W, Y, P, or C; C504 replaced with D, E, H, K, R, A, G, I, L, S, T, M, V, N, Q, F, W, Y,or P; Q505 replaced with D, E, H, K, R, A, G, I, L, S, T, M, V, F, W, Y, P, or C; T506 replaced with D, E, H, K, R, N, Q, F, W, Y, P, or C; K507 replaced with D, E, A, G, I, L, S, T, M, V, N, Q, F, W, Y, P, or C; H508 replaced with D, E, A, G, I, L, S, T, M, V, N, Q, F, W, Y, P, or C; F509 replaced with D, E, H, K, R, N, Q, A, G, I, L, S, T, M, V, P, or C; P510 replaced with D, E, H, K, R, A, G, I, L, S, T, M, V, N, Q, F, W, Y, or C; W511 replaced with D, E, H, K, R, N, Q, A, G, I, L, S, T, M, V, P, or C; A512 replaced with D, E, H, K, R, N, Q, F, W, Y, P, or C; D513 replaced with H, K, R, A, G, I, L, S, T, M, V, N, Q, F, W, Y, P, or C; G514 replaced with D, E, H, K, R, N, Q, F, W, Y, P, or C; T515 replaced with D, E, H, K, R, N, Q, F, W, Y, P, or C; S516 replaced with D, E, H, K, R, N, Q, F, W, Y, P, or C; C517 replaced with D, E, H, K, R, A, G, I, L, S, T, M, V, N, Q, F, W, Y, or P; G518 replaced with D, E, H, K, R, N, Q, F, W, Y, P, or C; E519 replaced with H, K, R, A, G, I, L, S, T, M, V, N, Q, F, W, Y, P, or C; G520 replaced with D, E, H, K, R, N, Q, F, W, Y, P, or C; K521 replaced with D, E, A, G, I, L, S, T, M, V, N, Q, F, W, Y, P, or C; W522 replaced with D, E, H, K, R, N, Q, A, G, I, L, S, T, M, V, P, or C; C523 replaced with D, E, H, K, R, A, G, I, L, S, T, M, V, N, Q, F, W, Y, or P; I524 replaced with D, E, H, K, R, N, Q, F, W, Y, P, or C; N525 replaced with D, E, H, K, R, A, G, I, L, S, T, M, V, F, W, Y, P, or C; G526 replaced with D, E, H, K, R, N, Q, F, W, Y, P, or C; K527 replaced with D, E, A, G, I, L, S, T, M, V, N, Q, F, W, Y, P, or C; C528 replaced with D, E, H, K, R, A, G, I, L, S, T, M, V, N, Q, F, W, Y, or P; V529 replaced with D, E, H, K, R, N, Q, F, W, Y, P, or C; N530 replaced with D, E, H, K, R, A, G, I, L, S, T, M, V, F, W, Y, P, or C; K531 replaced with D, E, A, G, I, L, S, T, M, V, N, Q, F, W, Y, P, or C; T532 replaced with D, E, H, K, R, N, Q, F, W, Y, P, or C; D533 replaced with H, K, R, A, G, I, L, S, T, M, V, N, Q, F, W, Y, P, or C; R534 replaced with D, E, A, G, I, L, S, T, M, V, N, Q, F, W, Y, P, or C; K535 replaced with D, E, A, G, I, L, S, T, M, V, N, Q, F, W, Y, P, or C; H536 replaced with D, E, A, G, I, L, S, T, M, V, N, Q, F, W, Y, P, or C; F537 replaced with D, E, H, K, R, N, Q, A, G, I, L, S, T, M, V, P, or C; D538 replaced with H, K, R, A, G, I, L, S, T, M, V, N, Q, F, W, Y, P, or C; T539 replaced with D, E, H, K, R, N, Q, F, W, Y, P, or C; P540 replaced with D, E, H, K, R, A, G, I, L, S, T, M, V, N, Q, F, W, Y, or C; F541 replaced with D, E, H, K, R, N, Q, A, G, I, L, S, T, M, V, P, or C; H542 replaced with D, E, A, G, I, L, S, T, M, V, N, Q, F, W, Y, P, or C; G543 replaced with D, E, H, K, R, N, Q, F, W, Y, P, or C; S544 replaced with D, E, H, K, R, N, Q, F, W, Y, P, or C; W545 replaced with D, E, H, K, R, N, Q, A, G, I, L, S, T, M, V, P, or C; G546 replaced with D, E, H, K, R, N, Q, F, W, Y, P, or C; M547 replaced with D, E, H, K, R, N, Q, F, W, Y, P, or C; W548 replaced with D, E, H, K, R, N, Q, A, G, I, L, S, T, M, V, P, or C; G549 replaced with D, E, H, K, R, N, Q, F, W, Y, P, or C; P550 replaced with D, E, H, K, R, A, G, I, L, S, T, M, V, N, Q, F, W, Y, or C; W551 replaced with D, E, H, K, R, N, Q, A, G, I, L, S, T, M, V, P, or C; G552 replaced with D, E, H, K, R, N, Q, F, W, Y, P, or C; D553 replaced with H, K, R, A, G, I, L, S, T, M, V, N, Q, F, W, Y, P, or C; C554 replaced with D, E, H, K, R, A, G, I, L, S, T, M, V, N, Q, F, W, Y, or P; S555 replaced with D, E, H, K, R, N, Q, F, W, Y, P, or C; R556 replaced with D, E, A, G, I, L, S, T, M, V, N, Q, F, W, Y, P, or C; T557 replaced with D, E, H, K, R, N, Q, F, W, Y, P, or C; C558 replaced with D, E, H, K, R, A, G, I, L, S, T, M, V, N, Q, F, W, Y, or P; G559 replaced with D, E, H, K, R, N, Q, F, W, Y, P, or C; G560 replaced with D, E, H, K, R, N, Q, F, W, Y, P, or C; G561 replaced with D, E, H, K, R, N, Q, F, W, Y, P, or C; V562 replaced with D, E, H, K, R, N, Q, F, W, Y, P, or C; Q563 replaced with D, E, H, K, R, A, G, I, L, S, T, M, V, F, W, Y, P, or C; Y564 replaced with D, E, H, K, R, N, Q, A, G, I, L, S, T, M, V, P, or C; T565 replaced with D, E, H, K, R, N, Q, F, W, Y, P, or C; M566 replaced with D, E, H, K, R, N, Q, F, W, Y, P, or C; R567 replaced with D, E, A, G, I, L, S, T, M, V, N, Q, F, W, Y, P, or C; E568 replaced with H, K, R, A, G, I, L, S, T, M, V, N, Q, F, W, Y, P, or C; C569 replaced with D, E, H, K, R, A, G, I, L, S, T, M, V, N, Q, F, W, Y, or P; D570 replaced with H, K, R, A, G, I, L, S, T, M, V, N, Q, F, W, Y, P, or C; N571 replaced with D, E, H, K, R, A, G, I, L, S, T, M, V, F, W, Y, P, or C; P572 replaced with D, E, H, K, R, A, G, I, L, S, T, M, V, N, Q, F, W, Y, or C; V573 replaced with D, E, H, K, R, N, Q, F, W, Y, P, or C; P574 replaced with D, E, H, K, R, A, G, I, L, S, T, M, V, N, Q, F, W, Y, or C; K575 replaced with D, E, A, G, I, L, S, T, M, V, N, Q, F, W, Y, P, or C; N576 replaced with D, E, H, K, R, A, G, I, L, S, T, M, V, F, W, Y, P, or C; G577 replaced with D, E, H, K, R, N, Q, F, W, Y, P, or C; G578 replaced with D, E, H, K, R, N, Q, F, W, Y, P, or C; K579 replaced with D, E, A, G, I, L, S, T, M, V, N, Q, F, W, Y, P, or C; Y580 replaced with D, E, H, K, R, N, Q, A, G, I, L, S, T, M, V, P, or C; C581 replaced with D, E, H, K, R, A, G, I, L, S, T, M, V, N, Q, F, W, Y, or P; E582 replaced with H, K, R, A, G, I, L, S, T, M, V, N, Q, F, W, Y, P, or C; G583 replaced with D, E, H, K, R, N, Q, F, W, Y, P, or C; K584 replaced with D, E, A, G, I, L, S, T, M, V, N, Q, F, W, Y, P, or C; R585 replaced with D, E, A, G, I, L, S, T, M, V, N, Q, F, W, Y, P, or C; V586 replaced with D, E, H, K, R, N, Q, F, W, Y, P, or C; R587 replaced with D, E, A, G, I, L, S, T, M, V, N, Q, F, W, Y, P, or C; Y588 replaced with D, E, H, K, R, N, Q, A, G, I, L, S, T, M, V, P, or C; R589 replaced with D, E, A, G, I, L, S, T, M, V, N, Q, F, W, Y, P, or C; S590 replaced with D, E, H, K, R, N, Q, F, W, Y, P, or C; C591 replaced with D, E, H, K, R, A, G, I, L, S, T, M, V, N, Q, F, W, Y, or P; N592 replaced with D, E, H, K, R, A, G, I, L, S, T, M, V, F, W, Y, P, or C; L593 replaced with D, E, H, K, R, N, Q, F, W, Y, P, or C; E594 replaced with H, K, R, A, G, I, L, S, T, M, V, N, Q, F, W, Y, P, or C; D595 replaced with H, K, R, A, G, I, L, S, T, M, V, N, Q, F, W, Y, P, or C; C596 replaced with D, E, H, K, R, A, G, I, L, S, T, M, V, N, Q, F, W, Y, or P; P597 replaced with D, E, H, K, R, A, G, I, L, S, T, M, V, N, Q, F, W, Y, or C; D598 replaced with H, K, R, A, G, I, L, S, T, M, V, N, Q, F, W, Y, P, or C; N599 replaced with D, E, H, K, R, A, G, I, L, S, T, M, V, F, W, Y, P, or C; N600 replaced with D, E, H, K, R, A, G, I, L, S, T, M, V, F, W, Y, P, or C; G601 replaced with D, E, H, K, R, N, Q, F, W, Y, P, or C; K602 replaced with D, E, A, G, I, L, S, T, M, V, N, Q, F, W, Y, P, or C; T603 replaced with D, E, H, K, R, N, Q, F, W, Y, P, or C; F604 replaced with D, E, H, K, R, N, Q, A, G, I, L, S, T, M, V, P, or C; R605 replaced with D, E, A, G, I, L, S, T, M, V, N, Q, F, W, Y, P, or C; E606 replaced with H, K, R, A, G, I, L, S, T, M, V, N, Q, F, W, Y, P, or C; E607 replaced with H, K, R, A, G, I, L, S, T, M, V, N, Q, F, W, Y, P, or C; Q608 replaced with D, E, H, K, R, A, G, I, L, S, T, M, V, F, W, Y, P, or C; C609 replaced with D, E, H, K, R, A, G, I, L, S, T, M, V, N, Q, F, W, Y, or P; E610 replaced with H, K, R, A, G, I, L, S, T, M, V, N, Q, F, W, Y, P, or C; A611 replaced with D, E, H, K, R, N, Q, F, W, Y, P, or C; H612 replaced with D, E, A, G, I, L, S, T, M, V, N, Q, F, W, Y, P, or C; N613 replaced with D, E, H, K, R, A, G, I, L, S, T, M, V, F, W, Y, P, or C; E614 replaced with H, K, R, A, G, I, L, S, T, M, V, N, Q, F, W, Y, P, or C; F615 replaced with D, E, H, K, R, N, Q, A, G, I, L, S, T, M, V, P, or C; S616 replaced with D, E, H, K, R, N, Q, F, W, Y, P, or C; K617 replaced with D, E, A, G, I, L, S, T, M, V, N, Q, F, W, Y, P, or C; A618 replaced with D, E, H, K, R, N, Q, F, W, Y, P, or C; S619 replaced with D, E, H, K, R, N, Q, F, W, Y, P, or C; F620 replaced with D, E, H, K, R, N, Q, A, G, I, L, S, T, M, V, P, or C; G621 replaced with D, E, H, K, R, N, Q, F, W, Y, P, or C; S622 replaced with D, E, H, K, R, N, Q, F, W, Y, P, or C; G623 replaced with D, B, H, K, R, N, Q, F, W, Y, P, or C; P624 replaced with D, E, H, K, R, A, G, I, L, S, T, M, V, N, Q, F, W, Y, or C; A625 replaced with D, E, H, K, R, N, Q, F, W, Y, P, or C; V626 replaced with D, E, H, K, R, N, Q, F, W, Y, P, or C; E627 replaced with H, K, R, A, G, I, L, S, T, M, V, N, Q, F, W, Y, P, or C; W628 replaced with D, E, H, K, R, N, Q, A, G, I, L, S, T, M, V, P, or C; I629 replaced with D, E, H, K, R, N, Q, F, W, Y, P, or C; P630 replaced with D, E, H, K, R, A, G, I, L, S, T, M, V, N, Q, F, W, Y, or C; K631 replaced with D, E, A, G, I, L, S, T, M, V, N, Q, F, W, Y, P, or C; Y632 replaced with D, E, H, K, R, N, Q, A, G, I, L, S, T, M, V, P, or C; A633 replaced with D, E, H, K, R, N, Q, F, W, Y, P, or C; G634 replaced with D, E, H, K, R, N, Q, F, W, Y, P, or C; V635 replaced with D, E, H, K, R, N, Q, F, W, Y, P, or C; S636 replaced with D, E, H, K, R, N, Q, F, W, Y, P, or C; P637 replaced with D, E, H, K, R, A, G, I, L, S, T, M, V, N, Q, F, W, Y, or C; K638 replaced with D, E, A, G, I, L, S, T, M, V, N, Q, F, W, Y, P, or C; D639 replaced with H, K, R, A, G, I, L, S, T, M, V, N, Q, F, W, Y, P, or C; R640 replaced with D, E, A, G, I, L, S, T, M, V, N, Q, F, W, Y, P, or C; C641 replaced with D, E, H, K, R, A, G, I, L, S, T, M, V, N, Q, F, W, Y, or P; K642 replaced with D, E, A, G, I, L, S, T, M, V, N, Q, F, W, Y, P, or C; L643 replaced with D, E, H, K, R, N, Q, F, W, Y, P, or C; I644 replaced with D, E, H, K, R, N, Q, F, W, Y, P, or C; C645 replaced with D, E, H, K, R, A, G, I, L, S, T, M, V, N, Q, F, W, Y, or P; Q646 replaced with D, E, H, K, R, A, G, I, L, S, T, M, V, F, W, Y, P, or C; A647 replaced with D, E, H, K, R, N, Q, F, W, Y, P, or C; K648 replaced with D, E, A, G, I, L, S, T, M, V, N, Q, F, W, Y, P, or C; G649 replaced with D, E, H, K, N, Q, F, W, Y, P, or C; I650 replaced with D, E, H, K, R, N, Q, F, W, Y, P, or C; G651 replaced with D, E, H, K, R, N, Q, F, W, Y, P, or C; Y652 replaced with D, E, H, K, R, N, Q, A, G, I, L, S, T, M, V, P, or C; F653 replaced with D, E, H, K, R, N, Q, A, G, I, L, S, T, M, V, P, or C; F654 replaced with D, E, H, K, R, N, Q, A, G, I, L, S, T, M, V, P, or C; V655 replaced with D, E, H, K, R, N, Q, F, W, Y, P, or C; L656 replaced with D, E, H, K, R, N, Q, F, W, Y, P, or C; Q657 replaced with D, E, H, K, R, A, G, I, L, S, T, M, V, F, W, Y, P, or C; P658 replaced with D, E, H, K, R, A, G, I, L, S, T, M, V, N, Q, F, W, Y, or C; K659 replaced with D, E, A, G, I, L, S, T, M, V, N, Q, F, W, Y, P, or C; V660 replaced with D, E, H, K, R, N, Q, F, W, Y, P, or C; V661 replaced with D, E, H, K, R, N, Q, F, W, Y, P, or C; D662 replaced with H, K, R, A, G, I, L, S, T, M, V, N, Q, F, W, Y, P, or C; G663 replaced with D, E, H, K, R, N, Q, F, W, Y, P, or C; T664 replaced with D, E, H, K, R, N, Q, F, W, Y, P, or C; P665 replaced with D, E, H, K, R, A, G, I, L, S, T, M, V, N, Q, F, W, Y, or C; C666 replaced with D, E, H, K, R, A, G, I, L, S, T, M, V, N, Q, F, W, Y, or P; S667 replaced with D, E, H, K, R, N, Q, F, W, Y, P, or C; P668 replaced with D, E, H, K, R, A, G, I, L, S, T, M, V, N, Q, F, W, Y, or C; D669 replaced with H, K, R, A, G, I, L, S, T, M, V, N, Q, F, W, Y, P, or C; S670 replaced with D, E, H, K, R, N, Q, F, W, Y, P, or C; T671 replaced with D, E, H, K, R, N, Q, F, W, Y, P, or C; S672 replaced with D, E, H, K, R, N, Q, F, W, Y, P, or C; V673 replaced with D, E, H, K, R, N, Q, F, W, Y, P, or C; C674 replaced with D, E, H, K, R, A, G, I, L, S, T, M, V, N, Q, F, W, Y, or P; V675 replaced with D, E, H, K, R, N, Q, F, W, Y, P, or C; Q676 replaced with D, E, H, K, R, A, G, I, L, S, T, M, V, F, W, Y, P, or C; G677 replaced with D, E, H, K, R, N, Q, F, W, Y, P, or C; Q678 replaced with D, E, H, K, R, A, G, I, L, S, T, M, V, F, W, Y, P, or C; C679 replaced with D, E, H, K, R, A, G, I, L, S, T, M, V, N, Q, F, W, Y, or P; V680 replaced with D, E, H, K, R, N, Q, F, W, Y, P, or C; K681 replaced with D, E, A, G, I, L, S, T, M, V, N, Q, F, W, Y, P, or C; A682 replaced with D, E, H, K, R, N, Q, F, W, Y, P, or C; G683 replaced with D, E, H, K, R, N, Q, F, W, Y, P, or C; C684 replaced with D, E, H, K, R, A, G, I, L, S, T, M, V, N, Q, F, W, Y, or P; D685 replaced with H, K, R, A, G, I, L, S, T, M, V, N, Q, F, W, Y, P, or C; R686 replaced with D, E, A, G, I, L, S, T, M, V, N, Q, F, W, Y, P, or C; I687 replaced with D, E, H, K, R, N, Q, F, W, Y, P, or C; I688 replaced with D, E, H, K, R, N, Q, F, W, Y, P, or C; D689 replaced with H, K, R, A, G, I, L, S, T, M, V, N, Q, F, W, Y, P, or C; S690 replaced with D, E, H, K, R, N, Q, F, W, Y, P, or C; K691 replaced with D, E, A, G, I, L, S, T, M, V, N, Q, F, W, Y, P, or C; K692 replaced with D, E, A, G, I, L, S, T, M, V, N, Q, F, W, Y, P, or C; K693 replaced with D, E, A, G, I, L, S, T, M, V, N, Q, F, W, Y, P, or C; F694 replaced with D, E, H, K, R, N, Q, A, G, I, L, S, T, M, V, P, or C; D695 replaced with H, K, R, A, G, I, L, S, T, M, V, N, Q, F, W, Y, P, or C; K696 replaced with D, E, A, G, I, L, S, T, M, V, N, Q, F, W, Y, P, or C; C697 replaced with D, E, H, K, R, A, G, I, L, S, T, M, V, N, Q, F, W, Y, or P; G698 replaced with D, E, H, K, R, N, Q, F, W, Y, P, or C; V699 replaced with D, E, H, K, R, N, Q, F, W, Y, P, or C; C700 replaced with D, E, H, K, R, A, G, I, L, S, T, M, V, N, Q, F, W, Y, or P; G701 replaced with D, E, H, K, R, N, Q, F, W, Y, P, or C; G702 replaced with D, E, H, K, R, N, Q, F, W, Y, P, or C; N703 replaced with D, E, H, K, R, A, G, I, L, S, T, M, V, F, W, Y, P, or C; G704 replaced with D, E, H, K, R, N, Q, F, W, Y, P, or C; S705 replaced with D, E, H, K, R, N, Q, F, W, Y, P, or C; T706 replaced with D, E, H, K, R, N, Q, F, W, Y, P, or C; C707 replaced with D, E, H, K, R, A, G, I, L, S, T, M, V, N, Q, F, W, Y, or P; K708 replaced with D, E, A, G, I, L, S, T, M, V, N, Q, F, W, Y, P, or C; K709 replaced with D, E, A, G, I, L, S, T, M, V, N, Q, F, W, Y, P, or C; I710 replaced with D, E, H, K, R, N, Q, F, W, Y, P, or C; S711 replaced with D, E, H, K, R, N, Q, F, W, Y, P, or C; G712 replaced with D, E, H, K, R, N, Q, F, W, Y, P, or C; S713 replaced with D, E, H, K, R, N, Q, F, W, Y, P, or C; V714 replaced with D, E, H, K, R, N, Q, F, W, Y, P, or C; T715 replaced with D, E, H, K, R, N, Q, F, W, Y, P, or C; S716 replaced with D, E, H, K, R, N, Q, F, W, Y, P, or C; A717 replaced with D, E, H, K, R, N, Q, F, W, Y, P, or C; K718 replaced with D, E, A, G, I, L, S, T, M, V, N, Q, F, W, Y, P, or C; P719 replaced with D, E, H, K, R, A, G, I, L, S, T, M, V, N, Q, F, W, Y, or C; G720 replaced with D, E, H, K, R, N, Q, F, W, Y, P, or C; Y721 replaced with D, E, H, K, R, N, Q, A, G, I, L, S, T, M, V, P, or C; H722 replaced with D, E, A, G, I, L, S, T, M, V, N, Q, F, W, Y, P, or C; D723 replaced with H, K, R, A, G, I, L, S, T, M, V, N, Q, F, W, Y, P, or C; I724 replaced with D, E, H, K, R, N, Q, F, W, Y, P, or C; I725 replaced with D, E, H, K, R, N, Q, F, W, Y, P, or C; T726 replaced with D, E, H, K, R, N, Q, F, W, Y, P, or C; I727 replaced with D, E, H, K, R, N, Q, F, W, Y, P, or C; P728 replaced with D, E, H, K, R, A, G, I, L, S, T, M, V, N, Q, F, W, Y, or C; T729 replaced with D, E, H, K, R, N, Q, F, W, Y, P, or C; G730 replaced with D, E, H, K, R, N, Q, F, W, Y, P, or C; A731 replaced with D, E, H, K, R, N, Q, F, W, Y, P, or C; T732 replaced with D, E, H, K, R, N, Q, F, W, Y, P, or C; N733 replaced with D, E, H, K, R, A, G, I, L, S, T, M, V, F, W, Y, P, or C; I734 replaced with D, E, H, K, R, N, Q, F, W, Y, P, or C; E735 replaced with H, K, R, A, G, I, L, S, T, M, V, N, Q, F, W, Y, P, or C; V736 replaced with D, E, H, K, R, N, Q, F, W, Y, P, or C; K737 replaced with D, E, A, G, I, L, S, T, M, V, N, Q, F, W, Y, P, or C; Q738 replaced with D, E, H, K, R, A, G, I, L, S, T, M, V, F, W, Y, P, or C; R739 replaced with D, E, A, G, I, L, S, T, M, V, N, Q, F, W, Y, P, or C; N740 replaced with D, E, H, K, R, A, G, I, L, S, T, M, V, F, W, Y, P, or C; Q741 replaced with D, E, H, K, R, A, G, I, L, S, T, M, V, F, W, Y, P, or C; R742 replaced with D, E, A, G, I, L, S, T, M, V, N, Q, F, W, Y, P, or C; G743 replaced with D, E, H, K, R, N, Q, F, W, Y, P, or C; S744 replaced with D, E, H, K, R, N, Q, F, W, Y, P, or C; R745 replaced with D, E, A, G, I, L, S, T, M, V, N, Q, F, W, Y, P, or C; N746 replaced with D, E, H, K, R, A, G, I, L, S, T, M, V, F, W, Y, P, or C; N747 replaced with D, E, H, K, R, A, G, I, L, S, T, M, V, F, W, Y, P, or C; G748 replaced with D, E, H, K, R, N, Q, F, W, Y, P, or C; S749 replaced with D, E, H, K, R, N, Q, F, W, Y, P, or C; F750 replaced with D, E, H, K, R, N, Q, A, G, I, L, S, T, M, V, P, or C; L751 replaced with D, E, H, K, R, N, Q, F, W, Y, P, or C; A752 replaced with D, E, H, K, R, N, Q, F, W, Y, P, or C; I753 replaced with D, E, H, K, R, N, Q, F, W, Y, P, or C; K754 replaced with D, E, A, G, I, L, S, T, M, V, N, Q, F, W, Y, P, or C; A755 replaced with D, E, H, K, R, N, Q, F, W, Y, P, or C; A756 replaced with D, E, H, K, R, N, Q, F, W, Y, P, or C; D757 replaced with H, K, R, A, G, I, L, S, T, M, V, N, Q, F, W, Y, P, or C; G758 replaced with D, E, H, K, R, N, Q, F, W, Y, P, or C; T759 replaced with D, E, H, K, R, N, Q, F, W, Y, P, or C; Y760 replaced with D, E, H, K, R, N, Q, A, G, I, L, S, T, M, V, P, or C; I761 replaced with D, E, H, K, R, N, Q, F, W, Y, P, or C; L762 replaced with D, E, H, K, R, N, Q, F, W, Y, P, or C; N763 replaced with D, E, H, K, R, A, G, I, L, S, T, M, V, F, W, Y, P, or C; G764 replaced with D, E, H, K, R, N, Q, F, W, Y, P, or C; D765 replaced with H, K, R, A, G, I, L, S, T, M, V, N, Q, F, W, Y, P, or C; Y766 replaced with D, E, H, K, R, N, Q, A, G, I, L, S, T, M, V, P, or C; T767 replaced with D, E, H, K, R, N, Q, F, W, Y, P, or C; L768 replaced with D, E, H, K, R, N, Q, F, W, Y, P, or C; S769 replaced with D, E, H, K, R, N, Q, F, W, Y, P, or C; T770 replaced with D, E, H, K, R, N, Q, F, W, Y, P, or C; L771 replaced with D, E, H, K, R, N, Q, F, W, Y, P, or C; E772 replaced with H, K, R, A, G, I, L, S, T, M, V, N, Q, F, W, Y, P, or C; Q773 replaced with D, E, H, K, R, A, G, I, L, S, T, M, V, F, W, Y, P, or C; D774 replaced with H, K, R, A, G, I, L, S, T, M, V, N, Q, F, W, Y, P, or C; I775 replaced with D, E, H, K, R, N, Q, F, W, Y, P, or C; M776 replaced with D, E, H, K, R, N, Q, F, W, Y, P, or C; Y777 replaced with D, E, H, K, R, N, Q, A, G, I, L, S, T, M, V, P, or C; K778 replaced with D, E, A, G, I, L, S, T, M, V, N, Q, F, W, Y, P, or C; G779 replaced with D, E, H, K, R, N, Q, F, W, Y, P, or C; V780 replaced with D, E, H, K, R, N, Q, F, W, Y, P, or C; V781 replaced with D, E, H, K, R, N, Q, F, W, Y, P, or C; L782 replaced with D, E, H, K, R, N, Q, F, W, Y, P, or C; R783 replaced with D, E, A, G, I, L, S, T, M, V, N, Q, F, W, Y, P, or C; Y784 replaced with D, E, H, K, R, N, Q, A, G, I, L, S, T, M, V, P, or C; S785 replaced with D, E, H, K, R, N, Q, F, W, Y, P, or C; G786 replaced with D, E, H, K, R, N, Q, F, W, Y, P, or C; S787 replaced with D, E, H, K, R, N, Q, F, W, Y, P, or C; S788 replaced with D, E, H, K, R, N, Q, F, W, Y, P, or C; A789 replaced with D, E, H, K, R, N, Q, F, W, Y, P, or C; A790 replaced with D, E, H, K, R, N, Q, F, W, Y, P, or C; L791 replaced with D, E, H, K, R, N, Q, F, W, Y, P, or C; E792 replaced with H, K, R, A, G, I, L, S, T, M, V, N, Q, F, W, Y, P, or C; R793 replaced with D, E, A, G, I, L, S, T, M, V, N, Q, F, W, Y, P, or C; I794 replaced with D, E, H, K, R, N, Q, F, W, Y, P, or C; R795 replaced with D, E, A, G, I, L, S, T, M, V, N, Q, F, W, Y, P, or C; S796 replaced with D, E, H, K, R, N, Q, F, W, Y, P, or C; F797 replaced with D, E, H, K, R, N, Q, A, G, I, L, S, T, M, V, P, or C; S798 replaced with D, E, H, K, R, N, Q, F, W, Y, P, or C; P799 replaced with D, E, H, K, R, A, G, I, L, S, T, M, V, N, Q, F, W, Y, or C; L800 replaced with D, E, H, K, R, N, Q, F, W, Y, P, or C; K801 replaced with D, E, A, G, I, L, S, T, M, V, N, Q, F, W, Y, P, or C; E802 replaced with H, K, R, A, G, I, L, S, T, M, V, N, Q, F, W, Y, P, or C; P803 replaced with D, E, H, K, R, A, G, I, L, S, T, M, V, N, Q, F, W, Y, or C; L804 replaced with D, E, H, K, R, N, Q, F, W, Y, P, or C; T805 replaced with D, E, H, K, R, N, Q, F, W, Y, P, or C; I806 replaced with D, E, H, K, R, N, Q, F, W, Y, P, or C; Q807 replaced with D, E, H, K, R, A, G, I, L, S, T, M, V, F, W, Y, P, or C; V808 replaced with D, E, H, K, R, N, Q, F, W, Y, P, or C; L809 replaced with D, E, H, K, R, N, Q, F, W, Y, P, or C; T810 replaced with D, E, H, K, R, N, Q, F, W, Y, P, or C; V811 replaced with D, E, H, K, R, N, Q, F, W, Y, P, or C; G812 replaced with D, E, H, K, R, N, Q, F, W, Y, P, or C; N813 replaced with D, E, H, K, R, A, G, I, L, S, T, M, V, F, W, Y, P, or C; A814 replaced with D, E, H, K, R, N, Q, F, W, Y, P, or C; L815 replaced with D, E, H, K, R, N, Q, F, W, Y, P, or C; R816 replaced with D, E, A, G, I, L, S, T, M, V, N, Q, F, W, Y, P, or C; P817 replaced with D, E, H, K, R, A, G, I, L, S, T, M, V, N, Q, F, W, Y, or C; K818 replaced with D, E, A, G, I, L, S, T, M, V, N, Q, F, W, Y, P, or C; I819 replaced with D, E, H, K, R, N, Q, F, W, Y, P, or C; K820 replaced with D, E, A, G, I, L, S, T, M, V, N, Q, F, W, Y, P, or C; Y821 replaced with D, E, H, K, R, N, Q, A, G, I, L, S, T, M, V, P, or C; T822 replaced with D, E, H, K, R, N, Q, F, W, Y, P, or C; Y823 replaced with D, E, H, K, R, N, Q, A, G, I, L, S, T, M, V, P, or C; F824 replaced with D, E, H, K, R, N, Q, A, G, I, L, S, T, M, V, P, or C; V825 replaced with D, E, H, K, R, N, Q, F, W, Y, P, or C; K826 replaced with D, E, A, G, I, L, S, T, M, V, N, Q, F, W, Y, P, or C; K827 replaced with D, E, A, G, I, L, S, T, M, V, N, Q, F, W, Y, P, or C; K828 replaced with D, E, A, G, I, L, S, T, M, V, N, Q, F, W, Y, P, or C; K829 replaced with D, E, A, G, I, L, S, T, M, V, N, Q, F, W, Y, P, or C; E830 replaced with H, K, R, A, G, I, L, S, T, M, V, N, Q, F, W, Y, P, or C; S831 replaced with D, E, H, K, R, N, Q, F, W, Y, P, or C; F832 replaced with D, E, H, K, R, N, Q, A, G, I, L, S, T, M, V, P, or C; N833 replaced with D, E, H, K, R, A, G, I, L, S, T, M, V, F, W, Y, P, or C; A834 replaced with D, E, H, K, R, N, Q, F, W, Y, P, or C; I835 replaced with D, E, H, K, R, N, Q, F, W, Y, P, or C; P836 replaced with D, E, H, K, R, A, G, I, L, S, T, M, V, N, Q, F, W, Y, or C; T837 replaced with D, E, H, K, R, N, Q, F, W, Y, P, or C; F838 replaced with D, E, H, K, R, N, Q, A, G, I, L, S, T, M, V, P, or C; S839 replaced with D, E, H, K, R, N, Q, F, W, Y, P, or C; A840 replaced with D, E, H, K, R, N, Q, F, W, Y, P, or C; W841 replaced with D, E, H, K, R, N, Q, A, G, I, L, S, T, M, V, P, or C; V842 replaced with D, E, H, K, R, N, Q, F, W, Y, P, or C; I843 replaced with D, E, H, K, R, N, Q, F, W, Y, P, or C; E844 replaced with H, K, R, A, G, I, L, S, T, M, V, N, Q, F, W, Y, P, or C; E845 replaced with H, K, R, A, G, I, L, S, T, M, V, N, Q, F, W, Y, P, or C; W846 replaced with D, E, H, K, R, N, Q, A, G, I, L, S, T, M, V, P, or C; G847 replaced with D, E, H, K, R, N, Q, F, W, Y, P, or C; E848 replaced with H, K, R, A, G, I, L, S, T, M, V, N, Q, F, W, Y, P, or C; C849 replaced with D, E, H, K, R, A, G, I, L, S, T, M, V, N, Q, F, W, Y, or P; S850 replaced with D, E, H, K, R, N, Q, F, W, Y, P, or C; K851 replaced with D, E, A, G, I, L, S, T, M, V, N, Q, F, W, Y, P, or C; S852 replaced with D, E, H, K, R, N, Q, F, W, Y, P, or C; C853 replaced with D, E, H, K, R, A, G, I, L, S, T, M, V, N, Q, F, W, Y, or P; E854 replaced with H, K, R, A, G, I, L, S, T, M, V, N, Q, F, W, Y, P, or C; L855 replaced with D, E, H, K, R, N, Q, F, W, Y, P, or C; G856 replaced with D, E, H, K, R, N, Q, F, W, Y, P, or C; W857 replaced with D, E, H, K, R, N, Q, A, G, I, L, S, T, M, V, P, or C; Q858 replaced with D, E, H, K, R, A, G, I, L, S, T, M, V, F, W, Y, P, or C; R859 replaced with D, E, A, G, I, L, S, T, M, V, N, Q, F, W, Y, P, or C; R860 replaced with D, E, A, G, I, L, S, T, M, V, N, Q, F, W, Y, P, or C; L861 replaced with D, E, H, K, R, N, Q, F, W, Y, P, or C; V862 replaced with D, E, H, K, R, N, Q, F, W, Y, P, or C; E863 replaced with H, K, R, A, G, I, L, S, T, M, V, N, Q, F, W, Y, P, or C; C864 replaced with D, E, H, K, R, A, G, I, L, S, T, M, V, N, Q, F, W, Y, or P; R865 replaced with D, E, A, G, I, L, S, T, M, V, N, Q, F, W, Y, P, or C; D866 replaced with H, K, R, A, G, I, L, S, T, M, V, N, Q, F, W, Y, P, or C; I867 replaced with D, E, H, K, R, N, Q, F, W, Y, P, or C; N868 replaced with D, E, H, K, R, A, G, I, L, S, T, M, V, F, W, Y, P, or C; G869 replaced with D, E, H, K, R, N, Q, F, W, Y, P, or C; Q870 replaced with D, E, H, K, R, A, G, I, L, S, T, M, V, F, W, Y, P, or C; P871 replaced with D, E, H, K, R, A, G, I, L, S, T, M, V, N, Q, F, W, Y, or C; A872 replaced with D, E, H, K, R, N, Q, F, W, Y, P, or C; S873 replaced with D, E, H, K, R, N, Q, F, W, Y, P, or C; E874 replaced with H, K, R, A, G, I, L, S, T, M, V, N, Q, F, W, Y, P, or C; C875 replaced with D, E, H, K, R, A, G, I, L, S, T, M, V, N, Q, F, W, Y, or P; A876 replaced with D, E, H, K, R, N, Q, F, W, Y, P, or C; K877 replaced with D, E, A, G, I, L, S, T, M, V, N, Q, F, W, Y, P, or C; E878 replaced with H, K, R, A, G, I, L, S, T, M, V, N, Q, F, W, Y,or C; V879 replaced with D, E, H, K, R, N, Q, F, W, Y, P, or C; K880 replaced with D, E, A, G, I, L, S, T, M, V, N, Q, F, W, Y, P, or C; P881 replaced with D, E, H, K, R, A, G, I, L, S, T, M, V, N, Q, F, W, Y, or C; A882 replaced with D, E, H, K, R, N, Q, F, W, Y, P, or C; S883 replaced with D, E, H, K, R, N, Q, F, W, Y, P, or C; T884 replaced with D, E, H, K, R, N, Q, F, W, Y, P, or C; R885 replaced with D, E, A, G, I, L, S, T, M, V, N, Q, F, W, Y, P, or C; P886 replaced with D, E, H, K, R, A, G, I, L, S, T, M, V, N, Q, F, W, Y, or C; C887 replaced with D, E, H, K, R, A, G, I, L, S, T, M, V, N, Q, F, W, Y, or P; A888 replaced with D, E, H, K, R, N, Q, F, W, Y, P, or C; D889 replaced with H, K, R, A, G, I, L, S, T, M, V, N, Q, F, W, Y, P, or C; H890 replaced with D, E, A, G, I, L, S, T, M, V, N, Q, F, W, Y, P, or C; P891 replaced with D, E, H, K, R, A, G, I, L, S, T, M, V, N, Q, F, W, Y, or C; C892 replaced with D, E, H, K, R, A, G, I, L, S, T, M, V, N, Q, F, W, Y, or P; P893 replaced with D, E, H, K, R, A, G, I, L, S, T, M, V, N, Q, F, W, Y, or C; Q894 replaced with D, E, H, K, R, A, G, I, L, S, T, M, V, F, W, Y, P, or C; W895 replaced with D, E, H, K, R, N, Q, A, G, I, L, S, T, M, V, P, or C; Q896 replaced with D, E, H, K, R, A, G, I, L, S, T, M, V, F, W, Y, P, or C; L897 replaced with D, E, H, K, R, N, Q, F, W, Y, P, or C; G898 replaced with D, E, H, K, R, N, Q, F, W, Y, P, or C; E899 replaced with H, K, R, A, G, I, L, S, T, M, V, N, Q, F, W, Y, P, or C; W900 replaced with D, E, H, K, R, N, Q, A, G, I, L, S, T, M, V, P, or C; S901 replaced with D, E, H, K, R, N, Q, F, W, Y, P, or C; S902 replaced with D, E, H, K, R, N, Q, F, W, Y, P, or C; C903 replaced with D, E, H, K, R, A, G, I, L, S, T, M, V, N, Q, F, W, Y, or P; S904 replaced with D, E, H, K, R, N, Q, F, W, Y, P, or C; K905 replaced with D, E, A, G, I, L, S, T, M, V, N, Q, F, W, Y, P, or C; T906 replaced with D, E, H, K, R, N, Q, F, W, Y, P, or C; C907 replaced with D, E, H, K, R, A, G, I, L, S, T, M, V, N, Q, F, W, Y, or P; G908 replaced with D, E, H, K, R, N, Q, F, W, Y, P, or K909 replaced with D, E, A, G, I, L, S, T, M, V, N, Q, F, W, Y, P, or C; G910 replaced with D, E, H, K, R, N, Q, F, W, Y, P, or C; Y911 replaced with D, E, H, K, R, N, Q, A, G, I, L, S, T, M, V, P, or C; K912 replaced with D, E, A, G, I, L, S, T, M, V, N, Q, F, W, Y, P, or C; K913 replaced with D, E, A, G, I, L, S, T, M, V, N, Q, F, W, Y, P, or C; R914 replaced with D, E, A, G, I, L, S, T, M, V, N, Q, F, W, Y, P, or C; S915 replaced with D, E, H, K, R, N, Q, F, W, Y, P, or C; L916 replaced with D, E, H, K, R, N, Q, F, W, Y, P, or C; K917 replaced with D, E, A, G, I, L, S, T, M, V, N, Q, F, W, Y, P, or C; C918 replaced with D, E, H, K, R, A, G, I, L, S, T, M, V, N, Q, F, W, Y, or P; L919 replaced with D, E, H, K, R, N, Q, F, W, Y, P, or C; S920 replaced with D, E, H, K, R, N, Q, F, W, Y, P, or C; H921 replaced with D, E, A, G, I, L, S, T, M, V, N, Q, F, W, Y, P, or C; D922 replaced with H, K, R, A, G, I, L, S, T, M, V, N, Q, F, W, Y, P, or C; G923 replaced with D, E, H, K, R, N, Q, F, W, Y, P, or C; G924 replaced with D, E, H, K, R, N, Q, F, W, Y, P, or C; V925 replaced with D, E, H, K, R, N, Q, F, W, Y, P, or C; L926 replaced with D, E, H, K, R, N, Q, F, W, Y, P, or C; S927 replaced with D, E, H, K, R, N, Q, F, W, Y, P, or C; H928 replaced with D, E, A, G, I, L, S, T, M, V, N, Q, F, W, Y, P, or C; E929 replaced with H, K, R, A, G, I, L, S, T, M, V, N, Q, F, W, Y, P, or C; S930 replaced with D, E, H, K, R, N, Q, F, W, Y, P, or C; C931 replaced with D, E, H, K, R, A, G, I, L, S, T, M, V, N, Q, F, W, Y, or P; D932 replaced with H, K, R, A, G, I, L, S, T, M, V, N, Q, F, W, Y, P, or C; P933 replaced with D, E, H, K, R, A, G, I, L, S, T, M, V, N, Q, F, W, Y, or C; L934 replaced with D, E, H, K, R, N, Q, F, W, Y, P, or C; K935 replaced with D, E, A, G, I, L, S, T, M, V, N, Q, F, W, Y, P, or C; K936 replaced with D, E, A, G, I, L, S, T, M, V, N, Q, F, W, Y, P, or C; P937 replaced with D, E, H, K, R, A, G, I, L, S, T, M, V, N, Q, F, W, Y, or C; K938 replaced with D, E, A, G, I, L, S, T, M, V, N, Q, F, W, Y, P, or C; H939 replaced with D, E, A, G, I, L, S, T, M, V, N, Q, F, W, Y, P, or C; F940 replaced with D, E, H, K, R, N, Q, A, G, I, L, S, T, M, V, P, or C; I941 replaced with D, E, H, K, R, N, Q, F, W, Y, P, or C; D942 replaced with H, K, R, A, G, I, L, S, T, M, V, N, Q, F, W, Y, P, or C; F943 replaced with D, E, H, K, R, N, Q, A, G, I, L, S, T, M, V, P, or C; C944 replaced with D, E, H, K, R, A, G, I, L, S, T, M, V, N, Q, F, W, Y, or P; T945 replaced with D, E, H, K, R, N, Q, F, W, Y, P, or C; M946 replaced with D, E, H, K, R, N, Q, F, W, Y, P, or C; A947 replaced with D, E, H, K, R, N, Q, F, W, Y, P, or C; E948 replaced with H, K, R, A, G, I, L, S, T, M, V, N, Q, F, W, Y, P, or C; C949 replaced with D, E, H, K, R, A, G, I, L, S, T, M, V, N, Q, F, W, Y, or P; S950 replaced with D, E, H, K, R, N, Q, F, W, Y, P, or C.

Also preferred are METH2 polypeptides with one or more of the following conservative amino acid substitutions: M1 replaced with A, G, I, L, S, T, or V; F2 replaced with W, or Y; A4 replaced with G, I, L, S, T, M, or V; A6 replaced with G, I, L, S, T, M, or V; A7 replaced with G, I, L, S, T, M, or V; R9 replaced with H, or K; W10 replaced with F, or Y; L11 replaced with A, G, I, S, T, M, or V; F13 replaced with W, or Y; L14 replaced with A, G, I, S, T, M, or V; L15 replaced with A, G, I, S, T, M, or V; L16 replaced with A, G, I, S, T, M, or V; L17 replaced with A, G, I, S, T, M, or V; L18 replaced with A, G, I, S, T, M, or V; L19 replaced with A, G, I, S, T, M, or V; L20 replaced with A, G, I, S, T, M, or V; L21 replaced with A, G, I, S, T, M, or V; L22 replaced with A, G, I, S, T, M, or V; L24 replaced with A, G, I, S, T, M, or V; A25 replaced with G, I, L, S, T, M, or V; R26 replaced with H, or K; G27 replaced with A, I, L, S, T, M, or V; A28 replaced with G, I, L, S, T, M, or V; A30 replaced with G, I, L, S, T, M, or V; R31 replaced with H, or K; A33 replaced with G, I, L, S, T, M, or V; A34 replaced with G, I, L, S, T, M, or V; G35 replaced with A, I, L, S, T, M, or V; G36 replaced with A, I, L, S, T, M, or V; Q37 replaced with N; A38 replaced with G, I, L, S, T, M, or V; S39 replaced with A, G, I, L, T, M, or V; E40 replaced with D; L41 replaced with A, G, I, S, T, M, or V; V42 replaced with A, G, I, L, S, T, or M; V43 replaced with A, G, I, L, S, T, or M; T45 replaced with A, G, I, L, S, M, or V; R46 replaced with H, or K; L47 replaced with A, G, I, S, T, M, or V; G49 replaced with A, I, L, S, T, M, or V; S50 replaced with A, G, I, L, T, M, or V; A51 replaced with G, I, L, S, T, M, or V; G52 replaced with A, I, L, S, T, M, or V; E53 replaced with D; L54 replaced with A, G, I, S, T, M, or V; A55 replaced with G, I, L, S, T, M, or V; L56 replaced with A, G, I, S, T, M, or V; H57 replaced with K, or R; L58 replaced with A, G, I, S, T, M, or V; S59 replaced with A, G, I, L, T, M, or V; A60 replaced with G, I, L, S, T, M, or V; F61 replaced with W, or Y; G62 replaced with A, I, L, S, T, M, or V; K63 replaced with H, or R; G64 replaced with A, I, L, S, T, M, or V; F65 replaced with W, or Y; V66 replaced with A, G, I, L, S, T, or M; L67 replaced with A, G, I, S, T, M, or V; R68 replaced with H, or K; L69 replaced with A, G, I, S, T, M, or V; A70 replaced with G, I, L, S, T, M, or V; D72 replaced with E; D73 replaced with E; S74 replaced with A, G, I, L, T, M, or V; F75 replaced with W, or Y; L76 replaced with A, G, I, S, T, M, or V; A77 replaced with G, I, L, S, T, M, or V; E79 replaced with D; F80 replaced with W, or Y; K81 replaced with H, or R; I82 replaced with A, G, L, S, T, M, or V; E83 replaced with D; R84 replaced with H, or K; L85 replaced with A, G, I, S, T, M, or V; G86 replaced with A, I, L, S, T, M, or V; G87 replaced with A, I, L, S, T, M, or V; S88 replaced with A, G, I, L, T, M, or V; G89 replaced with A, I, L, S, T, M, or V; R90 replaced with H, or K; A91 replaced with G, I, L, S, T, M, or V; T92 replaced with A, G, I, L, S, M, or V; G93 replaced with A, I, L, S, T, M, or V; G94 replaced with A, I, L, S, T, M, or V; E95 replaced with D; R96 replaced with H, or K; G97 replaced with A, I, L, S, T, M, or V; L98 replaced with A, G, I, S, T, M, or V; R99 replaced with H, or K; G100 replaced with A, I, L, S, T, M, or V; F102 replaced with W, or Y; F103 replaced with W, or Y; S104 replaced with A, G, I, L, T, M, or V; G105 replaced with A, I, L, S, T, M, or V; T106 replaced with A, G, I, L, S, M, or V; V107 replaced with A, G, I, L, S, T, or M; N108 replaced with Q; G109 replaced with A, I, L, S, T, M, or V; E110 replaced with D; E112 replaced with D; S113 replaced with A, G, I, L, T, M, or V; L114 replaced with A, G, I, S, T, M, or V; A115 replaced with G, I, L, S, T, M, or V; A116 replaced with G, I, L, S, T, M, or V; V117 replaced with A, G, I, L, S, T, or M; S118 replaced with A, G, I, L, T, M, or V; L119 replaced with A, G, I, S, T, M, or V; R121 replaced with H, or K; G122 replaced with A, I, L, S, T, M, or V; L123 replaced with A, G, I, S, T, M, or V; S124 replaced with A, G, I, L, T, M, or V; G125 replaced with A, I, L, S, T, M, or V; S126 replaced with A, G, I, L, T, M, or V; F127 replaced with W, or Y; L128 replaced with A, G, I, S, T, M, or V; L129 replaced with A, G, I, S, T, M, or V; D130 replaced with E; G131 replaced with A, I, L, S, T, M, or V; E132 replaced with D; E133 replaced with D; F134 replaced with W, or Y; T135 replaced with A, G, I, L, S, M, or V; I136 replaced with A, G, L, S, T, M, or V; Q137 replaced with N; Q139 replaced with N; G140 replaced with A, I, L, S, T, M, or V; A141 replaced with G, I, L, S, T, M, or V; G142 replaced with A, I, L, S, T, M, or V; G143 replaced with A, I, L, S, T, M, or V; S144 replaced with A, G, I, L, T, M, or V; L145 replaced with A, G, I, S, T, M, or V; A146 replaced with G, I, L, S, T, M, or V; Q147 replaced with N; H149 replaced with K, or R; R150 replaced with H, or K; L151 replaced with A, G, I, S, T, M, or V; Q152 replaced with N; R153 replaced with H, or K; W154 replaced with F, or Y; G155 replaced with A, I, L, S, T, M, or V; A157 replaced with G, I, L, S, T, M, or V; G158 replaced with A, I, L, S, T, M, or V; A159 replaced with G, I, L, S, T, M, or V; R160 replaced with H, or K; L162 replaced with A, G, I, S, T, M, or V; R164 replaced with H, or K; G165 replaced with A, I, L, S, T, M, or V; E167 replaced with D; W168 replaced with F, or Y; E169 replaced with D; V170 replaced with A, G, I, L, S, T, or M; E171 replaced with D; T172 replaced with A, G, I, L, S, M, or V; G173 replaced with A, I, L, S, T, M, or V; E174 replaced with D; G175 replaced with A, I, L, S, T, M, or V; Q176 replaced with N; R177 replaced with H, or K; Q178 replaced with N; E179 replaced with D; R180 replaced with H, or K; G181 replaced with A, I, L, S, T, M, or V; D182 replaced with E; H183 replaced with K, or R; Q184 replaced with N; E185 replaced with D; D186 replaced with E; S187 replaced with A, G, I, L, T, M, or V; E188 replaced with D; E189 replaced with D; E190 replaced with D; S191 replaced with A, G, I, L, T, M, or V; Q192 replaced with N; E193 replaced with D; E194 replaced with D; E195 replaced with D; A196 replaced with G, I, L, S, T, M, or V; E197 replaced with D; G198 replaced with A, I, L, S, T, M, or V; A199 replaced with G, I, L, S, T, M, or V; S200 replaced with A, G, I, L, T, M, or V; E201 replaced with D; L206 replaced with A, G, I, S, T, M, or V; G207 replaced with A, I, L, S, T, M, or V; A208 replaced with G, I, L, S, T, M, or V; T209 replaced with A, G, I, L, S, M, or V; S210 replaced with A, G, I, L, T, M, or V; R211 replaced with H, or K; T212 replaced with A, G, I, L, S., M, or V; K213 replaced with H, or R; R214 replaced with H, or K; F215 replaced with W, or Y; V216 replaced with A, G, I, L, S, T, or M; S217 replaced with A, G, I, L, T, M, or V; E218 replaced with D; A219 replaced with G, I, L, S, T, M, or V; R220 replaced with H, or K; F221 replaced with W, or Y; V222 replaced with A, G, I, L, S, T, or M; E223 replaced with D; T224 replaced with A, G, I, L, S, M, or V; L225 replaced with A, G, I, S, T, M, or V; L226 replaced with A, G, I, S, T, M, or V; V227 replaced with A, G, I, L, S, T, or M; A228 replaced with G, I, L, S, T, M, or V; D229 replaced with E; A230 replaced with G, I, L, S, T, M, or V; S231 replaced with A, G, I, L, T, M, or V; M232 replaced with A, G, I, L, S, T, or V; A233 replaced with G, I, L, S, T, M, or V; A234 replaced with G, I, L, S, T, M, or V; F235 replaced with W, or Y; Y236 replaced with F, or W; G237 replaced with A, I, L, S, T, M, or V; A238 replaced with G, I, L, S, T, M, or V; D239 replaced with E; L240 replaced with A, G, I, S, T, M, or V; Q241 replaced with N; N242 replaced with Q; H243 replaced with K, or R; I244 replaced with A, G, L, S, T, M, or V; L245 replaced with A, G, I, S, T, M, or V; T246 replaced with A, G, I, L, S, M, or V; L247 replaced with A, G, I, S, T, M, or V; M248 replaced with A, G, I, L, S, T, or V; S249 replaced with A, G, I, L, T, M, or V; V250 replaced with A, G, I, L, S, T, or M; A251 replaced with G, I, L, S, T, M, or V; A252 replaced with G, I, L, S, T, M, or V; R253 replaced with H, or K; I254 replaced with A, G, L, S, T, M, or V; Y255 replaced with F, or W; K256 replaced with H, or R; H257 replaced with K, or R; S259 replaced with A, G, I, L, T, M, or V; I260 replaced with A, G, L, S, T, M, or V; K261 replaced with H, or R; N262 replaced with Q; S263 replaced with A, G, I, L, T, M, or V; I264 replaced with A, G, L, S, T, M, or V; N265 replaced with Q; L266 replaced with A, G, I, S, T, M, or V; M267 replaced with A, G, I, L, S, T, or V; V268 replaced with A, G, I, L, S, T, or M; V269 replaced with A, G, I, L, S, T, or M; K270 replaced with H, or R; V271 replaced with A, G, I, L, S, T, or M; L272 replaced with A, G, I, S, T, M, or V; I273 replaced with A, G, L, S, T, M, or V; V274 replaced with A, G, I, L, S, T, or M; E275 replaced with D; D276 replaced with E; E277 replaced with D; K278 replaced with H, or R; W279 replaced with F, or Y; G280 replaced with A, I, L, S, T, M, or V; E282 replaced with D; V283 replaced with A, G, I, L, S, T, or M; S284 replaced with A, G, I, L, T, M, or V; D285 replaced with E; N286 replaced with Q; G287 replaced with A, I, L, S, T, M, or V; G288 replaced with A, I, L, S, T, M, or V; L289 replaced with A, G, I, S, T, M, or V; T290 replaced with A, G, I, L, S, M, or V; L291 replaced with A, G, I, S, T, M, or V; R292 replaced with H, or K; N293 replaced with Q; F294 replaced with W, or Y; N296 replaced with Q; W297 replaced with F, or Y; Q298 replaced with N; R299 replaced with H, or K; R300 replaced with H, or K; F301 replaced with W, or Y; N302 replaced with Q; Q303 replaced with N; S305 replaced with A, G, I, L, T, M, or V; D306 replaced with E; R307 replaced with H, or K; H308 replaced with K, or R; E310 replaced with D; H311 replaced with K, or R; Y312 replaced with F, or W; D313 replaced with E; T314 replaced with A, G, I, L, S, M, or V; A315 replaced with G, I, L, S, T, M, or V; I316 replaced with A, G, L, S, T, M, or V; L317 replaced with A, G, I, S, T, M, or V; L318 replaced with A, G, I, S, T, M, or V; T319 replaced with A, G, I, L, S, M, or V; R320 replaced with H, or K; Q321 replaced with N; N322 replaced with Q; F323 replaced with W, or Y; G325 replaced with A, I, L, S, T, M, or V; Q326 replaced with N; E327 replaced with D; G328 replaced with A, I, L, S, T, M, or V; L329 replaced with A, G, I, S, T, M, or V; D331 replaced with E; T332 replaced with A, G, I, L, S, M, or V; L333 replaced with A, G, I, S, T, M, or V; G334 replaced with A, I, L, S, T, M, or V; V335 replaced with A, G, I, L, S, T, or M; A336 replaced with G, I, L, S, T, M, or V; D337 replaced with E; I338 replaced with A, G, L, S, T, M, or V; G339 replaced with A, I, L, S, T, M, or V; T340 replaced with A, G, I, L, S, M, or V; I341 replaced with A, G, L, S, T, M, or V; D343 replaced with E; N345 replaced with Q; K346 replaced with H, or R; S347 replaced with A, G, I, L, T, M, or V; S349 replaced with A, G, I, L, T, M, or V; V350 replaced with A, G, I, L, S, T, or M; I351 replaced with A, G, L, S, T, M, or V; E352 replaced with D; D353 replaced with E; E354 replaced with D; G355 replaced with A, I, L, S, T, M, or V; L356 replaced with A, G, I, S, T, M, or V; Q357 replaced with N; A358 replaced with G, I, L, S, T, M, or V; A359 replaced with G, I, L, S, T, M, or V; H360 replaced with K, or R; T361 replaced with A, G, I, L, S, M, or V; L362 replaced with A, G, I, S, T, M, or V; A363 replaced with G, I, L, S, T, M, or V; H364 replaced with K, or R; E365 replaced with D; L366 replaced with A, G, I, S, T, M, or V; G367 replaced with A, I, L, S, T, M, or V; H368 replaced with K, or R; V369 replaced with A, G, I, L, S, T, or M; L370 replaced with A, G, I, S, T, M, or V; S371 replaced with A, G, I, L, T, M, or V; M372 replaced with A, G, I, L, S, T, or V; H374 replaced with K, or R; D375 replaced with E; D376 replaced with E; S377 replaced with A, G, I, L, T, M, or V; K378 replaced with H, or R; T381 replaced with A, G, I, L, S, M, or V; R382 replaced with H, or K; L383 replaced with A, G, I, S, T, M, or V; F384 replaced with W, or Y; G385 replaced with A, I, L, S, T, M, or V; M387 replaced with A, G, I, L, S, T, or V; G388 replaced with A, I, L, S, T, M, or V; K389 replaced with H, or R; H390 replaced with K, or R; H391 replaced with K, or R; V392 replaced with A, G, I, L, S, T, or M; M393 replaced with A, G, I, L, S, T, or V; A394 replaced with G, I, L, S, T, M, or V; L396 replaced with A, G, I, S, T, M, or V; F397 replaced with W, or Y; V398 replaced with A, G, I, L, S, T, or M; H399 replaced with K, or R; L400 replaced with A, G, I, S, T, M, or V; N401 replaced with Q; Q402 replaced with N; T403 replaced with A, G, I, L, S, M, or V; L404 replaced with A, G, I, S, T, M, or V; W406 replaced with F, or Y; S407 replaced with A, G, I, L, T, M, or V; S410 replaced with A, G, I, L, T, M, or V; A411 replaced with G, I, L, S, T, M, or V; M412 replaced with A, G, I, L, S, T, or V; Y413 replaced with F, or W; L414 replaced with A, G, I, S, T, M, or V; T415 replaced with A, G, I, L, S, M, or V; E416 replaced with D; L417 replaced with A, G, I, S, T, M, or V; L418 replaced with A, G, I, S, T, M, or V; D419 replaced with E; G420 replaced with A, I, L, S, T, M, or V; G421 replaced with A, I, L, S, T, M, or V; H422 replaced with K, or R; G423 replaced with A, I, L, S, T, M, or V; D424 replaced with E; L426 replaced with A, G, I, S, T, M, or V; L427 replaced with A, G, I, S, T, M, or V; D428 replaced with E; A429 replaced with G, I, L, S, T, M, or V; G431 replaced with A, I, L, S, T, M, or V; A432 replaced with G, I, L, S, T, M, or V; A433 replaced with G, I, L, S, T, M, or V; L434 replaced with A, G, I, S, T, M, or V; L436 replaced with A, G, I, S, T, M, or V; T438 replaced with A, G, I, L, S, M, or V; G439 replaced with A, I, L, S, T, M, or V; L440 replaced with A, G, I, S, T, M, or V; G442 replaced with A, I, L, S, T, M, or V; R443 replaced with H, or K; M444 replaced with A, G, I, L, S, T, or V; A445 replaced with G, I, L, S, T, M, or V; L446 replaced with A, G, I, S, T, M, or V; Y447 replaced with F, or W; Q448 replaced with N; L449 replaced with A, G, I, S, T, M, or V; D450 replaced with E; Q451 replaced with N; Q452 replaced with N; R454 replaced with H, or K; Q455 replaced with N; I456 replaced with A, G, L, S, T, M, or V; F457 replaced with W, or Y; G458 replaced with A, I, L, S, T, M, or V; D460 replaced with E; F461 replaced with W, or Y; R462 replaced with H, or K; H463 replaced with K, or R; N466 replaced with Q; T467 replaced with A, G, I, L, S, M, or V; S468 replaced with A, G, I, L, T, M, or V; A469 replaced with G, I, L, S, T, M, or V; Q470 replaced with N; D471 replaced with E; V472 replaced with A, G, I, L, S, T, or M; A474 replaced with G, I, L, S, T, M, or V; Q475 replaced with N; L476 replaced with A, G, I, S, T, M, or V; W477 replaced with F, or Y; H479 replaced with K, or R; T480 replaced with A, G, I, L, S, M, or V; D481 replaced with E; G482 replaced with A, I, L, S, T, M, or V; A483 replaced with G, I, L, S, T, M, or V; E484 replaced with D; L486 replaced with A, G, I, S, T, M, or V; H488 replaced with K, or R; T489 replaced with A, G, I, L, S, M, or V; K490 replaced with H, or R; N491 replaced with Q; G492 replaced with A, I, L, S, T, M, or V; S493 replaced with A, G, I, L, T, M, or V; L494 replaced with A, G, I, S, T, M, or V; W496 replaced with F, or Y; A497 replaced with G, I, L, S, T, M, or V; D498 replaced with E; G499 replaced with A, I, L, S, T, M, or V; T500 replaced with A, G, I, L, S, M, or V; G503 replaced with A, I, L, S, T, M, or V; G505 replaced with A, I, L, S, T, M, or V; H506 replaced with K, or R; L507 replaced with A, G, I, S, T, M, or V; S509 replaced with A, G, I, L, T, M, or V; E510 replaced with D; G511 replaced with A, I, L, S, T, M, or V; S512 replaced with A, G, I, L, T, M, or V; L514 replaced with A, G, I, S, T, M, or V; E516 replaced with D; E517 replaced with D; E518 replaced with D; V519 replaced with A, G, I, L, S, T, or M; E520 replaced with D; R521 replaced with H, or K; K523 replaced with H, or R; V525 replaced with A, G, I, L, S, T, or M; V526 replaced with A, G, I, L, S, T, or M; D527 replaced with E; G528 replaced with A, I, L, S, T, M, or V; G529 replaced with A, I, L, S, T, M, or V; W530 replaced with F, or Y; A531 replaced with G, I, L, S, T, M, or V; W533 replaced with F, or Y; G534 replaced with A, I, L, S, T, M, or V; W536 replaced with F, or Y; G537 replaced with A, I, L, S, T, M, or V; E538 replaced with D; S540 replaced with A, G, I, L, T, M, or V; R541 replaced with H, or K; T542 replaced with A, G, I, L, S, M, or V; G544 replaced with A, I, L, S, T, M, or V; G545 replaced with A, I, L, S, T, M, or V; G546 replaced with A, I, L, S, T, M, or V; V547 replaced with A, G, I, L, S, T, or M; Q548 replaced with N; F549 replaced with W, or Y; S550 replaced with A, G, I, L, T, M, or V; H551 replaced with K, or R; R552 replaced with H, or K; E553 replaced with D; K555 replaced with H, or R; D556 replaced with E; E558 replaced with D; Q560 replaced with N; N561 replaced with Q; G562 replaced with A, I, L, S, T, M, or V; G563 replaced with A, I, L, S, T, M, or V; R564 replaced with H, or K; Y565 replaced with F, or W; L567 replaced with A, G, I, S, T, M, or V; G568 replaced with A, I, L, S, T, M, or V; R569 replaced with H, or K; R570 replaced with H, or K; A571 replaced with G, I, L, S, T, M, or V; K572 replaced with H, or R; Y573 replaced with F, or W; Q574 replaced with N; S575 replaced with A, G, I, L, T, M, or V; H577 replaced with K, or R; T578 replaced with A, G, I, L, S, M, or V; E579 replaced with D; E580 replaced with D; D584 replaced with E; G585 replaced with A, I, L, S, T, M, or V; K586 replaced with H, or R; S587 replaced with A, G, I, L, T, M, or V; F588 replaced with W, or Y; R589 replaced with H, or K; E590 replaced with D; Q591 replaced with N; Q592 replaced with N; E594 replaced with D; K595 replaced with H, or R; Y596 replaced with F, or W; N597 replaced with Q; A598 replaced with G, I, L, S, T, M, or V; Y599 replaced with F, or W; N600 replaced with Q; Y601 replaced with F, or W; T602 replaced with A, G, I, L, S, M, or V; D603 replaced with E; M604 replaced with A, G, I, L, S, T, or V; D605 replaced with E; G606 replaced with A, I, L, S, T, M, or V; N607 replaced with Q; L608 replaced with A, G, I, S, T, M, or V; L609 replaced with A, G, I, S, T, M, or V; Q610 replaced with N; W611 replaced with F, or Y; V612 replaced with A, G, I, L, S, T, or M; K614 replaced with H, or R; Y615 replaced with F, or W; A616 replaced with G, I, L, S, T, M, or V; G617 replaced with A, I, L, S, T, M, or V; V618 replaced with A, G, I, L, S, T, or M; S619 replaced with A, G, I, L, T, M, or V; R621 replaced with H, or K; D622 replaced with E; R623 replaced with H, or K; K625 replaced with H, or R; L626 replaced with A, G, I, S, T, M, or V; F627 replaced with W, or Y; R629 replaced with H, or K; A630 replaced with G, I, L, S, T, M, or V; R631 replaced with H, or K; G632 replaced with A, I, L, S, T, M, or V; R633 replaced with H, or K; S634 replaced with A, G, I, L, T, M, or V; E635 replaced with D; F636 replaced with W, or Y; K637 replaced with H, or R; V638 replaced with A, G, I, L, S, T, or M; F639 replaced with W, or Y; E640 replaced with D; A641 replaced with G, I, L, S, T, M, or V; K642 replaced with H, or R; V643 replaced with A, G, I, L, S, T, or M; I644 replaced with A, G, L, S, T, M, or V; D645 replaced with E; G646 replaced with A, I, L, S, T, M, or V; T647 replaced with A, G, I, L, S, M, or V; L648 replaced with A, G, I, S, T, M, or V; G650 replaced with A, I, L, S, T, M, or V; E652 replaced with D; T653 replaced with A, G, I, L, S, M, or V; L654 replaced with A, G, I, S, T, M, or V;

A655 replaced with G, I, L, S, T, M, or V; I656 replaced with A, G, L, S, T, M, or V; V658 replaced with A, G, I, L, S, T, or M; R659 replaced with H, or K; G660 replaced with A, I, L, S, T, M, or V; Q661 replaced with N; V663 replaced with A, G, I, L, S, T, or M; K664 replaced with H, or R; A665 replaced with G, I, L, S, T, M, or V; G666 replaced with A, I, L, S, T, M, or V; D668 replaced with E; H669 replaced with K, or R; V670 replaced with A, G, I, L, S, T, or M; V671 replaced with A, G, I, L, S, T, or M; D672 replaced with E; S673 replaced with A, G, I, L, T, M, or V; R675 replaced with H, or K; K676 replaced with H, or R; L677 replaced with A, G, I, S, T, M, or V; D678 replaced with E; K679 replaced with H, or R; G681 replaced with A, I, L, S, T, M, or V; V682 replaced with A, G, I, L, S, T, or M; G684 replaced with A, I, L, S, T, M, or V; G685 replaced with A, I, L, S, T, M, or V; K686 replaced with H, or R; G687 replaced with A, I, L, S, T, M, or V; N688 replaced with Q; S689 replaced with A, G, I, L, T, M, or V; R691 replaced with H, or K; K692 replaced with H, or R; V693 replaced with A, G, L, S, T, or M; S694 replaced with A, G, I, L, T, M, or V; G695 replaced with A, I, L, S, T, M, or V; S696 replaced with A, G, I, L, T, M, or V; L697 replaced with A, G, I, S, T, M, or V; T698 replaced with A, G, I, L, S, M, or V; T700 replaced with A, G, I, L, S, M, or V; N701 replaced with Q; Y702 replaced with F, or W; G703 replaced with A, I, L, S, T, M, or V; Y704 replaced with F, or W; N705 replaced with Q; D706 replaced with E; I707 replaced with A, G, L, S, T, M, or V; V708 replaced with A, G, I, L, S, T, or M; T709 replaced with A, G, I, L, S, M, or V; I710 replaced with A, G, L, S, T, M, or V; A712 replaced with G, I, L, S, T, M, or V; G713 replaced with A, I, L, S, T, M, or V; A714 replaced with G, I, L, S, T, M, or V; T715 replaced with A, G, I, L, S, M, or V; N716 replaced with Q; I717 replaced with A, G, L, S, T, M, or V; D718 replaced with E; V719 replaced with A, G, I, L, S, T, or M; K720 replaced with H, or R; Q721 replaced with N; R722 replaced with H, or K; S723 replaced with A, G, I, L, T, M, or V; H724 replaced with K, or R; G726 replaced with A, I, L, S, T, M, or V; V727 replaced with A, G, I, L, S, T, or M; Q728 replaced with N; N729 replaced with Q; D730 replaced with E; G731 replaced with A, I, L, S, T, M, or V; N732 replaced with Q; Y733 replaced with F, or W; L734 replaced with A, G, I, S, T, M, or V; A735 replaced with G, I, L, S, T, M, or V; L736 replaced with A, G, I, S, T, M, or V; K737 replaced with H, or R; T738 replaced with A, G, I, L, S, M, or V; A739 replaced with G, I, L, S, T, M, or V; D740 replaced with E; G741 replaced with A, I, L, S, T, M, or V; Q742 replaced with N; Y743 replaced with F, or W; L744 replaced with A, G, I, S, T, M, or V; L745 replaced with A, G, I, S, M, or V; N746 replaced with Q; G747 replaced with A, I, L, S, T, M, or V; N748 replaced with Q; L749 replaced with A, G, I, S, T, M, or V; A750 replaced with G, I, L, S, T, M, or V; I751 replaced with A, G, L, S, T, M, or V; S752 replaced with A, G, I, L, T, M, or V; A753 replaced with G, I, L, S, T, M, or V; I754 replaced with A, G, L, S, T, M, or V; E755 replaced with D; Q756 replaced with N; D757 replaced with E; I758 replaced with A, G, L, S, T, M, or V; L759 replaced with A, G, I, S, T, M, or V; V760 replaced with A, G, I, L, S, T, or M; K761 replaced with H, or R; G762 replaced with A, I, L, S, T, M, or V; T763 replaced with A, G, I, L, S, M, or V; I764 replaced with A, G, L, S, T, M, or V; L765 replaced with A, G, I, S, T, M, or V; K766 replaced with H, or R; Y767 replaced with F, or W; S768 replaced with A, G, I, L, T, M, or V; G769 replaced with A, I, L, S, T, M, or V; S770 replaced with A, G, I, L, T, M, or V; I771 replaced with A, G, L, S, T, M, or V; A772 replaced with G, I, L, S, T, M, or V; T773 replaced with A, G, I, L, S, M, or V; L774 replaced with A, G, I, S, T, M, or V; E775 replaced with D; R776 replaced with H, or K; L777 replaced with A, G, I, S, T, M, or V; Q778 replaced with N; S779 replaced with A, G, I, L, T, M, or V; F780 replaced with W, or Y; R781 replaced with H, or K; L783 replaced with A, G, I, S, T, M, or V; E785 replaced with D; L787 replaced with A, G, I, S, T, M, or V; T788 replaced with A, G, I, L, S, M, or V; V789 replaced with A, G, I, L, S, T, or M; Q790 replaced with N; L791 replaced with A, G, I, S, T, M, or V; L792 replaced with A, G, I, S, T, M, or V; T793 replaced with A, G, I, L, S, M, or V; V794 replaced with A, G, I, L, S, T, or M; G796 replaced with A, I, L, S, T, M, or V; E797 replaced with D; V798 replaced with A, G, I, L, S, T, or M; F799 replaced with W, or Y; K802 replaced with H, or R; V803 replaced with A, G, I, L, S, T, or M; K804 replaced with H, or R; Y805 replaced with F, or W; T806 replaced with A, G, I, L, S, M, or V; F807 replaced with W, or Y; F808 replaced with W, or Y; V809 replaced with A, G, I, L, S, T, or M; N811 replaced with Q; D812 replaced with E; V813 replaced with A, G, I, L, S, T, or M; D814 replaced with E; F815 replaced with W, or Y; S816 replaced with A, G, I, L, T, M, or V; M817 replaced with A, G, I, L, S, T, or V; Q818 replaced with N; S819 replaced with A, G, I, L, T, M, or V; S820 replaced with A, G, I, L, T, M, or V; K821 replaced with H, or R; E822 replaced with D; R823 replaced with H, or K; A824 replaced with G, I, L, S, T, M, or V; T825 replaced with A, G, I, L, S, M, or V; T826 replaced with A, G, I, L, S, M, or V; N827 replaced with Q; I828 replaced with A, G, L, S, T, M, or V; I829 replaced with A, G, L, S, T, M, or V; Q830 replaced with N; L832 replaced with A, G, I, S, T, M, or V; L833 replaced with A, G, I, S, T, M, or V; H834 replaced with K, or R; A835 replaced with G, I, L, S, T, M, or V; Q836 replaced with N; W837 replaced with F, or Y; V838 replaced with A, G, I, L, S, T, or M; L839 replaced with A, G, I, S, T, M, or V; G840 replaced with A, I, L, S, T, M, or V; D841 replaced with E; W842 replaced with F, or Y; S843 replaced with A, G, I, L, T, M, or V; E844 replaced with D; S846 replaced with A, G, I, L, T, M, or V; S847 replaced with A, G, I, L, T, M, or V; T848 replaced with A, G, I, L, S, M, or V; G850 replaced with A, I, L, S, T, M, or V; A851 replaced with G, I, L, S, T, M, or V; G852 replaced with A, I, L, S, T, M, or V; W853 replaced with F, or Y; Q854 replaced with N; R855 replaced with H, or K; R856 replaced with H, or K; T857 replaced with A, G, I, L, S, M, or V; V858 replaced with A, G, I, L, S, T, or M; E859 replaced with D; R861 replaced with H, or K; D862 replaced with E; S864 replaced with A, G, I, L, T, M, or V; G865 replaced with A, I, L, S, T, M, or V; Q866 replaced with N; A867 replaced with G, I, L, S, T, M, or V; S868 replaced with A, G, I, L, T, M, or V; A869 replaced with G, I, L, S, T, M, or V; T870 replaced with A, G, I, L, S, M, or V; N872 replaced with Q; K873 replaced with H, or R; A874 replaced with G, I, L, S, T, M, or V; L875 replaced with A, G, I, S, T, M, or V; K876 replaced with H, or R; E878 replaced with D; D879 replaced with E; A880 replaced with G, I, L, S, T, M, or V; K881 replaced with H, or R; E884 replaced with D; S885 replaced with A, G, I, L, T, M, or V; Q886 replaced with N; L887 replaced with A, G, I, S, T, M, or V; L890 replaced with A, G, I, S, T, M, or V.

Also preferred are METH2 polypeptides with one or more of the following conservative amino acid substitutions: M1 replaced with D, E, H, K, R, N, Q, F, W, Y, P, or C; F2 replaced with D, E, H, K, R, N, Q, A, G, I, L, S, T, M, V, P, or C; P3 replaced with D, E, H, K, R, A, G, I, L, S, T, M, V, N, Q, F, W, Y, or C; A4 replaced with D, E, H, K, R, N, Q, F, W, Y, P, or C; P5 replaced with D, E, H, K, R, A, G, I, L, S, T, M, V, N, Q, F, W, Y, or C; A6 replaced with D, E, H, K, R, N, Q, F, W, Y, P, or C; A7 replaced with D, E, H, K, R, N, Q, F, W, Y, P, or C; P8 replaced with D, E, H, K, R, A, G, I, L, S, T, M, V, N, Q, F, W, Y, or C; R9 replaced with D, E, A, G, I, L, S, T, M, V, N, Q, F, W, Y, P, or C; W10 replaced with D, E, H, K, R, N, Q, A, G, I, L, S, T, M, V, P, or C; L11 replaced with D, E, H, K, R, N, Q, F, W, Y, P, or C; P12 replaced with D, E, H, K, R, A, G, I, L, S, T, M, V, N, Q, F, W, Y, or C; F13 replaced with D, E, H, K, R, N, Q, A, G, I, L, S, T, M, V, P, or C; L14 replaced with D, E, H, K, R, N, Q, F, W, Y, P, or C; L15 replaced with D, E, H, K, R, N, Q, F, W, Y, P, or C; L16 replaced with D, E, H, K, R, N, Q, F, W, Y, P, or C; L17 replaced with D, E, H, K, R, N, Q, F, W, Y, P, or replaced with H, K, R, A, G, I, L, S, T, M, V, N, Q, F, W, Y, P, or C; F134 replaced with D, E, H, K, R, N, Q, A, G, I, L, S, T, M, V, P, or C; T135 replaced with D, E, H, K, R, N, Q, F, W, Y, P, or C; I136 replaced with D, E, H, K, R, N, Q, F, W, Y, P, or C; Q137 replaced with D, E, H, K, R, A, G, I, L, S, T, M, V, F, W, Y, P, or C; P138 replaced with D, E, H, K, R, A, G, I, L, S, T, M, V, N, Q, F, W, Y, or C; Q139 replaced with D, E, H, K, R, A, G, I, L, S, T, M, V, F, W, Y, P, or C; G140 replaced with D, E, H, K, R, N, Q, F, W, Y, P, or C; A141 replaced with D, E, H, K, R, N, Q, F, W, Y, P, or C; G142 replaced with D, E, H, K, R, N, Q, F, W, Y, P, or C; G143 replaced with D, E, H, K, R, N, Q, F, W, Y, P, or C; S144 replaced with D, E, H, K, R, N, Q, F, W, Y, P, or C; L145 replaced with D, E, H, K, R, N, Q, F, W, Y, P, or C; A146 replaced with D, E, H, K, R, N, Q, F, W, Y, P, or C; Q147 replaced with D, E, H, K, R, A, G, I, L, S, T, M, V, F, W, Y, P, or C; P148 replaced with D, E, H, K, R, A, G, I, L, S, T, M, V, N, Q, F, W, Y, or C; H149 replaced with D, E, A, G, I, L, S, T, M, V, N, Q, F, W, Y, P, or C; R150 replaced with D, E, A, G, I, L, S, T, M, V, N, Q, F, W, Y, P, or C; L151 replaced with D, E, H, K, R, N, Q, F, W, Y, P, or C; Q152 replaced with D, E, H, K, R, A, G, I, L, S, T, M, V, F, W, Y, P, or C; R153 replaced with D, E, A, G, I, L, S, T, M, V, N, Q, F, W, Y, P, or C; W154 replaced with D, E, H, K, R, N, Q, A, G, I, L, S, T, M, V, P, or C; G155 replaced with D, E, H, K, R, N, Q, F, W, Y, P, or C; P156 replaced with D, E, H, K, R, A, G, I, L, S, T, M, V, N, Q, F, W, Y, or C; A157 replaced with D, E, H, K, R, N, Q, F, W, Y, P, or C; G158 replaced with D, E, H, K, R, N, Q, F, W, Y, P, or C; A159 replaced with D, E, H, K, R, N, Q, F, W, Y, P, or C; R160 replaced with D, E, A, G, I, L, S, T, M, V, N, Q, F, W, Y, P, or C; P161 replaced with D, E, H, K, R, A, G, I, L, S, T, M, V, N, Q, F, W, Y, or C; L162 replaced with D, E, H, K, R, N, Q, F, W, Y, P, or C; P163 replaced with D, E, H, K, R, A, G, I, L, S, T, M, V, N, Q, F, W, Y, or C; R164 replaced with D, E, A, G, I, L, S, T, M, V, N, Q, F, W, Y, P, or C; G165 replaced with D, E, H, K, R, N, Q, F, W, Y, P, or C; P166 replaced with D, E, H, K, R, A, G, I, L, S, T, M, V, N, Q, F, W, Y, or C; E167 replaced with H, K, R, A, G, I, L, S, T, M, V, N, Q, F, W, Y, P, or C; W168 replaced with D, E, H, K, R, N, Q, A, G, I, L, S, T, M, V, P, or C; E169 replaced with H, K, R, A, G, I, L, S, T, M, V, N, Q, F, W, Y, P, or C; V170 replaced with D, E, H, K, R, N, Q, F, W, Y, P, or C; E171 replaced with H, K, R, A, G, I, L, S, T, M, V, N, Q, F, W, Y, P, or C; T172 replaced with D, E, H, K, R, N, Q, F, W, Y, P, or C; G173 replaced with D, E, H, K, R, N, Q, F, W, Y, P, or C; E174 replaced with H, K, R, A, G, I, L, S, T, M, V, N, Q, F, W, Y, P, or C; G175 replaced with D, E, H, K, R, N, Q, F, W, Y, P, or C; Q176 replaced with D, E, H, K, R, A, G, I, L, S, T, M, V, F, W, Y, P, or C; R177 replaced with D, E, A, G, I, L, S, T, M, V, N, Q, F, W, Y, P, or C; Q178 replaced with D, E, H, K, R, A, G, I, L, S, T, M, V, F, W, Y, P, or C; E179 replaced with H, K, R, A, G, I, L, S, T, M, V, N, Q, F, W, Y, P, or C; R180 replaced with D, E, A, G, I, L, S, T, M, V, N, Q, F, W, Y, P, or C; G181 replaced with D, E, H, K, R, N, Q, F, W, Y, P, or C; D182 replaced with H, K, R, A, G, I, L, S, T, M, V, N, Q, F, W, Y, P, or C; H183 replaced with D, E, A, G, I, L, S, T, M, V, N, Q, F, W, Y, P, or C; Q184 replaced with D, E, H, K, R, A, G, I, L, S, T, M, V, F, W, Y, P, or C; E185 replaced with H, K, R, A, G, I, L, S, T, M, V, N, Q, F, W, Y, P, or C; D186 replaced with H, K, R, A, G, I, L, S, T, M, V, N, Q, F, W, Y, P, or C; S187 replaced with D, E, H, K, R, N, Q, F, W, Y, P, or C; E188 replaced with H, K, R, A, G, I, L, S, T, M, V, N, Q, F, W, Y, P, or C; E189 replaced with H, K, R, A, G, I, L, S, T, M, V, N, Q, F, W, Y, P, or C; E190 replaced with H, K, R, A, G, I, L, S, T, M, V, N, Q, F, W, Y, P, or C; S191 replaced with D, E, H, K, R, N, Q, F, W, Y, P, or C; Q192 replaced with D, E, H, K, R, A, G, I, L, S, T, M, V, F, W, Y, P, or C; E193 replaced with H, K, R, A, G, I, L, S, T, M, V, N, Q, F, W, Y, P, or C; E194 replaced with H, K, R, A, G, I, L, S, T, M, V, N, Q, F, W, Y, P, or C; E195 replaced with H, K, R, A, G, I, L, S, T, M, V, N, Q, F, W, Y, P, or C; A196 replaced with D, E, H, K, R, N, Q, F, W, Y, P, or C; E197 replaced with H, K, R, A, G, I, L, S, T, M, V, N, Q, F, W, Y, P, or C; G198 replaced with D, E, H, K, R, N, Q, F, W, Y, P, or C; A199 replaced with D, E, H, K, R, N, Q, F, W, Y, P, or C; S200 replaced with D, E, H, K, R, N, Q, F, W, Y, P, or C; E201 replaced with H, K, R, A, G, I, L, S, T, M, V, N, Q, F, W, Y, P, or C; P202 replaced with D, E, H, K, R, A, G, I, L, S, T, M, V, N, Q, F, W, Y, or C; P203 replaced with D, E, H, K, R, A, G, I, L, S, T, M, V, N, Q, F, W, Y, or C; P204 replaced with D, E, H, K, R, A, G, I, L, S, T, M, V, N, Q, F, W, Y, or C; P205 replaced with D, E, H, K, R, A, G, I, L, S, T, M, V, N, Q, F, W, Y, or C; L206 replaced with D, E, H, K, R, N, Q, F, W, Y, P, or C; G207 replaced with D, E, H, K, R, N, Q, F, W, Y, P, or C; A208 replaced with D, E, H, K, R, N, Q, F, W, Y, P, or C; T209 replaced with D, E, H, K, R, N, Q, F, W, Y, P, or C; S210 replaced with D, E, H, K, R, N, Q, F, W, Y, P, or C; R211 replaced with D, E, A, G, I, L, S, T, M, V, N, Q, F, W, Y, P, or C; T212 replaced with D, E, H, K, R, N, Q, F, W, Y, P, or C; K213 replaced with D, E, A, G, I, L, S, T, M, V, N, Q, F, W, Y, P, or C; R214 replaced with D, E, A, G, I, L, S, T, M, V, N, Q, F, W, Y, P, or C; F215 replaced with D, E, H, K, R, N, Q, A, G, I, L, S, T, M, V, P, or C; V216 replaced with D, E, H, K, R, N, Q, F, W, Y, P, or C; S217 replaced with D, E, H, K, R, N, Q, F, W, Y, P, or C; E218 replaced with H, K, R, A, G, I, L, S, T, M, V, N, Q, F, W, Y, P, or C; A219 replaced with D, E, H, K, R, N, Q, F, W, Y, P, or C; R220 replaced with D, E, A, G, I, L, S, T, M, V, N, Q, F, W, Y, P, or C; F221 replaced with D, E, H, K, R, N, Q, A, G, I, L, S, T, M, V, P, or C; V222 replaced with D, E, H, K, R, N, Q, F, W, Y, P, or C; E223 replaced with H, K, R, A, G, I, L, S, T, M, V, N, Q, F, W, Y, P, or C; T224 replaced with D, E, H, K, R, N, Q, F, W, Y, P, or C; L225 replaced with D, E, H, K, R, N, Q, F, W, Y, P, or C; L226 replaced with D, E, H, K, R, N, Q, F, W, Y, P, or C; V227 replaced with D, E, H, K, R, N, Q, F, W, Y, P, or C; A228 replaced with D, E, H, K, R, N, Q, F, W, Y, P, or C; D229 replaced with H, K, R, A, G, I, L, S, T, M, V, N, Q, F, W, Y, P, or C; A230 replaced with D, E, H, K, R, N, Q, F, W, Y, P, or C; S231 replaced with D, E, H, K, R, N, Q, F, W, Y, P, or C; M232 replaced with D, E, H, K, R, N, Q, F, W, Y, P, or C; A233 replaced with D, E, H, K, R, N, Q, F, W, Y, P, or C; A234 replaced with D, E, H, K, R, N, Q, F, W, Y, P, or C; F235 replaced with D, E, H, K, R, N, Q, A, G, I, L, S, T, M, V, P, or C; Y236 replaced with D, E, H, K, R, N, Q, A, G, I, L, S, T, M, V, P, or C; G237 replaced with D, E, H, K, R, N, Q, F, W, Y, P, or C; A238 replaced with D, E, H, K, R, N, Q, F, W, Y, P, or C; D239 replaced with H, K, R, A, G, I, L, S, T, M, V, N, Q, F, W, Y, P, or C; L240 replaced with D, E, H, K, R, N, Q, F, W, Y, P, or C; Q241 replaced with D, E, H, K, R, A, G, I, L, S, T, M, V, F, W, Y, P, or C; N242 replaced with D, E, H, K, R, A, G, I, L, S, T, M, V, F, W, Y, P, or C; H243 replaced with D, E, A, G, I, L, S, T, M, V, N, Q, F, W, Y, P, or C; I244 replaced with D, E, H, K, R, N, Q, F, W, Y, P, or C; L245 replaced with D, E, H, K, R, N, Q, F, W, Y, P, or C; T246 replaced with D, E, H, K, R, N, Q, F, W, Y, P, or C; L247 replaced with D, E, H, K, R, N, Q, F, W, Y, P, or C; M248 replaced with D, E, H, K, R, N, Q, F, W, Y, P, or C; S249 replaced with D, E, H, K, R, N, Q, F, W, Y, P, or C; V250 replaced with D, E, H, K, R, N, Q, F, W, Y, P, or C; A251 replaced with D, E, H, K, R, N, Q, F, W, Y, P, or C; A252 replaced with D, E, H, K, R, N, Q, F, W, Y, P, or C; R253 replaced with D, E, A, G, I, L, S, T, M, V, N, Q, F, W, Y, P, or C; I254 replaced with D, E, H, K, R, N, Q, F, W, Y, P, or C; Y255 replaced with D, E, H, K, R, N, Q, A, G, I, L, S, T, M, V, P, or C; K256 replaced with D, E, A, G, I, L, S, T, M, V, N, Q, F, W, Y, P, or C; H257 replaced with D, E, A, G, I, L, S, T, M, V, N, Q, F, W, Y, P, or C; P258 replaced with D, E, H, K, R, A, G, I, L, S, T, M, V, N, Q, F, W, Y, or C; S259 replaced with D, E, H, K, R, N, Q, F, W, Y, P, or C; I260 replaced with D, E, H, K, R, N, Q, F, W, Y, P, or C; K261 replaced with D, E, A, G, I, L, S, T, M, V, N, Q, F, W, Y, P, or C; N262 replaced with D, E, H, K, R, A, G, I, L, S, T, M, V, F, W, Y, P, or C; S263 replaced with D, E, H, K, R, N, Q, F, W, Y, P, or C; I264 replaced with D, E, H, K, R, N, Q, F, W, Y, P, or C; N265 replaced with D, E, H, K, R, A, G, I, L, S, T, M, V, F, W, Y, P, or C; L266 replaced with D, E, H, K, R, N, Q, F, W, Y, P, or C; M267 replaced with D, E, H, K, R, N, Q, F, W, Y, P, or C; V268 replaced with D, E, H, K, R, N, Q, F, W, Y, P, or C; V269 replaced with D, E, H, K, R, N, Q, F, W, Y, P, or C; K270 replaced with D, E, A, G, I, L, S, T, M, V, N, Q, F, W, Y, P, or C; V271 replaced with D, E, H, K, R, N, Q, F, W, Y, P, or C; L272 replaced with D, E, H, K, R, N, Q, F, W, Y, P, or C; I273 replaced with D, E, H, K, R, N, Q, F, W, Y, P, or C; V274 replaced with D, E, H, K, R, N, Q, F, W, Y, P, or C; E275 replaced with H, K, R, A, G, I, L, S, T, M, V, N, Q, F, W, Y, P, or C; D276 replaced with H, K, R, A, G, I, L, S, T, M, V, N, Q, F, W, Y, P, or C; E277 replaced with H, K, R, A, G, I, L, S, T, M, V, N, Q, F, W, Y, P, or C; K278 replaced with D, E, A, G, I, L, S, T, M, V, N, Q, F, W, Y, P, or C; W279 replaced with D, E, H, K, R, N, Q, A, G, I, L, S, T, M, V, P, or C; G280 replaced with D, E, H, K, R, N, Q, F, W, Y, P, or C; P281 replaced with D, E, H, K, R, A, G, I, L, S, T, M, V, N, Q, F, W, Y, or C; E282 replaced with H, K, R, A, G, I, L, S, T, M, V, N, Q, F, W, Y, P, or C; V283 replaced with D, E, H, K, R, N, Q, F, W, Y, P, or C; S284 replaced with D, E, H, K, R, N, Q, F, W, Y, P, or C; D285 replaced with H, K, R, A, G, I, L, S, T, M, V, N, Q, F, W, Y, P, or C; N286 replaced with D, E, H, K, R, A, G, I, L, S, T, M, V, F, W, Y, P, or C; G287 replaced with D, E, H, K, R, N, Q, F, W, Y, P, or C; G288 replaced with D, E, H, K, R, N, Q, F, W, Y, P, or C; L289 replaced with D, E, H, K, R, N, Q, F, W, Y, P, or C; T290 replaced with D, E, H, K, R, N, Q, F, W, Y, P, or C; L291 replaced with D, E, H, K, R, N, Q, F, W, Y, P, or C; R292 replaced with D, E, A, G, I, L, S, T, M, V, N, Q, F, W, Y, P, or C; N293 replaced with D, E, H, K, R, A, G, I, L, S, T, M, V, F, W, Y, P, or C; F294 replaced with D, E, H, K, R, N, Q, A, G, I, L, S, T, M, V, P, or C; C295 replaced with D, E, H, K, R, A, G, I, L, S, T, M, V, N, Q, F, W, Y, or P; N296 replaced with D, E, H, K, R, A, G, I, L, S, T, M, V, F, W, Y, P, or C; W297 replaced with D, E, H, K, R, N, Q, A, G, I, L, S, T, M, V, P, or C; Q298 replaced with D, E, H, K, R, A, G, I, L, S, T, M, V, F, W, Y, P, or C; R299 replaced with D, E, A, G, I, L, S, T, M, V, N, Q, F, W, Y, P, or C; R300 replaced with D, E, A, G, I, L, S, T, M, V, N, Q, F, W, Y, P, or C; F301 replaced with D, E, H, K, R, N, Q, A, G, I, L, S, T, M, V, P, or C; N302 replaced with D, E, H, K, R, A, G, I, L, S, T, M, V, F, W, Y, P, or C; Q303 replaced with D, E, H, K, R, A, G, I, L, S, T, M, V, F, W, Y, P, or C; P304 replaced with D, E, H, K, R, A, G, I, L, S, T, M, V, N, Q, F, W, Y, or C; S305 replaced with D, E, H, K, R, N, Q, F, W, Y, P, or C; D306 replaced with H, K, R, A, G, I, L, S, T, M, V, N, Q, F, W, Y, P, or C; R307 replaced with D, E, A, G, I, L, S, T, M, V, N, Q, F, W, Y, P, or C; H308 replaced with D, E, A, G, I, L, S, T, M, V, N, Q, F, W, Y, P, or C; P309 replaced with D, E, H, K, R, A, G, I, L, S, T, M, V, N, Q, F, W, Y, or C; E310 replaced with H, K, R, A, G, I, L, S, T, M, V, N, Q, F, W, Y, P, or C; H311 replaced with D, E, A, G, I, L, S, T, M, V, N, Q, F, W, Y, P, or C; Y312 replaced with D, E, H, K, R, N, Q, A, G, I, L, S, T, M, V, P, or C; D313 replaced with H, K, R, A, G, I, L, S, T, M, V, N, Q, F, W, Y, P, or C; T314 replaced with D, E, H, K, R, N, Q, F, W, Y, P, or C; A315 replaced with D, E, H, K, R, N, Q, F, W, Y, P, or C; I316 replaced with D, E, H, K, R, N, Q, F, W, Y, P, or C; L317 replaced with D, E, H, K, R, N, Q, F, W, Y, P, or C; L318 replaced with D, E, H, K, R, N, Q, F, W, Y, P, or C; T319 replaced with D, E, H, K, R, N, Q, F, W, Y, P, or C; R320 replaced with D, E, A, G, I, L, S, T, M, V, N, Q, F, W, Y, P, or C; Q321 replaced with D, E, H, K, R, A, G, I, L, S, T, M, V, F, W, Y, P, or C; N322 replaced with D, E, H, K, R, A, G, I, L, S, T, M, V, F, W, Y, P, or C; F323 replaced with D, E, H, K, R, N, Q, A, G, I, L, S, T, M, V, P, or C; C324 replaced with D, E, H, K, R, A, G, I, L, S, T, M, V, N, Q, F, W, Y, or P; G325 replaced with D, E, H, K, R, N, Q, F, W, Y, P, or C; Q326 replaced with D, E, H, K, R, A, G, I, L, S, T, M, V, F, W, Y, P, or C; E327 replaced with H, K, R, A, G, I, L, S, T, M, V, N, Q, F, W, Y, P, or C; G328 replaced with D, E, H, K, R, N, Q, F, W, Y, P, or C; L329 replaced with D, E, H, K, R, N, Q, F, W, Y, P, or C; C330 replaced with D, E, H, K, R, A, G, I, L, S, T, M, V, N, Q, F, W, Y, or P; D331 replaced with H, K, R, A, G, I, L, S, T, M, V, N, Q, F, W, Y, P, or C; T332 replaced with D, E, H, K, R, N, Q, F, W, Y, P, or C; L333 replaced with D, E, H, K, R, N, Q, F, W, Y, P, or C; G334 replaced with D, E, H, K, R, N, Q, F, W, Y, P, or C; V335 replaced with D, E, H, K, R, N, Q, F, W, Y, P, or C; A336 replaced with D, E, H, K, R, N, Q, F, W, Y, P, or C; D337 replaced with H, K, R, A, G, I, L, S, T, M, V, N, Q, F, W, Y, P, or C; I338 replaced with D, E, H, K, R, N, Q, F, W, Y, P, or C; G339 replaced with D, E, H, K, R, N, Q, F, W, Y, P, or C; T340 replaced with D, E, H, K, R, N, Q, F, W, Y, P, or C; I341 replaced with D, E, H, K, R, N, Q, F, W, Y, P, or C; C342 replaced with D, E, H, K, R, A, G, I, L, S, T, M, V, N, Q, F, W, Y, or P; D343 replaced with H, K, R, A, G, I, L, S, T, M, V, N, Q, F, W, Y, P, or C; P344 replaced with D, E, H, K, R, A, G, I, L, S, T, M, V, N, Q, F, W, Y, or C; N345 replaced with D, E, H, K, R, A, G, I, L, S, T, M, V, F, W, Y, P, or C; K346 replaced with D, E, A, G, I, L, S, T, M, V, N, Q, F, W, Y, P, or C; S347 replaced with D, E, H, K, R, N, Q, F, W, Y, P, or C; C348 replaced with D, E, H, K, R, A, G, I, L, S, T, M, V, N, Q, F, W, Y, or P; S349 replaced with D, E, H, K, R, N, Q, F, W, Y, P, or C; V350 replaced with D, E, H, K, R, N, Q, F, W, Y, P, or C; I351 replaced with D, E, H, K, R, N, Q, F, W, Y, P, or C; E352 replaced with H, K, R, A, G, I, L, S, T, M, V, N, Q, F, W, Y, P, or C; D353 replaced with H, K, R, A, G, I, L, S, T, M, V, N, Q, F, W, Y, P, or C; E354 replaced with H, K, R, A, G, I, L, S, T, M, V, N, Q, F, W, Y, P, or C; G355 replaced with D, E, H, K, R, N, Q, F, W, Y, P, or C; L356 replaced with D, E, H, K, R, N, Q, F, W, Y, P, or C; Q357 replaced with D, E, H, K, R, A, G, I, L, S, T, M, V, F, W, Y, P, or C; A358 replaced with D, E, H, K, R, N, Q, F, W, Y, P, or C; A359 replaced with D, E, H, K, R, N, Q, F, W, Y, P, or C; H360 replaced with D, E, A, G, I, L, S, T, M, V, N, Q, F, W, Y, P, or C; T361 replaced with D, E, H, K, R, N, Q, F, W, Y, P, or C; L362 replaced with D, E, H, K, R, N, Q, F, W, Y, P, or C; A363 replaced with D, E, H, K, R, N, Q, F, W, Y, P, or C; H364 replaced with D, E, A, G, I, L, S, T, M, V, N, Q, F, W, Y, P, or C; E365 replaced with H, K, R, A, G, I, L, S, T, M, V, N, Q, F, W, Y, P, or C; L366 replaced with D, E, H, K, R, N, Q, F, W, Y, P, or C; G367 replaced with D, E, H, K, R, N, Q, F, W, Y, P, or C; H368 replaced with D, E, A, G, I, L, S, T, M, V, N, Q, F, W, Y, P, or C; V369 replaced with D, E, H, K, R, N, Q, F, W, Y, P, or C; L370 replaced with D, E, H, K, R, N, Q, F, W, Y, P, or C; S371 replaced with D, E, H, K, R, N, Q, F, W, Y, P, or C; M372 replaced with D, E, H, K, R, N, Q, F, W, Y, P, or C; P373 replaced with D, E, H, K, R, A, G, I, L, S, T, M, V, N, Q, F, W, Y, or C; H374 replaced with D, E, A, G, I, L, S, T, M, V, N, Q, F, W, Y, P, or C; D375 replaced with H, K, R, A, G, I, L, S, T, M, V, N, Q, F, W, Y, P, or C; D376 replaced with H, K, R, A, G, I, L, S, T, M, V, N, Q, F, W, Y, P, or C; S377 replaced with D, E, H, K, R, N, Q, F, W, Y, P, or C; K378 replaced with D, E, A, G, I, L, S, T, M, V, N, Q, F, W, Y, P, or C; P379 replaced with D, E, H, K, R, A, G, I, L, S, T, M, V, N, Q, F, W, Y, or C; C380 replaced with D, E, H, K, R, A, G, I, L, S, T, M, V, N, Q, F, W, Y, or P; T381 replaced with D, E, H, K, R, N, Q, F, W, Y, P, or C; R382 replaced with D, E, A, G, I, L, S, T, M, V, N, Q, F, W, Y, P, or C; L383 replaced with D, E, H, K, R, N, Q, F, W, Y, P, or C; F384 replaced with D, E, H, K, R, N, Q, A, G, I, L, S, T, M, V, P, or C; G385 replaced with D, E, H, K, R, N, Q, F, W, Y, P, or C; P386 replaced with D, E, H, K, R, A, G, I, L, S, T, M, V, N, Q, F, W, Y, or C; M387 replaced with D, E, H, K, R, N, Q, F, W, Y, P, or C; G388 replaced with D, E, H, K, R, N, Q, F, W, Y, P, or C; K389 replaced with D, E, A, G, I, L, S, T, M, V, N, Q, F, W, Y, P, or C; H390 replaced with D, E, A, G, I, L, S, T, M, V, N, Q, F, W, Y, P, or C; H391 replaced with D, E, A, G, I, L, S, T, M, V, N, Q, F, W, Y, P, or C; V392 replaced with D, E, H, K, R, N, Q, F, W, Y, P, or C; M393 replaced with D, E, H, K, R, N, Q, F, W, Y, P, or C; A394 replaced with D, E, H, K, R, N, Q, F, W, Y, P, or C; P395 replaced with D, E, H, K, R, A, G, I, L, S, T, M, V, N, Q, F, W, Y, or C; L396 replaced with D, E, H, K, R, N, Q, F, W, Y, P, or C; F397 replaced with D, E, H, K, R, N, Q, A, G, I, L, S, T, M, V, P, or C; V398 replaced with D, E, H, K, R, N, Q, F, W, Y, P, or C; H399 replaced with D, E, A, G, I, L, S, T, M, V, N, Q, F, W, Y, P, or C; L400 replaced with D, E, H, K, R, N, Q, F, W, Y, P, or C; N401 replaced with D, E, H, K, R, A, G, I, L, S, T, M, V, F, W, Y, P, or C; Q402 replaced with D, E, H, K, R, A, G, I, L, S, T, M, V, F, W, Y, P, or C; T403 replaced with D, E, H, K, R, N, Q, F, W, Y, P, or C; L404 replaced with D, E, H, K, R, N, Q, F, W, Y, P, or C; P405 replaced with D, E, H, K, R, A, G, I, L, S, T, M, V, N, Q, F, W, Y, or C; W406 replaced with D, E, H, K, R, N, Q, A, G, I, L, S, T, M, V, P, or C; S407 replaced with D, E, H, K, R, N, Q, F, W, Y, P, or C; P408 replaced with D, E, H, K, R, A, G, I, L, S, T, M, V, N, Q, F, W, Y, or C; C409 replaced with D, E, H, K, R, A, G, I, L, S, T, M, V, N, Q, F, W, Y, or P; S410 replaced with D, E, H, K, R, N, Q, F, W, Y, P, or C; A411 replaced with D, E, H, K, R, N, Q, F, W, Y, P, or C; M412 replaced with D, E, H, K, R, N, Q, F, W, Y, P, or C; Y413 replaced with D, E, H, K, R, N, Q, A, G, I, L, S, T, M, V, P, or C; L414 replaced with D, E, H, K, R, N, Q, F, W, Y, P, or C; T415 replaced with D, E, H, K, R, N, Q, F, W, Y, P, or C; E416 replaced with H, K, R, A, G, I, L, S, T, M, V, N, Q, F, W, Y, P, or C; L417 replaced with D, E, H, K, R, N, Q, F, W, Y, P, or C; L418 replaced with D, E, H, K, R, N, Q, F, W, Y, P, or C; D419 replaced with H, K, R, A, G, I, L, S, T, M, V, N, Q, F, W, Y, P, or C; G420 replaced with D, E, H, K, R, N, Q, F, W, Y, P, or C; G421 replaced with D, E, H, K, R, N, Q, F, W, Y, P, or C; H422 replaced with D, E, A, G, I, L, S, T, M, V, N, Q, F, W, Y, P, or C; G423 replaced with D, E, H, K, R, N, Q, F, W, Y, P, or C; D424 replaced with H, K, R, A, G, I, L, S, T, M, V, N, Q, F, W, Y, P, or C; C425 replaced with D, E, H, K, R, A, G, I, L, S, T, M, V, N, Q, F, W, Y, or P; L426 replaced with D, E, H, K, R, N, Q, F, W, Y, P, or C; L427 replaced with D, E, H, K, R, N, Q, F, W, Y, P, or C; D428 replaced with H, K, R, A, G, I, L, S, T, M, V, N, Q, F, W, Y, P, or C; A429 replaced with D, E, H, K, R, N, Q, F, W, Y, P, or C; P430 replaced with D, E, H, K, R, A, G, I, L, S, T, M, V, N, Q, F, W, Y, or C; G431 replaced with D, E, H, K, R, N, Q, F, W, Y, P, or C; A432 replaced with D, E, H, K, R, N, Q, F, W, Y, P, or C; A433 replaced with D, E, H, K, R, N, Q, F, W, Y, P, or C; L434 replaced with D, E, H, K, R, N, Q, F, W, Y, P, or C; P435 replaced with D, E, H, K, R, A, G, I, L, S, T, M, V, N, Q, F, W, Y, or C; L436 replaced with D, E, H, K, R, N, Q, F, W, Y, P, or C; P437 replaced with D, E, H, K, R, A, G, I, L, S, T, M, V, N, Q, F, W, Y, or C; T438 replaced with D, E, H, K, R, N, Q, F, W, Y, P, or C; G439 replaced with D, E, H, K, R, N, Q, F, W, Y, P, or C; L494 replaced with D, E, H, K, R, N, Q, F, W, Y, P, or C; P495 replaced with D, E, H, K, R, A, G, I, L, S, T, M, V, N, Q, F, W, Y, or C; W496 replaced with D, E, H, K, R, N, Q, A, G, I, L, S, T, M, V, P, or C; A497 replaced with D, E, H, K, R, N, Q, F, W, Y, P, or C; D498 replaced with H, K, R, A, G, I, L, S, T, M, V, N, Q, F, W, Y, P, or C; G499 replaced with D, E, H, K, R, N, Q, F, W, Y, P, or C; T500 replaced with D, E, H, K, R, N, Q, F, W, Y, P, or C; P501 replaced with D, E, H, K, R, A, G, I, L, S, T, M, V, N, Q, F, W, Y, or C; C502 replaced with D, E, H, K, R, A, G, I, L, S, T, M, V, N, Q, F, W, Y, or P; G503 replaced with D, E, H, K, R, N, Q, F, W, Y, P, or C; P504 replaced with D, E, H, K, R, A, G, I, L, S, T, M, V, N, Q, F, W, Y, or C; G505 replaced with D, E, H, K, R, N, Q, F, W, Y, P, or C; H506 replaced with D, E, A, G, I, L, S, T, M, V, N, Q, F, W, Y, P, or C; L507 replaced with D replaced with D, E, H, K, R, N, Q, F, W, Y, P, or C; Q610 replaced with D, E, H, K, R, A, G, I, L, S, T, M, V, F, W, Y, P, or C; W611 replaced with D, E, H, K, R, N, Q, A, G, I, L, S, T, M, V, P, or C; V612 replaced with D, E, H, K, R, N, Q, F, W, Y, P, or C; P613 replaced with D, E, H, K, R, A, G, I, L, S, T, M, V, N, Q, F, W, Y, or C; K614 replaced with D, E, A, G, I, L, S, T, M, V, N, Q, F, W, Y, P, or C; Y615 replaced with D, E, H, K, R, N, Q, A, G, I, L, S, T, M, V, P, or C; A616 replaced with D, E, H, K, R, N, Q, F, W, Y, P, or C; G617 replaced with D, E, H, K, R, N, Q, F, W, Y, P, or C; V618 replaced with D, E, H, K, R, N, Q, F, W, Y, P, or C; S619 replaced with D, E, H, K, R, N, Q, F, W, Y, P, or C; P620 replaced with D, E, H, K, R, A, G, I, L, S, T, M, V, N, Q, F, W, Y, or C; R621 replaced with D, E, A, G, I, L, S, T, M, V, N, Q, F, W, Y, P, or C; D622 replaced with H, K, R, A, G, I, L, S, T, M, V, N, Q, F, W, Y, P, or C; R623 replaced with D, E, A, G, I, L, S, T, M, V, N, Q, F, W, Y, P, or C; C624 replaced with D, E, H, K, R, A, G, I, L, S, T, M, V, N, Q, F, W, Y, or P; K625 replaced with D, E, A, G, I, L, S, T, M, V, N, Q, F, W, Y, P, or C; L626 replaced with D, E, H, K, R, N, Q, F, W, Y, P, or C; F627 replaced with D, E, H, K, R, N, Q, A, G, I, L, S, T, M, V, P, or C; C628 replaced with D, E, H, K, R, A, G, I, L, S, T, M, V, N, Q, F, W, Y, or P; R629 replaced with D, E, A, G, I, L, S, T, M, V, N, Q, F, W, Y, P, or C; A630 replaced with D, E, H, K, R, N, Q, F, W, Y, P, or C; R631 replaced with D, E, A, G, I, L, S, T, M, V, N, Q, F, W, Y, P, or C; G632 replaced with D, E, H, K, R, N, Q, F, W, Y, P, or C; R633 replaced with D, E, A, G, I, L, S, T, M, V, N, Q, F, W, Y, P, or C; S634 replaced with D, E, H, K, R, N, Q, F, W, Y, P, or C; E635 replaced with H, K, R, A, G, I, L, S, T, M, V, N, Q, F, W, Y, P, or C; F636 replaced with D, E, H, K, R, N, Q, A, G, I, L; S, T, M, V, P, or C; K637 replaced with D, E, A, G, I, L, S, T, M, V, N, Q, F, W, Y, P, or C; V638 replaced with D, E, H, K, R, N, Q, F, W, Y, P, or C; F639 replaced with D, E, H, K, R, N, Q, A, G, I, L, S, T, M, V, P, or C; E640 replaced with H, K, R, A, G, I, L, S, T, M, V, N, Q, F, W, Y, P, or C; A641 replaced with D, E, H, K, R, N, Q, F, W, Y, P, or C; K642 replaced with D, E, A, G, I, L, S, T, M, V, N, Q, F, W, Y, P, or C; V643 replaced with D, E, H, K, R, N, Q, F, W, Y, P, or C; I644 replaced with D, E, H, K, R, N, Q, F, W, Y, P, or C; D645 replaced with H, K, R, A, G, I, L, S, T, M, V, N, Q, F, W, Y, P, or C; G646 replaced with D, E, H, K, R, N, Q, F, W, Y, P, or C; T647 replaced with D, E, H, K, R, N, Q, F, W, Y, P, or C; L648 replaced with D, E, H, K, R, N, Q, F, W, Y, P, or C; C649 replaced with D, E, H, K, R, A, G, I, L, S, T, M, V, N, Q, F, W, Y, or P; G650 replaced with D, E, H, K, R, N, Q, F, W, Y, P, or C; P651 replaced with D, E, H, K, R, A, G, I, L, S, T, M, V, N, Q, F, W, Y, or C; E652 replaced with H, K, R, A, G, I, L, S, T, M, V, N, Q, F, W, Y, P, or C; T653 replaced with D, E, H, K, R, N, Q, F, W, Y, P, or C; L654 replaced with D, E, H, K, R, N, Q, F, W, Y, P, or C; A655 replaced with D, E, H, K, R, N, Q, F, W, Y, P, or C; I656 replaced with D, E, H, K, R, N, Q, F, W, Y, P, or C; C657 replaced with D, E, H, K, R, A, G, I, L, S, T, M, V, N, Q, F, W, Y, or P; V658 replaced with D, E, H, K, R, N, Q, F, W, Y, P, or C; R659 replaced with D, E, A, G, I, L, S, T, M, V, N, Q, F, W, Y, P, or C; G660 replaced with D, E, H, K, R, N, Q, F, W, Y, P, or C; Q661 replaced with D, E, H, K, R, A, G, I, L, S, T, M, V, F, W, Y, P, or C; C662 replaced with D, E, H, K, R, A, G, I, L, S, T, M, V, N, Q, F, W, Y, or P; V663 replaced with D, E, H, K, R, N, Q, F, W, Y, P, or C; K664 replaced with D, E, A, G, I, L, S, T, M, V, N, Q, F, W, Y, P, or C; A665 replaced with D, E, H, K, R, N, Q, F, W, Y, P, or C; G666 replaced with D, E, H, K, R, N, Q, F, W, Y, P, or C; C667 replaced with D, E, H, K, R, A, G, I, L, S, T, M, V, N, Q, F, W, Y, or P; D668 replaced with H, K, R, A, G, I, L, S, T, M, V, N, Q, F, W, Y, P, or C; H669 replaced with D, E, A, G, I, L, S, T, M, V, N, Q, F, W, Y, P, or C; V670 replaced with D, E, H, K, R, N, Q, F, W, Y, P, or C; V671 replaced with D, E, H, K, R, N, Q, F, W, Y, P, or C; D672 replaced with H, K, R, A, G, I, L, S, T, M, V, N, Q, F, W, Y, P, or C; S673 replaced with D, E, H, K, R, N, Q, F, W, Y, P, or C; P674 replaced with D, E, H, K, R, A, G, I, L, S, T, M, V, N, Q, F, W, Y, or C; R675 replaced with D, E, A, G, I, L, S, T, M, V, N, Q, F, W, Y, P, or C; K676 replaced with D, E, A, G, I, L, S, T, M, V, N, Q, F, W, Y, P, or C; L677 replaced with D, E, H, K, R, N, Q, F, W, Y, P, or C; D678 replaced with H, K, R, A, G, I, L, S, T, M, V, N, Q, F, W, Y, P, or C; K679 replaced with D, E, A, G, I, L, S, T, M, V, N, Q, F, W, Y, P, or C; C680 replaced with D, E, H, K, R, A, G, I, L, S, T, M, V, N, Q, F, W, Y, or P; G681 replaced with D, E, H, K, R, N, Q, F, W, Y, P, or C; V682 replaced with D, E, H, K, R, N, Q, F, W, Y, P, or C; C683 replaced with D, E, H, K, R, A, G, I, L, S, T, M, V, N, Q, F, W, Y, or P; G684 replaced with D, E, H, K, R, N, Q, F, W, Y, P, or C; G685 replaced with D, E, H, K, R, N, Q, F, W, Y, P, or C; K686 replaced with D, E, A, G, I, L, S, T, M, V, N, Q, F, W, Y, P, or C; G687 replaced with D, E, H, K, R, N, Q, F, W, Y, P, or C; N688 replaced with D, E, H, K, R, A, G, I, L, S, T, M, V, F, W, Y, P, or C; S689 replaced with D, E, H, K, R, N, Q, F, W, Y, P, or C; C690 replaced with D, E, H, K, R, A, G, I, L, S, T, M, V, N, Q, F, W, Y, or P; R691 replaced with D, E, A, G, I, L, S, T, M, V, N, Q, F, W, Y, P, or C; K692 replaced with D, E, A, G, I, L, S, T, M, V, N, Q, F, W, Y, P, or C; V693 replaced with D, E, H, K, R, N, Q, F, W, Y, P, or C; S694 replaced with D, E, H, K, R, N, Q, F, W, Y, P, or C; G695 replaced with D, E, H, K, R, N, Q, F, W, Y, P, or C; S696 replaced with D, E, H, K, R, N, Q, F, W, Y, P, or C; L697 replaced with D, E, H, K, R, N, Q, F, W, Y, P, or C; T698 replaced with D, E, H, K, R, N, Q, F, W, Y, P, or C; P699 replaced with D, E, H, K, R, A, G, I, L, S, T, M, V, N, Q, F, W, Y, or C; T700 replaced with D, E, H, K, R, N, Q, F, W, Y, P, or C; N701 replaced with D, E, H, K, R, A, G, I, L, S, T, M, V, F, W, Y, P, or C; Y702 replaced with D, E, H, K, R, N, Q, A, G, I, L, S, T, M, V, P, or C; G703 replaced with D, E, H, K, R, N, Q, F, W, Y, P, or C; Y704 replaced with D, E, H, K, R, N, Q, A, G, I, L, S, T, M, V, P, or C; N705 replaced with D, E, H, K, R, A, G, I, L, S, T, M, V, F, W, Y, P, or C; D706 replaced with H, K, R, A, G, I, L, S, T, M, V, N, Q, F, W, Y, P, or C; I707 replaced with D, E, H, K, R, N, Q, F, W, Y, P, or C; V708 replaced with D, E, H, K, R, N, Q, F, W, Y, P, or C; T709 replaced with D, E, H, K, R, N, Q, F, W, Y, P, or C; I710 replaced with D, E, H, K, R, N, Q, F, W, Y, P, or C; P711 replaced with D, E, H, K, R, A, G, I, L, S, T, M, V, N, Q, F, W, Y, or C; A712 replaced with D, E, H, K, R, N, Q, F, W, Y, P, or C; G713 replaced with D, E, H, K, R, N, Q, F, W, Y, P, or C; A714 replaced with D, E, H, K, R, N, Q, F, W, Y, P, or C; T715 replaced with D, E, H, K, R, N, Q, F, W, Y, P, or C; N716 replaced with D, E, H, K, R, A, G, I, L, S, T, M, V, F, W, Y, P, or C; I717 replaced with D, E, H, K, R, N, Q, F, W, Y, P, or C; D718 replaced with H, K, R, A, G, I, L, S, T, M, V, N, Q, F, W, Y, P, or C; V719 replaced with D, E, H, K, R, N, Q, F, W, Y, P, or C; K720 replaced with D, E, A, G, I, L, S, T, M, V, N, Q, F, W, Y, P, or C; Q721 replaced with D, E, H, K, R, A, G, I, L, S, T, M, V, F, W, Y, P, or C; R722 replaced with D, E, A, G, I, L, S, T, M, V, N, Q, F, W, Y, P, or C; S723 replaced with D, E, H, K, R, N, Q, F, W, Y, P, or C; H724 replaced with D, E, A, G, I, L, S, T, M, V, N, Q, F, W, Y, P, or C; P725 replaced with D, E, H, K, R, A, G, I, L, S, T, M, V, N, Q, F, W, Y, or C; G726 replaced with D, E, H, K, R, N, Q, F, W, Y, P, or C; V727 replaced with D, E, H, K, R, N, Q, F, W, Y, P, or C; Q728 replaced with D, E, H, K, R, A, G, I, L, S, T, M, V, F, W, Y, P, or C; N729 replaced with D, E, H, K, R, A, G, I, L, S, T, M, V, F, W, Y, P, or C; D730 replaced with H, K, R, A, G, I, L, S, T, M, V, N, Q, F, W, Y, P, or C; G731 replaced with D, E, H, K, R, N, Q, F, W, Y, P, or C; N732 replaced with D, E, H, K, R, A, G, I, L, S, T, M, V, F, W, Y, P, or C; Y733 replaced with D, E, H, K, R, N, Q, A, G, I, L, S, T, M, V, P, or C; L734 replaced with D, E, H, K, R, N, Q, F, W, Y, P, or C; A735 replaced with D, E, H, K, R, N, Q, F, W, Y, P, or C; L736 replaced with D, E, H, K, R, N, Q, F, W, Y, P, or C; K737 replaced with D, E, A, G, I, L, S, T, M, V, N, Q, F, W, Y, P, or C; T738 replaced with D, E, H, K, R, N, Q, F, W, Y, P, or C; A739 replaced with D, E, H, K, R, N, Q, F, W, Y, P, or C; D740 replaced with H, K, R, A, G, I, L, S, T, M, V, N, Q, F, W, Y N, Q, F, W, Y, P, or C; G852 replaced with D, E, H, K, R, N, Q, F, W, Y, P, or C; W853 replaced with D, E, H, K, R, N, Q, A, G, I, L, S, T, M, V, P, or C; Q854 replaced with D, E, H, K, R, A, G, I, L, S, T, M, V, F, W, Y, P, or C; R855 replaced with D, E, A, G, I, L, S, T, M, V, N, Q, F, W, Y, P, or C; R856 replaced with D, E, A, G, I, L, S, T, M, V, N, Q, F, W, Y, P, or C; T857 replaced with D, E, H, K, R, N, Q, F, W, Y, P, or C; V858 replaced with D, E, H, K, R, N, Q, F, W, Y, P, or C; E859 replaced with H, K, R, A, G, I, L, S, T, M, V, N, Q, F, W, Y, P, or C; C860 replaced with D, E, H, K, R, A, G, I, L, S, T, M, V, N, Q, F, W, Y, or P; R861 replaced with D, E, A, G, I, L, S, T, M, V, N, Q, F, W, Y, P, or C; D862 replaced with H, K, R, A, G, I, L, S, T, M, V, N, Q, F, W, Y, P, or C; P863 replaced with D, E, H, K, R, A, G, I, L, S, T, M, V, N, Q, F, W, Y, or C; S864 replaced with D, E, H, K, R, N, Q, F, W, Y, P, or C; G865 replaced with D, E, H, K, R, N, Q, F, W, Y, P, or C; Q866 replaced with D, E, H, K, R, A, G, I, L, S, T, M, V, F, W, Y, P, or C; A867 replaced with D, E, H, K, R, N, Q, F, W, Y, P, or C; S868 replaced with D, E, H, K, R, N, Q, F, W, Y, P, or C; A869 replaced with D, E, H, K, R, N, Q, F, W, Y, P, or C; T870 replaced with D, E, H, K, R, N, Q, F, W, Y, P, or C; C871 replaced with D, E, H, K, R, A, G, I, L, S, T, M, V, N, Q, F, W, Y, or P; N872 replaced with D, E, H, K, R, A, G, I, L, S, T, M, V, F, W, Y, P, or C; K873 replaced with D, E, A, G, I, L, S, T, M, V, N, Q, F, W, Y, P, or C; A874 replaced with D, E, H, K, R, N, Q, F, W, Y, P, or C; L875 replaced with D, E, H, K, R, N, Q, F, W, Y, P, or C; K876 replaced with D, E, A, G, I, L, S, T, M, V, N, Q, F, W, Y, P, or C; P877 replaced with D, E, H, K, R, A, G, I, L, S, T, M, V, N, Q, F, W, Y, or C; E878 replaced with H, K, R, A, G, I, L, S, T, M, V, N, Q, F, W, Y, P, or C; D879 replaced with H, K, R, A, G, I, L, S, T, M, V, N, Q, F, W, Y, P, or C; A880 replaced with D, E, H, K, R, N, Q, F, W, Y, P, or C; K881 replaced with D, E, A, G, I, L, S, T, M, V, N, Q, F, W, Y, P, or C; P882 replaced with D, E, H, K, R, A, G, I, L, S, T, M, V, N, Q, F, W, Y, or C; C883 replaced with D, E, H, K, R, A, G, I, L, S, T, M, V, N, Q, F, W, Y, or P; E884 replaced with H, K, R, A, G, I, L, S, T, M, V, N, Q, F, W, Y, P, or C; S885 replaced with D, E, H, K, R, N, Q, F, W, Y, P, or C; Q886 replaced with D, E, H, K, R, A, G, I, L, S, T, M, V, F, W, Y, P, or C; L887 replaced with D, E, H, K, R, N, Q, F, W, Y, P, or C; C888 replaced with D, E, H, K, R, A, G, I, L, S, T, M, V, N, Q, F, W, Y, or P; P889 replaced with D, E, H, K, R, A, G, I, L, S, T, M, V, N, Q, F, W, Y, or C; L890 replaced with D, E, H, K, R, N, Q, F, W, Y, P, or C.

METH1 or METH2 polypeptides may contain 50, 40, 30, 10, 20, 19, 18, 17, 16, 15, 14, 13, 12, 11, 10, 9, 8, 7, 6, 5, 4, 3, 2 or 1 conservative or non-conservative amino acid substitutions. Additionally, METH1 or METH2 polypeptides may contain both conservative or non-conservative substitutions, in any combination. A METH1 or METH2 polypeptide may contain 50, 40, 30, 10, 20, 19, 18, 17, 16, 15, 14, 13, 12, 11, 10, 9, 8, 7, 6, 5, 4, 3, 2 or 1 conservative amino acids substitutions, and 50, 40, 30, 10, 20, 19, 18, 17, 16, 15, 14, 13, 12, 11, 10, 9, 8, 7, 6, 5, 4, 3, 2 or 1 non-conservative amino acid substitutions in the same polypeptide. For example, a particular polypeptide may contain 10 conservative amino acid substitutions and 10 non-conservative amino acid substitutions. Polynucleotides encoding such METH1 or METH2 polypeptides with substitutions are also encompassed within the present invention.

The substitutions may be made in full-length METH1 or METH2, mature METH1 or METH2, and any other METH1 or METH2 variant disclosed herein, including METH1 or METH2 polypeptides with N- and/or C-terminal amino acid deletions; METH1 or METH2 polypeptides which lack one or more domains; or hybrid METH1/METH2 molecules.

Amino acids in the METH1 and METH2 proteins of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as in vitro or in vivo inhibition of angiogenesis. Sites that are critical for inhibition of angiogenesis can also be determined by structural analysis such as crystallization, nuclear magnetic resonance or photoaffinity labeling (Smith et al., *J. Mol. Biol.* 224: 899–904 (1992) and de Vos et al., *Science* 255:306–312 (1992)).

Particularly preferred are polypeptides with amino acid substitutions at the boundaries of each domain (for example, at the boundary of the metalloprotease domain). Amino acid substitutions at these boundaries may be made to change the activity of the protein, for example, to prevent cleavage. Amino acid substitutions may also be made which do not affect the activity of the protein. For example, the following amino acids may be replaced in METH1, with the following amino acids: L-19 may be replaced with A, C, D, E, F, G, H, I, K, M, N, P, Q, R, S, T, V, W or Y; L-20 may be replaced with A, C, D, E, F, G, H, I, K, M, N, P, Q, R, S, T, V, W or Y; L-21 maybe replaced with A, C, D, E, F, G, H, I, K, M, N, P, Q, R, S, T, V, W or Y; L-22 may be replaced with A, C, D, E, F, G, H, I, K, M, N, P, Q, R, S, T, V, W or Y; A-23 may be replaced with may be replaced with C, D, E, F, G, H, I, K, L, M, N, P, Q, R, S, T, V, W or Y; A-24 may be replaced with C, D, E, F, G, H, I, K, L, M, N, P, Q, R, S, T, V, W or Y; A-25 may be replaced with C, D, E, F, G, H, I, K, L, M, N, P, Q, R, S, T, V, W or Y; L-26 maybe replaced with A, C, D, E, F, G, H, I, K, M, N, P, Q, R, S, T, V, W or Y; L-27 may be replaced with A, C, D, E, F, G, H, I, K, M, N, P, Q, R, S, T, V, W or Y; A-28 may be replaced with C, D, E, F, G, H, I, K, L, M, N, P, Q, R, S, T, V, W or Y; V-29 maybe replaced with A, C, D, E, F, G, H, I, K, L, M, N, P, Q, R, S, T, W or Y; S-30 may be replaced with A, C, D, E, F, G, H, I, K, L, M, N, P, Q, R, T, V, W or Y; D-31 may be replaced with A, C, E, F, G, H, I, K, L, M, N, P, Q, R, S, T, V, W or Y; A-32 may be replaced with C, D, E, F, G, H, I, K, L, M, N, P, Q, R, S, T, V, W or Y; L-33 may be replaced with A, C, D, E, F, G, H, I, K, M, N, P, Q, R, S, T, V, W or Y; G-34 may be replaced with A, C, D, E, F, H, I, K, L, M, N, P, Q, R, S, T, V, W or Y; R-35 may be replaced with A, C, D, E, F, G, H, I, K, L, M, N, P, Q, S, T, V, W or Y; P-36 may be replaced with A, C, D, E, F, G, H, I, K, L, M, N, Q, R, S, T, V, W or Y; S-37 may be replaced with A, C, D, E, F, G, H, I, K, L, M, N, P, Q, R, T, V, W or Y; E-38 may be replaced with A, C, D, F, G, H, I, K, L, M, N, P, Q, R, S, T, V, W or Y; E-39 may be replaced with A, C, D, E, F, G, H, I, K, L, M, N, P, Q, R, S, T, V, W or Y; P-225 may be replaced with A, C, D, E, F, G, H, I, K, L, M, N, Q, R, S, T, V, W or Y; T-226 may be replaced with A, C, D, E, F, G, H, I, K, L, M, N, P, Q, R, S, V, W or Y; G-227 may be replaced with A, C, D, E, F, H, I, K, L, M, N, P, Q, R, S, T, V, W or Y; T-228 may be replaced with A, C, D, E, F, G, H, I, K, L, M, N, P, Q, R, S, V, W or Y; G-229 may be replaced with A, C, D, E, F, H, I, K, L, M, N, P, Q, R, S, T, V, W or Y; S-230 may be replaced with A, C, D, E, F, G, H, I, K, L, M, N, P, Q, R, T, V, W or Y; I-231 may be replaced with A, C, D, E, F, G, H, K, L, M, N, P, Q, R, S, T, V, W or Y; R-232 may be replaced with A, C, D, E, F, G, H, I, K, L, M, N, P, Q, S, T, V, W or Y; K-233 may be replaced with A, C, D, E, F, G, H, I, L, M, N, P, Q, R, S, T, V, W or Y; K-234 may be replaced with A, C, D, E, F, G, H, I, L, M, N, P, Q, R, S, T, V, W or Y; R-235 may be replaced with A, C, D, E, F, G, H, I, K, L, M, N, P, Q, S, T, V, W or Y; F-236 may be replaced with A, C, D, E, G, H, I, K, L, M, N, P, Q, R, S, T, V, W or Y; V-237 may be replaced with A, C, D, E, F, G, H, I, K, L, M, N, P, Q, R, S, T, W or Y; S-238 may be replaced with A, C, D, E, F, G, H, I, K, L, M, N, P, Q, R, T, V, W or Y; S-239 may be replaced with A, C, D, E, F, G, H, I, K, L, M, N, P, Q, R, T, V, W or Y; H-240 may be replaced with A, C, D, E, F, G, I, K, L, M, N, P, Q, R, S, T, V, W or Y; R-241 may be replaced with A, C, D, E, F, G, H, I, K, L, M, N, P, Q, S, T, V, W or Y; Y-242 may be replaced with A, C, D, E, F, G, H, I, K, L, M, N, P, Q, R, S, T, V, or W; V-243 may be replaced with A, C, D, E, F, G, H, I, K, L, M, N, P, Q, R, S, T, W or Y; E-244 may be replaced with A, C, D, F, G, H, I, K, L, M, N, P, Q, R, S, T, V, W or Y; T-245 may be replaced with A, C, D, E, F, G, H, I, K, L, M, N, P, Q, R, S, V, W or Y; K-449 may be replaced with A, C, D, E, F, G, H, I, L, M, N, P, Q, R, S, T, V, W or Y; P-450 may be replaced with A, C, D, E, F, G, H, I, K, L, M, N, Q, R, S, T, V, W or Y; Q-451 may be replaced with A, C, D, E, F, G, H, I, K, L, M, N, P, R, S, T, V, W or Y; N-452 may be replaced with A, C, D, E, F, G, H, I, K, L, M, P, Q, R, S, T, V, W or Y; P-453 may be replaced with A, C, D, E, F, G, H, I, K, L, M, N, Q, R, S, T, V, W or Y; I-454 may be replaced with A, C, D, E, F, G, H, K, L, M, N, P, Q, R, S, T, V, W or Y; Q-455 may be replaced with A, C, D, E, F, G, H, I, K, L, M, N, P, R, S, T, V, W or Y; L-456 may be replaced with A, C, D, E, F, G, H, I, K, M, N, P, Q, R, S, T, V, W or Y; P-457 may be replaced with A, C, D, E, F, G, H, I, K, L, M, N, Q, R, S, T, V, W or Y; G-458 may be replaced with A, C, D, E, F, H, I, K, L, M, N, P, Q, R, S, T, V, W or Y; D-459 may be replaced with A, C, E, F, G, H, I, K, L, M, N, P, Q, R, S, T, V, W or Y; L-460 may be replaced with A, C, D, E, F, G, H, I, K, M, N, P, Q, R, S, T, V, W or Y; P-461 may be replaced with A, C, D, E, F, G, H, I, K, L, M, N, Q, R, S, T, V, W or Y; G-462 may be replaced with A, C, D, E, F, H, I, K, L, M, N, P, Q, R, S, T, V, W or Y; T-463 may be replaced with A, C, D, E, F, G, H, I, K, L, M, N, P, Q, R, S, V, W or Y; S-464 may be replaced with A, C, D, E, F, G, H, I, K, L, M, N, P, Q, R, T, V, W or Y; Y-465 may be replaced with A, C, D, E, F, G, H, I, K, L, M, N, P, Q, R, S, T, V, or W; D-466 may be replaced with A, C, E, F, G, H, I, K, L, M, N, P, Q, R, S, T, V, W or Y; A-467 may be replaced with C, D, E, F, G, H, I, K, L, M, N, P, Q, R, S, T, V, W or Y; N-468 may be replaced with A, C, D, E, F, G, H, I, K, L, M, P, Q, R, S, T, V, W or Y; R-469 may be replaced with A, C, D, E, F, G, H, I, K, L, M, N, P, Q, S, T, V, W or Y; R-534 may be replaced with A, C, D, E, F, G, H, I, K, L, M, N, P, Q, S, T, V, W or Y; K-535 may be replaced with A, C, D, E, F, G, H, I, L, M, N, P, Q, R, S, T, V, W or Y; H-536 may be replaced with A, C, D, E, F, G, I, K, L, M, N, P, Q, R, S, T, V, W or Y; F-537 may be replaced with A, C, D, E, G, H, I, K, L, M, N, P, Q, R, S, T, V, W or Y; D-538 may be replaced with A, C, E, F, G, H, I, K, L, M, N, P, Q, R, S, T, V, W or Y; T-539 may be replaced with A, C, D, E, F, G, H, I, K, L, M, N, P, Q, R, S, V, W or Y; P-540 may be replaced with A, C, D, E, F, G, H, I, K, L, M, N, Q, R, S, T, V, W or Y; F-541 may be replaced with A, C, D, E, G, H, I, K, L, M, N, P, Q, R, S, T, V, W or Y; H-542 may be replaced with A, C, D, E, F, G, I, K, L, M, N, P, Q, R, S, T, V, W or Y; G-543 may be replaced with A, C, D, E, F, H, I, K, L, M, N, P, Q, R, S, T, V, W or Y; S-544 may be replaced with A, C, D, E, F, G, H, I, K, L, M, N, P, Q, R, T, V, W or Y; W-545 may be replaced with A, C, D, E, F, G, H, I, K, L, M, N, P, Q, R, S, T, V, or Y; G-546 may be replaced with A, C, D, E, F, H, I, K, L, M, N, P, Q, R, S, T, V, W or Y; M-547 may be replaced with A, C, D, E, F, G, H, I, K, L, N, P, Q, R, S, T, V, W or Y; W-548 may be replaced with A, C, D, E, F, G, H, I, K, L, M, N, P, Q, R, S, T, V, or Y; G-549 may be replaced with A, C, D, E, F, H, I, K, L, M, N, P, Q, R, S, T, V, W or Y; P-550 may be replaced with A, C, D, E, F, G, H, I, K, L, M, N, Q, R, S, T, V, W or Y; W-551 may be replaced with A, C, D, E, F, G, H, I, K, L, M, N, P, Q, R, S, T, V, or Y; G-552 may be replaced with A, C, D, E, F, H, I, K, L, M, N, P, Q, R, S, T, V, W or Y; D-553 may be replaced with A, C, E, F, G, H, I, K, L, M, N, P, Q, R, S, T, V, W or Y; G-554 may be replaced with A, C, D, E, F, H, I, K, L, M, N, P, Q, R, S, T, V, W or Y; S-831 may be replaced with A, C, D, E, F, G, H, I, K, L, M, N, P, Q, R, T, V, W or Y; F-832 may be replaced with A, C, D, E, G, H, I, K, L, M, N, P, Q, R, S, T, V, W or Y; N-833 may be replaced with A, C, D, E, F, G, H, I, K, L, M, P, Q, R, S, T, V, W or Y; A-834 may be replaced with C, D, E, F, G, H, I, K, L, M, N, P, Q, R, S, T, V, W or Y; I-835 may be replaced with A, C, D, E, F, G, H, K, L, M, N, P, Q, R, S, T, V, W or Y; P-836 may be replaced with A, C, D, E, F, G, H, I, K, L, M, N, Q, R, S, T, V, W or Y; T-837 may be replaced with A, C, D, E, F, G, H, I, K, L, M, N, P, Q, R, S, V, W or Y; F-838 may be replaced with A, C, D, E, G, H, I, K, L, M, N, P, Q, R, S, T, V, W or Y; S-839 may be replaced with A, C, D, E, F, G, H, I, K, L, M, N, P, Q, R, T, V, W or Y; A-840 may be replaced with C, D, E, F, G, H, I, K, L, M, N, P, Q, R, S, T, V, W or Y; W-841 may be replaced with A, C, D, E, F, G, H, I, K, L, M, N, P, Q, R, S, T, V or Y; V-842 may be replaced with A, C, D, E, F, G, H, I, K, L, M, N, P, Q, R, S, T, W or Y; I-843 may be replaced with A, C, D, E, F, G, H, K, L, M, N, P, Q, R, S, T, V, W or Y; E-844 may be replaced with A, C, D, F, G, H, I, K, L, M, N, P, Q, R, S, T, V, W or Y; E-845 may be replaced with A, C, D, F, G, H, I, K, L, M, N, P, Q, R, S, T, V, W or Y; W-846 may be replaced with A, C, D, E, F, G, H, I, K, L, M, N, P, Q, R, S, T, V, or Y; G-847 may be replaced with A, C, D, E, F, H, I, K, L, M, N, P, Q, R, S, T, V, W or Y; E-848 may be replaced with A, C, D, F, G, H, I, K, L, M, N, P, Q, R, S, T, V, W or Y; C-849 may be replaced with A, D, E, F, G, H, I, K, L, M, N, P, Q, R, S, T, V, W or Y; S-850 may be replaced with A, C, D, E, F, G, H, I, K, L, M, N, P, Q, R, T, V, W or Y; K-851 may be replaced with A, C, D, E, F, G, H, I, L, M, N, P, Q, R, S, T, V, W or Y; R-885 may be replaced with A, C, D, E, F, G, H, I, K, L, M, N, P, Q, S, T, V, W or Y; P-886 may be replaced with A, C, D, E, F, G, H, I, K, L, M, N, Q, R, S, T, V, W or Y; C-887 may be replaced with A, D, E, F, G, H, I, K, L, M, N, P, Q, R, S, T, V, W or Y; A-888 may be replaced with C, D, E, F, G, H, I, K, L, M, N, P, Q, R, S, T, V, W or Y; D-889 may be replaced with A, C, E, F, G, H, I, K, L, M, N, P, Q, R, S, T, V, W or Y; H-890 may be replaced with A, C, D, E, F, G, I, K, L, M, N, P, Q, R, S, T, V, W or Y; P-891 may be replaced with A, C, D, E, F, G, H, I, K, L, M, N, Q, R, S, T, V, W or Y; C-892 may be replaced with A, D, E, F, G, H, I, K, L, M, N, P, Q, R, S, T, V, W or Y; P-893 may be replaced with A, C, D, E, F, G, H, I, K, L, M, N, Q, R, S, T, V, W or Y; Q-894 may be replaced with A, C, D, E, F, G, H, I, K, L, M, N, P, R, S, T, V, W or Y; W-895 may be replaced with A, C, D, E, F, G, H, I, K, L, M, N, P, Q, R, S, T, V, or Y; Q-896 may be replaced with A, C, D, E, F, G, H, I, K, L, M, N, P, R, S, T, V, W or Y; L-897 may be replaced with A, C, D, E, F, G, H, I, K, M, N, P, Q, R, S, T, V, W or Y; C-898 may be replaced with A, C, D, E, F, H, I, K, L, M, N, P, Q, R, S, T, V, W or Y; E-899 may be replaced with A, C, D, F, G, H, I, K, L, M, N, P, Q, R, S, T, V, W or Y; W-900 may be replaced with A, C, D, E, F, G, H, I, K, L, M, N, P, Q, R, S, T, V, or Y; S-901 may be replaced with A, C, D, E, F, G, H, I, K, L, M, N, P, Q, R, T, V, W or Y; S-902 may be replaced with A, C, D, E, F, G, H, I, K, L, M, N, P, Q, R, T, V, W or Y; C-903 may be replaced with A, D, E, F, G, H, I, K, L, M, N, P, Q, R, S, T, V, W or Y; S-904 may be replaced with A, C, D, E, F, G, H, I, K, L, M, N, P, Q, R, T, V, W or Y; and/or K-905 may be replaced with A, C, D, E, F, G, H, I, L, M, N, P, Q, R, S, T, V, W or Y.

In addition, the following amino acids may be replaced in METH2 with the following amino acids: L-14 may be replaced with A, C, D, E, F, G, H, I, K, M, N, P, Q, R, S, T, V, W or Y; L-15 maybe replaced with A, C, D, E, F, G, H, I, K, M, N, P, Q, R, S, T, V, W or Y; L-16 may be replaced with A, C, D, E, F, G, H, I, K, M, N, P, Q, R, S, T, V, W or Y; L-17 may be replaced with A, C, D, E, F, G, H, I, K, M, N, P, Q, R, S, T, V, W or Y; L-18 may be replaced with A, C, D, E, F, G, H, I, K, M, N, P, Q, R, S, T, V, W or Y; L-19 may be replaced with A, C, D, E, F, G, H, I, K, M, N, P, Q, R, S, T, V, W or Y; L-20 may be replaced with A, C, D, E, F, G, H, I, K, M, N, P, Q, R, S, T, V, W or Y; L-21 may be replaced with A, C, D, E, F, G, H, I, K, M, N, P, Q, R, S, T, V, W or Y; L-22 may be replaced with A, C, D, E, F, G, H, I, K, M, N, P, Q, R, S, T, V, W or Y; P-23 may be replaced with A, C, D, E, F, G, H, I, K, L, M, N, Q, R, S, T, V, W or Y; L-24 may be replaced with A, C, D, E, F, G, H, I, K, M, N, P, Q, R, S, T, V, W or Y; A-25 may be replaced with C, D, E, F, G, H, I, K, L, M, N, P, Q, R, S, T, V, W or Y; R-26 may be replaced with A, C, D, E, F, G, H, I, K, L, M, N, P, Q, S, T, V, W or Y; G-27 may be replaced with A, C, D, E, F, H, I, K, L, M, N, P, Q, R, S, T, V, W or Y; A-28 may be replaced with C, D, E, F, G, H, I, K, L, M, N, P, Q, R, S, T, V, W or Y; P-29 may be replaced with A, C, D, E, F, G, H, I, K, L, M, N, Q, R, S, T, V, W or Y; A-30 may be replaced with C, D, E, F, G, H, I, K, L, M, N, P, Q, R, S, T, V, W or Y; R-31 may be replaced with A, C, D, E, F, G, H, I, K, L, M, N, P, Q, S, T, V, W or Y; P-32 may be replaced with A, C, D, E, F, G, H, I, K, L, M, N, Q, R, S, T, V, W or Y; A-33 may be replaced with C, D, E, F, G, H, I, K, L, M, N, P, Q, R, S, T, V, W or Y; A-34 may be replaced with C, D, E, F, G, H, I, K, L, M, N, P, Q, R, S, T, V, W or Y; P-204 may be replaced with A, C, D, E, F, G, H, I, K, L, M, N, Q, R, S, T, V, W or Y; P-205 may be replaced with A, C, D, E, F, G, H, I, K, L, M, N, Q, R, S, T, V, W or Y; L-206 may be replaced with A, C, D, E, F, G, H, I, K, M, N, P, Q, R, S, T, V, W or Y; G-207 may be replaced with A, C, D, E, F, H, I, K, L, M, N, P, Q, R, S, T, V, W or Y; A-208 may be replaced with C, D, E, F, G, H, I, K, L, M, N, P, Q, R, S, T, V, W or Y; T-209 may be replaced with A, C, D, E, F, G, H, I, K, L, M, N, P, Q, R, S, V, W or Y; S-210 may be replaced with A, C, D, E, F, G, H, I, K, L, M, N, P, Q, R, T, V, W or Y; R-211 may be replaced with A, C, D, E, F, G, H, I, K, L, M, N, P, Q, S, T, V, W or Y; T-212 may be replaced with A, C, D, E, F, G, H, I, K, L, M, N, P, Q, R, S, V, W or Y; K-213 may be replaced with A, C, D, E, F, G, H, I, L, M, N, P, Q, R, S, T, V, W or Y; R-214 may be replaced with A, C, D, E, F, G, H, I, K, L, M, N, P, Q, S, T, V, W or Y; F-215 may be replaced with A, C, D, E, G, H, I, K, L, M, N, P, Q, R, S, T, V, W or Y; V-216 may be replaced with A, C, D, E, F, G, H, I, K, L, M, N, P, Q, R, S, T, W or Y; S-217 may be replaced with A, C, D, E, F, G, H, I, K, L, M, N, P, Q, R, T, V, W or Y; E-218 may be replaced with A, C, D, F, G, H, I, K, L, M, N, P, Q, R, S, T, V, W or Y; A-219 may be replaced with C, D, E, F, G, H, I, K, L, M, N, P, Q, R, S, T, V, W or Y; R-220 may be replaced with A, C, D, E, F, G, H, I, K, L, M, N, P, Q, S, T, V, W or Y; F-221 may be replaced with A, C, D, E, G, H, I, K, L, M, N, P, Q, R, S, T, V, W or Y; V-222 may be replaced with A, C, D, E, F, G, H, I, K, L, M, N, P, Q, R, S, T, W or Y; E-223 may be replaced with A, C, D, F, G, H, I, K, L, M, N, P, Q, R, S, T, V, W or Y; T-224 may be replaced with A, C, D, E, F, G, H, I, K, L, M, N, P, Q, R, S, V, W or Y; P-430 may be replaced with A, C, D, E, F, G, H, I, K, L, M, N, Q, R, S, T, V, W or Y; G-431 may be replaced with A, C, D, E, F, H, I, K, L, M, N, P, Q, R, S, T, V, W or Y; A-432 may be replaced with C, D, E, F, G, H, I, K, L, M, N, P, Q, R, S, T, V, W or Y; A-433 may be replaced with C, D, E, F, G, H, I, K, L, M, N, P, Q, R, S, T, V, W or Y; L-434 may be replaced with A, C, D, E, F, G, H, I, K, M, N, P, Q, R, S, T, V, W or Y; P-435 may be replaced with A, C, D, E, F, G, H, I, K, L, M, N, Q, R, S, T, V, W or Y; L-436 may be replaced with A, C, D, E, F, G, H, I, K, M, N, P, Q, R, S, T, V, W or Y; P-437 may be replaced with A, C, D, E, F, G, H, I, K, L, M, N, Q, R, S, T, V, W or Y; T-438 may be replaced with A, C, D, E, F, G, H, I, K, L, M, N, P, Q, R, S, V, W or Y; G-439 may be replaced with A, C, D, E, F, H, I, K, L, M, N, P, Q, R, S, T, V, W or Y; L-440 may be replaced with A, C, D, E, F, G, H, I, K, M, N, P, Q, R, S, T, V, W or Y; P-441 may be replaced with A, C, D, E, F, G, H, I, K, L, M, N, Q, R, S, T, V, W or Y; G-442 may be replaced with A, C, D, E, F, H, I, K, L, M, N, P, Q, R, S, T, V, W or Y; R-443 may be replaced with A, C, D, E, F, G, H, I, K, L, M, N, P, Q, S, T, V, W or Y; M-444 may be replaced with A, C, D, E, F, G, H, I, K, L, N, P, Q, R, S, T, V, W or Y; A-445 may be replaced with C, D, E, F, G, H, I, K, L, M, N, P, Q, R, S, T, V, W or Y; L-446 may be replaced with A, C, D, E, F, G, H, I, K, M, N, P, Q, R, S, T, V, W or Y; Y-447 may be replaced with A, C, D, E, F, G, H, I, K, L, M, N, P, Q, R, S, T, V or W; Q-448 may be replaced with A, C, D, E, F, G, H, I, K, L, M, N, P, R, S, T, V, W or Y; L-449 may be replaced with A, C, D, E, F, G, H, I, K, M, N, P, Q, R, S, T, V, W or Y; D-450 may be replaced with A, C, E, F, G, H, I, K, L, M, N, P, Q, R, S, T, V, W or Y; E-520 may be replaced with A, C, D, F, G, H, I, K, L, M, N, P, Q, R, S, T, V, W or Y; R-521 may be replaced with A, C, D, E, F, G, H, I, K, L, M, N, P, Q, S, T, V, W or Y; P-522 may be replaced with A, C, D, E, F, G, H, I, K, L, M, N, Q, R, S, T, V, W or Y; K-523 may be replaced with A, C, D, E, F, G, H, I, L, M, N, P, Q, R, S, T, V, W or Y; P-524 may be replaced with A, C, D, E, F, G, H, I, K, L, M, N, Q, R, S, T, V, W or Y; V-525 may be replaced with A, C, D, E, F, G, H, I, K, L, M, N, P, Q, R, S, T, W or Y; V-526 may be replaced with A, C, D, E, F, G, H, I, K, L, M, N, P, Q, R, S, T, W or Y; D-527 may be replaced with A, C, E, F, G, H, I, K, L, M, N, P, Q, R, S, T, V, W or Y; G-528 may be replaced with A, C, D, E, F, H, I, K, L, M, N, P, Q, R, S, T, V, W or Y; G-529 may be replaced with A, C, D, E, F, H, I, K, L, M, N, P, Q, R, S, T, V, W or Y; W-530 may be replaced with A, C, D, E, F, G, H, I, K, L, M, N, P, Q, R, S, T, V, or Y; A-531 may be replaced with C, D, E, F, G, H, I, K, L, M, N, P, Q, R, S, T, V, W or Y; P-532 may be replaced with A, C, D, E, F, G, H, I, K, L, M, N, Q, R, S, T, V, W or Y; W-533 may be replaced with A, C, D, E, F, G, H, I, K, L, M, N, P, Q, R, S, T, V, or Y; G-534 may be replaced with A, C, D, E, F, H, I, K, L, M, N, P, Q, R, S, T, V, W or Y; P-535 may be replaced with A, C, D, E, F, G, H, I, K, L, M, N, Q, R, S, T, V, W or Y; W-536 may be replaced with A, C, D, E, F, G, H, I, K, L, M, N, P, Q, R, S, T, V or Y; G-537 may be replaced with A, C, D, E, F, H, I, K, L, M, N, P, Q, R, S, T, V, W or Y; E-538 may be replaced with A, C, D, F, G, H, I, K, L, M, N, P, Q, R, S, T, V, W or Y; C-539 may be replaced with A, D, E, F, G, H, I, K, L, M, N, P, Q, R, S, T, V, W or Y; S-540 may be replaced with A, C, D, E, F, G, H, I, K, L, M, N, P, Q, R, T, V, W or Y; N-827 may be replaced with A, C, D, E, F, G, H, I, K, L, M, P, Q, R, S, T, V, W or Y; I-828 may be replaced with A, C, D, E, F, G, H, K, L, M, N, P, Q, R, S, T, V, W or Y; I-829 may be replaced with A, C, D, E, F, G, H, K, L, M, N, P, Q, R, S, T, V, W or Y; Q-830 may be replaced with A, C, D, E, F, G, H, I, K, L, M, N, P, R, S, T, V, W or Y; P-831 may be replaced with A, C, D, E, F, G, H, I, K, L, M, N, Q, R, S, T, V, W or Y; L-832 may be replaced with A, C, D, E, F, G, H, I, K, M, N, P, Q, R, S, T, V, W or Y; L-833 may be replaced with A, C, D, E, F, G, H, I, K, M, N, P, Q, R, S, T, V, W or Y; H-834 may be replaced with A, C, D, E, F, G, I, K, L, M, N, P, Q, R, S, T, V, W or Y; A-835 may be replaced with C, D, E, F, G, H, I, K, L, M, N, P, Q, R, S, T, V, W or Y; Q-836 may be replaced with A, C, D, E, F, G, H, I, K, L, M, N, P, R, S, T, V, W or Y; W-837 may be replaced with A, C, D, E, F, G, H, I, K, L, M, N, P, Q, R, S, T, V, or Y; V-838 may be replaced with A, C, D, E, F, G, H, I, K, L, M, N, P, Q, R, S, T, W or Y; L-839 may be replaced with A, C, D, E, F, G, H, I, K, M, N, P, Q, R, S, T, V, W or Y; G-840 may be replaced with A, C, D, E, F, H, I, K, L, M, N, P, Q, R, S, T, V, W or Y; D-841 may be replaced with A, C, E, F, G, H, I, K, L, M, N, P, Q, R, S, T, V, W or Y; W-842 may be replaced with A, C, D, E, F, G, H, I, K, L, M, N, P, Q, R, S, T, V or Y; S-843 may be replaced with A, C, D, E, F, G, H, I, K, L, M, N, P, Q, R, T, V, W or Y; E-844 may be replaced with A, C, D, F, G, H, I, K, L, M, N, P, Q, R, S, T, V, W or Y; C-845 may be replaced with A, D, E, F, G, H, I, K, L, M, N, P, Q, R, S, T, V, W or Y; S-846 may be replaced with A, C, D, E, F, G, H, I, K, L, M, N, P, Q, R, T, V, W or Y; and/or S-847 may be replaced with A, C, D, E, F, G, H, I, K, L, M, N, P, Q, R, T, V, W or Y.

METH1 or METH2 polypeptide variants, including substitution, deletion and/or addition variants, which contain amino acid substitutions can be tested for activity in any of the assays described herein, for example, the chorioallantoic assay or the cornea pocket assay. Preferred are METH1 or METH2 polypeptides with conservative substitutions that: maintain all the activities and/or properties of the wild type protein; or have one or more enhanced activities and/or properties compared to the wild type protein. Also preferred are METH1 or METH2 polypeptides with nonconservative substitutions which: lack an activity and/or property of the wild type protein, while maintaining all other activities and/or properties; or lack more than one activity and/or property of the wild type protein.

For example, activities or properties of METH1 or METH2 that may be altered in METH1 or METH2 polypeptides with conservative or nonconservative substitutions include, but are not limited to: stimulation of angiogenesis; stimulation of epithelial cell proliferation; antibody binding; ligand binding; stability; solubility; and/or properties which affect purification.

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or from a native source. For example, a recombinantly produced version of the METH1 or METH2 polypeptide can be substantially purified by the one-step method described in Smith and Johnson, *Gene* 67:31–40 (1988).

The polypeptides of the present invention include the METH1 polypeptide encoded by the deposited cDNA including the leader; the mature METH1 polypeptide encoded by the deposited the cDNA minus the leader (i.e., the mature protein); a polypeptide comprising amino acids about 1 to about 950 in SEQ ID NO:2; a polypeptide comprising amino acids about 2 to about 950 in SEQ ID NO:2; a polypeptide comprising amino acids about 29 to about 950 in SEQ ID NO:2; a polypeptide comprising amino acids about 30 to about 950 in SEQ ID NO:2; a polypeptide comprising the metalloprotease domain of METH1, amino acids 235 to 459 in SEQ ID NO:2; a polypeptide comprising the disintegrin domain of METH1, amino acids 460 to 544 in SEQ ID NO:2; a polypeptide comprising the first TSP-like domain of METH1, amino acids 545 to 598 in SEQ ID NO:2; a polypeptide comprising the second TSP-like domain of METH1, amino acids 841 to 894 in SEQ ID NO:2; a polypeptide comprising the third TSP-like domain of METH1, amino acids 895 to 934 in SEQ ID NO:2; a polypeptide comprising amino acids 536 to 613 in SEQ ID NO:2; a polypeptide comprising amino acids 549 to 563 in SEQ ID NO:2; the METH2 polypeptide encoded by the deposited cDNA including the leader; the mature METH2 polypeptide encoded by the deposited the cDNA minus the leader (i.e., the mature protein); a polypeptide comprising amino acids about 1 to about 890 in SEQ ID NO:4; a polypeptide comprising amino acids about 2 to about 890 in SEQ ID NO:4; a polypeptide comprising amino acids about 24 to about 890 in SEQ ID NO:4; a polypeptide comprising amino acids about 112 to about 890 in SEQ ID NO:4; a polypeptide comprising the metalloprotease domain of METH2, amino acids 214 to 439 in SEQ ID NO:4; a polypeptide comprising the disintegrin domain of METH2, amino acids 440 to 529 in SEQ ID NO:4; a polypeptide comprising the first TSP-like domain of METH2, amino acids 530 to 583 in SEQ ID NO:4; a polypeptide comprising the second TSP-like domain of METH2, amino acids 837 to 890 in SEQ ID NO:4; a polypeptide comprising amino acids 280 to 606 in SEQ ID NO:4; a polypeptide comprising amino acids 529 to 548 in SEQ ID NO:4; as well as polypeptides which are at least 95% identical, and more preferably at least 96%, 97%, 98% or 99% identical to the polypeptides described above and also include portions of such polypeptides with at least 30 amino acids and more preferably at least 50 amino acids.

By a polypeptide having an amino acid sequence at least, for example, 95% "identical" to a reference amino acid sequence of a METH1 or METH2 polypeptide is intended that the amino acid sequence of the polypeptide is identical to the reference sequence except that the polypeptide sequence may include up to five amino acid alterations per each 100 amino acids of the reference amino acid of the METH1 or METH2 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:2 or SEQ ID NO:4 or to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

A preferred method for determining the best overall match between a query sequence (a sequence of the present invention) and a subject sequence, also referred to as a global sequence alignment, can be determined using the FASTDB computer program based on the algorithm of Brutlag et al., Comp. App. Biosci. 6:237–245 (1990). In a sequence alignment, the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total residues of the query sequence. Whether a residue is matched/aligned is determined by the results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched, the final percent identity would be 90%. In another example, a 90 residue subject sequence is compared with a 100 residue query sequence. This time, the deletions are internal, so there are no residues at the N- or C-termini of the subject sequence which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of the present invention.

The polypeptides of the present invention are useful as a molecular weight marker on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998–4002 (1983).

As to the selection of peptides or polypeptides bearing an antigenic epitope (i.e., that contain a region of a protein molecule to which an antibody can bind), it is well known in the art that relatively short synthetic peptides that mimic part of a protein sequence are routinely capable of eliciting an antiserum that reacts with the partially mimicked protein. See, for instance, Sutcliffe, J. G. et al., "Antibodies that react with predetermined sites on proteins", Science 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., Cell 37:767–778 (1984) at 777.

Antigenic epitope-bearing peptides and polypeptides of the invention preferably contain a sequence of at least seven, more preferably at least nine and most preferably between about at least about 15 to about 30 amino acids contained within the amino acid sequence of a polypeptide of the invention.

The epitope-bearing peptides and polypeptides of the invention may be produced by any conventional means. Houghten, R. A., "General method for the rapid solid-phase synthesis of large numbers of peptides: specificity of antigen-antibody interaction at the level of individual amino acids", Proc. Natl. Acad. Sci. USA 82:5131–5135 (1985). This "Simultaneous Multiple Peptide Synthesis (SMPS)" process is further described in U.S. Pat. No. 4,631,211 to Houghten et al. (1986).

As one of skill in the art will appreciate, METH1 or METH2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331: 84–86 (1988)). Fusion proteins that have a disulfide-linked dimeric structure due to the IgG part can also be more efficient in binding and neutralizing other molecules than the monomeric METH1 or METH2 protein or protein fragment alone (Fountoulakis et al., J. Biochem. 270:3958–3964 (1995)).

METH1 and METH2 Polynucleotide and Polypeptide Fragments

In the present invention, a "polynucleotide fragment" refers to a short polynucleotide having a nucleic acid sequence contained in the deposited clones or shown in SEQ ID NO:1 or SEQ ID NO:3. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clones or the nucleotide sequence shown in SEQ ID NO:1 or SEQ ID NO:3. These nucleotide fragments are useful as diagnostic probes and primers as discussed herein. Of course, larger fragments (e.g., 50, 150, 500, 600, 2000 nucleotides) are preferred.

Moreover, representative examples of METH1 or METH2 polynucleotide fragments include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:1 or SEQ ID NO:3 or the cDNA contained in the deposited clones. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:2 or SEQ ID NO:4 or encoded by the cDNA contained in the deposited clones. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, 161–180, 181–200, 201–220, 221–240, 241–260, 261–280, or 281 to the end of the coding region of SEQ ID NO:2 or SEQ ID NO:4. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted METH1 or METH2 protein as well as the mature form. Further preferred polypeptide fragments include the secreted METH1 or METH2 protein or the mature form having a continuous series of deleted residues from the amino or the carboxy terminus, or both. For example, any number of amino acids, ranging from 1–60, can be deleted from the amino terminus of either the secreted METH1 or METH2 polypeptide or the mature form. Similarly, any number of amino acids, ranging from 1–30, can be deleted from the carboxy terminus of the secreted METH1 or METH2 protein or mature form. Furthermore, any combination of the above amino and carboxy terminus deletions are preferred. Similarly, polynucleotide fragments encoding these METH1 or METH2 polypeptide fragments are also preferred.

Particularly, N-terminal deletions of the METH1 polypeptide can be described by the general formula m-950, where m is an integer from 2 to 949, where m corresponds to the position of the amino acid residue identified in SEQ ID NO:2. Preferably, N-terminal deletions of the METH1 polypeptide of the invention shown as SEQ ID NO:2 include polypeptides comprising the amino acid sequence of residues: G-2 to S-950; N-3 to S-950; A-4 to S-950; E-5 to S-950; R-6 to S-950; A-7 to S-950; P-8 to S-950; G-9 to S-950; S-10 to S-950; R-11 to S-950; S-12 to S-950; F-13 to S-950; G-14 to S-950; P-15 to S-950; V-16 to S-950; P-17 to S-950; T-18 to S-950; L-19 to S-950; L-20 to S-950; L-21 to S-950; L-22 to S-950; A-23 to S-950; A-24 to S-950; A-25 to S-950; L-26 to S-950; L-27 to S-950; A-28 to S-950; V-29 to S-950; S-30 to S-950; D-31 to S-950; A-32 to S-950; L-33 to S-950; G-34 to S-950; R-35 to S-950; P-36 to S-950; S-37 to S-950; E-38 to S-950; E-39 to S-950; D-40 to S-950; E-41 to S-950; E-42 to S-950; L-43 to S-950; V-44 to S-950; V-45 to S-950; P-46 to S-950; E-47 to S-950; L-48 to S-950; E-49 to S-950; R-50 to S-950; A-51 to S-950; P-52 to S-950; G-53 to S-950; H-54 to S-950; G-55 to S-950; T-56 to S-950; T-57 to S-950; R-58 to S-950; L-59 to S-950; R-60 to S-950; L-61 to S-950; H-62 to S-950; A-63 to S-950; F-64 to S-950; D-65 to S-950; Q-66 to S-950; Q-67 to S-950; L-68 to S-950; D-69 to S-950; L-70 to S-950; E-71 to S-950; L-72 to S-950; R-73 to S-950; P-74 to S-950; D-75 to S-950; S-76 to S-950; S-77 to S-950; F-78 to S-950; L-79 to S-950; A-80 to S-950; P-81 to S-950; G-82 to S-950; F-83 to S-950; T-84 to S-950; L-85 to S-950; Q-86 to S-950; N-87 to S-950; V-88 to S-950; G-89 to S-950; R-90 to S-950; K-91 to S-950; S-92 to S-950; G-93 to S-950; S-94 to S-950; E-95 to S-950; T-96 to S-950; P-97 to S-950; L-98 to S-950; P-99 to S-950; E-100 to S-950; T-101 to S-950; D-102 to S-950; L-103 to S-950; A-104 to S-950; H-105 to S-950; C-106 to S-950; F-107 to S-950; Y-108 to S-950; S-109 to S-950; G-110 to S-950; T-111 to S-950; V-112 to S-950; N-113 to S-950; G-114 to S-950; D-115 to S-950; P-116 to S-950; S-117 to S-950; S-118 to S-950; A-119 to S-950; A-120 to S-950; L-122 to S-950; S-123 to S-950; L-124 to S-950; C-125 to S-950; E-126 to S-950; G-127 to S-950; V-128 to S-950; R-129 to S-950; G-130 to S-950; A-131 to S-950; F-132 to S-950; Y-133 to S-950; L-134 to S-950; L-135 to S-950; G-136 to S-950; E-137 to S-950; A-138 to S-950; Y-139 to S-950; F-140 to S-950; I-141 to S-950; Q-142 to S-950; P-143 to S-950; L-144 to S-950; P-145 to S-950; A-146 to S-950; A-147 to S-950; S-148 to S-950; E-149 to S-950; R-150 to S-950; L-151 to S-950; A-152 to S-950; T-153 to S-950; A-154 to S-950; A-155 to S-950; P-156 to S-950; G-157 to S-950; E-158 to S-950; K-159 to S-950; P-160 to S-950; P-161 to S-950; A-162 to S-950; P-163 to S-950; L-164 to S-950; Q-165 to S-950; F-166 to S-950; H-167 to S-950; L-168 to S-950; L-169 to S-950; R-170 to S-950; R-171 to S-950; N-172 to S-950; R-173 to S-950; Q-174 to S-950; G-175 to S-950; D-176 to S-950; V-177 to S-950; G-178 to S-950; G-179 to S-950; T-180 to S-950; C-181 to S-950; G-182 to S-950; V-183 to S-950; V-184 to S-950; D-185 to S-950; D-186 to S-950; E-187 to S-950; P-188 to S-950; R-189 to S-950; P-190 to S-950; T-191 to S-950; G-192 to S-950; K-193 to S-950; A-194 to S-950; E-195 to S-950; T-196 to S-950; E-197 to S-950; D-198 to S-950; E-199 to S-950; D-200 to S-950; E-201 to S-950; G-202 to S-950; T-203 to S-950; E-204 to S-950; G-205 to S-950; E-206 to S-950; D-207 to S-950; E-208 to S-950; G-209 to S-950; P-210 to S-950; Q-211 to S-950; W-212 to S-950; S-213 to S-950; P-214 to S-950; Q-215 to S-950; D-216 to S-950; P-217 to S-950; A-218 to S-950; L-219 to S-950; Q-220 to S-950; G-221 to S-950; V-222 to S-950; G-223 to S-950;

Q-224 to S-950; P-225 to S-950; T-226 to S-950; G-227 to S-950; T-228 to S-950; G-229 to S-950; S-230 to S-950; I-231 to S-950; R-232 to S-950; K-233 to S-950; K-234 to S-950; R-235 to S-950; F-236 to S-950; V-237 to S-950; S-238 to S-950; S-239 to S-950; H-240 to S-950; R-241 to S-950; Y-242 to S-950; V-243 to S-950; E-244 to S-950; T-245 to S-950; M-246 to S-950; L-247 to S-950; V-248 to S-950; A-249 to S-950; D-250 to S-950; Q-251 to S-950; S-252 to S-950; M-253 to S-950; A-254 to S-950; E-255 to S-950; F-256 to S-950; H-257 to S-950; G-258 to S-950; S-259 to S-950; G-260 to S-950; L-261 to S-950; K-262 to S-950; H-263 to S-950; Y-264 to S-950; L-265 to S-950; L-266 to S-950; T-267 to S-950; L-268 to S-950; F-269 to S-950; S-270 to S-950; V-271 to S-950; A-272 to S-950; A-273 to S-950; R-274 to S-950; L-275 to S-950; Y-276 to S-950; K-277 to S-950; H-278 to S-950; P-279 to S-950; S-280 to S-950; I-281 to S-950; R-282 to S-950; N-283 to S-950; S-284 to S-950; V-285 to S-950; S-286 to S-950; L-287 to S-950; V-288 to S-950; V-289 to S-950; V-290 to S-950; K-291 to S-950; I-292 to S-950; L-293 to S-950; V-294 to S-950; I-295 to S-950; H-296 to S-950; D-297 to S-950; E-298 to S-950; Q-299 to S-950; K-300 to S-950; G-301 to S-950; P-302 to S-950; E-303 to S-950; V-304 to S-950; T-305 to S-950; S-306 to S-950; N-307 to S-950; A-308 to S-950; A-309 to S-950; L-310 to S-950; T-311 to S-950; L-312 to S-950; R-313 to S-950; N-314 to S-950; F-315 to S-950; C-316 to S-950; N-317 to S-950; W-318 to S-950; Q-319 to S-950; K-320 to S-950; Q-321 to S-950; H-322 to S-950; N-323 to S-950; P-324 to S-950; P-325 to S-950; S-326 to S-950; D-327 to S-950; R-328 to S-950; D-329 to S-950; A-330 to S-950; E-331 to S-950; H-332 to S-950; Y-333 to S-950; D-334 to S-950; T-335 to S-950; A-336 to S-950; I-337 to S-950; L-338 to S-950; F-339 to S-950; T-340; S-950; R-341 to S-950; Q-342 to S-950; D-343 to S-950; L-344 to S-950; C-345 to S-950; G-346 to S-950; S-347 to S-950; Q-348 to S-950; T-349 to S-950; C-350 to S-950; D-351 to S-950; T-352 to S-950; L-353 to S-950; G-354 to S-950; M-355 to S-950; A-356 to S-950; D-357 to S-950; V-358 to S-950; G-359 to S-950; T-360 to S-950; V-361 to S-950; C-362 to S-950; D-363 to S-950; P-364 to S-950; S-365 to S-950; R-366 to S-950; S-367 to S-950; C-368 to S-950; S-369 to S-950; V-370 to S-950; I-371 to S-950; E-372 to S-950; D-373 to S-950; D-374 to S-950; G-375 to S-950; L-376 to S-950; Q-377 to S-950; A-378 to S-950; A-379 to S-950; F-380 to S-950; T-381 to S-950; T-382 to S-950; A-383 to S-950; H-384 to S-950; E-385 to S-950; L-386 to S-950; G-387 to S-950; H-388 to S-950; V-389 to S-950; F-390 to S-950; N-391 to S-950; M-392 to S-950; P-393 to S-950; H-394 to S-950; D-395 to S-950; D-396 to S-950; A-397 to S-950; K-398 to S-950; Q-399 to S-950; C-400 to S-950; A-401 to S-950; S-402 to S-950; L-403 to S-950; N-404 to S-950; G-405 to S-950; V-406 to S-950; N-407 to S-950; Q-408 to S-950; D-409 to S-950; S-410 to S-950; H-411 to S-950; M-412 to S-950; M-413 to S-950; A-414 to S-950; S-415 to S-950; M-416 to S-950; L-417 to S-950; S-418 to S-950; N-419 to S-950; L-420 to S-950; D-421 to S-950; H-422 to S-950; S-423 to S-950; Q-424 to S-950; P-425 to S-950; W-426 to S-950; S-427 to S-950; P-428 to S-950; C-429 to S-950; S-430 to S-950; A-431 to S-950; Y-432 to S-950; M-433 to S-950; I-434 to S-950; T-435 to S-950; S-436 to S-950; F-437 to S-950; L-438 to S-950; D-439 to S-950; N-440 to S-950; G-441 to S-950; H-442 to S-950; G-443 to S-950; E-444 to S-950; C-445 to S-950; L-446 to S-950; M-447 to S-950; D-448 to S-950; K-449 to S-950; P-450 to S-950; Q-451 to S-950; N-452 to S-950; P-453 to S-950; I-454 to S-950; Q-455 to S-950; L-456 to S-950; P-457 to S-950; G-458 to S-950; D-459 to S-950; L-460 to S-950; P-461 to S-950; G-462 to S-950; T-463 to S-950; S-464 to S-950; Y-465 to S-950; D-466 to S-950; A-467 to S-950; N-468 to S-950; R-469 to S-950; Q-470 to S-950; C-471 to S-950; Q-472 to S-950; F-473 to S-950; T-474 to S-950; F-475 to S-950; G-476 to S-950; E-477 to S-950; D-478 to S-950; S-479 to S-950; K-480 to S-950; H-481 to S-950; C-482 to S-950; P-483 to S-950; D-484 to S-950; A-485 to S-950; A-486 to S-950; S-487 to S-950; T-488 to S-950; C-489 to S-950; S-490 to S-950; T-491 to S-950; L-492 to S-950; W-493 to S-950; C-494 to S-950; T-495 to S-950; G-496 to S-950; T-497 to S-950; S-498 to S-950; G-499 to S-950; G-500 to S-950; V-501 to S-950; L-502 to S-950; V-503 to S-950; C-504 to S-950; Q-505 to S-950; T-506 to S-950; K-507 to S-950; H-508 to S-950; F-509 to S-950; P-510 to S-950; W-511 to S-950; A-512 to S-950; D-513 to S-950; G-514 to S-950; T-515 to S-950; S-516 to S-950; C-517 to S-950; G-518 to S-950; E-519 to S-950; G-520 to S-950; K-521 to S-950; W-522 to S-950; C-523 to S-950; I-524 to S-950; N-525 to S-950; G-526 to S-950; K-527 to S-950; C-528 to S-950; V-529 to S-950; N-530 to S-950; K-531 to S-950; T-532 to S-950; D-533 to S-950; R-534 to S-950; K-535 to S-950; H-536 to S-950; F-537 to S-950; D-538 to S-950; T-539 to S-950; P-540 to S-950; F-541 to S-950; H-542 to S-950; G-543 to S-950; S-544 to S-950; W-545 to S-950; G-546 to S-950; M-547 to S-950; W-548 to S-950; G-549 to S-950; P-550 to S-950; W-551 to S-950; G-552 to S-950; D-553 to S-950; C-554 to S-950; S-555 to S-950; R-556 to S-950; T-557 to S-950; C-558 to S-950; G-559 to S-950; G-560 to S-950; G-561 to S-950; V-562 to S-950; Q-563 to S-950; Y-564 to S-950; T-565 to S-950; M-566 to S-950; R-567 to S-950; E-568 to S-950; C-569 to S-950; D-570 to S-950; N-571 to S-950; P-572 to S-950; V-573 to S-950; P-574 to S-950; K-575 to S-950; N-576 to S-950; G-577 to S-950; G-578 to S-950; K-579 to S-950; Y-580 to S-950; C-581 to S-950; E-582 to S-950; G-583 to S-950; K-584 to S-950; R-585 to S-950; V-586 to S-950; R-587 to S-950; Y-588 to S-950; R-589 to S-950; S-590 to S-950; C-591 to S-950; N-592 to S-950; L-593 to S-950; E-594 to S-950; D-595 to S-950; C-596 to S-950; P-597 to S-950; D-598 to S-950; N-599 to S-950; N-600 to S-950; G-601 to S-950; K-602 to S-950; T-603 to S-950; F-604 to S-950; R-605 to S-950; E-606 to S-950; E-607 to S-950; Q-608 to S-950; C-609 to S-950; E-610 to S-950; A-611 to S-950; H-612 to S-950; N-613 to S-950; E-614 to S-950; F-615 to S-950; S-616 to S-950; K-617 to S-950; A-618 to S-950; S-619 to S-950; F-620 to S-950; G-621 to S-950; S-622 to S-950; G-623 to S-950; P-624 to S-950; A-625 to S-950; V-626 to S-950; E-627 to S-950; W-628 to S-950; I-629 to S-950; P-630 to S-950; K-631 to S-950; Y-632 to S-950; A-633 to S-950; G-634 to S-950; V-635 to S-950; S-636 to S-950; P-637 to S-950; K-638 to S-950; D-639 to S-950; R-640 to S-950; C-641 to S-950; K-642 to S-950; L-643 to S-950; I-644 to S-950; C-645 to S-950; Q-646 to S-950; A-647 to S-950; K-648 to S-950; to S-950; I-644 to S-950; C-645 to S-950; Q-646 to S-950; A-647 to S-950; K-648 to S-950; G-649 to S-950; I-650 to S-950; G-651 to S-950; Y-652 to S-950; F-653 to S-950; F-654 to S-950; V-655 to S-950; L-656 to S-950; Q-657 to S-950; P-658 to S-950; K-659 to S-950; V-660 to S-950; V-661 to S-950; D-662 to S-950; G-663 to S-950; T-664 to S-950; P-665 to S-950; C-666 to S-950; S-667 to S-950; P-668 to S-950; D-669 to S-950; S-670 to S-950; T-671 to S-950; S-672 to S-950; V-673 to S-950; C-674 to S-950; V-675 to S-950; Q-676 to S-950; G-677 to S-950; Q-678 to S-950; C-679 to S-950; V-680 to S-950; K-681 to S-950; A-682 to S-950; G-683 to S-950; C-684 to S-950; D-685 to S-950; R-686 to S-950; I-687 to

S-950; I-688 to S-950; D-689 to S-950; S-690 to S-950; K-691 to S-950; K-692 to S-950; K-693 to S-950; F-694 to S-950; D-695 to S-950; K-696 to S-950; C-697 to S-950; G-698 to S-950; V-699 to S-950; C-700 to S-950; G-701 to S-950; G-702 to S-950; N-703 to S-950; G-704 to S-950; S-705 to S-950; T-706 to S-950; C-707 to S-950; K-708 to S-950; K-709 to S-950; I-710 to S-950; S-711 to S-950; G-712 to S-950; S-713 to S-950; V-714 to S-950; T-715 to S-950; S-716 to S-950; A-717 to S-950; K-718 to S-950; P-719 to S-950; G-720 to S-950; Y-721 to S-950; H-722 to S-950; D-723 to S-950; I-724 to S-950; I-725 to S-950; T-726 to S-950; I-727 to S-950; D-728 to S-950; T-729 to S-950; G-730 to S-950; A-731 to S-950; T-732 to S-950; N-733 to S-950; I-734 to S-950; E-735 to S-950; V-736 to S-950; K-737 to S-950; Q-738 to S-950; R-739 to S-950; N-740 to S-950; Q-741 to S-950; R-742 to S-950; G-743 to S-950; S-744 to S-950; R-745 to S-950; N-746 to S-950; N-747 to S-950; G-748 to S-950; S-749 to S-950; F-750 to S-950; L-751 to S-950; A-752 to S-950; I-753 to S-950; K-754 to S-950; A-755 to S-950; A-756 to S-950; D-757 to S-950; G-758 to S-950; T-759 to S-950; Y-760 to S-950; I-761 to S-950; L-762 to S-950; N-763 to S-950; G-764 to S-950; D-765 to S-950; Y-766 to S-950; T-767 to S-950; L-768 to S-950; S-769 to S-950; T-770 to S-950; L-771 to S-950; E-772 to S-950; Q-773 to S-950; D-774 to S-950; I-775 to S-950; M-776 to S-950; Y-777 to S-950; K-778 to S-950; G-779 to S-950; V-780 to S-950; V-781 to S-950; L-782 to S-950; R-783 to S-950; Y-784 to S-950; S-785; S-950; G-786 to S-950; S-787 to S-950; S-788 to S-950; A-789 to S-950; A-790 to S-950; L-791 to S-950; E-792 to S-950; R-793 to S-950; I-794 to S-950; R-795 to S-950; S-796 to S-950; F-797 to S-950; S-798 to S-950; P-799 to S-950; L-800 to S-950; K-801 to S-950; E-802 to S-950; P-803 to S-950; L-804 to S-950; T-805 to S-950; I-806 to S-950; Q-807 to S-950; V-808 to S-950; L-809 to S-950; T-810 to S-950; V-811 to S-950; G-812 to S-950; N-813 to S-950; A-814 to S-950; L-815 to S-950; R-816 to S-950; P-817 to S-950; K-818 to S-950; I-819 to S-950; K-820 to S-950; Y-821 to S-950; T-822 to S-950; Y-823 to S-950; F-824 to S-950; V-825 to S-950; K-826 to S-950; K-827 to S-950; K-828 to S-950; K-829 to S-950; E-830 to S-950; S-831 to S-950; F-832 to S-950; N-833 to S-950; A-834 to S-950; I-835 to S-950; P-836 to S-950; T-837 to S-950; F-838 to S-950; S-839 to S-950; A-840 to S-950; W-841 to S-950; V-842 to S-950; I-843 to S-950; E-844 to S-950; E-845 to S-950; W-846 to S-950; G-847 to S-950; E-848 to S-950; C-849 to S-950; S-850 to S-950; K-851 to S-950; S-852 to S-950; C-853 to S-950; E-854 to S-950; L-855 to S-950; G-856 to S-950; W-857 to S-950; Q-858 to S-950; R-859 to S-950; R-860 to S-950; L-861 to S-950; V-862 to S-950; E-863 to S-950; C-864 to S-950; R-865 to S-950; D-866 to S-950; I-867 to S-950; N-868 to S-950; G-869 to S-950; Q-870 to S-950; P-871 to S-950; A-872 to S-950; S-873 to S-950; E-874 to S-950; C-875 to S-950; A-876 to S-950; K-877 to S-950; E-878 to S-950; V-879 to S-950; K-880 to S-950; P-881 to S-950; A-882 to S-950; S-883 to S-950; T-884 to S-950; R-885 to S-950; P-886 to S-950; C-887 to S-950; A-888 to S-950; D-889 to S-950; H-890 to S-950; P-891 to S-950; C-892 to S-950; P-893 to S-950; Q-894 to S-950; W-895 to S-950; Q-896 to S-950; L-897 to S-950; G-898 to S-950; E-899 to S-950; W-900 to S-950; S-901 to S-950; S-902 to S-950; C-903 to S-950; S-904 to S-950; K-905 to S-950; T-906 to S-950; C-907 to S-950; G-908 to S-950; K-909 to S-950; G-910 to S-950; Y-911 to S-950; K-912 to S-950; K-913 to S-950; R-914 to S-950; S-915 to S-950; L-916 to S-950; K-917 to S-950; C-918 to S-950; L-919 to S-950; S-920 to S-950; H-921 to S-950; D-922 to S-950; G-923 to S-950; G-924 to S-950; V-925 to S-950; L-926 to S-950; S-927 to S-950; H-928 to S-950; E-929 to S-950; S-930 to S-950; C-931 to S-950; D-932 to S-950; P-933 to S-950; L-934 to S-950; K-935 to S-950; K-936 to S-950; P-937 to S-950; K-938 to S-950; H-939 to S-950; F-940 to S-950; I-941 to S-950; D-942 to S-950; F-943 to S-950; C-944 to S-950; T-945 to S-950; of SEQ ID NO:2.

Moreover, C-terminal deletions of the METH1 polypeptide can also be described by the general formula 1-$n_1$, where $n_1$ is an integer from 2 to 950, where n corresponds to the position of amino acid residue identified in SEQ ID NO:2. Preferably, C-terminal deletions of the METH1 polypeptide of the invention shown as SEQ ID NO:2 include polypeptides comprising the amino acid sequence of residues: M-1 to C-949; M-1 to E-948; M-1 to A-947; M-1 to M-946; M-1 to T-945; M-1 to C-944; M-1 to F-943; M-1 to D-942; M-1 to I-941; M-1 to F-940; M-1 to H-939; M-1 to K-938; M-1 to P-937; M-1 to K-936; M-1 to K-935; M-1 to L-934; M-1 to P-933; M-1 to D-932; M-1 to C-931; M-1 to S-930; M-1 to E-929; M-1 to H-928; M-1 to S-927; M-1 to L-926; M-1 to V-925; M-1 to G-924; M-1 to G-923; M-1 to D-922; M-1 to H-921; M-1 to S-920; M-1 to L-919; M-1 to C-918; M-1 to K-917; M-1 to L-916; M-1 to S-915; M-1 to R-914; M-1 to K-913; M-1 to K-912; M-1 to Y-911; M-1 to G-910; M-1 to K-909; M-1 to G-908; M-1 to C-907; M-1 to T-906; M-1 to E-905; M-1 to S-904; M-1 to C-903; M-1 to S-902; M-1 to S-901; M-1 to W-900; M-1 to P-899; M-1 to G-898; M-1 to L-897; M-1 to Q-896; M-1 to W-895; M-1 to Q-894; M-1 to P-893; M-1 to C-892; M-1 to P-891; M-1 to H-890; M-1 to D-889; M-1 to A-888; M-1 to C-887; M-1 to P-886; M-1 to R-885; M-1 to T-884; M-1 to S-883; M-1 to A-882; M-1 to P-881; M-1 to K-880; M-1 to V-879; M-1 to E-878; M-1 to K-877; M-1 to A-876; M-1 to C-875; M-1 to E-874; M-1 to S-873; M-1 to A-872; M-1 to P-871; M-1 to Q-870; M-1 to G-869; M-1 to N-868; M-1 to I-867; M-1 to D-866; M-1 to R-865; M-1 to C-864; M-1 to E-863; M-1 to V-862; M-1 to L-861; M-1 to R-860; M-1 to R-859; M-1 to Q-858; M-1 to W-857; M-1 to G-856; M-1 to L-855; M-1 to E-854; M-1 to C-853; M-1 to S-852; M-1 to K-851; M-1 to S-850; M-1 to C-849; M-1 to E-848; M-1 to G-847; M-1 to W-846; M-1 to E-845; M-1 to E-844; M-1 to I-843; M-1 to V-842; M-1 to W-841; M-1 to A-840; M-1 to S-839; M-1 to F-838; M-1 to T-837; M-1 to P-836; M-1 to I-835; M-1 to A-834; M-1 to N-833; M-1 to F-832; M-1 to S-831; M-1 to E-830; M-1 to K-829; M-1 to K-828; M-1 to K-827; M-1 to K-826; M-1 to V-825; M-1 to F-824; M-1 to Y-823; M-1 to T-822; M-1 to Y-821; M-1 to K-820; M-1 to I-819; M-1 to K-818; M-1 to P-817; M-1 to R-816; M-1 to L-815; M-1 to A-814; M-1 to N-813; M-1 to G-812; M-1 to V-811; M-1 to T-810; M-1 to L-809; M-1 to V-808; M-1 to Q-807; M-1 to I-806; M-1 to T-805; M-1 to L-804; M-1 to P-803; M-1 to E-802; M-1 to K-801; M-1 to L-800; M-1 to P-799; M-1 to S-798; M-1 to F-797; M-1 to S-796; M-1 to R-795; M-1 to I-794; M-1 to R-793; M-1 to E-792; M-1 to L-791; M-1 to A-790; M-1 to A-789; M-1 to S-788; M-1 to S-787; M-1 to G-786; M-1 to S-785; M-1 to Y-784; M-1 to R-783; M-1 to L-782; M-1 to V-781; M-1 to V-780; M-1 to G-779; M-1 to K-778; M-1 to Y-777; M-1 to M-776; M-1 to I-775; M-1 to D-774; M-1 to Q-773; M-1 to E-772; M-1 to L-771; M-1 to T-770; M-1 to S-769; M-1 to L-768; M-1 to T-767; M-1 to Y-766; M-1 to D-765; M-1 to G-764; M-1 to N-763; M-1 to L-762; M-1 to I-761; M-1 to Y-760; M-1 to T-759; M-1 to G-758; M-1 to D-757; M-1 to A-756; M-1 to A-755; M-1 to K-754; M-1 to I-753; M-1 to A-752; M-1 to L-751; M-1 to F-750; M-1 to S-749; M-1 to G-748; M-1 to N-747; M-1 to N-746; M-1 to R-745; M-1 to S-744; M-1 to G-743; M-1 to R-742; M-1 to Q-741; M-1 to N-740; M-1 to R-739; M-1 to Q-738; M-1 to K-737; M-1 to V-736; M-1 to E-735; M-1 to I-734; M-1 to N-733; M-1 to T-732; M-1 to A-731; M-1 to G-730; M-1 to T-729; M-1 to P-728; M-1 to I-727; M-1 to T-726; M-1 to I-725; M-1 to I-724; M-1 to D-723; M-1 to H-722; M-1 to Y-721; M-1 to G-720; M-1 to P-719; M-1 to K-718; M-1 to A-717; M-1 to S-716; M-1 to T-715; M-1 to V-714; M-1 to S-713; M-1 to G-712; M-1 to S-711; M-1 to I-710; M-1 to K-709; M-1 to K-708; M-1 to C-707; M-1 to T-706; M-1 to S-705; M-1 to G-704; M-1 to N-703; M-1 to G-702; M-1 to G-701; M-1 to C-700; M-1 to V-699; M-1 to G-698; M-1 to C-697; M-1 to K-696; M-1 to D-695; M-1 to F-694; M-1 to K-693; M-1 to K-692; M-1 to K-691; M-1 to S-690; M-1 to D-689; M-1 to I-688; M-1 to I-687; M-1 to R-686; M-1 to D-685; M-1 to C-684; M-1 to G-683; M-1 to A-682; M-1 to K-681; M-1 to V-680; M-1 to C-679; M-1 to Q-678; M-1 to G-677; M-1 to Q-676; M-1 to V-675; M-1 to C-674; M-1 to V-673; M-1 to S-672; M-1 to T-671; M-1 to S-670; M-1 to D-669; M-1 to P-668; M-1 to S-667; M-1 to C-666; M-1 to P-665; M-1 to T-664; M-1 to G-663; M-1 to D-662; M-1 to V-661; M-1 to V-660; M-1 to K-659; M-1 to P-658; M-1 to Q-657; M-1 to L-656; M-1 to V-655; M-1 to F-654; M-1 to F-653; M-1 to Y-652; M-1 to G-651; M-1 to I-650; M-1 to G-649; M-1 to K-648; M-1 to A-647; M-1 to Q-646; M-1 to C-645; M-1 to I-644; M-1 to L-643; M-1 to K-642; M-1 to V-641; M-1 to R-640; M-1 to D-639; M-1 to K-638; M-1 to P-637; M-1 to S-636; M-1 to V-635; M-1 to G-634; M-1 to A-633; M-1 to Y-632; M-1 to K-631; M-1 to P-630; M-1 to I-629; M-1 to W-628; M-1 to E-627; M-1 to V-626; M-1 to A-625; M-1 to P-624; M-1 to G-623; M-1 to S-622; M-1 to G-621; M-1 to F-620; M-1 to S-619; M-1 to A-618; M-1 to K-617; M-1 to S-616; M-1 to F-615; M-1 to E-614; M-1 to N-613; M-1 to H-612; M-1 to A-611; M-1 to E-610; M-1 to C-609; M-1 to Q-608; M-1 to E-607; M-1 to E-606; M-1 to R-605; M-1 to F-604; M-1 to T-603; M-1 to K-602; M-1 to G-601; M-1 to N-600; M-1 to N-599; M-1 to D-598; M-1 to P-597; M-1 to C-596; M-1 to D-595; M-1 to E-594; M-1 to L-593; M-1 to N-592; M-1 to C-591; M-1 to S-590; M-1 to R-589; M-1 to Y-588; M-1 to R-587; M-1 to V-586; M-1 to R-585; M-1 to K-584; M-1 to G-583; M-1 to E-582; M-1 to C-581; M-1 to Y-580; M-1 to K-579; M-1 to G-578; M-1 to G-577; M-1 to N-576; M-1 to K-575; M-1 to P-574; M-1 to V-573; M-1 to P-572; M-1 to N-571; M-1 to D-570; M-1 to C-569; M-1 to E-568; M-1 to R-567; M-1 to M-566; M-1 to T-565; M-1 to Y-564; M-1 to Q-563; M-1 to V-562; M-1 to G-561; M-1 to G-560; M-1 to G-559; M-1 to C-558; M-1 to T-557; M-1 to R-556; M-1 to S-555; M-1 to C-554; M-1 to D-553; M-1 to G-552; M-1 to W-551; M-1 to P-550; M-1 to G-549; M-1 to W-548; M-1 to M-547; M-1 to G-546; M-1 to W-545; M-1 to S-544; M-1 to G-543; M-1 to H-542; M-1 to F-541; M-1 to P-540; M-1 to T-539; M-1 to D-538; M-1 to F-537; M-1 to H-536; M-1 to K-535; M-1 to R-534; M-1 to D-533; M-1 to T-532; M-1 to K-531; M-1 to N-530; M-1 to V-529; M-1 to C-528; M-1 to K-527; M-1 to G-526; M-1 to N-525; M-1 to I-524; M-1 to C-523; M-1 to W-522; M-1 to K-521; M-1 to G-520; M-1 to E-519; M-1 to G-518; M-1 to C-517; M-1 to S-516; M-1 to T-515; M-1 to G-514; M-1 to D-513; M-1 to A-512; M-1 to W-511; M-1 to P-510; M-1 to F-509; M-1 to H-508; M-1 to K-507; M-1 to T-506; M-1 to Q-505; M-1 to C-504; M-1 to V-503; M-1 to L-502; M-1 to V-501; M-1 to G-500; M-1 to G-499; M-1 to S-498; M-1 to T-497; M-1 to G-496; M-1 to T-495; M-1 to C-494; M-1 to W-493; M-1 to L-492; M-1 to T-491; M-1 to S-490; M-1 to C-489; M-1 to T-488; M-1 to S-487; M-1 to A-486; M-1 to A-485; M-1 to D-484; M-1 to P-483; M-1 to C-482; M-1 to H-481; M-1 to K-480; M-1 to S-479; M-1 to D-478; M-1 to E-477; M-1 to G-476; M-1 to F-475; M-1 to T-474; M-1 to F-473; M-1 to Q-472; M-1 to C-471; M-1 to Q-470; M-1 to R-469; M-1 to N-468; M-1 to A-467; M-1 to D-466; M-1 to Y-465; M-1 to S-464; M-1 to T-463; M-1 to G-462; M-1 to P-461; M-1 to L-460; M-1 to D-459; M-1 to G-458; M-1 to P-457; M-1 to L-456; M-1 to Q-455; M-1 to I-454; M-1 to P-453; M-1 to N-452; M-1 to Q-451; M-1 to P-450; M-1 to K-449; M-1 to D-448; M-1 to M-447; M-1 to L-446; M-1 to C-445; M-1 to E-444; M-1 to G-443; M-1 to H-442; M-1 to G-441; M-1 to N-440; M-1 to D-439; M-1 to L-438; M-1 to F-437; M-1 to S-436; M-1 to T-435; M-1 to I-434; M-1 to M-433; M-1 to Y-432; M-1 to A-431; M-1 to S-430; M-1 to C-429; M-1 to P-428; M-1 to S-427; M-1 to W-426; M-1 to P-425; M-1 to Q-424; M-1 to S-423; M-1 to H-422; M-1 to D-421; M-1 to L-420; M-1 to N-419; M-1 to S-418; M-1 to L-417; M-1 to M-416; M-1 to S-415; M-1 to A-414; M-1 to M-413; M-1 to M-412; M-1 to H-411; M-1 to S-410; M-1 to D-409; M-1 to Q-408; M-1 to N-407; M-1 to V-406; M-1 to G-405; M-1 to N-404; M-1 to L-403; M-1 to S-402; M-1 to A-401; M-1 to C-400; M-1 to Q-399; M-1 to K-398; M-1 to A-397; M-1 to D-396; M-1 to D-395; M-1 to H-394; M-1 to P-393; M-1 to M-392; M-1 to N-391; M-1 to F-390; M-1 to V-389; M-1 to H-388; M-1 to G-387; M-1 to L-386; M-1 to E-385; M-1 to H-384; M-1 to A-383; M-1 to T-382; M-1 to T-381; M-1 to F-380; M-1 to A-379; M-1 to A-378; M-1 to Q-377; M-1 to L-376; M-1 to G-375; M-1 to D-374; M-1 to D-373; M-1 to E-372; M-1 to I-371; M-1 to V-370; M-1 to S-369; M-1 to C-368; M-1 to S-367; M-1 to R-366; M-1 to S-365; M-1 to P-364; M-1 to D-363; M-1 to C-362; M-1 to V-361; M-1 to T-360; M-1 to G-359; M-1 to V-358; M-1 to D-357; M-1 to A-356; M-1 to M-355; M-1 to G-354; M-1 to L-353; M-1 to T-352; M-1 to D-351; M-1 to C-350; M-1 to T-349; M-1 to Q-348; M-1 to S-347; M-1 to G-346; M-1 to C-345; M-1 to L-344; M-1 to D-343; M-1 to Q-342; M-1 to R-341; M-1 to T-340; M-1 to F-339; M-1 to L-338; M-1 to I-337; M-1 to A-336; M-1 to T-335; M-1 to D-334; M-1 to Y-333; M-1 to H-332; M-1 to E-331; M-1 to A-330; M-1 to D-329; M-1 to R-328; M-1 to D-327; M-1 to S-326; M-1 to P-325; M-1 to P-324; M-1 to N-323; M-1 to H-322; M-1 to Q-321; M-1 to K-320; M-1 to Q-319; M-1 to W-318; M-1 to N-317; M-1 to C-316; M-1 to F-315; M-1 to N-314; M-1 to R-313; M-1 to L-312; M-1 to T-311; M-1 to L-310; M-1 to A-309; M-1 to A-308; M-1 to N-307; M-1 to S-306; M-1 to T-305; M-1 to V-304; M-1 to E-303; M-1 to P-302; M-1 to G-301; M-1 to K-300; M-1 to Q-299; M-1 to E-298; M-1 to D-297; M-1 to H-296; M-1 to I-295; M-1 to V-294; M-1 to L-293; M-1 to I-292; M-1 to K-291; M-1 to V-290; M-1 to V-289; M-1 to V-288; M-1 to L-287; M-1 to S-286; M-1 to V-285; M-1 to S-284; M-1 to N-283; M-1 to R-282; M-1 to I-281; M-1 to S-280; M-1 to P-279; M-1 to H-278; M-1 to K-277; M-1 to Y-276; M-1 to L-275; M-1 to R-274; M-1 to A-273; M-1 to A-272; M-1 to V-271; M-1 to S-270; M-1 to F-269; M-1 to L-268; M-1 to T-267; M-1 to L-266; M-1 to L-265; M-1 to Y-264; M-1 to H-263; M-1 to K-262; M-1 to L-261; M-1 to G-260; M-1 to S-259; M-1 to G-258; M-1 to H-257; M-1 to F-256; M-1 to E-255; M-1 to A-254; M-1 to M-253; M-1 to S-252; M-1 to Q-251; M-1 to D-250; M-1 to A-249; M-1 to V-248; M-1 to L-247; M-1 to M-246; M-1 to T-245; M-1 to E-244; M-1 to V-243; M-1 to Y-242; M-1 to R-241; M-1 to I-240; M-1 to S-239; M-1 to S-238; M-1 to V-237; M-1 to F-236; M-1 to R-235; M-1 to K-234; M-1 to K-233; M-1 to R-232; M-1 to I-231; M-1 to S-230; M-1 to G-229; M-1 to T-228; M-1 to G-227; M-1 to T-226; M-1 to P-225; M-1 to Q-224; M-1 to G-223; M-1 to V-222; M-1 to G-221; M-1 to Q-220; M-1 to L-219; M-1 to A-218; M-1 to P-217; M-1 to D-216; M-1 to Q-215; M-1 to P-214; M-1 to S-213; M-1 to W-212; M-1 to Q-211; M-1 to P-210; M-1 to G-209; M-1 to E-208; M-1 to D-207; M-1 to E-206; M-1 to G-205; M-1 to E-204; M-1 to T-203; M-1 to G-202; M-1 to E-201; M-1 to D-200; M-1 to E-199; M-1 to D-198; M-1 to E-197; M-1 to T-196; M-1 to E-195; M-1 to A-194; M-1 to K-193; M-1 to G-192; M-1 to T-191; M-1 to P-109; M-1 to R-189; M-1 to P-188; M-1 to E-187; M-1 to D-186; M-1 to D-185; M-1 to V-184; M-1 to V-183; M-1 to G-182; M-1 to C-181; M-1 to T-180; M-1 to G-179; M-1 to G-178; M-1 to V-177; M-1 to D-176; M-1 to G-175; M-1 to Q-174; M-1 to R-173; M-1 to N-172; M-1 to R-171; M-1 to R-170; M-1 to L-169; M-1 to L-168; M-1 to H167; M-1 to F-166; M-1 to Q-165; M-1 to L-164; M-1 to P-163; M-1 to A-162; M-1 to P-161; M-1 to P-160; M-1 to K-159; M-1 to E-158; M-1 to G-157; M-1 to P-156; M-1 to A-155; M-1 to A-154; M-1 to T-153; M-1 to A-152; M-1 to L-151; M-1 to R-150; M-1 to E-149; M-1 to S-148; M-1 to A-147; M-1 to A-146; M-1 to P-145; M-1 to L-144; M-1 to P-143; M-1 to Q-142; M-1 to I-141; M-1 to F-140; M-1 to Y-139; M-1 to A-138; M-1 to E-137; M-1 to G-136; M-1 to L-135; M-1 to L-134; M-1 to Y-133; M-1 to F-132; M-1 to A-131; M-1 to G-130; M-1 to R-129; M-1 to V-128; M-1 to G-127; M-1 to E-126; M-1 to C-125; M-1 to L-124; M-1 to S-123; M-1 to L-122; M-1 to A-121; M-1 to A-120; M-1 to A-119; M-1 to S-118; 118; M-1 to S-117; M-1 to P-116; M-1 to D-115; M-1 to G-114; M-1 to N-113; M-1 to V-112; M-1 to T-111; M-1 to G-110; M-1 to S-109; M-1 to Y-108; M-1 to F-107; M-1 to C-106; M-1 to H-105; M-1 to A-104; M-1 to L-103; M-1 to D-102; M-1 to T-101; M-1 to E-100; M-1 to P-99; M-1 to L-98; M-1 to P-97; M-1 to T-96; M-1 to E-95; M-1 to S-94; M-1 to G-93; M-1 to S-92; M-1 to K-91; M-1 to R-90; M-1 to G-89; M-1 to V-88; M-1 to N-87; M-1 to Q-86; M-1 to L-85; M-1 to T-84; M-1 to F-83; M-1 to G-82; M-1 to P-81; M-1 to A-80; M-1 to L-79; M-1 to F-78; M-1 to S-77; M-1 to S-76; M-1 to D-75; M-1 to P-74; M-1 to R-73; M-1 to L-72; M-1 to E-71; M-1 to L-70; M-1 to D-69; M-1 to L-68; M-1 to Q-67; M-1 to Q-66; M-1 to D-65; M-1 to F-64; M-1 to A-63; M-1 to H-62; M-1 to L-61; M-1 to R-60; M-1 to L-59; M-1 to R-58; M-1 to T-57; M-1 to T-56; M-1 to G-55; M-1 to H-54; M-1 to G-53; M-1 to P-52; M-1 to A-51; M-1 to R-50; M-1 to E-49; M-1 to L-48; M-1 to E-47; M-1 to P-46; M-1 to V-45; M-1 to V-44; M-1 to L-43; M-1 to E-42; M-1 to E-41; M-1 to D-40; M-1 to E-39; M-1 to E-38; M-1 to S-37; M-1 to P-36; M-1 to R-35; M-1 to G-34; M-1 to L-33; M-1 to A-32; M-1 to D-31; M-1 to S-30; M-1 to V-29; M-1 to A-28; M-1 to L-27; M-1 to L-26; M-1 to A-25; M-1 to A-24; M-1 to A-23; M-1 to L-22; M-1 to L-21; M-1 to L-20; M-1 to L-19; M-1 to T-18; M-1 to P-17; M-1 to V-16; M-1 to P-15; M-1 to G-14; M-1 to F-13; M-1 to S-12; M-1 to R-11; M-1 to S-10; M-1 to G-9; M-1 to P-8; M-1 to A-7; of SEQ ID NO:2. For example, any of the above listed N- or C-terminal deletions can be combined to produce a N- and C-terminal deleted METH1 polypeptide. Particularly preferred fragment of SEQ ID NO2 are H542-Q894 and K801-S950.

Deletion mutants of METH1 may also be made which comprise all or part of the additional sequence described in SEQ ID NO:126. For example, exemplary deletion mutants include: Q-2 to S-967; R-3 to S-967; A-4 to S-967; V-5 to S-967; P-6 to S-967; E-7 to S-967; G-8 to S-967; F-9 to S-967; G-10 to S-967; R-11 to S-976; R-12 to S-967; K-13 to S-967; L-14 to S-967; G-15 to S-967; S-16 to S-967; D-17 to S-967; and M-18 to S-967.

Moreover, N-terminal deletions of the METH2 polypeptide can be described by the general formula $m_2$-890, where $m_2$ is an integer from 2 to 889, where m corresponds to the position of the amino acid residue identified in SEQ ID NO:4. Preferably, N-terminal deletions of the METH2 polypeptide of the invention shown as SEQ ID NO:4 include polypeptides comprising the amino acid sequence of residues: F-2 to L-890; P-3 to L-890; A-4 to L-890; P-5 to L-890; A-6 to L-890; A-7 to L-890; P-8 to L-890; R-9 to L-890; W-10 to L-890; L-11 to L-890; P-12 to L-890; F-13 to L-890; L-14 to L-890; L-15 to L-890; L-16 to L-890; L-17 to L-890; L-18 to L-890; L-19 to L-890; L-20 to L-890; L-21 to L-890; L-22 to L-890; P-23 to L-890; L-24 to L-890; A-25 to L-890; R-26 to L-890; G-27 to L-890; A-28 to L-890; P-29 to L-890; A-30 to L-890; R-31 to L-890; P-32 to L-890; A-33 to L-890; A-34 to L-890; G-35 to L-890; G-36 to L-890; Q-37 to L-890; A-38 to L-890; S-39 to L-890; E-40 to L-890; L-41 to L-890; V-42 to L-890; V-43 to L-890; P-44 to L-890; T-45 to L-890; R-46 to L-890; L-47 to L-890; P-48 to L-890; G-49 to L-890; S-50 to L-890; A-51 to L-890; G-52 to L-890; E-53 to L-890; L-54 to L-890; A-55 to L-890; L-56 to L-890; H-57 to L-890; L-58 to L-890; S-59 to L-890; A-60 to L-890; F-61 to L-890; G-62 to L-890; K-63 to L-890; G-64 to L-890; F-65 to L-890; V-66 to L-890; L-67 to L-890; R-68 to L-890; L-69 to L-890; A-70 to L-890; P-71 to L-890; D-72 to L-890; D-73 to L-890; S-74 to L-890; F-75 to L-890; L-76 to L-890; A-77 to L-890; P-78 to L-890; E-79 to L-890; F-80 to L-890; K-81 to L-890; I-82 to L-890; E-83 to L-890; R-84 to L-890; L-85 to L-890; G-86 to L-890; G-87 to L-890; S-88 to L-890; G-89 to L-890; R-90 to L-890; A-91 to L-890; T-92 to L-890; G-93 to L-890; G-94 to L-890; E-95 to L-890; R-96 to L-890; G-97 to L-890; L-98 to L-890; R-99 to L-890; G-100 to L-890; C-101 to L-890; F-102 to L-890; F-103 to L-890; S-104 to L-890; G-105 to L-890; T-106 to L-890; V-107 to L-890; N-108 to L-890; G-109 to L-890; E-110 to L-890; P-111 to L-890; E-112 to L-890; S-113 to L-890; L-114 to L-890; A-115 to L-890; A-116 to L-890; V-117 to L-890; S-118 to L-890; L-119 to L-890; C-120 to L-890; R-121 to L-890; G-122 to L-890; L-123 to L-890; S-124 to L-890; G-125 to L-890; S-126 to L-890; F-127 to L-890; L-128 to L-890; L-129 to L-890; D-130 to L-890; G-131 to L-890; E-132 to L-890; E-133 to L-890; F-134 to L-890; T-135 to L-890; I-136 to L-890; Q-137 to L-890; P-138 to L-890; Q-139 to L-890; G-140 to L-890; A-141 to L-890; G-142 to L-890; G-143 to L-890; S-144 to L-890; L-145 to L-890; A-146 to L-890; Q-147 to L-890; P-148 to L-890; H-149 to L-890; R-150 to L-890; L-151 to L-890; Q-152 to L-890; R-153 to L-890; W-154 to L-890; G-155 to L-890; P-156 to L-890; A-157 to L-890; G-158 to L-890; A-159 to L-890; R-160 to L-890; P-161 to L-890; L-162 to L-890; P-163 to L-890; R-164 to L-890; G-165 to L-890; P-166 to L-890; E-167 to L-890; W-168 to L-890; E-169 to L-890; V-170 to L-890; E-171 to L-890; T-172 to L-890; G-173 to L-890; E-174 to L-890; G-175 to L-890; Q-176 to L-890; R-177 to L-890; Q-178 to L-890; E-179 to L-890; R-180 to L-890; G-181 to L-890; D-182 to L-890; H-183 to L-890; Q-184 to L-890; E-185 to L-890; D-186 to L-890; S-187 to L-890; E-188 to L-890; E-189 to L-890; E-190 to L-890; S-191 to L-890; Q-192 to L-890; E-193 to L-890; E-194 to L-890; E-195 to L-890; A-196 to L-890; E-197 to L-890; G-198 to L-890; A-199 to L-890; S-200 to L-890; E-201 to L-890; P-202 to L-890; P-203 to L-890; P-204 to L-890; P-205 to L-890; L-206 to L-890; G-207 to L-890; A-208 to L-890; T-209 to L-890; S-210 to L-890; R-211 to L-890; T-212 to L-890; K-213 to L-890; R-214 to L-890; F-215 to L-890; V-216 to L-890; S-217 to L-890; E-218 to L-890; A-219 to L-890; R-220 to L-890; F-221 to L-890; V-222 to L-890; E-223 to L-890; T-224 to L-890; L-225 to L-890; L-226 to L-890; V-227 to L-890; A-228 to L-890; D-229 to L-890; A-230 to L-890; S-231 to L-890; M-232 to L-890; A-233 to L-890; A-234 to L-890; F-235 to L-890; Y-236 to L-890; G-237 to L-890; A-238 to L-890; D-239 to L-890; L-240 to L-890; Q-241 to L-890; N-242 to L-890; H-243 to L-890; I-244 to L-890; L-245 to L-890; T-246 to L-890; L-247 to L-890; M-248 to L-890; S-249 to L-890; V-250 to L-890; A-251 to L-890; A-252 to L-890; R-253 to L-890; I-254 to L-890; Y-255 to L-890; K-256 to L-890; H-257 to L-890; P-258 to L-890; S-259 to L-890; I-260 to L-890; K-261 to L-890; N-262 to L-890; S-263 to L-890; I-264 to L-890; N-265 to L-890; L-266 to L-890; M-267 to L-890; V-268 to L-890; V-269 to L-890; K-270 to L-890; V-271 to L-890; L-272 to L-890; I-273 to L-890; V-274 to L-890; E-275 to L-890; D-276 to L-890; E-277 to L-890; K-278 to L-890; W-279 to L-890; G-280 to L-890; P-281 to L-890; E-282 to L-890; V-283 to L-890; S-284 to L-890; D-285 to L-890; N-286 to L-890; G-287 to L-890; G-288 to L-890; L-289 to L-890; T-290 to L-890; L-291 to L-890; R-292 to L-890; N-293 to L-890; F-294 to L-890; C-295 to L-890; N-296 to L-890; W-297 to L-890; Q-298 to L-890; R-299 to L-890; R-300 to L-890; F-301 to L-890; N-302 to L-890; Q-303 to L-890; P-304 to L-890; S-305 to L-890; D-306 to L-890; R-307 to L-890; H-308 to L-890; P-309 to L-890; E-310 to L-890; H-311 to L-890; Y-312 to L-890; D-313 to L-890; T-314 to L-890; A-315 to L-890; I-316 to L-890; L-317 to L-890; L-318 to L-890; T-319 to L-890; R-320 to L-890; Q-321 to L-890; N-322 to L-890; F-323 to L-890; C-324 to L-890; G-325 to L-890; Q-326 to L-890; E-327 to L-890; G-328 to L-890; L-329 to L-890; C-330 to L-890; D-331 to L-890; T-332 to L-333 to L-890; G-334 to L-890; V-335 to L-890; A-336 to L-890; D-337 to L-890; I-338 to L-890; G-339 to L-890; T-340 to L-890; I-341 to L-890; C-342 to L-890; D-343 to L-890; P-344 to L-890; N-345 to L-890; K-346 to L-890; S-347 to L-890; C-348 to L-890; S-349 to L-890; V-350 to L-890; I-351 to L-890; E-352 to L-890; D-353 to L-890; E-354 to L-890; G-355 to L-890; L-356 to L-890; Q-357 to L-890; A-358 to L-890; A-359 to L-890; H-360 to L-890; T-361 to L-890; L-362 to L-890; A-363 to L-890; H-364 to L-890; E-365 to L-890; L-366 to L-890; G-367 to L-890; H-368 to L-890; V-369 to L-890; L-370 to L-890; S-371 to L-890; M-372 to L-890; P-373 to L-890; H-374 to L-890; D-375 to L-890; D-376 to L-890; S-377 to L-890; K-378 to L-890; P-379 to L-890; C-380 to L-890; T-381 to L-890; R-382 to L-890; L-383 to L-890; F-384 to L-890; G-385 to L-890; P-386 to L-890; M-387 to L-890; G-388 to L-890; K-389 to L-890; H-390 to L-890; H-391 to L-890; V-392 to L-890; M-393 to L-890; A-394 to L-890; P-395 to L-890; L-396 to L-890; F-397 to L-890; V-398 to L-890; H-399 to L-890; L-400 to L-890; N-401 to L-890; Q-402 to L-890; T-403 to L-890; L-404 to L-890; P-405 to L-890; W-406 to L-890; S-407 to L-890; P-408 to L-890; C-409 to L-890; S-410 to L-890; A-411 to L-890; M-412 to L-890; Y-413 to L-890; L-414 to L-890; T-415 to L-890; E-416 to L-890; L-417 to L-890; L-418 to L-890; D-419 to L-890; G-420 to L-890; G-421 to L-890; H-422 to L-890; G-423 to L-890; D-424 to L-890; C-425 to L-890; L-426 to L-890; L-427 to L-890; D-428 to L-890; A-429 to L-890; P-430 to L-890; G-431 to L-890; A-432 to L-890; A-433 to L-890; L-434 to L-890; P-435 to L-890; L-436 to L-890; P-437 to L-890; T-438 to L-890; G-439 to L-890; L-440 to L-890; P-441 to L-890; G-442 to L-890; R-443 to L-890; M-444 to L-890; A-445 to L-890; L-446 to L-890; Y-447 to L-890; Q-448 to L-890; L-449 to L-890; D-450 to L-890; Q-451 to L-890; Q-452 to L-890; C-453 to L-890; R-454 to L-890; Q-455 to L-890; I-456 to L-890; F-457 to L-890; G-458 to L-890; P-459 to L-890; D-460 to L-890; F-461 to L-890; R-462 to L-890; H-463 to L-890; C-464 to L-890; P-465 to L-890; N-466 to L-890; T-467 to L-890; S-468 to L-890; A-469 to L-890; Q-470 to L-890; D-471 to L-890; V-472 to L-890; C-473 to L-890; A-474 to L-890; Q-475 to L-890; L-476 to L-890; W-477 to L-890; C-478 to L-890; H-479 to L-890; T-480 to L-890; D-481 to L-890; G-482 to L-890; A-483 to L-890; E-484 to L-890; P-485 to L-890; L-486 to L-890; C-487 to L-890; H-488 to L-890; T-489 to L-890; K-490 to L-890; N-491 to L-890; G-492 to L-890; S-493 to L-890; L-494 to L-890; P-495 to L-890; W-496 to L-890; A-497 to L-890; D-498 to L-890; G-499 to L-890; T-500 to L-890; P-501 to L-890; C-502 to L-890; G-503 to L-890; P-504 to L-890; G-505 to L-890; H-506 to L-890; L-507 to L-890; C-508 to L-890; S-509 to L-890; E-510 to L-890; G-511 to L-890; S-512 to L-890; C-513 to L-890; L-514 to L-890; P-515 to L-890; E-516 to L-890; E-517 to L-890; E-518 to L-890; V-519 to L-890; E-520 to L-890; R-521 to L-890; P-522 to L-890; K-523 to L-890; P-524 to L-890; V-525 to L-890; V-526 to L-890; D-527 to L-890; G-528 to L-890; G-529 to L-890; W-530 to L-890; A-531 to L-890; P-532 to L-890; W-533 to L-890; G-534 to L-890; P-535 to L-890; W-536 to L-890; G-537 to L-890; E-538 to L-890; C-539 to L-890; S-540 to L-890; R-541 to L-890; T-542 to L-890; C-543 to L-890; G-544 to L-890; G-545 to L-890; G-546 to L-890; V-547 to L-890; Q-548 to L-890; F-549 to L-890; S-550 to L-890; H-551 to L-890; R-552 to L-890; E-553 to L-890; C-554 to L-890; K-555 to L-890; D-556 to L-890; P-557 to L-890; E-558 to L-890; P-559 to L-890; Q-560 to L-890; N-561 to L-890; G-562 to L-890; G-563 to L-890; R-564 to L-890; Y-565 to L-890; C-566 to L-890; L-567 to L-890; G-568 to L-890; R-569 to L-890; R-570 to L-890; A-571 to L-890; K-572 to L-890; Y-573 to L-890; Q-574 to L-890; S-575 to L-890; C-576 to L-890; H-577 to L-890; T-578 to L-890; E-579 to L-890; E-580 to L-890; C-581 to L-890; P-582 to L-890; P-583 to L-890; D-584 to L-890; G-585 to L-890; K-586 to L-890; S-587 to L-890; F-588 to L-890; R-589 to L-890; E-590 to L-890; Q-591 to L-890; Q-592 to L-890; C-593 to L-890; E-594 to L-890; K-595 to L-890; Y-596 to L-890; N-597 to L-890; A-598 to L-890; Y-599 to L-890; N-600 to L-890; Y-601 to L-890; T-602 to L-890; D-603 to L-890; M-604 to L-890; D-605 to L-890; G-606 to L-890; N-607 to L-890; L-608 to L-890; L-609 to L-890; Q-610 to L-890; W-611 to L-890; V-612 to L-890; P-613 to L-890; K-614 to L-890; Y-615 to L-890; A-616 to L-890; G-617 to L-890; V-618 to L-890; S-619 to L-890; P-620 to L-890; R-621 to L-890; D-622 to L-890; R-623 to L-890; C-624 to L-890; K-625 to L-890; L-626 to L-890; F-627 to L-890; C-628 to L-890; R-629 to L-890; A-630 to L-890; R-631 to L-890; G-632 to L-890; R-633 to L-890; S-634 to L-890; E-635 to L-890; F-636 to L-890; K-637 to L-890; V-638 to L-890; F-639 to L-890; E-640 to L-890; A-641 to L-890; K-642 to L-890; V-643 to L-890; I-644 to L-890; D-645 to L-890; G-646 to L-890; T-647 to L-890; L-648 to L-890; C-649 to L-890; G-650 to L-890; P-651 to L-890; E-652 to L-890; T-653 to L-890; L-654 to L-890; A-655 to L-890; I-656 to L-890; C-657 to L-890; V-658 to L-890; R-659 to L-890; G-660 to L-890; Q-661 to L-890; C-662 to L-890; V-663 to L-890; K-664 to L-890; A-665 to L-890; G-666 to L-890; C-667 to L-890; D-668 to L-890; H-669 to L-890; V-670 to L-890; V-671 to L-890; D-672 to L-890; S-673 to L-890; P-674 to L-890; R-675 to L-890; K-676 to L-890; L-677 to L-890; D-678 to L-890; K-679 to L-890; C-680 to L-890; G-681 to L-890; V-682 to L-890; C-683 to L-890; G-684 to L-890; G-685 to L-890; K-686 to L-890; G-687 to L-890; N-688 to L-890; S-689 to L-890; C-690 to L-890; R-691 to L-890; K-692 to L-890; V-693 to L-890; S-694 to L-890; G-695 to L-890; S-696 to L-890; L-697 to L-890; T-698 to L-890; P-699 to L-890; T-700 to L-890; N-701 to L-890; Y-702 to L-890; G-703 to L-890; Y-704 to L-890; N-705 to L-890; D-706 to L-890; I-707 to L-890; V-708 to L-890; T-709 to L-890;

I-710 to L-890; P-711 to L-890; A-712 to L-890; G-713 to L-890; A-714 to L-890; T-715 to L-890; N-716 to L-890; I-717 to L-890; D-718 to L-890; V-719 to L-890; K-720 to L-890; Q-721 to L-890; R-722 to L-890; S-723 to L-890; H-724 to L-890; P-725 to L-890; G-726 to L-890; V-727 to L-890; Q-728 to L-890; N-729 to L-890; D-730 to L-890; G-731 to L-890; N-732 to L-890; Y-733 to L-890; L-734 to L-890; A-735 to L-890; L-736 to L-890; K-737 to L-890; T-738 to L-890; A-739 to L-890; D-740 to L-890; G-741 to L-890; Q-742 to L-890; Y-743 to L-890; L-744 to L-890; L-745 to L-890; N-746 to L-890; G-747 to L-890; N-748 to L-890; L-749 to L-890; A-750 to L-890; I-751 to L-890; S-752 to L-890; A-753 to L-890; I-754 to L-890; E-755 to L-890; Q-756 to L-890; D-757 to L-890; I-758 to L-890; L-759 to L-890; V-760 to L-890; K-761 to L-890; G-762 to L-890; T-763 to L-890; I-764 to L-890; L-765 to L-890; K-766 to L-890; Y-767 to L-890; S-768 to L-890; G-769 to L-890; S-770 to L-890; I-771 to L-890; A-772 to L-890; T-773 to L-890; L-774 to L-890; E-775 to L-890; R-776 to L-890; L-777 to L-890; Q-778 to L-890; S-779 to L-890; F-780 to L-890; R-781 to L-890; P-782 to L-890; L-783 to L-890; P-784 to L-890; E-785 to L-890; P-786 to L-890; L-787 to L-890; T-788 to L-890; V-789 to L-890; Q-790 to L-890; L-791 to L-890; L-792 to L-890; T-793 to L-890; V-794 to L-890; P-795 to L-890; G-796 to L-890; E-797 to L-890; V-798 to L-890; F-799 to L-890; P-800 to L-890; P-801 to L-890; K-802 to L-890; V-803 to L-890; K-804 to L-890; Y-805 to L-890; T-806 to L-890; F-807 to L-890; F-808 to L-890; V-798 to L-890; P-810 to L-890; N-811 to L-890; D-812 to L-890; V-813 to L-890; D-814 to L-890; F-815 to L-890; S-816 to L-890; M-817 to L-890; Q-818 to L-890; S-819 to L-890; S-820 to L-890; K-821 to L-890; E-822 to L-890; R-823 to L-890; A-824 to L-890; T-825 to L-890; T-826 to L-890; N-827 to L-890; I-828 to L-890; I-829 to L-890; Q-830 to L-890; P-831 to L-890; L-832 to L-890; L-833 to L-890; H-834 to L-890; A-835 to L-890; Q-836 to L-890; W-837 to L-890; V-838 to L-890; L-839 to L-890; G-840 to L-890; D-841 to L-890; W-842 to L-890; S-843 to L-890; E-844 to L-890; C-845 to L-890; S-846 to L-890; S-847 to L-890; T-848 to L-890; C-849 to L-890; G-850 to L-890; A-851 to L-890; G-852 to L-890; W-853 to L-890; Q-854 to L-890; R-855 to L-890; R-856 to L-890; T-857 to L-890; V-858 to L-890; E-859 to L-890; C-860 to L-890; R-861 to L-890; D-862 to L-890; P-863 to L-890; S-864 to L-890; G-865 to L-890; Q-866 to L-890; A-867 to L-890; S-868 to L-890; A-869 to L-890; T-870 to L-890; C-871 to L-890; N-872 to L-890; K-873 to L-890; A-874 to L-890; L-875 to L-890; K-876 to L-890; P-877 to L-890; E-878 to L-890; D-879 to L-890; A-880 to L-890; K-881 to L-890; P-882 to L-890; C-883 to L-890; E-884 to L-890; S-885 to L-890; of SEQ ID NO:4.

Moreover, C-terminal deletions of the METH2 polypeptide can also be described by the general formula 1-$n_2$, where $n_2$ is an integer from 2 to 890 where n corresponds to the position of amino acid residue identified in SEQ ID NO:4. Preferably, C-terminal deletions of the METH2 polypeptide of the invention shown as SEQ ID NO:4 include polypeptides comprising the amino acid sequence of residues: M-1 to P-889; M-1 to C-888; M-1 to L-887; M-1 to Q-886; M-1 to S-885; M-1 to E-884; M-1 to C-883; M-1 to P-882; M-1 to K-881; M-1 to A-880; M-1 to D-879; M-1 to E-878; M-1 to P-877; M-1 to K-876; M-1 to K-875; M-1 to A-874; M-1 to K-873; M-1 to N-872; M-1 to C-871; M-1 to T-870; M-1 to A-869; M-1 to S-868; M-1 to A-867; M-1 to Q-866; M-1 to G-865; M-1 to S-864; M-1 to 863; M-1 to D-862; M-1 to R-861; M-1 to C-860; M-1 to E-859; M-1 to V-858; M-1 to T-857; M-1 to R-856; M-1 to R-855; M-1 to Q-854; M-1 to W-853; M-1 to G-852; M-1 to A-851; M-1 to G-850; M-1 to C-849; M-1 to T-848; M-1 to S-847; M-1 to S-846; M-1 to C-845; M-1 to E-844; M-1 to S-843; M-1 to W-842; M-1 to D-841; M-1 to G-840; M-1 to L-839; M-1 to V-838; to M-1 to W-837; M-1 to Q-836; M-1 to A-835; M-1 to H-834; M-1 to L-833; M-1 to L-832; M-1 to P-831; M-1 to Q-830; M-1 to I-829; M-1 to I-828; M-1 to N-827; M-1 to T-826; M-1 to T-825; M-1 to A-824; M-1 to R-823; M-1 to E-822; M-1 to K-821; M-1 to S-820; M-1 to S-819; M-1 to Q-818; M-1 to M-817; M-1 to S-816; M-1 to F-815; M-1 to D-814; M-1 to V-813; M-1 to D-812; M-1 to N-811; M-1 to P-810; M-1 to V-809; M-1 to F-808; M-1 to F-807; M-1 to T-806; M-1 to Y-805; to M-1 to K-804; M-1 to V-803; M-1 to K-802; M-1 to P-801; M-1 to P-800; M-1 to F-799; M-1 to V-798; M-1 to E-797; M-1 to G-796; M-1 to P-795; M-1 to V-794; M-1 to T-793; M-1 to L-792; M-1 to L-791; M-1 to Q-790; M-1 to V-789; M-1 to T-788; M-1 to L-787; M-1 to P-786; M-1 to E-785; M-1 to P-784; M-1 to L-783; M-1 to P-782; M-1 to R-781; M-1 to F-780; M-1 to S-779; M-1 to Q-778; M-1 to L-777; M-1 to R-776; M-1 to E-775; M-1 to L-774; M-1 to T-773; M-1 to A-772; M-1 to I-771; M-1 to S-770; M-1 to G-769; M-1 to S-768; M-1 to Y-767; M-1 to K-766; M-1 to L-765; M-1 to I-764; M-1 to T-763; M-1 to G-762; M-1 to K-761; M-1 to V-760; M-1 to L-759; M-1 to I-758; M-1 to D-757; M-1 to Q-756; M-1 to E-755; I-754; M-1 to A-753; M-1 to S-752; M-1 to I-751; M-1 to A-750; M-1 to L-749; M-1 to N-748; M-1 to G-747; M-1 to N-746; M-1 to L-745; M-1 to L-744; M-1 to Y-743; M-1 to Q-742; M-1 to G-741; M-1 to D-740; M-1 to A-739; M-1 to T-738; M-1 to K-737; M-1 to L-736; M-1 to A-735; M-1 to L-734; M-1 to Y-733; M-1 to N-732; M-1 to G-731; M-1 to D-730; M-1 to N-729; M-1 to Q-728; M-1 to V-727; M-1 to G-726; M-1 to P-725; M-1 to H-724; M-1 to S-723; M-1 to R-722; M-1 to Q-721; M-1 to K-720; M-1 to V-719; M-1 to D-718; M-1 to I-717; M-1 to N-716; M-1 to T-715; M-1 to A-714; M-1 to G-713; M-1 to A-712; M-1 to P-711; M-1 to I-710; M-1 to T-709; M-1 to V-708; M-1 to I-707; M-1 to D-706; M-1 to N-705; M-1 to Y-704; M-1 to G-703; M-1 to Y-702; M-1 to N-701; M-1 to T-700; M-1 to P-699; M-1 to T-698; M-1 to L-697; M-1 to S-696; M-1 to G-695; M-1 to S-694; M-1 to V-693; M-1 to K-692; M-1 to R-691; M-1 to C-690; M-1 to S-689; M-1 to N-688; M-1 to G-687; M-1 to K-686; M-1 to G-685; M-1 to G-684; M-1 to C-683; M-1 to V-682; M-1 to G-681; M-1 to C-680; M-1 to K-679; M-1 to D-678; M-1 to L-677; M-1 to K-676; M-1 to R-675; M-1 to P-674; M-1 to S-673; M-1 to D-672; M-1 to V-671; M-1 to V-676; M-1 to H-669; M-1 to D-668; M-1 to C-667; M-1 to G-666; M-1 to A-665; M-1 to K-664; M-1 to V-663; M-1 to C-662; M-1 to Q-661; M-1 to G-660; M-1 to R-659; M-1 to V-658; M-1 to C-657; M-1 to I-656; M-1 to A-655; M-1 to L-654; M-1 to T-653; M-1 to E-652; M-1 to P-651; M-1 to G-650; M-1 to C-649; M-1 to L-648; M-1 to T-647; M-1 to G-646; M-1 to D-645; M-1 to I-644; M-1 to V-643; M-1 to K-642; M-1 to A-641; M-1 to E-640; M-1 to F-639; M-1 to V-638; M-1 to K-637; M-1 to F-636; M-1 to E-635; M-1 to S-634; M-1 to R-633; M-1 to G-632; M-1 to R-631; M-1 to A-630; M-1 to R-629; M-1 to C-628; M-1 to F-627; M-1 to L-626; M-1 to K-625; M-1 to C-624; M-1 to R-623; M-1 to D-622; M-1 to R-621; M-1 to P-620; M-1 to S-619; M-1 to V-618; M-1 to G-617; M-1 to A-616; M-1 to Y-615; M-1 to K-614; M-1 to P-613; M-1 to V-612; M-1 to W-611; M-1 to Q-610; M-1 to L-609; M-1 to L-608; M-1 to N-607; M-1 to G-606; M-1 to D-605; M-1 to M-604; M-1 to D-603; M-1 to T-602; M-1 to Y-601; M-1 to N-600; M-1 to Y-599; M-1 to A-598; M-1 to N-597; M-1 to Y-596; M-1 to K-595; M-1 to E-594; M-1 to C-593; M-1 to Q-592; M-1 to Q-591; M-1 to E-590; M-1 to R-589; M-1 to F-588; M-1 to S-587; M-1 to K-586; M-1 to G-585; M-1 to D-584; M-1 to P-583; M-1 to P-582; M-1 to C-581; M-1 to E-580; M-1 to E-579; M-1 to T-578; M-1 to H-577; M-1 to C-576; M-1 to S-575; M-1 to Q-574; M-1 to Y-573; M-1 to K-572; M-1 to A-571; M-1 to R-570; M-1 to R-569; M-1 to G-568; M-1 to L-567; M-1 to C-566; M-1 to Y-565; M-1 to R-564; M-1 to G-563; M-1 to G-562; M-1 to N-561; M-1 to Q-560; M-1 to P-559; M-1 to E-558; M-1 to P-557; M-1 to D-556; M-1 to K-555; M-1 to C-554; M-1 to E-553; M-1 to R-552; M-1 to H-551; M-1 to S-550; M-1 to F-549; M-1 to Q-548; M-1 to V-547; M-1 to G-546; M-1 to G-545; M-1 to G-544; M-1 to C-543; M-1 to T-542; M-1 to R-541; M-1 to S-540; M-1 to C-539; M-1 to E-538; M-1 to G-537; M-1 to W-536; M-1 to P-535; M-1 to G-534; M-1 to W-533; M-1 to P-532; M-1 to A-531; M-1 to W-530; M-1 to G-529; M-1 to G-528; M-1 to D-527; M-1 to V-526; M-1 to V-525; M-1 to P-524; M-1 to K-523; M-1 to P-522; M-1 to R-521; M-1 to E-520; M-1 to V-519; M-1 to E-518; M-1 to E-517; M-1 to E-516; M-1 to P-515; M-1 to L-514; M-1 to C-513; M-1 to S-512; M-1 to G-511; M-1 to E-510; M-1 to S-509; M-1 to C-508; M-1 to L-507; M-1 to H-506; M-1 to G-505; M-1 to P-504; M-1 to G-503; M-1 to C-502; M-1 to P-501; M-1 to T-500; M-1 to G-499; M-1 to D-498; M-1 to A-497; M-1 to W-496; M-1 to P-495; M-1 to L-494; M-1 to S-493; M-1 to G-492; M-1 to N-491; M-1 to K-490; M-1 to T-489; M-1 to H-488; M-1 to C-487; M-1 to L-486; M-1 to P-485; M-1 to E-484; M-1 to A-483; M-1 to G-482; M-1 to D-481; M-1 to T-480; M-1 to H-479; M-1 to C-478; M-1 to W-477; M-1 to L-476; M-1 to Q-475; M-1 to A-474; M-1 to C-473; M-1 to V-472; M-1 to D-471; M-1 to Q-470; M-1 to A-469; M-1 to S-468; M-1 to T-467; M-1 to N-466; M-1 to P-465; M-1 to C-464; M-1 to H-463; M-1 to R-462; M-1 to F-461; M-1 to D-460; M-1 to P-459; M-1 to G-458; M-1 to F-457; M-1 to I-456; M-1 to Q-455; M-1 to R-454; M-1 to C-453; M-1 to Q-452; M-1 to Q-451; M-1 to D-450; M-1 to L-449; M-1 to Q-448; M-1 to Y-447; M-1 to L-446; M-1 to A-445; M-1 to M-444; M-1 to R-443; M-1 to G-442; M-1 to P-441; M-1 to L-440; M-1 to G-439; M-1 to T-438; M-1 to P-437; M-1 to L-436; M-1 to P-435; M-1 to L-434; M-1 to A-433; M-1 to A-432; M-1 to G-431; M-1 to P-430; M-1 to A-429; M-1 to D-428; M-1 to L-427; M-1 to L-426; M-1 to C-425; M-1 to D-424; M-1 to G-423; M-1 to H-422; M-1 to G-421; M-1 to G-420; M-1 to D-419; M-1 to L-418; M-1 to L-417; M-1 to E-416; M-1 to T-415; M-1 to L-414; M-1 to Y-413; M-1 to M-412; M-1 to A-411; M-1 to S-410; M-1 to C-409; M-1 to P-408; M-1 to S-407; M-1 to W-406; M-1 to P-405; M-1 to L-404; M-1 to T-403; M-1 to Q-402; M-1 to N-401; M-1 to L-400; M-1 to H-399; M-1 to V-398; M-1 to F-397; M-1 to L-396; M-1 to P-395; M-1 to A-394; M-1 to M-393; M-1 to V-392; M-1 to H-391; M-1 to H-390; M-1 to K-389; M-1 to G-388; M-1 to M-387; M-1 to P-386; M-1 to G-385; M-1 to F-384; M-1 to L-383; M-1 to R-382; M-1 to T-381; M-1 to C-380; M-1 to P-379; M-1 to K-378; M-1 to S-377; M-1 to D-376; M-1 to D-375; M-1 to H-374; M-1 to P-373; M-1 to M-372; M-1 to S-371; M-1 to L-370; M-1 to V-369; M-1 to H-368; M-1 to G-367; M-1 to L-366; M-1 to E-365; M-1 to H-364; M-1 to A-363; M-1 to L-362; M-1 to T-361; M-1 to H-360; M-1 to A-359; M-1 to A-358; M-1 to Q-357; M-1 to L-356; M-1 to G-355; M-1 to E-354; M-1 to D-353; M-1 to E-352; M-1 to I-351; M-1 to V-350; M-1 to S-349; M-1 to C-348; M-1 to S-347; M-1 to K-346; M-1 to N-345; M-1 to P-344; M-1 to D-343; M-1 to C-342; M-1 to I-341; M-1 to T-340; M-1 to G-339; M-1 to I-338; M-1 to D-337; M-1 to A-336; M-1 to V-335; M-1 to G-334; M-1 to L-333; M-1 to T-332; M-1 to D-331; M-1 to C-330; M-1 to L-329; M-1 to G-328; M-1 to E-327; M-1 to Q-326; M-1 to G-325; M-1 to C-324; M-1 to F-323; M-1 to N-322; M-1 to Q-321; M-1 to R-320; M-1 to T-319; M-1 to L-318; M-1 to L-317; M-1 to I-316; M-1 to A-315; M-1 to T-314; M-1 to D-313; M-1 to Y-312; M-1 to H-311; M-1 to E-310; M-1 to P-309; M-1 to H-308; M-1 to R-307; M-1 to D-306; M-1 to S-305; M-1 to P-304; M-1 to Q-303; M-1 to N-302; M-1 to F-301; M-1 to R-300; M-1 to R-299; M-1 to Q-298; M-1 to W-297; M-1 to N-296; M-1 to C-295; M-1 to F-294; M-1 to N-293; M-1 to R-292; M-1 to L-291; M-1 to T-290; M-1 to L-289; M-1 to G-288; M-1 to G-287; M-1 to N-286; M-1 to D-285; M-1 to S-284; M-1 to V-283; M-1 to E-282; M-1 to P-281; M-1 to G-280; M-1 to W-279; M-1 to K-278; M-1 to E-277; M-1 to D-276; M-1 to E-275; M-1 to V-274; M-1 to I-273; M-1 to L-272; M-1 to V-271; M-1 to K-270; M-1 to V-269; M-1 to V-268; M-1 to M-267; M-1 to L-266; M-1 to N-265; M-1 to I-264; M-1 to S-263; M-1 to N-262; M-1 to K-261; M-1 to I-260; M-1 to S-259; M-1 to P-258; M-1 to H-257; M-1 to K-256; M-1 to K-255; M-1 to I-254; M-1 to R-253; M-1 to A-252; M-1 to A-251; M-1 to V-250; M-1 to S-249; M-1 to M-248; M-1 to L-247; M-1 to T-246; M-1 to L-245; M-1 to I-244; M-1 to H-243; M-1 to N-242; M-1 to Q-241; M-1 to L-240; M-1 to D-239; M-1 to A-238; M-1 to G-237; M-1 to Y-236; M-1 to F-235; M-1 to A-234; M-1 to A-233; M-1 to M-232; M-1 to S-231; M-1 to A-230; M-1 to D-229; M-1 to A-228; M-1 to V-227; M-1 to L-226; M-1 to A-225; M-1 to T-224; M-1 to E-223; M-1 to V-222; M-1 to F-221; M-1 to R-220; M-1 to A-219; M-1 to E-218; M-1 to L-217; M-1 to V-216; M-1 to F-215; M-1 to R-214; M-1 to K-213; M-1 to T-212; M-1 to R-211; M-1 to S-210; M-1 to T-209; M-1 to A-208; M-1 to G-207; M-1 to L-206; M-1 to P-205; M-1 to P-204; M-1 to P-203; M-1 to P-202; M-1 to E-201; M-1 to S-200; M-1 to A-199; M-1 to G-198; M-1 to E-197; M-1 to A-196; M-1 to E-195; M-1 to E-194; M-1 to E-193; M-1 to Q-192; M-1 to S-191; M-1 to E-190; M-1 to E-189; M-1 to E-188; M-1 to S-187; M-1 to D-186; M-1 to E-185; M-1 to Q-184; M-1 to H-183; M-1 to D-182; M-1 to G-181; M-1 to R-180; M-1 to E-179; M-1 to Q-178; M-1 to R-177; M-1 to Q-176; M-1 to G-175; M-1 to E-174; M-1 to G-173; M-1 to T-172; M-1 to E-171; M-1 to V-170; M-1 to E-169; M-1 to W-168; M-1 to E-167; M-1 to P-166; M-1 to G-165; M-1 to R-164; M-1 to P-163; M-1 to L-162; M-1 to P-161; M-1 to R-160; M-1 to A-159; M-1 to G-158; M-1 to A-157; M-1 to P-156; M-1 to G-155; M-1 to W-154; M-1 to R-153; M-1 to Q-152; M-1 to L-151; M-1 to R-150; M-1 to H-149; M-1 to P-148; M-1 to Q-147; M-1 to A-146; M-1 to L-145; M-1 to S-144; M-1 to G-143; M-1 to G-142; M-1 to A-141; M-1 to G-140; M-1 to Q-139; M-1 to P-138; M-1 to Q-137; M-1 to I-136; M-1 to T-135; M-1 to F-134; M-1 to E-133; M-1 to E-132; M-1 to G-131; M-1 to D-130; M-1 to L-129; M-1 to L-128; M-1 to F-127; M-1 to S-126; M-1 to G-125; M-1 to S-124; M-1 to L-123; M-1 to G-122; M-1 to R-121; M-1 to C-120; M-1 to L-119; M-1 to S-118; M-1 to V-117; M-1 to A-116; M-1 to A-115; M-1 to L-114; M-1 to S-113; M-1 to E-112; M-1 to P-111; M-1 to E-110; M-1 to G-109; M-1 to N-108; M-1 to V-107; M-1 to T-106; M-1 to G-105; M-1 to S-104; M-1 to F-103; M-1 to F-102; M-1 to C-101; M-1 to G-100; M-1 to R-99; M-1 to L-98; M-1 to G-97; M-1 to R-96; M-1 to E-95; M-1 to G-94; M-1 to G-93; M-1 to T-92; M-1 to A-91; M-1 to R-90; M-1 to G-89; M-1 to S-88; M-1 to G-87; M-1 to G-86; M-1 to L-85; M-1 to R-84; M-1 to E-83; M-1 to I-82; M-1 to K-81; M-1 to F-80; M-1 to E-79; M-1 to P-78; M-1 to A-77; M-1 to L-76; M-1 to F-75; M-1 to S-74; M-1 to D-73; M-1 to D-72; M-1 to P-71; M-1 to A-70; M-1 to L-69; M-1 to R-68; M-1 to L-67; M-1 to V-66; M-1 to F-65; M-1 to G-64; M-1 to K-63; M-1 to G-62; M-1 to F-61; M-1 to A-60; M-1 to S-59; M-1 to L-58; M-1 to H-57; M-1 to L-56; M-1 to A-55; M-1 to L-54; M-1 to E-40; M-1 to G-52; M-1 to A-51; M-1 to S-50; M-1 to G-49; M-1 to P-48; M-1 to L-47; M-1 to R-46; M-1 to T-45; M-1 to P-44; M-1 to V-43; M-1 to V-42; M-1 to L-41; M-1 to E-40; M-1 to S-39; M-1 to A-38; M-1 to Q-37; M-1 to G-36; M-1 to G-35; M-1 to A-34; M-1 to A-33; M-1 to P-32; M-1 to R-31; M-1 to A-30; M-1 to P-29; M-1 to A-28; M-1 to G-27; M-1 to R-26; M-1 to A-25; M-1 to L-24; M-1 to P-23; M-1 to L-22; M-1 to L-21; M-1 to L-20; M-1 to L-19; M-1 to L-18; M-1 to L-17; M-1 to L-16; M-1 to L-15; M-1 to L-14; M-1 to F-13; M-1 to P-12; M-1 to L-11; M-1 to W-10; M-1 to R-9; M-1 to P-8; M-1 to A-7; SEQ ID NO:4. Preferably, any of the above listed N- or C-terminal deletions can be combined to produce a N- and C-terminal deleted METH2 polypeptide.

The invention also provides polypeptides having one or more amino acids deleted from both the amino and the carboxyl termini, which may be described generally as having residues $m_1$–$n_1$ of SEQ ID NO:2 or $m_2$–$n_2$ SEQ ID NO:4, where n and m are integers as described above.

The invention also provides mutants of the metalloprotease domain of METH1, which are described by the general formula $m_3$–$n_3$, where $m_3$ is an integer from 205 to 265, and $n_3$ is an integer from 285 to 950, where $m_3$ and $n_3$ correspond to the position of the amino acid residue identified in SEQ ID NO:2. The invention further provides mutants of the metalloprotease domain of METH1, which are described by the general formula $m_4$–$n_4$, where $m_4$ is an integer from 1 to 409, and $n_4$ is an integer from 429 to 489, where $m_4$ and $n_4$ correspond to the position of the amino acid residue identified in SEQ ID NO:2.

The invention also provides mutants of the disintegrin domain of METH1, which are described by the general formula $m_5$–$n_5$, where $m_5$ is an integer from 430 to 490, and $n_5$ is an integer from 510 to 950, where $m_5$ and $n_5$ correspond to the position of the amino acid residue identified in SEQ ID NO:2. The invention further provides mutants of the disintegrin domain of METH1, which are described by the general formula $m_6$–$n_6$, where $m_6$ is an integer from 1 to 494, and $n_6$ is an integer from 514 to 574, where $m_6$ and $n_6$ correspond to the position of the amino acid residue identified in SEQ ID NO:2.

The invention further provides mutants of the TSP1 domain of METH1, which are described by the general formula $m_7$–$n_7$, where $m_7$ is an integer from 515 to 575, and $n_7$ is an integer from 595 to 950, where $m_7$ an $n_7$ correspond to the position of the amino acid residue identified in SEQ ID NO:2. The invention also provides mutants of the TSP1 domain of METH1, which are described by the general formula $m_8$–$n_8$, where $m_8$ is an integer from 1 to 548, and $n_8$ is an integer from 568 to 628, where $m_8$ and $n_8$ correspond to the position of the amino acid residue identified in SEQ ID NO:2.

The invention further provides mutants of the TSP2 domain of METH1, which are described by the general formula $m_9$–$n_9$, where $m_9$ is an integer from 801 to 871, and $n_9$ is an integer from 891 to 950, where $m_9$ and $n_9$ correspond to the position of the amino acid residue identified in SEQ ID NO:2. The invention also provides mutants of the TSP2 domain of METH1, which are described by the general formula $m_{10}$–$n_{10}$, where $m_{10}$ is an integer from 1 to 834, and $n_1$ is an integer from 864 to 924, where $m_{10}$ and $n_{10}$ correspond to the position of the amino acid residue identified in SEQ ID NO:2.

The invention further provides mutants of the TSP3 domain of METH1, which are described by the general formula $m_{11}$–$n_{11}$, where $m_{11}$ is an integer from 865 to 925, and $n_{11}$ is an integer from 945 to 950, where $m_{11}$ and $n_{11}$ correspond to the position of the amino acid residue identified in SEQ ID NO:2. The invention also provides mutants of the TSP3 domain of METH1, which are described by the general formula $m_{12}$–$n_{12}$, where $m_{12}$ is an integer from 1 to 884, and $n_{12}$ is an integer from 904 to 950, where $m_{12}$ and $n_{12}$ correspond to the position of the amino acid residue identified in SEQ ID NO:2.

The invention further provides mutants of the metalloprotease domain of METH2, which are described by the general formula $m_{13}$–$n_{13}$, where $m_{13}$ is an integer from 184 to 244, and $n_{13}$ is an integer from 264 to 890, where $m_{13}$ and $n_{13}$ correspond to the position of the amino acid residue identified in SEQ ID NO:4. The invention also provides mutants of the metalloprotease domain of METH2, which are described by the general formula $m_{14}$–$n_{14}$, where $m_{14}$ is an integer from 1 to 389, and $n_{14}$ is an integer from 409 to 469, where $m_{14}$ and $n_{14}$ correspond to the position of the amino acid residue identified in SEQ ID NO:4.

The invention further provides mutants of the disintegrin domain of METH2, which are described by the general formula $m_{15}$–$n_{15}$, where $m_{15}$ is an integer from 400 to 470, and $n_{15}$ is an integer from 490 to 890, where $m_{15}$ and $n_{15}$ correspond to the position of the amino acid residue identified in SEQ ID NO:4. The invention also provides mutants of the disintegrin domain of METH2, which are described by the general formula $m_{16}$–$n_{16}$, where $m_{16}$ is an integer from 1 to 479, and $n_{16}$ is an integer from 499 to 559, where $m_{16}$ and $n_{16}$ correspond to the position of the amino acid residue identified in SEQ ID NO:4.

The invention further provides mutants of the TSP1 domain of METH2, which are described by the general formula $m_{17}$–$n_{17}$, where $m_{17}$ is an integer from 500 to 560, and $n_{17}$ is an integer from 580 to 890, where $m_{17}$ and $n_{17}$ correspond to the position of the amino acid residue identified in SEQ ID NO:4. The invention also provides mutants of the TSP1 domain of METH2, which are described by the general formula $m_{18}$–$n_{18}$, where $m_{18}$ is an integer from 1 to 533, and $n_{18}$ is an integer from 553 to 613, where $m_{18}$ and $n_{18}$ correspond to the position of the amino acid residue identified in SEQ ID NO:4.

The invention further provides mutants of the TSP2 domain of METH2, which are described by the general formula $m_{19}$–$n_{19}$, where $m_{19}$ is an integer from 807 to 867, and $n_{19}$ is an integer from 887 to 890, where $m_{19}$ and $n_{19}$ correspond to the position of the amino acid residue identified in SEQ ID NO:4. The invention also provides mutants of the TSP2 domain of METH2, which are described by the general formula $m_{20}$–$n_{20}$, where $m_{20}$ is an integer from 1 to 840, and $n_{20}$ is an integer from 860 to 890, where $m_{20}$ and $n_{20}$ correspond to the position of the amino acid residue identified in SEQ ID NO:4.

Also preferred are METH1 or METH2 polypeptide and polynucleotide fragments characterized by structural or functional domains. Preferred embodiments of the invention include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions, substrate binding region, and high antigenic index regions. As set out in the Figures, such preferred regions include Garnier-Robson alpha-regions, beta-regions, turn-regions, and coil-regions, Chou-Fasman alpha-regions, beta-regions, and turn-regions, Kyte-Doolittle hydrophilic regions and hydrophobic regions, Eisenberg alpha and beta amphipathic regions, Karplus-Schulz flexible regions, Emini surface-forming regions, and Jameson-Wolf high antigenic index regions.

Polypeptide fragments of SEQ ID NO:2 falling within conserved domains are specifically contemplated by the present invention. (See FIGS. 10 & 11 and Tables 1& 2.) Moreover, polynucleotide fragments encoding these domains are also contemplated.

Other preferred fragments are biologically active METH1 or METH2 fragments. Biologically active fragments are those exhibiting activity similar, but not necessarily identical, to an activity of the METH1 or METH2 polypeptide. The biological activity of the fragments may include an improved desired activity, or a decreased undesirable activity.

However, many polynucleotide sequences, such as EST sequences, are publicly available and accessible through sequence databases. Some of these sequences are related to SEQ ID NO:1 or SEQ ID NO:3 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 936 of SEQ ID NO:1, b is an integer of 15 to 950, where both a and b correspond to the positions of nucleotide residues shown in SEQ ID NO:1, and where the b is greater than or equal to a+14. Moreover, preferably excluded from the present invention are one or more polynucleotides comprising a nucleotide sequence described by the general formula of a-b, where a is any integer between 1 to 876 of SEQ ID NO:3, b is an integer of 15 to 890, where both a and b correspond to the positions of nucleotide residues shown in SEQ ID NO:3, and where the b is greater than or equal to a+14.

The above-described fragments may be used to make fusion proteins, for example Fc or Flag fusion proteins, as described below.

Epitopes & Antibodies

In another aspect, the invention provides peptides and polypeptides comprising epitope-bearing portions of the polypeptides of the present invention. These epitopes are immunogenic or antigenic epitopes of the polypeptides of the present invention. An "immunogenic epitope" is defined as a part of a protein that elicits an antibody response in vivo when the whole polypeptide of the present invention, or fragment thereof, is the immunogen. On the other hand, a region of a polypeptide to which an antibody can bind is defined as an "antigenic determinant" or "antigenic epitope." The number of in vivo immunogenic epitopes of a protein generally is less than the number of antigenic epitopes. See, e.g., Geysen, et al. (1983) *Proc. Natl. Acad. Sci. USA* 81:3998–4002. However, antibodies can be made to any antigenic epitope, regardless of whether it is an immunogenic epitope, by using methods such as phage display. See e.g., Petersen G. et al. (1995) *Mol. Gen. Genet.* 249:425–431. Therefore, included in the present invention are both immunogenic epitopes and antigenic epitopes.

A list of exemplified amino acid sequences comprising immunogenic epitopes are shown in Tables 1 and 2. It is pointed out that Tables 1 and 2 only list amino acid residues comprising epitopes predicted to have the highest degree of antigenicity using the algorithm of Jameson and Wolf, (1988) *Comp. Appl. Biosci.* 4:181–186 (said references incorporated by reference in their entireties). The Jameson-Wolf antigenic analysis was performed using the computer program PROTEAN, using default parameters (Version 3.11 for the Power MacIntosh, DNASTAR, Inc., 1228 South Park Street Madison, Wis.). Tables 1 and 2 and portions of polypeptides not listed in Tables 1 and 2 are not considered non-immunogenic. The immunogenic epitopes of Tables 1 and 2 are exemplified lists, not exhaustive lists, because other immunogenic epitopes are merely not recognized as such by the particular algorithm used. Amino acid residues comprising other immunogenic epitopes may be routinely determined using algorithms similar to the Jameson-Wolf analysis or by in vivo testing for an antigenic response using methods known in the art. See, e.g., Geysen et al., supra; U.S. Pat. Nos. 4,708,781; 5,194,392; 4,433,092; and 5,480,971 (said references incorporated by reference in their entireties).

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention.

Using DNAstar analysis, SEQ ID NO:2 was found antigenic at amino acids: 2–14, 32–44, 47–60, 66–78, 87–103, 109–118, 146–162, 168–180, 183–219, 223–243, 275–284, 296–306, 314–334, 341–354, 357–376, 392–399, 401–410, 418–429, 438–454, 456–471, 474–488, 510–522, 524–538, 550–561, 565–626, 630–643, 659–671, 679–721, 734–749, 784–804, 813–820, 825–832, 845–854, 860–894, 899–917, 919–924 and 928–939.

Using DNAstar analysis, SEQ ID NO:4 was found antigenic at amino acids: 26–38, 45–52, 69–76, 80–99, 105–113, 129–136, 138–217, 254–263, 273–289, 294–313, 321–331, 339–356, 371–383, 417–427, 438–443, 459–471, 479–505, 507–526, 535–546, 550–607, 615–640, 648–653, 660–667, 669–681, 683–704, 717–732, 737–743, 775–787, 797–804, 811–825, 840–867 and 870–884.

Thus, these regions of METH1 and/or METH2 are non-limiting examples of antigenic polypeptides or peptides that can be used to raise METH1 and/or METH2-specific antibodies include.

It is particularly pointed out that the amino acid sequences of Tables 1 and 2 comprise immunogenic epitopes. Tables 1 and 2 list only the critical residues of immunogenic epitopes determined by the Jameson-Wolf analysis. Thus, additional flanking residues on either the N-terminal, C-terminal, or both N- and C-terminal ends may be added to the sequences of Tables 1 and 2 to generate an epitope-bearing polypeptide of the present invention. Therefore, the immunogenic epitopes of Tables 1 and 2 may include additional N-terminal or C-terminal amino acid residues. The additional flanking amino acid residues may be contiguous flanking N-terminal and/or C-terminal sequences from the polypeptides of the present invention, heterologous polypeptide sequences, or may include both contiguous flanking sequences from the polypeptides of the present invention and heterologous polypeptide sequences.

Polypeptides of the present invention comprising immunogenic or antigenic epitopes are at least 7 amino acids residues in length. "At least" means that a polypeptide of the present invention comprising an immunogenic or antigenic epitope may be 7 amino acid residues in length or any integer between 7 amino acids and the number of amino acid residues of the full length polypeptides of the invention. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. However, it is pointed out that each and every integer between 7 and the number of amino acid residues of the full length polypeptide are included in the present invention.

The immuno and antigenic epitope-bearing fragments may be specified by either the number of contiguous amino acid residues, as described above, or further specified by N-terminal and C-terminal positions of these fragments on the amino acid sequence of SEQ ID NO:2 or 4. Every combination of a N-terminal and C-terminal position that a fragment of, for example, at least 7 or at least 15 contiguous amino acid residues in length could occupy on the amino acid sequence of SEQ ID NO:2 or 4 is included in the invention. Again, "at least 7 contiguous amino acid residues in length" means 7 amino acid residues in length or any integer between 7 amino acids and the number of amino acid residues of the full length polypeptide of the present invention. Specifically, each and every integer between 7 and the number of amino acid residues of the full length polypeptide are included in the present invention.

Immunogenic and antigenic epitope-bearing polypeptides of the invention are useful, for example, to make antibodies which specifically bind the polypeptides of the invention, and in immunoassays to detect the polypeptides of the present invention. The antibodies are useful, for example, in affinity purification of the polypeptides of the present invention. The antibodies may also routinely be used in a variety of qualitative or quantitative immunoassays, specifically for the polypeptides of the present invention using methods known in the art. See, e.g., Harlow et al., Antibodies: A Laboratory Manual, (Cold Spring Harbor Laboratory Press; 2nd Ed. 1988).

The epitope-bearing polypeptides of the present invention may be produced by any conventional means for making polypeptides including synthetic and recombinant methods known in the art. For instance, epitope-bearing peptides may be synthesized using known methods of chemical synthesis. For instance, Houghten has described a simple method for the synthesis of large numbers of peptides, such as 10–20 mgs of 248 individual and distinct 13 residue peptides representing single amino acid variants of a segment of the HA1 polypeptide, all of which were prepared and characterized (by ELISA-type binding studies) in less than four weeks (Houghten, R. A. Proc. Natl. Acad. Sci. USA 82:5131–5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously (Houghten et al. (1985) Proc. Natl. Acad. Sci. 82:5131–5135 at 5134).

Epitope-bearing polypeptides of the present invention are used to induce antibodies according to methods well known in the art including, but not limited to, in vivo immunization, in vitro immunization, and phage display methods. See, e.g., Sutcliffe, et al., supra; Wilson, et al., supra, and Bittle, et al. (1985) J. Gen. Virol. 66:2347–2354. If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as m-maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins. See, e.g., EPA 0,394,827; Traunecker et al. (1988) Nature 331:84–86. Fusion proteins that have a disulfide-linked dimeric structure due to the IgG portion can also be more efficient in binding and neutralizing other molecules than monomeric polypeptides or fragments thereof alone. See, e.g., Fountoulakis et al. (1995) J. Biochem. 270:3958–3964. Nucleic acids encoding the above epitopes can also be recombined with a gene of interest as an epitope tag to aid in detection and purification of the expressed polypeptide.

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention including, but not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes monoclonal, polyclonal, chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity.

Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991) *J. Immunol.* 147:60–69; U.S. Pat. Nos. 5,573,920, 4,474,893, 5,601,819, 4,714,681, 4,925,648; Kostelny, S. A. et al. (1992) *J. Immunol.* 148:1547–1553.

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., ANTIBODIES: A LABORATORY MANUAL, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "monoclonal antibody" refers to an antibody that is derived from a single clone, including eukaryotic, prokaryotic, or phage clones, and not by the method which it is produced. Monoclonal antibodies can be prepared using a wide variety of techniques known in the art including the use of hybridoma, recombinant and phage display technology.

Hybridoma techniques include those known in the art and taught in Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981) (said references incorporated by reference in their entireties). Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA and phage display technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995) *J. Immunol. Methods* 182:41–50; Ames, R. S. et al. (1995) *J. Immunol. Methods* 184:177–186; Kettleborough, C. A. et al. (1994) *Eur. J. Immunol.* 24:952–958; Persic, L. et al. (1997) *Gene* 187:9–18; Burton, D. R. et al. (1994) *Advances in Immunology* 57:191–280; PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al. (1992) *BioTechniques* 12(6):864–869; and Sawai, H. et al. (1995) *AJRI* 34:26–34; and Better, M. et al. (1988) *Science* 240:1041–1043 (said references incorporated by reference in their entireties).

Examples of techniques which can be used to produce single-chain Fvs and antibodies include those described in U.S. Pat. Nos. 4,946,778 and 5,258,498; Huston et al. (1991)

*Methods in Enzymology* 203:46–88; Shu, L. et al. (1993) *PNAS* 90:7995–7999; and Skerra, A. et al. (1988) *Science* 240:1038–1040. For some uses, including in vivo use of antibodies in humans and in vitro detection assays, it may be preferable to use chimeric, humanized, or human antibodies. Methods for producing chimeric antibodies are known in the art. See e.g., Morrison, *Science* 229:1202 (1985); Oi et al., *BioTechniques* 4:214 (1986); Gillies, S. D. et al. (1989) *J. Immunol. Methods* 125:191–202; and U.S. Pat. No. 5,807,715. Antibodies can be humanized using a variety of techniques including CDR-grafting (EP 0 239 400; WO91/09967; U.S. Pat. Nos. 5,530,101; and 5,585,089), veneering or resurfacing (EP 0 592 106; EP 0 519 596; Padlan E. A., (1991) *Molecular Immunology* 28(4/5):489–498; Studnicka G. M. et al. (1994) *Protein Engineering* 7(6):805–814; Roguska M. A. et al. (1994) *PNAS* 91:969–973), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and WO 98/46645 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al. (1994) *Immunol. Lett.* 39:91–99; U.S. Pat. No. 5,474,981; Gillies, S. O. et al. (1992) *PNAS* 89:1428–1432; Fell, H. P. et al. (1991) *J. Immunol.* 146:2446–2452 (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991) *PNAS* 88:10535–10539; Zheng, X. X. et al. (1995) *J. Immunol.* 154:5590–5600; and Vil, H. et al. (1992) *PNAS* 89:11337–11341 (said references incorporated by reference in their entireties).

The invention further relates to antibodies that act as agonists or antagonists of the polypeptides of the present invention. Antibodies which act as agonists or antagonists of the polypeptides of the present invention include, for example, antibodies which disrupt receptor/ligand interactions with the polypeptides of the invention either partially or fully. For example, the present invention includes antibodies that disrupt the ability of the proteins of the invention to multimerize. In another example, the present invention includes antibodies which allow the proteins of the invention to multimerize, but disrupt the ability of the proteins of the invention to bind one or more METH1 and/or METH2 receptor(s)/ligand(s). In yet another example, the present invention includes antibodies which allow the proteins of the invention to multimerize, and bind METH1 and/or METH2 receptor(s)/ligand(s), but blocks biological activity associated with the METH1 and/or METH2/receptor/ligand complex.

Antibodies which act as agonists or antagonists of the polypeptides of the present invention also include, both receptor-specific antibodies and ligand-specific antibodies. Included are receptor-specific antibodies that do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al., *Blood* 92(6):1981–1988 (1998); Chen, Z. et al., *Cancer Res.* 58(16):3668–3678 (1998); Harrop, J. A. et al., *J. Immunol.* 161(4): 1786–1794 (1998); Zhu, Z. et al., *Cancer Res.* 58(15):3209–3214 (1998); Yoon, D. Y. et al., *J. Immunol.* 160(7):3170–3179 (1998); Prat, M. et al., *J. Cell. Sci.* 111(Pt2):237–247 (1998); Pitard, V. et al., *J. Immunol. Methods* 205(2):177–190 (1997); Liautard, J. et al., *Cytokine* 9(4):233–241 (1997); Carlson, N. G. et al., *J. Biol. Chem.* 272(17): 11295–11301 (1997); Taryman, R. E. et al., *Neuron* 14(4):755–762 (1995); Muller, Y. A. et al., *Structure* 6(9): 1153–1167 (1998); Bartunek, P. et al., *Cytokine* 8(1):14–20 (1996)(said references incorporated by reference in their entireties).

As discussed above, antibodies to the METH1 and/or METH2 proteins of the invention can, in turn, be utilized to generate anti-idiotype antibodies that "mimic" METH1 and/or METH2 using techniques well known to those skilled in the art. (See, e.g., Greenspan & Bona, *FASEB J.* 7(5): 437–444; (1989) and Nissinoff, *J. Immunol* 147(8):2429–2438 (1991)). For example, antibodies which bind to METH1 and/or METH2 and competitively inhibit METH1 and/or METH2 multimerization and/or binding to ligand can be used to generate anti-idiotypes that "mimic" the METH1 and/or METH2 mutimerization and/or binding domain and, as a consequence, bind to and neutralize METH1 and/or METH2 and/or its ligand. Such neutralizing anti-idiotypes or Fab fragments of such anti-idiotypes can be used in therapeutic regimens to neutralize METH1 and/or METH2 ligand. For example, such anti-idiotypic antibodies can be used to bind METH1 and/or METH2, or to bind METH1 and/or METH2 ligands/receptors, and thereby block METH1 and/or METH2 biological activity.

Fusion Proteins

Any METH1 or METH2 polypeptide can be used to generate fusion proteins. For example, the METH1 or METH2 polypeptide, when fused to a second protein, can be used as an antigenic tag. Antibodies raised against the METH1 or METH2 polypeptide can be used to indirectly detect the second protein by binding to the METH1 or METH2. Moreover, because secreted proteins target cellular locations based on trafficking signals, the METH1 or METH2 polypeptides can be used as a targeting molecule once fused to other proteins.

Examples of domains that can be fused to METH1 or METH2 polypeptides include not only heterologous signal sequences, but also other heterologous functional regions. The fusion does not necessarily need to be direct, but may occur through linker sequences.

In certain preferred embodiments, METH1 or METH2 proteins of the invention comprise fusion proteins wherein the METH1 or METH2 polypeptides are those described above as $m_1-n_1$ or $m_2-n_2$, respectively. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

Moreover, fusion proteins may also be engineered to improve characteristics of the METH1 or METH2 polypeptide. For instance, a region of additional amino acids, particularly charged amino acids, may be added to the N-terminus of the METH1 or METH2 polypeptide to improve stability and persistence during purification from the host cell or subsequent handling and storage. Also, peptide moieties may be added to the METH1 or METH2 polypeptide to facilitate purification. Such regions may be removed prior to final preparation of the METH1 or METH2 polypeptide. The addition of peptide moieties to facilitate handling of polypeptides are familiar and routine techniques in the art.

Moreover, METH1 or METH2 polypeptides, including fragments, and specifically epitopes, can be combined with parts of the constant domain of immunoglobulins (IgG), an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270: 9459–9471 (1995).)

Moreover, the METH1 or METH2 polypeptides can be fused to marker sequences, such as a peptide which facilitates purification of METH1 or METH2. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the METH1 or METH2 polynucleotides or the polypeptides.

Biological Activities of METH1 and/or METH2

METH1 and/or METH2 polynucleotides or polypeptides, or agonists or antagonists of METH1 and/or METH2, can be used in assays to test for one or more biological activities. If METH1 and/or METH2 polynucleotides or polypeptides, or agonists or antagonists of METH1 and/or METH2, do exhibit activity in a particular assay, it is likely that METH1 and/or METH2 may be involved in the diseases associated with the biological activity. Therefore, METH1 and/or METH2 could be used to treat the associated disease.

Immune Activity

METH1 and/or METH2 polynucleotides or polypeptides, or agonists or antagonists of METH1 and/or METH2, may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, METH1 and/or METH2 polynucleotides or polypeptides, or agonists or antagonists of METH1 and/or METH2, can be used as a marker or detector of a particular immune system disease or disorder.

METH1 and/or METH2 polynucleotides or polypeptides, or agonists or antagonists of METH1 and/or METH2, may be useful in treating or detecting deficiencies or disorders of hematopoietic cells. METH1 and/or METH2 polynucleotides or polypeptides, or agonists or antagonists of METH1 and/or METH2, could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, METH1 and/or METH2 polynucleotides or polypeptides, or agonists or antagonists of METH1 and/or METH2, can also be used to modulate hemostatic (the stopping of bleeding) or thrombolytic activity (clot formation). For example, by increasing hemostatic or thrombolytic activity, METH1 and/or METH2 polynucleotides or polypeptides, or agonists or antagonists of METH1 and/or METH2, could be used to treat blood coagulation disorders (e.g., afibrinogenemia, factor deficiencies), blood platelet disorders (e.g. thrombocytopenia), or wounds resulting from trauma, surgery, or other causes. Alternatively, METH1 and/or METH2 polynucleotides or polypeptides, or agonists or antagonists of METH1 and/or METH2, that can decrease hemostatic or thrombolytic activity could be used to inhibit or dissolve clotting, important in the treatment of heart attacks (infarction), strokes, or scarring.

METH1 and/or METH2 polynucleotides or polypeptides, or agonists or antagonists of METH1 and/or METH2, may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of METH1 and/or METH2 polynucleotides or polypeptides, or agonists or antagonists of METH1 and/or METH2, that can inhibit an immune response, particularly the proliferation, differentiation, or chemotaxis of T-cells, may be an effective therapy in preventing autoimmune disorders.

Examples of autoimmune disorders that can be treated or detected include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by METH1 and/or METH2 polynucleotides or polypeptides, or agonists or antagonists of METH1 and/or METH2. Moreover, these molecules can be used to treat anaphylaxis, hypersensitivity to an antigenic molecule, or blood group incompatibility.

METH1 and/or METH2 polynucleotides or polypeptides, or agonists or antagonists of METH1 and/or METH2, may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of METH1 and/or METH2 polynucleotides or polypeptides, or agonists or antagonists of METH1 and/or METH2, that inhibits an immune response, particularly the proliferation, differentiation, or chemotaxis of T-cells, may be an effective therapy in preventing organ rejection or GVHD.

Similarly, METH1 and/or METH2 polynucleotides or polypeptides, or agonists or antagonists of METH1 and/or METH2, may also be used to modulate inflammation. For example, METH1 and/or METH2 polynucleotides or polypeptides, or agonists or antagonists of METH1 and/or METH2, may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

METH1 and/or METH2 polynucleotides or polypeptides, or agonists or antagonists of METH1 and/or METH2, can be used to treat or detect hyperproliferative disorders, including neoplasms. METH1 and/or METH2 polynucleotides or polypeptides, or agonists or antagonists of METH1 and/or METH2, may inhibit the proliferation of the disorder through direct or indirect interactions. Alternatively, METH1 and/or METH2 polynucleotides or polypeptides, or agonists or antagonists of METH1 and/or METH2, may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response maybe increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by METH1 and/or METH2 polynucleotides or polypeptides, or agonists or antagonists of METH1 and/or METH2, include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by METH1 and/or METH2 polynucleotides or polypeptides, or agonists or antagonists of METH1 and/or METH2. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Cardiovascular Disorders

METH1 and/or METH2 polynucleotides or polypeptides, or agonists or antagonists of METH1 and/or METH2, encoding METH1 and/or METH2 may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, post-pericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve diseases include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, heredi-tary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include airembolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

METH1 and/or METH2 polynucleotides or polypeptides, or agonists or antagonists of METH1 and/or METH2, are especially effective for the treatment of critical limb ischemia and coronary disease.

METH1 and/or METH2 polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. METH1 and/or METH2 polypeptides may be administered as part of a pharmaceutical composition, described in more detail below. Methods of delivering METH1 and/or METH2 polynucleotides are described in more detail herein.

Diseases at the Cellular Level

Diseases associated with increased cell survival or the inhibition of apoptosis that could be treated or detected by METH1 and/or METH2 polynucleotides or polypeptides, as well as antagonists or agonists of METH1 and/or METH2, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, METH1 and/or METH2 polynucleotides, polypeptides, and/or antagonists of the invention are used to inhibit growth, progression, and/or metasis of cancers, in particular those listed above.

Additional diseases or conditions associated with increased cell survival that could be treated or detected by METH1 and/or METH2 polynucleotides or polypeptides, or agonists or antagonists of METH1 and/or METH2, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by METH1 and/or METH2 polynucleotides or polypeptides, as well as agonists or antagonists of METH1 and/or METH2, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing METH1 and/or METH2 polynucleotides or polypeptides, as well as agonists or antagonists of METH1 and/or METH2, for therapeutic purposes, for example, to stimulate epithelial cell proliferation and basal keratinocytes for the purpose of wound healing, and to stimulate hair follicle production and healing of dermal wounds. METH1 and/or METH2 polynucleotides or polypeptides, as well as agonists or antagonists of METH1 and/or METH2, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. METH1 and/or METH2 polynucleotides or polypeptides, as well as agonists or antagonists of METH1 and/or METH2, could be used to promote dermal reestablishment subsequent to dermal loss.

METH1 and/or METH2 polynucleotides or polypeptides, as well as agonists or antagonists of METH1 and/or METH2, could be used to increase the adherence of skin grafts to a wound bed and to stimulate re-epithelialization from the wound bed. The following are types of grafts that METH1 and/or METH2 polynucleotides or polypeptides, agonists or antagonists of METH1 and/or METH2, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. METH1 and/or METH2 polynucleotides or polypeptides, as well as agonists or antagonists of METH1 and/or METH2, can be used to promote skin strength and to improve the appearance of aged skin.

It is believed that METH1 and/or METH2 polynucleotides or polypeptides, as well as agonists or antagonists of METH1 and/or METH2, will also produce changes in hepatocyte proliferation, and epithelial cell proliferation in the lung, breast, pancreas, stomach, small intesting, and large intestine. METH1 and/or METH2 polynucleotides or polypeptides, as well as agonists or antagonists of METH1 and/or METH2, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. METH1 and/or METH2 polynucleotides or polypeptides, agonists or antagonists of METH1 and/or METH2, may promote proliferation of endothelial cells, keratinocytes, and basal keratinocytes.

METH1 and/or METH2 polynucleotides or polypeptides, as well as agonists or antagonists of METH1 and/or METH2, could also be used to reduce the side effects of gut toxicity that result from radiation, chemotherapy treatments or viral infections. METH1 and/or METH2 polynucleotides or polypeptides, as well as agonists or antagonists of METH1 and/or METH2, may have a cytoprotective effect on the small intestine mucosa. METH1 and/or METH2 polynucleotides or polypeptides, as well as agonists or antagonists of METH1 and/or METH2, may also stimulate healing of mucositis (mouth ulcers) that result from chemotherapy and viral infections.

METH1 and/or METH2 polynucleotides or polypeptides, as well as agonists or antagonists of METH1 and/or METH2, could further be used in full regeneration of skin in full and partial thickness skin defects, including burns, (i.e., repopulation of hair follicles, sweat glands, and sebaceous glands), treatment of other skin defects such as psoriasis. METH1 and/or METH2 polynucleotides or polypeptides, as well as agonists or antagonists of METH1 and/or METH2, could be used to treat epidermolysis bullosa, a defect in adherence of the epidermis to the underlying dermis which results in frequent, open and painful blisters by accelerating reepithelialization of these lesions. METH1 and/or METH2 polynucleotides or polypeptides, as well as agonists or antagonists of METH1 and/or METH2, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, METH1 and/or METH2 polynucleotides or polypeptides, as well as agonists or antagonists of METH1 and/or METH2, could be used to promote the resurfacing of the mucosal surface to aid more rapid healing and to prevent progression of inflammatory bowel disease. Treatment with METH1 and/or METH2 polynucleotides or polypeptides, agonists or antagonists of METH1 and/or METH2, is expected to have a significant effect on the production of mucus throughout the gastrointestinal tract and could be used to protect the intestinal mucosa from injurious substances that are ingested or following surgery. METH1 and/or METH2 polynucleotides or polypeptides, as well as agonists or antagonists of METH1 and/or METH2, could be used to treat diseases associate with the under expression of METH1 and/or METH2.

Moreover, METH1 and/or METH2 polynucleotides or polypeptides, as well as agonists or antagonists of METH1 and/or METH2, could be used to prevent and heal damage to the lungs due to various pathological states. A growth factor such as METH1 and/or METH2 polynucleotides or polypeptides, as well as agonists or antagonists of METH1 and/or METH2, could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated using METH1 and/or METH2 polynucleotides or polypeptides, agonists or antagonists of METH1 and/or METH2. Also, METH1 and/or METH2 polynucleotides or polypeptides, as well as agonists or antagonists of METH1 and/or METH2, could be used to stimulate the proliferation and differentiation of type II pneumocytes, which may help treat or prevent diseases such as hyaline membrane diseases, such as infant respiratory distress syndrome and bronchopulmonary displasia, in premature infants.

METH1 and/or METH2 polynucleotides or polypeptides, as well as agonists or antagonists of METH1 and/or METH2, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, METH1 and/or METH2 polynucleotides or polypeptides, as well as agonists or antagonists of METH1 and/or METH2, could be used treat or prevent the onset of diabetes mellitus. In patients with newly diagnosed Types I and II diabetes, where some islet cell function remains, METH1 and/or METH2 polynucleotides or polypeptides, as well as agonists or antagonists of METH1 and/or METH2, could be used to maintain the islet function so as to alleviate, delay or prevent permanent manifestation of the disease. Also, METH1 and/or METH2 polynucleotides or polypeptides, as well as agonists or antagonists of METH1 and/or METH2, could be used as an auxiliary in islet cell transplantation to improve or promote islet cell function.

Infectious Disease

METH1 and/or METH2 polynucleotides or polypeptides, or agonists or antagonists of METH1 and/or METH2, can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, METH1 and/or METH2 polynucleotides or polypeptides, or agonists or antagonists of METH1 and/or METH2, may also directly inhibit the infectious agent, without necessarily eliciting an immune response.

Viruses are one example of an infectious agent that can cause disease or symptoms that can be treated or detected by METH and/or METH2 polynucleotides or polypeptides, or agonists or antagonists of METH1 and/or METH2. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. METH1 and/or METH2 polynucleotides or polypeptides, or agonists or antagonists of METH1 and/or METH2, can be used to treat or detect any of these symptoms or diseases.

Similarly, bacterial or fungal agents that can cause disease or symptoms and that can be treated or detected by METH1 and/or METH2 polynucleotides or polypeptides, or agonists or antagonists of METH1 and/or METH2, include, but not limited to, the following Gram-Negative and Gram-positive bacterial families and fungi: Actinomycetales (e.g., *Corynebacterium, Mycobacterium, Norcardia*), Aspergillosis, Bacillaceae (e.g., *Anthrax, Clostridium*), Bacteroidaceae, Blastomycosis, *Bordetella, Borrelia*, Brucellosis, Candidiasis, *Campylobacter*, Coccidioidomycosis, Cryptococcosis, Dermatocycoses, Enterobacteriaceae (*Klebsiella, Salmo-*

*nella, Serratia, Yersinia*), *Erysipelothrix, Helicobacter,* Legionellosis, Leptospirosis, *Listeria,* Mycoplasmatales, Neisseriaceae (e.g., *Acinetobacter, Gonorrhea, Menigococcal*), Pasteurellacea Infections (e.g., *Actinobacillus, Heamophilus, Pasteurella*), *Pseudomonas,* Rickettsiaceae, Chlamydiaceac, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. METH1 and/or METH2 polynucleotides or polypeptides, or agonists or antagonists of METH1 and/or METH2, can be used to treat or detect any of these symptoms or diseases.

Moreover, parasitic agents causing disease or symptoms that can be treated or detected by METH1 and/or METH2 polynucleotides or polypeptides, or agonists or antagonists of METH1 and/or METH2, include, but are not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. METH1 and/or METH2 polynucleotides or polypeptides, or agonists or antagonists of METH1 and/or METH2, can be used to treat or detect any of these symptoms or diseases.

Preferably, treatment using METH1 and/or METH2 polynucleotides or polypeptides, or agonists or antagonists of METH1 and/or METH2, could either be by administering an effective amount of METH1 and/or METH2 polypeptide to the patient, orbyremoving cells from the patient, supplying the cells with METH1 and/or METH2 polynucleotide, and returning the engineered cells to the patient (ex vivo therapy). Moreover, the METH1 and/or METH2 polypeptide or polynucleotide can be used as an antigen in a vaccine to raise an immune response against infectious disease.

Regeneration

METH1 and/or METH2 polynucleotides or polypeptides, or agonists or antagonists of METH1 and/or METH2, can be used to differentiate, proliferate, and attract cells, leading to the regeneration of tissues. (See, Science 276:59–87 (1997) .) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, METH1 and/or METH2 polynucleotides or polypeptides, or agonists or antagonists of METH1 and/or METH2, may increase regeneration of tissues difficult to heal. For example, increased tendon/ligament regeneration would quicken recovery time after damage. METH1 and/or METH2 polynucleotides or polypeptides, or agonists or antagonists of METH1 and/or METH2, of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using METH1 and/or METH2 polynucleotides or polypeptides, or agonists or antagonists of METH1 and/or METH2, to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the METH1 and/or METH2 polynucleotides or polypeptides, or agonists or antagonists of METH1 and/or METH2.

Chemotaxis

METH1 and/or METH2 polynucleotides or polypeptides, or agonists or antagonists of METH1 and/or METH2, may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as a site of inflammation, infection, or hyperproliferation. The mobilized cells can then fight off and/or heal the particular trauma or abnormality.

METH1 and/or METH2 polynucleotides or polypeptides, or agonists or antagonists of METH1 and/or METH2, may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. As a chemotactic molecule, METH1 and/or METH2 could also attract fibroblasts, which can be used to treat wounds.

It is also contemplated that METH1 and/or METH2 polynucleotides or polypeptides, or agonists or antagonists of METH1 and/or METH2, may inhibit chemotactic activity. These molecules could also be used to treat disorders. Thus, METH1 and/or METH2 polynucleotides or polypeptides, or agonists or antagonists of METH1 and/or METH2, could be used as an inhibitor of chemotaxis.

Binding Activity

METH1 and/or METH2 polypeptides may be used to screen for molecules that bind to METH1 and/or METH2 or for molecules to which METH1 and/or METH2 binds. The binding of METH1 and/or METH2 and the molecule may activate (agonist), increase, inhibit (antagonist), or decrease activity of the METH1 and/or METH2 or the molecule bound. Examples of such molecules include antibodies, oligonucleotides, proteins (e.g., receptors), or small molecules.

Preferably, the molecule is closely related to the natural ligand of METH1 and/or METH2, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which METH1 and/or METH2 binds, or at least, a fragment of the receptor capable of being bound by METH1 and/or METH2 (e.g., active site). In either case, the molecule can be rationally designed using known techniques.

Preferably, the screening for these molecules involves producing appropriate cells which express METH1 and/or METH2, either as a secreted protein or on the cell membrane. Preferred cells include cells from mammals, yeast, *Drosophila*, or *E. coli*. Cells expressing METH1 and/or METH2(or cell membrane containing the expressed polypeptide) are then preferably contacted with a test compound potentially containing the molecule to observe binding, stimulation, or inhibition of activity of either METH1 and/or METH2 or the molecule.

The assay may simply test binding of a candidate compound to METH1 and/or METH2, wherein binding is detected by a label, or in an assay involving competition with a labeled competitor. Further, the assay may test whether the candidate compound results in a signal generated by binding to METH1 and/or METH2.

Alternatively, the assay can be carried out using cell-free preparations, polypeptide/molecule affixed to a solid support, chemical libraries, or natural product mixtures. The assay may also simply comprise the steps of mixing a candidate compound with a solution containing METH1 and/or METH2, measuring METH1 and/or METH2/molecule activity or binding, and comparing the METH1 and/or METH2/molecule activity or binding to a standard.

Preferably, an ELISA assay can measure METH1 and/or METH2 level or activity in a sample (e.g., biological sample) using a monoclonal or polyclonal antibody. The antibody can measure METH1 and/or METH2 level or activity by either binding, directly or indirectly, to METH1 and/or METH2 or by competing with METH1 and/or METH2 for a substrate.

Additionally, the receptor to which METH1 and/or METH2 binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of METH1 or METH2 thereby effectively generating agonists and antagonists of METH1 or METH2. See generally, U.S. Pat. Nos. 5,605,793, 5,811,238, 5,830,721, 5,834,252, and 5,837,458; and Patten, P. A. et al., *Curr. Opinion Biotechnol.* 8:724–733 (1997); Harayama, S. *Trends Biotechnol.* 16(2):76–82 (1998); Hansson, L. O. et al., *J. Mol. Biol.* 287:265–276 (1999); and Lorenzo, M. M. and Blasco, R. *Biotechniques* 24(2):308–313 (1998) (each of these patents and publications are hereby incorporated by reference). In one embodiment, alteration of METH1 or METH2 polynucleotides and corresponding polypeptides may be achieved by DNA shuffling. DNA shuffling involves the assembly of two or more DNA segments into a desired METH1 or METH2 molecule by homologous, or site-specific, recombination.

In another embodiment, METH1 or METH2 polynucleotides and corresponding polypeptides may be altered by being subjected to random mutagenesis by error-prone PCR, random nucleotide insertion, or other methods prior to recombination. In another embodiment, one or more components, motifs, sections, parts, domains, fragments, etc., or METH1 or METH2 may be recombined with one or more components, motifs, sections, parts, domains, fragments, etc. of one or more heterologous molecules. In preferred embodiments, the heterologous molecule is a growth factor such as, for example, platelet-derived growth factor (PDGF), insulin-like growth factor (IGI-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-6, BMP-7, activins A and B, decapentaplegic (dpp), 60A, OP-2, dorsalin, growth differentiation factors (GDFs), nodal, MIS, inhibin-alpha, TGF-beta1, TGF-beta2, TGF-beta3, TGF-beta5, and glial-derived neutrophic factor (GDNF).

Other preferred fragments are biologically active METH1 or METH2 fragments. Biologically active fragments are those exhibiting activity similar, but not necessarily identical, to an activity of the METH1 or METH2 polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the METH1 and/or METH2 receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat disease or to bring about a particular result in a patient (e.g., blood vessel growth) by activating or inhibiting the METH1 and/or METH2/molecule. Moreover, the assays can discover agents which may inhibit or enhance the production of METH1 and/or METH2 from suitably manipulated cells or tissues. Therefore, the invention includes a method of identifying compounds which bind to METH1 and/or METH2 comprising the steps of: (a) incubating a candidate binding compound with METH1 and/or METH2; and (b) determining if binding has occurred. Moreover, the invention includes a method of identifying agonists/antagonists comprising the steps of: (a) incubating a candidate compound with METH1 and/or METH2, (b) assaying a biological activity, and (b) determining if a biological activity of METH1 and/or METH2 has been altered.

Figure 10:
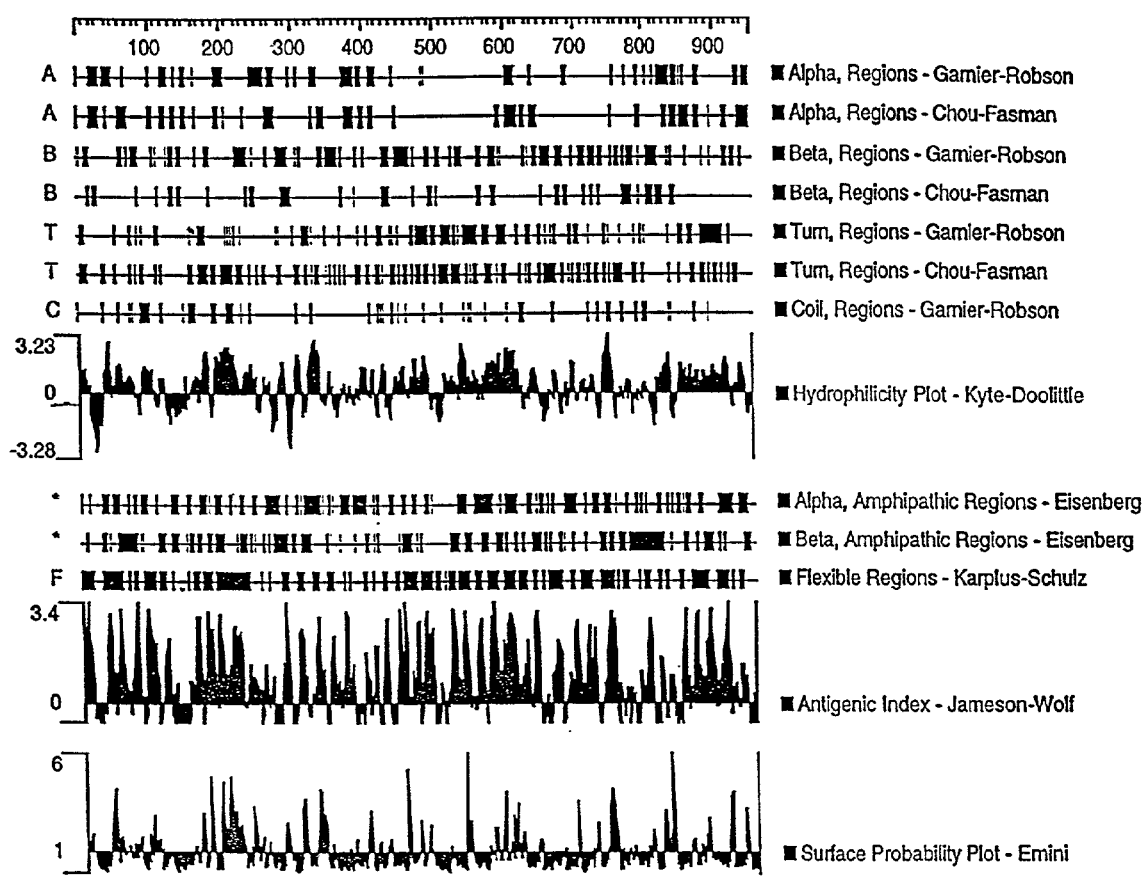
FIG. 10 shows an analysis of the METH1 amino acid sequence. Alpha, beta, turn and coil regions; hydrophilicity and hydrophobicity; amphipathic regions; flexible regions; antigenic index and surface probability are shown, and all were generated using the default settings. In the "Antigenic Index or Jameson-Wolf" graph, the positive peaks indicate locations of the highly antigenic regions of the METH1 or METH2 protein, i.e., regions from which epitope-bearing peptides of the invention can be obtained. The domains defined by these graphs are contemplated by the present invention. Tabular representation of the data summarized graphically in FIG. 10 can be found in Table 1.
Figure 11:
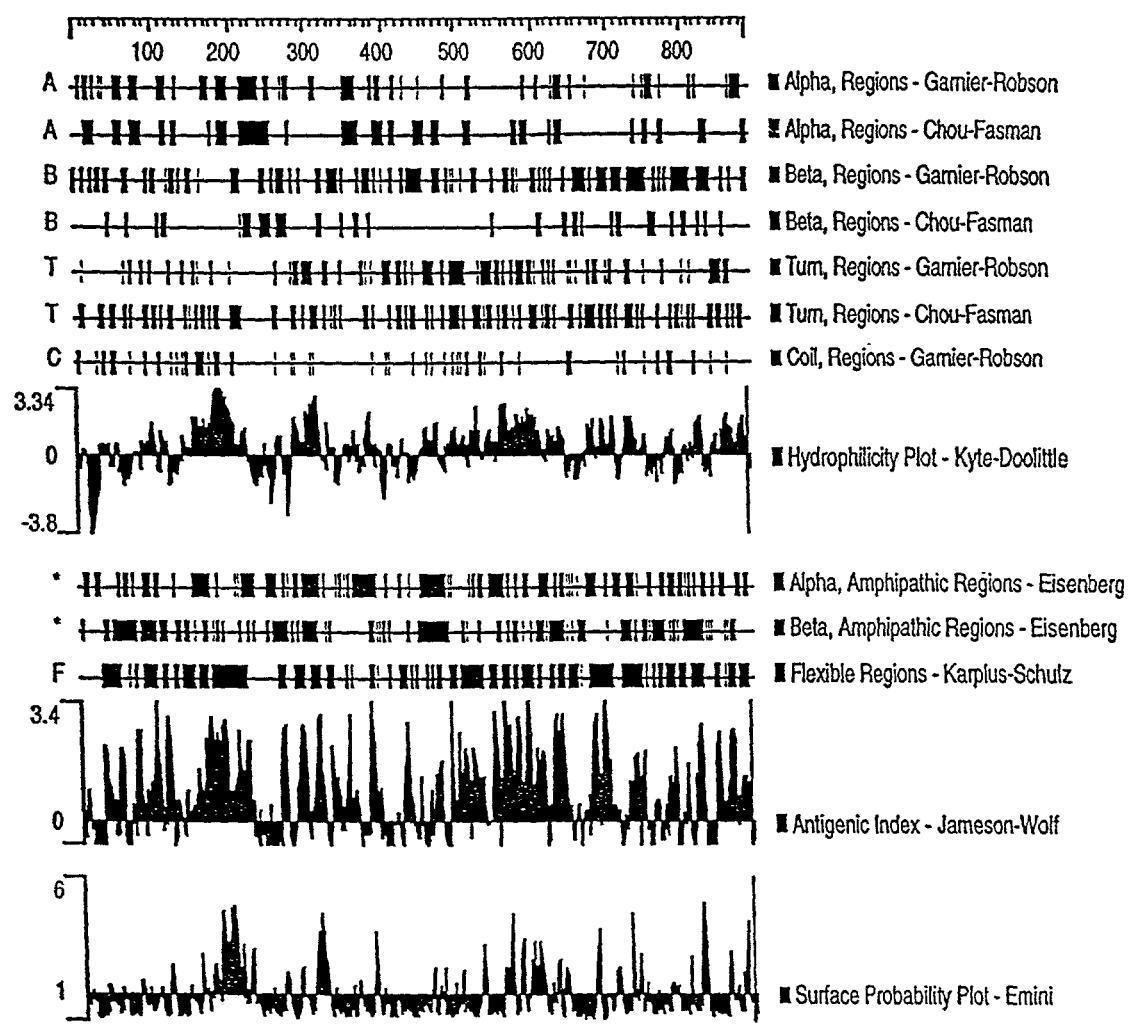
FIG. 11 shows an analysis of the METH2 amino acid sequence. Alpha, beta, turn and coil regions; hydrophilicity and hydrophobicity; amphipathic regions; flexible regions; antigenic index and surface probability are shown, and all were generated using the default settings. In the "Antigenic Index or Jameson-Wolf" graph, the positive peaks indicate locations of the highly antigenic regions of the METH1 or METH2 protein, i.e., regions from which epitope-bearing peptides of the invention can be obtained. The domains defined by these graphs are contemplated by the present invention. Tabular representation of the data summarized graphically in FIG. 11 can be found in Table 2.

Also, one could identify molecules which bind METH1 and/or METH2 experimentally by using the beta-pleated sheet regions disclosed in FIGS. 10 and 11 and Tables 1 and 2. Accordingly, specific embodiments of the invention are directed to polynucleotides encoding polypeptides which comprise, or alternatively consist of, the amino acid sequence of each beta pleated sheet regions disclosed in FIG. 10/Table 1 and FIG. 11/Table 2. Additional embodiments of the invention are directed to polynucleotides encoding METH1 and/or METH2 polypeptides which comprise, or alternatively consist of, any combination or all of the beta pleated sheet regions disclosed in FIG. 10/Table 1 and FIG. 11/Table 2. Additional preferred embodiments of the invention are directed to polypeptides which comprise, or alternatively consist of, the METH1 and/or METH2 amino acid sequence of each of the beta pleated sheet regions disclosed in FIG. 10/Table 1 and FIG. 11/Table 2. Additional embodiments of the invention are directed to METH1 and/or METH2 polypeptides which comprise, or alternatively consist of, any combination or all of the beta pleated sheet regions disclosed in FIG. 10/Table 1 and FIG. 11/Table 2.

Antisense And Ribozyme (Antagonists)

In specific embodiments, antagonists according to the present invention are nucleic acids corresponding to the sequences contained in SEQ ID NO:1 or 3, or the complementary strand thereof, and/or to nucleotide sequences contained in the deposited clones. In one embodiment, antisense sequence is generated internally by the organism, in another embodiment, the antisense sequence is separately administered (see, for example, O'Connor, J., Neurochem. 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the METH1 and/or METH2 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the METH1 and/or METH2 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding METH1 and/or METH2, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of a METH1 and/or METH2 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded METH1 and/or METH2 antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a METH1 and/or METH2 RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, *Nature* 372:333–335. Thus, oligonucleotides complementary to either the 5'- or 3'-non-translated, non-coding regions of METH1 and/or METH2 shown in FIG. 1 could be used in an antisense approach to inhibit translation of endogenous METH1 and/or METH2 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of METH1 and/or METH2 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brainbarrier (see, e.g., PCT Publication No. WO89/10134, published Apr. 25, 1988), hybridization-triggered cleavage agents. (See, e.g., Krol et al., 1988, *BioTechniques* 6:958–976) or intercalating agents. (See, e.g., Zon, 1988, *Pharm. Res.* 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, *Nucl. Acids Res.* 15:6625–6641). The oligonucleotide is a 2'-O-methylribonucleotide (Inoue et al., 1987, *Nucl. Acids Res.* 15:6131–6148), or a chimeric RNA-DNA analogue (Inoue et al., 1987, *FEBS Lett.* 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, *Proc. Natl. Acad. Sci. U.S.A.* 85:7448–7451), etc.

While antisense nucleotides complementary to the METH1 and/or METH2 coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al., *Science* 247:1222–1225 (1990). While ribozymes that cleave mRNA at site specific recognition sequences can be used to destroy METH1 and/or METH2 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585–591 (1988). There are numerous potential hammerhead ribozyme cleavage sites within the nucleotide sequence of METH1 and/or METH2 (FIGS. 1 and 2). Preferably, the ribozyme is engineered so that the cleavage recognition site is located near the 5' end of the METH1 and/or METH2 mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express METH1 and/or METH2 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous METH1 and/or METH2 messages and inhibit translation. Since ribozymes, unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Other Activities

As stated below, METH1 and METH2 share structural and sequence homology with memebrs of the ADAM family. ADAM proteins have been shown to proteolytically process membrane-anchored proteins, including TNF (Black et al., Nature 385:729 (1997); Moss et al., Nature 385:733 (1997)). Thus, METH1 and/or METH2 may be useful in proteolytic processing of membrane-anchored proteins. Membrane-anchored proteins which may be proteolytically processed by METH1 and/or METH2 include cytokines, growth factors, cytokine receptors and growth factor receptors.

METH1 or METH2 polypeptides or polynucleotides, or agonists or antagonists of METH1 and/or METH2, may also increase or decrease the differentiation or proliferation of embryonic stem cells, besides, as discussed above, hematopoietic lineage.

METH1 or METH2 polypeptides or polynucleotides, or agonists or antagonists of METH1 and/or METH2, may also be used to modulate mammalian characteristics, such as body height, weight, hair color, eye color, skin, percentage of adipose tissue, pigmentation, size, and shape (e.g., cosmetic surgery). Similarly, METH1 or METH2 polypeptides or polynucleotides, or agonists or antagonists of METH1 and/or METH2, may be used to modulate mammalian metabolism affecting catabolism, anabolism, processing, utilization, and storage of energy.

As angiogenesis is a key factor in supporting adipose tissue, METH1 or METH2 polypeptides or polynucleotides, or agonists or antagonists of METH1 and/or METH2 may be used to control weight, reduce weight, treat obesity, and/or control adipose tissue in an individual.

METH1 or METH2 polypeptides or polynucleotides, or agonists or antagonists of METH1 and/or METH2, may be used to change a mammal's mental state or physical state by influencing biorhythms, circadian rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

METH1 or METH2 polypeptides or polynucleotides, or agonists or antagonists of METH1 and/or METH2, may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Anti-angiogenesis

As shown in Examples 4 and 5, METH1 and METH2 inhibit angiogenesis. Thus, the present invention provides a method of treating an angiogenesis-related disease and/or disorder, comprising administering to an individual in need thereof a therapeutically effective amount of a METH1 and/or METH2 polynucleotide, polypeptide, and/or agonist.

For example, METH1 and/or METH2 polynucleotides, polypeptides, and/or agonists may be utilized in a variety of additional methods in order to therapeutically treat a cancer or tumor. Cancers which may be treated with METH1 and/or METH2 polynucleotides, polypeptides and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, METH1 and/or METH2 polynucleotides, polypeptides, and/or agonists may be delivered topically, in order to treat cancers such as skin cancer, head and neck tumors, breast tumors, and Kaposi's sarcoma. Within yet other aspects, METH1 and/or METH2 polynucleotides, polypeptides, and/or agonists may be utilized to treat superficial forms of bladder cancer by, for example, intravesical administration. METH1 and/or METH2 polynucleotides, polypeptides and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

METH1 and/or METH2 polynucleotides, polypeptides and/or agonists maybe useful in treating other disorders, besides cancers, which involve angiogenesis. These disorders include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating hypertrophic scars and keloids, comprising the step of administering a METH1 and/or METH2 polynucleotide, polypeptide, and/or agonist to a hypertrophic scar or keloid. Within one embodiment of the present invention METH1 and/or METH2 polynucleotides, polypeptides, and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development.

As noted above, the present invention also provides methods for treating neovascular diseases of the eye, including for example, corneal neovascularization, neovascular glaucoma, proliferative diabetic retinopathy, retrolental fibroplasia and macular degeneration, as well as other eye inflammatory diseases, ocular tumors and diseases associated with choroidal or iris neovascularization. See, e.g., reviews by Waltman et al., *Am. J. Ophthal* 85:704–710 (1978) and Gartner et al., *Surv. Ophthal.* 22:291–312 (1978).

Thus, within one aspect of the present invention methods are provided for treating neovascular diseases of the eye such as corneal neovascularization (including corneal graft neovascularization), comprising the step of administering to a patient a therapeutically effective amount of a METH1 and/or METH2 compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates.

A wide variety of disorders can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, METH1 and/or METH2 may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy.

Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself Within another aspect of the present invention, methods are provided for treating neovascular glaucoma, comprising the step of administering to a patient a therapeutically effective amount of a METH1 and/or METH2 polypeptide, polynucleotide, and/or agonist to the eye, such that the formation of blood vessels is inhibited. In one embodiment, the compound may be administered topically to the eye in order to treat early forms of neovascular glaucoma. Within other embodiments, the compound may be implanted by injection into the region of the anterior chamber angle. Within other embodiments, the compound may also be placed in any location such that the compound is continuously released into the aqueous humor.

Within another aspect of the present invention, methods are provided for treating proliferative diabetic retinopathy, comprising the step of administering to a patient a therapeutically effective amount of a METH1 and/or METH2 polynucleotide, polypeptide, and/or agonist to the eyes, such that the formation of blood vessels is inhibited. Within particularly preferred embodiments of the invention, proliferative diabetic retinopathy may be treated by injection into the aqueous humor or the vitreous, in order to increase the local concentration of the METH1 and/or METH2 polynucleotide, polypeptide, and/or agonist in the retina. Preferably, this treatment should be initiated prior to the acquisition of severe disease requiring photocoagulation.

Within another aspect of the present invention, methods are provided for treating retrolental fibroplasia, comprising the step of administering to a patient a therapeutically effective amount of a METH1 and/or METH2 polynucleotide, polypeptide, and/or agonist to the eye, such that the formation of blood vessels is inhibited. The compound may be administered topically, via intravitreous injection and/or via intraocular implants.

METH1 and/or METH2 polynucleotides, polypeptides and/or agonists may be used to treat diseases that have angiogenesis as a pathologic consequence such as cat scratch disease (Rochele minalia quintosa), ulcers (Helicobacter pylori), Bartonellosis and bacillary angiomatosis.

METH1 and/or METH2 polynucleotides, polypeptides and/or agonists may be used as a birth control agent by preventing vascularization required for embryo implantation. In one aspect of the birth control method, an amount of the compound sufficient to block embryo implantation is administered before or after intercourse and fertilization have occurred, thus providing an effective method of birth control, possibly a "morning after" method.

METH1 and/or METH2 polynucleotides, polypeptides and/or agonists may also be used in controlling menstruation or administered as either a peritoneal lavage fluid or for peritoneal implantation in the treatment of endometriosis.

METH1 and/or METH2 polynucleotides, polypeptides, and/or agonists of the present invention may be incorporated into surgical sutures in order to prevent stitch granulomas.

METHL and/or and METH2 polynucleotides, polypeptides, and/or agonists may be utilized in a wide variety of surgical procedures. For example, within one aspect of the present invention a METH1 and/or METH2 compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, METH1 and/or METH2 compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a METH1 and/or METH2 polynucleotide, polypeptide, and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, METH1 and/or METH2 polynucleotides, polypeptides, and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The METH1 and/or METH2 polynucleotides, polypeptides, and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, $\alpha,\alpha$-dipyridyl, $\beta$-aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); $\beta$-Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); $\beta$-1-anticollagenase-serum; $\alpha$2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Diagnostic Methods

The invention also relates to the use of METH1 or METH2 polynucleotides for use as diagnostic reagents. Detection of a mutated form of the METH1 or METH2 gene associated with a dysfunction will provide a diagnostic tool that can add to or define a diagnosis of a disease or susceptibility to a disease which results from under-expression, overexpression or altered expression of METH1 or METH2. Individuals carrying mutations in the METH1 or METH2 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled METH1 or METH2 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., Science 230:1242 (1985). Sequence changes at specific locations may also be revealed by nuclease protection assays, such as RNase and S1 protection or the chemical cleavage method. See Cotton et al., Proc Natl Acad Sci USA 85:4397–4401 (1985). In another embodiment, an array of oligonucleotides probes comprising METH1 or METH2 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See, for example, M. Chee et al., Science 274:610–613 (1996).

The diagnostic assays offer a process for diagnosing or determining a susceptibility to angiogenic diseases (cancer, cancer metastasis, chronic inflammatory disorders, rheumatoid arthritis, altherosclerosis, macular degeneration, diabetic retinopathy), restenosis, Alzheimer's disease and tissue remodeling through detection of mutation in the METH1 or METH2 gene by the methods described.

In addition, angiogenic diseases (cancer, cancer metastasis, chronic inflammatory disorders, rheumatoid arthritis, altherosclerosis, macular degeneration, diabetic retinopathy), restenosis, Alzheimer's disease and tissue remodeling can be diagnosed by methods comprising determining from a sample derived from a subject an abnormally decreased or increased level of the METH1 or METH2 polypeptide or METH1 or METH2 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an METH1 or METH2 polypeptide, in a sample derived from a host are well-known to those of skill in the art. Such assay methods include radioimmunoassays, competitive-binding assays, Western Blot analysis and ELISA assays.

Cancer Diagnosis and Prognosis

It is believed that certain tissues in mammals with cancer express significantly diminished levels of the METH1 or METH2 protein and mRNA encoding the METH1 or METH2 protein when compared to a corresponding "standard" mammal, i.e., a mammal of the same species not having the cancer. Further, it is believed that diminished levels of the METH1 or METH2 protein can be detected in certain body fluids (e.g., sera, plasma, urine, and spinal fluid) from mammals with cancer when compared to sera from mammals of the same species not having the cancer. Thus, the invention provides a diagnostic method useful during tumor diagnosis, which involves assaying the expression level of the gene encoding the METH1 protein in mammalian cells or body fluid and comparing the gene expression level with a standard METH1 gene expression level, whereby a decrease in the gene expression level under the standard is indicative of certain tumors. The invention also provides a diagnostic method useful during tumor diagnosis, which involves assaying the expression level of the gene encoding the METH2 protein in mammalian cells or body fluid and comparing the gene expression level with a standard METH2 gene expression level, whereby a decrease in the gene expression level under the standard is indicative of certain tumors.

Where a tumor diagnosis has already been made according to conventional methods, the present invention is useful as a prognostic indicator, whereby patients exhibiting diminished METH1 or METH2 gene expression will experience a worse clinical outcome relative to patients expressing the gene at a lower level.

By "assaying the expression level of the gene encoding the METH1 or METH2 protein" is intended qualitatively or quantitatively measuring or estimating the level of the METH1 or METH2 protein or the level of the mRNA encoding the METH1 or METH2 protein in a first biological sample either directly (e.g., by determining or estimating absolute protein level or mRNA level) or relatively (e.g., by comparing to the METH1 or METH2 protein level or mRNA level in a second biological sample).

Preferably, the METH1 or METH2 protein level or mRNA level in the first biological sample is measured or estimated and compared to a standard METH1 or METH2 protein level or mRNA level, the standard being taken from a second biological sample obtained from an individual not having the cancer. As will be appreciated in the art, once a standard METH1 or METH2 protein level or mRNA level is known, it can be used repeatedly as a standard for comparison.

By "biological sample" is intended any biological sample obtained from an individual, cell line, tissue culture, or other source which contains METH1 or METH2 protein or mRNA. Biological samples include mammalian body fluids (such as sera, plasma, urine, synovial fluid and spinal fluid) which contain secreted mature METH1 or METH2 protein, and adrenal, thyroid, stomach, brain, heart, placenta, lung, liver, muscle, kidney, pancreas, testis and ovarian tissue (for METH1); and prostate, small intestine, colon, brain and lung tissue (for METH2).

The present invention is useful for detecting cancer in mammals. In particular the invention is useful during diagnosis of the of following types of cancers in mammals: breast, ovarian, prostate, liver, lung, pancreatic, colon, and testicular. Preferred mammals include monkeys, apes, cats, dogs, cows, pigs, horses, rabbits and humans. Particularly preferred are humans.

Total cellular RNA can be isolated from a biological sample using the single-step guanidinium-thiocyanate-phenol-chloroform method described in Chomczynski and Sacchi, Anal. Biochem. 162:156–159 (1987). Levels of mRNA encoding the METH1 or METH2 protein are then assayed using any appropriate method. These include Northern blot analysis (Harada et al., Cell 63:303–312 (1990)), S1 nuclease mapping (Fujita et al., Cell 49:357–367 (1987)), the polymerase chain reaction (PCR), reverse transcription in combination with the polymerase chain reaction (RT-PCR) (Makino et al., Technique 2:295–301 (1990)), and reverse transcription in combination with the ligase chain reaction (RT-LCR).

Assaying METH1 or METH2 protein levels in a biological sample can occur using antibody-based techniques. For example, METH1 or METH2 protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)).

Other antibody-based methods useful for detecting METH1 or METH2 protein gene expression include immunoassays, such as the enzyme linked immunosorbent assay (ELISA) and the radioimmunoassay (RIA).

Suitable labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

Vaccines

Another aspect of the invention relates to a method for inducing an immunological response in a mammal which comprises inoculating the mammal with METH1 or METH2 polypeptide, or a fragment thereof, adequate to produce antibody and/or T cell immune response to protect said animal from angiogenic diseases (cancer, cancer metastasis, chronic inflammatory disorders, rheumatoid arthritis, altherosclerosis, macular degeneration, diabetic retinopathy), restenosis, Alzheimer's disease and tissue remodeling, among others. Yet another aspect of the invention relates to a method of inducing immunological response in a mammal which comprises delivering METH1 or METH2 polypeptide via a vector directing expression of METH1 or METH2 polynucleotide in vivo in order to induce such an immunological response to produce antibody to protect such animal from diseases.

Further aspect of the invention relates to an immunological/vaccine formulation (composition) which, when introduced into a mammalian host, induces an immunological response in that mammal to a METH1 or METH2 polypeptide wherein the composition comprises a METH1 or METH2 polypeptide or METH1 or METH2 gene. The vaccine formulation may further comprise a suitable carrier. Since METH1 or METH2 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Modes of administration

It is recognized than an increase in the vascular supply plays a central role in tumor progression and metastasis; therefore, inhibitors of angiogenesis can prove effective as adjuvant therapy for cancer patients. Some of the currently recognized angiogenic suppressors are poor candidates for systemic treatment due to severe collateral effect. The present inventors have found that METH1 and METH2 are potent inhibitors of angiogenesis both in vitro and in vivo. The advantage of METH1 and METH1 is that these inhibitors are normally associated with suppression of physiological angiogenesis; therefore, they offer lack of toxicity and endothelial specificity over other angiogenic inhibitors. Furthermore, METH1 and METH2 present a restricted pattern of expression providing a possible advantage on organ specificity.

Accordingly, the polypeptides of the present invention may be employed to treat cancer. The METH1 and METH2 polypeptides of the present invention can also be used to treat individuals with other disorders that are related to angiogenesis, including abnormal wound healing, inflammation, rheumatoid arthritis, psoriasis, endometrial bleeding disorders, diabetic retinopathy, some forms of macular degeneration, hemangiomas, and arterial-venous malformations.

Thus, the invention provides a method of inhibiting angiogenesis in an individual comprising administering to such an individual a pharmaceutical composition comprising an effective amount of an isolated METH1 polypeptide of the invention, effective to increase the METH1 activity level in such an individual. The invention also provides a method of inhibiting angiogenesis in an individual comprising administering to such an individual a pharmaceutical composition comprising an effective amount of an isolated METH2 polypeptide of the invention, effective to increase the METH2 activity level in such an individual.

METH1 polypeptides which may be used to inhibit angiogenesis in this manner include: METH1 polypeptide encoded by the deposited cDNA including the leader; the mature METH1 polypeptide encoded by the deposited the cDNA minus the leader (i.e., the mature protein); a polypeptide comprising amino acids about 1 to about 950 in SEQ ID NO:2; a polypeptide comprising amino acids about 2 to about 950 in SEQ ID NO:2; a polypeptide comprising amino acids about 29 to about 950 in SEQ ID NO:2; a polypeptide comprising amino acids about 30 to about 950 in SEQ ID NO:2; a polypeptide comprising the metalloprotease domain of METH1, amino acids 235 to 459 in SEQ ID NO:2; a polypeptide comprising the disintegrin domain of METH1, amino acids 460 to 544 in SEQ ID NO:2; a polypeptide comprising the first TSP-like domain of METH1, amino acids 545 to 598 in SEQ ID NO:2; a polypeptide comprising the second TSP-like domain of METH1, amino acids 841 to 894 in SEQ ID NO:2; a polypeptide comprising the third TSP-like domain of METH1, amino acids 895 to 934 in SEQ ID NO:2; a polypeptide comprising amino acids 536 to 613 in SEQ ID NO:2; a polypeptide comprising amino acids 549 to 563 in SEQ ID NO:2; a polypeptide comprising amino acids 542 to 894 of SEQ ID NO:2; and a polypeptide comprising amino acids 801 to 950 of SEQ ID NO:2.

METH2 polypeptides which may be used to inhibit angiogenesis in this manner include: the METH2 polypeptide encoded by the deposited cDNA including the leader; the mature METH2 polypeptide encoded by the deposited the cDNA minus the leader (i.e., the mature protein); a polypeptide comprising amino acids about 1 to about 890 in SEQ ID NO:4; a polypeptide comprising amino acids about 2 to about 890 in SEQ ID NO:4; a polypeptide comprising amino acids about 24 to about 890 in SEQ ID NO:4; a polypeptide comprising amino acids about 112 to about 890 in SEQ ID NO:4; a polypeptide comprising the metalloprotease domain of METH2, amino acids 214 to 439 in SEQ ID NO:4; a polypeptide comprising the disintegrin domain of METH2, amino acids 440 to 529 in SEQ ID NO:4; a polypeptide comprising the first TSP-like domain of METH2, amino acids 530 to 583 in SEQ ID NO:4; a polypeptide comprising the second TSP-like domain of METH2, amino acids 837 to 890 in SEQ ID NO:4; a polypeptide comprising amino acids 280 to 606 in SEQ ID NO:4; and a polypeptide comprising amino acids 529 to 548 in SEQ ID NO:4.

Also included are METH1 or METH2 proteins lacking TSP3; a METH1 or METH2 protein lacking TSP2 and TSP3; a METH1 or METH2 protein lacking TSP3, TSP2, and TSP1; a METH1 or METH2 protein lacking the cysteine-rich domain, TSP1, TSP2, and TSP3; a METH1 or METH2 protein lacking the metalloprotease domain, the cysteine-rich domain, TSP1, TSP2 and TSP3; and a METH1 or METH2 protein lacking the prodomain, the metalloprotease domain, the cysteine-rich domain, TSP1, TSP2, and TSP3. Finally, any combination of these domains are also preferred. For example, the cysteine-rich domain of METH1 may be combined with 1, 2, or 3 TSP domains of METH1. The cysteine-rich domain of METH2 may be combined with 1, 2, or 3 TSP domain of METH2. The metalloprotease domain and the cysteine-rich domain of METH1 may be combined with 1,2 or 3 TSP domains of METH1. The metalloprotease domain and the cysteine-rich domain of METH2 may be combined with 1,2 or 3 TSP domains of METH2. The prodomain, the metalloprotease domain, and the cysteine-rich domain of METH1 may be combined with 1,2 or 3 TSP domains of METH1. The prodomain, the metalloprotease domain, and the cysteine-rich domain of METH2 may be combined with 1,2 or 3 TSP domains of METH2. The signal sequence, the prodomain, the metalloprotease domain, and the cysteine-rich domain of METH1 may be combined with 1,2, or 3 TSP domains of METH1. The signal sequence, the prodomain, the metalloprotease domain, and the cysteine-rich domain of METH2 may be combined with 1,2, or 3 TSP domains of METH2.

As a general proposition, the total pharmaceutically effective amount of METH1 or METH2 polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the polypeptide. If given continuously, the METH1 or METH2 polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed.

Pharmaceutical compositions containing the METH1 or METH2 of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Gene Therapy Methods

Another aspect of the present invention is to gene therapy methods for treating disorders, diseases and conditions. The gene therapy methods relate to the introduction of nucleic acid (DNA, RNA and antisense DNA or RNA) sequences into an animal to achieve expression of the METH1 and/or METH2 polypeptide of the present invention. This method requires a polynucleotide which codes for a METH1 and/or METH2 polypeptide operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a METH1 and/or METH2 polynucleotide ex vivo, with the engineered cells then being provided to a patient to be treated with the polypeptide. Such methods are well-known in the art. For example, see Belldegrun, A., et al., *J. Natl. Cancer Inst.* 85:207–216 (1993); Ferrantini, M. et al., *Cancer Research* 53:1107–1112 (1993); Ferrantini, M. et al, *J. Immunology* 153:4604–4615 (1994); Kaido, T., et al., *Int. J. Cancer* 60: 221–229 (1995); Ogura, H., et al., *Cancer Research* 50:5102–5106 (1990); Santodonato, L., et al., *Human Gene Therapy* 7:1–10 (1996); Santodonato, L., et al., Gene Therapy 4:1246–1255 (1997); and Zhang, J.-F. et al., *Cancer Gene Therapy* 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the METH1 and/or METH2 polynucleotide constructs can be delivered by any method that delivers injectable materials to the cells of an animal, such as, injection into the interstitial space of tissues (heart, muscle, skin, lung, liver, and the like). The METH1 and/or METH2 polynucleotide constructs may be delivered in a pharmaceutically acceptable liquid or aqueous carrier.

In one embodiment, the METH1 and/or METH2 polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the METH1 and/or METH2 polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The METH1 and/or METH2 polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of METH1 and/or METH2 DNA. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs;

the b-actin promoter; and human growth hormone promoters. The promoter also may be the native promoter for METH1 and/or METH2.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The METH1 and/or METH2 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked METH1 and/or METH2 DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the METH1 and/or METH2 polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., *Proc. Natl. Acad. Sci. USA* (1987) 84:7413–7416, which is herein incorporated by reference); mRNA (Malone et al., *Proc. Natl. Acad. Sci. USA* (1989) 86:6077–6081, which is herein incorporated by reference); and purified transcription factors (Debs et al., *J. Biol. Chem.* (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., *Proc. Natl Acad. Sci. USA* (1987) 84:7413–7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., *Proc. Natl. Acad. Sci. USA* 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., *Methods of Immunology* (1983), 101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., *Biochim. Biophys. Acta* (1975) 394:483; Wilson et al., *Cell* (1979) 17:77); ether injection (Deamer, D. and Bangham, A., *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); detergent dialysis (Enoch, H. and Strittmatter, P., *Proc. Natl. Acad. Sci. USA* (1979) 76:145); and reverse-phase evaporation (REV) (Fraley et al., *J. Biol. Chem.* (1980) 255:10431; Szoka, F. and Papahadjopoulos, D., *Proc. Natl. Acad. Sci. USA* (1978) 75:145; Schaefer-Ridder et al., *Science* (1982) 215:166), which are herein incorporated by reference.

Generally, the ratio of DNA to liposomes will be from about 10:1 to about 1:10. Preferably, the ration will be from about 5:1 to about 1:5. More preferably, the ratio will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/29469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/29469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding METH1 and/or METH2. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+en-vAm12, and DAN cell lines as described in Miller, *Human Gene Therapy* 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding METH1 and/or METH2. Such retroviral vector particles then may be employed, to transduce eukaryotic cells, either in vitro or in vivo. The transduced eukaryotic cells will express METH1 and/or METH2.

In certain other embodiments, cells are engineered, ex vivo or in vivo, with METH1 and/or METH2 polynucleotide contained in an adenovirus vector. Adenovirus can be manipulated such that it encodes and expresses METH1 and/or METH2, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) *Am. Rev. Respir. Dis.* 109:233–238). Finally, adenovirus mediated gene transfer has been demonstrated in a number of instances including transfer of alpha-1-antitrypsin and CFTR to the lungs of cotton rats (Rosenfeld, M. A. et al. (1991) *Science* 252:431–434; Rosenfeld et al., (1992) *Cell* 68:143–155). Furthermore, extensive studies to attempt to establish adenovirus as a causative agent in human cancer were uniformly negative (Green, M. et al. (1979) *Proc. Natl. Acad. Sci. USA* 76:6606).

Suitable adenoviral vectors useful in the present invention are described, for example, in Kozarsky and Wilson, *Curr. Opin. Genet. Devel.* 3:499–503 (1993); Rosenfeld et al., *Cell* 68:143–155 (1992); Engelhardt et al., *Human Genet. Ther.* 4:759–769 (1993); Yang et al., *Nature Genet.* 7:362–369 (1994); Wilson et al., *Nature* 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., *Curr. Topics in Microbiol. Immunol.* 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The METH1 and/or METH2 polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the METH1 and/or METH2 polynucleotide construct. These viral particles are then used to transduce eukaryotic cells, either ex vivo or in vivo. The transduced cells will contain the METH1 and/or METH2 polynucleotide construct integrated into its genome, and will express METH1 and/or METH2.

Another method of gene therapy involves operably associating heterologous control regions and endogenous polynucleotide sequences (e.g. encoding METH1 and/or METH2) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:8932–8935 (1989); and Zijlstra et al.,*Nature* 342:435–438(1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the METH1 and/or METH2 desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous METH1 and/or METH2 sequence is placed under the control of the promoter. The promoter then drives the expression of the endogenous METH1 and/or METH2 sequence.

The polynucleotides encoding METH1 and/or METH2 may be administered along with other polynucleotides encoding other proteins. Such proteins include, but are not limited to, acidic and basic fibroblast growth factors, VEGF-1, VEGF-2, VEGF-3, VEGF-E, PlGF 1 and 2, epidermal growth factor alpha and beta, platelet-derived endothelial cell growth factor, platelet-derived growth factor alpha and beta, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding METH1 and/or METH2 contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., *Science* 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., *Proc. Natl. Acad. Sci. USA* 189: 11277–11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a METH1 or METH2 protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Other mapping strategies that can similarly be used to map to its chromosome include radiation hybrid mapping, prescreening with labeled flow-sorted chromosomes and preselection by hybridization to construct chromosome specific-cDNA libraries. Radiation hybrid (RH) mapping relies upon fragmentation of human chromosomes with X-rays, and retention of these random fragments in Hamster A23 host cells. The DNAs for RH mapping are supplied by Research Genetics (USA). Oligo pairs are designed from EST sequences that will amplify products of between 80 bp and 300 bp. The PCRs are performed on 93 human/hamster hybrid DNAs and the results compared with a framework map (http://www-genome.wi.mit.edu/cgi-bin/contig/rhmapper.pl; Gyapay et al., *Human Molecular Genetics* 5:39–346 (1996)). RH mapping provides greater precision than FISH and indicates clusters of genes as well as disease locus/gene correlations.

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

The METH1 gene maps between STS markers D21S1435 and D21S1442 which translates as 21q21. This is a similar chromosomal location to amyloid precursor protein (APP). APP and METH1 are approximately 3 million bases apart which is not a massive distance in human genomics. The chromosomal location includes important genes such as enterokinases (enzymes that activate trypsinogen by converting it to trypsin) and genes responsible for Alzheimer's disease.

The METH1 gene can be mapped to 21q21 using the following oligos for radiation hybrid mapping:

```
5' primer:      ACTGTGTGTGATCCGAG
3' primer:      GTTGGAAAGCATTGACG
```

Having generally described the invention, the same will be more readily understood by reference to the following examples, which are provided by way of illustration and are not intended as limiting.

EXAMPLES

Example 1

Identification and Cloning of METH1 and METH2

To search for novel genes with TSP-like domains, a large human cDNA database consisting of approximately 900,000 expressed sequence tags (ESTs) was screened for sequences homologous to the second type I repeat of TSP1. Several ESTs were predicted to encode proteins with TSP-like domains. Two cDNA clones originated from human heart and lung libraries were further sequenced and chosen for functional analysis.

The amino-terminal end of METH1 was obtained using 5' rapid amplification of cDNA ends (RACE) PCR technique (Marathon cDNA amplification kit, Clontech) according to manufacturer instructions. The amino-terminal end of METH2 was obtained partially through 5'RACE PCR and later confirmed and completed by genomic screening. For the genomic screen, BAC clones (Genome Systems) were initially identified by PCR. Positive BAC clones containing 150–200 bp of sequence were subsequently subcloned into pGEM vector as small fragments and sequenced.

Analysis and comparison of the deduced amino acid sequence with the GenBank, EMBL and SwissProt databases suggested that these genes belong to a new family of metalloproteases with homology to the reprolysin family in their NH2-terminal end and with several TSP-like motifs in the COOH-terminal end. These cDNAs were named METH1 and METH2; ME, for metalloprotease and TH, for thrombospondin. The mouse homologue of METH1 was identified and named ADAMTS1 (Kuno, K., et al., *J. Biol. Chem.* 272:556–562 (1997)). Direct comparison of the human and mouse sequences revealed a high level of conservation (83.4% amino acid identity). Thus far no homologues for METH2 have been identified.

Interestingly, a recently identified protein named pNPI (procollagen IN-proteinase; (Colidge, A., et al., *Proc. Natl. Acad. Sci. USA* 94:2374–2379 (1997)) showed a striking sequence and structural similarity to METH1 and METH2 (FIG. 3). As the novel proteins described here, pNPI also contains metalloproteinase (reprolysin subfamily) and TSP domains at the carboxy-terminal end. Although the sequence for pNPI is of bovine origin, sequence alignment revealed identical structural features. The amino acid similarity between METH1 and METH2 is 51.7%, and between METH1 or METH2 and pNPI the homology is lesser 33.9% and 36.3%, respectively.

Sequence analysis showed that the ORF of METH1 and METH2 coded for proteins of 950 and 890 amino acids, respectively. In all three proteins, the $NH_2$ terminal end contains a putative signal peptide followed by another putative transmembrane domain around amino acid 300, deduced from the hydrophilicity plots. It is not clear whether these proteins are bound to the membrane. However, given preliminary data, it is more likely that this second transmembrane domain will consist of a hydrophobic pocket and that METH1, METH2 and pNPI are in fact secreted proteins. The $NH_2$-terminal end past the signal peptide has homology to the superfamily of zinc metalloproteases and can be subdivided in a prodomain, a metalloprotease domain, and a cysteine-rich region.

The double underlined sequence in METH1 (amino acids 232–235) and METH2 (amino acids 211–214) in FIG. 3 localized at the boundary between the prodomain and the metalloprotease domain, are potential cleavage sites for mammalian subtilisins, such as furins (Barr, 1991). Proteolytical processing occurs in SVMPs to yield soluble metalloproteases and disintegrins (Bjarnason, J. B. & Fox, J. W., *Methods Enzymol.* 248:345–368 (1995)) and has also been detected in some ADAMs (reviewed by Wolsberg, T. G. & White, J. M., *Developmental Biology* 180:389–401 (1996)). Proteolytical processing occurs in both METH1 and 2 (see below). Additionally, both METH1 and METH2 present a $Zn^{2+}$-binding site (dotted line in FIG. 3) that is presumed to be catalytically active due to the conservation of certain functionally important amino acids (Rawlings, N. D. & Barrett, A. J., *Methods Enzymol.* 248:183–228 (1995)) suggesting that these proteins may be active proteases.

Following the metalloprotease domain, there is a cysteine-rich region which contains two putative disintegrin loops (Wolsberg, T. G. & White, J. M., *Developmental Biology* 180:389–401 (1996)) (marked by arrows in FIG. 3). Disintegrin domains are found within the superfamily of metalloproteases in snake venom metalloproteases (SVMPs) and ADAMs (mammalian proteins containing a disintegrin and a metalloprotease domain) and have a possible function inhibiting binding of integrins to their ligands in SVMPs. Conversely, the ADAM-disintegrin-like domain, as part of membrane anchored proteins, may promote rather than disrupt, cell-cell interactions (Wolsberg, T. G. & White, J. M., *Developmental Biology* 180:389–401 (1996)). The TSP-like domains are located in the COOH-half of METH1 and METH2 proteins. METH1 contains two conserved TSP domains separated by a spacer region with unknown function, and a subdomain with less homology, and only 5 cysteines, following the second anti-angiogenic region. METH2 contains two TSP domains separated by the spacer region. The alignment of the TSP-like domains of METH1 and METH2 with those of TSP1 and TSP2 are shown in FIG. 5. The homology varies between 19.2% to 52% amino acid similarity among all the TSP repeats. The cysteines, numbered 1 to 6, and the tryptophans, labeled by asterisks, are highly conserved.

Southern blot of human genomic DNA revealed the presence of METH1 and METH2 in the genome. METH1 and METH2 probes revealed bands of different size suggesting that they are transcribed from different genes.

The consensus sequence for the type I repeats includes 16 residues with 6 perfectly conserved cysteines. Typically it begins with the sequence motif WSXWS (SEQ ID NO:82) that has also been shown to bind to heparin (Guo, N., et al., *J. Biol. Chem.* 267:19349–19355 (1992)). The affinity of this region to heparin has been proposed to the part of the anti-angiogenic activity of TSP-1 (Guo, N., et al., *J. Peptide Res.* 49 (1997)). Among the five members of the TSP family of proteins, only TSP-1 and TSP-2 inhibit angiogenesis and contain the type I repeats (Tolsma, S. S., et al., *J. Cell. Biol.* 122:497–511 (1993); Kyriakides, T. R., et al, *J. Cell Biol.* 140:419–430 (1998)). The type I or properdin repeats were probably added to the precursor of TSP1 and 2 by exon shuffling between 500 and 900 million years ago (Adams, J., et al., *The Thrombospondin Gene Family*, 1 Ed. Molecular Biology Intelligence Unit (Springer, Ed.), R. G. Landes Company, Germany (1995)). It is likely that the acquisition of this domain provided the precursor of TSP1 and TSP2 with functions, such as regulation of new vessel formation. More recently, BAI-1 (brain angiogenic inhibitor-1), a protein isolated from a brain library for its ability to be regulated by p53, has also been shown to contain the type I repeat of TSP-1 and to provide anti-angiogenic potential to this molecule (Nishimori, H., et al., *Oncogene* 15:2145–2150 (1997)). Nevertheless, it appears that additional sequences or context are also important, since other proteins containing the type I repeats appear not to have clear or more established anti-angiogenic properties such as: properdin, F-spondin, and other members of the complement family.

Because of the presence of TSP-repeats in METH1 and METH2, along with their anti-angiogenic properties, these proteins were originally considered members of the TSP superfamily. Nevertheless, they have no additional homology to other TSPs, and in fact, the similarity to TSP1 and TSP2 is restricted to the type I repeats. Furthermore, the proteins also have strong sequence and structural homology to members of the ADAM family. These features led Kuno and colleagues to name ADAMTS to the mouse homolog of METH1 (Kuno, K., et al., *J. Biol. Chem.* 272:556–562 (1997)). The recent identification of pNPI and its striking sequence homology to the proteins here described, prompt all these three proteins to be grouped in a subfamily named metallospondins. At this point, it is not clear whether pNIP has anti-angiogenic properties or whether METH1 and/or METH2 participate in the cleavage of the amino terminal pro-peptide of α1(I) procollagen.

Example 2

Northern and Southern Blot Analysis

Total RNA was purified from cells by guanidinium-isothiocyanate extraction, as previously described (Chomczynski, P. & Sacchi, N., *Anal. Biochem.* 162:156–159 (1987)) Poly(A)+RNA was extracted using a Boehringer Mannheim (BMB, Indianapolis, Ind.) kit according to the manufacturer conditions. Other poly(A)+RNA blots were purchased from Clontech (Palo Alto, Calif.). Pre-hybridization was performed in a solution containing: 50% formamide, 6×SSPE, 1× Denhardt's solution, 0.1% SDS and 100 µg/ml of heat denatured salmon sperm DNA for 12–18 h at 42° C. Hybridization with labeled cDNA probes proceeded in the same solution at 42° C. for 12–18 h. TSP1 and METH1 probes corresponded to the entire human cDNAs. The METH2 probe corresponded to a KpnI-EcoRI fragment from the human cDNA. A 1.3 Kb PstI fragment of the glyceraldehyde-3-phosphate-dehydrogenase (GPDH) was used to normalize for loading and transfer efficiency. Membranes were exposed to Kodak Biomax MS film (Kodak, New Haven, Conn.).

For Southern blots, human genomic DNA, purchased from Promega (Madison, Wis.), was heated at 65° C. for 10 min and digested with EcoRI and PstI overnight at 37° C. 5 µg of digested DNA was separated in a 1% agarose gel, transferred to a nytran membrane and cross-linked by ultraviolet light. cDNA probes, as well as, prehybridization and hybridization conditions were identical to those described for Northern blots. Blots were washed with high stringency (0.2×SSC, 0.2% SDS at 50° C.).

The expression patterns of METH1 and METH2 were examined in both adult and embryonic tissues. Northern blot analysis was performed under high-stringency conditions with blots that included poly(A)+RNA from human tissues. METH1 and METH2 transcripts revealed a single band of 4.6 and 3.7 Kb, respectively. Abundant METH1 mRNA expression was observed in adrenal, heart, placenta, followed by skeletal muscle, thyroid and stomach. From the embryonic tissues analyzed, kidney showed the highest expression of METH1 mRNA. Nevertheless, weaker expression of METH1 mRNA was seen in all tissues analyzed. Distribution of METH2 mRNA was more restricted and weaker than that of METH1. The highest expression was seen in lung, both embryonic and adult. Interestingly, METH1 and METH2 expression do not appear to overlap. In combination, the structural similarities and their pattern of expression suggest functional redundancy yet different transcriptional regulation. The expression levels of TSP1 transcripts in the same blots were also analyzed, for purpose of comparison. TSP1 mRNA highest expression was seen in the adult placenta and in all embryonic tissues analyzed. In contrast to METH1 and METH2 we observed constant levels of TSP1 transcript in all the other tissues examined.

The cell type distribution was also studied by Northern blot analysis of poly(A)+RNA. METH1 mRNA was detectable, at low levels, in dermal fibroblasts, vascular smooth muscle, endometrial stromal cells, and in two cancer cell lines, HeLa and G631, an adenocarcinoma and a melanoma, respectively. METH2 mRNA was detected only on SW480, a colon carcinoma cell line, but no expression was seen in any other of the cell lines or primary strains analyzed.

The possibility that groups of angiogenic and anti-angiogenic factors regulate vascular network formation in specific organs has been a frequently discussed hypothesis likely to be true, yet unproven. The expression patterns of METH1 and METH2, which are clearly distinct and almost non-overlapping, were puzzling, at least with concern to overall levels. TSP1 and TSP2 also share identical structure, high level of amino acid similarity, yet their pattern of expression differs significantly (Iruela-Arispe, M. L., *Dev. Dyn.* 197: 40–56 (1993)). The differences are likely based on dissimilar cis-acting elements in their promoters and different regulatory mechanisms, as previously suggested. Although the promoters for METH1 and 2 have not been characterized, it is likely that they provide unique features for the regulation of each gene. Nevertheless, the possibility that one motif, the anti-angiogenic/type I repeat, with demonstrated anti-angiogenic properties is present in several proteins with different tissue specificities is appealing. Alternatively, the small differences in sequence between closely related members of the same family could possess significance that goes beyond functional redundancy. In the case of TSP1 and TSP2, aside from the striking structural similarities and perhaps having functionally common anti-angiogenic properties, TSP1 and TSP2 also appear to display functions of their own and not likely shared by their similar relative. This became evident with the outcome of the two knock-outs for these genes. TSP1 null animals exhibited primarily lung disorders (Lawler, J., et al., *J. Clin. Invest.* 101:982–992 (1998)) and secondarily vascular abnormalities, but only under specific pathological settings or on a restricted set of organs. In contrast TSP2 knock-out mice exhibited unpredicted collagen assembly anomalies, with carry-on consequences to the skin, tendons, and bone (Kyriakides, T. R., et al., *J. Cell Biol.* 140:419–430 (1998)). In addition, these animals also appear to have overall increase in capillary density in the dermis. It is not understood how the resemblance between the newly described members of the metallospondin family translate functionally. Clearly, pNIP has been shown to display active proteolytic activity by cleaving the N-terminus of type I procollagen (Colidge, A., et al., *Proc. Natl. Acad. Sci. USA* 94:2374–2379 (1997)).

A second region of functional interest corresponds to the disintegrin domain. This domain has been more fully characterized in related members of the snake venom metalloproteases that have been shown to bind to αIIbβ3 and inhibit platelet interaction blocking coagulation (Pfaff, M., et al., *Cell Adhes Commun.* 2:491–501 (1994); Usami, Y., et al., *Biochem. Biophys. Res. Commun.* 201:331–339 (1994)). The disintegrin motif consists of a thirteen to fifteen domain which frequently contain an RGD or a negatively charged residue at the position of the aspartic acid. The RGD, or equivalent, binds to integrins and serve as antagonist or signaling ligands (Wolsberg, T. G. & White, J. M., *Developmental Biology* 180:389–401 (1996)). METH2, but not METH1, has an RGD sequence located amino-terminal to the disintegrin domain. In addition, both molecules present relatively high, but not perfect, degree of conservation of cysteines within the disintegrin motif. This appears to display an important role in the tertiary structure of this region and its ability to interact with integrins. In addition, some of these domains have been shown to act as functional adhesion molecules, particularly those with transmembrane regions (Wolsberg, T. G. & White, J. M., *Developmental Biology* 180:389–401 (1996)). It is unlikely that this will be the case for METH1 and METH2, since both these proteins appear to be secreted.

Example 3

Expression and Purification of Recombinant Proteins

Recombinant constructs for expression of His-tagged fusion proteins were generated for expression in bacteria. METH1 nt 605–1839 (from ATG) was amplified by polymerase chain reaction using primers containing BamHI and PstI sites and subcloned into the pRSET vector (Invitrogen, Carlsbad, Calif.). The construct was sequenced to verify frame and sequence fidelity and were then transformed into BL21;DE3 *E. Coli* strain (Stratagene Cloning Systems, La Jolla, Calif.). Purification was performed by affinity chromatography on Ni-NTA columns. Recombinant protein was eluted with 500 mM imidazole in PBS. Fractions containing recombinant protein were dialyzed against phenol-red free DMEM and used to generate antisera.

Antisera was generated by intramuscular injection of a 1:1 mixture of recombinant protein (500 μg/ml) and Freud's adjuvant. Eight animals, including five guinea pigs and three rabbits were injected every 15 days for three cycles. After the third injection, serum was evaluated for presence of anti-METH1 antibodies, only two of the guinea pigs showed significant titers. The antibodies recognized recombinant protein on Western blots, were able to immunoprecipitate METH1 protein from cell extracts and recognize the protein by immunocytochemistry. Pre-immune sera was always included as control. One of the guinea pig antibodies was also able to recognize METH2.

For mammalian expression, full-length METH1 and METH2 cDNA were cloned into pcDNA3.1 expression vector (Invitrogen). The vector is under the regulatory control of the CMV promoter. Cloning was performed so that constructs contained their own termination codons.

Recombinant protein was obtained by transient transfection of the expression vectors in 293T cells using standard calcium phosphate precipitation. Upon transfection, cells were incubated for 6 to 16 h in serum-containing media and then switched to serum-free media for 36 h for accumulation of recombinant protein. As control, pcDNA3.1 vector alone was transiently transfected in parallel plates. Purification of the protein included 30% ammonium sulfate precipitation followed by dialysis on HS buffer (DB=10 mM HEPES, 150 mM NaCl, 1 mM $CaCl_2$ and 1 mM $MgSO_4$). Samples were then subjected to heparin-affinity chromatography. Elution from heparin columns was achieved with HS buffer containing 550 mM NaCl. Fractions were then loaded on 5–30% sucrose gradients and spun at 48K. Separation on sucrose gradients was assessed by Western blotting and purity was determined by Commmassie blue and silver nitrate staining.

Generation of recombinant protein was initially done in bacteria. A METH1 expression vector was generated containing an amino terminal His Tag to aid on the purification. The resulting protein coded for all METH1 translated sequence except the prodomain. Affinity chromatography on $Ni^{++}$-beads showed an unique band of 68 kD. Isolation and purification was always performed under denatured conditions and attempts to refold the protein met with little success, probably due to a significant number of intramolecular disulfide bonds associated with the large number of cysteines. Nonetheless, the protein was used to generate antibodies. From eight animals injected, only two were able to mount an immune response and generate specific antibodies, possibly due to the high conservation across species. Both antibodies recognized recombinant METH1 protein before and after purification on $Ni^{++}$ columns. The antibody was also used to evaluate expression of the protein on Western blots of cell lysates. A single band of approximately 105–110 kD was detected in stromal fibroblasts and smooth muscle cells.

To test the hypothesis that METH1 and METH2 could function as regulators of angiogenesis, recombinant full length protein was generated in mammalian cells. Evaluation of correct reading frame and molecular weight was initially tested by in vitro translation. Translation of the METH-1 open reading frame revealed a 110 kD protein, slightly higher than the size predicted by translation of the cDNA sequence. As previously indicated, there are two putative glycosylation sites, the higher size of the protein is likely due to addition of sugar residues. Similarly, METH2 was also slightly higher than its predicted size, showing a 98 kD protein.

Recombinant proteins were isolated from 293T supernatants under native conditions to preserve secondary structure. From analysis of the deduced amino acid sequence and published information on the murine homolog, ADAMTS, it was predicted that both proteins could bind to heparin and used affinity chromatography for purification. Both cell layer and conditioned media of 293T cells transfected with METH1, METH2 and vector control were used for purification. The molecular weight of METH1 and 2 were similar to those from the reticulocyte lysate. As predicted, both proteins are secreted. Interestingly, the media contains both full length (110 kD) and two processed forms of 85 and 67 kD for METH1, and 79 and 64 kD for METH2. The 85 and 79 kD molecular weights agree with the predicted size for both proteins after cleavage at the consensus sublisin site. However, a second processing event must take place to generate the most abundant fragments observed at 67 and 64 kD respectively. These forms are stable after purification even in the absence of proteinase inhibitors. For purification, proteins were initially concentrated by ammonium sulfate precipitation, followed by dialysis. The resulting protein suspension was then subjected to heparin-sepharose columns. Recombinant METH1 and METH2 were eluted with washing buffer containing 550 mM NaCl. Fractions contained both pro-METH1, as well as the processed forms. Because it was unclear whether processing was relevant for function of the proteins, both forms were separated on sucrose gradients. Both full-length and processed forms were used in angiogenesis assays.

Recombinant constructs for expression of truncated fusion proteins were as follows: (1) pRSET-METH1-Type I: METH1 nt 1605–1839 (from the start codon) was amplified by polymerase chain reaction using the following primers: 5'-GCA TTT TGG ATC CGC CTT TTC ATG-3' (SEQ ID NO:78) and 5'-GTT GTG TGC TGC AGA TTG TTC C-3' (SEQ ID NO:79). The amplified fragment was then subcloned into the BamHI and PstI sites of the pRSET vector; (2) pGEX-METH1-TSP was generated by ligating the BamHI-EcoRI fragment from the pRSET-METH1-TSP into the SmaI site of the pGEX-5X vector (Pharmacia Biotech Inc., Piscataway, N.J.) by blunt-end ligation; (3) pGEX-1.0-METH2: the fragment nt 838–1818 of METH2 cDNA (from the start codon) was ligated into BamHI-EcoRI sites of pGEM-2TK. The METH2 fragment was amplified by PCR using the following primers: 5'-GAAAAATGGGGATC-CGAGGTG-3' (SEQ ID NO:80) and 5'-GCAGGAGAAT-TCCGTCCATG-3' (SEQ ID NO:81) to generate BamHI and EcoRI restriction sites; (4) pGEX-METH2-TSP: a 0.5 Kb XmaI-EcoRI fragment isolated from pGEX-1.0-METH2 was subcloned into the XmaI and EcoRI sites of pGEX-2TK vector. All constructs were sequenced to verify sequence fidelity and correct open reading frame.

The recombinant proteins were named 6H-METH1, the recombinant protein expressed with the plasmid pRSET-METH1-TSP, GST-METH1, the protein expressed with the plasmid pGEX-METH1-TSP and GST-METH2, the protein expressed with the plasmid pGEX-METH2-TSP.

Expression plasmids were transformed into BL21:DE3 E. coli strain (Stratagene Cloning Systems, La Jolla, Calif.) and fusion proteins were induced following manufacturer recommendations. Briefly, induced bacteria pellets were resuspended in PBS and sonicated on ice for 1 min. The suspension was, subsequently, incubated at RT for 20 min in the presence of 1% triton X-100 and centrifuged at 4° C. Histidine tagged fusion proteins were then purified on Ni-NTA beads (Qiagen, Chatsworth, Calif.) by incubating 20 ml of supernatant with 1 ml of beads (50% slurry) for 2 h at 4° C. The suspension was transferred into a column and washed with 10 columns volume of PBS containing 10 mM imidazole, followed by 50 mM imidazole and finally 100 mM imidazole. The protein was eluted with 500 mM imidazole in PBS. Fractions containing the recombinant protein were dialyzed against phenol-red free DMEM. Samples were centrifuged for 30 min at 4° C., part of the protein was not soluble and was lost during centrifugation. The supernatant was stored at −70° C. and used for proliferation, cornea pocket and chorioallantoic membrane (CAM) assays.

For purification of GST-fusion proteins, the extract was cleared by centrifugation and applied to a GST-affinity column (Pharmacia). The column was washed with PBS-1% triton X-100 in the presence of 0.1 mM reduced glutathione and, subsequently, with the same buffer in the presence of 0.5 mM reduced glutathione. Fusion proteins were eluted with 10 mM reduced glutathione in 50 mM Tris-HCl, pH 7.5. Fractions containing the protein were dialyzed against DMEM, stored at −70° C. and used for proliferation, cornea pocket and chorioallantoic membrane (CAM) assays.

Integrity and purity of recombinant proteins was analyzed in 12.5% or 15% acrylamide gels stained with Coomassie blue.

A recombinant GST fusion protein containing the first two type I repeats of TSP was also dialyzed against DMEM before used in functional assays. Intact TSP1 was purified from platelets as previously described (Roberts, D. D., et al., *J. Tissue Cult. Methods* 16:217–222 (1994)).

To test the hypothesis that METH1 and METH2 TSP domains could function as regulators of angiogenesis recombinant fusion proteins were generated in bacteria. The constructs included the first TSP domain of METH1 or METH2. This domain is the most conserved, 52% amino acid similarity with the second type I repeat of TSP1, (this domain contains a putative binding site for CD36). All recombinant proteins were isolated under native conditions to preserve their secondary structure as much as possible. 6H-METH1 and GST-METH1 contained the first TSP-like domain of METH1 fused to a histidine tag or a GST, respectively. METH1 recombinant protein was made with two different tags because of purification and structural advantages. The differences in size are due to the size of the tag, 6 KDa the histidine and 27 KDa the GST. GST-METH2 contained the first TSP domain of METH2 also fused to a GST. A fragment corresponding to the last two type I repeats of TSP1, also fused to a GST, and intact TSP1 purified from platelets were used as positive controls. In addition, GST alone was included in all experiments as negative control.

Example 4

TSP Domains in METH1 and METH2 Disrupt Angiogenesis In Vivo

Cornea Pocket Assay

Swiss Webster females and males, were purchased from Charles River (Boston, Mass.) and used between 8–10 weeks-old for implantation of the pellets. Cornea pockets were performed as described by Kenyon and colleagues (Kenyon, B. M., et al., *Invest. Ophthalmol. Vis. Sci.* 37:1625–1632 (1996)) with few modifications. Briefly, a solution of 10 μg of recombinant bFGF plus 5 mg of sucralfate were mixed with 10 μl of Hydron (200 mg/ml in ethanol; New Brunswick, N.J.) and the recombinant protein of interest (2 μg). The suspension was then smeared onto a sterile nylon mesh square (pore size 500 μm; Tetko Inc., Briarcliff Manor, N.Y.) and allowed to dry for 30 min. The fibers of the mesh were pulled to produce pellets of 500 μm³ that were stored at −20° C. Uniformly sized pellets were selected under a microscope and used for the assays.

Mice were anesthetized with Avertin. An incision was made in the cornea using a Nikon SMZ-U dissecting microscope with the aid of a surgical blade. A single pellet was implanted into the pocket. Five days after pellet implantation, corneal angiogenesis was evaluated and photographed.

CAM Assay

Chorioallantoic membrane assays were performed on Leghorn chicken embryos (SPAFAS, MA) at 12–14 days of embryonic development. Matrigel (750 μg/ml), VEGF (250 ng/mesh) and the protein or peptide to be tested were mixed, placed onto nylon meshes (pore size 250 μm; Tetko Inc.) and incubated sequentially at 37° C. for 30 min and at 4° C. for 2 h to induce polymerization. A positive (matrigel and VEGF) and a negative (VEGF alone) control were also prepared for each CAM. Polymerized meshes were placed onto the third outer region of the CAM and incubated for 24 h. To visualize vessels, 400 μl of fluorescein isothiocyanate dextran (10 mg/ml, SIGMA) was injected in the chick blood stream. After 5–10 min incubation, the chick was topically fixed with 3.7% formaldehyde for 5 min. The meshes were then dissected and mounted onto slides. Fluorescence intensity was analyzed with a computer-assisted image program (NIH Image 1.59).

Peptides used on these assays were synthesized by Chiron (Raleigh, N.C.). Sequence corresponded to amino acids: P-TSP1, 430–447; P-METH1, 549–563; P-METH2, 529–548.

The evaluation of angiogenic or anti-angiogenic responses relies heavily on the sensitivity and specificity of the assays used to assess the response. To evaluate the anti-angiogenic activity of these fragments in vivo, two popular and well-accepted angiogenesis assays were used: the corneal pocket and the chorioallantoic membrane. The visibility, accessibility, and avascularity of the cornea are highly advantageous and facilitate the visualization of the neovascular response and the topical application of the test substances. A known amount of angiogenesis factor(s) is implanted, as a pellet, in a pocket made in the cornea eye. To test an angiogenesis inhibitor, the molecule is implanted with the stimulator in the same pellet, and the response is compared to the stimulator alone.

In these experiments, bFGF was used as the vascularization stimulator. Pellets containing the recombinant protein were implanted in mouse corneas and their ability to inhibit the bFGF-induced angiogenic response was compared to that of controls. When a bFGF pellet containing GST was implanted new capillary vessels grew from the cornea limbus, across the cornea and into the pellet within 5 days. In contrast, addition of GST-METH1 or GST-METH2 to the bFGF pellets completely abolished blood vessel growth. Table 4 contains a summary of the results obtained from 41 assays performed. Intact TSP1 purified from platelets and GST-TSP1 were used as positive controls. All assays were performed at identical concentrations, suggesting that METH1 and METH2 have similar potency to that of TSP1 in the inhibition of angiogenesis. In addition, when half of the standard concentration was used, a weak, however noticeable response was seen, indicating a dose-dependent effect.

TABLE 4

Activity of METH1 and METH2 recombinant proteins in the corneal pocket assay

| bFGF Pellets | Vascularized corneas/Total corneas |
| --- | --- |
| Vehicle | 5/5 |
| TSP1 | 0/5 |
| GST | 11/11 |
| GST-TSP1-TI | 1/4 |
| GST-METH1-TSP | 0/8 |
| GST-METH2-TSP | 0/8 |

Figure 6:
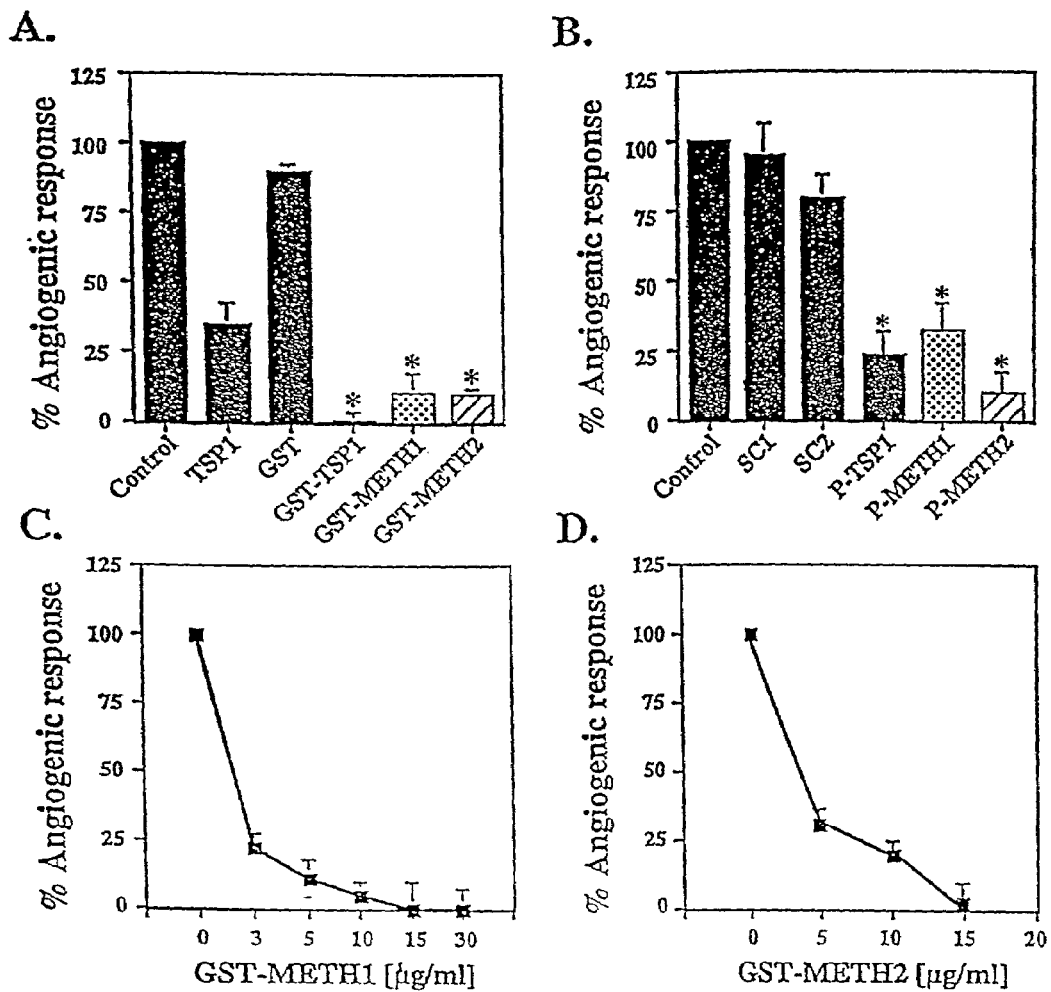
FIG. 6 shows that peptides and recombinant protein derived from the TSP-like domain of METH1 and METH2 block VEGF-induced angiogenesis. Angiogenesis was induced on CAMs from 12–14-day-old embryos using a nylon mesh containing VEGF casted on matrigel and in the presence or absence of the peptides or recombinant protein. Capillary density was evaluated as described in Example 4. Positive and negative control included VEGF alone and vehicle alone, respectively. (A) Quantification of the angiogenic response induced by VEGF in the presence of recombinant proteins. TSP1, purified platelet TSP1, GST, purified GST, GST-TSP1, GST-METH1, and GST-METH2 are described in Example 4. (B) Quantification of the angiogenic response induced by VEGF in the presence or absence of the peptides; P-TSP1, P-METH1, and P-METH2 (peptide derived from the Type I repeats of TSP, METH1 and METH2, respectively); SC1 and SC2 are scramble peptides used as controls. (C) Dose-response of the VEGF-induced angiogenesis in the presence of GST-METH1. (D) Dose-response of the VEGF-induced angiogenesis in the presence of GST-METH2. The angiogenic index was expressed considering the vascular response from the VEGF-matrigel as 100% and subtracting the background levels (matrigel alone). Assays were repeated, at least, twice. Each treatment was done in triplicate. Values represent the mean, bars indicate standard deviations. *p<0.001.

In the CAM assay, the angiogenic response is analyzed by measuring the number of vessels that grow within a matrix polymer containing the angiogenic growth factor. To determine whether recombinant METH1 and METH2 proteins inhibited neovascularization in the CAM assay induced by VEGF, a matrigel polymer containing VEGF and the recombinant protein were implanted in the CAM. Quantitative analysis of the experiments, which included three different polymers per treatment are shown in FIG. 6A. Matrigels polymers containing VEGF plus 5 µg of GST-METH1 or GST-METH2 caused greater than 80% inhibition in blood vessel growth. A similar potency was found using the GST recombinant protein derived from the type I repeats of TSP1. Furthermore, the anti-angiogenic effect of the TSP domains in METH1 and METH2 was dose-dependent with a complete inhibition of blood vessel growth when 15 µg/ml of protein was used (FIG. 6C and D). GST alone, at identical concentrations, had no significant effect on VEGF-stimulated angiogenesis. CAM assays performed with the unprocessed form of METH-1 and METH2 provided similar results to the processed forms. It was unclear whether processing is not required for function or if the CAM tissue lead to processing of our proteins. Thus, the intact protein was incubated with CAM tissue for 24 h and was evaluated the protein on Western blots. The results demonstrate that the CAM tissue was able to generate a 68 kD METH1 processed protein.

Synthetic peptides from the second or the third type I repeats of human TSP1 can mimic the anti-angiogenic effects of the intact TSP1 (Tolsma, S. S., et al., *J. Cell. Biol.* 122:497–511 (1993)). In fact, a 19-residue polypeptide was shown to be sufficient to block in vivo neovascularization in the rat cornea and to inhibit the bFGF-induced migration of cultured endothelial cells (Vogel, T., et al., *J. Cell. Biochem.* 53:74–84 (1993); Tolsma, S. S., et al., *J. Cell. Biol.* 122: 497–511 (1993)). To test whether the same was true for the METH1 and METH2 TSP domains, peptides derived from the same region were synthesized and their anti-angiogenic activity was evaluated in the CAM assay. The results are shown in FIG. 6B. Peptides derived from both the TSP domain of METH1 and METH2 blocked VEGF-induced angiogenesis similarly to that of TSP1. In contrast, scramble peptides had no significant effects.

Example 5

Proliferation Assays

Human dermal endothelial cells (HDEC) were isolated and grown on Vitrogen™ coated petri-dishes in EBM (Clonetics, San Diego, Calif.) supplemented with 15% fetal calf serum, 25 µg/ml cAMP, and 1 µg/ml of hydrocortisone-21-acetate and were used from passages 3 to 6. Cells were made quiescent by incubation of confluent monolayers with phenol red-free EBM containing 0.2% BSA for 48 h. Human dermal fibroblasts were isolated from neonatal foreskin and by enzymatic dissociation. Both fibroblasts and smooth muscle cells were maintained in DMEM supplemented with 10% fetal calf serum. Human mammary epithelial cells (HMEC) were purchased from Clonetics and maintained in the recommended media (mammary epithelial growth media, MEGM).

Quiescent human dermal endothelial cells, between passage 3 and 6, were plated on Vitrogen™ coated 24-well plates in EBM supplemented with 0.2% BSA, 0.1% fetal calf serum and 1 ng/ml of bFGF in the presence or absence of the recombinant protein and incubated at 5% $CO_2$ at 37° C. for 48 h. For vascular smooth muscle (VSM) and fibroblast proliferation assays, cells were incubated under the same conditions but using DMEM instead of EBM. Human mammary epithelial cells were incubated on their growth media. A pulse of [$^3$H]-Thymidine (1 µCi/µl) was added during the last 4 h prior harvesting. Cells were washed and fixed in 10% TCA. Incorporation of [$^3$H]-thymidine was determined by scintillation counting, as previously described (Iruela-Arispe, M. L. & Sage, E. H., *J. Cell. Biochem.* 52:414 (1993)).

Statistical analyses were done using In-Stat software (Graph Pad Software) for Macintosh. Assuming normal distributions, data were analyzed by one-way ANOVA, followed by either T-test Dunnett test for comparisons between groups, or student-Newman-Kleus test for multiple comparisons between groups.

Figure 7:
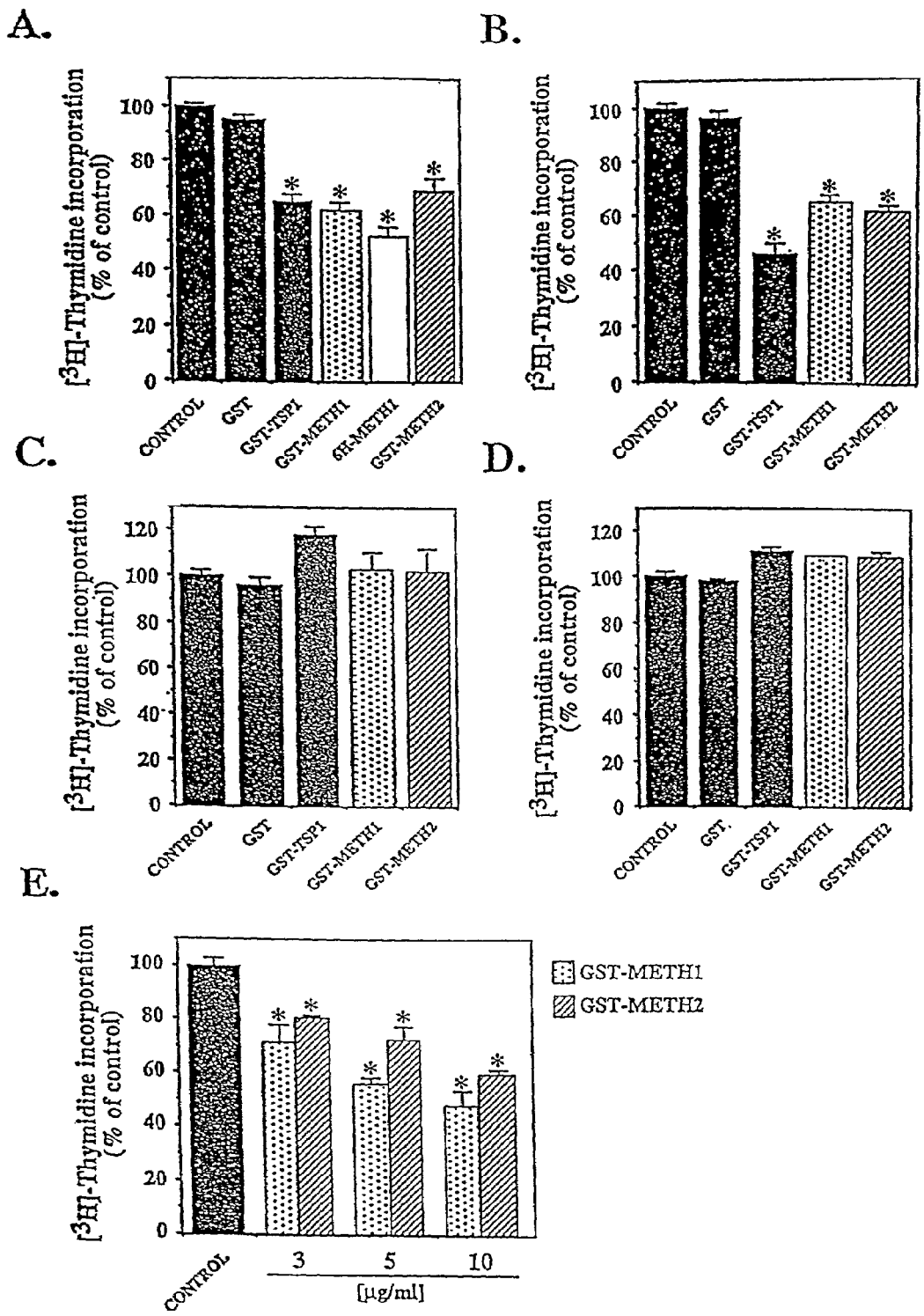
FIG. 7 shows the effect of METH1 and METH2 recombinant proteins on bFGF-stimulated cell proliferation. Cells were cultured on 24-well plates in media containing bFGF and the recombinant protein to be tested (3 μg/ml, unless indicated in the graph). Controls included vehicle or GST recombinant protein alone. (A), HDEC, human dermal endothelial cells; (B), HMEC, human mammary epithelial cells; (C), HDF, human dermal fibroblasts; (D), SMC, smooth muscle cells; (E) Dose-response of GST-METH1 and GST-METH2 on HDEC proliferation. Experiments were repeated, at least, twice. Each treatment was done in triplicate. Values represent the mean, bars indicate standard deviations. *p<0.01.

To gain insight into the mechanism by which METH1 and METH2 inhibit neovascularization, the direct effect of the purified recombinant fusion proteins on endothelial cell proliferation was tested. Serum-starved endothelial cells were plated into growth medium containing bFGF and FCS. Recombinant proteins (3 µg/ml) were added at the same time of plating. 40% (GST-METH1), 45% (6H-GST) or 36% (GST-METH2) inhibition was observed, in contrast to a non-significant effect when GST alone was added. The recombinant protein from the type I repeats of TSP1 had similar inhibitory effects. (FIG. 7A). Furthermore, suppression of proliferation mediated by METH1 or METH2 was dose-dependent, as shown in FIG. 7E. The inhibition was observed as early as one day after treatment and the inhibitory effect was not toxic and reversible since the removal of the recombinant protein and subsequent addition of growth factor alone led to the resumption of endothelial cell proliferation.

The cell specificity of the anti-proliferative effects for METH1 and METH2 on the endothelium was evaluated by additional proliferation assays on a variety of non-endothelial cells. No significant inhibition of proliferation was seen on fibroblasts or smooth muscle cell cultures. In contrast, a non significant, but reproducible stimulation of proliferation for these two cell types could be observed. This result rules out the presence of any potential nonspecific inhibitor of cell growth in the recombinant protein preparations. On mammary epithelial cell, however, METH1 and METH2 inhibited cell proliferation to the same degree as endothelial cells. Interestingly, TSP1 also suppresses mammary epithelial cell proliferation both in vitro and in a transgenic model.

The possibility that METH1 and METH2 might act as disintegrins is consistent with their anti-angiogenic properties. Clearly blockade of αvβ3 and β1 integrins with antibodies has been shown to inhibit neovascularization both during development and in tumors (Brooks, P. C., et al., *Cell* 85:683–693 (1996); Brooks, P. C., et al., *Cell* 92:391–400 (1998); Senger, D. R., et al., *Proc. Natl. Acad. Sci. USA*

94:13612–13617 (1997)). Integrins are essential for the mediation of both proliferative and migratory signals (Schwartz, M. A. & Ingber, D. E., *Mol. Biol. Cell* 5:389–393 (1994)), therefore interference with those signals can be highly deleterious to the angiogenic process. The angiogenic functional assays were performed with recombinant protein containing only the type I repeats in METH1 and METH2.

The mechanism of action of METH1 and METH2 with regards to their angio-inhibitory activity is not known. To date we have evidence that these proteins are secreted and bind to endothelial cells. Further investigations are guided towards the identification of receptors and signal transduction mechanisms. A likely hypothesis resulting from the lessons learned from TSP1 is that both METH1 and METH2 bind to CD36. Recently, this scavenger receptor has been implicated in the mediation of signals by which TSP-1 exert its anti-angiogenic effects (Dawson, D. W., et al., *J. Cell. Biol.* 138:707–717 (1997)). Both the CSVTCG (SEQ ID NO:83) (Asch, A. S., et al., *Nature* 262:1436–1439 (1993); Catimel, B., et al., *Biochem. J.* 284:231–236 (1992)) and the GCQXR (SEQ ID NO:84) sequences have been proposed as primary binding motifs to CD36 (Dawson, D. W., et al., *J. Cell. Biol.* 138:707–717 (1997)). METH1 and METH2 have almost entire conservation in both these regions. A complementary and also likely occurrence is binding of METH1 and METH2 to bFGF. Binding to heparin and bFGF has been proposed as part of the anti-angiogenic activity of TSP1 (Guo, N., et al., *J. Peptide Res.* 49 (1997)). This property appears to be mediated through the WSXWS (SEQ ID NO:82) motif, also conserved in METH1 and METH2. Future efforts will focus on the signals implicated in the anti-angiogenic properties mediated by these novel proteins and on their potential as proteases of the extracellular milieu.

Example 6

Isolation of the METH1 or METH2 cDNA Clone from the Deposited Sample

Two approaches can be used to isolate METH1 or METH2 from the deposited sample. First, the deposited clone is transformed into a suitable host (such as XL-1 Blue (Stratagene)) using techniques known to those of skill in the art, such as those provided by the vector supplier or in related publications or patents. The transformants are plated on 1.5% agar plates (containing the appropriate selection agent, e.g., ampicillin) to a density of about 150 transformants (colonies) per plate. A single colony is then used to generate DNA using nucleic acid isolation techniques well known to those skilled in the art. (e.g., Sambrook et al., Molecular Cloning: A Laboratory Manual, 2nd Edit., (1989), Cold Spring Harbor Laboratory Press.)

Alternatively, two primers of 17–20 nucleotides derived from both ends of the SEQ ID NO:1 or SEQ ID NO:3 (i.e., within the region of SEQ ID NO:1 or SEQ ID NO:3 bounded by the 5' NT and the 3' NT of the clone) are synthesized and used to amplify the METH1 or METH2 cDNA using the deposited cDNA plasmids as templates. The polymerase chain reaction is carried out under routine conditions, for instance, in 25 µl of reaction mixture with 0.5 µg of the above cDNA template. A convenient reaction mixture is 1.5–5 mM MgCl$_2$, 0.01% (w/v) gelatin, 20 µM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of the METH1 or METH2 gene which may not be present in the deposited clones. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., *Nucleic Acids Res.* 21(7):1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the METH1 or METH2 gene of interest is used to PCR amplify the 5' portion of the METH1 or METH2 full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the METH1 or METH2 gene.

Example 7

Bacterial Expression of METH1 or METH2

A METH1 or METH2 polynucleotide encoding a METH1 or METH2 polypeptide invention is amplified using PCR oligonucleotide primers corresponding to the 5' and 3' ends of the DNA sequence, as outlined in Example 5, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Amp$^r$), a bacterial origin of replication (ori), an IPTG-regulatable promoter/operator (P/O), a ribosome binding site (RBS), a 6-histidine tag (6-His), and restriction enzyme cloning sites. The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4

(Qiagen, Inc.) which contains multiple copies of the plasmid pREP4, which expresses the lacd repressor and also confers kanamycin resistance (Kan'). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 µg/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacd repressor, clearing the P/O leading to increased gene expression. Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra). Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified METH1 or METH2 protein is then renatured by dialyzing it against phosphate-buffered saline (PBS) or 50 mM Na-acetate, pH 6 buffer plus 200 mM NaCl. Alternatively, the METH1 or METH2 protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Inmidazole is removed by a final dialyzing step against PBS or 50 mM sodium acetate pH 6 buffer plus 200 mM NaCl. The purified METH1 or METH2 protein is stored at 4° C. or frozen at −80° C.

In addition to the above expression vector, the present invention further includes an expression vector comprising phage operator and promoter elements operatively linked to a METH1 or METH2 polynucleotide, called pHE4a. (ATCC Accession Number 209645, deposited Feb. 25, 1998.) This vector contains: 1) a neomycinphosphotransferase gene as a selection marker, 2) an E. coli origin of replication, 3) a T5 phage promoter sequence, 4) two lac operator sequences, 5) a Shine-Delgarno sequence, and 6) the lactose operon repressor gene (1acIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 5, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 8

Purification of METH1 or METH2 Polypeptide from an Inclusion Body

The following alternative method can be used to purify METH1 or METH2 polypeptide expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the METH1 or METH2 polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant METH1 or METH2 polypeptide should exhibit greaterthan 95% purity after the above refolding and purification steps. No major contaminant bands should be observed from Coomassie blue stained 16% SDS-PAGE gel when 5 ug of purified protein is loaded. The purified METH1 or METH2 protein can also be tested for endotoxin/LPS contamination, and typically the LPS content is less than 0.1 ng/ml according to LAL assays.

Example 9

Cloning and Expression of METH1 or METH2 in a Baculovirus Expression System

In this example, the plasmid shuttle vector pA2 is used to insert METH1 or METH2 polynucleotide into a baculovirus to express METH1 or METH2. This expression vector contains the strong polyhedrin promoter of the *Autographa californica* nuclear polyhedrosis virus (AcMNPV) followed by convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that expresses the cloned METH1 or METH2 polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

Specifically, the METH1 or METH2 cDNA sequence contained in the deposited clone, including the AUG initiation codon and any naturally associated leader sequence, is amplified using the PCR protocol described in Example 5. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB 101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transfected with 1.0 ug of a commercially available linearized baculovirus DNA ("BaculoGold$^a$ baculovirus DNA", Pharmingen, San Diego, Calif.), using the lipofection method described by Felgner et al., *Proc. Natl. Acad. Sci. USA* 84:7413–7417 (1987). One ug of BaculoGold$^a$ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of $^{35}$S-methionine and 5 uCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced METH1 or METH2 protein.

Example 10

Expression of METH1 or METH2 in Mammalian Cells

METH1 or METH2 polypeptide can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2DHFR (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC-1-3 cells, mouse L cells and Chinese hamster ovary (CHO) cells.

Alternatively, METH1 or METH2 polypeptide can be expressed in stable cell lines containing the METH1 or METH2 polynucleotide integrated into a chromosome. The co-transfection with a selectable marker such as DHFR, gpt, neomycin, hygromycin allows the identification and isolation of the transfected cells.

The transfected METH1 or METH2 gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., *J. Biol. Chem.* 253:1357–1370 (1978); Hamlin, J. L. and Ma, C., *Biochem. et Biophys. Acta* 1097:107–143 (1990); Page, M. J. and Sydenham, M. A., *Biotechnology* 9:64–68 (1991).) Another useful selection marker is the enzyme glutamine synthase (GS) (Murphy et al., *Biochem J.* 227:277–279 (1991); Bebbington et al., *Bio/Technology* 10: 169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-DBFR (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985).) Multiple cloning sites, e.g., with the restriction enzyme cleavage sites BamHI, XbaI and Asp718, facilitate the cloning of METH1 or METH2. The vectors also contain the 3' intron, the polyadenylation and termination signal of the rat preproinsulin gene, and the mouse DHFR gene under control of the SV40 early promoter.

If a naturally occurring signal sequence is used to produce a secreted protein, the vector does not need a second signal peptide. Alternatively, if a naturally occurring signal sequence is not used, the vector can be modified to include a heterologous signal sequence in an effort to secrete the protein from the cell. (See, e.g., WO 96/34891.)

The amplified fragment is then digested with the appropriate restriction enzyme and purified on a 1% agarose gel using acommercially available kit ("Geneclean," BIO 101 Inc., La Jolla, Calif.). The isolated fragment and the dephosphorylated vector are then ligated with T4 DNA ligase. *E. coli* HB 101 or XL-1 Blue cells are then transformed and bacteria are identified that contain the fragment inserted into plasmid pC6 or pC4 using, for instance, restriction enzyme analysis.

Chinese hamster ovary cells lacking an active DHFR gene are used for transfection. Five µg of the expression plasmid pC6 or pC4 is cotransfected with 0.5 µg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of metothrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of METH1 or METH2 is analyzed, for instance, by SDS-PAGE and Western blot or by reversed phase HPLC analysis.

Example 11

Construction of N-Terminal and/or C-Terminal Deletion Mutants

The following general approach may be used to clone a N-terminal or C-terminal deletion METH1 or METH2 deletion mutant. Generally, two oligonucleotide primers of about 15–25 nucleotides are derived from the desired 5' and 3' positions of a polynucleotide of SEQ ID NO:1 or SEQ ID NO:3. The 5' and 3' positions of the primers are determined based on the desired METH1 or METH2 polynucleotide fragment. An initiation and stop codon are added to the 5' and 3' primers respectively, if necessary, to express the METH1 or METH2 polypeptide fragment encoded by the polynucleotide fragment. Preferred METH1 or METH2 polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the METH1 or METH2 polynucleotide fragment in a desired vector may also be added to the 5' and 3' primer sequences. The METH1 or METH2 polynucleotide fragment is amplified from genomic DNA or from the deposited cDNA clone using the appropriate PCR oligonucleotide primers and conditions discussed herein or known in the art. The METH1 or METH2 polypeptide fragments encoded by the METH1 or METH2 polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the METH1 polypeptide fragment R-235 to L-934 or the METH2 polypeptide fragment R-214 to Q-836 is amplified and cloned as follows: A 5' primer is generated comprising a restriction enzyme site followed by an initiation codon in frame with the polynucleotide sequence encoding the N-terminal portion of the polypeptide fragment beginning with R-235 or R-214, respectively. A complementary 3' primer is generated comprising a restriction enzyme site followed by a stop codon in frame with the polynucleotide sequence encoding C-terminal portion of the METH1 or METH2 polypeptide fragment ending with L-934 or Q-836, respectively.

The amplified polynucleotide fragment and the expression vector are digested with restriction enzymes which recognize the sites in the primers. The digested polynucleotides are then ligated together. The METH1 or METH2 polynucleotide fragment is inserted into the restricted expression vector, preferably in a manner which places the METH1 or METH2 polypeptide fragment coding region downstream from the promoter. The ligation mixture is transformed into competent E. coli cells using standard procedures and as described in the Examples herein. Plasmid DNA is isolated from resistant colonies and the identity of the cloned DNA confirmed by restriction analysis, PCR and DNA sequencing.

Example 12

Protein Fusions of METH1 or METH2

METH1 or METH2 polypeptides are preferably fused to other proteins. These fusion proteins can be used for a variety of applications. For example, fusion of METH1 or METH2 polypeptides to His-tag, HA-tag, protein A, IgG domains, and maltose binding protein facilitates purification. (See Example 7; see also EP A 394,827; Traunecker, et al., Nature 331:84–86 (1988).) Similarly, fusion to IgG-1, IgG-3, and albumin increases the halflife time in vivo. Nuclear localization signals fused to METH1 or METH2 polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 7.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and METH1 or METH2 polynucleotide, isolated by the PCR protocol described in Example 5, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc Region (SEQ ID NO:85)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT

Example 13

Production of an Antibody a) The antibodies of the present invention can be prepared by a variety of methods. (See, Current Protocols, Chapter 2.) For example, cells expressing METH1 or METH2 is administered to an animal to induce the production of sera containing polyclonal antibodies. In a preferred method, a preparation of METH1 or METH2 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with METH1 or METH2 polypeptide or, more preferably, with a secreted METH1 or METH2 polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (*Gastroenterology* 80:225–232 (1981).) The hybridoma cells obtained through such a selection are then assayed to identify clones which secrete antibodies capable of binding the METH1 or METH2 polypeptide.

Alternatively, additional antibodies capable of binding to METH1 or METH2 polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the METH1 or METH2 protein-specific antibody can be blocked by METH1 or METH2. Such antibodies comprise anti-idiotypic antibodies to the METH1 or METH2 protein-specific antibody and can be used to immunize an animal to induce formation of further METH1 or METH2 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted METH1 or METH2 protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).)

b) Isolation of antibody fragments directed against METH1 and/or METH2 from a library of scFvs.

Naturally occuring V-genes isolated from human PBLs are constructed into a large library of antibody fragments which contain reactivities against METH1 and/or METH2 to which the donor may or may not have been exposed (see e.g., U.S. Pat. No. 5,885,793 incorporated herein in its entirety by reference).

Rescue of the Library. A library of scFvs is constructed from the RNA of human PBLs as described in WO92/01047. To rescue phage displaying antibody fragments, approximately $10^9$ *E. coli* harbouring the phagemid are used to inoculate 50 ml of 2×TY containing 1% glucose and 100 ug/ml of ampicillin (2×TY-AMP-GLU) and grown to an O.D. of 0.8 with shaking. Five ml of this culture is used to innoculate 50 ml of 2×TY-AMP-GLU, $2×10^8$ TU of delta gene 3 helper (M13 delta gene III, see WO92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of of 2×TY containing 100 ug/ml ampicillin and 50 ug/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harbouring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the Library. Immunotubes (Nunc) are coated overnight in PBS with 4 ml of either 100 ug/ml or 10 ug/ml of a polypeptide of the present invention. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylarnine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 ug/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

Example 14

Production of METH1 or METH2 Protein for High-Throughput Screening Assays

The following protocol produces a supernatant containing METH1 or METH2 polypeptide to be tested. This supernatant can then be used in the Screening Assays described in Examples 16–23.

First, dilute Poly-D-Lysine (644 587 Boehringer-Mannheim) stock solution (1 mg/ml in PBS) 1:20 in PBS (w/o calcium or magnesium 17–516F Biowhittaker) for a working solution of 50 ug/ml. Add 200 ul of this solution to each well (24 well plates) and incubate pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM(Dulbecco's Modified Eagle Medium)(with 4.5 G/L glucose and L-glutamine (12-604F Biowhittaker))/10% heat inactivated FBS(14-503F Biowhittaker)/1×Penstrep(17-602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 10–12, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a12-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either 1% BSA in DMEM with 1× penstrep, or HGS CHO-5 media (116.6 mg/L of $CaCl_2$ (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$—$H_2O$; 71.02 mg/L of $Na_2HPO_4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/mil of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Gistidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-2$H_2O$; and 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; 10 mg/L of Methyl-B-Cyclodextrin complexed with Retinal Acetate. Adjust osmolarity to 327 mOsm with 2 mm glutamine and 1× penstrep. (BSA (81–068–3 Bayer) 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37° C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 16–23.

It is specifically understood that when activity is obtained in any of the assays described below using a supernatant, the activity originates from either the METH1 or METH2 polypeptide directly (e.g., as a secreted protein) or by METH1 or METH2 inducing expression of other proteins, which are then secreted into the supernatant. Thus, the invention further provides a method of identifying the protein in the supernatant characterized by an activity in a particular assay.

Example 15

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, *Ann. Rev. Biochem.* 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proxial region encoding Trp-Ser-Xxx-Trp-Ser (SEQ ID NO:82)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

ISRE elements can be used instead. The 5' primer also contains 18 bp of sequence complementary to the SV40 early promoter sequence and is flanked with an XhoI site. The sequence of the 5' primer is:

(SEQ ID NO:86)
5':GCGCCTCGAGATTTCCCCGAAATCTAGATTTCCCCGAAATGATTTCC
CCGAAATGATTTCCCCGAAATATCTGCCATCTCAATTAG:3'

The downstream primer is complementary to the SV40 promoter and is flanked with a Hind III site: 5':GCG-GCAAGCTTTTTGCAAAGCCTAGGC:3' (SEQ ID NO:87)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

| | JAKs | | | | | |
|---|---|---|---|---|---|---|
| Ligand | tyk2 | Jak1 | Jak2 | Jak3 | STATS | GAS/(elements) or ISRE |
| IFN family | | | | | | |
| IFN-a/B | + | + | − | − | 1,2,3 | ISRE |
| IFN-g | | + | + | − | 1 | GAS (IRF1>Lys6>IFP) |
| Il-10 | + | ? | ? | − | 1,3 | |
| gp130 family | | | | | | |
| IL-6 (Pleiotrophic) | + | + | + | ? | 1,3 | GAS (IRF1>Lys6>IFP) |
| Il-11(Pleiotrophic) | ? | + | ? | ? | 1,3 | |
| OnM(Pleiotrophic) | ? | + | + | ? | 1,3 | |
| LIF(Pleiotrophic) | ? | + | + | ? | 1,3 | |
| CNTF(Pleiotrophic) | −/+ | + | + | ? | 1,3 | |
| G-CSF(Pleiotrophic) | ? | + | ? | ? | 1,3 | |
| IL-12(Pleiotrophic) | + | − | + | + | 1,3 | |
| g-C family | | | | | | |
| IL-2 (lymphocytes) | − | + | − | + | 1,3,5 | GAS |
| IL-4 (lymph/myeloid) | − | + | − | + | 6 | GAS (IRF1 = IFP>>Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1>IFP>>Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1,3,5 | GAS(B-CAS>IRF1 = IFP>>Ly6) |
| EPO | ? | − | + | − | 5 | |
| Receptor Tyrosine Kinases | | | | | | |
| EGF | ? | + | + | − | 1,3 | GAS (IRF1) |
| PDGF | ? | + | + | − | 1,3 | GAS (not IRF1) |
| CSF-1 | ? | + | + | − | 1,3 | |

To construct a synthetic GAS containing promoter element, which is used in the Biological Assays described in Examples 16–17, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., *Immunity* 1:457–468 (1994).), although other GAS or (SEQ ID NO:88)
5':CTCGAGATTTCCCCGAAATCTAGATTTCCCCGAAATGATTTCCCCGA
AATGATTTCCCCGAAATATCTGCCATCTCAATTAGTCAGCAACCATAGTC
CCGCCCCTAACTCCGCCCATCCCGCCCCTAACTCCGCCCAGTTCCGCCCA -continued
```
TTCTCCGCCCCATGGCTGACTAATTTTTTTTATTTATGCAGAGGCCGAGG

CCGCCTCGGCCTCTGAGCTATTCCAGAAGTAGTGAGGAGGCTTTTTTGGA

GGCCTAGGCTTTTGCAAAAAGCTT:3'
```

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can used be instead of SEAP, in this or in any of the other Examples. Well known reporter molecules that can be used instead of SEAP include chloramphenicol acetyltransferase (CAT), luciferase, alkaline phosphatase, β-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 16–17.

Other constructs can be made using the above description and replacing GAS with a different promoter sequence. For example, construction of reporter molecules containing NFK-B and EGR promoter sequences are described in Examples 18 and 19. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, II-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 16

High-Throughput Screening Assay for T-cell Activity

The following protocol is used to assess T-cell activity of METH1 or METH2 by determining whether METH1 or METH2 supernatant proliferates and/or differentiates T-cells. T-cell activity is assessed using the GAS/SEAP/Neo construct produced in Example 15. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing METH1 or METH2 polypeptides or METH1 or METH2 induced polypeptides as produced by the protocol described in Example 14.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20° C. until SEAP assays are performed according to Example 20. The plates containing the remaining treated cells are placed at 4° C. and serve as a source of material for repeating the assay on a specific well if desired.

As a positive control, 100 Unit/ml interferon gamma can be used which is known to activate Jurkat T cells. Over 30 fold induction is typically observed in the positive control wells.

Example 17

High-Throughput Screening Assay Identifying Myeloid Activity

The following protocol is used to assess myeloid activity of METH1 or METH2 by determining whether METH1 or METH2 proliferates and/or differentiates myeloid cells.

Myeloid cell activity is assessed using the GAS/SEAP/Neo construct produced in Example 15. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 15, a DEAE-Dextran method (Kharbanda et. al., 1994, *Cell Growth & Differentiation* 5:259–265) is used. First, harvest 2×10e⁷ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4 \cdot 7H_2O$, 1 mM $MgCl_2$, and 675 uM $CaCl_2$. Incubate at 37° C. for 45

Wash the cells with RPMI 1640 medium containing 10% FBS and then resuspend in 10 ml complete medium and incubate at 37° C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting 1×10⁸ cells (this is enough for ten 96-well plates assay) and wash with PBS. Suspend the cells in 200 ml above described growth medium, with a final density of 5×10⁵ cells/ml. Plate 200 ul cells per well in the 96-well plate (or 1×10⁵ cells/well).

Add 50 ul of the supernatant prepared by the protocol described in Example 14. Incubate at 37° C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 20.

Example 18

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed by METH1 or METH2.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells by METH1 or METH2 can be assessed.

The EGR/SEAP reporter construct can be assembled by the following protocol. The EGR-1 promoter sequence (−633 to +1)(Sakamoto K et al., *Oncogene* 6:867–871 (1991)) can be PCR amplified from human genomic DNA using the following primers:

5'GCGCTCGAGGGATGACAGCGATAGAACCCCGG-3' (SEQ ID NO:89)

5'GCGAAGCTTCGCGACTCCCCGGATCCGCCTC-3' (SEQ ID NO:90)

Using the GAS:SEAP/Neo vector produced in Example 15, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. # 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 14. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as 5×10⁵ cells/ml.

Add 200 ul of the cell suspension to each well of 96-well plate (equivalent to 1×10⁵ cells/well). Add 50 ul supernatant produced by Example 14, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 20.

Example 19

High-Throughput Screening Assay for T-cell Activity

NF-KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KB regulates the expression of genes involved in immune cell activation, control of apoptosis (NF-KB appears to shield cells from apoptosis), B and T-cell development, anti-viral and antimicrobial responses, and multiple stress responses. In non-stimulated conditions, NF-KB is retained in the cytoplasm with I-KB (Inhibitor KB). However, upon stimulation, I-KB is phosphorylated and degraded, causing NF-KB to shuttle to the nucleus, thereby activating transcription of target genes. Target genes activated by NF-KB include IL-2, IL-6, GM-CSF, ICAM-1 and class 1 MHC.

Due to its central role and ability to respond to a range of stimuli, reporter constructs utilizing the NF-KB promoter element are used to screen the supernatants produced in Example 14. Activators or inhibitors of NF-KB would be useful in treating diseases. For example, inhibitors of NF-KB could be used to treat those diseases related to the acute or chronic activation of NF-KB, such as rheumatoid arthritis.

To construct a vector containing the NF-KB promoter element, a PCR based strategy is employed. The upstream primer contains four tandem copies of the NF-KB binding site (GGGGACTTTCCC) (SEQ ID NO:91), 18 bp of sequence complementary to the 5' end of the SV40 early promoter sequence, and is flanked with an XhoI site:

```
                                              (SEQ ID NO:92)
5':GCGGCCTCGAGGGGACTTTCCCGGGGACTTTCCGGGGACTTTCCGGG
                      ACTTTCCATCCTGCCATCTCAATTAG:3'
```

The downstream primer is complementary to the 3' end of the SV40 promoter and is flanked with a Hind III site: 5':GCGGCAAGCTTTTTGCAAAGCCTAGGC:3' (SEQ ID NO:93)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

```
                                              (SEQ ID NO:88)
5':CTCGAGGGGACTTTCCCGGGGACTTTCCGGGGACTTTCCGGGACTTT

CCATCTGCCATCTCAATTAGTCAGCAACCATAGTCCCGCCCCTAACTCCG

CCCATCCCGCCCCTAACTCCGCCCAGTTCCGCCCATTCTCCGCCCCATGG

CTGACTAATTTTTTTTATTTATGCAGAGGCCGAGGCCGCCTCGGCCTCTG

AGCTATTCCAGAAGTAGTGAGGAGGCTTTTTTGGAGGCCTAGGCTTTTGC

AAAAAGCTT:3'
```

Next, replace the SV40 minimal promoter element present in the pSEAP2-promoter plasmid (Clontech) with this NF-KB/SV40 fragment using XhoI and HindIII. However, this vector does not contain a neomycin resistance gene, and therefore, is not preferred for mammalian expression systems.

In order to generate stable mammalian cell lines, the NF-KB/SV40/SEAP cassette is removed from the above NF-KB/SV40/SEAP vector using restriction enzymes SalI and NotI, and inserted into a vector containing neomycin resistance. Particularly, the NF-KB/SV40/SEAP cassette was inserted into pGFP-1 (Clontech), replacing the GFP gene, after restricting pGFP-1 with SalI and NotI.

Once NF-KB/SV40/SEAP/Neo vector is created, stable Jurkat T-cells are created and maintained according to the protocol described in Example 16. Similarly, the method for assaying supernatants with these stable Jurkat T-cells is also described in Example 16. As a positive control, exogenous TNF alpha (0.1,1, 10 ng) is added to wells H9, H10, and H11, with a 5–10 fold activation typically observed.

Example 20

Assay for SEAP Activity

As a reporter molecule for the assays described in Examples 16–19, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 ul of 2.5× dilution buffer into Optiplates containing 35 ul of a supernatant. Seal the plates with a plastic sealer and incubate at 65° C. for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| Reaction Buffer Formulation: | | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |

-continued

Reaction Buffer Formulation:

| # of plates | Rxn buffer diluent (ml) | CSPD (ml) |
|---|---|---|
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 21

High-Throughput Screening Assay Idenfifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-3, used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-3 is made in 10% pluronic acid DMSO. To load the cells with fluo-3, 50 ul of 12 ug/ml fluo-3 is added to each well. The plate is incubated at 37° C. in a $CO_2$ incubator for 60 min. The plate is washed four times in the Biotek washer with HBSS leaving 100 ul of buffer.

For non-adherent cells, the cells are spun down from culture media. Cells are re-suspended to $2$–$5 \times 10^6$ cells/ml with HBSS in a 50-ml conical tube. 4 ul of 1 mg/ml fluo-3 solution in 10% pluronic acid DMSO is added to each ml of cell suspension. The tube is then placed in a 37° C. water bath for 30–60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-3. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event caused by the a molecule, either METH1 or METH2 or a molecule induced by METH1 or METH2, which has resulted in an increase in the intracellular $Ca^{++}$ concentration.

Example 22

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, identifying whether METH1 or METH2 or a molecule induced by METH1 or METH2 is capable of activating tyrosine kinase signal transduction pathways is of interest. Therefore, the following protocol is designed to identify such molecules capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4° C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 14, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (# 1836170) obtained from Boehringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4° C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg$^{2+}$ (5 mM ATP/50 mM MgCl2), then 10 ul of 5× Assay Buffer (40 mM imidazole hydrochloride, pH7.3, 40 mM beta-glycerophosphate, 1 mM EGTA, 100 mM MgCl$_2$, 5 mM MnCl$_2$, 0.5 mg/ml BSA), then 5 ul of Sodium Vanadate(1 mM), and then 5 ul of water. Mix the components gently and preincubate the reaction mix at 30° C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37° C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase (anti-P-Tyr-POD(0.5 u/ml)) to each well and incubate at 37° C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 23

High-Throughput Screening Assay Identifying Phosphorylation Activity

As a potential alternative and/or compliment to the assay of protein tyrosine kinase activity described in Example 22, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4° C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 14 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation by METH1 or METH2 or a molecule induced by METH1 or METH2.

Example 24

Method of Determining Alterations in the METH1 or METH2 Gene

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95° C. for 30 seconds; 60–120 seconds at 52–58° C.; and 60–120 seconds at 70° C., using buffer solutions described in Sidransky, D. et al., *Science* 252:706 (1991).

PCR products are then sequenced using primers labeled at their 5' end with T4 polynucleotide kinase, employing SequiTherm Polymerase. (Epicentre Technologies). The intron-exon borders of selected exons of METH1 or METH2 is also determined and genomic PCR products analyzed to confirm the results. PCR products harboring suspected mutations in METH1 or METH2 is then cloned and sequenced to validate the results of the direct sequencing.

PCR products of METH1 or METH2 are cloned into T-tailed vectors as described in Holton, T. A. and Graham, M. W., *Nucleic Acids Research* 19:1156 (1991) and sequenced with T7 polymerase (United States Biochemical). Affected individuals are identified by mutations in METH1 or METH2 not present in unaffected individuals.

Genomic rearrangements are also observed as a method of determining alterations in the METH1 or METH2 gene. Isolated genomic clones are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the METH1 or METH2 genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl. 8:75 (1991).) Image collection, analysis and chromosomal fractional length measurements are performed using the ISee Graphical Program System. (Inovision Corporation, Durham, N.C.) Chromosome alterations of the genomic region of METH1 or METH2 (hybridized by the probe) are identified as insertions, deletions, and translocations. These METH1 or METH2 alterations are used as a diagnostic marker for an associated disease.

Example 25

Method of Detecting Abnormal Levels of METH1 or METH2 in a Biological Sample

METH1 or METH2 polypeptides can be detected in a biological sample, and if an increased or decreased level of METH1 or METH2 is detected, this polypeptide is a marker for a particular phenotype. Methods of detection are numerous, and thus, it is understood that one skilled in the art can modify the following assay to fit their particular needs.

For example, antibody-sandwich ELISAs are used to detect METH1 or METH2 in a sample, preferably a biological sample. Wells of a microtiter plate are coated with specific antibodies to METH1 or METH2, at a final concentration of 0.2 to 10 ug/ml. The antibodies are either monoclonal or polyclonal and are produced by the method described in Example 13. The wells are blocked so that non-specific binding of METH1 or METH2 to the well is reduced.

The coated wells are then incubated for >2 hours at RT with a sample containing METH1 or METH2. Preferably, serial dilutions of the sample should be used to validate results. The plates are then washed three times with deionized or distilled water to remove unbounded METH1 or METH2.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot METH1 or METH2 polypeptide concentration on the X-axis (log scale) and fluorescence or absorbance on the Y-axis (linear scale). Interpolate the concentration of the METH1 or METH2 in the sample using the standard curve.

Example 26

Formulating a Polypeptide

The METH1 or METH2 composition will be formulated and dosed in a fashion consistent with good medical practice, taking into account the clinical condition of the individual patient (especially the side effects of treatment with the METH1 or METH2 polypeptide alone), the site of delivery, the method of administration, the scheduling of administration, and other factors known to practitioners. The "effective amount" for purposes herein is thus determined by such considerations.

As a general proposition, the total pharmaceutically effective amount of METH1 or METH2 administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, METH1 or METH2 is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing METH1 or METH2 are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

METH1 or METH2 is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al.) or poly-D-(–)-3-hydroxybutyric acid (EP 133,988). Sustained-release compositions also include liposomally entrapped METH1 or METH2 polypeptides. Liposomes containing the METH1 or METH2 are prepared by methods known per se: DE 3,218,121; Epstein et al., *Proc. Natl. Acad. Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, METH1 or METH2 is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting METH1 or METH2 uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

METH1 or METH2 is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

METH1 or METH2 used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

METH1 or METH2 polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous METH1 or METH2 polypeptide solution, and the resulting mixture is lyophilized. The infusion solution is prepared by reconstituting the lyophilized METH1 or METH2 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, METH1 or METH2 may be employed in conjunction with other therapeutic compounds.

The compositions of the invention maybe administered alone or in combination with other therapeutic agents. Therapeutic agents that may be administered in combination with the compositions of the invention include, but are not limited to, other members of the TNF family, chemotherapeutic agents, antibiotic, steroidal and non-steroidal anti-inflammatories, conventional immunotherapeutic agents, cytokines and/or growth factors. Combination may be administered either concomitantly, e.g. as an admixture; separately but simultaneously or concurrently; or sequentially. This includes presentations in which the combined agents are administered together as a therapeutic mixture, and also procedures in which the combined agents are administered separately but simultaneously, e.g. as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin alpha (LT-alpha, also known as TNF-beta), LT-beta (found in complex heterotrimer LT-alph2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921), OX40, and nerve growth factor (NGF) and soluble forms of Fas, CD30, CD27, CD40 and 4-IBB, TR2 (International Publication No. WO 98/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms of CD154, CD70 and CD153.

Conventional nonspecific immunosuppressive agents that may be administered in combination with the compositions of the invention include, but are not limited to, steroids, cyclosporine, cyclosporine analogs, ayclophosphamide methylprednisone, prednisone, azathioprine, FK-506, 15-deoxyspergulain, and other immunosuppressive agents that act by suppressing the function of responding T cells.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, eacetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethenyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL2, IL3, IL4, IL5, IL6, IL7, IL10, IL12, IL13, IL15, anti-CD40, CD40L, IFN-gamma and TNF-alpha.

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Growth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B 186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

Example 27

Method of Treating Decreased Levels of METH1 or METH2

The present invention relates to a method for treating an individual in need of a decreased level of METH1 or METH2 activity in the body comprising, administering to such an individual a composition comprising a therapeutically effective amount of METH1 or METH2 antagonist. Preferred antagonists for use in the present invention are METH1 or METH2-specific antibodies.

Moreover, it will be appreciated that conditions caused by a decrease in the standard or normal expression level of METH1 or METH2 in an individual can be treated by administering METH1 or METH2, preferably in the secreted form. Thus, the invention also provides a method of treatment of an individual in need of an increased level of METH1 or METH2 polypeptide comprising administering to such an individual a pharmaceutical composition comprising an amount of METH1 or METH2 to increase the activity level of METH1 or METH2 in such an individual.

For example, a patient with decreased levels of METH1 or METH2 polypeptide receives a daily dose 0.1–100 ug/kg of the polypeptide for six consecutive days. Preferably, the polypeptide is in the secreted form. The exact details of the dosing scheme, based on administration and formulation, are provided in Example 26.

Example 28

Method of Treating Increased Levels of METH1 or METH2

The present invention also relates to a method for treating an individual in need of an increased level of METH1 or METH2 activity in the body comprising administering to such an individual a composition comprising a therapeutically effective amount of METH1 or METH2 or an agonist thereof.

Antisense technology is used to inhibit production of METH1 or METH2. This technology is one example of a method of decreasing levels of METH1 or METH2 polypeptide, preferably a secreted form, due to a variety of etiologies, such as cancer.

For example, a patient diagnosed with abnormally increased levels of METH1 or METH2 is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 26.

Example 29

Method of Treatment Using Gene Therapy—Ex Vivo

One method of gene therapy transplants fibroblasts, which are capable of expressing METH1 or METH2 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA* 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding METH1 or METH2 can be amplified using PCR primers which correspond to the 5' and 3' end sequences respectively as set forth in Example 5. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted METH1 or METH2.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the METH1 or METH2 gene is then added to the media and the packaging cells transduced with the vector. The packaging cells now produce infectious viral particles containing the METH1 or METH2 gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether METH1 or METH2 protein is produced.

The engineered fibroblasts are then transplanted onto the host, either alone or after having been grown to confluence on cytodex 3 microcarrier beads.

Example 30

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) METH1 or METH2 sequences into an animal to increase or decrease the expression of the METH1 or METH2 polypeptide. The METH1 or METH2 polynucleotide may be operatively linked to a promoter or any other genetic elements necessary for the expression of the METH1 or METH2 polypeptide by the target tissue. Such gene therapy and delivery techniques and methods are known in the art, see, for example, WO 90/11092, W098/11779; U.S. Pat. Nos. 5,693,622, 5,705,151, 5,580,859; Tabata, H. et al. (1997) *Cardiovasc. Res.* 35(3):470–479, Chao, J. et al (1997) *Pharmacol. Res.* 35(6):517–522, Wolff, J. A. (1997) *Neuromuscul. Disord.* 7(5):314–318, Schwartz, B. et al. (1996) *Gene Ther.* 3(5):405–411, Tsurumi, Y. et al. (1996) *Circulation* 94(12):3281–3290 (incorporated herein by reference).

The METH1 or METH2 polynucleotide constructs may be delivered by any method that delivers injectable materials to the cells of an animal, such as, injection into the interstitial space of tissues (heart, muscle, skin, lung, liver, intestine and the like). The METH1 or METH2 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the METH1 or METH2 polynucleotides may also be delivered in liposome formulations (such as those taught in Felgner, P. L. et al. (1995) *Ann. NY Acad. Sci.* 772:126–139 and Abdallah, B. et al. (1995) *Biol. Cell* 85(1):1–7) which can be prepared by methods well known to those skilled in the art.

The METH1 or METH2 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The METH1 or METH2 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked METH1 or METH2 polynucleotide injection, an effective dosage amount of DNA or RNA will be in the range of from about 0.0005 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked METH1 or METH2 polynucleotide constructs can be delivered to arteries during angioplasty by the catheter used in the procedure.

The dose response effects of injected METH1 or METH2 polynucleotide in muscle in vivo is determined as follows. Suitable METH1 or METH2 template DNA for production of mRNA coding for METH1 or METH2 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The METH1 or METH2 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for METH1 or METH2 protein expression. A time course for METH1 or METH2 protein expression may be done in a similar fashion except that quadriceps from different mice are harvested at different times. Persistence of METH1 or METH2 DNA in muscle following injection maybe determined by Southern blot analysis after preparing total cellular DNA and HIRT supernatants from injected and control mice. The results of the above experimentation in mice can be use to extrapolate proper dosages and other treatment parameters in humans and other animals using METH1 or METH2 naked DNA.

Example 31

Gene Therapy Using Endogenous METH1 and/or METH2 Gene

Another method of gene therapy according to the present invention involves operably associating the endogenous METH1 and/or METH2 sequence with a promoter via homologous recombination as described, for example, in U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous METH1 and/or METH2, flanking the promoter. The targeting sequence will be sufficiently near the 5' end of METH1 and/or METH2 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous METH1 and/or METH2 sequence. This results in the expression of METH1 and/or METH2 in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately 3×10⁶ cells/ml. Electroporation should be performed immediately following resuspension.

Plasmid DNA is prepared according to standard techniques. For example, to construct a plasmid for targeting to the METH1 and/or METH2 locus, plasmid pUC18 (MBI Fermentas, Amherst, N.Y.) is digested with HindIII. The CMV promoter is amplified by PCR with an XbaI site on the 5' end and a BamHI site on the 3' end. Two METH1 and/or METH2 non-coding sequences are amplified via PCR: one METH1 and/or METH2 non-coding sequence (METH1 and/or METH2 fragment 1) is amplified with a HindIII site at the 5' end and an Xba site at the 3'end; the other METH1 and/or METH2 non-coding sequence (METH1 and/or METH2 fragment 2) is amplified with a BamHI site at the 5'end and a HindIII site at the 3'end. The CMV promoter and METH1 and/or METH2 fragments are digested with the appropriate enzymes (CMV promoter—XbaI and BamHI; METH1 and/or METH2 fragment 1—XbaI; METH1 and/or METH2 fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately 1.5×10⁶ cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 32

METH1 and/or METH2 Transgenic Animals

The METH1 and/or METH2 polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., *Appl. Microbiol. Biotechnol.* 40:691–698 (1994); Carver et al., *Biotechnology* (NY) 11:1263–1270 (1993); Wright et al., *Biotechnology* (NY) 9:830–834 (1991); and Hoppe et al., U.S. Pat. No. 4,873,191 (1989)); retrovirus mediated gene transfer into germ lines (Van der Putten et al., *Proc. Natl. Acad. Sci. USA* 82:6148–6152 (1985)), blastocysts or embryos; gene targeting in embryonic stem cells (Thompson et al., *Cell* 56:313–321 (1989)); electroporation of cells or embryos (Lo, 1983, *Mol Cell. Biol.* 3:1803–1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64–66 (1996); Wilmut et al., *Nature* 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., *Proc. Natl. Acad. Sci. USA* 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., *Science* 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of METH1 and/or METH2 polypeptides, studying conditions and/or disorders associated with aberrant METH1 and/or METH2 expression, and in screening for compounds effective in ameliorating such conditions and/or disorders.

Example 33

METH1 and/or METH2 Knock-Out Animals

Endogenous METH1 and/or METH2 gene expression can also be reduced by inactivating or "knocking out" the METH1 and/or METH2 gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the et al.METH1 and/or METH2 polypeptides. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of METH1 and/or METH2 polypeptides, studying conditions and/or disorders associated with aberrant METH1 and/or METH2 expression, and in screening for compounds effective in ameliorating such conditions and/or disorders.

Example 34

Assays Detecting Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In vitro Assay—Purified METH1 and/or METH2 protein, or truncated forms thereof, is assessed for its ability to induce activation, proliferation, differentiation or inhibition and/or death in B-cell populations and their precursors. The activity of METH1 and/or METH2 protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed Staphylococcus aureus Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5 \times 10^{-5}$M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In vivo Assay—BALB/c mice are injected (i.p.) twice per day with buffer only, or 2 mg/Kg of METH1 and/or METH2 protein, or truncated forms thereof. Mice receive this treatment for 4 consecutive days, at which time they are sacrificed and various tissues and serum collected for analyses. Comparison of H&E sections from normal and METH1 and/or METH2 protein-treated spleens identify the results of the activity of METH1 and/or METH2 protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from METH1 and/or METH2 protein-treated mice is used to indicate whether METH1 and/or METH2 protein specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and METH1 and/or METH2 protein-treated mice.

The studies described in this example test activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 35

T Cell Proliferation Assay

A CD3-induced proliferation assay is performed on PBMCs and is measured by the uptake of $^3$H-thymidine. The assay is performed as follows. Ninety-six well plates are coated with 100 μl/well of mAb to CD3 (HIT3a, Pharmingen) or isotype-matched control mAb (B33.1) overnight at 4° C. (1 mg/ml in 0.05M bicarbonate buffer, pH 9.5), then washed three times with PBS. PBMC are isolated by F/H gradient centrifugation from human peripheral blood and added to quadruplicate wells ($5 \times 10^4$/well) of mAb coated plates in RPMI containing 10% FCS and P/S in the presence of varying concentrations of et al.METH1 and/or METH2 protein (total volume 200 μl). Relevant protein buffer and medium alone are controls. After 48 hr. culture at 37° C., plates are spun for 2 min. at 1000 rpm and 100 μl of supernatant is removed and stored −20° C. for measurement of IL-2 (or other cytokines) if effect on proliferation is observed. Wells are supplemented with 100 μl of medium containing 0.5 μCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative control for the effects of METH1 and/or METH2 proteins.

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 36

Effect of METH1 and/or METH2 on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of METH1 and/or METH2 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of METH1 and/or METH2 for 24 hours. LPS (100 ng/ml) is added to the cell culture as positive control. Supernatants from the cell cultures are then collected and analyzed for IL-12 content using commercial ELISA kit (e.g, R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of METH1 and/or METH2 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. METH1 and/or METH2, agonists, or antagonists of METH1 and/or METH2 can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

1. Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation.

Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 µg/ml, and then incubated at room temperature for 5 minutes before FACScan analysis. PI uptake has been demonstrated to correlate with DNA fragmentation in this experimental paradigm.

2. Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of $5\times10^5$ cells/ml with increasing concentrations of METH1 and/or METH2 and under the same conditions, but in the absence of METH1 and/or METH2. For IL-12 production, the cells are primed overnight with IFN (100 U/ml) in presence of METH1 and/or METH2. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g, R & D Systems (Minneapolis, Minn.)) and applying the standard protocols provided with the kit.

3. Oxidative burst. Purified monocytes are plated in 96-w plate at $2-1\times10^5$ cell/well. Increasing concentrations of METH1 and/or METH2 are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 µl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity in METH1 and/or METH2 protein. However, one skilled in the art could easily modify the exemplified studies to test the activity of METH1 and/or METH2 polynucleotides (e.g., genetherapy), agonists, and/or antagonists of METH1 and/or METH2.

Example 37

METH1 and/or METH2 Biological Effects

Astrocyte and Neuronal Assays. Recombinant METH1 and/or METH2, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate METH1 and/or METH2's activity on these cells.

Moreover, previous reports describing the biological effects of FGF-2 (basic FGF) on cortical or hippocampal neurons in vitro have demonstrated increases in both neuron survival and neurite outgrowth (Walicke, P. et al., "Fibroblast growth factor promotes survival of dissociated hippocampal neurons and enhances neurite extension." *Proc. Natl. Acad. Sci. USA* 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of METH1 and/or METH2 to induce neurite outgrowth can be compared to the response achieved with FGF-2 using, for example, a thymidine incorporation assay.

Fibroblast and endothelial cell assays. Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or METH1 and/or METH2 with or without IL-1α for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or METH1 and/or METH2 with or without IL-1α for 24 hours. The supernatants are collected and assayed for IL-6 by ELISA kit (Endogen, Cambridge, Mass.).

Human lung fibroblasts are cultured with FGF-2 or METH1 and/or METH2 for 3 days in basal medium before the addition of Alamar Blue to assess effects on growth of the fibroblasts. FGF-2 should show a stimulation at 10–2500 ng/ml which can be used to compare stimulation with METH1 and/or METH2.

Parkinson Models. The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in *mitochondria* by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, METH1 and/or METH2 can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of METH1 and/or METH2 is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/cm$^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if METH1 and/or METH2 acts to prolong the survival of dopaminergic neurons, it would suggest that METH1 and/or METH2 may be involved in Parkinson's Disease.

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 38

The Effect of METH1 and/or METH2 on the Growth of Vascular Endothelial Cells

On day 1, human umbilical vein endothelial cells (HUVEC) are seeded at $2–5\times10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. METH1 and/or METH2 protein of SEQ ID NO. 2, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that METH1 and/or METH2 may proliferate vascular endothelial cells.

The studies described in this example tested activity in METH1 and/or METH2 protein. However, one skilled in the art could easily modify the exemplified studies to test the activity of meth1 and/or METH2 polynucleotides (e.g., gene therapy), agonists, and/or antagonists of METH1 and/or METH2.

Example 39

Stimulatory Effect of METH1 and/or METH2 on the Proliferation of Vascular Endothelial Cells For evaluation of mitogenic activity of growth factors, the calorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) is performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, VEGF$_{165}$ or METH1 and/or METH2 in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. in vitro *Cell. Dev. Biol.* 30A:512–518 (1994).

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 40

Inhibition of PDGF-induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4° C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., *J. Biol. Chem.* 6:271(36): 21985–21992 (1996). The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 41

Stimulation of Endothelial Migration

This example will be used to explore the possibility that METH1 and/or METH2 may stimulate lymphatic endothelial cell migration.

Endothelial cell migration assays are performed using a 48 well microchemotaxis chamber (Neuroprobe Inc., Cabin John, MD; Falk, W., et al., *J. Immunological Methods* 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, 2.5×10$^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 42

Stimulation of Nitric Oxide Production by Endothelial Cells

Nitric oxide released by the vascular endothelium is believed to be a mediator of vascular endothelium relaxation. Thus, METH1 and/or METH2 activity can be assayed by determining nitric oxide production by endothelial cells in response to METH1 and/or METH2.

Nitric oxide is measured in 96-well plates of confluent microvascular endothelial cells after 24 hours starvation and a subsequent 4 hr exposure to various levels of a positive control (such as VEGF-1) and METH1 and/or METH2. Nitric oxide in the medium is determined by use of the Griess reagent to measure total nitrite after reduction of nitric oxide-derived nitrate by nitrate reductase. The effect of METH1 and/or METH2 on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

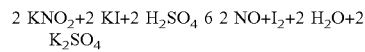

$$2\ KNO_2 + 2\ KI + 2\ H_2SO_4 \rightarrow 2\ NO + I_2 + 2\ H_2O + 2\ K_2SO_4$$

The standard calibration curve is obtained by adding graded concentrations of KNO$_2$ (0, 5, 10, 25, 50, 100, 250, and 500 nmol/L) into the calibration solution containing KI and H$_2$SO$_4$. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) to maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per 1×10⁶ endothelial cells. All values reported are means of four to six measurements in each group (number of cell culture wells). See, Leak et al. *Biochem. and Biophys. Res. Comm.* 217: 96–105 (1995).

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 43

Effect of METH1 and/or METH2 on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or METH1 and/or METH2 (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 44

Rescue of Ischemia in Rabbit Lower Limb Model

To study the in vivo effects of METH1 and/or METH2 on ischemia, a rabbit hindlimb ischemia model is created by surgical removal of one femoral arteries as described previously (Takeshita, S. et al., *Am J. Pathol* 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al. *Am J. Pathol* 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked METH1 and/or METH2 expression plasmid by arterial gene transfer technology using a hydrogel-coated balloon catheter as described (Riessen, R. et al. *Hum Gene Ther*. 4:749–758 (1993); Leclerc, G. et al. *J. Clin. Invest*. 90:936–944 (1992)). When METH1 and/or METH2 is used in the treatment, a single bolus of 500 mg METH1 and/or METH2 protein or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 45

Effect of METH1 and/or METH2 on Vasodilation

Since dilation of vascular endothelium is important in reducing blood pressure, the ability of METH1 and/or METH2 to affect the blood pressure in spontaneously hypertensive rats (SHR) is examined. Increasing doses (0, 10, 30, 100, 300, and 900 mg/kg) of the METH1 and/or METH2 are administered to 13–14 week old spontaneously hypertensive rats (SHR). Data are expressed as the mean+/−SEM. Statistical analysis are performed with a paired t-test and statistical significance is defined as $p<0.05$ vs. the response to buffer alone.

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 46

Rat Ischemic Skin Flap Model

The evaluation parameters include skin blood flow, skin temperature, and factor III immunohistochemistry or endothelial alkaline phosphatase reaction. METH1 and/or METH2 expression, during the skin ischemia, is studied using in situ hybridization.

The study in this model is divided into three parts as follows:
a) Ischemic skin
b) Ischemic skin wounds
c) Normal wounds The experimental protocol includes:
a) Raising a 3×4 cm, single pedicle full-thickness random skin flap (myocutaneous flap over the lower back of the animal).
b) An excisional wounding (4–6 mm in diameter) in the ischemic skin (skin-flap).
c) Topical treatment with METH1 and/or METH2 of the excisional wounds (day 0, 1, 2, 3, 4 post-wounding) at the following various dosage ranges: 1 mg to 100 mg.
d) Harvesting the wound tissues at day 3, 5, 7, 10, 14 and 21 post-wounding for histological, immunohistochemical, and in situ studies.

The studies described in this example tested activity in METH1 and/or METH2 protein. However, one skilled in the art could easily modify the exemplified studies to test the activity of METH1 and/or METH2 polynucleotides (e.g., genetherapy), agonists, and/or antagonists of METH1 and/or METH2.

Example 47

Peripheral Arterial Disease Model

Angiogenic therapy using METH1 and/or METH2 is a novel therapeutic strategy to obtain restoration of blood flow around the ischemia in case of peripheral arterial diseases.

The experimental protocol includes:
a) One side of the femoral artery is ligated to create ischemic muscle of the hindlimb, the other side of hindlimb serves as a control.
b) METH1 and/or METH2 protein, in a dosage range of 20 mg–500 mg, is delivered intravenously and/or intramuscularly 3 times (perhaps more) per week for 2–3 weeks.
c) The ischemic muscle tissue is collected after ligation of the femoral artery at 1, 2, and 3 weeks for the analysis of METH1 and/or METH2 expression and histology. Biopsy is also performed on the other side of normal muscle of the contralateral hindlimb.

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 48

Ischemic Myocardial Disease Model

METH1 and/or METH2 is evaluated as a potent mitogen capable of stimulating the development of collateral vessels, and restructuring new vessels after coronary artery occlusion. Alteration of METH1 and/or METH2 expression is investigated in situ. The experimental protocol includes:

a) The heart is exposed through a left-side thoracotomy in the rat. Immediately, the left coronary artery is occluded with a thin suture (6-0) and the thorax is closed.
b) METH1 and/or METH2 protein, in a dosage range of 20 mg–500 mg, is delivered intravenously and/or intramuscularly 3 times (perhaps more) per week for 2–4 weeks.
c) Thirty days after the surgery, the heart is removed and cross-sectioned for morphometric and in situ analyzes.

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 49

Rat Corneal Wound Healing Model

This animal model shows the effect of METH1 and/or METH2 on neovascularization. The experimental protocol includes:
a) Making a 1–1.5 mm long incision from the center of cornea into the stromal layer.
b) Inserting a spatula below the lip of the incision facing the outer corner of the eye.
c) Making a pocket (its base is 1–1.5 mm form the edge of the eye).
d) Positioning a pellet, containing 50 ng–5 ug of METH1 and/or METH2, within the pocket.
e) METH1 and/or METH2 treatment can also be applied topically to the corneal wounds in a dosage range of 20 mg–500 mg (daily treatment for five days).

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 50

Diabetic Mouse and Glucocorticoid-Impaired Wound Healing Models

A. Diabetic db+/db+Mouse Model.

To demonstrate that METH1 and/or METH2 has an effect on the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al., *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., *Diabetes* 29(1):60–67 (1980); Giacomelli et al., *Lab Invest.* 40(4):460–473 (1979); Coleman, D. L., *Diabetes* 31 (Suppl):1–6 (1982)). These homozygous diabetic mice develop hyperglycemia that is resistant to insulin analogous to human type II diabetes (Mandel et al., *J. Immunol.*

120:1375–1377 (1978)). The characteristics observed in these animals suggests that healing in this model may be similar to the healing observed in human diabetes (Greenhalgh, et al., *Am. J. of Pathol.* 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

METH1 and/or METH2 is administered using at a range different doses of METH1 and/or METH2, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) METH1 and/or 3) METH2.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 mm$^2$, the corresponding size of the dermal punch. Calculations are made using the following formula:

[Open area on day 8]–[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with METH1 and/or METH2. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer served as a positive tissue control and human brain tissue is used as a negative tissue control. Each specimen included a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, S. M. Glucocorticoids and Wound healing. In: Anti-Inflammatory Steroid Action: Basic and Clinical Aspects. 280–302 (1989); Wahl, S. M. et al., *J. Immunol.* 115:476–481 (1975); Werb, Z. et al., *J. Exp. Med.* 147:1684–1694 (1978)). Glucocorticoids retard wound healing by inhibiting angiogenesis, decreasing vascular permeability (Ebert, R. H., et al., *An. Intern. Med.* 37:701–705 (1952)), fibroblast proliferation, and collagen synthesis (Beck, L. S. et al., *Growth Factors.* 5: 295–304 (1991); Haynes, B. F. et al., *J. Clin. Invest.* 61: 703–797 (1978)) and producing a transient reduction of circulating monocytes (Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck, L. S. et al., *Growth Factors.* 5: 295–304 (1991); Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989); Pierce, G. F. et al., *Proc. Natl. Acad. Sci. USA* 86: 2229–2233 (1989)).

To demonstrate that METH1 and/or METH2 has an effect on the healing process, the effects of multiple topical applications of METH1 and/or METH2 on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

METH1 and/or METH2 is administered using at a range different doses of METH1 and/or METH2, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) METH1 and 4) METH2 treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 $mm^2$, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with METH1 and/or METH2. A calibrated lens micrometer is used by a blinded observer to determine the distance of the wound gap.

Experimental data are analyzed using an unpaired t test. A p value of <0.05 is considered significant.

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 51

Lymphadema Animal Model

The purpose of this experimental approach is to create an appropriate and consistent lymphedema model for testing the therapeutic effects of METH1 and/or METH2 in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements: Blood is drawn, spun, and serum separated prior to surgery and then at conclusion for total protein and Ca2+ comparison.

Limb Weight Comparison: After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations: The transverse muscle located behind the knee (popliteal) area is dissected and arranged in a metal mold, filled with freezeGel, dipped into cold methylbutane, placed into labeled sample bags at −80EC until sectioning. Upon sectioning, the muscle is observed under fluorescent microscopy for lymphatics.

The studies described in this example tested activity in METH1 and/or METH2 protein. However, one skilled in the art could easily modify the exemplified studies to test the activity of METH1 and/or METH2 polynucleotides (e.g., gene therapy), agonists, and/or antagonists of METH1 and/or METH2.

Example 52

Generation of Constructs and Expression of METH1

Two constructs having either a Flag peptide sequence or a human IgG1 Fc domain fused to the full-length METH1 gene at its C-terminus were generated, using methods well known in the art. The construct names, pFlag-CMV-5a: METH1 (ID 822) and pC4Fc:METH1 (ID 821) were assigned.

The following primers were used for pFlag-CMV-5a: METH1:

```
5':AAGAATGCGGCCGCAGCCACCATGGGGAACGCGGAGCGGGCTCC

3':GATCGCGGTACCACTGCATTCTGCCATTGTGCAAAAGTCTATG
```

METH1 was amplified using the indicated primers, and digested with Asp718. The vector pFLAGCMV-5a was also digested with Asp718. The resulting restriction products were ligated together.

The following primers were used for pC4Fc:METH1:

```
5':GATCTATGATCAGCCACCATGGGGAACGCGGAGCGGGCTCC

3':GACTGCTCTAGAACTGCATTCTGCCATTGTGCAAAAGTCTATG
```

METH1 was amplified using the indicated primers, and digested with BcII and Xba. The vector pC4Fc was also digested with BcII and Xba. The resulting restriction products were ligated together.

Constructs pA2 gp:METH1 (H542-Q894).Fc and pA2 gp:METH1(H542-Q894) can also be made.

Also, pC4Fc:Meth1.M1-P799 can be made using the following primers:

```
5' primer:
GATCTA TGATCA GCCACCATGGGGAACGCGGAGCGGGCTCC

3' primer:
GCGTGC TCTAGA AGGGCTAAAGCTGCGAATTC
```

METH1 is amplified using the indicated primers, and digested with BcII and Xba. The vector pC4Fc was also digested with BcII and Xba, and ligated to the digested METH1 fragment.

pFLAG-CMV-1:Meth1.F236-E614 can be made using the following primers:

```
5' primer:    GTACCC AAGCTT TTTGTGTCCAGTCACCGC

3' primer:    GCGTGC TCTAGA TTACTCGTTGTGTGCTTCAC
```

METH1 is amplified using the indicated primers and digested with Hind III and Xba. The vector pFLAG-CMV-1 is also digested with Hind III and Xba and ligated to the digested METH1 fragment.

The constructs were made in order to confirm the anti-angiogenesis activity of METH1. The full length METH1 gene was PCR cloned into pC4Fc and pFlagCMV5a vectors. Both pC4Fc:METH1 and pFLAGCMV5a:METH1 were obtained and the sequence confirmed.

Transient transfections on 293T cells were done using lipofectamine plus (LTI) reagent and held for production under serum-free conditions. Western analysis was done with either anti-huFc Ab or anti-Flag M2 Ab. METH1-Fc conditioned media showed at least five bands with varying degree of intensity. Their estimated MWs are 130–140 kD(weak), 110–120 kD(weak), 52 kD(strong), 45–48 kd(strong) and 32–35 kD(strongest). Two weaker bands at about 60 and 90 kD were also detectable. METH1-Flag conditioned medium revealed three major bands with equal intensity. They are about 100–110 kD, 70–80 kD and 22 kD. Transient transfection of METH1-Fc in 293T cells. A second batch of METH1-Fc protein was produced in medium with 1% serum as described above.

5.5 day conditioned medium from transiently transfected cells was run on a ProteinA column and eluted. The fractions containing protein were examined by SDS-PAGE under reduced and non-reduced conditions and stained with Coomassie Blue. A second gel was also prepared for N-terminal sequence analysis.

197 µg of protein were recovered which demonstrated 4 bands under reducing conditions. Three of the bands were strong, one was weak. N-terminal sequencing of the bands suggested that 2 of the bands contained proteins with a blocked N-termini. Of the 2 bands giving sequence, one was an Fc-derived fragment, the other a cleavage product of the METH1. Fc fusion starting at L800 (containing two of the thrombospondin-like domains). This suggests that METH1 is processed with at least 2 cleavage sites (possibly more) since only the C-terminal fragments still linked to the Fc fragment would be purified on the Protein A column.

The transfected 293T cells were conditioned in medium containing 1% dialyzed, low IgG, fetal calf serum to attempt to decrease the proteolysis of the recombinant secreted protein. The purification and analysis was as described above. The yield of protein was significantly higher than the first batch, possibly reflecting the effect of the serum in the medium. While some processing may have been slowed by the serum, the majority of the protein remained approximately 31 kD on a reducing gel.

N-terminal sequencing of resolved bands under reducing conditions indicated the protein is processed at L800 of the 950 residue METH1 orf, with other possible cleavage occurring N-terminal to this site. The observed cleavage site was considered unusual since it followed a Pro. A total of 197.4 µg of protein was isolated (HG12100-D293T1). Analysis of flag protein (pFlag-CMV-5a:METH1), consisting of at least three bands on the Western blot (120, 97 and 21 Kd) indicated that only one band (21 kd) could be confirmed as METH1 and the other bands were of non-METH1 origin.

Since sequencing of the purified METH1 Fc protein suggested an unusual cleavage site, a second batch of METH1 Fc was prepared with cells grown in 1% FBS, to possibly inhibit undesirable processing. A preliminary assessment of the product suggests that no difference in processing resulted from the change in medium, but protein yields were increased.

Functional assays of the initial Fc and Flag protein supernatants performed included proliferation of Human Microvascular Endothelial Cells (HMVECs) and in vitro cord formation using Bovine aortic endothelial cells (BAECs). The proliferation assay indicated increased rates of HMVEC proliferation in response to both culture supernatants, which may be attributable to high background stimulation from the conditioned medium. Cord formation assays of both the Fc and Flag supernatants indicated inhibition of cord formation relative to a medium/collagen control in two independent experiments.

Example 53

In Vitro Activity of METH1

Proliferation

HMVECs were used in an alamar blue assay to determine if METH1 supernatants have functional anti-angiogenic activity, detectable by an inhibition of EC proliferation. FGF-2 was used as the primary stimulus for proliferation and culture supernatants were used at a 1:4 final dilution. The proliferation assays indicated significantly increased rates of HMVEC proliferation in response to both culture supernatants, which may be attributable to high background stimulation from the conditioned medium. This problem should be reduced or eliminated by the use of purified proteins.

Cord Formation

The addition of soluble type I collagen to endothelial cells and the appropriate growth factors will induce the production of tube-like structures or cords of endothelial cells in culture which involves both the migration of endothelial cells and the selective deletion (apoptosis) of cells not involved in these structures. Bovine aortic endothelial cells (BAECs) were used to detect inhibition of stable cord formation when cultured with METH1-Fc and METH1-Flag containing culture supernatants at a 1:4 dilution. Qualitative assessment of the cord formation indicated inhibition with both of the tested supernatants relative to the collagen-treated control. However, a non-matched conditioned medium control also generated inhibition of cord formation, suggesting that non-specific cellular toxicity might also contribute to the observed inhibition.

The studies described in this example tested activity in METH1 protein. However, one skilled in the art could easily modify the exemplified studies to test the activity of METH2 polypeptides, METH1 and/or METH2 polynucleotides (e.g., gene therapy), agonists, and/or antagonists of METH1 and/or METH2.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated polynucleotide comprising a nucleotide sequence encoding amino acids 1 to 967 of SEQ ID NO:126.

2. The isolated polynucleotide of claim 1, wherein said polynucleotide comprises nucleotides 466 to 3366 of SEQ ID NO:125.

3. The isolated polynucleotide of claim 1, wherein said nucleotide sequence comprises the nucleotide sequence of SEQ ID NO:125.

4. The isolated polynucleotide of claim 1, which is RNA.
5. The isolated polynucleotide of claim 2, which is RNA.
6. The isolated polynucleotide of claim 3, which is RNA.
7. The isolated polynucleotide of claim 1, which is DNA.
8. The isolated polynucleotide of claim 2, which is DNA.
9. The isolated polynucleotide of claim 3, which is DNA.

10. A vector comprising the isolated polynucleotide of claim 1.

11. The vector of claim 10, wherein said polynucleotide is operably associated with a regulatory sequence that regulates gene expression.

12. An isolated host cell which comprises the isolated polynucleotide of claim 1.

13. A process for producing a host cell comprising transforming or transfecting an isolated cell with the vector of claim 10.

14. A process for producing a polypeptide comprising culturing the host cell of claim 13 under conditions sufficient for the production of said polypeptide and recovering said polypeptide from the culture.

15. An isolated polynucleotide comprising a nucleotide sequence which is fully complementary to a polynucleotide sequence encoding amino acids 1 to 967 of SEQ ID NO:126.

16. The isolated polynucleotide of claim 15, comprising a nucleotide sequence which is fully complementary to nucleotides of 466 to 3366 of SEQ ID NO:125.

17. An isolated polynucleotide comprising the entire nucleotide sequence of SEQ ID NO:1.

* * * * *

UNITED STATES PATENT AND TRADEMARK OFFICE
CERTIFICATE OF CORRECTION

PATENT NO. : 7,220,557 B2
APPLICATION NO. : 09/373658
DATED : May 22, 2007
INVENTOR(S) : Hastings et al.

It is certified that error appears in the above-identified patent and that said Letters Patent is hereby corrected as shown below:

On The Title Page,
Item (60) Related U.S. Application Data:
Please delete "provisional application No. 60/098,539, filed on Aug. 28, 1998." and replace with --provisional application No. 60/098,539, filed on Aug. 28, 1998, provisional application No. 60/072,298, filed on Jan. 23, 1998.--.

On The Title Page,
Item (56) References Cited, Foreign Patent Documents:
Last line, please delete "766767" and replace with --766787--.
On page 1, column 2, line 9, please delete "WO 1 004 674 A1" and replace with --EP 1 004 674 A1--.

In the Sequence Listing:
Replace the Sequence Listing with the accompanying Sequence Listing.

Signed and Sealed this

Twenty-seventh Day of November, 2007

JON W. DUDAS
*Director of the United States Patent and Trademark Office*

SEQUENCE LISTING

<160> NUMBER OF SEQ ID NOS: 125

<210> SEQ ID NO 1
<211> LENGTH: 3261
<212> TYPE: DNA
<213> ORGANISM: Homo sapiens
<220> FEATURE:
<221> NAME/KEY: CDS
<222> LOCATION: (1)..(2853)
<221> NAME/KEY: UNSURE
<222> LOCATION: (3095)
<223> OTHER INFORMATION: May be any nucleic acid
<221> NAME/KEY: UNSURE
<222> LOCATION: (3248)

```
<223> OTHER INFORMATION: May be any nucleic acid
<221> NAME/KEY: UNSURE
<222> LOCATION: (3255)
<223> OTHER INFORMATION: May be any nucleic acid
<221> NAME/KEY: UNSURE
<222> LOCATION: (3261)
<223> OTHER INFORMATION: May be any nucleic acid

<400> SEQUENCE: 1 atg ggg aac gcg gag cgg gct ccg ggg tct cgg agc ttt ggg ccc gta      48
Met Gly Asn Ala Glu Arg Ala Pro Gly Ser Arg Ser Phe Gly Pro Val
 1               5                  10                  15
ccc acg ctg ctg ctc gcc gcg gcg cta ctg gcc gtc gac gca              96
Pro Thr Leu Leu Leu Ala Ala Ala Leu Leu Ala Val Ser Asp Ala
             20                  25                  30
ctc ggg cgc ccc tcc gag gag gac gag gag cta gtg gtg ccg gag ctg     144
Leu Gly Arg Pro Ser Glu Glu Asp Glu Glu Leu Val Val Pro Glu Leu
         35                  40                  45
gag cgc gcc ccg gga cac ggg acc acg cgc ctc cgc ctg cac gcc ttt     192
Glu Arg Ala Pro Gly His Gly Thr Thr Arg Leu Arg Leu His Ala Phe
 50                  55                  60
gac cag cag ctg gat ctg gag ctg cgg ccc gac agc agc ttt ttg gcg     240
Asp Gln Gln Leu Asp Leu Glu Leu Arg Pro Asp Ser Ser Phe Leu Ala
 65                  70                  75                  80
ccc ggc ttc acg ctc cag aac gtg ggg cgc aaa tcc ggg tcc gag acg     288
Pro Gly Phe Thr Leu Gln Asn Val Gly Arg Lys Ser Gly Ser Glu Thr
                 85                  90                  95
ccg ctt ccg gaa acc gac ctg gcg cac tgc ttc tac tcc ggc acc gtg     336
Pro Leu Pro Glu Thr Asp Leu Ala His Cys Phe Tyr Ser Gly Thr Val
            100                 105                 110
aat ggc gat ccc agc tcg gct gcc gcc ctc agc ctc tgc gag ggc gtg     384
Asn Gly Asp Pro Ser Ser Ala Ala Ala Leu Ser Leu Cys Glu Gly Val
        115                 120                 125
cgc ggc gcc ttc tac ctg ctg ggg gag gcg tat ttc atc cag ccg ctg     432
Arg Gly Ala Phe Tyr Leu Leu Gly Glu Ala Tyr Phe Ile Gln Pro Leu
    130                 135                 140
ccc gcc gcc agc gag cgc ctc gcc acc gcc gcc cca ggg gag aag ccg     480
Pro Ala Ala Ser Glu Arg Leu Ala Thr Ala Ala Pro Gly Glu Lys Pro
145                 150                 155                 160
ccg gca cca cta cag ttc cac ctc ctg cgg aat cgg cag ggc gac         528
Pro Ala Pro Leu Gln Phe His Leu Leu Arg Asn Arg Gln Gly Asp
                165                 170                 175
gta ggc ggc acg tgc ggg gtc gtg gac gac gag ccc cgg ccg act ggg     576
Val Gly Gly Thr Cys Gly Val Val Asp Asp Glu Pro Arg Pro Thr Gly
            180                 185                 190
aaa gcg gag acc gaa gac gag gac gaa ggg act gag ggc gag gac gaa     624
Lys Ala Glu Thr Glu Asp Glu Asp Glu Gly Thr Glu Gly Glu Asp Glu
        195                 200                 205
ggg cct cag tgg tcg ccg cag gac ccg gca ctg caa ggc gta gga cag     672
Gly Pro Gln Trp Ser Pro Gln Asp Pro Ala Leu Gln Gly Val Gly Gln
    210                 215                 220
ccc aca gga act gga agc ata aga aag aag cga ttt gtg tcc agt cac     720
Pro Thr Gly Thr Gly Ser Ile Arg Lys Lys Arg Phe Val Ser Ser His
225                 230                 235                 240
cgc tat gtg gaa acc atg ctt gtg gca gac cag tcg atg gca gaa ttc     768
Arg Tyr Val Glu Thr Met Leu Val Ala Asp Gln Ser Met Ala Glu Phe
                245                 250                 255
cac ggc agt ggt cta aag cat tac ctt ctc acg ttg ttt tcg gtg gca     816
His Gly Ser Gly Leu Lys His Tyr Leu Leu Thr Leu Phe Ser Val Ala
            260                 265                 270
gcc aga ttg tac aaa cac ccc agc att cgt aat tca gtt agc ctg gtg     864
Ala Arg Leu Tyr Lys His Pro Ser Ile Arg Asn Ser Val Ser Leu Val
        275                 280                 285
gtg gtg aag atc ttg gtc atc cac gat gaa cag aag ggg ccg gaa gtg     912
Val Val Lys Ile Leu Val Ile His Asp Glu Gln Lys Gly Pro Glu Val
    290                 295                 300
acc tcc aat gct gcc ctc act ctg cgg aac ttt tgc aac tgg cag aag     960
Thr Ser Asn Ala Ala Leu Thr Leu Arg Asn Phe Cys Asn Trp Gln Lys
305                 310                 315                 320
cag cac aac cca ccc agt gac cgg gat gca gag cac tat gac aca gca    1008
Gln His Asn Pro Pro Ser Asp Arg Asp Ala Glu His Tyr Asp Thr Ala
                325                 330                 335
att ctt ttc acc aga cag gac ttg tgt ggg tcc cag aca tgt gat act    1056
Ile Leu Phe Thr Arg Gln Asp Leu Cys Gly Ser Gln Thr Cys Asp Thr
            340                 345                 350
ctt ggg atg gct gat gtt gga act gtg tgt gat ccg agc aga agc tgc    1104
Leu Gly Met Ala Asp Val Gly Thr Val Cys Asp Pro Ser Arg Ser Cys
        355                 360                 365
```

```
tcc gtc ata gaa gat gat ggt tta caa gct gcc ttc acc aca gcc cat    1152
Ser Val Ile Glu Asp Asp Gly Leu Gln Ala Ala Phe Thr Thr Ala His
        370                 375                 380
gaa tta ggc cac gtg ttt aac atg cca cat gat gat gca aag cag tgt    1200
Glu Leu Gly His Val Phe Asn Met Pro His Asp Asp Ala Lys Gln Cys
385                 390                 395                 400
gcc agc ctt aat ggt gtg aac cag gat tcc cac atg atg gcg tca atg    1248
Ala Ser Leu Asn Gly Val Asn Gln Asp Ser His Met Met Ala Ser Met
                405                 410                 415
ctt tcc aac ctg gac cac agc cag cct tgg tct cct tgc agt gcc tac    1296
Leu Ser Asn Leu Asp His Ser Gln Pro Trp Ser Pro Cys Ser Ala Tyr
            420                 425                 430
atg att aca tca ttt ctg gat aat ggt cat ggg gaa tgt ttg atg gac    1344
Met Ile Thr Ser Phe Leu Asp Asn Gly His Gly Glu Cys Leu Met Asp
        435                 440                 445
aag cct cag aat ccc ata cag ctc cca ggc gat ctc cct ggc acc tcg    1392
Lys Pro Gln Asn Pro Ile Gln Leu Pro Gly Asp Leu Pro Gly Thr Ser
    450                 455                 460
tac gat gcc aac cgg cag tgc cag ttt aca ttt ggg gag gac tcc aaa    1440
Tyr Asp Ala Asn Arg Gln Cys Gln Phe Thr Phe Gly Glu Asp Ser Lys
465                 470                 475                 480
cac tgc cct gat gca gcc agc aca tgt agc acc ttg tgg tgt acc ggc    1488
His Cys Pro Asp Ala Ala Ser Thr Cys Ser Thr Leu Trp Cys Thr Gly
                485                 490                 495
acc tct ggt ggg gtg ctg gtg tgt caa acc aaa cac ttc ccg tgg gcg    1536
Thr Ser Gly Gly Val Leu Val Cys Gln Thr Lys His Phe Pro Trp Ala
            500                 505                 510
gat ggc acc agc tgt gga gaa ggg aaa tgg tgt atc aac ggc aag tgt    1584
Asp Gly Thr Ser Cys Gly Glu Gly Lys Trp Cys Ile Asn Gly Lys Cys
        515                 520                 525
gtg aac aaa acc gac aga aag cat ttt gat acg cct ttt cat gga agc    1632
Val Asn Lys Thr Asp Arg Lys His Phe Asp Thr Pro Phe His Gly Ser
    530                 535                 540
tgg gga atg tgg ggg cct tgg gga gac tgt tcg aga acg tgc ggt gga    1680
Trp Gly Met Trp Gly Pro Trp Gly Asp Cys Ser Arg Thr Cys Gly Gly
545                 550                 555                 560
gga gtc cag tac acg atg agg gaa tgt gac aac cca gtc cca aag aat    1728
Gly Val Gln Tyr Thr Met Arg Glu Cys Asp Asn Pro Val Pro Lys Asn
                565                 570                 575
gga ggg aag tac tgt gaa ggc aaa cga gtg cgc tac aga tcc tgt aac    1776
Gly Gly Lys Tyr Cys Glu Gly Lys Arg Val Arg Tyr Arg Ser Cys Asn
            580                 585                 590
ctt gag gac tgt cca gac aat aat gga aaa acc ttt aga gag gaa caa    1824
Leu Glu Asp Cys Pro Asp Asn Asn Gly Lys Thr Phe Arg Glu Glu Gln
        595                 600                 605
tgt gaa gca cac aac gag ttt tca aaa gct tcc ttt ggg agt ggg cct    1872
Cys Glu Ala His Asn Glu Phe Ser Lys Ala Ser Phe Gly Ser Gly Pro
    610                 615                 620
gcg gtg gaa tgg att ccc aag tac gct ggc gtc tca cca aag gac agg    1920
Ala Val Glu Trp Ile Pro Lys Tyr Ala Gly Val Ser Pro Lys Asp Arg
625                 630                 635                 640
tgc aag ctc atc tgc caa gcc aaa ggc att ggc tac ttc ttc gtt ttg    1968
Cys Lys Leu Ile Cys Gln Ala Lys Gly Ile Gly Tyr Phe Phe Val Leu
                645                 650                 655
cag ccc aag gtt gta gat ggt act cca tgt agc cca gat tcc acc tct    2016
Gln Pro Lys Val Val Asp Gly Thr Pro Cys Ser Pro Asp Ser Thr Ser
            660                 665                 670
gtc tgt gtg caa gga cag tgt gta aaa gct ggt tgt gat cgc atc ata    2064
Val Cys Val Gln Gly Gln Cys Val Lys Ala Gly Cys Asp Arg Ile Ile
        675                 680                 685
gac tcc aaa aag aag ttt gat aaa tgt ggt gtt tgc ggg gga aat gga    2112
Asp Ser Lys Lys Lys Phe Asp Lys Cys Gly Val Cys Gly Gly Asn Gly
    690                 695                 700
tct act tgt aaa aaa ata tca gga tca gtt act agt gca aaa cct gga    2160
Ser Thr Cys Lys Lys Ile Ser Gly Ser Val Thr Ser Ala Lys Pro Gly
705                 710                 715                 720
tat cat gat atc atc aca att cca act gga gcc acc aac atc gaa gtg    2208
Tyr His Asp Ile Ile Thr Ile Pro Thr Gly Ala Thr Asn Ile Glu Val
                725                 730                 735
aaa cag cgg aac cag agg gga tcc agg aac aat ggc agc ttt ctt gcc    2256
Lys Gln Arg Asn Gln Arg Gly Ser Arg Asn Asn Gly Ser Phe Leu Ala
            740                 745                 750
atc aaa gct gct gat ggc aca tat att ctt aat ggt gac tac act ttg    2304
Ile Lys Ala Ala Asp Gly Thr Tyr Ile Leu Asn Gly Asp Tyr Thr Leu
        755                 760                 765
tcc acc tta gag caa gac att atg tac aaa ggt gtt gtc ttg agg tac    2352
Ser Thr Leu Glu Gln Asp Ile Met Tyr Lys Gly Val Val Leu Arg Tyr
    770                 775                 780
agc ggc tcc tct gcg gca ttg gaa aga att cgc agc ttt agc cct ctc    2400
```

```
               Ser Gly Ser Ser Ala Ala Leu Glu Arg Ile Arg Ser Phe Ser Pro Leu
               785                 790                 795                 800
aaa gag ccc ttg acc atc cag gtt ctt act gtg ggc aat gcc ctt cga        2448
Lys Glu Pro Leu Thr Ile Gln Val Leu Thr Val Gly Asn Ala Leu Arg
                    805                 810                 815
cct aaa att aaa tac acc tac ttc gta aag aag aag gaa tct ttc            2496
Pro Lys Ile Lys Tyr Thr Tyr Phe Val Lys Lys Lys Glu Ser Phe
                820                 825                 830
aat gct atc ccc act ttt tca gca tgg gtc att gaa gag tgg ggc gaa        2544
Asn Ala Ile Pro Thr Phe Ser Ala Trp Val Ile Glu Glu Trp Gly Glu
            835                 840                 845
tgt tct aag tca tgt gaa ttg ggt tgg cag aga aga ctg gta gaa tgc        2592
Cys Ser Lys Ser Cys Glu Leu Gly Trp Gln Arg Arg Leu Val Glu Cys
        850                 855                 860
cga gac att aat gga cag cct gct tcc gag tgt gca aag gaa gtg aag        2640
Arg Asp Ile Asn Gly Gln Pro Ala Ser Glu Cys Ala Lys Glu Val Lys
865                 870                 875                 880
cca gcc agc acc aga cct tgt gca gac cat ccc tgc ccc cag tgg cag        2688
Pro Ala Ser Thr Arg Pro Cys Ala Asp His Pro Cys Pro Gln Trp Gln
                    885                 890                 895
ctg ggg gag tgg tca tca tgt tct aag acc tgt ggg aag ggt tac aaa        2736
Leu Gly Glu Trp Ser Ser Cys Ser Lys Thr Cys Gly Lys Gly Tyr Lys
                900                 905                 910
aaa aga agc ttg aag tgt ctg tcc cat gat gga ggg gtg tta tct cat        2784
Lys Arg Ser Leu Lys Cys Leu Ser His Asp Gly Gly Val Leu Ser His
            915                 920                 925
gag agc tgt gat cct tta aag aaa cct aaa cat ttc ata gac ttt tgc        2832
Glu Ser Cys Asp Pro Leu Lys Lys Pro Lys His Phe Ile Asp Phe Cys
        930                 935                 940
aca atg gca gaa tgc agt taa gtggtttaag tggtgttagc tttgaggcaa           2883
Thr Met Ala Glu Cys Ser
945                 950
ggcaaagtga ggaagggctg gtgcagggaa agcaagaagg ctggagggat ccagcgtatc      2943
ttgccagtaa ccagtgaggt gtatcagtaa ggtgggatta tgggggtaga tagaaaagga     3003
gttgaatcat cagagtaaac tgccagttgc aaatttgata ggatagttag tgaggattat     3063
taacctctga gcagtgatat agcataataa anccccgggc attattatta ttatttcttt     3123
tgttacatct attacaagtt tagaaaaaac aaagcaattg tcaaaaaaaa aaaaaaaaa      3183
aaaaaaaaa aaagggcggc cgctctagag gatccctcga ggggcccaag cttacgcgtg     3243
catgntgtca tnagtctn                                                   3261
```

<210> SEQ ID NO 2
<211> LENGTH: 950
<212> TYPE: PRT
<213> ORGANISM: Homo sapiens

<400> SEQUENCE: 2

```
Met Gly Asn Ala Glu Arg Ala Pro Gly Ser Arg Ser Phe Gly Pro Val
1               5                   10                  15
Pro Thr Leu Leu Leu Ala Ala Leu Leu Ala Val Ser Asp Ala
            20                  25                  30
Leu Gly Arg Pro Ser Glu Glu Asp Glu Glu Leu Val Val Pro Glu Leu
        35                  40                  45
Glu Arg Ala Pro Gly His Gly Thr Thr Arg Leu Arg Leu His Ala Phe
    50                  55                  60
Asp Gln Gln Leu Asp Leu Glu Leu Arg Pro Asp Ser Ser Phe Leu Ala
65                  70                  75                  80
Pro Gly Phe Thr Leu Gln Asn Val Gly Arg Lys Ser Gly Ser Glu Thr
                85                  90                  95
Pro Leu Pro Glu Thr Asp Leu Ala His Cys Phe Tyr Ser Gly Thr Val
            100                 105                 110
Asn Gly Asp Pro Ser Ser Ala Ala Ala Leu Ser Leu Cys Glu Gly Val
        115                 120                 125
Arg Gly Ala Phe Tyr Leu Leu Gly Glu Ala Tyr Phe Ile Gln Pro Leu
    130                 135                 140
Pro Ala Ala Ser Glu Arg Leu Ala Thr Ala Ala Pro Gly Glu Lys Pro
145                 150                 155                 160
Pro Ala Pro Leu Gln Phe His Leu Leu Arg Arg Asn Arg Gln Gly Asp
                165                 170                 175
Val Gly Gly Thr Cys Gly Val Val Asp Asp Glu Pro Arg Pro Thr Gly
            180                 185                 190
Lys Ala Glu Thr Glu Asp Glu Asp Glu Gly Thr Glu Gly Glu Asp Glu
        195                 200                 205
Gly Pro Gln Trp Ser Pro Gln Asp Pro Ala Leu Gln Leu Val Gly Gln
    210                 215                 220
Pro Thr Gly Thr Gly Ser Ile Arg Lys Lys Arg Phe Val Ser Ser His
225                 230                 235                 240
Arg Tyr Val Glu Thr Met Leu Val Ala Asp Gln Ser Met Ala Glu Phe
```

-continued

```
            245                 250                 255
His Gly Ser Gly Leu Lys His Tyr Leu Leu Thr Leu Phe Ser Val Ala
                260                 265                 270
Ala Arg Leu Tyr Lys His Pro Ser Ile Arg Asn Ser Val Ser Leu Val
            275                 280                 285
Val Val Lys Ile Leu Val Ile His Asp Glu Gln Lys Gly Pro Glu Val
            290                 295                 300
Thr Ser Asn Ala Ala Leu Thr Leu Arg Asn Phe Cys Asn Trp Gln Lys
305                 310                 315                 320
Gln His Asn Pro Pro Ser Asp Arg Asp Ala Glu His Tyr Asp Thr Ala
                325                 330                 335
Ile Leu Phe Thr Arg Gln Asp Leu Cys Gly Ser Gln Thr Cys Asp Thr
            340                 345                 350
Leu Gly Met Ala Asp Val Gly Thr Val Cys Asp Pro Ser Arg Ser Cys
            355                 360                 365
Ser Val Ile Glu Asp Asp Gly Leu Gln Ala Ala Phe Thr Thr Ala His
            370                 375                 380
Glu Leu Gly His Val Phe Asn Met Pro His Asp Asp Ala Lys Gln Cys
385                 390                 395                 400
Ala Ser Leu Asn Gly Val Asn Gln Asp Ser His Met Met Ala Ser Met
                405                 410                 415
Leu Ser Asn Leu Asp His Ser Gln Pro Trp Ser Pro Cys Ser Ala Tyr
            420                 425                 430
Met Ile Thr Ser Phe Leu Asp Asn Gly His Gly Glu Cys Leu Met Asp
            435                 440                 445
Lys Pro Gln Asn Pro Ile Gln Leu Pro Gly Asp Leu Pro Gly Thr Ser
            450                 455                 460
Tyr Asp Ala Asn Arg Gln Cys Gln Phe Thr Phe Gly Glu Asp Ser Lys
465                 470                 475                 480
His Cys Pro Asp Ala Ala Ser Thr Cys Ser Thr Leu Trp Cys Thr Gly
                485                 490                 495
Thr Ser Gly Gly Val Leu Val Cys Gln Thr Lys His Phe Pro Trp Ala
            500                 505                 510
Asp Gly Thr Ser Cys Gly Glu Gly Lys Trp Cys Ile Asn Gly Lys Cys
            515                 520                 525
Val Asn Lys Thr Asp Arg Lys His Phe Asp Thr Pro Phe His Gly Ser
            530                 535                 540
Trp Gly Met Trp Gly Pro Trp Gly Asp Cys Ser Arg Thr Cys Gly Gly
545                 550                 555                 560
Gly Val Gln Tyr Thr Met Arg Glu Cys Asp Asn Pro Val Pro Lys Asn
                565                 570                 575
Gly Gly Lys Tyr Cys Glu Gly Lys Arg Val Arg Tyr Arg Ser Cys Asn
            580                 585                 590
Leu Glu Asp Cys Pro Asp Asn Asn Gly Lys Thr Phe Arg Glu Glu Gln
            595                 600                 605
Cys Glu Ala His Asn Glu Phe Ser Lys Ala Ser Phe Gly Ser Gly Pro
            610                 615                 620
Ala Val Glu Trp Ile Pro Lys Tyr Ala Gly Val Ser Pro Lys Asp Arg
625                 630                 635                 640
Cys Lys Leu Ile Cys Gln Ala Lys Gly Ile Gly Tyr Phe Phe Val Leu
                645                 650                 655
Gln Pro Lys Val Val Asp Gly Thr Pro Cys Ser Pro Asp Ser Thr Ser
            660                 665                 670
Val Cys Val Gln Gly Gln Cys Val Lys Ala Gly Cys Asp Arg Ile Ile
            675                 680                 685
Asp Ser Lys Lys Lys Phe Asp Lys Cys Gly Val Cys Gly Gly Asn Gly
            690                 695                 700
Ser Thr Cys Lys Lys Ile Ser Gly Ser Val Thr Ser Ala Lys Pro Gly
705                 710                 715                 720
Tyr His Asp Ile Ile Thr Ile Pro Thr Gly Ala Thr Asn Ile Glu Val
                725                 730                 735
Lys Gln Arg Asn Gln Arg Gly Ser Arg Asn Asn Gly Ser Phe Leu Ala
            740                 745                 750
Ile Lys Ala Ala Asp Gly Thr Tyr Ile Leu Asn Gly Asp Tyr Thr Leu
            755                 760                 765
Ser Thr Leu Glu Gln Asp Ile Met Tyr Lys Gly Val Val Leu Arg Tyr
            770                 775                 780
Ser Gly Ser Ser Ala Ala Leu Glu Arg Ile Arg Ser Phe Ser Pro Leu
785                 790                 795                 800
Lys Glu Pro Leu Thr Ile Gln Val Leu Thr Val Gly Asn Ala Leu Arg
                805                 810                 815
Pro Lys Ile Lys Tyr Thr Tyr Phe Val Lys Lys Lys Glu Ser Phe
            820                 825                 830
Asn Ala Ile Pro Thr Phe Ser Ala Trp Val Ile Glu Glu Trp Gly Glu
            835                 840                 845
Cys Ser Lys Ser Cys Glu Leu Gly Trp Gln Arg Arg Leu Val Glu Cys
            850                 855                 860
Arg Asp Ile Asn Gly Gln Pro Ala Ser Glu Cys Ala Lys Glu Val Lys
865                 870                 875                 880
```

-continued

```
        Pro Ala Ser Thr Arg Pro Cys Ala Asp His Pro Cys Pro Gln Trp Gln
                        885                 890                 895
        Leu Gly Glu Trp Ser Ser Cys Ser Lys Thr Cys Gly Lys Gly Tyr Lys
                    900                 905                 910
        Lys Arg Ser Leu Lys Cys Leu Ser His Asp Gly Val Leu Ser His
                915                 920                 925
        Glu Ser Cys Asp Pro Leu Lys Lys Pro Lys His Phe Ile Asp Phe Cys
            930                 935                 940
        Thr Met Ala Glu Cys Ser
        945                 950

<210> SEQ ID NO 3
<211> LENGTH: 3008
<212> TYPE: DNA
<213> ORGANISM: Homo sapiens
<220> FEATURE:
<221> NAME/KEY: CDS
<222> LOCATION: (1)..(2670)
<221> NAME/KEY: UNSURE
<222> LOCATION: (2887)
<223> OTHER INFORMATION: May be any nucleic acid
<221> NAME/KEY: UNSURE
<222> LOCATION: (2957)
<223> OTHER INFORMATION: May be any nucleic acid
<221> NAME/KEY: UNSURE
<222> LOCATION: (2970)
<223> OTHER INFORMATION: May be any nucleic acid
<221> NAME/KEY: UNSURE
<222> LOCATION: (2981)
<223> OTHER INFORMATION: May be any nucleic acid

<400> SEQUENCE: 3 atg ttc ccc gcc ccc gcc gcc ccc cgg tgg ctt ccg ttc ctg ctg ctg     48
        Met Phe Pro Ala Pro Ala Ala Pro Arg Trp Leu Pro Phe Leu Leu Leu
        1               5                   10                  15
        ctg ctg ctg ctg ctg ctg ccg ctg gcc cgc ggc gcc ccg gcc cgg ccc     96
        Leu Leu Leu Leu Leu Leu Pro Leu Ala Arg Gly Ala Pro Ala Arg Pro
                        20                  25                  30
        gca gcc ggg ggg cag gcc tcg gag ctg gtg gtg ccc acg cgg ttg ccc    144
        Ala Ala Gly Gly Gln Ala Ser Glu Leu Val Val Pro Thr Arg Leu Pro
                    35                  40                  45
        ggc agc gcg ggc gag ctc gcg ctc cac ctg tcc gcc ttc ggc aag ggc    192
        Gly Ser Ala Gly Glu Leu Ala Leu His Leu Ser Ala Phe Gly Lys Gly
                50                  55                  60
        ttc gtg ttg cgc ctg gcg ccc gac gac agc ttc ctg gcg ccc gag ttc    240
        Phe Val Leu Arg Leu Ala Pro Asp Asp Ser Phe Leu Ala Pro Glu Phe
        65                  70                  75                  80
        aag atc gag cgc ctc ggg ggc tcc ggc cgg gcg acc ggg ggc gag cgg    288
        Lys Ile Glu Arg Leu Gly Gly Ser Gly Arg Ala Thr Gly Gly Glu Arg
                        85                  90                  95
        ggg ctg cgc ggc tgt ttt ttt tcc ggc acc gtg aat ggg gag ccc gag    336
        Gly Leu Arg Gly Cys Phe Phe Ser Gly Thr Val Asn Gly Glu Pro Glu
                    100                 105                 110
        tcg ctg gcg gcg gtc agc ctg tgc cgc ggg ctg agc ggc tcc ttc ctg    384
        Ser Leu Ala Ala Val Ser Leu Cys Arg Gly Leu Ser Gly Ser Phe Leu
                115                 120                 125
        ctg gac ggc gag gag ttc acc atc cag ccg cag ggc gcg ggg ggc tcc    432
        Leu Asp Gly Glu Glu Phe Thr Ile Gln Pro Gln Gly Ala Gly Gly Ser
            130                 135                 140
        ctg gct cag ccg cac cgc ctg cag cgc tgg ggt ccc gcc gga gcc cgc    480
        Leu Ala Gln Pro His Arg Leu Gln Arg Trp Gly Pro Ala Gly Ala Arg
        145                 150                 155                 160
        ccc ctc ccg cga gga ccc gag tgg gag gtg gag acg gga gag ggt cag    528
        Pro Leu Pro Arg Gly Pro Glu Trp Glu Val Glu Thr Gly Glu Gly Gln
                        165                 170                 175
        agg cag gag aga gga gac cac cag gag gac agc gag gag agc caa        576
        Arg Gln Glu Arg Gly Asp His Gln Glu Asp Ser Glu Glu Ser Gln
                    180                 185                 190
        gaa gag gag gca gaa ggc gct agc gag ccg cca ccg ccc ctg ggg gcc    624
        Glu Glu Glu Ala Glu Gly Ala Ser Glu Pro Pro Pro Pro Leu Gly Ala
                195                 200                 205
        acg agt agg acc aag cgg ttt gtg tct gag gcg cgc ttc gtg gag acg    672
        Thr Ser Arg Thr Lys Arg Phe Val Ser Glu Ala Arg Phe Val Glu Thr
            210                 215                 220
        ctg ctg gtg gcc gat gcg tcc atg gct gcc ttc tac ggg gcc gac ctg    720
        Leu Leu Val Ala Asp Ala Ser Met Ala Ala Phe Tyr Gly Ala Asp Leu
        225                 230                 235                 240
```

```
cag aac cac atc ctg acg tta atg tct gtg gca gcc cga atc tac aag      768
Gln Asn His Ile Leu Thr Leu Met Ser Val Ala Ala Arg Ile Tyr Lys
                245                 250                 255
cac ccc agc atc aag aat tcc atc aac ctg atg gta aaa gtg ctg          816
His Pro Ser Ile Lys Asn Ser Ile Asn Leu Met Val Val Lys Val Leu
            260                 265                 270
atc gta gaa gat gaa aaa tgg ggc cca gag gtg tcc gac aat ggg ggg      864
Ile Val Glu Asp Glu Lys Trp Gly Pro Glu Val Ser Asp Asn Gly Gly
        275                 280                 285
ctt aca ctg cgt aac ttc tgc aac tgg cag cgg cgt ttc aac cag ccc      912
Leu Thr Leu Arg Asn Phe Cys Asn Trp Gln Arg Arg Phe Asn Gln Pro
290                 295                 300
agc gac cgc cac cca gag cac tac gac acg gcc atc ctg ctc acc aga      960
Ser Asp Arg His Pro Glu His Tyr Asp Thr Ala Ile Leu Leu Thr Arg
305                 310                 315                 320
cag aac ttc tgt ggg cag gag ggg ctg tgt gac acc ctg ggt gtg gca     1008
Gln Asn Phe Cys Gly Gln Glu Gly Leu Cys Asp Thr Leu Gly Val Ala
                325                 330                 335
gac atc ggg acc att tgt gac ccc aac aaa agc tgc tcc gtg atc gag     1056
Asp Ile Gly Thr Ile Cys Asp Pro Asn Lys Ser Cys Ser Val Ile Glu
            340                 345                 350
gat gag ggg ctc cag gcg gcc cac acc ctg gcc cat gaa cta ggg cac     1104
Asp Glu Gly Leu Gln Ala Ala His Thr Leu Ala His Glu Leu Gly His
        355                 360                 365
gtc ctc agc atg ccc cac gac tcc aag ccc tgc acg cgg ctc ttc         1152
Val Leu Ser Met Pro His Asp Ser Lys Pro Cys Thr Arg Leu Phe
370                 375                 380
ggg ccc atg ggc aag cac cac gtg atg gca ccg ctg ttc gtc cac ctg     1200
Gly Pro Met Gly Lys His His Val Met Ala Pro Leu Phe Val His Leu
385                 390                 395                 400
aac cag acg ctg ccc tgg tcc ccc tgc agc gcc atg tat ctc aca gag     1248
Asn Gln Thr Leu Pro Trp Ser Pro Cys Ser Ala Met Tyr Leu Thr Glu
                405                 410                 415
ctt ctg gac ggc ggg cac gga gac tgt ctc ctg gat gcc cct ggt gcg     1296
Leu Leu Asp Gly Gly His Gly Asp Cys Leu Leu Asp Ala Pro Gly Ala
            420                 425                 430
gcc ctg ccc ctc ccc aca ggc ctc ccg ggc cgc atg gcc ctg tac cag     1344
Ala Leu Pro Leu Pro Thr Gly Leu Pro Gly Arg Met Ala Leu Tyr Gln
        435                 440                 445
ctg gac cag cag tgc agg cag atc ttt ggg ccg gat ttc cgc cac tgc     1392
Leu Asp Gln Gln Cys Arg Gln Ile Phe Gly Pro Asp Phe Arg His Cys
450                 455                 460
ccc aac acc tct gct cag gac gtc tgc gcc cag ctt tgg tgc cac act     1440
Pro Asn Thr Ser Ala Gln Asp Val Cys Ala Gln Leu Trp Cys His Thr
465                 470                 475                 480
gat ggg gct gag ccc ctg tgc cac acg aag aat ggc agc ctg ccc tgg     1488
Asp Gly Ala Glu Pro Leu Cys His Thr Lys Asn Gly Ser Leu Pro Trp
                485                 490                 495
gct gac ggc acg ccg tgc ggg cct ggg cac ctc tgc tca gaa ggc agc     1536
Ala Asp Gly Thr Pro Cys Gly Pro Gly His Leu Cys Ser Glu Gly Ser
            500                 505                 510
tgt cta cct gag gag gaa gtg gag agg ccc aag ccc gtg gta gat gga     1584
Cys Leu Pro Glu Glu Glu Val Glu Arg Pro Lys Pro Val Val Asp Gly
        515                 520                 525
ggc tgg gca ccg tgg gga ccc tgg gga gaa tgt tct cgg acc tgt gga     1632
Gly Trp Ala Pro Trp Gly Pro Trp Gly Glu Cys Ser Arg Thr Cys Gly
530                 535                 540
gga gga gta cag ttt tca cac cgt gag tgc aag gac ccc gag cct cag     1680
Gly Gly Val Gln Phe Ser His Arg Glu Cys Lys Asp Pro Glu Pro Gln
545                 550                 555                 560
aat gga gga aga tac tgc ctg ggt cgg aga gcc aag tac cag tca tgc     1728
Asn Gly Gly Arg Tyr Cys Leu Gly Arg Arg Ala Lys Tyr Gln Ser Cys
                565                 570                 575
cac acg gag gaa tgc ccc cct gac ggg aaa agc ttc agg gag cag cag     1776
His Thr Glu Glu Cys Pro Pro Asp Gly Lys Ser Phe Arg Glu Gln Gln
            580                 585                 590
tgt gag aag tat aat gcc tac aat tac act gac atg gac ggg aat ctc     1824
Cys Glu Lys Tyr Asn Ala Tyr Asn Tyr Thr Asp Met Asp Gly Asn Leu
        595                 600                 605
ctg cag ttg tgg gtc ccc aag tat gct ggg gtg tcc ccc cgg gac cgc tgc 1872
Leu Gln Trp Val Pro Lys Tyr Ala Gly Val Ser Pro Arg Asp Arg Cys
610                 615                 620
aag ttg ttc tgc cga gcc cgg ggg agg agc gag ttc aaa gtg ttc gag     1920
Lys Leu Phe Cys Arg Ala Arg Gly Arg Ser Glu Phe Lys Val Phe Glu
625                 630                 635                 640
gcc aag gtg att gat ggc acc ctg tgt ggg cca gaa aca ctg gcc atc     1968
Ala Lys Val Ile Asp Gly Thr Leu Cys Gly Pro Glu Thr Leu Ala Ile
                645                 650                 655
tgt gtc cgt ggc cag tgt gtc aag gcc ggc tgt gac cat gtg gtg gac     2016
```

```
                Cys Val Arg Gly Gln Cys Val Lys Ala Gly Cys Asp His Val Val Asp
                                660                 665                 670
    tcg cct cgg aag ctg gac aaa tgc ggg gtg tgt ggg ggc aaa ggc aac         2064
    Ser Pro Arg Lys Leu Asp Lys Cys Gly Val Cys Gly Gly Lys Gly Asn
                675                 680                 685
    tcc tgc agg aag gtc tcc ggg tcc ctc acc ccc acc aat tat ggc tac         2112
    Ser Cys Arg Lys Val Ser Gly Ser Leu Thr Pro Thr Asn Tyr Gly Tyr
            690                 695                 700
    aat gac att gtc acc atc cca gct ggt gcc act aat att gac gtg aag         2160
    Asn Asp Ile Val Thr Ile Pro Ala Gly Ala Thr Asn Ile Asp Val Lys
    705                 710                 715                 720
    cag cgg agc cac ccg ggt gtg cag aac gat ggg aac tac ctg gcg ctg         2208
    Gln Arg Ser His Pro Gly Val Gln Asn Asp Gly Asn Tyr Leu Ala Leu
                725                 730                 735
    aag acg gct gat ggg cag tac ctg ctc aac ggc aac ctg gcc atc tct         2256
    Lys Thr Ala Asp Gly Gln Tyr Leu Leu Asn Gly Asn Leu Ala Ile Ser
                740                 745                 750
    gcc ata gag cag gac atc ttg gtg aag ggg acc atc ctg aag tac agc         2304
    Ala Ile Glu Gln Asp Ile Leu Val Lys Gly Thr Ile Leu Lys Tyr Ser
            755                 760                 765
    ggc tcc atc gcc acc ctg gag cgc ctg cag agc ttc cgg ccc ttg cca         2352
    Gly Ser Ile Ala Thr Leu Glu Arg Leu Gln Ser Phe Arg Pro Leu Pro
    770                 775                 780
    gag cct ctg aca gtg cag ctc ctg aca gtc cct ggc gag gtc ttc ccc         2400
    Glu Pro Leu Thr Val Gln Leu Leu Thr Val Pro Gly Glu Val Phe Pro
    785                 790                 795                 800
    cca aaa gtc aaa tac acc ttc ttt gtt cct aat gac gtg gac ttt agc         2448
    Pro Lys Val Lys Tyr Thr Phe Phe Val Pro Asn Asp Val Asp Phe Ser
                805                 810                 815
    atg cag agc agc aaa gag aga gca acc acc aac atc atc cag ccg ctg         2496
    Met Gln Ser Ser Lys Glu Arg Ala Thr Thr Asn Ile Ile Gln Pro Leu
                820                 825                 830
    ctc cac gca cag tgg gtg ctg ggg gac tgg tct gag tgc tct agc acc         2544
    Leu His Ala Gln Trp Val Leu Gly Asp Trp Ser Glu Cys Ser Ser Thr
                835                 840                 845
    tgc ggg gcc ggc tgg cag agg cga act gta gag tgc agg gac ccc tcc         2592
    Cys Gly Ala Gly Trp Gln Arg Arg Thr Val Glu Cys Arg Asp Pro Ser
    850                 855                 860
    ggc cag gcc tct gcc acc tgc aac aag gct ctg aaa ccc gag gat gcc         2640
    Gly Gln Ala Ser Ala Thr Cys Asn Lys Ala Leu Lys Pro Glu Asp Ala
    865                 870                 875                 880
    aag ccc tgc gaa agc cag ctg tgc ccc ctg tgattcaggg gggcaggggc           2690
    Lys Pro Cys Glu Ser Gln Leu Cys Pro Leu
                885                 890
    cagtcttgtg ctcctggaca tgcggtactg aggtgcagac aaggtctcca ctgtggtgac      2750
    tgggtcccctt ggccatatca aggcagcacg gcccacccag gcctcccatt gccgcaaccc      2810
    ctccagtact gcacaaattc ctaaggggga agagaaaagg tatgggggcgg caaaacctat     2870
    catcaactgt ccawtgnaat ggaacttgct cgggttcaat taaaggcata agttaaagta      2930
    aattcattat gatcaacaga cctcacntca tctgttgcan gatacaacta ntaaaaaaaa     2990
    aaaaaaaaaa aaaaaaaa                                                    3008

<210> SEQ ID NO 4
<211> LENGTH: 890
<212> TYPE: PRT
<213> ORGANISM: Homo sapiens

<400> SEQUENCE: 4

Met Phe Pro Ala Pro Ala Ala Pro Arg Trp Leu Pro Phe Leu Leu Leu
    1               5                   10                  15
    Leu Leu Leu Leu Leu Pro Leu Ala Arg Gly Ala Pro Ala Arg Pro
                20                  25                  30
    Ala Ala Gly Gly Gln Ala Ser Glu Leu Val Val Pro Thr Arg Leu Pro
            35                  40                  45
    Gly Ser Ala Gly Glu Leu Ala Leu His Leu Ser Ala Phe Gly Lys Gly
        50                  55                  60
    Phe Val Leu Arg Leu Ala Pro Asp Asp Ser Phe Leu Ala Pro Glu Phe
    65                  70                  75                  80
    Lys Ile Glu Arg Leu Gly Gly Ser Gly Arg Ala Thr Gly Gly Glu Arg
                    85                  90                  95
    Gly Leu Arg Gly Cys Phe Phe Ser Gly Thr Val Asn Gly Glu Pro Glu
                100                 105                 110
    Ser Leu Ala Ala Val Ser Leu Cys Arg Gly Leu Ser Gly Ser Phe Leu
            115                 120                 125
    Leu Asp Gly Glu Glu Phe Thr Ile Gln Pro Gln Gly Ala Gly Gly Ser
        130                 135                 140
    Leu Ala Gln Pro His Arg Leu Gln Arg Trp Gly Pro Ala Gly Ala Arg
    145                 150                 155                 160
```

```
Pro Leu Pro Arg Gly Pro Glu Trp Glu Val Glu Thr Gly Glu Gly Gln
            165                 170                 175
Arg Gln Glu Arg Gly Asp His Gln Glu Asp Ser Glu Glu Ser Gln
        180                 185                 190
Glu Glu Glu Ala Glu Gly Ala Ser Glu Pro Pro Pro Leu Gly Ala
        195                 200                 205
Thr Ser Arg Thr Lys Arg Phe Val Ser Glu Ala Arg Phe Val Glu Thr
        210                 215                 220
Leu Leu Val Ala Asp Ala Ser Met Ala Ala Phe Tyr Gly Ala Asp Leu
225                 230                 235                 240
Gln Asn His Ile Leu Thr Leu Met Ser Val Ala Ala Arg Ile Tyr Lys
            245                 250                 255
His Pro Ser Ile Lys Asn Ser Ile Asn Leu Met Val Val Lys Val Leu
            260                 265                 270
Ile Val Glu Asp Glu Lys Trp Gly Pro Glu Val Ser Asp Asn Gly Gly
            275                 280                 285
Leu Thr Leu Arg Asn Phe Cys Asn Trp Gln Arg Arg Phe Asn Gln Pro
            290                 295                 300
Ser Asp Arg His Pro Glu His Tyr Asp Thr Ala Ile Leu Leu Thr Arg
305                 310                 315                 320
Gln Asn Phe Cys Gly Gln Glu Gly Leu Cys Asp Thr Leu Gly Val Ala
            325                 330                 335
Asp Ile Gly Thr Ile Cys Asp Pro Asn Lys Ser Cys Ser Val Ile Glu
            340                 345                 350
Asp Glu Gly Leu Gln Ala Ala His Thr Leu Ala His Glu Leu Gly His
            355                 360                 365
Val Leu Ser Met Pro His Asp Asp Ser Lys Pro Cys Thr Arg Leu Phe
370                 375                 380
Gly Pro Met Gly Lys His His Val Met Ala Pro Leu Phe Val His Leu
385                 390                 395                 400
Asn Gln Thr Leu Pro Trp Ser Pro Cys Ser Ala Met Tyr Leu Thr Glu
            405                 410                 415
Leu Leu Asp Gly Gly His Gly Asp Cys Leu Leu Asp Ala Pro Gly Ala
            420                 425                 430
Ala Leu Pro Leu Pro Thr Gly Leu Pro Gly Arg Met Ala Leu Tyr Gln
            435                 440                 445
Leu Asp Gln Gln Cys Arg Gln Ile Phe Gly Pro Asp Phe Arg His Cys
            450                 455                 460
Pro Asn Thr Ser Ala Gln Asp Val Cys Ala Gln Leu Trp Cys His Thr
465                 470                 475                 480
Asp Gly Ala Glu Pro Leu Cys His Thr Lys Asn Gly Ser Leu Pro Trp
            485                 490                 495
Ala Asp Gly Thr Pro Cys Gly Pro Gly His Leu Cys Ser Glu Gly Ser
            500                 505                 510
Cys Leu Pro Glu Glu Glu Val Glu Arg Pro Lys Pro Val Val Asp Gly
            515                 520                 525
Gly Trp Ala Pro Trp Gly Pro Trp Gly Glu Cys Ser Arg Thr Cys Gly
            530                 535                 540
Gly Gly Val Gln Phe Ser His Arg Glu Cys Lys Asp Pro Glu Pro Gln
545                 550                 555                 560
Asn Gly Gly Arg Tyr Cys Leu Gly Arg Arg Ala Lys Tyr Gln Ser Cys
            565                 570                 575
His Thr Glu Glu Cys Pro Pro Asp Gly Lys Ser Phe Arg Glu Gln Gln
            580                 585                 590
Cys Glu Lys Tyr Asn Ala Tyr Asn Tyr Thr Asp Met Asp Gly Asn Leu
            595                 600                 605
Leu Gln Trp Val Pro Lys Tyr Ala Gly Val Ser Pro Arg Asp Arg Cys
            610                 615                 620
Lys Leu Phe Cys Arg Ala Arg Gly Arg Ser Glu Phe Lys Val Phe Glu
625                 630                 635                 640
Ala Lys Val Ile Asp Gly Thr Leu Cys Gly Pro Glu Thr Leu Ala Ile
            645                 650                 655
Cys Val Arg Gly Gln Cys Val Lys Ala Gly Cys Asp His Val Val Asp
            660                 665                 670
Ser Pro Arg Lys Leu Asp Lys Cys Gly Val Cys Gly Gly Lys Gly Asn
            675                 680                 685
Ser Cys Arg Lys Val Ser Gly Ser Leu Thr Pro Thr Asn Tyr Gly Tyr
            690                 695                 700
Asn Asp Ile Val Thr Ile Pro Ala Gly Ala Thr Asn Ile Asp Val Lys
705                 710                 715                 720
Gln Arg Ser His Pro Gly Val Gln Asn Asp Gly Asn Tyr Leu Ala Leu
            725                 730                 735
Lys Thr Ala Asp Gly Gln Tyr Leu Leu Asn Gly Asn Leu Ala Ile Ser
            740                 745                 750
Ala Ile Glu Gln Asp Ile Leu Val Lys Gly Thr Ile Leu Lys Tyr Ser
            755                 760                 765
Gly Ser Ile Ala Thr Leu Glu Arg Leu Gln Ser Phe Arg Pro Leu Pro
770                 775                 780
Glu Pro Leu Thr Val Gln Leu Leu Thr Val Pro Gly Glu Val Phe Pro
```

```
          785                 790                 795                 800
    Pro Lys Val Lys Tyr Thr Phe Phe Val Pro Asn Asp Val Asp Phe Ser
                        805                 810                 815
    Met Gln Ser Ser Lys Glu Arg Ala Thr Thr Asn Ile Ile Gln Pro Leu
                    820                 825                 830
    Leu His Ala Gln Trp Val Leu Gly Asp Trp Ser Glu Cys Ser Ser Thr
                835                 840                 845
    Cys Gly Ala Gly Trp Gln Arg Arg Thr Val Glu Cys Arg Asp Pro Ser
            850                 855                 860
    Gly Gln Ala Ser Ala Thr Cys Asn Lys Ala Leu Lys Pro Glu Asp Ala
    865                 870                 875                 880
    Lys Pro Cys Glu Ser Gln Leu Cys Pro Leu
                    885                 890

<210> SEQ ID NO 5
<211> LENGTH: 1203
<212> TYPE: PRT
<213> ORGANISM: Bovine

<400> SEQUENCE: 5

Met Asp Pro Pro Ala Gly Ala Ala Gly Arg Leu Leu Cys Pro Ala Leu
    1               5                   10                  15
    Leu Leu Leu Leu Leu Pro Leu Pro Ala Asp Ala Arg Leu Leu Ala Ala
                    20                  25                  30
    Ala Ala Ala Asp Pro Pro Gly Gly Pro Gln Gly His Gly Ala Glu Arg
                35                  40                  45
    Ile Leu Ala Val Pro Val Arg Thr Asp Ala Gln Gly Arg Leu Val Ser
        50                  55                  60
    His Val Val Ser Ala Ala Thr Ala Pro Ala Gly Val Arg Thr Arg Arg
    65                  70                  75                  80
    Ala Ala Pro Ala Gln Ile Pro Gly Leu Ser Gly Gly Ser Glu Glu Asp
                    85                  90                  95
    Pro Gly Gly Arg Leu Phe Tyr Asn Val Thr Val Phe Gly Arg Asp Leu
                    100                 105                 110
    His Leu Arg Leu Arg Pro Asn Ala Arg Leu Val Ala Pro Gly Ala Thr
                115                 120                 125
    Val Glu Trp Gln Gly Glu Ser Gly Ala Thr Arg Val Glu Pro Leu Leu
            130                 135                 140
    Gly Thr Cys Leu Tyr Val Gly Asp Val Ala Gly Leu Ala Glu Ser Ser
    145                 150                 155                 160
    Ser Val Ala Leu Ser Asn Cys Asp Gly Leu Ala Gly Leu Ile Arg Met
                    165                 170                 175
    Glu Glu Glu Glu Phe Phe Ile Glu Pro Leu Glu Lys Gly Leu Ala Ala
                    180                 185                 190
    Lys Glu Ala Glu Gln Gly Arg Val His Val Val Tyr His Arg Pro Thr
                195                 200                 205
    Thr Ser Arg Pro Pro Leu Gly Gln Ala Leu Asp Thr Gly Ile Ser
            210                 215                 220
    Ala Asp Ser Leu Asp Ser Leu Ser Arg Ala Leu Gly Val Leu Glu Glu
    225                 230                 235                 240
    Arg Val Asn Ser Ser Arg Arg Arg Met Arg Arg His Ala Ala Asp Asp
                    245                 250                 255
    Asp Tyr Asn Ile Glu Val Leu Leu Gly Val Asp Asp Ser Val Val Gln
                    260                 265                 270
    Phe His Gly Thr Glu His Val Gln Lys Tyr Leu Leu Thr Leu Met Asn
                275                 280                 285
    Ile Val Asn Glu Ile Tyr His Asp Glu Ser Leu Gly Ala His Ile Asn
            290                 295                 300
    Val Val Leu Val Arg Ile Ile Leu Leu Ser Tyr Gly Lys Ser Met Ser
    305                 310                 315                 320
    Leu Ile Glu Ile Gly Asn Pro Ser Gln Ser Leu Glu Asn Val Cys Arg
                    325                 330                 335
    Trp Ala Tyr Leu Gln Gln Lys Pro Asp Thr Asp His Asp Glu Tyr His
                    340                 345                 350
    Asp His Ala Ile Phe Leu Thr Arg Gln Asp Phe Gly Pro Ser Gly Met
                355                 360                 365
    Gln Gly Tyr Ala Pro Val Thr Gly Met Cys His Pro Val Arg Ser Cys
            370                 375                 380
    Thr Leu Asn His Glu Asp Gly Phe Ser Ser Ala Phe Val Val Ala His
    385                 390                 395                 400
    Glu Thr Gly His Val Leu Gly Met Glu His Asp Gly Gln Gly Asn Arg
                    405                 410                 415
    Cys Gly Asp Glu Val Arg Leu Gly Ser Ile Met Ala Pro Leu Val Gln
                    420                 425                 430
    Ala Ala Phe His Arg Phe His Trp Ser Arg Cys Ser Gln Gln Glu Leu
                435                 440                 445
    Ser Arg Tyr Leu His Ser Tyr Asp Cys Leu Arg Asp Asp Pro Phe Thr
```

-continued

```
            450                 455                 460
His Asp Trp Pro Ala Leu Pro Gln Leu Pro Gly Leu His Tyr Ser Met
465                 470                 475                 480
Asn Glu Gln Cys Arg Phe Asp Phe Gly Leu Gly Tyr Met Met Cys Thr
                    485                 490                 495
Ala Phe Arg Thr Phe Asp Pro Cys Lys Gln Leu Trp Cys Ser His Pro
                500                 505                 510
Asp Asn Pro Tyr Phe Cys Lys Thr Lys Lys Gly Pro Pro Leu Asp Gly
            515                 520                 525
Thr Met Cys Ala Pro Gly Lys His Cys Phe Lys Gly His Cys Ile Trp
        530                 535                 540
Leu Thr Pro Asp Ile Leu Lys Arg Asp Gly Asn Trp Gly Ala Trp Ser
545                 550                 555                 560
Pro Phe Gly Ser Cys Ser Arg Thr Cys Gly Thr Gly Val Lys Phe Arg
                    565                 570                 575
Thr Arg Gln Cys Asp Asn Pro His Pro Ala Asn Gly Gly Arg Thr Cys
                580                 585                 590
Ser Gly Leu Ala Tyr Asp Phe Gln Leu Cys Asn Ser Gln Asp Cys Pro
            595                 600                 605
Asp Ala Leu Ala Asp Phe Arg Glu Glu Gln Cys Arg Gln Trp Asp Leu
        610                 615                 620
Tyr Phe Glu His Gly Asp Ala Gln His His Trp Leu Pro His Glu His
625                 630                 635                 640
Arg Asp Ala Lys Glu Arg Cys His Leu Tyr Cys Glu Ser Lys Glu Thr
                    645                 650                 655
Gly Glu Val Val Ser Met Lys Arg Met Val His Asp Gly Thr Arg Cys
                660                 665                 670
Ser Tyr Lys Asp Ala Phe Ser Leu Cys Val Arg Gly Asp Cys Arg Lys
            675                 680                 685
Val Gly Cys Asp Gly Val Ile Gly Ser Ser Lys Gln Glu Asp Lys Cys
        690                 695                 700
Gly Val Cys Gly Gly Asp Asn Ser His Cys Lys Val Val Lys Gly Thr
705                 710                 715                 720
Phe Ser Arg Ser Pro Lys Lys Leu Gly Tyr Ile Lys Met Phe Glu Ile
                    725                 730                 735
Pro Ala Gly Ala Arg His Leu Leu Ile Gln Glu Ala Asp Thr Thr Ser
                740                 745                 750
His His Leu Ala Val Lys Asn Leu Glu Thr Gly Lys Phe Ile Leu Asn
            755                 760                 765
Glu Glu Asn Asp Val Asp Pro Asn Ser Lys Thr Phe Ile Ala Met Gly
        770                 775                 780
Val Glu Trp Glu Tyr Arg Asp Glu Asp Gly Arg Glu Thr Leu Gln Thr
785                 790                 795                 800
Met Gly Pro Leu His Gly Thr Ile Thr Val Leu Val Ile Pro Glu Gly
                    805                 810                 815
Asp Ala Arg Ile Ser Leu Thr Tyr Lys Tyr Met Ile His Glu Asp Ser
                820                 825                 830
Leu Asn Val Asp Asp Asn Asn Val Leu Glu Asp Asp Ser Val Gly Tyr
            835                 840                 845
Glu Trp Ala Leu Lys Lys Trp Ser Pro Cys Ser Lys Pro Cys Gly Gly
        850                 855                 860
Gly Ser Gln Phe Thr Lys Tyr Gly Cys Arg Arg Leu Asp His Lys
865                 870                 875                 880
Met Val His Arg Gly Phe Cys Asp Ser Val Ser Lys Pro Lys Ala Ile
                    885                 890                 895
Arg Arg Thr Cys Asn Pro Gln Glu Cys Ser Gln Pro Val Trp Val Thr
                900                 905                 910
Gly Glu Trp Glu Pro Cys Ser Arg Ser Cys Gly Arg Thr Gly Met Gln
            915                 920                 925
Val Arg Ser Val Arg Cys Val Gln Pro Leu His Asn Asn Thr Thr Arg
        930                 935                 940
Ser Val His Thr Lys His Cys Asn Asp Ala Arg Pro Glu Gly Arg Arg
945                 950                 955                 960
Ala Cys Asn Arg Glu Leu Cys Pro Gly Arg Trp Arg Ala Gly Ser Trp
                    965                 970                 975
Ser Gln Cys Ser Val Thr Cys Gly Asn Gly Thr Gln Glu Arg Pro Val
                980                 985                 990
Leu Cys Arg Thr Ala Asp Asp Ser Phe Gly Val Cys Arg Glu Glu Arg
            995                 1000                1005
Pro Glu Thr Ala Arg Ile Cys Arg Leu Gly Pro Cys Pro Arg Asn Thr
        1010                1015                1020
Ser Asp Pro Ser Lys Lys Ser Tyr Val Val Gln Trp Leu Ser Arg Pro
1025                1030                1035                1040
Asp Pro Asn Ser Pro Val Gln Glu Thr Ser Ser Lys Gly Arg Cys Gln
                    1045                1050                1055
Gly Asp Lys Ser Val Phe Cys Arg Met Glu Val Leu Ser Arg Tyr Cys
                1060                1065                1070
Ser Ile Pro Gly Tyr Asn Lys Leu Cys Cys Lys Ser Cys Asn Pro His
            1075                1080                1085
```

```
        Asp Asn Leu Thr Asp Val Asp Asp Arg Ala Glu Pro Pro Ser Gly Lys
            1090                1095                1100
        His Asn Asp Ile Glu Glu Leu Met Pro Thr Leu Ser Val Pro Thr Leu
        1105                1110                1115                1120
        Val Met Glu Val Gln Pro Pro Gly Ile Pro Leu Glu Val Pro Leu
                        1125                1130                1135
        Asn Thr Ser Ser Thr Asn Ala Thr Glu Asp His Pro Glu Thr Asn Ala
                    1140                1145                1150
        Val Asp Val Pro Tyr Lys Ile Pro Gly Leu Glu Asp Glu Val Gln Pro
                1155                1160                1165
        Pro Asn Leu Ile Pro Arg Arg Pro Ser Pro Tyr Glu Lys Thr Arg Asn
            1170                1175                1180
        Gln Arg Ile Gln Glu Leu Ile Asp Glu Met Arg Lys Lys Glu Met Leu
        1185                1190                1195                1200
        Gly Lys Phe

<210> SEQ ID NO 6
<211> LENGTH: 50
<212> TYPE: PRT
<213> ORGANISM: Homo sapiens

<400> SEQUENCE: 6

Asp Asp Gly Trp Ser Pro Trp Ser Glu Trp Thr Ser Cys Ser Thr Ser
        1                   5                   10                  15
        Cys Gly Asn Gly Ile Gln Gln Arg Gly Arg Ser Cys Asp Ser Leu Asn
                        20                  25                  30
        Asn Arg Cys Glu Gly Ser Ser Val Gln Thr Arg Thr Cys His Ile Gln
                    35                  40                  45
        Glu Cys
            50

<210> SEQ ID NO 7
<211> LENGTH: 57
<212> TYPE: PRT
<213> ORGANISM: Homo sapiens

<400> SEQUENCE: 7

Asp Gly Gly Trp Ser His Trp Ser Pro Trp Ser Ser Cys Ser Val Thr
        1                   5                   10                  15
        Cys Gly Asp Gly Val Ile Thr Arg Ile Arg Leu Cys Asn Ser Pro Ser
                        20                  25                  30
        Pro Gln Met Asn Gly Lys Pro Cys Glu Gly Glu Ala Arg Glu Thr Lys
                    35                  40                  45
        Ala Cys Lys Lys Asp Ala Cys Pro Ile
            50                  55

<210> SEQ ID NO 8
<211> LENGTH: 57
<212> TYPE: PRT
<213> ORGANISM: Homo sapiens

<400> SEQUENCE: 8

Asn Gly Gly Trp Gly Pro Trp Ser Pro Trp Asp Ile Cys Ser Val Thr
        1                   5                   10                  15
        Cys Gly Gly Gly Val Gln Lys Arg Ser Arg Leu Cys Asn Asn Pro Thr
                        20                  25                  30
        Pro Gln Phe Gly Gly Lys Asp Cys Val Gly Asp Val Thr Glu Asn Gln
                    35                  40                  45
        Ile Cys Asn Lys Gln Asp Cys Pro Ile
            50                  55

<210> SEQ ID NO 9
<211> LENGTH: 50
<212> TYPE: PRT
<213> ORGANISM: Homo sapiens

<400> SEQUENCE: 9

Glu Glu Gly Trp Ser Pro Trp Ala Glu Trp Thr Gln Cys Ser Val Thr
        1                   5                   10                  15
        Cys Gly Ser Gly Thr Gln Gln Arg Gly Arg Ser Cys Asp Val Thr Ser
                        20                  25                  30
```

```
        Asn Thr Cys Leu Gly Pro Ser Ile Gln Thr Arg Ala Cys Ser Leu Ser
                    35                  40                  45
        Lys Cys
         50
```

<210> SEQ ID NO 10
<211> LENGTH: 57
<212> TYPE: PRT
<213> ORGANISM: Homo sapiens

<400> SEQUENCE: 10

```
        Asp Gly Gly Trp Ser His Trp Ser Pro Trp Ser Ser Cys Ser Val Thr
         1               5                  10                  15
        Cys Gly Val Gly Asn Ile Thr Arg Ile Arg Leu Cys Asn Ser Pro Val
                    20                  25                  30
        Pro Gln Met Gly Gly Lys Asn Cys Lys Gly Ser Gly Arg Glu Thr Lys
                    35                  40                  45
        Ala Cys Gln Gly Ala Pro Cys Pro Ile
         50                  55
```

<210> SEQ ID NO 11
<211> LENGTH: 56
<212> TYPE: PRT
<213> ORGANISM: Homo sapiens

<400> SEQUENCE: 11

```
        Asp Gly Arg Trp Ser Pro Trp Ser Pro Trp Ser Ala Cys Thr Val Thr
         1               5                  10                  15
        Cys Ala Gly Gly Ile Arg Glu Arg Thr Arg Val Cys Asn Ser Pro Glu
                    20                  25                  30
        Pro Gln Tyr Gly Gly Lys Ala Cys Val Gly Asp Val Gln Glu Arg Gln
                    35                  40                  45
        Met Cys Asn Lys Arg Ser Cys Pro
         50                  55
```

<210> SEQ ID NO 12
<211> LENGTH: 3974
<212> TYPE: DNA
<213> ORGANISM: Homo sapiens

<400> SEQUENCE: 12

```
        ggtacctaag tgagtagggc gtccgatcga cggacgcctt ttttttgaat tcgtaatcat    60
        ggtcatagct gtttcctgtg tgaaattgtt atccgctcac aattccacac aacatacgag   120
        ccggaagcat aaagtgtaaa gcctggggtg cctaatgagt gagctaactc acattaattg   180
        cgttgcgctc actgcccgct ttccagtcgg gaaacctgtc gtgccagctg cattaatgaa   240
        tcggccaacg cgcggggaga ggcggtttgc gtattgggcg ctcttccgct tcctcgctca   300
        ctgactcgct gcgctcggtc gttcggctgc ggcgagcggt atcagctcac tcaaaggcgg   360
        taatacggtt atccacagaa tcagggggata acgcaggaaa gaacatgtga gcaaaaggcc   420
        agcaaaaggc caggaaccgt aaaaaggccg cgttgctggc gtttttccat aggctccgcc   480
        cccctgacga gcatcacaaa aatcgacgct caagtcagag gtggcgaaac ccgacaggac   540
        tataaagata ccaggcgttt ccccctggaa gctccctcgt gcgctctcct gttccgaccc   600
        tgccgcttac cggatacctg tccgcctttc tcccttcggg aagcgtggcg ctttctcata   660
        gctcacgctg taggtatctc agttcggtgt aggtcgttcg ctccaagctg ggctgtgtgc   720
        acgaaccccc cgttcagccc gaccgctgcg ccttatccgg taactatcgt cttgagtcca   780
        acccggtaag acacgactta tcgccactgg cagcagccac tggtaacagg attagcagag   840
        cgaggtatgt aggcggtgct acagagttct tgaagtggtg gcctaactac ggctacacta   900
        gaagaacagt atttggtatc tgcgctctgc tgaagccagt taccttcgga aaaagagttg   960
        gtagctcttg atccggcaaa caaaccaccg ctggtagcgg tggtttttttt gtttgcaagc  1020
        agcagattac gcgcagaaaa aaggatctca agaagatcc tttgatcttt tctacggggt  1080
        ctgacgctca gtggaacgaa aactcacgtt aagggatttt ggtcatgaga ttatcgtcga  1140
        caattcgcgc gcgaaggcga agcggcatgc atttacgttg acaccatcga atggtgcaaa  1200
        acctttcgcg gtatggcatg atagcgcccg gaagagagtc aattcagggt ggtgaatgtg  1260
        aaaccagtaa cgttatacga tgtcgcagag tatgccggtg tctcttatca gaccgtttcc  1320
        cgcgtggtga accaggccag ccacgttttct gcgaaaacgc gggaaaaagt ggaagcggcg  1380
        atggcggagc tgaattacat tcccaaccgc gtggcacaac aactggcggg caaacagtcg  1440
        ttgctgattg gcgttgccac ctccagtctg gccctcacg cgccgtcgca aattgtcgcg  1500
        gcgattaaat ctcgcgccga tcaactgggt gccagcgtgg tggtgtcgat ggtagaacga  1560
        agcggcgtcg aagcctgtaa agcggcggtg cacaatcttc tcgcgcaacg cgtcagtggg  1620
        ctgatcatta actatcgct ggatgaccag gatgccattg ctgtggaagc tgcctgcact  1680
        aatgttccgg cgttatttct tgatgtctct gaccagacac ccatcaacag tattatttttc  1740
        tcccatgaag acggtacgcg actgggcgtg gagcatctgg tcgcattggg tcaccagcaa  1800
        atcgcgctgt tagcgggccc attaagttct gtctcggcgc gtctgcgtct ggctggctgg  1860
        cataaatatc tcactcgcaa tcaaattcag ccgatagcgg aacgggaagg cgactggagt  1920
```

```
gccatgtccg gttttcaaca aaccatgcaa atgctgaatg agggcatcgt tcccactgcg 1980
atgctggttg ccaacgatca gatggcgctg ggcgcaatgc gcgccattac cgagtccggg 2040
ctgcgcgttg gtgcggatat ctcggtagtg ggatacgacg ataccgaaga cagctcatgt 2100
tatatcccgc cgttaaccac catcaaacag gattttcgcc tgctgggggca aaccagcgtg 2160
gaccgcttgc tgcaactctc tcagggccag gcggtgaagg gcaatcagct gttgcccgtc 2220
tcactggtga aaagaaaaac caccctggcg cccaatacgc aaaccgcctc tccccgcgcg 2280
ttggccgatt cattaatgca gctggcacga caggtttccc gactggaaag cgggcagtga 2340
gcgcaacgca attaatgtaa gttagcgcga attgtcgacc aaagcggcca tcgtgcctcc 2400
ccactcctgc agttcggggg catggatgcg cggatagccg ctgctggttt cctggatgcc 2460
gacggatttg cactgccggt agaactccgc gaggtcgtcc agcctcaggc agcagctgaa 2520
ccaactcgcg aggggatcga gcccggggtg ggcgaagaac tccagcatga tccccgcg 2580
ctggaggatc atccagccgg cgtcccggaa aacgattccg aagcccaacc tttcatagaa 2640
ggcggcgtg gaatcgaaat ctcgtgatgg caggtttggc gtcgcttggt cggtcatttc 2700
gaaccccaga gtcccgctca aagaactcg tcaagaaggc gatagagggc gatgcgctgc 2760
gaatcgggag cggcgatacc gtaaagcacg aggaagcggt cagcccattc gccgccaagc 2820
tcttcagcaa tatcacgggt agccaacgct atgtcctgat agcggtccgc cacacccagc 2880
cggccacagt cgatgaatcc agaaaagcgg ccatttttcca ccatgatatt cggcaagcag 2940
gcatcgccat gggtcacgac gagatcctcg ccgtcgggca tgcgcgcctt gagcctggcg 3000
aacagttcgg ctggcgcgag cccctgatgc tcttcgtcca gatcatcctg atcgacaaga 3060
ccggcttcca tccgagtacg tgctcgctcg atgcgatgtt tcgcttggtg gtcgaatggg 3120
caggtagccg gatcaagcgt atgcagccgc cgcattgcat cagccatgat ggatactttc 3180
tcggcaggag caaggtgaga tgcaggaga tcctgccccg gcacttcgcc caatagcagc 3240
cagtcccttc ccgcttcagt gacaacgtcg agcacagctg cgcaaggaac gcccgtcgtg 3300
gccagccacg atagccgcgc tgcctcgtcc tgcagttcat tcagggcacc ggacaggtcg 3360
gtcttgacaa aaagaaccgg gcgccctgc gctgacagag ggacacggc ggcatcagag 3420
cagccgattg tctgttgtgc ccagtcatag ccgaatagcc tctccaccca agcggccgga 3480
gaacctgcgt gcaatccatc ttgttcaatc atgcgaaacg atcctcatcc tgtctcttga 3540
tcagatcttg atcccctgcg ccatcagatc cttggcggca agaaagccat ccagtttact 3600
ttgcagggct tcccaacctt accagagggc gcccagctg gcaattccgg ttcgcttgct 3660
gtccataaaa ccgcccagtc tagctatcgc catgtaagcc cactgcaagc tacctgcttt 3720
ctctttgcgc ttgcgttttc ccttgtccag atagcccagt agctgacatt catccggggt 3780
cagcaccgtt tctgcggact ggctttctac gtgttccgct tcctttagca gcccttgcgc 3840
cctgagtgct tgcggcagcg tgaagcttaa aaaactgcaa aaaatagttt gacttgtgag 3900
cggataacaa ttaagatgta cccaattgtg agcggataac aatttcacac attaaagagg 3960
agaaattaca tatg                                                    3974
```

<210> SEQ ID NO 13
<211> LENGTH: 112
<212> TYPE: DNA
<213> ORGANISM: Homo sapiens

<400> SEQUENCE: 13

```
aagcttaaaa aactgcaaaa aatagtttga cttgtgagcg gataacaatt aagatgtacc  60
caattgtgag cggataacaa tttcacacat taaagaggag aaattacata tg          112
```

<210> SEQ ID NO 14
<211> LENGTH: 542
<212> TYPE: DNA
<213> ORGANISM: Mus musculus
<220> FEATURE:
<221> NAME/KEY: UNSURE
<222> LOCATION: (3)
<223> OTHER INFORMATION: May be any nucleic acid
<221> NAME/KEY: UNSURE
<222> LOCATION: (21)
<223> OTHER INFORMATION: May be any nucleic acid
<221> NAME/KEY: UNSURE
<222> LOCATION: (22)
<223> OTHER INFORMATION: May be any nucleic acid
<221> NAME/KEY: UNSURE
<222> LOCATION: (361)
<223> OTHER INFORMATION: May be any nucleic acid
<221> NAME/KEY: UNSURE
<222> LOCATION: (369)
<223> OTHER INFORMATION: May be any nucleic acid
<221> NAME/KEY: UNSURE
<222> LOCATION: (407)
<223> OTHER INFORMATION: May be any nucleic acid
<221> NAME/KEY: UNSURE
<222> LOCATION: (427)
<223> OTHER INFORMATION: May be any nucleic acid
<221> NAME/KEY: UNSURE
<222> LOCATION: (479)
<223> OTHER INFORMATION: May be any nucleic acid
<221> NAME/KEY: UNSURE
<222> LOCATION: (482)

<223> OTHER INFORMATION: May be any nucleic acid
<221> NAME/KEY: UNSURE
<222> LOCATION: (535)
<223> OTHER INFORMATION: May be any nucleic acid

<400> SEQUENCE: 14

```
gtncgaattt cggcacgaga nnttagacgc cttttcatgg aagctgggga atgtggggc    60
cttggggaga ctgttcgaga acgtgcggtg gaggagtcca gtacacgatg agggaatgtg   120
acaacccagt cccaaagaat ggagggaagt actgtgaagg caaacgagtg cgctacagat   180
cctgtaacct tgaggactgt ccagacaata atgaaaaac  ctttagagag gaacaatgtg   240
aagcacacaa cgagttttca aaagcttcct ttgggagtgg gcctgcgctg gaatggattc   300
ccaagtacgc tggcgtctca ccaaaggaca ggtgcaagtt catgttgcca agccaaaggc   360
nttggctant tctttcgttt tgcagcccaa ggttgttagg tgggtantcc atgttaggcc   420
cagattncac ctttgtctgt gtgcaaggac agtgtgttaa agttggttg  tgatccgcnt   480
cntagattcc aaaaggagtt ttgttaatgt ggtgttttcn ggggaatgg  tctantttta   540
aa                                                                 542
```

<210> SEQ ID NO 15
<211> LENGTH: 320
<212> TYPE: DNA
<213> ORGANISM: Unknown
<220> FEATURE:
<223> OTHER INFORMATION: Description of Unknown Organism:Unknown

<400> SEQUENCE: 15

```
cagagaacat tcgccccact cttcaatgac ccatgctgaa aaagtgggga tagcattgaa    60
agattccttc ttcttcttta cgaagtaggt gtatttaatt ttaggtcgaa gggcattgcc   120
cacagtaaga acctggatgg tcaagggctc tttgagaggg ctaaagctgc gaattctttc   180
caatgccgca gaggagccgc tgtacctcaa gacaacacct tgtacataa  tgtcttgctc   240
taaggtggac aaagtgtagt caccattaag aatatatgtg ccatcagcag ctttgatggc   300
aagaaagctg cccttgttcc                                              320
```

<210> SEQ ID NO 16
<211> LENGTH: 316
<212> TYPE: DNA
<213> ORGANISM: Eimeria tenella

<400> SEQUENCE: 16

```
aatgccgaga cattaatgga cagcctgctt ccgagtgtgc aaaggaagtg aagccagcca    60
gcaccagacc ttgtgcagac catccctgcc cccagtggca gctggggag  tggtcatcat   120
gttctaagac ctgtgggaag ggttacaaaa aaagaagctt gaagtgtctg tcccatgatg   180
gaggggtgtt atctcatgag agctgtgatc cttttaaagaa acctaaacat tcatagact   240
tttgcacaat ggcagaatgc agttaagtgg tttaagtggt gttagctttg agggcaaggc   300
aaagtgagga agggct                                                  316
```

<210> SEQ ID NO 17
<211> LENGTH: 383
<212> TYPE: DNA
<213> ORGANISM: Caenorhabditis elegans
<220> FEATURE:
<221> NAME/KEY: UNSURE
<222> LOCATION: (160)
<223> OTHER INFORMATION: May be any nucleic acid
<221> NAME/KEY: UNSURE
<222> LOCATION: (326)
<223> OTHER INFORMATION: May be any nucleic acid
<221> NAME/KEY: UNSURE
<222> LOCATION: (358)
<223> OTHER INFORMATION: May be any nucleic acid
<221> NAME/KEY: UNSURE
<222> LOCATION: (366)
<223> OTHER INFORMATION: May be any nucleic acid
<221> NAME/KEY: UNSURE
<222> LOCATION: (377)
<223> OTHER INFORMATION: May be any nucleic acid
<221> NAME/KEY: UNSURE
<222> LOCATION: (379)
<223> OTHER INFORMATION: May be any nucleic acid

<400> SEQUENCE: 17

```
gtcgacccac gcgtccggat ggtactccat gtagcccaga ttccacctct gtctgtgtgc    60
aaggacagtg tgtaaaagct ggttgtgatc gcatcataga ctccaaaaag aagtttgata   120
```

```
            aatgtggtgt tgcgggga  aatggatcta cttgtaaaan aatatcagga tcagttacta    180
            gtgcaaaacc tgggatatca tgatatcatc acaattccaa ctgggagcca ccaacatcga    240
            agtgaaacag cggaaccaga ggggatccag ggaacaatgg gcagctttct tgccatcaaa    300
            gctgctggat ggcacatata ttcttnaatg gtgactacac tttgtccacc ttagaganag    360
            acattntgtg acaaagngnt tgt                                            383
```

<210> SEQ ID NO 18
<211> LENGTH: 404
<212> TYPE: DNA
<213> ORGANISM: Crotalus atrox
<220> FEATURE:
<221> NAME/KEY: UNSURE
<222> LOCATION: (21)
<223> OTHER INFORMATION: May be any nucleic acid
<221> NAME/KEY: UNSURE
<222> LOCATION: (301)
<223> OTHER INFORMATION: May be any nucleic acid
<221> NAME/KEY: UNSURE
<222> LOCATION: (335)
<223> OTHER INFORMATION: May be any nucleic acid
<221> NAME/KEY: UNSURE
<222> LOCATION: (373)
<223> OTHER INFORMATION: May be any nucleic acid
<221> NAME/KEY: UNSURE
<222> LOCATION: (378)
<223> OTHER INFORMATION: May be any nucleic acid
<221> NAME/KEY: UNSURE
<222> LOCATION: (382)
<223> OTHER INFORMATION: May be any nucleic acid
<221> NAME/KEY: UNSURE
<222> LOCATION: (383)
<223> OTHER INFORMATION: May be any nucleic acid

<400> SEQUENCE: 18

```
            cccacgcgtc cgcccacggt nccgggactt gtgtgggtcc cagacatgtg atactcttgg     60
            gatggctgat gttggaactg tgtgtgatcc gagcagaagc tgctccgtca tagaagatga    120
            tggtttacaa gctgccttca ccacagccca tgaattaggc cacgtgttta acatgccaca    180
            tgatggatgc aaagcagtgt gccagcctta aatggtgtga accagggatt cccacatgat    240
            ggcgtcaatg ctttccaacc tgggaccaca gccagccttg ggtcctcctt gcagtggcct    300
            nacatggatt gacatcattt ctgggatgaa tggtncatgg gggaatgttt tgattggaca    360
            agccttcaga atnccctnac annttcccag gggttctccc tggg                     404
```

<210> SEQ ID NO 19
<211> LENGTH: 152
<212> TYPE: DNA
<213> ORGANISM: Homo sapiens
<220> FEATURE:
<221> NAME/KEY: UNSURE
<222> LOCATION: (105)
<223> OTHER INFORMATION: May be any nucleic acid
<221> NAME/KEY: UNSURE
<222> LOCATION: (122)
<223> OTHER INFORMATION: May be any nucleic acid
<221> NAME/KEY: UNSURE
<222> LOCATION: (135)
<223> OTHER INFORMATION: May be any nucleic acid

<400> SEQUENCE: 19

```
            atcgtagaag atgaaaaatg gggcccagag gtgtccgaca atgggggct tacactgcgt      60
            aacttctgca actggcagcg gcgtttcaac cagcccagcg accgncaccc agagcactac    120
            gncacggcca tcctnctcac cagacagaac tt                                   152
```

<210> SEQ ID NO 20
<211> LENGTH: 4180
<212> TYPE: DNA
<213> ORGANISM: Unknown
<220> FEATURE:
<223> OTHER INFORMATION: Description of Unknown Organism:Unknown

<400> SEQUENCE: 20

```
            gcagctccga gctaggtgct atcgcaaggc cagagcgcac agcccggcgg agagagcaga     60
            tccttgctca gatcgagtca aatcgggcca aggcggagga cgaagagtcc aggctcctat    120
            tctggacttg ttccccagct ccggggggcgc ttctaggtcc tgcagcagcc agcagtgcgg    180
```

-continued

```
agccaccaac tcggtgctgg aatgaaaaaa ttcccgcgcg ccagtgcaga atctttctaa    240
gtgacccgga gcttcgggtg ctagctctgc acgaactttc ccatcaaagt gatcgtgaat    300
tttaagcatc aggagcaggc cagcgaagct ctacgcgtct aaacgtctat ccagaccaag    360
agttctctgc ggtgcagggt gcggtgccat gcagccaaaa gtccctttg  gggtcacgca    420
agcagaagcc ctgctccgac atggggacg  tccagcgggc agcgagatct cggggctctc    480
tgtccgcaca catgctgttg ctgctcctcg cttccataac aatgctgcta tgtgcgcggg    540
gcgcacacgg gcgcccacg  gaggaagatg aggagctggt cctgccctcg ctggagcgcg    600
ccccgggcca cgattccacc accacacgcc ttcgtctgga cgcctttggc cagcagctac    660
atctgaagtt gcagccgac  agcggtttct tggcgcctgg cttcaccctg cagactgtgg    720
ggcgcagtcc cggtccgag  gcacaacatc tggacccccac cggggacctg gctcactgct    780
tctactctgg cacggtgaac ggtgatcccg gctctgccgc agccctcagc ctctgtgaag    840
gtgtgcgtgg tgccttctac ctacaaggag aggagttctt cattcagcca gcgcctggag    900
tggccaccga gcgcctggcc cctgccgtgc ccgaggagga gtcatccgca cggccgcagt    960
tccacatcct gaggcgaagg cggcggggca gtggcggcgc caagtccggc gtcatggacg   1020
acgagaccct gccaaccagc gactcgcgac ccgagagcca gaacacccgg aaccagtggc   1080
ctgtgcggga ccccacgcct caggacgcgg gaaagccatc aggaccagga agcataagga   1140
agaagcgatt tgtgtccagc ccccgttatg tggaaaccat gctcgtagct gaccagtcca   1200
tggccgactt ccacggcagc ggtctaaagc attaccttct aaccctgttc tcggtggcag   1260
ccaggtttta caagcatccc agcattagga attcaattag cctggtggtg gtgaagatct   1320
tggtcatata cgaggagcag aagggaccag aagttacctc caatgcagct ctcacccttc   1380
ggaatttctg cagctggcag aaacaacaca acagcccag  tgaccgggat ccagagcact   1440
atgacactgc aattctgttc accagacagg atttatgtgg ctcccacacg tgtgacactc   1500
tcggaatggc agatgttgga accgtatgtg accccagcag gagctgctca gtcatagaag   1560
atgatggttt gcaagccgcc ttcaccacag cccatgaatt gggccatgtg tttaacatgc   1620
cgcacgatga tgctaagcac tgtgccagct tgaatggtgt ggctggcagt tctcatctga   1680
tggcctcgat gctctccagc ttagaccata gccagccctg gtcacccttgc agtgcctaca   1740
tggtcacgtc cttcctagat aatggacacg gggaatgttt gatgacaag  ccccagaatc   1800
caatcaagct cccttctgat cttcccggta ccttgtacga tgccaaccgc cagtgtcagt   1860
ttacattcgg agaggaatcc aagcactgcc ctgatgcagc cagcacatgt actaccctgt   1920
ggtgcactgg cacctccggt ggcttactgg tgtgccaaac aaaacacttc ccttgggcag   1980
atggcaccag ctgtggagaa gggaagtggt gtgtcagtgg caagtgcgtg aacaagacag   2040
acatgaagca ttttgctact cctgttcatg gaagctgggg accatgggga ccgtggggag   2100
actgctcaag aacctgtggt ggtggagttc aatacacaat ggagaatgt  gacaacccag   2160
tcccaaagaa cggagggaag tactgtgaag gcaaacgagt ccgctacagg tcctgtaaca   2220
tcgaggactg tccagacaat aacggaaaaa cgttcagaga ggagcagtgc gaggcgcaca   2280
atgagttttc caaagcttcc tttgggaatg agcccactgt agagtggaca cccaagtacg   2340
ccggcgtctc gccaaaggac aggtgcaagc tcacctgtga agccaaaggc attggctact   2400
ttttcgtctt acagcccaag gttgtagatg gcactccctg tagtccagac tctacctctg   2460
tctgtgtgca agggcagtgt gtgaaagctg gctgtgatcg catcatagac tccaaaaaga   2520
agtttgataa gtgtggcgtt tgtggaggaa acggttccac atgcaagaag atgtcaggaa   2580
tagtcactag tacaagacct gggtatcatg acattgtcac aattcctgct ggagccacca   2640
acattgaagt gaaacatcgg aatcaaaggg ggtccagaaa caatggcagc tttctggcta   2700
ttagagccgc tgatggtacc tatattctga atggaaactt cactctgtcc acactagagc   2760
aagacctcac ctacaaaggt actgtcttaa ggtacagtgg ttcctcggct gcgctggaaa   2820
gaatccgcag cttagtcca  ctcaaagaac ccttaacctat ccaggttctt atggtaggcc   2880
atgctctccg acccaaaatt aaattcacct actttatgaa gaagaagaca gagtcattca   2940
acgccattcc cacatttct  gagtgggtga ttgaagagtg ggggagtgc  tccaagacat   3000
gcggctcagg ttggcagaga agagtagtgc agtgcagaga cattaacgga caccctgctt   3060
ccgaatgtgc aaaggaagtg aagccagcca gtaccagacc ttgtgcagac cttccttgcc   3120
cacactgtca ggtggggat  tggtcaccat gttccaaaac ttgcgggaag ggttacaaga   3180
agagaacctt gaaatgtgtg tcccacgatg ggggcgtgtt atcaaatgag agctctgatc   3240
ctttgaagaa gccaaagcat tacattgact tttgcacact gacacagtgc agttaagagg   3300
cgttagagga caaggtagcg tggggagggg ctgatacact gagtgcaaga gtactggagg   3360
gatccagtga gtcaaaccag taagcagtga ggtgtggcag gagggtgtg  taggggata   3420
catagcaaag gaggtagatc aggacactac cctgccagtt acattctgat aaggtagtta   3480
atgaggcaca gtagcatctg aaagaccata cagagcacta aggagcccca aagcactatt   3540
agtatctctt ttcttatatc tatcgcccaa ataattttca gagtctggca gaagccctgt   3600
tgcactgtac taactagata cttcttatca caaagattgt gaaaggcaaa gcagaaagat   3660
ggtaagactg ggtttcaaac aaggcttggt ttcaatcact ggaggcaagg aggagggga   3720
aaacaagatc attattcgaa gtcgctggtt gctgtggttt tacgaaggt tgatgcatca    3780
ttcctatcaa cagtgaaaag ttcagcttgt tcaacgtgac agaaaggctc atctccgtga   3840
aagagctcct gatttcttct tacaccatct cagttcttaa ctatagttca tgttgaggta   3900
gaaacaattc atctatttat aaaatgtaca ttggaaaaaa aaagtgaagt ttatgaggta   3960
cacataaaaa ctgaaggaaa caatgagcaa catgcctcct gctttgcttc ctcctgaggt   4020
aaacctgcct ggggattgag gttgtttaag attatccatg gctcacaaga ggcagtaaaa   4080
taatacatgt tgtgccagag ttagaatggg gtatagagat cagggtccca tgagatgggg   4140
aacatggtga tcactcatct cacatgggag gctgctgcag                         4180
```

<210> SEQ ID NO 21
<211> LENGTH: 9248
<212> TYPE: DNA
<213> ORGANISM: Unknown
<220> FEATURE:
<223> OTHER INFORMATION: Description of Unknown Organism:Unknown

<400> SEQUENCE: 21

```
gcagctccga gctaggtgct atcgcaaggc cagagcgcac agcccggcgg agagagcaga     60
```

-continued

```
tccttgctca gatcgagtca aatcggggcc aaggcggagg acgaagagtc caggctccta 120
ttctggactt gttccccagc tccggggcg cttctaggtc ctgcagcagc caggagtgcg 180
gagccaccaa ctcggtgctg gaatgaaaaa attcccgcgc gccagtgcag aatctttcta 240
agtgacccgg agcttcgggt gctagctctg cacgaacttt cccatcaaag tgatcgtgaa 300
tttaagcat caggagcagg ccagcgaagc tctacgcgtc taaacgtcta tccagaccaa 360
gagttctctg cggtgcaggt tgcggtgcca tgcagccaaa agtccctttg gggtcacgca 420
agcagaagcc ctgctccgac atggggggacg tccagcgggc agcgagatct cggggctctc 480
tgtccgcaca catgctgttg ctgctcctcg cttccataac aatgctgcta tgtgcgcggg 540
gcgcacacgg gcgccccacg gaggaagatg aggagctggt cctgccctcg ctggagcgcg 600
ccccgggcca cgattccacc accacacgcc ttcgtctgga cgcctttggc cagcagctac 660
atctgaagtt gcagccggac agcggtttct ggcgcctggg cttcaccctg cagactgtgg 720
ggcgcagtcc cgggtccgag gcacaacatc tggaccccac cggggacctg gctcactgct 780
tctactctgg cacggtgaac ggtgatcccg gctctgccgc agccctcagc ctctgtgaag 840
gtgtgcgtgg tgccttctac ctacaaggag aggagttctt cattcagcca gcgcctggag 900
tggccaccga gcgcctggcc cctgccgtgc ccgaggagga gtcatccgca cggccgcagt 960
tccacatcct gaggcgaagg cggcgggggca gtggcggcgc caagtgcggc gtcatggacg 1020
acgagaccct gccaaccagc gactcgcgac ccgagagcca gaacaccggg aaccagtggc 1080
ctgtgcggga ccccacgcct caggacgcgg gaaagccatc aggtataaga gtgaccccca 1140
tctctcagtc tttacgaggc gtgacttggg gtcacactcc agatcgcctc taaatgcgaa 1200
tgactcagac ttgcagtgaa ttgaagttct gggtcgtgac cttcccgctc ccccccccc 1260
aaaaaagtg tgaccatact ctgctagaac acttatttgc ccgaatagtt aataatttga 1320
gaaagagaga aagaatcgga ggtcctgtag ataagggcta agcgtttcct ccgcgaagcc 1380
aataacccga ctccttacac tggagaatct ctctccatcc ctttaatgcc tttagtgaat 1440
gtatgagttc actttaacta ggttgtagtt tcgcgctgag ttttgtaacg tcagtccgtg 1500
tgagcacgta gcgctcaaag gagggcggaa tagaggagcc atggtgacct ggatgtgcgt 1560
tcaggagcct gggcaacggc agtggtgatc tcatttctgt ggccttccgt ctgtccccttt 1620
cccccatttg aaaagctgac cccgatggct ggtggctccg ttgggcccct ctgcagaacc 1680
tgcttgggag gtctttgctt ggttcgcccc gcctccacgc gcctcctacc tcggcctcgt 1740
tgctcgcact ccctctcccg gcagaggttg gactccccag cgctgtggaa tgttagcctg 1800
gactgatcct ccctgctaca cattcgcctg actctgccgt gttcagtctc taccagccag 1860
ttagttcttt ttaatcattc aaatttcttt ttgcccttt ctagatttct ccctctttc 1920
cgacttgtcc ctaggagctg gtattcatat cctactttac gatttctctg accgctgagt 1980
ctcagcagcc cgaaaaagcc cattttccaa attggcaacc ctggtttgag aaaggaactt 2040
attccccccg gggcactggg agtgagagga ggcaggaaaa cactgctggg cagagtgggt 2100
ggtcctagtg cccggaactg gatcaagcag agaaccccct gggacccctt gaatgagaga 2160
gctgagcctt acagactgag actcctcaag cccaccccct tggctgagct ccccgccctg 2220
ccccatgcct tccacgtgga gctggatgat ctcattcggg atttcagccc tggcttcaat 2280
agtgaaaggg tgactcaggg cgtccgcctg cttctcttgc caagttttta ctacagctgg 2340
gtagaaatga tagccatact gcctcactca ggctgtggag tcttcaaaga ccacaaaaga 2400
aatctgcgga cacatatata gacagtttga tcactctgtt gcttgctttg ttttgttttg 2460
ttttgtctta tttaaagcaa aagaaaaaag acttaaaaat aactcacagt ttttagaaga 2520
tgcaaatatt tgttttattt ttgttccagg tgtatttcag ttttatttac tttgactagg 2580
ttgactttcc taatataccc cgagaaggtc actattagga gaaggactgc ccatgagcaa 2640
acttccttt cttttttacag gaccaggaag cataaggaag aagcgatttg tgtccagccc 2700
ccgttatgtg gaaaccatgc tcgtggctga ccagtccagc gccgacttcc acggcacgcgg 2760
tctaaagcat taccttctaa ccctgttctc ggtggcagcc aggttttaca agcatcccag 2820
cattaggaat tcaattagcc tggtggtggt gaagatcttg gtcatatatg aggagcagaa 2880
gggaccagaa gttacctcca atgcagctct caccttcgg aatttctgca actggcagaa 2940
acaacacaac agcccagtg accgggatcc agagcactat gacactgcaa ttctgttcac 3000
cagacaggta agacaggagc ttatcaacca tttcatcaac tcaactcgga ggtcagcgtt 3060
gtgttggatg ggatgagagg gtggggggtgt ggcggagagg aaacccagaa ggggatgaca 3120
tttgaaatgt aaacaaaata accaattaaa aaaaaaggc atctcatctg tattgcctca 3180
tttcctttcg gttataggct agctcaatct gtcttgctta tttctatttt aaacttccac 3240
atctcaagtt ctacagttct attttaaaag cattacagtg aatcttgctt agagtcagtc 3300
cttcaagccc agcaataatg aatggacagg cttcaaagtg catgtgaaga cacgcccaac 3360
tgaagagcta agtatcactc tctcctactt aaaagggatt tcccttgcct ctttgtagga 3420
tttatgtggc tcccacacgt gtgacactct cgggatggca gatgttgaa ctgtatgtga 3480
cccagcagg agctgctcag tcatagaaga tgatgttttg caagccgcct tcaccacagc 3540
ccacgaattg ggtaagtcgg cttcagagta caagttaagc ccaaatgcat ggatacaacc 3600
caataagtca atctgatgtg acgagagaga aaacatctca gactatgttg ctacctcagc 3660
caccagcaat tttagaaggg gtagggtata ttttccacga tttcaagtat ggtcttacta 3720
ggacaggaga aagtggtaca acatttgaa cgttgacatt tttatacttg ccctgatcaa 3780
agtgagtatg agccccaata caggttgtct aataagagag ccattgagcc tcactcaata 3840
atacagctga atgtccttct tgtctgcttc ccaggccatg tgtttaacat gccgcacgat 3900
gatgctaagc actgtgccag cttgaatggt gtgactggcg attctcatct gatggcctcg 3960
atgctctcca gcttagacca tagccagccc tggtcaccttt gcagtgccta catgtcacg 4020
tccttcctag ataatggaca cggtaagatg acagctcctg tttccagatg gtgttcaacg 4080
ttccttgtgt agggctctct ctggctaagt gagctccatg gctcttctc atttccctc 4140
cttcagagtt ttctctggca ggatcataag tagtagatct ttacctccat tgcatcctgc 4200
tcccaaagtc cattcattca taaacaataa cttctcgcca ttgtaaaatc agaagtcccc 4260
tattgaggat aacgtctcga taaaaatcta attgtccta gcattgattt tcccaaaaat 4320
gcatgatttc accaaacatg tattaataat tgcctctttt ttcttttcct ttttttttt 4380
tattattta ggggaatgtt tgatggacaa gccccagaat ccaatcaagc tccccttctga 4440
tcttcccggt accttgtacg atgccaaccg ccagtgtcag tttacattcg gagaggaatc 4500
caagcactgc cctgatgcag ccagcacatg tactaccctg gcacctccgg 4560
tggcttactg gtgtgccaaa caaacactt cccttgggca gatggcacca gctgtggaga 4620
agggaagtgg tgtgtcagtg gcaagtgcgt gaacaagaca gacatgaagc attttgctgt 4680
gagttttccc aatgaaacat atccgtttgc aactcagggt tgagaagggc aaagtgatgg 4740
tttagttcct ttcctagaca aactcctcta cctgtgtcct gtagtgggac tatgagatgg 4800
```

-continued

```
tagcgtattt tgagaattga ttgtctgttt tacatttttc tctgattccc taaaatgtct 4860
ttatagttct aacactgata tctgtatctc catttagact cctgttcatg gaagctgggg 4920
accatgggga ccgtggggag actgctcaag aacctgtggt ggtggagttc aatacacaat 4980
gagagaatgt gacaacccag tcccaaagaa cggagggaga tactgtgaag gcaaacgagt 5040
ccgctacagg tcctgtaaca tcgaggactg tccagacaat aacggtgagt catactggac 5100
ttcagctctc agaaaccggg caaaggcggc gtgccacaac atgtggttgg aagttggaaa 5160
ctgggaacat catcgccgtc gttctctttt caggaaaaac gttcagagag gagcagtgcg 5220
aggcgcacaa tgagttttcc aaagcttcct ttgggaatga gcccactgta gagtggacac 5280
ccaagtacgc cggcgtctcg ccaaaggaca ggtgcaagct cacctgtgaa gccaaaggca 5340
ttggctactt tttcgtctta cagcccaagg taggtgcttt tacacttgaa tctttgcaaa 5400
ggagcctcag ctgggcttgc tgccatgcca tacaaatgtt tgggctgtct ttacctattg 5460
atctgtgttc cgttttgaat ttggaatact tctaaatgca ggaacaactc cttgctttgg 5520
gatttgttgt tgccttctgt tgggaaggaa gcttaaatct agctagcact taaaagagtc 5580
ttgcatgtgt ttaatattgc ttctctatcc ccaaagaatg gccctttgaa aactcaagag 5640
ccctctctgt ataactaggt ttcacataca aaaattcatg gttagataaa ttatatatta 5700
acatggcacc caggagtttt agaaagtagt ccaaagtact tgttactggg tacctagcag 5760
ccgcacatac gagcacacta actaaggtaa gagtttgaga attaaaaatt catcgttgga 5820
acatgtactt tgaccaaaga gactcgccat ttcttttggt gttttgcaga aaggataaat 5880
cctgctttga agaagaaaat tgaatgaaat ttgcttaagc ttgtcatgta ttcttagcat 5940
tataagatag caaactatat ccaagttgtg gatgaagtat ttagcaagtg atttataaag 6000
taccttcaac tacagcatat tattctaggt actgaccatg gaacaataat cagtgtgaca 6060
gtgaaccctg cttccattga cctaggccag caaatatata aaatcaagac atttataagc 6120
cttacagata gctatatgaa ctgttgaaaa agccaaaatg aaagtgaaca tgtggcacgt 6180
gacaaggaga ctacttgtag cctgggagga gagcattccc agttgccatc acatcagatg 6240
tttaaccacc atggtgcatg ttgtctccac aggttgtaga tggcactccc tgtagtccag 6300
actctacctc tgtctgtgtg caagggcagt gtgtgaaagc tggctgtgat cgcatcatag 6360
actccaaaaa gaagtttgat aagtgtggcg tttgtggagg aaacggttcc acatgcaaga 6420
agatgtcagg aatagtcact agtacaaggt gagtttcaga acgctcactt ctgcagtaga 6480
cacgctgtgt tgctcagttg gtccctagca tctacaagac cttgggttca atccgcatgc 6540
atgtacctgt agtcccagtg tatgggagac agagacaagt gtgacaagac ggtcagatgt 6600
tcaggtcatc tttgctcat agtgactttc agttcaccctt ggggaacatg aaaaacctga 6660
ctggaaacac aaacacacac aaaacaatta acccaggtac ttcatgtaat cccagtgttc 6720
agtaggctga cttgggagga tggttgctat aaggcctagg ttagcttggt ctacataatg 6780
agttccagta taacctggcc cacaagtgaa ccctaaagtt aattaatcga cacatgaaac 6840
aaaacacatg ctttggagac cctgtaattt tgatatacga ttttgtagga ctaaggaaaa 6900
gtcacattta aaagaattgc ctattttaa agcaatgtga ttgattaact cattgaaaga 6960
catatacctg ttttctttgt ccacagacct gggtatcatg acattgtcac aattcctgct 7020
ggagccacca acattgaagt gaaacatcgg aatcaaaggg ggtccagaaa caatggcagc 7080
tttctggcta ttagagccgc tgatggtacc tatattctga atggaaactt cactctgtcc 7140
acactagagc aagacctcac ctacaaaggt actgtcttaa ggtacagtgg ttcctcggct 7200
gcgctggaga gaatccgcag ctttagtcca ctcaaagaac ccttaaccat ccaggttctt 7260
atggtaggcc atgctctccg acccaaaatt aaattcacct actttatgaa gaagaagaca 7320
gagtcattca acgccattcc cacattttct gagtgggtga ttgaagagtg gggggagtgc 7380
tccaagacat gcggctcagg ttggcagaga agagtagtgc agtgcagaga cattaatgga 7440
caccctgctt ccgaatgtgc aaaggaagtg aagccagcca gtaccagcc ttgtgcagac 7500
cttccttgcc cacactggca ggtgggggat tggtcaccat gttccaaaac ttgcgggaag 7560
ggttacaaga agagaaccctt gaaatgtgtg tcccacgatg ggggcgtgtt atcaaatgag 7620
agctgtgatc cttttgaagaa gccaaagcat tacattgact tttgcacact gacacagtgc 7680
agttaagagg cgttagagga caaggtagcg tggggagggg ctgatacact gagtgctgga 7740
gggatccagt gagtcaaacc agtaagcagt gaggtgtggc aaggaggtgt gtgtagggga 7800
tacatagcaa aggaggtaga tcaggacact accctgccag ttacattctg ataaggtagt 7860
taatgaggca cagtagcatc tgaaagacca tacagagcac taaggagccc caaagcacta 7920
ttagtatctc ttttcttata tctatcgccc aaataatttt cagagtctgg cagaagccct 7980
gttgcactgt actgactaga tacttcttat cacaaagatt gggaaaggca aagcagaaag 8040
atggtaagac tgggtttcaa acaaggcttg gtttctatca ctggaggcaa ggaggagggg 8100
acaaacaaga tcattattcg aagtcgctgg ttgctgtggt tttacggaag gttgatgcat 8160
cattcctatc aacagtgaaa agttcagctt gttcaacgtg acagaaaggc tcatctccgt 8220
gaaagagctc ctgatttctt cttacaccat ctcagttctt aactataatt catgttgagg 8280
tagaaacaat tcatctattt ataaaatgta cattggaaaa aaaaaagtga agtttatgag 8340
gtacacataa aaactgaagg aaacaatgag caacatgcct cctgcttttgc ttcctcctga 8400
ggtaaacctg cctggggatt gaggttgttt aagattatcc atggctcaca agaggcagta 8460
aaataataca tgttgtgcca gagttagaat gggtataga gatcagggtc ccatgagatg 8520
gggaacatgg tgatcactca tctcacatgg gaggctgctg cagggtagca ggtccactcc 8580
tggcagctgg tccaacagtc gtatcctggt gaatgtctgt tcagctcttc tactgagaga 8640
gaatatgact gtttccatat gtatatgtat atagtaaaat atgttactat gaattgcatg 8700
tactttataa gtattggtgt gtctgttcct tctaagaagg actatagtt ataatatg 8760
cctataataa catattttatt tttatacatt tatttctaat gataaaaccct ttaagttata 8820
tcgcttttgt aaaagtgcat ataaaaatag agtatttata caatatatgt taactagaaa 8880
taataaaaga acacttttga atgtgtatgc ctattttctg gagtgggatt aacttctggg 8940
caagaaatct gatgagacac aaacattgga cttcaagaca gttttaaaat ttgggtaaat 9000
gaactgtatt tcctgtttat agacgtacta ataaaaagaa agttgatgat gtcttttagtg 9060
gtaagattgt tactaatgtg gttggcaaat tgctgtaaag agccagatag taagcattta 9120
tggcattgta ggctatcttt cctgccacaa ccatgtgaca gtgagtgctt tgtaggactg 9180
agagcagcca taaatgacat gtaaatgata aactgtggct gtgctttaat aaaactttat 9240
ttacaaaa                                                       9248
```

<210> SEQ ID NO 22
<211> LENGTH: 5722

<212> TYPE: DNA
<213> ORGANISM: Unknown
<220> FEATURE:
<223> OTHER INFORMATION: Description of Unknown Organism:Unknown

<400> SEQUENCE: 22

```
ggacgcacag gcattccccg cgcccctcca gccctcgccg ccctcgccac cgctcccggc   60
cgccgcgctc cggtacacac aggatccctg ctgggcacca acagctccac catggggctg  120
gcctggggac taggcgtcct gttcctgatg catgtgtgtg gcaccaaccg cattccagag  180
tctggcggag acaacagcgt gtttgacatc tttgaactca ccggggccgc ccgcaagggg  240
tctgggcgcc gactggtgaa gggccccgac ccttccagcc cagctttccg catcgaggat  300
gccaacctga tccccccgtg gcctgatgac aagttccaag acctggtgga tgctgtgcgg  360
gcagaaaagg gtttcctcct tctggcatcc ctgaggcaga tgaagaagac ccggggcacg  420
ctgctggccc tggagcgaaa agaccactct ggccaggtct tcagcgtggt gtccaatggc  480
aaggcgggca ccctggacct cagcctgacc gtccaaggaa agcagcacgt ggtgtctgtg  540
gaagaagctc tcctggcaac cggccagtgg aagagcatca ccctgtttgt gcaggaagac  600
agggcccagc tgtacatcga ctgtgaaaag atggagaatg ctgagttgga cgtccccatc  660
caaagcgtct tcaccagaga cctggccagc atcgccagac tccgcatcgc aaagggggc  720
gtcaatgaca atttccaggg ggtgctgcaa aatgtgaggt ttgtctttgg aaccacacca  780
gaagacatcc tcaggaacaa aggctgctcc agctctacca gtgtcctcct caccccttgac  840
aacaacgtgg tgaatggttc cagccctgcc atccgcacta actacattgg ccacaagaca  900
aaggacttgc aagccatctg cggcatctcc tgtgatgagc tgtccagcat ggtcctggaa  960
ctcagggggcc tgcgcaccat tgtgaccacg ctgcaggaca gcatccgcaa agtgactgaa 1020
gagaacaaag agttggccaa tgagctgagg cggcctcccc tatgctatca caacggagtt 1080
cagtacagaa ataacgagga atgggactgtt gatagctgca ctgagtgtca ctgtcagaac 1140
tcagttacca tctgcaaaaa ggtgtcctgc cccatcatgc cctgctccaa tgccacagtt 1200
cctgatggag aatgctgtcc tcgctgttgg cccagcgact ctgcggacga tggctggtct 1260
ccatggtccg agtgacctc ctgttctacg agctgtggca atggaattca gcagcgcggc 1320
cgctcctgcg atagcctcaa caaccgatgt gagggctcct cggtccagac acggacctgc 1380
cacattcagg agtgtgacaa aagatttaaa caggatggtg gctggagcca ctggtccccg 1440
tggtcatctt gttctgtgac atgtggtgat ggtgtgatca caaggatccg gctctgcaac 1500
tctcccagcc ccagatgaa tgggaaaccc tgtgaaggcg aagcgcggga gaccaaagcc 1560
tgcaagaaag acgcctgccc catcaatgga ggctgggtc cttggtcacc atgggacatc 1620
tgttctgtca cctgtggagg aggggtacag aaacgtagtc gtctctgcaa caaccccgca 1680
ccccagtttg gaggcaagga ctgcgttggt gatgtaacag aaaaccagat ctgcaacaag 1740
caggactgtc caattgatgg atgcctgtcc aatccctgct ttgccggcgt gaagtgtact 1800
agctaccctg atggcagctg gaaatgtggt gcttgtcccc ctggttacag tggaaatggc 1860
atccagtgca cagatgttga tgagtgcaaa gaagtgcctg atgcctgctt caaccacaat 1920
ggagagcacc ggtgtgagaa cacggacccc ggctacaact gcctgccctg ccccccacgc 1980
ttcaccggct cacagcccct cggccagggt gtcgaacatg ccacgccaa caacaggtg 2040
tgcaagcccc gtaaccctg cacggatggg acccacgact gcaacaagaa cgccaagtg 2100
aactacctgg gccactatag cgacccatg taccgctgcg agtgcaagcc tggctacgct 2160
ggcaatggca tcatctgcgg ggaggacaca gacctggatg gctgccaa tgagaacctg 2220
gtgtgcgtgg ccaatgcgac ttaccactgc aaaaaggata attgccccaa ccttcccaac 2280
tcagggcagg aagactatga caaggatgga attggtgatg cctgtgatga tgacgatgac 2340
aatgataaaa ttccagatga cagggacaac tgtccattcc attacaaccc agctcagtat 2400
gactatgaca gagatgatgt gggagaccgc tgtgacaact gtccctacaa ccacaaccca 2460
gatcaggcag acacagacaa caatggggaa ggagacgcct gtgctgcaga cattgatgga 2520
gacggtatcc tcaatgaacg ggacaactgc cagtacgtct acaatgtgga ccagagagac 2580
actgatatgg atggggttgg agatcagtgt gacaattgcc ccttggaaca caatccggat 2640
cagctggact ctgactcaga ccgcattgga gatacctgtg acaacatca ggatattgat 2700
gaagatggcc accagaacaa tctggacaac tgtccctatg tgcccaatgc caaccaggct 2760
gaccatgaca aagatggcaa gggagatgcc tgtgaccaag atgatgacaa cgatggcatt 2820
cctgatgaca aggacaactg cagactcgtg cccaatcccg accagaagga ctctgacggc 2880
gatggtcgag gtgatgcctg caaagatgat tttgaccatg acagtgtgcc agacatcgat 2940
gacatctgtc ctgagaatgt tgacatcagt gagaccgatt ccgccgatt ccagatgatt 3000
cctctggacc ccaaagggac atcccaaat gaccctaact gggttgtacg ccatcagggt 3060
aaagaactcg tccagactgt caactgtgat cctggactcg ctgtaggtta tgatgagttt 3120
aatgctgtgg acttcagtgg caccttcttc atcaacaccg aaagggacga tgactatgct 3180
ggatttgtct ttggctacca gtccagcagc cgcttttatg ttgtgatgtg gaagcaagtc 3240
acccagtcct actgggacac caacccccacg agggctcagg gatactcggg ccttttctgtg 3300
aaagttgtaa actccaccac agggcctggc gagcacctgc ggaacgccct gtggcacaca 3360
ggaaacaccc ctgcccaggt gcgcacccctg tggcatgacc ctcgtcacat aggctggaaa 3420
gatttcaccg cctacagatg gcgtctcagc cacaggccaa agacgggttt cattagagtg 3480
gtgatgtatg aagggaagaa aatcatggct gactcaggac ccatctatga taaacctat 3540
gctggtggta gactagggt gtttgtcttc tctcaagaaa tggtgttctt ctctgacctg 3600
aaatacgaat gtagagatcc ctaatcatca aattgttgat tgaaagactg atcataaacc 3660
aatgctggta ttgcaccttc tggaactatg gcttgagaa acccccaggg atcacttctc 3720
cttggcttcc ttcttttctg tgcttgcatc agtgtggact cctagaacgt gcgacctgcc 3780
tcaagaaaat gcagttttca aaaacagact catcagcatt cagcctccaa tgaataagac 3840
atcttccaag catataaaca attgctttgg tttcctttg aaaagcatc tacttgcttc 3900
agttgggaag gtgcccattc cactctgcct ttgtcacaga gcagggtgct attgtgagc 3960
catctctgag cagtggactc aaaagcattt tcaggcatgt cagagaaggg aggactcact 4020
agaattagca aacaaaacca ccctgacatc ctccttcagg aacacgggga gcagaggcca 4080
aagcactaag gggagggcgc atacccgaga cgattgtatg aagaaaatat ggaggaactg 4140
ttacatgttc ggtactaagt cattttcagg ggattgaaag actattgctg gatttcatga 4200
tgctgactgg cgttagctga ttaacccatg taaataggca cttaaataga agcaggaaag 4260
ggagacaaag actggcttct ggacttcctc cctgatcccc accccttactc atcaccttgc 4320
```

```
agtggccaga attagggaat cagaatcaaa ccagtgtaag gcagtgctgg ctgccattgc 4380
ctggtcacat tgaaattggt ggcttcattc tagatgtagc ttgtgcagat gtagcaggaa 4440
aataggaaaa cctaccatct cagtgagcac cagctgcctc ccaaaggagg ggcagccgtg 4500
cttatatttt tatgcttaca atggcacaaa attattatca acctaactaa aacattcctt 4560
ttctctttttt tccgtaatta ctaggtagtt ttctaattct ctcttttgga agtatgattt 4620
ttttaaagtc tttacgatgt aaaatattta ttttttactt attctggaag atctggctga 4680
aggattattc atggaacagg aagaagcgta aagactatcc atgtcatctt tgttgagagt 4740
cttcgtgact gtaagattgt aaatacagat tatttattaa ctctgttctg cctgaaatt 4800
taggcttcat acggaaagtg tttgagagca agtagttgac atttatcagc aaatctcttg 4860
caagaacagc acaaggaaaa tcagtctaat aagctgctct gcccttgtg ctcagagtgg 4920
atgttatggg attcctttt tctctgtttt atctttcaa gtggaattag ttggttatcc 4980
atttgcaaat gttttaaatt gcaaagaaag cctatgaggtc ttcaatactg ttttacccca 5040
tcccttgtgc atatttccag ggagaaggaa agcatataca ctttttttctt tcatttttcc 5100
aaaagagaaa aaaatgacaa aaggtgaaac ttcatacaa atattacctc atttgttgtg 5160
tgactgagta aagaattttt ggatcaagcg gaaagagttt aagtgtctaa caaacttaaa 5220
gctactgtag tacctaaaaa gtcagtgttg tacatagcat aaaaactctg cagagaagta 5280
ttcccaataa ggaaatagca ttgaaatgtt aaatacaatt tctgaaagtt atgttttttt 5340
tctatcatct ggtataccat tgctttattt ttataaatta ttttctcatt gccattggaa 5400
tagaatattc agattgtgta gatatgctat ttaaataatt tatcaggaaa tactgcctgt 5460
agagttagta tttctatttt tatataatgt ttgcacactg aattgaagaa ttgttggttt 5520
tttctttttt ttgttttttt ttttttttt cttttgacct cccatttta 5580
ctatttgcca ataccttttt ctaggaatgt gctttttttt gtacacattt ttatccattt 5640
tacattctaa agcagtgtaa gttgtatatt actgtttctt atgtacaagg aacaacaata 5700
aatcatatgg aaatttatat tt                                          5722
```

<210> SEQ ID NO 23
<211> LENGTH: 42521
<212> TYPE: DNA
<213> ORGANISM: Unknown
<220> FEATURE:
<223> OTHER INFORMATION: Description of Unknown Organism:Unknown

<400> SEQUENCE: 23

```
gatcgttttc cagacatttt tgttctctgt tcatttcctt atcgtattca aaaagttatc 60
acaaatgacc ttctctatct gtctgcgtct cttttaactc tcaccgtttg ggacctttca 120
aatagttttt cgctatcaaa tctaaacatt agttgcgttg actcgacatt tgaccctca  180
ctatcatctc cagttctctt ttttgttaca ctttagcagt ggcagcagag agcaagtagg 240
tggagccaaa gtgtgcgcca ttcatcggga aaaattgtgt tcttcatcaa attttgggca 300
atttactcgg gatttgcgct aatttggaaa caaaaattca aattcctgcc aattgtttg  360
tttgcttttt ttctttttt tttgctcctc ccatctctca tcaaattgct ctttttttcga 420
ttctaacata tcagccatct tcagagtgtg tcactaaccc ccattttat tcaaggttag 480
tgatatagta tcctaactac agacgtcaca ccatgaggtt gctgctcttc tcggcagccc 540
ttcttctgtg ctccgtccca acgtgggcct tctctctgtc atcattcttc ggaagcgatg 600
ttgcacaagt aagcaagctc tcctatacct agaatcttgt aaattgaaaa ctctaatttc 660
cagaagccat accttcatcc aaactcccca ccgggagcgtg acccggcgag ttccagaatg 720
aagagacagg catatcaagt gtacgttgat ggagatgttt ccgttactgt tgacaagtct 780
ggacaaaagg aaaccggcaa ctggggacca tgggtgcccg agaacgagtg ctcacgttcg 840
tgtggtggag gagttcaact cgagaagaga cagtgcaggt tcgtggactt ttcatttttt 900
agggaattc ctagacgttc taaaagctta ttttcaaaaa ttttggtttc ctgatcttca 960
tgccttatg aacgtggtga aagatcaacc taggctagcc tgtgacatac attttttgaa 1020
gcagatccaa ctttatcaag agccatcgaa ttctcgtttt aaagtgtttt ttttttctga 1080
taacttttttt ctaatagctt tacccatttt tatgtcaaga ctgaaagcaa tgaatcacaa 1140
gaggctatct acgtttgttt ttgaagctct gtaggaatca tcttaaaaaa ttaagtaaag 1200
taatggagat gaaattctaa ttttttaaaa tcataatcat tactttctgt attatcttca 1260
agttcaaact tttcaaacgg ttattctcaa gaaactcaca tagaatttta acaatttcct 1320
ctatctatttt cttgcaagca acccaccgaa ctcaaatctt atccaaacta aacttttagt 1380
ggtgactgca ctggagcttc agtccgctac atctcgtgta acttgaacgc atgcgagtct 1440
ggtactgatt tccgtgctga gcaatgctcc aaattcaacg atgaggctct tgatggaaac 1500
taccacaagt ggactccata caagggaaag aacaagtaag ttaacttct tcaagatgtt 1560
tttctaattt tcgagttttc aggtgcgagc tcgtctgtaa gccagaatct ggaaacttct 1620
actacaagtg ggctgataag gttgttgatg gaaccaagtg cgactccaag agcaacgata 1680
tctgtgttga tgggaatgt cttccagttg gatgtgacgg aaagcttgga tcttgtaagt 1740
ttaaaattta attcaaaatc ttcatttcat gccgaatatt tcagctctca aattcgacaa 1800
gtgcggaaag tgcgatggag atggttctac ctgcaagact attgaaggac gtttcgatga 1860
gcgcaatctc tctccaggat accatgtatt tatcaaactt ccagaaggag ccaccaacat 1920
taagattcag gaagccagaa agagcaccaa caacttggct ctgaagaacg gttccgatca 1980
ctttttatttg aatggaaatg gattgatcca agttgagaag gaggttgaag tcggaggaac 2040
tatcttcgtt tacgatgacg ctgaaccaga aactctcagt gctcaaggac cactctccga 2100
ggagctcacc gttgctcttc tcttcagaaa gggaagccgt gatactgcta tcaagtacga 2160
gttctctatt ccacttgagg aggaagttga ctacatgtac aagtttgaca actggactcc 2220
gtgctctgta tcatgcggaa agggtgttca aacccgtaat ctctactgta ttgatggaaa 2280
gaacaaggga cgcgttgagg atgatctctg cgaggagaac aatgccacaa agccagagtt 2340
cgaaaagagc tgtgaaactg ttgactgtga agccgaatgg tcactggag actgggaatc 2400
ttgctcatcc acctgcggag atcaaggaca gcaataccgt gtcgtctact gccatcaagt 2460
attcgctaac ggacgtcgtg ttaccgttga ggatgaaaac tgcaccgttg agaccaccc 2520
agtaaagcag acttgcaatc ggtaagttga ttttataaat gcataaacaa ctctgtgaat 2580
ctatttgttt atgcgatgct atccatatat attaccagat ggtgttggtg cccaaaaactt 2640
```

```
ataaacaatt attttctctt tgcagttttg cctgcccaga gtggcaagct ggtccgtggt 2700
cggcttgctc agagaagtgt ggagacgcct tccaatacag atcggtgacc tgccgcagtg 2760
agaaggaagg agaagaggga aaactcttgg ccgctgatgc ttgcccagct gatgagcaag 2820
agaagttcga cacagagaga acttgcaatt tgggaccata cgagggactt acatttgtca 2880
ctggagaatg gaacttggtt agattttgca aaatatgggg acctggggaa aagcatacta 2940
aataagatca actttatgaa acaaataatt tttagtgcac ccgctgcaac gatactgagg 3000
agactcgtga agtcacctgc aaggactccc aaggaagagc ctatccactc gagaagtgtt 3060
tggttgataa ctccaccgag attccaactg atactaggtg agtcattcca gatatgacat 3120
tgaacttgga ttaattttt tcttccagat catgcgccac ccaaccacca tgtgagtacg 3180
agtggaccgt cagtgagtgg agcaagtgta ccaccgaatg cggacacgga cacaagactc 3240
gtcgtgttat ctgtgccatc caccaaaacg gaggactcga ggttgttgat gaaggacact 3300
gtcaagctga gaagccagaa ggaaagacta actgcaccaa tgaggagaag tgtactggaa 3360
catggtacac atcttcatgg tccgagtgta ccgctgaatg tggtggtgga tcccaagatc 3420
gtgtcgctgt ttgcttgaac tacgataaga agccagttcc agaatggtgc gacgaagccg 3480
tcaagccatc tgagaaacaa gattgtaacg ttgatgactg cccaacttgc gttgactctg 3540
agttcggatg ctgcccagat aactctactt ttgctaccgg agaattcaac ttccgatgct 3600
ctaactgctc ggaaacagaa ttcggatgct gtgctgacaa tgttaccgtt gccactggac 3660
ctaactccaa gggatgcgaa gaattcgttg agtctccact taaccttgaa gctgatgttg 3720
ccaatgctga cgctgaagct tcaggagatg ctccagaact ctgcagcgtc acaaacgaga 3780
acggagaagc tgtttgatgt tgagtgtgcc accattgctc aatcactgct cttcttggag 3840
atggggaact tatcggaaat gatactgatg cttccaatga gaccatacac tgctcgaaga 3900
ccgaattcgg atgctgtcca gattggtaca ccgccgcctc tggaaagggt aacgaaggat 3960
gcccatcgtt cactcttgga ggatgtaacg agactcaatt cggatgttgt cacgatgatg 4020
tcactcttgc tcgtggagcc aaccttgaag atgcggaga gccatctgc gctgcttccc 4080
tctatggatg ctgtaaagat cgtaagacaa ttgccttcgg accacactat tctgatgtg 4140
agcgatcatc cttcccatgt gagcttagcg acttcggatg ctgcccagat ggtgagactg 4200
ctgctcttgg aaagaatgga accggatgcg gagagaactg cttgaccacc aagttcggat 4260
gctgccctga tggaaagacc accgccaagg ggtcccacaa cgagggatgc ggatgcgagt 4320
tcgcccaata cggatgctgc ccagacggaa aatcagttgc cagggagcc ggattttacg 4380
gatgcccaga aagctgcgcc cagagccagt tcggatgctg cccagacgga aagactcgtg 4440
ctcgcggaga gaacaaggaa ggatgtccat gccagtacac ccgttacgga tgctgcccag 4500
atggggagac tactgctctt ggaccacgca atgatggatg tgataactgc cgctacgcca 4560
agcacggatg ttgcccagat ggagagacca aggctcttgg accagatgga gccggatgcc 4620
caccaactac cacgccacca ttcctcatgg gaggaactgt tgccccacat aaaatcgccg 4680
cctgtaatca gacacaagaa agtggaaccg tctgcggagc cggatacaag cttgtaagta 4740
attaacctca tgaaaagaa ttggagcaac acatttcatg tataaatatt tcaatttcag 4800
gcatgcatt atgataccac tgaggggacgt tgcaaccagt tctggtacgg aggatgcggt 4860
ggaaatgaca acaactttgc tagccaggat atgtgcgaga ctatctgcgt cgaaccacca 4920
ggcaagggaa gatgttacct gccacgtgtt gatggaccac tccggtgtga ccaacttcag 4980
ccaagatact attatgatca ttccaagaag cactgtgtgg ccttctggtg gagaggatgt 5040
ctcggaaatg ccaacaactt caactcttc gaagaatgct ccatgttctg taaggacgtt 5100
ggaccgtacg atgctccaac caccgctgct ccaccaccac caccacagca aaatgctcag 5160
caataccttc caactccaga agttcaacag attgagattc aatctgctga gcaacctcaa 5220
ccacaacagc cacaacaaca gcaacagcaa caacagcaac aaccacagca accacgtcaa 5280
tcaatggaag acatctgcag atcccgccaa gacgccggac catgcgagac ttactccgat 5340
caatggttct acaacgcttt cagccaagaa tgcgaaacct tcacttatgg aggatgtgga 5400
ggaaatctca atcgtttccg cagcaaggat gaatgcgagc agcgttgttt cttcgttcac 5460
ggagctcagc catccgctgc ccggcaggaa caagctcagc cagcagctca accagctcaa 5520
ccagctcagc caagtaacat cgtctctcca ccacaacagt cagctagtcc agttgtggtt 5580
ccatgtaagt tctttagaat gcatttattt cttactataa gtttctataa gttccgcatgt 5640
gaagcatccc catttcagcg aacagcaaaa aacgcgatgc ttgccacctc aacgttgacc 5700
aaggacgttg taaggggggct tttgactcct ggtactacga agttgccacc ggatcctgcg 5760
tcacattcaa gtacaccgga tgcggaggaa acgccaacag atttgctagc aaggatcagt 5820
gcgagtcact ctgtgtgaag ccagcttctg aagctgcttc ggccggaatt ggtatgcttt 5880
gagttataga gaatgttcac tatttttgtt aaatgtttga gtaaatgaga aactggctca 5940
gtttgaaaat gtttgcacca tgtttcaaaa agttttttga gttgaatagt tgaggccatg 6000
aaaatcttaa ttacactcca gaagtacatt ttaaaacatt tttgagaatt aggtcttcaa 6060
aaaaaggttt aatattgagg tttcaaatta gaaatattaa tatacggagg tttgggttta 6120
aaactgattt ttaaaatctt attttgaag tttcgcttg atattcgtgc aaaaaaaaaa 6180
ccaactttt cagacggtgc agctggaatc aactcagttt gtgacgaagc caaggacacc 6240
ggaccgtgca ccaactttgt cacgaaatgg tactacaaca aagccgacgg aacctgcaac 6300
cgattccatt acggtggatg ccaaggaaca acaatcgat tcgacaacga gcaacagtgc 6360
aaggctgctt gtcaaaatca taaggatgct tgtcaacttc caaaggttca aggaccatgc 6420
tctggaaagc attcctatta ttactacaac actgccagtc atcaatgcga gacgttcact 6480
tatggtggct gcctcggaaa tactaacaga ttcgctacca ttgaggagtg tcaagcgaga 6540
tgcccgagta agttctaagt taatagtgat atatgcttg ttttccccttt attctttgac 6600
aatttctcaaa tactttttgc ataattacct tatttctatt ccctctgtt tcccatttct 6660
ctccacccgc tacaaattgt ttcccgtact ctctcctttc tcactttccc gtccgaaggg 6720
acacgcaat gctgcctaaa tgaactgcct aataatattt atgaattttc caatttttcta 6780
aaaaaaaaca attctctcaa aaaattcccct gccgttccgc cactgctttc ttcacccatt 6840
gttcgcgtat ttttttttaa taaatgaata aagctgaaat agttaacagt ttctgaaatt 6900
gcatgtaagt ttgtagtgta tcagtgtgtt tgtcgtgaaa gttttttttt acctgcatga 6960
tttcctgaac tgcatgaaac tgttcttatt acgttttaga tttgctgaag tgtgctagaa 7020
gtgtgatttt gtttcagaag acgaccagac tacaacaaca tcacaaccag aagagctccc 7080
aagtttgcca cttgttcaag aagatcctca gccacgaccg gcattttcat tgaagtaagc 7140
acgtgtagtc caagtgccta cttctcgtat gaccaaaaaa tttaatataa ggtttccaag 7200
tattaaggaa tcagtagcat gtaaattgtg tggattgttc tcctgggttg atgggttttt 7260
ttctcactca caatcagata tggagtagct tatatgggaa tttatttgag aaatagaata 7320
tgtcataaca tccaaattta attattaaaa agttgtgaag tttctcatta tgtatataaa 7380
```

```
attcgccttt caaataagaa caaaaattaa ctgtatgaaa gagctgaatt caatttgaaa 7440
ttgagaaaat aactggttca aaaagaagaa aaacgttgga aaatctagac gtaaatctat 7500
ggattttctt ttcaggtcgg ggaaatttcg acgatttta tattttcaaa aatcattcac 7560
aaatatacac caaaaattat ttttaccata ataaaatacg gaattactgt ggattactgt 7620
agtattcatg taaggttact gtattgttac tctagggata ctacaagaat atttttgcaa 7680
agttgtaaga agtatagaga ttactgtaga ttgaaaatct agacaaaaat catttccgt 7740
aataatctgt ggggatagaa tgttgaaggc acaaggctta taaagcacca tgggaaaaaa 7800
ttttaacagt gattttttta agcatatcct ctttcccagg aaatccactt ttcaaatata 7860
ttcccactaa actctttaag acaatcctt gcccatagtc gtcgccgtga tgctccattt 7920
gcacgttccg tatccgcccg tcaccatact cctgattccg aagaggaacg agttgactgt 7980
tatgctgttc cagatccagg atcttgcggg taataaatct cacctatcca ttacaaccat 8040
taccgtctta atgattcaga gactaccgtc ttgtttggca ctactctgcc acgagtaact 8100
catgccgtca attctactat ggtggatgtg ctgggaatac gaatcgcttc gagacccggg 8160
ataaatgtga aacatcgtgt gttgctaaga ttgaagaacg cgtgaaagt gtgtcagaag 8220
cttcaaaatc tctggaagag gttagactaa cggatccaag gatggattct cactttggat 8280
atcatgatcc agaagttgat caaatcgaag aagaagccga atatgtcatt gttgataccg 8340
gagctctacc tgaattatgc atgcttccag aacaaagagg gtcttgttat gataacattt 8400
tgagatggag gtaagtcaaa tcaagaatag aaaattcgaa aatccgaaaa actttataat 8460
tatactaaaa gcaaaatctt aaaatctttc agattcgact ctgaaaagtc tcaatgtgta 8520
accttcatgt attctggatg taatccaaat gcaaatcact tcactagtca ggttagtttc 8580
attattttgt gtcctttcgt ggaactggcc ccttggtttc taacttgatc ttctccttcc 8640
gaatacccaa tttgagcacc gctggctcac ttttttcgacg gtgacgttcc tcaattctag 8700
cggcctctgt attttctgag cactcttgag caacagtttc ctcactggaa atgtttgttt 8760
ttcaagaggg agtgagagag agaaataaac gtacaatttt tgaagccgca catgatttgt 8820
tagaagtcga tgccgttctg cagtatcctt catgttttcgt agttgtttct gtagtaattt 8880
ttatggatta ggaactaaga aatcatcact cactgcggta gttgcatttt tgtgcatgca 8940
tcttcccata aaagcaacaa atgcaacaac tgatagagcc gccacacaaa ttgcaataat 9000
tcgaagtcga tttctaattc cttttcttac tttttgtcta tgctcagctg ctttttcgat 9060
gtgcttcttc ttgctggggt cgagctcgca atgaggaaat ggttcgatga gtggaccgtg 9120
tttttttgcat tgttcacaac ggcgtccagt gtatttgtct gggcagtcac acgaaagagt 9180
gcggttttg aaatctgaaa attttaaatt taagaacagg atctatagca gttttgccca 9240
tcacagtcct atgtctatat taaaaaaaat tatcggacat taaaaaaaat gttttctcat 9300
ttttcagta tttctataaa aactgcattc gcatttaatc ataacttta atcgttaaaa 9360
acttagtctt taagtacctg gggatccgta aacacagaca atttcatcac aataatcgcc 9420
ttcaaatccc acatcacaga tgcatcttcc atttctcaaa aaccctctcga cacatttact 9480
tgtatattgg cattcacttc caaaatatga gcccacacat tcacatcggt ccccttcca 9540
ttctccttg tttccgcact gaaataattc aatagatttt ggaagtttag ggcctcaaaa 9600
atatacctt tccgctggcc gatagtcaca catttcacct ttccatccga cttcgcaaat 9660
gcacggctca ctgaatagaa ggctttccgg gtcgaagcgg aatccgaccg agagtccgtg 9720
aactgtaaat tgaaaatttg taattccaaa aaaaaaacag cttttgcaaa aatcgtccaa 9780
aagaatttta gagttagaca ttatttttct caaaaagttc aaagttgtat cagtttttaaa 9840
ataaaatatt taataggatt gtagagcttg ttagaaaaaa taaaagctac ttgaaaaaag 9900
aaaggtatcc aaaaaggtat tgagatagtt tcaagcaact ctatttgtaa actgtcgagt 9960
ttttaagttc tacaaatctc ttataacatc gctacatcta ctatcaaact ttgaaaaaaa 10020
accataccac attcaaaatg ttcacattta tctccagtct gtcccttgat acaatgacaa 10080
atccctccag catagattcc tccattacga cattcggctc tcggatcatc cagacgaaca 10140
ttgtctagaa tacttctctt ttgaagaata cgatgcacgt cgctcaatat attttcatct 10200
agatctagtg agtcatcctg tgattgtgct tttgttgttg ataaaaatag gaagagtaaa 10260
gtggaaaatt gtaaacagta catagcgtta gatactgaca agtctactat caattgattt 10320
atttattgcg tcttgaaagg ggtatcaatg agagaaatag aggagatgggt aaaatgcatt 10380
tataagagaa tacaaaagat gacgtaattg attaatcaga gatcagttga aaatacttt 10440
aagtatcaat tattatctgt gaagacagtc acgtgactct gactcgaact caatttgcat 10500
gttgatagtt ccaatgttaa agaaagtctt tgggttttct ccagatgaaa caaatgattt 10560
tggaatatta aacgtgactc ttctctgaca aggttttgat ccgtcatcac aatcgtgata 10620
gatattaagt tttgatcaa tagtcatcac ttcggaagtg tgtccggtaa gaaggaattg 10680
accaagagag tctgtagttc cttcggcaag aagatcgtca agatccggtc ctgaaaaaaa 10740
ctttatttt gaaaatttc aatgagttgc ttcatgttag aatttggaat ttttaaagat 10800
gttagcaatt ggtatttaaa tgttcaagct aacgtaatta gagttattca aacaagcttt 10860
atataaaaac tttgtgtaag attcggtcta attagaacat caattttaa cgcagctgat 10920
aaaaaacttt aatttcaagc ttcacataat tctacttacc ggtatcatca tcgtagagct 10980
tcaccttcgt gttagccagt ggttgtctc cacacatcag aacacccta actccagctg 11040
attgggtgaa tacagcttcg gagccaattg cacaaagtat gaaaagtgat gaaatgcacg 11100
cgagtcgtga cattattttt gtctgaaaat acaaacactg actgatctga ccttcatcgg 11160
agaaactctc ttatagcaca gttggttaga aaaagatacg gagaggagaa gtgggaaatc 11220
gaattgacca aacaaagaa ctggttttca cttgaaatag aagacgatga aagatataca 11280
acagagaaga tcggaagtga ttcatctgga gaagaaaatt agagggacca acttcttgta 11340
ttttccactt atttatatac ccaatagaat tcacctgatt ctttccgatt tgtgtacatt 11400
tcgctgacta acgtgtgctt cttcggtttt gtcatttctt attgttcatt gaaaataaac 11460
agaacaaagc aatcataagg tcgaaaatcc catttagaga tcaagaggtg tacctttaat 11520
tgtgcggcat ggcatagttt tatcttgctg aactctcacc aattgatgag tatgtcagta 11580
gaatggattc catccgatcg ttgctccacg gtgatctctt ccgccgcctt ttcatccacc 11640
atacccgttg tgtatggctg gcaactgtga acagcgcctc agtgtgaatgt ttagtttgat 11700
atacagttta aaataatttt ctaaactaaa gaaatcagtt tttgaaacca gtcttgtagg 11760
catgtcgggc gcaggcacgc taacgtgaaa aatagaattt cgagtggtta actatttat 11820
tttcaattaa aatacaatca actacacaat gaatgaccg gataaatgaa atacaaatac 11880
aagaatttaa aaaaaacatg gaaatttaaa cttttccatc atctccctt gctggaatat 11940
tatatttcat tcgataagct tccaattcgg cttttctctg atcggatcgt acactgtgtc 12000
tctcatccat ctcttgttga gctgtcattc tcttctcatt ccatttctga gcttttgctt 12060
ttttgtggat tctgttgtat tctttgcact tgcagcagca ataacagaag caggcaatga 12120
```

```
gaattacagc aatgattcca gcgcagatgg caataacgat tgcggcggct gatgtgctca 12180
cccagcagac attgtatttg acatgcttga tattacagtc tggatagtac cagtcgaatg 12240
gcatacatct tttcgttttt ccaccacacc agaagcaatt ctgaaaaaat gtgttttttga 12300
aattttcaat atgtttgctt ataaaattga atttaatttt tcaaacagtg tttcagaaac 12360
tcaacttctg aaattaggaa agtattctca attgagagct gttttttgtat taaaagtttc 12420
agtttagaac tacaggtgtg aaaaaatctg agcaagtgaa caccaacgta ttgcatcaca 12480
gtttacgcgt caatttattc gagtgttcat tgtagagaaa gttaggtcac cttccagaaa 12540
attaagaaac ttgtttcaga catttttgct cttttagagg aatttttttt tagaggaaac 12600
acgcaagttt ctttgaaaac aaaaacaaaa tatattttt atccacttac cgagcccttg 12660
ccaacacatg tttcacaagt gttcaaatcg ttcgatccaa ttctacagta ttcttgtttc 12720
tctgaccatg tcatgttatc cgcacatact gatactagaa caattgagaa aaagagtagt 12780
aatcggtgaa tcatcgttct gaaaaatcaa taaatagtaa caacttgagc aagtctcgta 12840
actgagcgac aaaaccaaag tagtaatgaa atagaaagat agaaaggtaa actcaaaggg 12900
ctcgcgtgtg tttgtctatc gagtgccaat gagttttagg agtagcgaca gaaataagtt 12960
ggcagaagaa gaacatacga actatgtcgg gctacaagat tcttgtgttt acttttgaa 13020
aaagaaaatg catttgagaa aatgcaaatg ttcggcagaa atcgaatgga gtttagagca 13080
gaatggtaaa aataaaggtg gatcagcaaa aatagttgaa caaatatttt gtagatttca 13140
tgaaagataa caaaaaaaaa taaatacaga aaacaatata tgacgtattt ttcaatcatt 13200
gtttttgtat agtgcaaatt cagtagttgt acctgttata agtacagcga agttatacat 13260
tttagagtgg gtcttgtcac gatccatatt ttttgaacgc aatatttgaa atccaaaaaa 13320
aaataaagaa actaggcgcc aagaagctat agtagctata cgcataaatt gtgaatacct 13380
tgaattacat taaattccaa caaaatagga aaatcatata aaaacgaagt tagttgtcaa 13440
ttcaaaaacg tttttaaaat tgttcataag cgccgagctg tccccctcag ttttcgttta 13500
ttcagctttt ctctctctct ctattctcta tcgtcaccta tatttcatag tccccttatc 13560
caaagtgga agtgaatgag gatggaaata tgataccgca tgcttcaaaa aaatttgctt 13620
atgagaaacc aacatttgaa aatttccagg aaacttgtga acgagcctgt ggtaaatgga 13680
gaaatgtggc agtgtgcgag ttgccggccg aacacggaga ttgccaactt gcgattccca 13740
ggtatgtact gttgacacat tttacaaatg gatgggaag tggtcggtga tcaggtggaa 13800
atgttgatgg caaggtttta aatagatgta gtaactgaaa acaaaatgac agatgtacat 13860
acataaatta ggattaaaac aaaaatacta tgcggagtca ggtgactaat ttttctggaa 13920
attccagaat ttgaaaatgt ttttctctgt ttgaaagtag aacgggacct tttacaaaat 13980
aggctgaggt aggtaggctg tagaaagtgc ctttggtgtc tttgtaattt ttgttttcaa 14040
aaaatcactt gtaagcacat gaaaatcaca tgaataatga tttaaaattt agaaaattag 14100
tataaagaag atttacattt taataataat aattccagat ggtaccatga cccaaaaaca 14160
tcccaatgtc aaatgatgat gtggactgga tgcggaggaa atggaaacgc gttctcttca 14220
aaagcagact gtgaatctct ttgccgagtt gagacattat ggtccaacaa cactgacttc 14280
tgtacattgg aacgatcggc cggtccatgt acagattcca tttcaattcg gtatttcgat 14340
tcaactcatc tcgattgtaa gccattcact tatggaggtt gccgtggaaa tcagaatcga 14400
ttcgttagca aagagcaatg tcagcagagc tgccgtcctg gagacacaaa atctgaggat 14460
atctgcacac tccgcccaga gccgggaccg tgtcggctgg gactcgagaa atacttttac 14520
gacccggtga tccaatcctg tcatatgttc cattatgagg gttgtgaggg aaatgcaaac 14580
cggttcgatt cagagttgga ctgcttccga cgatgctcga gtgtcaaggt tgaagcaagt 14640
gaaagcgaga gagtgggaca gctgacgtct gcatccacgc cagttatta tattgttaac 14700
aaaacagcga ttttgttgg aaatactgta agttattaat tttaattcga agatttctta 14760
atatttaaac tggtcccatg agagtttggt tcattttccg acaatagact gcaaaattga 14820
taacttttca tgaacactt agccgatttt agctagttt gtttattaaa atttggtaat 14880
tcaaaataaa aaccttacgc cactccactt ttgaatactt gtcaaaataca tttttttcagt 14940
tccgaatccg atgcaacagt acggagtgc ttccaataac atggtacaag aacggaggtc 15000
tcctccagtt cggctcgcga atcactgaag agaatgatga cactttggaa attgtggatg 15060
ctttaactgc tgacgccggt gtctacactt gcattgccgg ccaggatagt acaatgagcg 15120
agggagtcga ggttgtgatc aagagacttc ctggtcacag aactacatct cgtccaatgc 15180
tgacaccatc caagaacttc tccttgggaa ccccaccgac accatctcca tctacagttt 15240
ctacaacacc cttccgaatc tatacgcctg gatctgctcc atctgatgct cgtgtaagcc 15300
gcccgacaag caattcctgt atggatgtgg gtaacgcgag cacgtgcgat ttgatcgtga 15360
agaacggttt gtgcgggaag aagcgatatg gaacattctg ctgtcacact tgcacccggg 15420
ttcataattt taaattttaa gtttggattt tttgatttca aattttcatt aatctttaa 15480
tgttttctcc ttcataatat ctccattgcg agatctcttt ttcccttctc ttcctatact 15540
ttcccctcag acaattggct aattactgct tcgttccagt aaataaatat gaatttattt 15600
cttcttccta tactttggta tacataatca tggcatgaaa tacaagacaa aaaaaacaag 15660
aaaaaacaat ccacttgaaa tccattcagg tgtgaactaa catcttactc tattaacttc 15720
gtgccattac ttccacttat tttgcctatt cactaatgaa gtctctgaga attattttct 15780
gtctaactct gctgattgca agcttcccag ctcagcggag ccgccgaaaa cagaaatttg 15840
tacgccttcc tagtgggttc acgtttcctg cggatgcggc gagtaatttt caaagagatg 15900
cgtatattcc agcgacggta aattttcgct ttttgttaaa tgaatttcag gcttcaaatt 15960
attttctagg acaaaaattt aaagtaggct tgcgcatact catttccctg ccttacctgc 16020
caacaggcta gcttttggag agaaatcaaa agtttggtgt ctgtaaatct aagctttccg 16080
aagcgtccga aagtttttgg gaatccgcta tacactttaa gattgataaa tatttgaatc 16140
aggtttattt tgcactatta aggcgtgtag gcactaggcc ggcaaagctc gcctacgggg 16200
agccttacaa tcaagtatta ttcatgaagg tcttgatttg gttacagaat tccatctaaa 16260
attacttata caaaaacatg aaaaatttca gtttgcccg ccatcgtgaga agattcttca 16320
agctccacca cgctatttaa ctggagaaca caatccgact catgtgtaggc tcaattttt 16380
atctgatttt ctaaatttaa cttcaagctc acaataccga tgtgcaagga atgaactacg 16440
ctgagtacaa gcaagcgatg gccccacaac cacatccagt cgatgcttat tctccaccac 16500
ctcctgcacc aatggtccca ccggttactg tagttgaacc acctgcaatg ccgtatgaaa 16560
tgactacgat tgcatctgtt ggaccactta ctactcccgc atcagtccgc ttgaagaagg 16620
gaaagtttgt gattttagtt aattgatctt tcaagtcaatt ggatacaatt tccagcatcg 16680
gaggaattgc tcaaaacttg aacgacaggt acaccagctt aacaccagaa gctcaacgtg 16740
ctcagaaagg tcatacctat acggctctgg gcggtggaca attctatcaa agtttacttg 16800
gaggggtaag atgcaaggtt agaacttaca aactcaattc attttacaga aaggaggccc 16860
```

-continued

```
cggaggattc tcccccactct cgttctttct aaacggcggt ctaggaggta ctggtggtgg 16920
tggtaacaat ggattcttcg ttccggtgcc tgtagtcatt ccgcctccac cgccaccgcc 16980
accaggacca aactgtttca cgaacccgtc gggattcctt tgctgtaacg tgacacttga 17040
gaaaactatg gaagacgcgt acctggccgc aaaagcagat ggtgcatcac tgtgcaatgt 17100
acagaaaatg gcaactgcag tgcaagcggt ggggtttatg gatttcattt tataatgtaa 17160
tgtgctcttc cctagaattg aataagctta caacttgaat tacgacttga attacaactt 17220
gaataagctt aaaatatcca ccaaatttca gcaagccgaa aaaaattcg gaacaacttt 17280
cgaatcagtc gctgctcatt cggacttcgt cgcaaaaatt aattttgccg gtgacctgaa 17340
ctgtaaaata gaaatcgatg ggaaattcat actagcgtac gcaactccaa tcgccgagca 17400
agaggtgaac attgtcgatg ctagctcatt cttctcggga gctgctgata aggatttgga 17460
tggtgtcaat ggtaccaagc ccacctacat tgtctacggt cccattaaat aatggagggt 17520
ctagctttaa agatttctgt atattaaagc tgaaatgtga attaattgtt tatttgccaa 17580
tcacaataaa gttgaaaata tcatttgaat agttcgaaag ttttcaatcg gaatgggaga 17640
aaattcgaaa atttaggtgg aggtgaaaag ttgatgaagt aacacaatta actgtgctcg 17700
aatcctgaat agaaggagaa aagagcctat aaacagattt tcaatttaca catattacac 17760
aacaattcag gaagaagaca gtagttgcaa aagaaaatac gtagaaaaaa gagtgaagga 17820
ctggcgggat gtcagtttgg atgtacaaat agaactcctg aagcataaga aacagaagaa 17880
tcgaccgatg atcgaacctg aaatggattt attgttgatt gaaaaatatt aagcaattct 17940
gaatctctac cttgtttgat tgtgtgtaat gcaagaatct aaactcgtga gtgtgattgt 18000
tactgatccg gaaatgttcg gctgcttgca gcattatcaa tatcggatta cgcccacaaa 18060
tcgtgttctg ggtcttttg aggtagtcat taaaagctgc cggattaagc gtctcaattg 18120
cgctcattcc ctgcttatcc atattggtta tctgctcata atcggaata gaactatgac 18180
gatcgtacgg agaaaagctg aagcgttctc cccaatggca aaagtccgaa gagatcacaa 18240
acaagtttct tggatcctcc atgtaatgag caaaatatt tccatacgtt tgctgcctag 18300
atcctggtaa agatccaaca agtaccggaa caatggtgta acgttttgaa cccataacct 18360
ttgcaataaa tgggagttgc atttcaatac tatgctctga ttcttcatct cggcgatcca 18420
tcaaatcgaa atgacgagtg gcacgaagct cctcgttaac tgcaaagggc aatgttgtaa 18480
aagatgtact aagagtgcaa tagattactt ttgtgatcaa cgatcaagtc gccgagtgga 18540
gttctgtact tgctgcatgt ggttatagca catccattta gagcaacaac gtgagatgga 18600
ccaagaatga agactctttc actgaaagtt attgagtaag ccctgttgcc aagtacaaat 18660
ttcaacaact cacactgctg atgaaacaac ttgtttgaaa gcatatgcag ctgtttctcc 18720
acaatacgaa tatcccgcat gtctgaaagt tatcagaaaa taaatattaa atgcatttag 18780
agtattacgg tgaaatcaac gctcgagccg ttccaatccg gtgaccggcg ttgtcaagcc 18840
atttttgtgag ttgccgatca agatctcgct ggttggcgtt gtaccatgat ccggcatgtg 18900
aggcagatct cgtgtgctcg ccgaatccgt ttagtgacat tttaaattca gatggtctga 18960
atattaaagt tttgataaat tgttgtatac gacttgatta atatgtttag tagggttttc 19020
aactactgtg tgtttcccaa atagtcaaca ttgaaaaatg gaaaagtttg aatttaaata 19080
ttcaaataat tttaattaat taatattaaa attcacaata cagtgtaaca tcacacttaa 19140
ttcaagatgt tctaaaaata tgagccatcg ggctagctct acttcacgaa ttcgaatcaa 19200
gtccgggaa ctggctcgaa agaaaataaa ttttaatttt ggtttatgtc cgaaatagaa 19260
atgggaatct ggtttttcat tctgaataat ttccgagaaa cacttacaaa ataaaattca 19320
gatatcttgc aaaaggaagg ccaaatgtcc tgagaaatag agcacgagag ttttgaaata 19380
cctgcaacaa caggatttgc ttctatttg tttttttgaac tgaattttaa actattatct 19440
attctgaaaa cattttttgt ccaaaaaaaa tcaagaacaa tttagagcaa aatgtggcaa 19500
tccgaaaatg ttgatgcaac aaaaaagtgt ttttttttt attgaatttc agtttgaaa 19560
actgatttct ttccaaaaaa aaaacgaagg aaaattttga gaaaaaagtg aaaatccaaa 19620
aatgctgatt ttggtttttt tttcaaaaaa aaagcatttt gcaaagtgtg tgctttttttt 19680
cgaaagtttc agaaccttga gacaaaaaac caaaattgtg ttcccgagtg aagcccgcca 19740
cgtggacatg gtcagacgaa tcttgttcgt gttcgcagcc aattttcatt tttgctgaac 19800
gcataattgt tcaaagaaga ttccggtctaa aaagacgaaa ttgaaataga ttgtgggaatc 19860
ctttgaaatt ttcttttgac aaaaggtcac cgttattcaa aaattgagat ggtctcgtga 19920
ctaaaattaa acaatcaaga taatcatgat tgtgggcctg ttttaaaata cacttttcaa 19980
aaacgaaatg taggctccaa tccaaactgc gcatcaagac caagaatata aaattttaa 20040
actcgggaga cgtagagaaa cttgtgaatat taaacatcgc cgtcaagttt ccgtcagagc 20100
gcgcctgaaa ttttttagag gcttcttttca aaaagctacc catacaaata atcataagaa 20160
aaacgttta aaactttgca ttccacccaa aaatgtctga aattaccgt aaaaagaatg 20220
tgtgaaggga gtgatttgag ggttctgtca aacagtttga ctgtttcgcg ttcgacgtgt 20280
ctcgacgtgg atggtattga agaggaccgc gctgatcttg tgctggtcgt cgtcgtcttg 20340
tcggaccgcc gcgagtagtc ttcagtctac caattacctg aaaatttgac actttttgtg 20400
atgtgaaact ggctgcctga agcaatgcca tataaatc ataataatata taatgaagag 20460
ggatgaggat gcatgccaaa agaatgaaag gaaagacgct cttctacaac accagccgat 20520
agtatttaga agaaaaagaa gactaaaaag agagtattgg gtgatgggag aaagaacaca 20580
atagggggagg cagtgaaata gaacgagaac aatggaatcg gcagacattt gacactagag 20640
gggccactgt ttcagtcttt ttcgcacttg aatattggaa gagggccaag aaggggagtt 20700
ccaagaatgg aaaaagtggt aggtttgtag aaaatctgcc tttttttttt taaaatttcg 20760
tgttcactac tttattcgt gttcactcgt ttatgtcttc cattataggc aggcaaagtt 20820
tcatgcctac ataccctgcct catgcctatt tgactttcaa tataaaactt gattttggc 20880
attcttcatt ttataacaat tgtaactaat aataagcttt gcaaagtttt ctgaaagaaa 20940
ttgtctaaat tttcctggta cactgaacat ttttcggtat aaaatctatg cgtatcaagc 21000
ctatttctaa gagccgtaag tattttcagc tgaaatgtaa aaccacggag tcaatattta 21060
cttcgtatca tccatcttcc attccgtctt gtttacacct acggcaggta tttagacacg 21120
aatgattgtt tttctcgttg cctaatactt ttttcccccga aatattccca tattccagtt 21180
ctgaacaatg cacttttcag cggtcatcgg gtccatccag ccctcattca gccctttcat 21240
ttatcttcgt ttctactttt agacgaaaat gcaaaaaaa gagaaaaaga cactctcttt 21300
tgacgctcac attcgctcac attgctgtgg tagaaaaaca ctcactcggt ggctgctggg 21360
aagggaaaac gagaaaatgt ttggtcacgc aatacgccta tatctttgat ttgactttga 21420
atctttatac attttttcacg gggttcaaaa acaattatga agaaaattgt tgattaaat 21480
tagaatgtag attctttata ttttcaatca aaaattaatt ttggaaaaat aactatccaa 21540
aaaacgaaaa aagtaataaa tgagtacttg aaagtgaaat ggggcaatta aacaagataa 21600
```

```
aaaagactaa aacgtgagac atctcacaac gggtcacggg caagaagtac acgagaaatc  21660
gaacgtgagt ggggaggcag agacactcag ctgactgcct ggcctgacgc tcgctcacaa  21720
aacgctctca ctctcttcct cgctttgccc gctctccgcc ccgggtcgtc agttcggtcg  21780
atccatgttt gttcattttt ataggtgaaa atttatgtaa gggaacggaa aatgtaaagt  21840
gatcgtggga aaatagaaaa acaattacat tgtaactttt ctggaccaag ttgtacccag  21900
atgcaatatg tatattttc tcagaaaata ctgtgttggg tttcgacagg atcgatttat  21960
caaaagcaaa cgagtgtgcg tctcaacgag cactaaagtt cccaactaga gcatccttgt  22020
tgtggtagaa ctacatagaa attttaatt ttgatttcaa tagcttttct cttgttttct  22080
caaaatttat tgaaaaactt atttactata aaacgaccaa cgacggatct ggaaactaca  22140
gtactcctta atgcaaaagg caacgaaaaa tcagccagtg acttatttt tgttctggat  22200
aaaaatcggg aatatttgca ttttgaattc gcactgtatc gataaacaaa acaccgaaga  22260
tcacgccaaa atgactattg taactaacag gtacagagaa gggacgcttg ttctacaaaa  22320
ataattcaac aaattttccc caaaaaaatg tgaagtccgc aattctcgta gttttacgta  22380
aatcaaaccg agcatgacac tctgacacca cgtgcgcctg aagatgtgcc tgcctaccat  22440
ggatgcttta catttgctag ttccatgaca ccccatcctt tcagcttcca agatgaagga  22500
gttcggagaa aattcgaaaa aatattgaga aaaataaccc aaaacattgc gaaacattgc  22560
ggaaaaaagt tagaaattat gtcgaatata tctgaaccaa tcaacaattt caaataaaat  22620
acaaaaaaaa attggaagac cttaaatagt ctccgcccat attttggctt caaatgaccg  22680
tacttcggaa tatggccgat ggccgtggca agacctccaa tcgtagtttt gagcggtcag  22740
taagtgaaga ttaaaatagg aacagtaccg taagatcagc ccaggtgcgg atgtgggata  22800
gaggaactga aaataatcga agaagcatga taactaagcc acgttggcca cgttcgttttt  22860
gcgatgttaa tagatcgcca cttcgtccat tgtcgttttg tttgtactaa gtctccttag  22920
caattctctc gaaggcgggc cattgctatt agtaaaataa gctaccaatt ttacctttca  22980
atacattcat tcactgatgg ttttcctatc aggtgatcat ttttttgttc ttctcaatta  23040
cactatctaa aaatgatgaa gttttgctt cgcggctatt tggttgaagt gatgatatat  23100
ccattgattg tcgtctccac ttgtgctctt tttacgtctt acaacttctt tttaagtgtt  23160
ttgcgtattc actgtttcat ttatttttg cagaaaatga gcctgttcag caaatttttc  23220
ggaggcatga tgcaagaagc tccgattact ccacaagaat ctattcaaaa acttcgggaa  23280
acagaagata ttcttggaaa gaaacaagaa ttcttggaga aaaaaattga cgacgtaagt  23340
tggaagatca gtttggtcg aattaatcac attaaaagt gctgaaatcg aaatttttaa  23400
actctcgagt ctcaagtgac tgtgacgtaa ttaaaacatt gctcagcatt tacattgttt  23460
actgacgtct tttcgaagtt tagtcgagca aatccaaaaa agagcaataa aaatttctgc  23520
tacgatacgt ttgggaaatt ggaatcatag tttttttaaca tccatttttc aaaaaataca  23580
ttattagaaa atcagtaagt ttcggaaatt atttgagaaa cgtttcagga aagcaaaatg  23640
ccgtgaagta tggaacaaaa aacaagcgga tggctctcca gtgtttgagt aggaagaaag  23700
ctttcgagaa gcagttgatc catattgacg gagttttggc tactctcgaa catcaggttg  23760
gtatataaaa atattagaga aataaattga ataacacggt ttttcttcca gagagaaacc  23820
ctcgaaaatg cttcaacgaa tgctgaagtt ctcacggtta tgaaacttgc tagcgatgcg  23880
ttgaaagcgg ttcataataa catggatagc gaccaagttc gtgatatgat ggataacata  23940
gatgaacaac gagaagtggc gaaggaaatc gcggatgcta tttcaaaccc tggctttaac  24000
aacgcaattg acgaggccga gttgctgcgc gagttggtgg atcttgtaca ggttcgtcta  24060
taccaccaac atcgtgtaat tattagaaaa taccaggaa agcacttgac aaagatttgc  24120
ttgatgcgag agctcccca gtcacgcttc cggatactcc caatattgca cttccagcct  24180
ccagaccgag agctaaagaa gctgacaagg atctagaaga cctcgaaagt tgggcaaact  24240
aacttctcta agtcactttc atattaatt ttcggctatt tttgtttcat ttgcatccc  24300
ttcatcaatc ctaccattct ccggagattc tcctaaatca acttctaat tacgacaaat  24360
tcaaatagtt gaatgatttc tgtttagcca tttcattcga aacaaatttc cccaaggcta  24420
cgatcaacac tcatcaaaat tgtaacatat tatcgagctt tttgaaatt tgtcatttta  24480
tacatcttgg tcccttttctc caaaatcttc caagcatgca ttaaagttcc aacttttatt  24540
aaaaatttcat tctggcaaac atgttattg taccggttga aaacgaaaac caagcgagaa  24600
atagttacat ctcagatctc cctaacgatg gctcaacccc tttgacgctc atttactaat  24660
gtttatactt ttgctcattt actaatgaat ggctcattta ctaacttgct gagattttt  24720
aatttactac tgctaattgt aagatatata tcatttatca tttactatat ataaagcgct  24780
tattccgttt gtccatagtt gtcactctat gtagtctttg tagtctgtga cgttttggct  24840
tctggaagga tagtgagttg ggcttagtgt agggatatag ggggtactgt agtggtacaa  24900
tagtggtacg gtaggagtac tgtatgatta cggtagtttc agaaaaatta gttttcagct  24960
ccagaagtcg ggggccgcgc cggaggtgcg gtccacggct ggttttacat aaggtagttc  25020
caaaaaatgt cctacttcca attactcata actcagttag cgcgctatag ctatagcgtt  25080
tgagtttaaa aaaattgtgg ccaactgaaa tgctgtttgt cagagatgcg agctctaaaa  25140
gatgatcgaa atattctatt tctgcggatc tagaatattt cgatcatctt ttggagctga  25200
catctccgca atcgctaaag ataactaaaa ggtaccaatt aacaaaatgt gttttacaat  25260
attgccaaca acatttaagg tttctttcgc tgattgtttc cttttggttt tggtgatggt  25320
cccggagtgg tttttttcgc tggttctact atttttgga tcggcaggct ctgaacaatt  25380
ggttgtacaa tcttcttcaa cttcatcaaa ttatccagag ttatgttgtc gcttctgctg  25440
tccaacatat tcatgcattt gacggaactc ttcaactttc tgcattgtca ctggattctt  25500
cttttcgat tttattttat gaaaactta ctatcataaa caatagtatt tatcatgta  25560
caaatcagtt tggaatgatc tccttcattc aaaattctta atgatcagtc gattcactct  25620
tagagccacg aaaaatgtgg gacaattgtt tgagaagtga aaaatagtta ttaatgttgc  25680
aattagttgt acatataagt aatacatgaa aatacatctt aaaaatacag ttactactag  25740
gtattattgc ttaaaattgt gttccaatct gccagtacta tgagcgtaat tcgttgatcc  25800
aatcttcgaa tagccgtgag cacaggcttc gccggcactg cacacaaact tcacgattgc  25860
acgatttgca gaggtagagg acgaacgact ttcctgtaat tggcgaaata ttgttttaag  25920
ataaagttag taggaacgat cgtactgttt ttagaacgag actgtctagc tggtggccgc  25980
atcgagcatt gatggcatcc aagaccttga acttcttcgc tgaatgatat acgatgcttg  26040
aatatggatc cactgaaaat tgaggttata tgagattatt gggagctatt atgatttcac  26100
ccatgaagaa ctgcgtcagt aactcgtttc agattctcgc tatccttttc accgctttt  26160
cgttgtaatt ctatgagaaa acggtagaat ttggtgacat ttgtcgagtt aaacaattcc  26220
acgaggcaga caaacatctg aaatttgcgt tttttccaca aatgcataaa ctttcaataa  26280
aacaaaccgc ttctagggca acatcagcta aactgtgatc atgctcgtat tcggcgttta  26340
```

```
gcgagaagca taaatggtag aataaatgaa agatatcggt aggttcgcgg gaatccggat 26400
tgtagtcttt gagataatca acgcaatttt gtttcagatt cgtcatcagg tatttgtcgc 26460
atagcctgag aactgtgcac acgttttgtt ctgaaaataa atttggcatt cattgaaact 26520
acatcgatca tgaactacca tcaataacat ccggatataa accaagagaa ttgggagaaa 26580
tgacagtgat caacttgaga atatcttccg gtgactcatc aaggatattc agctgcttta 26640
tggcgccttc aaggaaaaac ttgttctcca tcaagatgcg gaaataatcc gaatttcttg 26700
caaagattgc tggatccaca aagtactttt gattaccaac aataataggc cagtttcgaa 26760
gcttgcttgt cgactcaaaa tcgacctgaa agaaaaatcg aaaaattcca atttaaaaaa 26820
cgtttgttta cgtaatcgga tccttctagg aaggtttcat gacttgttgt cggctgcatt 26880
agaatgacgt ttacggggaa atcattattt attccgaaac gtgcttgggc ttgttctgtt 26940
tgctgaaatt tgaaaggtt ctccgaatat taagcgaaaa aaacttacat taataatata 27000
aggtctcata gcgccgagta gctaaacaat taatatttga ttacagtttt ggaaagatct 27060
ttctgagctc gatcaggaag aaaaacttct tgaaactta gaagatgaaa tgtgtgctac 27120
cgtataaact ttaaaggtgc atgaataaat ttctccttt ggtcctgcga cgattaaact 27180
ttttaatcaa ttctctgggc tagttttat tcaataacta gaaatgttgt ttatttttgt 27240
tccctactta aatcatatgt tatttcttt ttcctttgtg tcttacaggc tttttagct 27300
gaagaaatag caattttccg ataaaatttg ttgctctatg taaaggcgc atgcatttat 27360
ttgagagacg ggtctcgcaa cgtgctcact cctcggcccg atttgttctt cgtttgcgcg 27420
gttttcaggc cttttaaaga tagttccgtc gttttttct caatttctgc tgaaataagg 27480
tttaattaaa tttattttca aaatcttggt aaacatttta actcatatat tcagaatttt 27540
cattcctctt tcacccagaa aaccgaattt caatattaag attaagaaca catctagaac 27600
atgcaaaaaa cacaattgct atctctctac tttcatttta aggctgattt tttgaagaaa 27660
aatcatgaaa tacgtccatt attgttgtat cccttgtttg catccaaagt tgactcgatt 27720
gatctcttaa atgtggtatt ccgttcgaaa ttcgattgat ttttagaagt taacacattc 27780
ggaatgatga taattcgtat caaaccaaaa ttgtcttctt ttcgccttt ttgtgcagtg 27840
tcagcattaa acaaaacgag aatattgaaa gttacgtggc gtttgcatct ctccaccacga 27900
tgacatcacg aaatgcagac gacaaagacc ggtgaaaaat agtgcgctga atggtgaaaa 27960
cttgcgaaga taacgtgtta cgggttgaga gagaaaacat tccgcgagac aatgcttttg 28020
gtgagaggcg cagatggttc agagaacact agagaaaacc acgcctctgt ccgctcacag 28080
ccagccccat caagcctctt cgggcatcga cgcatagaca cacatcattt tgccccaatt 28140
tcctttcatt ccgtcaagta tttcgcaact aatcgttatt gctcattaca atacacattt 28200
tacagaagtt cctcttcttc tacttggtcc gaccgcatca gataactggg agatccagtt 28260
gtgcatgttc ttgtgcccac acaaactcgc gcccatttac aattttatga tcgacaaccc 28320
tcaagaaggt aagcatttaa acgtgttggc cgtgcgtctc aaaaaattgt taaaaaacct 28380
ggcgacacgc gttttttccac aatttcattc cctagggcat tttgtatttg aagtaattct 28440
attacgcgta cgcaatcgga cgaatcctgc aggtttgttg gtagtcaatt ttatcaagtc 28500
gactgcctct tatgctttct gaaaaaagag aatgacagtt ttcgctaagt agtactaaag 28560
cgatctttta tctttggcaa aaccttgata taagcattat cacagcatat catgcagatt 28620
gatttagagt taagcatgaa atgtgcaagg ctaaaataaa ttacaaaata agtccatagt 28680
ccatttttagt aacagtatac atcagctgat agaatcacat gcgtaatgac aggtctaaaa 28740
cattatcaaa caaaagacat tacaaaaaca agaaaaatac aatataatag aacgactatt 28800
tgaaatgagc gtagttaaat tcggaacttc aatagattat catacgcgct tttaaaaaaa 28860
tgtgtgttcc cttttctccg cgtttgcccg ctacaaaccg gtgagtcgga aggcataatc 28920
gggttgaaaa aaagtatca aacactgatg gtgtcttttt tagggaggtt gtccagaaag 28980
agaaagaaac tgaagatttg cgaatcgata gcgcgtcgt ctctcgacgc cagtgaagtc 29040
aagatcggtt acaatagtgt atgcgattcc caaatccac atatcaaccg gactcgtgat 29100
atttatcatt tgtaagtact aacaagagat gtgaacgtat ttacactcaa cattagcaaa 29160
ttccagaaga agatctaaac aaaaactatc gaaatggctc tcaacgtgaa ccgcgctgtc 29220
gctgatccat tctaccgcta caagatgccc aagctgtcag caaaagtcga aggcaaagga 29280
aacggaatca aaacggtcat ttccaacatg tctgagatcg cgaaagctct cgagcgtccg 29340
ccgatgtgta tgtttatcgc cagttggctc gccattggac acaaaaataa ccattgtttt 29400
tcagacccca cgaagtactt tggctgtgag ctcggggctc aaacgaactt cgatgccaag 29460
aacgagcgtt acattgtcaa cggcgagcat gatgccaaca agctccagga tattttagat 29520
ggttttcatta aaagtttgt gctttgcaaa tcatgtgaaa accggaaac tcagttggta 29580
cgagatcatt gaattaataa tctgtctaat tttattatt cagtttgtcc gtaaaaataa 29640
catcaagagc aagtgcaagg catgtggatg ttcgttcgac attgatctca aacataagct 29700
gtctacattc atcatgaaga atcctccaaa gattgatgtc gattttgta agtatcgttt 29760
actaacattt ttcgattgaa ctattgcaaa attctgccaa aaattctatt tgcatttaa 29820
atcctttcaa ttcgattttc cgtgtgcttc cagtgcatac aaacatgcta atttttggtt 29880
tccagccaaa gccgaacaaa agaatgaaa gaagacatcg ggtgctgacg ccgccgccgc 29940
cgtggctgcc gacataatcc acaacagcga caaggcagt tcgaatgatg acgacgacga 30000
cgattgggaa cctgaaccag tcgagccgaa tggcatgctg tcggcgggaa tgggcaagct 30060
cgtgctggac aaggatcttg agaagagcga agaacagcgt ctcgacatgc ttcacacatt 30120
cttcttggaa gccaaggaag aaggtaagaa ttctgagcat tgataaaaag tattctcgtt 30180
atttcagata gaatttctga tgccaaggga caaactgctc tacgtgacga agctgagaga 30240
cttgagctga agcaaaaagc atctctcctt ctcgcgaacg tttttcttga tgagaaagta 30300
atcactgaca aacaaatcag caaacaccgc aatcttctgc ttcgcttcac gttgaatgac 30360
aagaaagctc aaagatacct gttgggagga gttgagcaag taattccaaa acatgaagcg 30420
gaacttctgt ctaaatcagc tcacatcatt aagtcattgt atgatgaaga tgtctgcgaa 30480
gaggattcgc ttattcatg gggagaagaag gttagtacca aatgagctt tgttcgaat 30540
taaagttat atttacagcc gtcgagtaag tatgtctccca aatcttttgc caagaagatt 30600
attgagaact ctcaaccagt gctcaactgg ctgaagaag cggaagaaga aaccgaagaa 30660
gagtccgacg atgagattgc ggtaagaaat atcagatttg tttttttttt ttcaatggtt 30720
ggttttcagt tcggaggaga cgtcaaggag agtgaattcc ttcgtcaaca gaaggaaag 30780
gctgctagag aagctcagca aaaatcagcc aaggctacag acggcaatgc tgctgctgca 30840
tccggagcaa atgatgaaga ggacttggat attgatgaca tttaattgta cagatgcttt 30900
tttaaaattt acctgggcta cttatgtttt ttgtgtattt cttcccatat tcgaaccaat 30960
tcaactaatt tcgaagaagc ctcagttttt ttttgctttc tccccctttc aatagtaagc 31020
atcatttcat ttctgtcttc tgtctttct gttcctacgc tgtttccct tcaccaaatc 31080
```

```
caattcattt attcgtaaag tcattactat ttgttgttaa tcgtaaacat ttgggaatat   31140
tcttgttcaa ttcagtctta tattacaaaa acacaatgtt caaaaaaaaa gaatcacttc   31200
agatgggaac ccgtcgaatt cggcggtccg atggagaata cacattgttt tttcggaaag   31260
ttagcccatt ttcaaatcat cacccagctg atttcatttg cgacgaagcg ataaattgta   31320
aagagccgaa aacctttgc tgctcggaac agtactatat gtacaataag gcttcactat    31380
tgatggattc aaaactgatg gcagcgattc tagaagcaac ttgtccgaaa acaatgaaga   31440
caatgtgttc taaatggtcg ttgaaaggat ggaaggattc ggtgtaagtt ttaaatcagt   31500
ttgataataa aatatgtttt tcttttacag atgggatgag aacaaagaag aagtgatgag   31560
aataggatgc ttggcaaaat tccgtgcttc tcgccatctt cgttatgctc tttttctcac   31620
aactggtagc aaactagtcg aatgtagtcc gttcgataaa atatggggaa tcggttagtt   31680
tccaacggat cgtcttattc ttccatcgcc catcacaatg caatcagaat cttcaaactg   31740
gaaatgtttt gaaatcattg aaatcatctt tgagctgata tggtgacgga agaaaaggac   31800
gtctgaaaat ggctgaatta ttataggaaa agatatgcaa gccgcacaat gggctccatt   31860
gagctctggc aagaatctgc tgggaaagat tttggatgga atccgagagg aattgtggga   31920
tgattcaaat tacaagttag ctctggaatc agaaaattat tattatataa aattactatt   31980
tcagagatga acgagaagaa gtggagaaac gaatgaaac tgaaagaat tatctattca    32040
ctgctataga gcacatggac ttgatgtaca aagaaagagc aacaaaaaga gtattgtaag   32100
aatcagaaaa tctgcgtaat tgtcgacaga aataacgtat tccagattgt tcgaggaaga   32160
attgttaact gatgatagat cctacatcac accagatatt cagaggctcc ttcccgactg   32220
ggcttggccg ccgatcctcg tgaaaaacga gcctattcaa ccatcgctgc ctgtaataat   32280
cgatttccct aggtacttgc cttgatcttt aatttatcag aattaacttt caaattccag   32340
atcatctcca cttcgagcag ctgaaatatc acgtaggaag agcacactctc attcgacaag   32400
cttgagtaaa aggcggtacc tcaggagcag atcgagaagt ctgtccaaaa gcccggctcg   32460
aagacgctcc agacatcttt cccgaagtgg atcccgtaca ccagctcaac ggcattccag   32520
aagatccgaa agtacatctc gaagacgttc cggacggcac tctagaagtc gatctagaag   32580
cccaccacga aaacgtccgg tacgccgatc aagaagcaga tccaggagca ggacaccaaa   32640
ccgaaattgg acaagagcac ggagcagaac aagaagtcag gctaaaagta gcagcacttt   32700
aacctggcca ctgagcccat cgagaagcag aagtaacagt aatgaaagga atttgaaaga   32760
gaagaaagac cggaaaaaga aaaaatctga gaagaaacgag aagcatcatt ctaaatccag   32820
aaaacaccgt tctaaaagat ccgaatccag agaagaacgt cacagaagac ggaaggagaa   32880
gaaaagagag aaaaagaaga acgacgtcg gagaagttcc actacttcag attaaacttt    32940
attttttgaaa actagtcata acttttaaag tcataacttt tttaaaagtc ataacactgg   33000
tttaatatca aatgtctttt caaatattct ctatttattt attcttcgta attaaactga   33060
gattaagtac tgggtatatc attaataaaa ttacgatact ttgccgaata aatcagttat   33120
aattacaatc tgtctgctgg tgaaaattgt acatgctatt ttcttgttcc tcattcttt    33180
ttcattctct gtaaggtttt gttcgttttt tggaaaattc tgagagtagc cggaaaaaaa   33240
aaaaaaaaaa actaaatacc tacagtaatg ccagagcat atgctcaata attatcaaaa    33300
attagttttc cgcggcgaga cccatcccca caaagtatg actcccttga aagtcgtaaa   33360
tgacaatttc ttgaaacaag aacatttgta tattaacgaa acacaaaatt ccgagaatgc   33420
gtattgagca gcatatttgc cgagccaaat atctcgtagc gaaaactaca ttaattctta   33480
aaaacactac tgtagcgctt gtgtcgattt acgggctctt tgaattatca ttgatttatc   33540
gatagaatat ttaaaaaata aattcatttc gaaattagag cccataaatc gacacaaaca   33600
ctacagtagc catttaaaga attactgtag ttttcgctat gagatatttt gcgcatcaaa   33660
tatgttgcgc aatacgcatt ctcagaattc tgtcttccgt aataatagac agtggcttcg   33720
ctaaaaacta agaacaaagt aaattaaagt tttttctgt tcacttcaaa ttttacacga    33780
tcttgaagca aagttcaaaa gagcatgaat caattggaaa gtgttcaatg cacccacag    33840
atatgatttc ggggcagtgt aaactacagg gcacagacat aaaaattta attgttgaag    33900
actaaaatat aaacatatga attcaagggt cataataaat gtattttttt aaataatatt   33960
tattaaatgt atgcatacaa ttaaatacaa cataattatc aaatacaaat attataattg   34020
caacctgtcg gacaacaact ttgctgaggt gtcgtgtgac agtcagaatc cttgtcacac   34080
cagctgaccg gctcagagac gatacatcgg aagttgagat gagtgactgg tggacattgc   34140
cgacgcgttg gagcacaaca ctcacgatat cgagtcatgt cgatgcagcg ctgaaactca   34200
ggaaactatg tggaatttag gtggatcacc caaccagctg ccctcaccg cactgataat    34260
ttggagtgca gtacatgtga tgggcagagc attgctgcat tgtcatcaca atcaatgaat   34320
ttgcaaaggg cctgagatt ggcttggctg aaagagttga tattatttct attgatataa    34380
taccctaaat ttacgaaaat tatgctaaat taggatttta gttataatcc tcgtcacatc   34440
tgatctctga aaacttaaaa atatcctttt tggtagtgtg gcaccaaatt cgtgctgtaa   34500
cagagaccaa aaacactact ttttcgacat ttcctctcct tgcagcgaaa aataaaattt   34560
tttgaaaatc tgtgttttct catacccgga aaaaccaac aaaaacggcc ttgttccaaa    34620
ggcggtgagt attttctattt tatgaaagtg gccgagattt ctcttttttct acgccaagta   34680
gttaattctt cgcggcaaga cccatcaatt ttctaacctc taatctcttt ttcaacatga   34740
atatccacgt catcatagaa tttgcactcg ggcttataga tttggagcct ttgaaagtat   34800
atgcaccagt ctatatgggt gttgggaaac gaataggcag tagtttttttg gaccaattgt   34860
agaatagaca gtagtaatag ggaagaatat aagaatttca taattcagat ttcaataaaa   34920
aataaattta attgagaaaa aaacggttg atattctttt gtttaagcag acaagtatgc    34980
ggaagtgaat cttgagcacc tcgtaaatca cgggaggcgt acttgtcag aagagagata    35040
agggattaag aggcgcaagc tttgccactt tgaagttaaa aaataaagaa agagacatgc   35100
aaattggtgg acaaatagcg gaaggttagc gggaggtggg aggggggaca ggtgcatgta   35160
acacaatgga ttttacaata ggaatattga aaatacgcat atgggaaatc ggaacagata   35220
tgaaggtgtc aatatttgag gtcaactgtc tggtttttcc ccgatttttg aattttttga   35280
aaaaagtgc ataattcaca gattgaaatt ggaaattgt cgagaaaaga ataggagtg     35340
ttatgaattg atggtggcaa caaaacacaa attctacatt tgtaccaaaa tgcccactaa   35400
aatgggcata ttcgcacaca ttccacacaa attgcataca tattccacaa tggggaatat   35460
tttgaatatt tagattaata aagatgaaat aattgagttt tatttgtaat taaatatttt   35520
ttctgtttat cattaattga aatgttgaa ttacttttta atagacgaat catcaaagaa    35580
cttgatccct gcattatcag gcaatcctac ataaccttc aacgttgtcg ttttaccaat    35640
tgcaacattt ctcgctactg gaacacgcat actggaatac gatgacgatt ccaattggaa   35700
gaatatattg gtgcccggtt ggaagttaac aattgaattg ttgttaagcg ataaaggata   35760
cacattgata acatccaaaa gttcagttat gtatatccat ccgtataaat cttgcgatct   35820
```

```
tccattcacc aaaagctggt cgccatcttg tataggaatg aatggagtta aggatcccgt 35880
aacagtacga gttgtgagcg tagttccact gaaaattact aaatatttag ttcaaaggtt 35940
ttctgttact acttttttggt tgcaacaact ctgagaaatt ttagttttca ccaaaatttt 36000
tcgattttgt acagaattgc acaatatatt ttggaatagc aagaaattgt tcagtgaatg 36060
tcaaatctga caaaaaaaaa ttttttttaaa aggtgcctat caattttaa aaatgttcta 36120
atattttgtt ggaaagtttc aataatttca ctacatttac tatttctttt ttaggcctat 36180
tttgggtatt caaaatatta accacacgac cttcaataca ggaaaactgt caaatttttt 36240
ttaaattatg aacaattaac tcactttaca ttttgtcctc cattccttgt agttaatata 36300
agacttccca acgcttcttg agaactattc gaaataatat aaatcttcga atttcttcct 36360
actatatatc ctagtgtgtt gctcgttgca acgtctagag tatccaatat aaacccacta 36420
gaagctgata taagaaaaa taatagaaat atattttca ttttttccaa atgactaaat 36480
gaccaacttc aagacatttt atatgcttaa aatcacgtca cagaactata atcatgttga 36540
tttttgatag aaaatgataa gaaatgcgac caaaatgtgt attttctccg tttgtcctct 36600
gaatgagtca aattcacgta aaacttggca tttgtcacag tgtgtcagac acaaggcaca 36660
tatgtattta ccggactttt caagactttta ttattattga gatcaaacca gattacagaa 36720
gacgggagaa aggtaccaac aaatatcaga atattgcaaa aaaaaattaa aaatttcaaa 36780
acgcaaactt caaactagga gagctaattc aaactttgaa atcatgttcc ataaccggta 36840
gcatttgttc ggtgacttgt ttgacagccc attgaaggaa gagaagtact cccgacaggc 36900
tgaaacatat gaaatagtcc aggccttcca ttagagaatg tgatgtttga aggaagaaca 36960
atgggacgta gagtactccg aatagagcag taagtccatt gatgagctga aacagtaaat 37020
aatcgaaaag ttagtaaata tgttcaagga atggaagtaa accggaatta tccgagtatg 37080
ggcgtttat agttttttct cttttttttga cttcgttttt catcctatta aatatcatc 37140
ggttttttcg agttccagaa aaaatattta aaaatcatc cgaaatccga acacaaatc 37200
cgaaggctac tccaaggtaa gttaaccta ctcggcaaat ctctcgtcct ggagcgcgga 37260
cggggcgcga ctagatcacg ggttcgcgct ccagtcaccc tttttttcgc gcttcttacg 37320
cgccacgtcc gcgcttcagg aggagcgatt tgcggagtac tttttatgca ttcagactcg 37380
tacttaaaaa ttaatcgatt tttttaaaaa gtgtcataaa cttttttctac gtctttttct 37440
gacacaatgt tgaaccgtac tagattgttg taaacacggt cttcaaattt gatttttcgcg 37500
aaaaaatttg aataattttt ttctaacttt tttcttttta aaatcttacc acacttagca 37560
aataaccatg aagcacaact tcataagtgg atcctatttt tcgtttgaag aggcaaaata 37620
ctgaaaacaa aagagctgat atggagcaag acacgtggat ccagaagagt atacgcacaa 37680
tcacactatc cccttcgatt ttgacgcgt acagaattct ggattttttt tttgaacttt 37740
aatgattgc gattcaaaag aaaacgtagc ttaatctcca gttaagctg attttcattg 37800
caaaatgtat ttagaaaaaa ctcacgctaa taaggcggag agtattgtct gtagaaccgc 37860
catgattact gtagatgcat agagtgagaa tgagcacata taagcgctcg gctgtttttg 37920
aacgacaatc gaattggccg ccatcatctc attcttcgac ctcccgtttt atttctgaaa 37980
atatatgaca ctttttaaat gaattgacag aaatctgtac ctaactacat tttaacttgt 38040
aggagtggtt caaatgattc ataaagggaa tacaatttct gaatgatcaa agaagaaaga 38100
aaaaaaatat tggtgaatgt ataattttt aggggtaaag taaataaata aacacaaggc 38160
cgaagattag caagagtttg gggataaccc ccgtgaagaa aaatatgaaa aaaaatggtt 38220
tgaaagaatt aaaaaaatcc tttcaaattt gagattcaaa ttttgttcat ctgttctgtt 38280
cgaacattga gcagaagaag cttttaccaa taaatccaaa atttgttaag agaatatagt 38340
ttaaggatat cacccagttc aaaatagtag ttcaaaaact cgagtcttaa ttttttttcagt 38400
attcgaattt ttacagtaca ttgatcgttt cgttatttga tcgctttttg ataaaacaaa 38460
aaatagataa tgaagctgcc aagtttaaaa aaatcggggc taaggctaat ggagcataca 38520
cggtatatca ctacctggat attagttttta gacttcatca gatatttagt cagaaaagta 38580
cgtcaagaag tcggatacga aatgtatataaa tttcttaaaa cttaaaactt cgagatatcc 38640
agactgtggc tctcaagctt cagtgcttgg agaaatagtt taatagtcag aatatgtttt 38700
aaatttctta attttttctga agaagtcgta aaagtataaa tgttgctaga tcaaacactc 38760
tagaaaacct tcaccacttg agaatactcc agtctcaaat tttccctcga cgcggaagtg 38820
tagaagggcg cgagattcag aagtaggtga aaattagacg gaaaactctc tcaaaattga 38880
aatcaatgaa taggacaact gagacaatgt gcaggtgtat gtgtatgcac atggcaccca 38940
cgtacacgca tacatcttat gttagagaag tacgtgtgct ccgctcatca tgtcttctcc 39000
ttctcctaca tctacatttt ttgctccgtg agccacgccg ggaaaaacga cgacgacgac 39060
ggcgacgggg gacgactact cgactctaat tggccctaaa cgcaagtaaa ttttttaggcc 39120
atgtatgttt gcgagagttg agagccccac cgccacgagg agaagtgggg gaagattccg 39180
aagagattcc ccctcctcct tctgatcacc tcgtctttcc ttttttgttc catttccgtg 39240
aaaaagctgt ggaagggagg agaagaactt accggctaaa tggaaaaaaa ggaactctaa 39300
cttattctga ctctacgaa ataggaagcc tacttgtcaa ttagaccgcc ctcgcacaga 39360
tttcttttttt tttgtagata caaatataaa aactaactgc gtgtgatgca gcagatatct 39420
tgaattggaa agtgtcagtg ctcagaggga atagccaatc attgacagaa atttgactac 39480
ttcagaagga atcaactaga acatttgacg cctgaaacct aacaagaaaa atctataatt 39540
tggagatccc tagattgatg ccaactttat taaaactaa gtataccttat atatatacga 39600
tttttttaaa aataaacctg attgtctgaa tttctacaag attgcgacca aattttccgt 39660
atttccaaaa tctaatatta gggggtttcta ctaaaattca acgagaactc ttaacattat 39720
ggttatttta acacatggtt caccgccggc tcaaacttca ttcttagtcc tctgattttt 39780
ggtaaatcga cgcctacgtc tcaacaatta gtttgtgcag aaaataagta aaaagagttg 39840
tgctccatct tgcacacata cacatcgcct gtaatgaaga ggttcggagt cagatgacta 39900
ggcgtagaaa tgtgcgaaat tcacggataa cagagatttt tgatgtttca tcagacttac 39960
acgttttgga agtatgaatt gggtctagac aacggagtgg cagatgttcg gaaaattttg 40020
cagaaaagag aacctaagag cgttgatggt ttggtgacta agaacttaa aagaaaattg 40080
gtcattgaaa atttttaaaat tttaaattttt gcttcagtt catctttctc tattaacaaa 40140
aattattttg tagcttttct caatttcagg caattaaaac atttcaattt attcttctat 40200
tatggaagtt tatctctaat tgaaactctc caattttgat caaagaacaa acgttctcgt 40260
tgtttgaaaa aaaaaacagt tctttttga aactcgcgcg caaattatta accaatcatc 40320
ctcgtttgcg cgcaaaattg tagaaaaaat catttaaatt tatcaaaaat agtttaccat 40380
tctgatgagt ttttcatata caaaaatgcc ctgcaattg ttgttttctc tgaaatagca 40440
cataataatt gaactctacc cacataaagt tcgttctgaa aaacaccttta caattattgt 40500
gattgagagc caccccaaga gggattagaa aaacgatgt aatctgtata ccttcgagat 40560
```

-continued

```
                  tcgtttattt ccttgtataa ccaatagcag gaaaattaca gcttttcta   40620
       agtaagcggt gaaactagag agattctata gaatatgggc gttaataatt gtatgttaaa   40680
       gttttagaat aacacaagtc cagagtaagg gcaagaaaag taatgagcaa cggaaaccag   40740
       catgcaagac acccgaattc cggttctctt ctgaaactaa aagttgcgtg tactaaacct   40800
       taaaccagca gctggctagt ctcaagaaat aatagaaaaa aggaaggaat gaagatatgg   40860
       gaataataca aattgaaaat gttgtgtgag ctccgaataa ttttcaatat caaaaattta   40920
       tgaattgtgt ggacgctgt gtgtgcgtgt gcgtatgcgt cggcaagaaa aagaagcgac   40980
       cgaataagaa aatggttgat tcagtgaaca aaaaaagaga gaaagatatc caaacaaaat   41040
       tattcaaaac tattatcaat cggtaggtat tgctctagag cacaccttc tggacactca   41100
       gcagacatgc gtagagaggg attatgtggt acatatagtg gatggaggaa cagatattta   41160
       taaatactta tggaaagag gatgaagata ggatgaggta gatgaattga gaagatttta   41220
       aaatgataat ggatattgaa tttgaataag gagattctaa attatccgaa gaacacaaac   41280
       tatatcaaga ctacaaaata atctagacga gtcccagttt tgcaaggtaa ggattaatct   41340
       taaaaggatc ttttaaatat ttatttcaat gctcctataa attttaaaaa gtaggtgcat   41400
       tctaatatgt acagtgatta ggagatatgt gacgttacgt gaggtctcga taagtacgg   41460
       tattcgagct aaattcaaa cattgtcaag gtagattcgg tacacagcca ccataaatgt   41520
       tccactaaaa atgtgttgtc cttctccttt ggaacacaaa tctagctgct gaacttttc   41580
       acttcactac atgtcaatgg gattgatatg catctaggac atttttttgg ttatcaatag   41640
       tccgcatagc ttgcgtaacc aatacaaccg attgtccaaa aaaatttgaa cactacaaaa   41700
       cgtatttatt attcggatac ccgttgcatt tcaatacaca aagttgatact tgctgcccct   41760
       cggggctctc agacactcat tgactgaaaa cagacgattg ctcgtcgtcg tagtctgaag   41820
       gctcggagag ctgaggaaga tatgaggaca taatgaattg atgtgtgaga atgagaaaat   41880
       gaaaaaggaa aaatgagaaa aaaaagatga tgaagaatgt acaaatgaat aatcaagtag   41940
       caatgacgag aaaagaacca ggtccttttg gcaggcaatt ttcgaaattt tcagatcaaa   42000
       tttgtcgcca ttgcttctgg attaataatg gatgacgctt tgacaatgct gctcaataca   42060
       agtgcaaaca gattggtttg ggatggcgta tagaaataga gccggtgaga cgatgtgatg   42120
       aagttctgag agacgagatg tgatcgaggc gtttgtagtc gaggcaaacc gaggccgcat   42180
       atgggggttcc gataggcaat cggagaccag tgtccatctg aaagagataa aagttattcg   42240
       agttgtgaat gttgcaagga aaattaaagg tacagtagga acaatcggca ctttttcgg   42300
       gaggacgcca 42300
       tctaaaaact gtggaagcac gtggctttgg tagcttgatg tcacagaagt tgattccata   42360
       agaattacat tagaaagctt gcgacgctaa atggataaat ctggtaacgg cttcctaata   42420
       gcaagttaag tttttcaca ataaattttt cagaattgaa tagatgcatt ttataactta   42480
       cacatcgagt gggcacgttg gtggacaaga caagcccga t                        42521
```

<210> SEQ ID NO 24
<211> LENGTH: 4434
<212> TYPE: DNA
<213> ORGANISM: Unknown
<220> FEATURE:
<223> OTHER INFORMATION: Description of Unknown Organism:Unknown
<400> SEQUENCE: 24

```
       gccgccctcg ccaccgctcc cggccgccgc gctccggtac acacaggatc cctgctgggc   60
       accaacagct ccaccatggg gctggcctgg ggactaggcg tcctgttcct gatgcatgtg   120
       tgtggcacca accgcattcc agagtctggc ggagacaaca gcgtgtttga catctttgaa   180
       ctcaccgggg ccgcccgcaa ggggtctggg cgccgactgg tgaagggccc cgacccttcc   240
       agcccagctt tccgcatcga ggatgccaac ctgatccccc ctgtgcctga tgacaagttc   300
       caagacctgg tggatgctgt gcggacagaa aagggtttcc tccttctggc atccctgagg   360
       cagatgaaga agacccgggg cacgctgctg gccctggagc ggaaagacca ctctgccag   420
       gtcttcagcg tggtgtccaa tgcaaggcg gcaccctgg acctcagcct gaccgtccaa   480
       ggaaagcagc acgtggtgtc tgtggaagaa gctctcctgg caaccggcca gtggaagagc   540
       atcaccctgt ttgtgcagga agacagggcc cagctgtaca tcgactgtga aaagatggag   600
       aatgctgagt tggacgtccc catccaaagc gtcttcacca gagacctggc cagcatcgcc   660
       agactccgca tcgcaaaggg gggcgtcaat gacaatttcc aggggggtgct gcagaatgtg   720
       aggtttgtct ttggaaccac accagaagac atcctcagga caaaggctg ctccagctct   780
       accagtgtcc tcctcaccct tgacaaccac gtggtgaatg gtccagccc tgccatccgc   840
       actaactaca ttggccacaa gacaaaggac ttgcaagcca tctgcggcat ctcctgtgat   900
       gagctgtcca gcatggtcct ggaactcagg ggcctgcgca ccattgtgac cacgctgcag   960
       gacagcatcc gcaaagtgac tgaagagaac aaaagagttgg ccaatgagct gaggcggcct   1020
       cccctatgct atcacaacg agttcagtac agaaataacg aggaatgac tgttgatagc   1080
       tgcactgagt gtcactgtca gaactcagtt accatctgca aaaaggtgtc ctgcccatc   1140
       atgccctgct ccaatgccac agttcctgat ggagaatgct gtcctgctg ttggccagc   1200
       gactctgcgg acgatggctg gtctccatgg tccgagtgga cctcctgttc tacgagctgt   1260
       ggcaatgaa ttcagcagcg cggccgctcc tgcgatagcc tcaacaaccg atgtgaggc   1320
       tcctcggtcc agacacggac ctgccacatt caggagtgtg acaagagatt taaacaggat   1380
       ggtggctgga gccactggtc ccgtggtca tcttgttctg tgacatgtgg tgatggtgtg   1440
       atcacaagga tccggctctg caactctccc agcccccaga tgaacgggaa accctgtgaa   1500
       ggcgaagcgc gggagaccaa agctgcaag aaagacgcct gccccatcaa tggaggctgg   1560
       ggtccttggt caccatggga catctgttct gtcacctgtg gaggagggt acagaaacgt   1620
       agtcgtctct gcaacaaccc cacaccccag tttggaggca aggactcgt tggtgatgta   1680
       acagaaaacc agatctgcaa caagcaggac tgtccaattg atggatgcct gtccaatccc   1740
       tgctttgccg gcgtgaagtg tactagctac cctgatggca gctggaaatg tggtgcttgt   1800
       cccctggtt acagtggaaa tggcatccag tgcacagttg ttgatgagtg caaagaagtg   1860
       cctgatgcct gcttcaacca caatggagag caccggtgtg agaacacgga ccccgcta   1920
       aactgcctgc cctgccccc acgcttcacc ggctcacagc ccttcggcca gggtgtcgaa   1980
       catgccacgg ccaacaaaca ggtgtgcaag cccgtaacc cctgcacgga tgggacccac   2040
       gactgcaaca agaacgccaa gtgcaactac ctgggccact atagcgaccc catgtaccgc   2100
```

-continued

```
tgcgagtgca agcctggcta cgctggcaat ggcatcatct gcggggagga cacagacctg 2160
gatggctggc ccaatgagaa cctggtgtgc gtggccaatg cgacttacca ctgcaaaaag 2220
gataattgcc ccaaccttcc caactcaggg caggaagact atgacaagga tggaattggt 2280
gatgcctgtg atgatgacga tgacaatgat aaaattccag atgacaagga caactgtcca 2340
ttccattaca acccagctca gtatgactat gacagagatg atgtgggaga ccgctgtgac 2400
aactgtccct acaaccacaa cccagatcag gcagacacag acaacaatgg ggaaggagac 2460
gcctgtgctg cagacattga tggagacggt atcctcaatg aacgggacaa ctgccagtac 2520
gtctacaatg tggaccagag agacactgat atggatgggg ttggagatca gtgtgacaat 2580
tgccccttgg aacacaatcc ggatcagctg gactctgact cagaccgcat tggagatacc 2640
tgtgacaaca atcaggatat tgatgaagat ggccaccaga acaatctgga caactgtccc 2700
tatgtgccca atgccaacca ggctgaccat gacaaagatg gcaagggaga tgcctgtgac 2760
cacgatgatg acaacgatgg cattcctgat gacaaggaca actgcagact cgtgcccaat 2820
cccgaccaga aggactctga cggcgatggt cgaggtgatg cctgcaaaga tgattttgac 2880
catgacagtg tgccagacat cgatgacatc tgtcctgaga atgttgacat cagtgagacc 2940
gatttccgcc gattccagat gattcctctg gaccccaaag ggacatccca aaatgaccct 3000
aactgggttg tacgccatca gggtaaagaa ctcgtccaga ctgtcaactg tgatcctgga 3060
ctcgctgtag gttatgatga gtttaatgct gtggacttca gtggcaccct cttcatcaac 3120
accgaaaggg acgatgacta tgctggattt gtctttggct accagtccag cagccgcttt 3180
tatgttgtga tgtggaagca agtcacccag tcctactggg acaccaaccc cacgagggct 3240
cagggatact cgggcctttc tgtgaaagtt gtaaactcca ccacagggcc tggcgagcac 3300
ctgcggaacg ccctgtgca cacaggaaac acccctggcc aggtgcgcac cctgtggcat 3360
gaccctcgtc acataggctg gaaagatttc accgcctaca gatgcgtct cagccacagg 3420
ccaaagacgg gtttcattag agtggtgatg tatgaaggga agaaaatcat ggctgactca 3480
ggacccatct atgataaaac ctatgctggt ggtagactag ggttgtttgt cttctctcaa 3540
gaaatggtgt tcttctctga cctgaaatac gaatgtagag atccctaatc atcaaattgt 3600
tgattgaaag actgatcata aaccaatgct ggtattgcac cttctggaac tatgggcttg 3660
agaaaacccc caggatcact tctccttggc ttccttcttt tctgtgcttg catcagtgtg 3720
gactcctaga acgtgcgacc tgcctcaaga aaatgcagtt ttcaaaaaca gactcagcat 3780
tcagcctcca atgaataaga catcttccaa gcatataaaa aattgctttg gttttccttt 3840
gaaaaagcat ctacttgctt cagttgggaa ggtgcccatt ccactctgcc tttgtcacag 3900
agcagggtgc tattgtgagg ccatctctga gcagtggact caaaagcatt tcaggcatg 3960
tcagagaagg gaggactcac tagaattagc aaacaaaacc ccctgacat cctccttcag 4020
gaacacgggg agcagaggcc aaagcactaa ggggagggcg cataccgag acgattgtat 4080
gaagaaaata tggaggaact gttacatgtt cggtactaag tcattttcag gggattgaaa 4140
gactattgct ggatttcatg atgctgactg gcgttagctg attaacccat gtaaataggc 4200
acttaaatag aagcaggaaa gggagacaaa gactggcttc tggacttcct ccctgatccc 4260
caccctttact catcacctgc agtggccaga attagggaat cagaatcgaa accagtgtaa 4320
ggcagtgctg gctgccattg cctggtcaca ttgaaattgg tggcttcatt ctagatgtag 4380
cttgtgcaga tgtagcagga aaataggaaa acctaccatc tcagtgagca ccag        4434
```

<210> SEQ ID NO 25
<211> LENGTH: 2837
<212> TYPE: DNA
<213> ORGANISM: Unknown
<220> FEATURE:
<223> OTHER INFORMATION: Description of Unknown Organism:Unknown

<400> SEQUENCE: 25

```
agagagccag tccgatgtct gcagcctccc tggccaggcc tctcctctcc tgccgcagct 60
agtcccctc aggacagaca gagtactggc gtcggtcacc attcacttgc aaacacacca 120
ggtcacgtga agaaacttcc tggtgacact caggctgtag ctgtgcactc ttcaaccacg 180
aggttggttt tctcctaagt gtcacaggtg gagacaagat gctctgggca ctggccctgc 240
tggctctggg catagggcca agagcttctg ctggtgacca cgtcaaggac acttcatttg 300
accttttcag catcagcaac attaaccgga agaccatcgg tgccaagcag ttccgagggc 360
ctgaccccgg ggtgcccgcc taccgttttg tacggtttga ctacatcccc ccagtgaaca 420
cagatgatct caacaggatt gtcaagcttg caaggacagg gagggcttc ttcctcacag 480
cccaactgaa gcaggaccgc aagtctcggg gaacgctcct ggtgttggaa ggccccggca 540
cctcccagag gcagtttgag attgtgtcca atgcccagg gacactttg gacctcaact 600
actgggtaga aggcaatcag catacccaact tcctggagga tgtgggcctg gctgactccc 660
agtggaagaa tgtgactgtg caggtggcca gtgacaccta tagcctgtat gtggctgcg 720
atcttatcga cagtgtcacc ctgaagaaac cattctatga gcagctagaa gtagacagga 780
gcaggatgta cgtggccaaa ggtgcatctc gagagagtca cttcaggggc ttgctgcaga 840
atgtccatct cgtgtttgca gattctgtgg aagatatctt aagcaagaaa agctgtcaac 900
acagccaggg agctgaagtc aacaccatca gtgaacatac agagactctc catctgagcc 960
ctcacatcac cacagatctc gtggtccagg gtgtggagaa ggcacaggag gtgtgtacgc 1020
actcctgcga ggagttgagc aacatgatga tgagctctc tggactgcac gtcatggtga 1080
accagctgag caagaacctg agagagtgt ctagtgataa ccagttcctt ttggagctca 1140
ttggggccc tctgaagaca agaaacatgt cagcctgtgt gcaggagggc cgaatcttg 1200
cagaaaatga aaccggtt gtggatagtt taccacatg cccctgcaag aaattaaa 1260
cagtctgcca tcagatcacc tgctcacctg caacttgtgc caacccatct tttgtggaag 1320
gcgagtgctg tccatcctgt tcacactctg cagacagtga tgagggctgg tctccgtggg 1380
cagagtggac cgagtgttct gtcacctgtg gctctgggac ccagcagaga ggccggtctt 1440
gtgatgtcac cagcaacacc tgcctgggcc cctccatcca gacaaggaca tgcacgctgg 1500
gcaaatgtga tacgagaatc cgtcagaatg gaggctggag tcactggtca ccctggtctt 1560
catgctccgt gacttgtgga gttggcaatg tcaccgcat acgtctctgc aactcaccag 1620
tgccccagat gggtggcaag aactgcaagg gcagcggccg ggaaaccaaa ccctgtcagc 1680
gtgatccgtg cccaattgat ggccgctgga gcccctggtc cccttggtca gcctgcacag 1740
```

-continued

```
ttacctgtgc tggagggatc cgtgagcgct cacgtgtttg caacagccct gagccccagt 1800
atggagggaa ggactgtgtc ggggatgtga cagaacacca aatgtgcaac aagagaagct 1860
gccctattga tgggtgctta tccaacccgt gttttcctgg agccaagtgc aacagcttcc 1920
ctgatgggtc ctggtcctgt ggctcctgcc cagtgggctt tctgggcaat ggtacccact 1980
gtgaggacct ggatgagtgt gctgtggtca cagatatttg cttctcaact aacaaagctc 2040
cccgctgtgt caacaccaac ccgggcttcc actgcctgcc ttgtccacca cgctacaagg 2100
ggaaccaacc cttcggtgtt ggcctggagg atgctaggac agaaaaacaa gtgtgtgagc 2160
cagagaatcc atgtaaggac aagactcaca gctgccacaa gaatgcagag tgcatctacc 2220
tgggccactt tagtgacccc atgtacaagt gtgagtgcca gattggctac gcaggtgatg 2280
ggctcatctg cggggaggac tcagacctgg atggctggcc caacaacaac ctggtgtgtg 2340
ctactaatgc cacctaccac tgcatcaagg acaactgccc caaactgcca aattccgggc 2400
aggaggattt tgataaggat ggaatcggag atgcttgtga cgaggacgat gacaatgacg 2460
gtgtgagcga tgagaaggac aattgccagc ttctcttcaa tccccgtcaa ttagactatg 2520
acaaggatga ggttggagac cgctgtgaca actgcccta tgtgcacaac ccagcacaga 2580
tcgacacaga caacaatggc gaggggatg cctgctctgt ggacattgac ggagacgatg 2640
ttttcaatga gcgagacaat tgtccatatg tctacaacac tgaccagaga gatacggatg 2700
gtgatggcgt gggtgaccac tgtgacaatt gtcctctgat gcacaaccca gatcagatcg 2760
atcaggacaa tgatctcgtt ggagaccagt gtgacaacaa tgaggacata gatgatgacg 2820
gccaccagaa caaccaa                                                 2837
```

<210> SEQ ID NO 26
<211> LENGTH: 4108
<212> TYPE: DNA
<213> ORGANISM: Unknown
<220> FEATURE:
<223> OTHER INFORMATION: Description of Unknown Organism:Unknown

<400> SEQUENCE: 26

```
agagagccag tccgatgtct gcagcctccc tggccaggcc tctcctctcc tgccgcagct 60
agtcccccct aggacagaca gagtactggc gtcggtcacc attcacttgc aaacacacca 120
ggtcacgtga agaaacttcc tggtgacact caggctgtag tgtgcactc ttcaaccacg 180
aggttggttt tctcctaagt gtcacaggtg gagacaagat gctctgggca ctggccctgc 240
tggctctggg catagggcca agagcttctg ctggtgacca cgtcaaggac acttcatttg 300
acctttcag catcagcaac attaaccgga agaccatcgg tgccaagcag ttccgagggc 360
ctgaccccgg ggtgcccgcc taccgttttg tacggtttga ctacatcccc ccagtgaaca 420
cagatgatct caacaggatt gtcaagcttg caaggagaaa ggagggcttc ttcctcacag 480
cccaactgaa gcaggaccgc aagtctcggg gaacgctcct ggtgttggaa ggccccggca 540
cctcccagag gcagtttgag attgtgtcca atggcccagg ggacactttg gacctcaact 600
actgggtaga aggcaatcag cataccaact tcctgaggac tgtgggcctg gctgactcc 660
agtggaagaa tgtgactgtg caggtggcca gtgacaccta tagcctgtat gtgggctgcg 720
atcttatcga cagtgtcacc ctggaagaac cattctatga gcagctagaa gtagacagga 780
gcaggatgta cgtggccaaa ggtgcatctc gagagagtca cttcaggggc ttgctgcaga 840
atgtccatct cgtgttttgca gattctgtgg aagatatctt aagcaagaaa agctgtcaac 900
acagccaggg agctgaagtc aacaccatca gtgaacatac agagactctc catctgagcc 960
ctcacatcac cacagatctc gtggtccagg gtgtggagaa ggcacaggag gtgtgtacgc 1020
actcctgcga ggagttgagc aacatgatga atgagctctc tggactgcac gtcatggtga 1080
accagctgag caagaacctg agagagtgt ctagtgataa ccagttcctt ttggagctca 1140
ttgggggccc tctgaagaca agaaacatgt cagcctgtgt gcaggagggc cgaatctttg 1200
cagaaaatga aacctgggtt gtggatagtt gtaccacatg cacctgcaag aaatttaaaa 1260
cagtctgcca tcagatcacc tgctcacctg caacttgtgc caacccatct tttgtggaag 1320
gcgagtgctg tccatcctgt tcacactctg cagacagtga tgagggctgg tctccgtggg 1380
cagagtggac cgagtgttct gtcacctgtg gctctgggca ccagagaggc cggtcttctt 1440
gtgatgtcac cagcaacacc tgcctgggcc cctccattca gacaaggaca tgcagcctgt 1500
gcaaatgtga tacgagaatc cgtcagaatg gaggctggag tcactggtca ccctggtctt 1560
catgctccgt gacttgtgga gttggcaatg tcacccgcat acgtctctgc aactcaccag 1620
tgccccagat gggtggcaag aactgcaagg gcagcgcacg ggaaaccaaa ccctgtcagg 1680
gtgatccgtg cccaattgat ggccgctgga gccctggtc cccttggtca gcctgcacag 1740
ttacctgtgc tggagggatc cgtgagcgct cacgtgttg caacagccct gagccccagt 1800
atggagggaa ggactgtgtc ggggatgtga cagaacacca aatgtgcaac aagagaagct 1860
gccctattga tgggtgctta tccaacccgt gttttcctgg agccaagtgc aacagcttcc 1920
ctgatgggtc ctggtcctgt ggctcctgcc cagtgggctt tctgggcaat ggtacccact 1980
gtgaggacct ggatgagtgt gctgtggtca cagatatttg cttctcaact aacaaagctc 2040
cccgctgtgt caacaccaac ccgggcttcc actgcctgcc ttgtccacca cgctacaagg 2100
ggaaccaacc cttcggtgtt ggcctggagg atgctaggac agaaaaacaa gtgtgtgagc 2160
cagagaatcc atgtaaggac aagactcaca gctgccacaa gaatgcagag tgcatctacc 2220
tgggccactt tagtgacccc atgtacaagt gtgagtgcca gattggctac gcaggtgatg 2280
ggctcatctg cggggaggac tcagacctgg atggctggcc caacaacaac ctggtgtgtg 2340
ctactaatgc cacctaccac tgcatcaagg acaactgccc caaactgcca aattccgggc 2400
aggaggattt tgataaggat ggaatcggag atgcttgtga cgaggacgat gacaatgacg 2460
gtgtgagcga tgagaaggac aattgccagc ttctcttcaa tccccgtcaa ttagactatg 2520
acaaggatga ggttggagac cgctgtgaca actgcccta tgtgcacaac ccagcacaga 2580
tcgacacaga caacaatggc gaggggatg cctgctctgt ggacattgac ggagacgatg 2640
ttttcaatga gcgagacaat tgtccatatg tctacaacac tgaccagaga gatacggatg 2700
gtgatggcgt gggtgaccac tgtgacaatt gtcctctgat gcacaaccca gatcagatcg 2760
atcaggacaa tgatctcgtt ggagaccagt gtgacaacaa tgaggacata gatgatgacg 2820
gccaccagaa caaccaagac aactgcccat acatctccaa ctccaaccag gctgaccatg 2880
acaacgacgg caagggcgat gcctgcgact ctgatgatga caatgatggt gttccagatg 2940
```

```
acagggacaa ctgtcggctt gtgttcaacc cagaccagga agactcggac ggtgacggcc 3000
gaggtgacat ttgtaaagat gactttgaca atgataatgt cccagatatt gatgatgtgt 3060
gccctgagaa caatgccatc actgagacag acttcagaaa cttccagatg gtccctctgg 3120
atcccaaggg gaccacacaa attgatccca actgggtact tcgtcaccaa ggcaaagagc 3180
tggtgcagac agcaaactca gaccctggca tcgctgtagg tttcgacgag tttgggtctg 3240
tggacttcag tggcactttc tatgtcaaca ctgaccggga tgatgactac gctggctttg 3300
tctttggcta tcagtcaagc agccgcttct atgtggtgat gtggaagcag gtgacccaga 3360
cctactggga agacaagccc agtcgggctt acggctactc tggtgtgtca ctcaaagtgg 3420
taaactccac gactggtact ggcgagcacc tgaggaatgc cctgtggcac acgggaaaca 3480
cagaaggcca ggtccggact ctatggcatg accccaaaaa cattggctgg aaagactaca 3540
ctgcctacag gtggcacctg attcacaggc ctaagacagg ctacatgaga gtcttagtgc 3600
atgaaggaaa gcaagtcatg gctgactcag gaccaattta tgaccaaacc tacgctggtg 3660
gacggctggg cctgtttgtc ttctcccaag agatggtcta tttctcggac ctcaagtatg 3720
agtgcagaga tgcctagaga gcagggctcc agctccagca atgtgctgca acaccccttt 3780
cttagacaca tcagtccatc ttggcacttg tggcttttct gtcatttggc atttcctgtt 3840
tcttgacctt aactgagtgg atctacacct ccttcatcag caccaagtcc aagtgtcttc 3900
aaaggagaaa catcaattgc actccaagag cttccagcct gctgctggaa aacatttgga 3960
tgagatatga ggctcaccgt ggagcgaaga ccgagcattc cgctgtgttg ccttttcttg 4020
tttgtttaaa agaatgacg tttacatgta aatgtaatta cttgcagtat ttatgtgtat 4080
atggagtcga agggagcttt agagcaca                                    4108
```

<210> SEQ ID NO 27
<211> LENGTH: 820
<212> TYPE: DNA
<213> ORGANISM: Unknown
<220> FEATURE:
<223> OTHER INFORMATION: Description of Unknown Organism:Unknown

<400> SEQUENCE: 27

```
tcgaccagag gagggaggc cagttcctct cccaagggtg ccacacaccc ctccctgttc 60
atcaccagac aggcccttcc ttcttagcca tatgctaacc ttctcctccc tgggaaattt 120
cctctgcagg agccaaagca gatgggagct ggagttgctg gagctcctgg tctgtatgca 180
gagcaggcat ccaggaaagg agaagagagt gtgacaatcc agcacctcag aatggagggg 240
cctcgtgttc agggcggaaa gtacagacgc aggcttgctg agggcctctg gacacaggct 300
ggaccagatg ctgtggatgt cgaccccctgc actgactatt ggataaagac ttctttcaac 360
taagagaaga tgcaaatcag cacactttttt tctttgttct gccagcttcc aggcctaaga 420
ctaggttttg ctgtctacag ccaactattc tattagttac aaaactcaat cattttattc 480
agcaactgga tgttgactgt taactagaag ctctgtccta cttcagcac tttggatcat 540
caaaaaaata aagtaaaata gaaaactgag aaaactcaat ccatgaccag ggagaactta 600
caggatgtta gagacaaaac aagcagacac ctgaaacaat caacgcccaa taaaacaaag 660
taggatgaaa attctcttag ttctttgata acaatttgtt cactcataga aacattatta 720
attggtaggg taagcagaca ctctgaaaca atgagaaaaa tactaaaaat tgacttgagt 780
tatttcaaat tgcctcattg acctgttata tcataactct              820
```

<210> SEQ ID NO 28
<211> LENGTH: 2397
<212> TYPE: DNA
<213> ORGANISM: Unknown
<220> FEATURE:
<223> OTHER INFORMATION: Description of Unknown Organism:Unknown

<400> SEQUENCE: 28

```
tttttttttt catcctactt tgttttattg ggcgttgatt gttacaggtc ccagcctgta 60
gacatctttt actccaattt cctgaataga tagcttttatt ccttcaaggt aatatagtgc 120
ggtggcttct ggctgagatg tttgctgttg ttttcttcat cttgtctttg atgacttgtc 180
agcctggggt aactgcacag gagaaggtga accagagagt aagacgggca gctacacccg 240
cagcagttac ctgccagctg agcaactggt cagagtggac agattgcttt ccgtgccagg 300
acaaaaagta ccgacaccgg agcctcttgc agccaaacag tttgggggga accatctgca 360
gtggtgacat ctgggatcaa gccagctgct ccagttctac aacttgtgta aggcaagcac 420
agtgtggaca ggatttccag tgtaaggaga caggtcgctg cctgaaacgc caccttgtgt 480
gtaatggaga ccaggactgc cttgatggct ctgatgagga cgactgtgaa gatgtcaggg 540
ccattgacga agactgcagc cagtatgaac caattccaga atcacagaag gcagccttgg 600
ggtacaatat cctgacccag gaagatgctc agagtgtgta cgatgccagt tattatgcgg 660
gccagtgtga gacggtatac aatgggggaat ggagggagct tcgatatgac tccacctgtg 720
aacgtctcta ctatgggagat gatgagaaat actttcggaa accctacaac tttctgaagt 780
accactttga agccctggca gatactgaaa tctcctcaga gttttatgat aatgcaaatg 840
accttctttc caaagttaaa aagacaagt ctgactcatt tggagtgacc atcggcatag 900
gcccagccgg cagcccttta ttggtgggtg taggtgtatc ccactcacaa gacacttcat 960
tcttgaacga attaaacaag tataatgaga agaaattcat tttcacaaga atcttcacaa 1020
aggtgcagac tgcacatttt aagatgagga aggatgacat tatgctggat gaaggaatgc 1080
tgcagtcatt aatggagctt ccagatcagt acaattatgg catgtatgcc aagttcatca 1140
atgactatgg cacccattac atcacatctg gatccatggg tgcatttat gaatatatcc 1200
tggtgattga caaagcaaaa atggaatccc ttggtattac cagcagagat atcacgacat 1260
gttttggagg ctccttgggc attcaatatg aagacaaaat aaatgttggt ggaggtttat 1320
caggagacca ttgtaaaaaa tttggaggtg gcaaaactga aagggccagg aaggccatgg 1380
```

```
ctgtggaaga cattatttct cgggtgcgag gtggcagttc tggctggagc ggtggcttgg 1440
cacagaacag gagcaccatt acataccgtt cctggggggag gtcattaaag tataatcctg 1500
ttgttatcga tttttgagatg cagcctatcc acgaggtgct gcggcacaca agcctgggc 1560
ctctggaggc caagcgccag aacctgcgcc gcgccttgca ccagtatctg atggaattca 1620
atgcctgccg atgtgggcct tgcttcaaca atgggtgcc catcctcgag ggcaccagct 1680
gcaggtgcca gtgccgcctg ggtagcttgg gtgctgcctg tgagcaaaca cagacagaag 1740
gagccaaagc agatgggagc tggagttgct ggagctcctg gtctgtatgc agagcaggca 1800
tccaggaaag gagaagagag tgtgacaatc cagcacctca gaatgagggg gcctcgtgtc 1860
cagggcggaa agtacagacg caggcttgct gagggcctct ggacacaggc tggaccagat 1920
gctgtggatg tcgacccctg cactgactat tggataaaga cttcttcaa ctaagagaag 1980
atgcaaatca gcacactttt ttctttgttc tgccagcttc caggcctaag actaggtttt 2040
gctgtctaca gccaactatt ctattagtta caaaactcaa tcattttatt cagcaactgg 2100
atgttgactg ttaactagaa gctctgtcct acttacagca ctttggatca tcaaaaaaat 2160
aaagtaaaat agaaaactga gaaaactcaa tccatgacca gggagaactt acaggatgtt 2220
agagacaaaa caagcagaca cctgaaacaa tcaacgccca ataaacaaa gtaggatgaa 2280
aattctctta gttctttgat aacaatttgt tcactcatag aaacattatt aattggtagg 2340
gtaagcagac actctgaaac aatgagaaaa atactaaaaa ttgacttgag ttatttc    2397
```

<210> SEQ ID NO 29
<211> LENGTH: 4100
<212> TYPE: DNA
<213> ORGANISM: Unknown
<220> FEATURE:
<223> OTHER INFORMATION: Description of Unknown Organism:Unknown

<400> SEQUENCE: 29

```
ggatccccc gctccgctac catcttcatc gacctcaccc aggacgacga ctgagctccc 60
tcttcctcgc cgcggactgg ggcgaccctg ttgctgctgc ggccgccgcc gctcctgccc 120
ccacttcggc tcccgctcct gctcctgctc ccggccccac tcctgttcct gttcctgttc 180
ctgttcctgt tcccggtcct gctccggctc ccggccccgc acccacctcc gctcctgctg 240
cgggtctcca ggcccagaca aaataaaaaa agatatattt tttcagtccg tctctcccgc 300
ccggtgtctt ctatggctga gggagtctgg ctctcggggc tctcgggtcg gctgggcggc 360
tcggctggtt ggctggctgg cgagatggac cgctccggcg cgcagcgtcc gcggctgctg 420
tgatgggtgg gcggagcgcg gaccggggat tatatacacg atgtgcatcc ataattgatg 480
ttgtttgaga aaaacaaagt cataaagtgg cactcagaca gcactttggc ctggcgtccg 540
gccaccatct gagtgcccaa ccgggcccgg cggttacatc accccccacat ggaccatcac 600
ggcccattag caccaattgg ccagagtgtc gggagccacc gctaattgca gtaacgcgcg 660
gctgccagac tgcaatttac cgcgcgatac tgcagtttac tgcagccgcg gtaaactgca 720
gtacgcggcg gccgcaggaa atctactgta gtatttggcg gcggcgcgg gtactgcaac 780
tgtagtaaac tgtagctgca gtagagttac tgcagccgca tcgggccggt gtggccgcca 840
gggtaactgc acccgcagta aatttactgc agccggactt tgtgcgctgt ggagaccgcg 900
ccgaactggg acccccccga ctccccccg actcccccc gactccccc 960
ccgactcccc cccgactccc cccgactc ccccgggacg cgtcgcgcgc 1020
tcgatgcgcc ccatcgcgcc ccgttccgct tcgccacgct ccagttgccc cgcccccggc 1080
acgtggcacg tatttccccc ccgtaaatca agaggggatta tgcggatgtc tagtttatgt 1140
ctcaatttcc tctttccgga gataaaagcc gggaccccg cgccgaaaaa ggatacacca 1200
gccgcgatgt cgccgctcgt ggcggtgctg gtgttttttt cggcggcgct ggggggttcct 1260
ggccccggc tcgcgggaaa cccccgtggg ctcgatgcca tcttcgaggc cccggtcacg 1320
cccgcgcccc ccactcgcca tcctcggcgc gaggagctgg agtgggacga tgaggatcac 1380
ccgctgctgg acctcgagcc gcccgtggga tcacgctgcc atccctacat cgcgtactcg 1440
ctgccgccgg acatgaacgc cgtcacgagc gtggtcgtga agccctactg ctcgccgccg 1500
gaggtcatcc tgtgggcgtc tggcaccgcc tacctggtca accccttgt cgccatccag 1560
gccctggccg tcggagagcc cttaaatgag gcggccctca aggagctcgg agaggtggcc 1620
gtgcacaagg actccctgcc gccgctgcgc tataatggag ggccccccgc cgagtaagag 1680
accctgcggc ctgccgcccg gggtgcgcct cgtcgtgcct gccgcgcgcc ccgcttctgc 1740
ctctaacgcc gccaccgccg ctgcagcagc agcccccgcc ggggccgggg ccggggcctc 1800
gaagccggcc cgacccccg ccgccgcccg gcccgcgaag ggcacgcccg cggcgtcggc 1860
ggcaacaaca gccacggggg ccgacgcctc cgccccggcc cccgacccg gggcgcccac 1920
gtgggacgcc ttcgccgccg agttcgacgt ggcccccctcg tggcgcgcgc tgctggagcc 1980
cgagatcgcc aagccgtacg cgcgcctgct gctggccgga taccgcggcc gctgcctgac 2040
cgaggaggtg ctgcccgcgc gcgaggacgt gttcgcctgg acgcgcctca cggcgcccga 2100
ggacgtcaag gtggtcatca tcggccagga cccgtaccac gggcgggccc aggcccacgg 2160
gctggccttc agcgtccggc gcggggtgcc gatcccccg agcctggcca acatcttcgc 2220
ggcggtccgg gcgacgtacc cgacgctgcc cgcgcccgcc cacgcgctgcc tggaggcctg 2280
ggcgcgccgc ggggtgctgc tgctgaacac gacgctgacc gtgcggcgcg gggtcccccgg 2340
ctcccacgcc ccgctcggct gggcgcggct cgtgcgcgcc gtcgtccagc ggctctgcga 2400
gacccgcccc aagctggtgt tcatgtctg gggcgcccac gctcaaaagg cctgcgcgcc 2460
ggacccgcgc cgccacaagg tgctcacctt cagccatccg tcgccgctgg cccgcacgcc 2520
cttcaggacc tgcccgcact ttggagaggc gaaccgctac ctcgtccaga cgggccgggc 2580
ccccgtcgac tggagcgtgg actgagtcgg gcgtgcgcgc acccgccgg cggaggacga 2640
ggaggggga gggggtggg atgacggag gagagcggat gatgagcccc gcgctcgccg 2700
gcgcccggc cagcgcgctg ccggtcctgg cggtgctgcg cgagtgggga tgggccgtgg 2760
aggaggtcga gccctccggg ccgtccccac aggacgcgga cgcgcccggg gagagcgcac 2820
cccctcccgg gagggggtg cgcgggagcg aagacgcgaga ggggcccgtg gaagacgcg 2880
aggaggggaa ggcgacggag aaggaggaga cggaagacga ggaagacggg gggacgaag 2940
ggacgacgac ggcggcgcg ggcccgcgcc gggcgcagca cgtgagttt gacacgctgt 3000
ttatggtcgc gtccgtggac gagctcgggc gccggcggct gacggacacg atccgccggg 3060
```

```
acctggccgc ggccctggcc ggcctccccg tcgcctgcac caagacgtcc gcgtttgcgc 3120
gcggcgcgcg cggcccgcgc ggcgcccccg ggcgcggcca taaaagcctg cagatgttta 3180
tcctgtgccg cagagcccac gcggcgcgcg tacgcgatca gctccggtcc gcggtgcgcg 3240
cccgacgccc acgcgagccc cgccgccgcc cgacgagccg acgggcgcgg ccggccgcgc 3300
cggtgttcat ccacgagttc atcacccccg agccggtgcg gctgcaccgg gacaacgtgt 3360
ttgcggcgcc atgagcacct tcggacgcgc gtccgtggcc acggtcgatg actaccaccg 3420
gttcctgcag gccaacgaga cggccgcccg gcgcctggcc gcggcctccc gccgcgtctc 3480
caccggcggg ggcgagacgc gggcccccgg gtcctcgccg ggccccacg acgatgaggc 3540
gccctgcgc gccggcggcc tgggcaccgg ccgcgggcgc tcgcgccagc gcggcgcgac 3600
cgagccggac cccgtctacg ccaccgtcgt ccagcctacc caccaccacc accagcagca 3660
ccaccaccgc tctcagcatc cgcagcagca gcaacaacag cagcgggccc acgccgccg 3720
cggcagcgtg cacgcctcgg cgacggccgc ggacggaccc gagtcgtgcg cggccgcacc 3780
cccgcgccgc cgcggcagcg tgcacgcctc ggcgacggcc gccccggcgg tccagctgcc 3840
ccggccccgg caacggagca tcaacgcctc gacgacggcc gccccgacgc cccagctgcc 3900
gagaccccgc cagcgcagcg tcaacgcctc ggcccgcgcc gccgtcccct cgacggccac 3960
cctcccgcgc ccccggaccc cgtcccgggg ccggcgcgcg cccccgcct catgctgtta 4020
tcgcgatcaa taaagggcga gcgcccacgg accagacaaa agacacaacc ggttcggtct 4080
ctctgtccgc gcacgcgcgg                                           4100
```

<210> SEQ ID NO 30
<211> LENGTH: 38734
<212> TYPE: DNA
<213> ORGANISM: Unknown
<220> FEATURE:
<223> OTHER INFORMATION: Description of Unknown Organism:Unknown

<400> SEQUENCE: 30

```
gatcctcgtg accgggtaca ccgacgcctc ctggacgccg ctgttcgcca tcgcgggcgg 60
ggtcgtcacc gacatcgggt cgatgctctc gcacagttcc atcgtggccc gcgagttcca 120
cgtcccgtcg gtggtgaaca ccaaggacgc cacccagcgc atcaacaccg gcgacctgat 180
cgtggtggac ggcgacgcgg gcacggtcga ggtcgtcgag agcgcggca ccagcccgca 240
gggcccggcc ggggccgccg ggacccgg cggagccacc accgactgaa gccggccacc 300
gccgcaacac cggaccacga ccgcccccgc gaggggcgga ccacacccca gacgggagac 360
gacccgatga tccccaacca gtggtatccc atcgtcgagg cgcaggaggt gggcaacgac 420
aaaccgctcg gtgtgcgccg catgggccag gacctcgtg tctggccgga catcgacggc 480
aacctcgtct gccagggcgc ccgctgcccg cacaagggcg ccaacctcgg cgacgccgc 540
atgaagggca acaccatcga atgcccgtac cacggcttcc gctacggagc cgacggtgcc 600
tgccgggtga tcccggcgat gggctccgag gcccgcatcc ccggctcgct gcgggtaccc 660
acctaccggg tccgggagca gttcggcctg gtgtggatgt ggtggggcga cgacgcccgc 720
acggccgacc tgccgccggt ggcggccccg gccgaggtga cggacaaccg gaagctgtac 780
gccaccaagc gctgaccccg cccggtgcac tacacccgtt acatcgagag cctgctcgag 840
ttctaccacg tgacctacgt gcaccgggac cactggttca actacatcga ctacctgctc 900
ctgtacggca cccgagcaa gttcggcctc gacggccgca gcgtacct ggccgccacc 960
cggatcacca accaccgggt ggagacggaa gcggagggc agaccatccg ctactccttc 1020
gaccactgcc aggaggacga ccccaccaaac accacccact acgtcatcac gttcaccttc 1080
ccgtgcatgg tgcacgtgca gaccgagcag ttcgagacca cctcctggct ggtgcccatc 1140
gacgaccaga acaccgagca catcctgcgc tggtacgagt acgaacaggt caagcccgtc 1200
ctgaggttcg aaccgctgcg ccgtctgctg ccctgggcgt ccctctacat ggagaagtgg 1260
gtgcaggacc ccaggacgt ccgcatcatg gaacaccagg aacccaagat cagcgccggc 1320
ggcgtgaaca agttcatccc gtcgacgag atgaacgcca gtacatctc gatgcgcgcc 1380
aagctgatcg cggacgcctc ggccgcgccc tcgtcaccgg cgcgggcgg ggagcccgag 1440
ccggaagcgg cgggcgggg cggatcagcg gccgtgcca cgggcaacgg caggggagcg 1500
gccggcggac gacgcggcac caagcccaag gaggacgccg ccgcgcccc gtagacccga 1560
agacggggga cggacaagag agacgagag tgagagatgt acggcggata cgacgcgtcg 1620
accggcccca aggccctggt gacgccttc aacaccgtcg ccgtggccgg cgccgtgtgg 1680
ttcctgttcg gcggcgcgga caccgtgcg gactggttcg gcaccgactt cgacggaggcg 1740
gtgaccctgc gccgggtcct gctggcgacc ctgtcggtgc tctacctgct gcgcttcatc 1800
gccacgaact tcgtgatgct ccagcgcaag atggagtggt cggagtcggc caccatcggg 1860
atctgggtcc tggtgatcca cggcacgatg gcgtacttcg gcggcaccaa cgacgccggc 1920
gtgagcgcgt tcacctggct gggcgtcgtg ctgtacctcc tcgggtccta cctgaacacg 1980
gggtcggagt accagccgcaa actctggaag aagcgcccgg agaacaaggg caagctctac 2040
accgaaggcc tgttcaagca ctcgatgcac atcaactact cggtgacgc cgtgctcttc 2100
tccgggttcg cgctggtcac gggcaccccg tgggccttcg ccatcccccct gatcatggtc 2160
tgcatgttcg tcttcctgaa catcccctg ctcgacaagt acctcgtcga gcgatacgc 2220
gaggccttcg acgagtacgc gtccccggacg gcgaagttgc tccctacgg gtactgaccc 2280
cgcccgtcac gcgcgtacgc cggcctcccc gggcgagggg ggccgccgta ccggtggca 2340
accacagatc ccacagatcc ccacagatcc ccacagagcc cctccacaga ccccctccag 2400
agatccacag atcccctcca cagatccgag acgaggcacg tatgaccgga gacattccct 2460
tcggagaggc cgaggcgtcc ctgaccgcca ggtgctctg gcggcggcg ccgggcgcgg 2520
ccgagcgtt cgcccggctg acctccgacg agggcgccgt cgacgacttc ggcttcgacc 2580
cggagctgac cgacgactac ctgctccccg ccctgcgcct gctgtacgag aagtacttcc 2640
gggtcgacct ggagggcactg gagaacgtgc cggccgaggg gggcgcactc ctggtcgcca 2700
accactccgg caccctgccg ctcgacgccc tgatgctcca gtgatgctcca cacgaccatc 2760
acagcacgca ccgcaggctc cggctgctcg ccgccgacct tgccttcgac ctccccgtcg 2820
tccgtgacct cgcccgcaag gccggccacg tacgcgcctg ccccgagaac gcgctgcggt 2880
tgctcggctc cggcgaactg gtcggcgtga tgccggaggg ctacaagggg ctcggcaagc 2940
ccttcgagga gcgctaccgg ctgcagcgct tcggccgggg aggcttcgcg gcggtggcac 3000
```

-continued

```
tgcggtcgcg gcgcccatg gtgccgtgct cgatcgtcgg cgccgaggag atctacccga 3060
tgatcggctc ggcccccacc ctggccggga tgctgaagct gccgtacttc ccgatcaccc 3120
cgaccttccc gctgctgggc gcgctgggcc tgatcccgat gccgaccaag tggaccatcc 3180
gcttcggtgc cccgatccac acggacggct tccccgagga ccgcgggag gaccgctgg 3240
tggtcgagaa gctcgccggc gaggtgaagg acaccatcca gcacacgctc aacgagatgt 3300
tggagggccg cggctcccg ttcgtctgag ggccgcggct cccggttcgc ccagggcgg 3360
cggctcccgg ttcgcccgag gaccgtccct ctcgtccggg gccccgcctc agccccccgc 3420
cgacgatccc cggcggcaga tgctgcgaac gctggcgaag gccagaacgg cgaggccgac 3480
gagcgtgacg ccgccgccga ccagctccgc ggacagatgc atgggatctc cctcaggggg 3540
acgacggacg gtgatggtca tatagccatg cgaacccgc cgtccgcccg atccgcagcc 3600
gcaccgcccc gcgaattcac ccgtagagca gaccggtgcg gccgaggagg ggtggcgatt 3660
gggtggtcgc gcgttcgaac gcttacgatc ctctgttgtg tccaaactga ccgacgtgcc 3720
caagcggatc ctcatcgggc gcgcactgcc cagcgaccgg ctgggtgaaa cgctcctgcc 3780
gaagcgcatc gcgcttcccg tgttcgcgtc cgaccgctg tcctccgtgg cgtacgcgcc 3840
cggcgaggtg ctgctcgtcc tgtccatcgc gggcgtgtcg gcctaccact tcagcccgtg 3900
gatcgcggtc gcggtcgtgg tcctgatgtt caccgtggtc gcctcctacc ggcagaacgt 3960
gcacgcctac ccgagccgcg gcggcgacta cgaggtggcc accaccaacc tcgggcccaa 4020
ggccggtctg accgtcgcca gcgccctgct ggtcgactac gtcctgaccg tcgcggtctc 4080
catctcctcc ggcatcgaga acctgggctc cgcgatcccc ttcgtcgtcg agcacaaggt 4140
cctgtgcgcg gtcgccgtga tcctgctgct cacgctgatg aacctgcgcg gggtcaggga 4200
gtcgggcacc ctgttcgcga ttccgacgta cgtcttcctg gcgggcgtct tcatcatgat 4260
cgtgtggggg gcgttccgcg gactggtcct ggacgacacc atgcgtgccc cgaccgcgga 4320
ctacgagatc aagccggagc acggcggcct ggccggcttc gcgctgatct tcctcctcct 4380
gcgcgccttc tcctccggct gtgccgcgct caccggtgtc gaggcgatct ccaacggcgt 4440
cccggcctc gcaagccca agtccaagaa cgcggggaac accctcgcga tgatgggtct 4500
gctggccgtc accatgttct gcggcatcat cgcgctggcc gccgcgaccg acgtgcggat 4560
gtcggagaac ccggccaccg acctcttcca caacggcgtc gcggtcggcg cggactacgt 4620
ccagcacccg gtgatctcgc aggtcgccga ggcggtcttc ggcgagggca gcttcctgtt 4680
catcgtgctg gccgcagcca ccgcgctggt cctcttcctc gcgggcgtct ccgcgtacaa 4740
cggcttcccg ctgctcggct cgatcctcgc ccaggaccgc tacctgccgc gccagctgca 4800
caccgcggc gaccgcctgg cctcctccaa cggcatcgtg ctcctcgccg gagccgccat 4860
gctcctggtc gtcgtctacg gcgccgactc gacccggctg atccagctct acatcgtcgg 4920
cgtcttcgtg tccttcacgc tcagccagat cggcatcgcg cgccactgga accgcaacct 4980
ggccgcgag cgggaccagt ccaagcgacg ccacatgatg cgctcccgcg cgatcaacgc 5040
cttcggcgcc ttcttccacg gcctcgtcct ggtggtggtc ctggcgacca agttcacgca 5100
cggcgcctgg gtcgcgctgc tcggcatgtg catcttcttc gcgaccatga cggcgatccg 5160
caagcactac gaccgggtcg ccgaggagat cgcggccccg gaggacccg aggaggcaca 5220
gagcgacgac atggtgcgcc cctcacgcgt tcactcggtg gtcctgatct ccaagatcca 5280
ccgccccacg ctccgcgccc tcgcctacgc caagctgatg cgctccgaca gcctggaggc 5340
gctcagcgtc aacgtcgacc cggccgagac gaaggcgctg cgcgaggagt gggagcgccg 5400
cggcatcgcc gtaccgctga aggtcctgga ctcgccgtac cgcagatca cccggccgct 5460
catcgagtac gtcaagagcc tgcgcaagga gtccccgcgc gacgcggtct cggtgatcat 5520
ccccgagtac gtggtcggcc actggtacga gcacctgctg cacaaccaga gcgcctgcg 5580
cctcaagggc cggctgctgt tcacgcccgg cgtcatggtc acgtcggtcc cgtaccagct 5640
ggagtcctcc gaggccgcca ggcgccgggc gcgcaagccg caggactgga gcgcgccggg 5700
tgcggtgcgg cgcggaccgg cccaccacca ccaggaccgt gaccgtacga ggactcccgg 5760
ctcgtccacg tagactggac ggctgttgtc cctgtcatcc ccccgttctc tggagtcacc 5820
ccgccatgca ggcagaaccg aagaagtcgc aggcggaaca gcgagcggtc gcggagccgg 5880
tctcggagcc ggtctcgctg gtgggcgagg agtacgaggt cgaggtcggc cccgtcgccc 5940
acggcggcca ctgcatcgcc cgcacgtccg agggccaggt gctgttcgtc cggcacacgc 6000
tgcccggcga gcgggtcgtg gcccgggtga cggaggcgca ggagggtgcc cgcttcctgc 6060
gggcggacgc ggtcgagatc ctggaccct ccaaggaccg catcgaagcc cctgccct 6120
tcgccggccc cggccgctgc ggcggctgcg actggcagca cgccaagccg ggcgcccagc 6180
gacgcctgaa gggcgaggtg gtcgccgagc agttgccagg cctggccggt ctcaccccgg 6240
aggaggccgg ctgggacggc acggtgatgc cggccgaggg cgacaagctg ccggccggcc 6300
aggtcccgtc gtggcgcacg cgcgtgcagt tcgcggtgga cgccgacggt cgcgccggtc 6360
tgcgccgcca ccgctcccac gagatcgagc cgatcgacca ctgcatgatc gcggcggagg 6420
gcgtcagcga actgggcatc gagccgcgtg actggcccgg catggcgacg gtcgaggcga 6480
tcgcgcgac gggctcccag gaccgccagg tcatcctgac ccgcgcccc ggcgcccgcc 6540
tccccatcgt cgaactggac cgcccggtct cggtcatgcg cgtcgggggag aaggacggcg 6600
gcgtccaccg cgtccacggc cgcccccttcg tccgcgagcg cgccgacgac cgcacctacc 6660
ggtcggctc cggcggcttc tggcaggtcc acccgaaggc cgccgacacc ctggtcaccg 6720
cggtcatgca gggcctgctg ccccgcaagg gcgacatggc cctggacctc tactgctccg 6780
tcggcctctt cgccggcgcc ctggccgacc gcgtcgggga ccagggagcg gtcctcggca 6840
tcgagtccgg caagcgcgcc gtcgaggacg cccgccacaa cctgccgccg ttcgaccgcg 6900
tccgcatcga gcagggcaag gtcgagtccg tcctgcccg caccggcatc gacgaggtcg 6960
acctcatcgt cctcgacccg cccgcgccg gcgccggccg caagacggtc cagcacctct 7020
cgaccctggg cgcccgcagg atcgcctacg tggcctgcga cccggccgcg ctggcccggg 7080
acctggggta cttccaggac ggggggtacc gggtgcggac gctgcgggtg ttcgatctgt 7140
tcccgatgac tgcgcacgtt gagtgcgtgg cgattttgga gcccgccgca aaggggctct 7200
gacctgcatt tttcttgct ggatcaggag cggcctgttg cgctcgacct gttctccaaa 7260
gcgcacgacg tagagcttgc ggaccgctcg tgaaagccgc ctgacctggc gttgcacgag 7320
cggtccgcgc atgtcggcgt ggtcggccct tctcctggcg cgaagggaaa ccgaaggtct 7380
tgacgctcgg gtgacgctat ttctgaaggg tcgtcaccga ctggggaggc agggccctgc 7440
ctctcgcgcc cgatgaagca ggttctctct gctccaggta atcgtcgagg gtgcctgac 7500
ggatcaggta gacggtcagg gaccgcaggg tgcagggcgt cgacgcccag gtcgaggatc 7560
atcagggcgc tgtcattggt gatggcgaag gcgccgatca caccgtcgac ggaacaggtt 7620
gcgttcagga gtctgtgcgg gcgccgcacc ggcacggtct ggaagctcgg ctccgaccgc 7680
agctcgccac cagtccgaga ggagccgata ctgtccggtg ccgggtgacc cttcgtgcaa 7740
```

```
gcgttgctgc ccccgctcgg cagaccgggg cagcaacgct tgcacgatcg gccggtactc 7800
aacgggatcg tgtggagttt cggaccggaa cggcttggca ggacgtgccc gagcggtacg 7860
gctcctgggc cacattgcac acccgcttcc gtcgatgggt gaaaggcggc acctttcagt 7920
gaaagggggt tccgccccc cccgggacct tgcgcccacc gtccgcgacc ggctgatgaa 7980
ccggctccgc gctcccgcca ccaacctgac ccgacgtgag accgaagtcc tctcaccggt 8040
cgccgacgga ctgtccgacc aggccatcgg cgcacgcctc cacttgaccg aaggcaccgt 8100
cgatatcacc tggcctgcat ctatgccaac ctcggaaccg actcgcgcac cgccgctgtg 8160
gccactgtca ccgccatcga cgacctcggg ctcatccgcc gctgaacagt atgtggtggg 8220
cggtgtttcc gttctccacg acttcagcgg cgtccggagt tgtggtgctg gctgggcttg 8280
gtgcccgctc ctctgaaccc atgtgaacgc ccacgccag ttcgagccgg acacgcccc 8340
cggacctggc ctccgccgcg gccagaatgc ccggcccctg cacctggtct gcctacctgt 8400
acaggcgagg gcggtccctc ggagccactg cctgtaactc cgaggggccg ccccttggccg 8460
actcggcggt caccgcggac gcggtgcggt caggaggcac cgtctgcgtc atcaggcgcg 8520
gctcggccga gcgagttatt ccggcacccg tgggaccaga aatgtcagcc ctgcgtgacc 8580
gcttcgaaga ccgtgacgcg gttgtcgtcg gagagcgagt gggtggggtc ggcgtgcgcg 8640
gcgcggaatg cctccgacga ggtgtaggcg gtgaatgcgg cgtcgtcctc gaagttgagg 8700
acggccaggt agccgtgtgc gcccttgcgg ggacgcagca gccgtgcgtt gcgcagcccc 8760
ggcacgttgg aaagggtggc gcgcatgctg gcggtgcagt tgttctcgaa cgcgccctgg 8820
gcggcgcgg cgacggtgaa ctcggtgacg gcggtgctca tttctgtctt ctctcggttg 8880
ttggtgtgat gtcggtggct gtcccgcccg gccggggccc gcacggcgat ggcgatgatg 8940
tgcaccgcgt gtccgatcga gttccgttgc ggggtgcggt tacagggctg gagttgggct 9000
cgggtccgcg gtcggctgag ggagcctgcc tgtgcggcgg gcccagatt cgaacgcgat 9060
agtcatgaac gggggtacgg cggccagcag ggcgaagatc gttgtccggc ccagccgcca 9120
cttcagccgg atcgcgacca ggacggtcag ggacacgtag acgatgaagg cggcgccgtg 9180
gagggtgccg aagatccgta cgccgagttc ggtggtttcg gggatgtact tgaggtacat 9240
cccggccagc agacctgccc acgtgcacgc ttcgatgatc gcgatccagg tgaacgcgcg 9300
cagcagacgg ctggtgccgg tttcggcagc ccgtgcgcc ggcgcgtcgg cggaaggcgg 9360
ttcggaggtg ggcgtggagg tgtctgcgg ggtgcctggg cgtgcgggcc acagggcgcg 9420
gttgccgagc aggcggacga tggcgggac caggagcggg cggatgagga aggtgtccag 9480
caggatgccg caggccatgg cgaagccgaa ctggaacagt tcgcggatcg gctgggtcat 9540
caggacggcg aaggtcgccg cgaggatgag gcccgcggag gagatgacgc cgccggtgcg 9600
tgtcagtgcg gcggtgatcg ccttcgctgg gggctgggtg cgcagttcct gcttgaaccg 9660
gctcatgatg aagatgttgt agtcgacgcc gagcgcgacg aggaagacga agatgtacgc 9720
ggtgacgcgg ttgccgatgc cgtcgtcacc gaggacgtc acggtgaaga aggtggtggc 9780
gcccagggtg gccaggaacg acaggagcag ggtcgcgacc aggtagagcg gggcaaggag 9840
cgagcggagc agcaggacga ggaccacggt gacgatggct aggaccagca gcacgatgag 9900
ggtcgtgtcg cggtcgaggg cggagcggat gtcggcgttc tgcgcggtct cgccgccgat 9960
gagcaccgtg gcgtcctgga cgccggcggc ctgggctgcg gattgtgtgg cctgcttgag 10020
gggaccgatc gcgtcgagtg ccttggagct gtaggggtcg aggtcgagga tgacgtcgta 10080
gaagacggtc ttgccgtcct tgcccatgcg ggggtctgcg acacggctga cgtgatcggc 10140
gtcggtgagc gcggtggcga tgtcggcggg tgcgggctg gagcgcaggt tgtcctggga 10200
atggacgacg acggtactgg gggcgatctc gccgggcccg aattcctccc gaatgaggtg 10260
ctgtccgtgc tccgactcgg tggcggcgcg gaagccgctg agggtgttga agctctcctg 10320
gtagccgagc agtcccgcgc tcagtaccac caggagtgcg atcacgccg aggccaccttt 10380
gacgggggcc cgtgcgacca gggcggcgat gcggtgccag atgcctgcgc gcgactgcg 10440
ttcggcgacg ttgtccacgc ccccggcca gaagacgctc ctgcccagca ggaggaccag 10500
ggcggggatg aaggtgaacg ccaccagcgc catgacggcc acgcccagag cgaggtacgg 10560
tccgaagccg tgaagtgccg ggggagacgg ccacgagcagg gcaaacatgc cgagcacgat 10620
ggtcgaggcg ctggcgagga cggactcgg ggtgcggcgc acggcggcct gcatcgcgcg 10680
ggcgcggtct ggctcgtcga gcagggtctc gcggtagcgg ggtgatga tcagcgcgta 10740
gtccgtgccc accccgaaca gcagcacggt catgatcgag gcggtctggg agctgaccgt 10800
gatgactccg gcgtccgcga gaatcgcgcc gagagtctcc gccacgcgca tagccacgcc 10860
cacggcaaga agcggcacga gcgccatcag gggcgagcgg tagatcgcca gcaggatgat 10920
caggacgagc acgacggtgg ccagcagcag gactttgtca ccgccgctga agaccttcac 10980
ggtgtcggtg gcgatcccgg cggggccggt caccgcgacg tcgcgcgggcc cggcccggtc 11040
ggacgcgagg gcacgcacct cgtcgaccgc attctggaag gactcgtccg aggggctgcc 11100
ctccatgggc acgatgacca gctgagcacc gcggtcctgc gagaccaact cggccgcagc 11160
gtcgggacgg gtcaccgtgg agaccacgct cacgacatgg tcgggtcggc tggttccgga 11220
aagggccgag gtgatgcgg cgaccgattg cgtggcgctc ttcgcggcgt cggtgccctt 11280
gccgcggacc acgatgatcg ccggcgtcgc gtcctggccc ggaagctggg cgcggacgag 11340
atcacgggcc ttcatggagt ccgaggcggc gggcggcagg ttggcggagg cgttgtcctc 11400
gacggattcc aggggcgggg cgacccggc gaggaggcc gcgatcagga cccgaaaggc 11460
caccaccacg gcggcgcgct tcttcgatcc caggagacat cgcagcagag cggggagtt 11520
catcggttgc atcgggcagc cttcggcagg aagtacggac agaacttagc gacagggtgt 11580
ctctaagttg cgtcaagcta acacgccccc tcggcctctc gggcgtgggg gtaggttggc 11640
gggagacggc acagcgtccg aggtgaagcg gagaaaatgc caagattga acgcggccga agccggcagc 11700
gtccgggagc accgggcgca cggctcgcg cagctcgcg ggagtcctg 11760
gaagagggcg gtgccgaagc cctcacagcc ggagcggttg ccgcgcagc cgggatcgcc 11820
cgcaacagca tctaccgcta cttcaactcc atcgacgacc tgctcgaact cgtcgtcacc 11880
cgcgaattcc ccgcctggat cgacgcagtg gagcaggcca tcgcggccga gaccacaccc 11940
gccgcccagg ctgccgccta cgtcagggcc aacctcgaac aggcagctcg cggcacccac 12000
ggctggcggg ccgcgctcac gcgcgactcg ctctcccgt cggcgcggga gcggttgagg 12060
aatctgcaca tctcgctaca cgaggcgctc gcccgggtcg tgcgcgaact ggggcagcca 12120
cagcccgagc tgaccgtggc ggtggtccaa gcagtcgtcg atgcgtgcat ccgcagaatc 12180
gaccaaggcg acgatctgac aaccgtgtc gacttcgcgg gcggagcgac gcgtcgactg 12240
ctcgcggatg acgacttgcc acatcacccg tgacgcaccc cgtccaggcg gctcgcaggc 12300
ccgtcgacag cgaagccccg gcagaacgag ccggatcttg agccgcaccg gagcgtgacg 12360
cagaccgctg gtggctcatg cctcgtctca tccgatcttg ccaccggggcg gccgaccggt 12420
cagtgcccga cgcccatcga ttacgacgtc cacgacccga accagcgcgt tcagtgcgtt 12480
```

```
gacgttcgtg gtgcgctcat tggtcacccg gcctctgggg gtcaccagcg cttttagggc 12540
acgagactcg acggtggcgc gtgataccag gcaggcatca tgaccttatg gcgatgacac 12600
tccggcttcc cgacgacctg gacacgaagc ttacggagcg ggctcgtggg gagggttgca 12660
gcaagcagga actttgccatc ggggccattc gtgatgcccg ggaccgggcc gagctgaagg 12720
tcgatgacgt tctggccggt ctgatggaca gcgatgcgga gattctggac tacctgaagt 12780
gagcggcgtg cgctacctcc agatcgacga gatcctggcc atcgtgcgca cggtcaacgg 12840
tgccgagcac agcgtgcgtg acatgggcct ccttgtgtcg gcgatcgaac ggccccggac 12900
gaacgtcttc ggagccgagc tgtatcccac cctgcacgag aagccgcggc actactgcac 12960
tccgtcgccc gcaatcacgc gctgatcgac ggcaacaagc gcaccgcctg gttcgccatg 13020
cgcgtcttcc tgcggttcaa cggcgcagc gccagtaccg tcccgcccca cgggcgccgg 13080
cccgacggac ccgaggcccg tcacgcgctg ctcaccagca gccctctcct cagcagcgca 13140
ctgggaccgg cgctgctgat cgccctgtcc gccctggggg ttctcgccct ggacacggcg 13200
ttgtgggtct cggtggtcag tgaggtggcg gcgccggccc ggtggggctt cgtgggcggg 13260
ctgcgtgtcg gcgccgggcg tctgggagcc ctgatcgccg gcgtactcaa cgccgtgatc 13320
ggtcttggcg tggtcgctgt caaactcatc gccgggcact gagagggcct gtggtggtgt 13380
tcgcggagcg catacggtgg cagaccggtc ggaatcctcg gcgccgcggc cggagcggtc 13440
ccggcaccc ggcgaacagc cgcacgtccc cgtccggtcg ggtcaggtcc gagccgtcag 13500
atccaggtca gtcgccacag gcgcagaagc ccggtgccgt ccaccgcgta ctggccgccg 13560
cccacgtcct ccccggacac cacgaagtcc ttggcctgcc acagcgggac gacgggcacg 13620
tcgcgggcga cgatccgctg aagggcttcg aggtcggctt cggcgtcgct ccggtcggcg 13680
aagcgctgac tgctcgtgat cagccggtcg gcggccatgc tgccgtaccc cgtcgccatg 13740
gtgccgtccg tgccgacgag aggaccgccg aaggtgtcgg gatcgggggta gtcggcgacc 13800
cagccgacgg cgtaggcgtc gagctctccc tcggcccagc tcttctggaa ttcgtcccat 13860
tcatatcctc tgagggtcac cttgaacagc ccgtcggcct ctagttgctt tttcacctcc 13920
gcagcctcct cgtgggctga tccgcgtccc gccgcgtaac cgtaggtgaa agacagcggg 13980
atttcctcac cggcctcgac gaggaggcgg cgtgccttt cggcgtcctt gtgagggtag 14040
ttgtcgaaga aggaggtggt gtggcccgtg atgctcgtcg ggatgaggga gtagagcggg 14100
tccacggttc cgtcgtagac gtcgtaggaa atccggtccc tgtctatcag ccaggccgcc 14160
gcctgccgtg gcgtctgtc gtgaaacggc ttgccgccgc gggttgttgag gtacaggttt 14220
cgagtctccg cgctctgcgc ctccgtcacg cgaagcccg gatcgctcgg gttcagatcg 14280
gcgagcattt cggggggaag ctgtctgagg gcgacatcga tgcggtggga tatccaggcc 14340
cgggcgagtg agtcggggt gtcgtagaaa tggagttcga tcggccggcc ggtgttctcg 14400
gcggcgccct tgtaccgagg gttgggcgaa agggagatct tctcgccctt cgcgtaggag 14460
acgacgccgt acggtccggt cccgtcgatc cggccgtccg agcgcaggga gtccgccggg 14520
tacgtggtcg agtcgacgat cgagcccgcc ccggtcgtca gcttgaaggg gaacgtggcg 14580
tccggtgcgg tcagtcggaa agtgacggtc cggtcgcggg cgtccatcga ctcgatggtg 14640
tccaggaggg acgacggcc cacgtcggaa tctatcttct tgacccgttc gaacgagaac 14700
cggacgtcct tggctgtcat tctgcgtccg ctggagaagg tgatgtcatc ccgcagccgg 14760
catcgatagg tgcgtaggcc ggaatcggtg aaggagcagc tttcggctgc gtcgggaacg 14820
ggctccgcca ctccgggctc cagggtcagc agtgtctgga agacattgct gtacagagtg 14880
gtcgagccgg agtcgtagcc gccggccgtg tcgagtgacg tcggcggttc cgtcgtcccg 14940
accttgatgg tggtgccctc ctggtcgtcc gtcgggtaaa gcagcagacc ggctgccagt 15000
gccgtggcga tcaccgtggg tgtgatgacg gacgcacgga tgtgcgcacg aataggtctc 15060
atgaggctcg tcctcgcaag atcgagacga acaggaattt tcgtacccct gggtggagag 15120
tgcgtcggcc aagtatgcgc aggcgtcgct tccttcggag cccgacggca cttccggaac 15180
gaagtcttat gactgacacg gtggaactgc tatgcccgt tcggcgagag ggccgccagg 15240
ggtcggcacc ccctctcagc agccgttccg cctcgtctcc ggtggtcctg cggacccgct 15300
tgcgcgggtc ccgcccacgg tctcactcct cgatgccatt ccctgtgcaa tgtcacctgt 15360
gccatgttcc gtgttgcagg gcgtggccat gccaagtcgg gaggtcgttc gtcttccgtc 15420
aggtgccagt gcggtactcc gtttcccacg tcctctcccc cttcagtcgg ccgtgctccg 15480
cacggccgga tccctcatgg gaggcgctgt gagaaagtca ctggtacggc gaggtctggg 15540
ggcggcgctg ccgctggccc tgaccgtcgc catgagcgtg ggcctgctgt cgcagccggc 15600
cggcgcagcc gggaacaccg gtccgtcgt gcacgtcgcg gcggacgacc cggagcacgc 15660
gggaccccg cccgtcgccg agtcccccac cgccgagacg gagcacgtcg cgcagggacg 15720
cacgagggcg tccgagcttc cgcccgtggc cgcgagtaag gacgcgctca aggaggtgta 15780
cggcaagacc gcgaaggcgc cggtccgtcc ctcgaagtcg acggacaagg cggtcgccgg 15840
caagaccggc aactcccgtg cgcgtgccgc cgcgtgcaac gtctccgact tcaccagccg 15900
gagcggcggc gcgctggtcc agcagatcaa ggcgtccacg accgactgcg tcaacaccct 15960
gttcaacctg accgggaacg acgcctacta cgccttccgt gagtcgcaga tgacctcggt 16020
cgcctacgcc ctgcgcgacg gctcgacgtc ctaccgggc aacgcctcca ccggtatgcc 16080
gcagctcgtg ctctacctgc gcgccggcta ctacgtgcac tactacaacg ccggcacggt 16140
gggcacctac ggcagcagcc tgcagaccgc ggatacgcgg gggatcgacg ccttcttcgc 16200
cagcccgcac tcccgcgacg tcaacgacgc caacggcgag acgtcgcccg aggccgtcac 16260
gctcatcgac agcgccgagg agaacgcccg ctacatccac gtcgtcaagc gactgctggc 16320
ggactacgac tccacctgga actcgtcgtg gtggatgctc aacgcggtca caacgtgta 16380
cacggtgacc ttccgcggtc accaggtcgc cgcgttcgtg agtcgctgc agtctgaccc 16440
cggcctgatc gacgcgctct acaacttcgc gagcgccac ctcgcgctgc tgggaacgga 16500
ccagtcctac ctcacgtcga acgcgggacg tgaactcggc cggttcctgc agcattccgc 16560
actgcgctcc aaggtcagcc ctctggccgg cggcctgctc aactccagct ccatcaaggg 16620
ccggacggcc ccgctgtggg tcggtgtcgc cgagatgacc gactactacg acaaggccaa 16680
ctgctcctac tacggcacct gcgacctcca ggcacaactg gcccgctccg tcctgacggt 16740
gacctaccca tgcagctcca gcatcaccat caaggcgcag cagatgacct cgggcgagct 16800
gtcctccagc tgcagcagcc tgcgcaacca ggacgcctac ttccacaacg tggtccgtga 16860
caacggcccc gtcgcgaacg acaacaacag caccatcgag gtcgtggtct tcgactccag 16920
caccgactac cagacctacg ccggcgcgat gtacgggatc ccaccaaca acggcggcat 16980
gtacctggag gggaatccgt cggcggccgg caaccagccg cgcttcatcg cctacgaggc 17040
cgagtggctg cgtccggact tccagatctg gaacctcaac cacgagtaca cccactacct 17100
cgacggccgc ttcgacatgt acggcgactt caacgccaac atcaccaccc cgaccatctg 17160
gtgggtcgaa ggcttcgccg agtacgtctc ctactcctac cgcggcgtcc cctacaccga 17220
```

```
ggccacgacc gaggcgggc  gtcgcacgta cgcgctgagc accctgttcg acaccacgta 17280
cagccacgac accacgcgca tctaccgctg gggctacctc gccgtgcggt acatgctcga 17340
aaaccaccgc gccgacatgg acaccgtcct cagccactac cgcgcgggaa actggaacgc 17400
cgcccgcagc tacctgaccg gcaccatcgg caccgctac  gacaacgact ggtacacctg 17460
gctggcggcc tgcgcggccg gcaactgcgg tggcggggc  accaacccgc ccgggaacca 17520
ggcgcccacc gccgcgttca ccaccgccgt ccagggcctg aacgtcacct tcaccgacca 17580
gtccaccgac gccgacggca ccatcgcctc ccgctcctgg agcttcggcg acggcaccac 17640
ctccacggcc accaacccg  tcaagacgta cgggtcggcc gggtcctaca cggtcaagct 17700
gaccgtcacc gacgacaagg gagccaccgc caccgccacg aggacggtca ccgtcggcag 17760
cggcggaggc ggcggcaccg aatgcaacgg gaccgacacc cgggaactgg ccagaactgg 17820
ccaacgcggc aaccagtccg ccaccaccgg caactacgcc tacctgtacc tctacgtccc 17880
ggccggcacc acccagctga agatcaccac ctccggcggg acgggcgacg cggacctgta 17940
ctacagcacc agcggctggc ccggcaccac gagctacacg cagcgggcca cgggagccgg 18000
caacaaccac accctgacca tcaccaaccc gccggccggc gccaactaca tcagcctgca 18060
cgccgtcagc agcttcagcg gcgtcaccgt gagttcgcc  tactgaccca cggctccgca 18120
ccaaggcacg accctcacga cggcccgggg cggctctccc cgccccgggc ggcgtccggg 18180
gcggcggcag gggggagacc tccgtcgccc cggaccgaga acacatcgcc cgcccgcaca 18240
cgggcatccc tacctcccag gaggcagagc gtgaagtcat acccgcacg  caggcgacgc 18300
cgcgccatgt ggtccctcat catgtccgtc ggtctcacct gcgcactcgc cacacccgcc 18360
gtcggcagcg gtgaccaggg cacgtcacgg ctcagcgcct cgcaacaggc cgcggccggc 18420
caactcgcag cggaccagca catctccacc caggaggcac agcggccgt  actgcggcag 18480
gagcggctca ccggcgtcgc aacagcgctg cgtgagcgcc tgggttcccg cttcgcagga 18540
gcctggatcg accagaagca cggcggcagg ctgaccgtcg ccgtcacccg gtcgacggcc 18600
acggccctcg tcgaggcccg gtccgctcag gctcaggcac ccgacacgac caccgtcgtc 18660
gtcgaccgca gcctgccgca actcgaccgc atgtccgcag gactggccca ccgtatcgcc 18720
gcagcgaaca agggcgccgc ccacgcctg  cagtccgcgg tggtggtgca ggacaacaag 18780
gttcgtctgg acctgccacg gggcaagacc ctcaccccg  cccagcacgc agtcgtggag 18840
tgggcgaagc ggaccctcgg cgatggcctc gaggtcagca cctacgcgca tgcctccgaa 18900
cccttctact gcggcggcca gtactcgtgc gacccccg   cctggccatc 18960
tacggcacga acgtccgctg ctccagcgcc ttcatggcgt acagcggcag cagctactac 19020
atgatgaccg ccggccactg tgcggaggac agctcgtact ggaggtccc  cacctacagc 19080
tacggctacc aggggtcgg  tcacgtcgcc gactacacct tcggctacta cggcgactcc 19140
gcgatcgtca gggtcgacga ccccggcttc tggcagccgc gcggctgggt ctaccctcg  19200
acccgcatca ccaactggga ctacgactac gtcggccagt acgtgtgcaa gcagggctcc 19260
acgaccggct acacctgcgg gcagatcacc gagaccaacg caacggtgtc ctacccaggc 19320
cgcaccctga ccggcatgac ctggtccacc gcatgcgacg ctcccggtga cagcggcagc 19380
ggcgtctacg acggctcaac ggcccacggc atcctcagcg gggggccgaa cagcggatgc 19440
ggcatgatcc acgaaccgat cagccgagca ctgcggacc  gcggggtcac gctgctggcc 19500
ggctaagcag cccggggcgga ccgtgagtac gccgcccggg tcacatcacg aggacgtcga 19560
ccgccgcacg cgcggtcggc gtctttcccc gtgctccgct ccgtccgcca cccagcggac 19620
tgggggcggg gcgtggcac  gtcgtgcacg ccgcaccgcc gtggaacccg tcggccgatt 19680
agaccgtacc gggggagcgc tttccggctc cgttcgtggg acgggcgggt gcgtatgcgc 19740
gcgtcaccca tttctggaag tgcggagcct gcgacagcag ttgccagtgg gcgcgtacgg 19800
catgatggtg caccacctcg acggccgacg cctcgaccga atcccgccgc cagacgagca 19860
gatgccgctg ccacagcgga tcccccgcga ggggtttaac cagtactccg cccaccgggc 19920
gcatggtggg ctggacgacg gccaccccca gaccttggc  gatcatccac tgcagttcgt 19980
cgagcatgtg gaactcgtgg gtgacggcgg gcctgaatcc gcggccccca caagcgtcgt 20040
agaaggcgcc gggccagccc accccgtcgt ccgcggagac gaaccacgcg tcctccgaca 20100
ggtcggccaa ggacacctcc agccggtgcg ccagtgggtg atcggcaggg gtggccacga 20160
acaccggcaa ggttctgata gtcggtggt  ccagcttcgg agagtgtcga agaggcagcc 20220
ctgggtagtc gcaacccagg gcgacgtcga gctcgccggc ctctaggaga tcgatgagtt 20280
ctccgtcgcg gtacacactg ctgaccgaga cggtcagatc ggggcaggct tcacggagga 20340
cgtcgagcaa ggtgggtacc accggtgtgt tgatgccccc gaggcgaagc cgacgtgtcg 20400
ccccggacga gcggggaggc cgcagccgtg cgagattgtc gagagcgccg aggatctccc 20460
gggcccggcc gacgacctgg gcgccgtagg cggtgagctc cacgcccgcg ctgctgcgca 20520
ggaagacccc ctcgccgagc agtccctcga tgcggcgcag ttgggtactc atcgccggct 20580
gggtgtatcc gagcgccgca gcagcccggc cgacgccccc cgcgtcggct atcgcacaca 20640
gcacgcgcaa gtggcgcaac tcaagttcca cgggggcacc tcgctccggg cgaacagagt 20700
tccattatgc gccaggagga aggcggtggg gaatccggga cggcctgacg ccttcggtcg 20760
accagtagcc cgagggttat ggatgagccg gagcctctgg tatgcctgg  ccggttgttc 20820
ccgggtgacc gccgtggaaa tctcggacct gcgtgttggt ccgcagaggc gactgcggaa 20880
gcctgaagcg caccgccatc gaggagcgac atcatgcctc acacctgcat cagcttcaca 20940
gtcgaagcga ccggggccgc ggttcaccgc gccgccacc  cgtctccac  cgcgctgagc 21000
tggtggggag ggccggtcga ggaagagctc cgcttcagcg cggaactcgt gacctccgag 21060
ctcctcacca acgggctgcg gcacgcgggc gggcccatga ccgtcgagtt gacgctggtg 21120
cacgacatgg tcgtcgtcgc ggtcctcgat gacagccgga agctgccgcg gcctcggcag 21180
acggaggcgg acgacgagtg cgggccggga ctcgccctga tcgaggacct cagtctgata 21240
cggggagtcg agaccacttc ccgcgggaag cgctgctggg cggttctgcc gctgcgacg  21300
ccacaggagc gggctatcga gtcggctccg gctgaggagg cggaccacgg cttcgaggca 21360
gaccgggaac gctggtcact ggctccccaa ggaagcggac tactggcgag tctgtttccg 21420
gcgatgtgag ttcgtcctcc tcgggcggca cagtagccga cagttgggtt tcccgaagcc 21480
ctgagggcgt gatgacgctc gtctgacgct ctggccgctt tcaagctgca cagcgagccg 21540
agaaacagcc tttgacctgg cctttttctgc ggctgcctca ggccgacatc tttccgatga 21600
cgcaccacgt ggagtacgtg gcgattctgg agcctgctgg caaggggttc tgacctgcgc 21660
ttttgttctc ctgcgcggg  cgcggcaagc tcgtcgcggg cagttgggtt tcccgaaagc 21720
cggtgctcgt gtgtccggcc ggcgggtggg ctgccttcgt ttcagtgggt gcgagagggc 21780
actcggacgc ctgagccgag atgcggttcg ttcggcacca tggggtccgg aggatgaccc 21840
ggtcagcgac cgctggcacc tgtggaagaa ccctttgcga caagggcctgg ccgaggttcg 21900
ctcccacagc gcctgctgga ccacagcgaa cacaccccgc ccggtcggcg tccatgagca 21960
```

```
gaccacccgc gaacgttggc atcagctcca cgacctcctc ggcaagggtg tcggcttgct 22020
cgaatgcgcc cgccgcctga acctgtccct caacaccgtc aagcgctacc cgcgcacccg 22080
cgatcctgaa gccctgcgcc ccgtgaagca gctgtttcgc gaggtccagg agcagggctg 22140
caccggcagc ttcaccctgc tctaccgcag cacccaggac gtcgaccggc cgaccggcc 22200
cgtcggaggg tcgcggcttg acgctcaccg tatccatcac tggaacggca acgtctgatc 22260
ccgtctgccc ggggcttggg tcccggctgc ggcccgtagg cccggctcac cccagcaccc 22320
atcactgttc gagagtgatt acctctccgc cggacacatg gaaatctgca tcggctggag 22380
tagacattgg gcagcagtgt ggttatgttt ctcctgtaac ccagaaggac cgcagggccc 22440
ggcagagacg aactgccggg cagcagtacc cgcagttgca ggacggtgcg gtggtggagt 22500
gtcgaagcca ggatggtgca ggacggcgac gggactgacg accgaccgg cggcccgca 22560
gtggtcaggg gccgccaccg cagtgcagta cccagcagcg aagtcagtga gcggtacctc 22620
ggtgaaggcg tcggctgcgg acgcgcgcgc cgggaggttc ggcagtggtg gttccaagcc 22680
agagcagacg caggacgggc aacggggccg actgtcggac agtggcgctg tcacaggtca 22740
ctgagaggtt cgtgtcacca gcagtagagc agtaccagag gaaagaacgg aggaaccaag 22800
cgccatcagg atcgcccggg cgcagttttg ggcccgggta ccgcaggaca tcgatagtga 22860
ggtggtctcc ggtcaagaaa ccgcgatccc cgcgccccg gcagcaggca ggtcgggtcc 22920
gcggacacag aaggccggtg cagtatcagg gccggcagat ggtgtaggag ttccttcggg 22980
gccctggtgc cgcatggcac cagggcccct ccatgcgttc cgcagagagg tgcagatgac 23040
agcagacgat tcgtacggcc gtctcgacga cgacgattac cccgcctaca ccatggggcg 23100
ggcggccgag atgctcggta cgaccccgc tttcctgcgg gccgtcggag aagcccggct 23160
gatcacgccg ctccgctcgg agggcggcca ccgccgctac tcccgctacc agttgcgcat 23220
cgcggcccgc gcccgcgaac tcgtcgacca gggcactccc gtcgaggcgg cctgccgcat 23280
cgtcatcctg gaagaccagc tccaagaagc gcggcgtatc aacgaggaac tgcagaggcg 23340
cccggccggc ctggtggaca aggccgaggg ctgaggccgc atctgccggc cggtcctgtg 23400
agggctcgcc tgccaagacg ggaagccctt gccgcaacga gaagaggcaa ctgtccgcac 23460
cgatgtgctg ggcccggtcc tggctaggac tcccgtctct ttgccggagc gatgcggctg 23520
tggacgcgga accggacggc agtgtcgtcg ggcgcggagc gcggggcgca cgtcgatggc 23580
gacaggaccg gcgaaggtgt attcgtgttc ggcggtgtga cggcgcacct ggccggcgag 23640
ggcggcgccg caggtgtcac agggacatcg gttccgactt ccaccaccg tccgggttcc 23700
accagcgtgt catccacctg atccaggctg ccgcgtagg tgctcgacgt cggggtgta 23760
cgggggcagt tgtaccgttc cgccgcgagg agtgaccga ttgaccaccg gcctgtggcg 23820
ctcaggaacg ggctggactg tcgcagtccg ggcaactca gcccgacca tgaggccgac 23880
cacggccgcg cgcgacccg accacagcta cacgcgtggc atgaccaagg cggcacatgc 23940
ttcgaacgag ccatctcatg tgtgccggta tgaacgtgat cgacgtcccc ggcactctgg 24000
tgcggacgca agccgtctgg ggcgccaccc acgactggct cgccgccccg ccccgcggc 24060
gccaccgtcc gtcccgccct gcgtcgtcgc ccgtgtggcg tcatgacggc gacagacttc 24120
ctcgcgtatg ggccgaccat acggccaacg ccagagtaa agcgctgtcc atggtgagtt 24180
ccctgaacag aagggctggc gggacctcct ttccaagacc gtgctgcagg agtccgtcag 24240
agcgcaggta atcccgtgct gtccgcgacc cagggctgtc ctccgtctgt ccgagggtcc 24300
tcgtcttctg ggcgacatcc ctttagcgtg ggcggtagcc gccgaaggga ggcgccatgt 24360
cggacgaatt gacgggcccg ttgggaacgg caatgcgggg ggtcacgttt ccggaccggt 24420
ctcgcgggat catcttggtg cgggctggaa caccgcaggc cgaggccgga gcaatggccg 24480
cccgtatgtg ggccgagatg ccggaaggct gacgtgcccg aacgcagaca acccgtaccg 24540
tcctcacacg cattcccctg agccgtcggc catggaacgg aaccagccgt acgaacccg 24600
gaggcgccgt tgcggtctct gcggcgaggc cggggccacg cagggcgaag aggccgcgcc 24660
gcgttctgcc gcctggccg gctgccggct gttcacgaga acaccgaggg aggagtcgcc 24720
cgcctcttgc ccggcgcgtt gccgggtgga gagcaggtgg tgaaggactg gctcgctgaa 24780
ggcggccgag gcgacctcgt cggccggcct gaacgctttt cactgtccca gcggcggcag 24840
gccgccgaca caggcatgct ttgccatctc ccctcgctgt tactgacccc agcagcagga 24900
tccagtacgg cgtcgcggcg ctgccgcctc actcgcgcat cgatcgggga atgcggcatg 24960
tggtgagggc ccggccggcg tgccggtcgg gccctcacac tgtttttggtg tcggcgcgtt 25020
tgtcgtgtcg gtcagacgga caggtggggg gcgccagca tggcggaagc ccgctgcaac 25080
ggactgtcgc tgcgcgcggg ggcggcctcg ggaagggtgc ggcaggtgaa gcccagctgg 25140
gccatggccc ttaggatttc gccggtgctg aagtcgcggc ggtcgtggcg ggtgatgacc 25200
tggccgacct gcttggcggg gtagtggcgt cgtccgatga tcacggactc gccggtgacc 25260
ggttcgggtt tgacgcccctt catcgattcc agcacgccgc tcttggtcag gtcgaacggg 25320
aagcgggcaa tgacacagcg catgatgcct cacaggcagg agagttacgg ggccggccgc 25380
cgtctgccgg ttcagcggga gagagcgagg acgcccaggc cgtgccgtg ttcgtcgacc 25440
acgggcacca gcccgagccg tccgaagggc accgcgtcct ggcttcctc cctcgtggcc 25500
gacggtgaga cgaagggctc gctgtcgtcg gtgatgtcac cgaggcgag ccggtcggtg 25560
tatcggggagc tgtcccggac ggcggtgagc cgggcctggg tgaccaggcc gacgcaccgg 25620
gcatcctcgt cgcagacgac cagatgctcg gcacgggccg cggccatcac ggacagccgc 25680
acctcgacgg tcatgtcgta ccagacctgt ggcccggcgg cgtccatgac gtcggccacc 25740
gtgccgcgca atgggagagc gcctacggag cgatcctgca actgtcctgc cgtcaagggg 25800
tgcctcctgc gcagacgggc gggttcctg atcaggacgg tcctaggcgg ccgcgccagc 25860
cgtggacttg agtgcgggg tacgccgcgt cgccgaggcg gggcggcgtc ggccgcgtga 25920
ggtggcgccg cgcttcttgg ggcgttcagt cgccggggcg gtgatgacga ccgggatgcc 25980
ggtcggggcc tgggctccgg tgatccggct gagggcctcg tcgcccgggc tgacctggt 26040
ggtctgcggc cggatcccgg cttccgacat gagacggacc atgccgcggc gctggttcgg 26100
ggtgacgagc gtgacgacgc tgccggactc gccggcgcgg gccgtgcggc cgccccggtg 26160
gaggtagtcc ttgtggtcgg tcggcgggtc gacgttgacg gcaggtcgg ggttgtcgac 26220
gtggattccg cgtgccgcga cgttggtcgc caccagcacg gtgacgtgcc cggtcttgaa 26280
ctgcgccaga gtgcgggtgc gctcgcgctg ggacttgccg ccgtgcaggg cggcggcccg 26340
taccccgctg ttgagcaggt cccggggtcag tctgtcgacg gcgtgcttgg tgtcgaggaa 26400
catgatcacg cggccgtcgc gtgcggcgat ctcggtggtg gcgcgtgct tgtcggcgcc 26460
gtggacatgg agtacgtggt gctccatcgt ggtgacggcg ccggccgagg ggtcgacgga 26520
gtgcacgacg gggtcgctga ggtagcggcg tacgagcagg tcgacgttgc ggtcgagggt 26580
ggcggagaac agcatgcgct ggccttcggg acgcacctgg tcgagcagtg cggtgacctg 26640
cggcatgaag cccatatcgg ccatctggtc ggcctcgtcg aggacggtga cggagacctg 26700
```

-continued

```
gttcaaccgg cagtcgccgc ggtcgatgag gtccttgaga cgtcccggag tggcgacgac 26760
gacctcggcg ccaccacgca gcgccgacgc ctgcctgccg atcgacatcc cgcccaccac 26820
cgtggccagc cgcagcttca cagagcgggc gtacgggtg agcgcgtcgg tgacctgctg 26880
cgccagctca cgtgtcggta cgaggaccag ccccagcggc tgccgaggct cggcccgccg 26940
gccggccgta cgggccagca gagccaggcc gaaggcgagg gtctttccgg aaccggtgcg 27000
cccgcggccc atgatgtcgc ggccggcgag ggagttcggc agggtcgcgg cctggatcgg 27060
gaacggcacg gtcaccccctt gttggccgag cgcggccagc agttccccgg gcatgtcgag 27120
atcggcgaag ccctccgcag cgggaagcgc gggggtgatc gtccgggga gggcgaactc 27180
cccctgaacg gcgccggccgc ggcggccgta accgccgag cggctgggtc cggccggccg 27240
gcgcggcgcc ggcgaaccga agcggctgcc gcccttccg gagtcggcac cgccatgacg 27300
ggtgcgagcg aagcggtcgt tcgtgcgtgt gcggttcata cggaaccttc ctcgatgcgg 27360
cacatatcaa ggaatttccg aagcaatgag cagcacggag aatcgcaaga atggaccggt 27420
gggccttgcc agcggatctg gccgacagaa aatctgtgcg cacgtgcgc tggaatgatt 27480
ggggggtgctg tgggctcgat attcgaagcg tccactgcac tgtagctatg aaggatgcgg 27540
ctgcaccttc gaaggacgat ccgtgtgcgg taaacacacg ctgtccgag cgtcgtccgc 27600
aggtgaaatc actgcgggaa acgcatgtag ctgggggccg cacccccgaag gatgcgggcc 27660
ccagctacaa gtacgtgaca gtcggcgtca ggcgggaacg atgttctcgg ccgtcgggcc 27720
cttctggccc tgcgcgatgt cgaagttcac cttctggcct tcgagcagct cgcggaagcc 27780
ctggcggcg atgttcgagt agtgggcgaa cacatcagcg ccgccaccgt cctgctcgat 27840
gaagccgaag cccttttccg cgttgaacca cttcacggta ccagcagcca tgtcatttct 27900
ccttcggggc agtcgtacgg gatccgcacc gcgcggacct cgtgtcgccg caatgatcac 27960
cccgcccgga aaaagaccgg agatgtaaaa gtgcttccag gggtactgag cccgaccgga 28020
gcacttgaaa tttcgggaac cacaactgca actgacatcg acagtagcac gccacagcag 28080
ccactgtgcg gtgaagaacg ccaccttgct tattgcggca gagaatctat ccgcatgctc 28140
cgatgaaaac tcaaaccgcg cgcacagata ttgaccttcg cgcgacgcca tatatcgcat 28200
gccgcgctcg cgtgatccgg tcccccacca cgctctccgc tactgcacgg gtcgcaccgc 28260
cgcgggggca gacaggtccg gccatgacgc cggccatgct cggggcgtag cggacgcctg 28320
ccggtcgggt gtacgtctcg cgcgcgcga gcactgcggg ggaggggccg gttgccagac 28380
gtcttgcctg gcaaccggct gtcggctcgg gctggttggt cagccgtggc aggtgatgtg 28440
gttctgcgcg cccgcttccg tgaacgcgcc gcagccccgg ctgccttcta ccaggccgac 28500
cctcaggagg cgtgacccgg ggaagccgag gatcagcggt agtcgtcagg ggaggcttcc 28560
ttgccgccgt aggtgacgtc ctcgaagtat gcccaggcat ccggccggct gccgtccacg 28620
tccgtcaccc cgtatgccct ggccagttcc ccgctggagg tggacttgcc gttccaccgc 28680
ttcgcgcggt ctgggtcggc ggccagcgcc gcgaccgtac gggccaggta gtgcggggac 28740
tccgcgatcg cgaacgtcgg ctccttgggcg atcgcgtcac gccagttctc ctcactcaca 28800
ccgaagtggg agagcatctg ctccgaacgc aggaagcccg gggacaccgc gaccgccgtg 28860
ccctcgtact ccgccagctc ctgagccagc ccgaacgcga ggcgttcttc 28920
gccaggtcgt agtagatgtt ctcgcggtag cggcggttgg agtgcgcggt accgtcggtg 28980
acttccacat gcagcggcgc gtcggagcgg atcagcagcg gaagcagcag cgccgccgtg 29040
atcacgtgcg agcgcgcgcc cagctccagg atccgcaggc cgtcggcgag cggtgtctcc 29100
cagctcttct tcccgaacac cgaggtggcc agaaggtgct cgccgcccca caggtcgttg 29160
acgagaatgt cgagccgctc gtactcccgg tcgatccgct cgacgagggc gcggacctgg 29220
gcttcgtcga gatggtcggt gggaactgcg attccggtgc cgcccgctgc ggtgacgagt 29280
tcggcggtct cctcgatggt ctcggtcgtc cggccgacct cgctggcccg ggcccgggtg 29340
gttcggccgg tcacatacac ggtagcgccg gcccgcccca gttccacagc ctgagctcgt 29400
cccgccccgc gggtagcgcc cgccacgagg gcgatccgtc ctgccagcgg acccttcgga 29460
ccggcctgct cggtgttctc agtggtctgc ctggtgatgt cctcgttgct catgtcatcc 29520
atcgttcacg ctaaaaccga cagaacacgt caccttttat gtgggggta ccgcgcatca 29580
tcccggccat agcgccaact acgtcctcgc actgagcgtt ttcagctgg gccaccgatc 29640
gggtgacgcc ggtcaggtcg gggtagggcc cgcaacgcac aaggctcgcg tgcacgacat 29700
ggccaccgcg cgcatgatct cccagcggga gcccagccgt ccccggcagc cccgaccgct 29760
gagaccagct cacccgggac acccggtccg acaccgcaca cgatcaagta gtcgacctcc 29820
agacgcgttc agcagcccac atcccaggag ccgtctaccg tcccaggaac ccctgctccg 29880
ggaccatcgg gctcggccac cgggagtgca agttgatcga taactggcaa cgagctcgtg 29940
cacggtaagc ggtgaggtgt cgaggtccag atgggcggcg gcggtggtgc ccccagcggt 30000
cggccgaccg gcatgccgag cgggcagccc accggtgtgc cgagcggcgg acccggcggc 30060
ggcacgggca tgggcggcac ccccacccccg cagcacctga agtcggtcag gaccggccgc 30120
gtgacgggct tcgggtcaga cctgtgcggg gaacagcagg cagtcgtccg ggcggatgat 30180
caggttgatc tcgccgtccg tgtgccggac ggggctctcg gcatggacgc gcacgtcgcc 30240
gatgctgagc tcgtactcga atcgcgctcc ggtgtacgag cactgctcga cctcgcccg 30300
gagcacgttg acggcaccgt cgtgcggggc gtcggcgcgg tcggtgagcg tgatgcgttc 30360
cgagcgcagc cccacggtgg cggacgacc cgcggagcag gcgccggcca ccctcaagcg 30420
ctgaccggtc tcacccagtt cgacctgtac ggctccgccc tcggtggcgc cgacgcgccc 30480
ctccaggagg ttgcagcggc cgatgaagcc ggcgacctcg ggagtggcgg gagtctcgta 30540
gatctcggtc ggtgtgccca cctgctggag gtgtccgtgc atgaacacg cgatgcggtc 30600
ggacagggac atggcctcga cctggtcgtg ggtgacgtaa acggtggtga tgccgacctc 30660
ccgctggagg tccttgagcc agacgggccc ctggtcgcgc atcttcgcgt ccaggttgga 30720
gagcggttcg tccaggagca gcacgccggc ggagtagacg atgcctcggg cgagggcgac 30780
gcgctgctgc tgtccgccgg agagctggtg gggtagcgg tcgcgcaggt gagccatgtc 30840
gaccttggtg aggacgtcgt cgatgaggcc ccgttgctcg cccttggtga ccttgcggag 30900
cttcagcggc agtcgaggt tgtcggcgac ggtcatgtgt ggccagacg atacgactg 30960
gaagaccagg ccgagattgc ggccttcggg gggcaccgtg ctgcgccggg tgccgtcgaa 31020
gaagacctgg tcgccgacac ggatggtgcc cgagtcgggg gtctccagac ccgcgacgca 31080
cgacaaggtg gtggacttgc cgcagcccga cgggccgagc agagtgaaga actccccgtc 31140
cgcgacgtg aagttgacgt cctccaggac cgcggtcccg tggaaggact tcttgatgtt 31200
ctcgacgacc agctcaggca tgcttcttcc ccttcaggag gagaccggcg aggccggcga 31260
cgacgcggt gacgcgatc tggaggggtgg cgaggcggc cacggagccg gtctcaccct 31320
gggtccacag atcgatggcg gtggtgccga tgacctgtga ctcggctccg gcgaggaaca 31380
tggcgggggc gtactcgcgg atcatctggg tccagatgag caggaacgag gcgagcatcg 31440
```

-continued

```
cgggcacgag gagacggagc atgatccggg acaccgtgcg ccaccagtcg gcgccggcga 31500
cgcgtgcggc gttgtcgagt tcggctccga gctgcatggt cgccggggag atcgcgccgt 31560
acgccgacgg gagtgcccgg atgccgaagg cgatgatcag cgcgaagagc gtgccgcgca 31620
ccgcgtcgcc gccgggtatc caggtgaagg cccagaacag ccgcgatgcg acgatcaggc 31680
ccgggaccgc gtgcggtgac tgcgctgtcg tctccaggag acgggcgaag cggaagtcgg 31740
agcggcgtgc cacgaggacg accaccgtgc cgaacagggt cacggccacc gccccacga 31800
aggccacggt gatgctgttg acgatcgact cggtgtaggg ggcgtagtcg aagatcagac 31860
ggaagttgtc cagggtgagc aggtcgaacg ggttcaccag cggagtgagc agcgaggtga 31920
acgcgcgcag gatgagcgcg agcatcggca gcagtgcgcc gaagacgacg tacagaccga 31980
cgaaggcgaa gcccagccac ttccaggcac cgatgtcgag caggtcggag cgggtcgcct 32040
tgccgcgcac cgacacgaac cgctgggcgt gccccagcag ccgcgtctgg aacacgacca 32100
gggcgatggt ggtgagcagc atgaaggtgg acgccgcgcc cagcaggccg tagtccggat 32160
tgatcgagtc gatgccctgc tcgtagagga agttggagaa gagggtgatg ccggcgggct 32220
cgcccaggat gagcgggatg gacagggtct cgatcgccgt gccgaagatc agcagacccg 32280
cgtagagcat cggcgggcgc agcatcggca ccacgaccga cgcaggacg cgcagaggcc 32340
ccgcgccgac gctgcgggcc gcgttctcca gagaggtgtc ggaggcggcc agcgcgttgg 32400
cgcagaacag gtaggcgatg gggacctggg cgacggccct gacgaacgcc ataccgggca 32460
gtgagtacag gttccagggc acccagccga agccctcgcg caccgcgccg gtcaggaagc 32520
cggccgggcc gtagacgacg atccacccga aggccaggac gagcggggag atgtagatgg 32580
gccagcgcag cacctgcccg aacaggcggg cggcggggaa gcgggtcgcg tccagcagaa 32640
tcgccatcgg caccgcgatg gcgagcgcga acacggtcgt caggacggcg aagaggaggg 32700
tgtcgaggac gatcgaaccg aagcccgccg acgtgaacag gtgggtgtag ttcgagaggg 32760
tgaaggcgcc gccggccgcg tacaggggct ggttgcggac cgactggtag aggatcggta 32820
cgacggggc gaggacgagc acggcggtga cgaggaacgt cagccagtgg atggtgacct 32880
cacgtccggc gccgaacagg cgccggtact ggggcgttgc cagctcgccc gcgcgcggga 32940
tgcgggacgg cgcgggtggc gccggggtg tctggatggc catgacgact ccgtacgaac 33000
ggggtgggga caggggcgtt gggcgggcgg gggcggctca gccggccgcc ttctcccagc 33060
gcgcgacgta cgcctcccgc acgcgctccg gcaccccgcac gggccggtac agatggacgc 33120
ggtccgcgcc gagccgccgc cgcatgtcct gcagactgtc catggcgtcc tggcgcacgt 33180
ccggccggta cggcaccagg ccgccctcgg cgaccgccgc ctgcccttcg gcggagagca 33240
ggaagtccag gaagagacgg gccgcgttcg ggtgcgggggc ggtcttcacg acggacagcg 33300
cgcgcggcat gacgacggtg ccctccgcgt agtagctcca ccccagcagt ccccgctgt 33360
gctcggcggc gggtatcgcg acgccatcac gtacggcagg atcccgcgt gccgcaggta 33420
ggccagttcc tggcgcgagt ggaggcgcag cctgagacgg accgtggcgc ggggtgcgtc 33480
gggccggacg agggacaggg cgacggggtt cgtgccgacg cacaggtcgg cgaggccgtc 33540
gaaggtgaat tcctcctctc cggtgaaggc gtgggccgat gcggtgtcgc cctcctcgaa 33600
ctccagggcg agtacaccca tgccgatcag gttgttgcgg tggatgcgct cgaaggactc 33660
ggctatcacc gcccgcactc ccagcagccg cctgtgccttg gcggccagt cgccggctgga 33720
gccggcgccg tagttgcggc ccgcgaccac gacgagatcg tggcccgcgg cgcggtaggt 33780
cgccgcggct tcgtggacgg gccccatccg cagttgcgtg ccccgatggc cgccctgcgc 33840
atggacgatg cggccgggtc ccttcgaggg cctggccgcc gggtcgttcc tgacccgagg 33900
cgccgatcag gacgacgccg tgcaacggac gcgaggacac cgtcagcttc gtccgcggcg 33960
acagcgacga ccccggtgac ttccgatgac gcgcacgccc ccgccgcccg aacccgagct 34020
gaccgtcgac cgcgccgcct gctctgggtc accctcccgc tccgcctgcg agatcagatc 34080
gccgacgcgc cgccgggcac cgtcgtccac gtcgtcgcca ccgacccccg cggcaccgct 34140
cgacctgccc acctggtgcc acatgacagg tcacacctgt ctcggcacgc cccgccgaa 34200
cggccggtgt acgccccgaa gctcaccgcc gacgcgcgcg ccacccgccc ggacgcaccc 34260
tggcacccgc tccggcggcg gcaggagcag ccccggaacc ggtgacgcat ctcgtcggcc 34320
ggccgtttcg agtggaccgc ggacgcggaa cgtcacgcg tccggaaacc ccggaaggtg 34380
accggcctgc gtgtcttgaa gccgagccgt tcgtacaagg cgatcgcgcc ggtgttcgcc 34440
tcggccacgt gcaggaaggg acgatcaccg cgcgccgaga tgcgctcggt gagagcgcgg 34500
acgaggcggg cggcataacc ctgcccgcgc gcctcgggag cggcgcagac ggcgctgatc 34560
tcggtccagc ccggaggacg caggcgttcc ccgccatcg ccaccagggt gccgtcgacc 34620
cggacaccca ggtaggtgcc gagttcatgg gtacggggcc agaacggccc cggctcggtc 34680
cgcgcggcga gatccagcat ctcaggcacg ctgtccgcgc ccagctcgac cacgtcggtg 34740
tcggacgcgg agcgagttcg gccggggcgg ccgtcgccgg gccaggtcat ctgacggccc 34800
tcaagactga aaaccggctc ccaacccggc ggcggaacgg ccggggagct gaacatgtcg 34860
gcgaaggcgc cgggaccgag taggccggcc aggtcggcgcc agtcctccgc gtccgggtcg 34920
acggacacgg aggagaaggt cgccacgtcg gtgagatagg tggctgctcg accgaaccgt 34980
cgggcgagat gagcgtgccg accactgagc gactgaccta ccgggtcgtc gagtgcgggg 35040
tcgtcgtcgt tcatcatcgt gccgtttcct tcctggtgag cgcggtggtc gaagggtggc 35100
cgcggtaggc gaaaagtcgg cggcgggggc cgtggcccga tagtcgtagc ccttgtcacc 35160
gtgcagtttg ccgggtcgcc tgaggacttc cggctgcgagg ccaatgccaa agcgctctcg 35220
tgccggcgga ggcacgcctt ctgacgtgcc tccaccggca ccactcagtt caggcagatt 35280
gagcttgagc gatgcagcgc cgccggaagt cgagcgcctc aatgcatcga gcggcgactt 35340
cctcgttctg ggtgagagca gtcctgcctt gtcgagtgat gcggcgttcg gaccgtcacc 35400
ccggtcaagg caaggacctg tcccacggag tggctcatcc acctcccct cctcggccca 35460
cagcttcagg cccgactag ggggaggggc gactcggaac ccggcgtccc gctcgcgaag 35520
gtcggtcaga cctgttcgaa gtggaacgcc ttgatgaagc agtcccgggg ttgggcgacg 35580
gcgaagagga tgcactccac gagggactgc gcgtgaggg cgtcctcggc ttcgcgtgaa 35640
gtggtcgccc actcctcgga gagcgggtcg gcgttgtcga gtcgggcgg gtagagcgag 35700
atcaccccgga ctccttgggc gcgcaggcgc ttggagagga tttcggtgaa ccctgcctgg 35760
gcgctcttgg ccgcgtagaa ggcgtcgtgt gcgtccgagc ggtggtggcc cggtgttccg 35820
caggcggaga ccatcgtcac gacgtcgggt gtgtccgagt tgagcaggag ggggaggaaa 35880
ctcctcgtgg tcaggaccgt cggcgtggct ccggaggcgt ggtcgtcacg gacgtcggcg 35940
tcggttgccg acagcaggtc cggcccggtg aggtagcggg agccgttgtt gacgagtacg 36000
tcgacgcggt cggtgtgttc cgcgcacgccg gaggcgaagt cgcggatcga gcaggatcc 36060
gtcaggtcgc aggcgaaggc gtgcacccgc tggtgtccgc ggtcgcggat ctcgtcgcgg 36120
acccgttggg cggcggcgag ccggcgtgcc gagaggaaga cctccgcgcc gaggtccgcg 36180
```

```
aggcggatgg ccagggttcg tccgaagtcc cggccggcgg ccgtgatgac gacgcggtgg   36240
ttgtcccatc tcatggtgtc gttccccagt cgccgtttcg tggatcgggt ggtgccgtgc   36300
accgcgtctc tacgctatcg gtcatggtcg ctcacgaacg gtcgttcacg gtcaatgatg   36360
atgttgaggt gcccaacccc ggtgcggacg aggtctggac cgtcggcgcg gtcatcctca   36420
atcggaagg  tcgtgccttt gcccagaagc ggagccggga ccgtcgcctg ttccccgggg   36480
cctgggacat cgtgggcggt catgtcgagg agggcgagac gcttctggag gccctcgcgc   36540
gtgaagtcga ggaggagacc ggctggcgcc tgacccgtgt gcggcggttc ctcggcacca   36600
cgacctggac ggggacgac  ggcggcggcc tgcgtcacga ggccgactac ctggtcgagg   36660
tggacggcga cctgaccac  ccgaggctgg aatggtccaa gcactccgcc tacgactggt   36720
tcggccccgg cgatctcacc cgcctcaagg agaaccgcgg accaggggag tacctgatcc   36780
acgacctcat agccggtgcc gttgccgact cgcctttcga cttgctccgg gcggacgccc   36840
tcaccagccc ggaccggctg cgcgagctct acccgcagcc gaacccgaac tcgctgcgca   36900
aggagaccga ccgcctgacc gaggagaccc gggcgctgat cggctgttcg tcactggtgt   36960
tcatcggcag cgcggaccgc gagggccggg cggacgtgac gccacgtggc ggcccggccg   37020
ggttcgtctc ggtgctggac gagcagaccc tggtgatccc cgacgcgacc ggcaacaaac   37080
ggctcgacac cctgcacaac gtgctggaga ccggacgcct ggggcgtctc ttcctcgtcc   37140
ccggccgccc gaccacgctg cggatcaacg gacgcgcctg tgtttcggcc cgcccggagc   37200
tgctcgcccg cctcactccc gtcggaaagc gccggtcac  cgcgctggtg gtgcaggtcg   37260
agcaggtgta tccgcactgc ccgaagtcac tgatgcgcgc cgacgcctgc cgacccgagc   37320
agtggatgcc cgccgacgcc cagccgagca gcgccgaggt gaccttgcg  cagctgaacc   37380
tgcccggcct gaccctggac cggatcgagg atgccaacg  gaggtcgctg cgcctgcggt   37440
acgaatgacg acgagtcgat gagcgccgat gagccgatga gaccgacgg  gatccgacgg   37500
gtcggcgtcc gcggcgagca gaccggtcgc gaaggtcacc gcccgcacgg cggcgaccct   37560
cgcgacggtc agtactgtcc ggtcaggtgc gggtccagcg ttggttgctg ccgttggagc   37620
aggtgtacag ctggatcagg gtgccgtttg ccgtgccgtt cccgacggcg tcgaggcaga   37680
ggccggactg gacgccgacg acggacccgt cggagttgag gcgccacttc tggttgtcgc   37740
cgccccagca gctgtagatc tggaccttgg agccgttgcc ggtgcctgcg gcgtccaggc   37800
acttgtcgcc gtagaccctg agctcgcccg cgtcagtggc ggcccactgc tggttggtgc   37860
cgctgtgca  gtcccacagc tggagctggg tgccgtggcg tgccgtacgt   37920
cgaggcagcg gcccgaaccg acgcccttga tctgtccccc gtccgcgggg ggctccgagg   37980
agtcgccgcc gttgagtgcg tcgaggacgg cggtgtacgc ggccttcttg ctgccgtcgt   38040
tgttgaacag caacggcgtc tgctccgacc gccaggagtc gctgtcgcgc acaccccaga   38100
cggtgatgcc gaggcagcgc gagacggcca ggcagtcgtt cgtcacgttg gcgtaggtcg   38160
aggccggggc gccctggatg tccagctcgg tgatggccac gtcgacgccg agggcggcga   38220
agttctgcag tgtggtgcgg aagttgctgt tgtaggggct gccgctgttg aagtgcgact   38280
ggaagccgac gcagtcgatc ggcacgccgc gctgcttgaa gtcccgcacc atgttgtaca   38340
tggcctgggt cttgcccag  gtccagttct cgacgttgta gtcgtttag cagagcttgg   38400
cggacgggtc ggcggcgcgc gcggtgcgga aggcgacctc gatccagtcg ttgccgctgc   38460
gttgcaggtt ggagtcccgc cgcgctcccg aactgccgtc ggcgaaggcc tcgttcacga   38520
cgtcccactg gacgatcttg cccttgtagt gggccatcac gccgttgatg tggtcgatca   38580
tcgcctggcg cagcgcgctg ccgctgaggc tctgcatcca gccgggctgc tgggagtgcc   38640
aggccagggt gtggccgcgc acctgcttgc cgttctgcac cgcccagttg tagacgcggt   38700
cggcggagct gaagttgaac tggccccgct gcgg                                38734
```

<210> SEQ ID NO 31  
<211> LENGTH: 3331  
<212> TYPE: DNA  
<213> ORGANISM: Unknown  
<220> FEATURE:  
<223> OTHER INFORMATION: Description of Unknown Organism:Unknown

<400> SEQUENCE: 31

```
tcggatctcc ccacacaaca tagatagagg atatccgcct gggttcacaa tgaagttact     60
ggtggttctc accaccctcg tgggctttag ctcagcacta agtttcggtt gtaattacag    120
accagtatta ggcttcaatt cacagtatat gctgggagga ctaagacttt tctgtatgcc    180
tgccatggtt tatgatccat gggcatgtgg ttgcgtttcg gcatggagca gtgcaggtct    240
ttacggtgtc ggaggggcg  gaggcgcctg gggagctggc ggtgctggag gagccgacgg    300
cggacgcggc ggcggcggt  gagattggga atatgactat gatgacgaca gcgatgacga    360
tgatgaatgg gactgggatg atgacggtgg aatgggagct ggcgccggag gtggtgctgg    420
tggtggtgcc ggaggtggtg ctggtgctgg tgctggagca ggcgcaggga caggagcagg    480
tgctggactc ggacttggat tgggcggagg tctcggaggt ggacttggcg gacttggagg    540
tcttggcgga cttggcggtg gagacgattt atttgattta gatttcgatg atcttggtgc    600
agctcttgcc ctcggtggag ctggtgagc  tggaggtgct gctgctgctg ctgcagctgc    660
cgctgctgcc gccggggggtg gagttggtgg agctgctgcc gcagccgcag ccgctgctgc    720
cgctgcagga ggaggcgcag gtagacttgg aggactcggt ggcggacttg gaggactcgg    780
tgccgctgca ggaggcgcag gtgacttgg  aggactcggt ggcggacttg gaggactcgg    840
tggcggactt ggaggcctcg gaggtcttgg tggcctcgga ggatatggag gatctgctgc    900
tgccgctgct gctgctgccg ccgctgctgc cggaggtgga ggactcggtg gtgtttggttt    960
ctacggtgga cgaagaggta acgcggtcg  aggaagagga ggccgacagc gtgctgctgc   1020
tgccgctgct gcagctgccg ccgcagccgc tggtggtggc ggaggaggtg gaggtggtga   1080
aggaggaggc ggaggcgctg gtgctgccgc tgccgctgca gccgctgctg catctgcttc   1140
agcttctaga caaatagagtg gtataaggga cgcattagga gacattaaag accttctcag   1200
gagtaatgga gcctctgcaa aagcctctgc taaagcatca gcagtagcaa gcacaaaatc   1260
tcaaattgac gatttgaagg atgtcttaaa ggatcttgca ggtctattga aaagctcagc   1320
atctgcttca gcatctgcat ctgcatcagc ttcagctgga ggtgaggcg  gtggtggtaa   1380
cggaggtggt aacgaggag  gaggcggcg  tggagctgga gctctagctg ctgctctcgc   1440
tgctgcagga gccggaggtg gacttggagg tggaggcgga ggcggagctt agccgctgca   1500
```

-continued

```
           actagctgct gctggtgcag gtggaggagg ttttggtgga cttggaggac taggcggtct 1560
           tggtggggga tctgccgcag ctgctgcagc cgctgccgct gctgcatcag gtggtggagg 1620
           aagagcactt agaagggctt tgagaagaca aatgcgtgga ggtggatccg ctgctgccgc 1680
           tgctgctgct gctgcagccg ctgctggagg tggatgggga gtggaatgg gtggaggatt 1740
           cggagtaggt ctcggtggag gattcggagg aggatttggt ggtggatcat cagcagcagc 1800
           tgctgccgct gctgcagccg ccgctggatt tggtggaggt ggacgaaaag gtagaggtag 1860
           aggacgtgga ggcgatggcg acggtaacgg agctagtgct gtagctgcag ccgccgccgc 1920
           tgctgctgct gctggaggat ctgctgctga tgttgccgct gccgctgctg cagccgcagc 1980
           tatgtacggt gacggtgctg atggacctga tttcgataat ggattcggtg gtgaaacgg 2040
           aaatgaggt ggcggatctg gtggtggcgg atccggcgga ggtggatccg gtggcggatc 2100
           tggaggtggc ggtggatctg gtggatcagg cggtggcggc ggatctggtg gttcaggcgg 2160
           tggcggatca ggcggcggtg gaaacaatgg atggggaaat aacggcaaca ataaaatatga 2220
           cgatgatgac tgtgatgaat atggtaaccc tattagaagg gggtaaatta tttgacatta 2280
           tccgccattt gactcatttt tcttagttct ctatgtttta tacttcacct tagattgttt 2340
           tagtttgatt gaataaatta tgttttcgat ataaattttt tttaaattaa attaaacttt 2400
           attagttgac ctgtaaactt tttcatggag ttataatcta aggaacaaaa aacatacata 2460
           atatgttcag tattgtggta aagcacctgt accgcaaaca caatcacctc tatacatgta 2520
           tacaaaatca gtaatgctga caaaatcttc tacactctca cctacacact cgcacacagt 2580
           cctcttacat acacagcact ataatatcct gaacatgaag tttgtgttga taaaaagttc 2640
           agaaaaatct cccctacatc acctgatctt tcactgaaaa tttacgacaa gtattgaaaa 2700
           tagcagaaag aaaacgggaa attgagaagt tttctataaa aaacaatcgg aacaatgact 2760
           ggaatgacaa ggatgaaaat aatgataact tacattaatt aaggccccaa taatctctct 2820
           attttcaaac tttttttttca aatgttctct ctaactcact tgcatctatg tggaaattca 2880
           catactatac taaattacca caagtatcaa ggtttcacaa cctctcatgc cttcatggca 2940
           gaccatgctg ggtatttgtc taacaatgcc tcataaatac ataaaactaa ctaacaaaat 3000
           aggtcagtct gtaacaaatt attaatgcac cattattgca ttttctaaaa caaagcatac 3060
           actggatatt ggcagacaaa atgttgttat tggataccctt tccattctat ctagacactt 3120
           gctttccaca agtcatcata aataaatccc ccctatccca aatgtcaatg gaatgcccca 3180
           acccttcccc cataatttta aaacctagaa taaattaaaa catctatagt tcgtcatgat 3240
           catctttcctt atcatcctct tcttcttcct cctcctcctt cttcttcttc ctcctcctca 3300
           ggttcttggc tgcctgctcc ttccttgcca a                               3331
```

<210> SEQ ID NO 32
<211> LENGTH: 5224
<212> TYPE: DNA
<213> ORGANISM: Unknown
<220> FEATURE:
<223> OTHER INFORMATION: Description of Unknown Organism:Unknown

<400> SEQUENCE: 32

```
           ggatcccctg ctcgacgccg gcggcccggt acacctccat cgtgcggacg ttgttcccgc   60
           gcccgcgagg gtggacggag gtgccggcgt gacgctccac cagcatgtgc cgcaccccga  120
           gccggcccag gaacacggac gtcgacaggc ccacgagcga tccgccgacg acgaggaccg  180
           gaaccctgtg gaccgttcc ccggcccgat cggctcttgc gttcatctttt ctcctccagc  240
           gcgtgatgtc cgcccactcg gccggtttcg gccggggtca tgcatgcccc gcgaggctgg  300
           agcgcggtgc gccgggggacc acacttcacc cgcttaaccc gctgcgttcg cgcaggggca  360
           cggcacgccc gacgatcgtg ctcacgggcc gacgcaccgt catgtgacgc gtcggccgcc  420
           ttaccgttcc tccaggaaga ggtgcgcctc aatgacggtc tctgccgctg tgtccacggt  480
           cccggaccgt gtccccctca ccgtgttcga cggttcccgg gtgcgggtcg tgctgatgct  540
           ggacatccgc gacgggacga aagcggaggt cctggacgcc tacgagcgga tgtccgaccg  600
           ggtcgccgcc gtgccgggc acatcagcga ccagctgtgc cagtcgctgg agaaccccac  660
           ccagtggctc atcaccagcg agtgggagag cgcaccggag ttcctcgcct gggccaacag  720
           cgaggaacac ctggagatgg tccgtcccct ggagccctac gtccgcggca cccactcgat  780
           gcgctactcg gtgctgcgcg agacggccga ggagcgggcc ggggcgggtg cggcggcccg  840
           gggcgcgctg cagccccggc cgcgcatcgg cgacaacgtg gtccggcacg ccgtcaccta  900
           caccgtcaag cccgacagcg tcaccgaggt cgtgaagatc tctccgcct acacctcgcc  960
           cgaggtgcgc gtggacgaca ccacgcggct cgtgcgcacc tccctcttcc tgtacggcaa 1020
           ccggggtcgtc cggccgatcg aggtgcgggg cgacctgcag gccgccctgc gccacgtggc 1080
           ccggcagccg gaggtgcgcg ccgtcgagga agccctcacc ccgcacatcg aacaggaccg 1140
           ggacctcacc gacccggcgt ccgcccggct gttcttcacc cgggccgcgc tgccggccgt 1200
           ccaccacgtg gtgtccggcc gcgggacggg cggcgacacg cagcggtgcg cgctgtacta 1260
           cccggcccac cccggcgccg gaccggcgct cgcccggctg ctggcgcggc agggcgaggc 1320
           caccgtgggc gacccgggca gtccggtcgt cgcctgcacc gtcttccacc gcgacgacct 1380
           cgtcgtacgg ctcgtcgaca cggcggggcg accggagcgc gcgcccgggg ccgtcctggc 1440
           cctgcacgag ccggacgccc tcgccgaggc cgggcggctg ctggacgcga ccgcgctcgg 1500
           cgccgacggc ccccggacg accgggcgct gccgacgttc ctcgcgcacg cccggatgcg 1560
           gcctctgaca gaccgtcagt cgccggcctc ctgacccccc gctcgcccga cctcagggag 1620
           tgaccgacat gacagaacag caggcacgca tcgtcgcctt cgacgacgtc ccgcccaacc 1680
           ggcggccgg cggcgacgtc cgggccctgc tcacgccaca gaccgcggg gcgaccagcg 1740
           gcttcatggg cgtggccgtc gtacggcccg gagaacgcat ctccgagcac taccacccgt 1800
           actccgagga gttcgtgtac gtcaccgccg gcgccttcga ggtgacctg gacgacgtgc 1860
           cgcatcccct gcgcaccggg cagggcctgc tcatccccaa ggacgtgcgc caccgcttcc 1920
           gcaacaccgg cgacgtgctc gcgcgcctcg tcttccacct ggacgtcgtc gccccccggg 1980
           cggacctcgg gcacgtcgac accgaggaga ccgacgagac cgcgccggcc ggggtggtgt 2040
           catgagccgc cggtcgtcg tcaccggcat aggcgtcgtc gccccggggg gcatcggcgc 2100
           ggcccggttc tgggacctgc tggccgcgg gcgtacgcg acgcgccgga tctcccctgtt 2160
           cgacccggcg cgcctgcgct cgcagatcgc cgcgagtgc gacttcgacc cgtccgcgca 2220
```

-continued

```
cggcctggac gacgagacgg tccggcggtg cgaccggtac gtgcagttcg cgctggtcgc 2280
caccgccgag gcggtccgcg acgcgggcct ggacaccacg cgcgaggacc cctggcgcat 2340
gggggccgtc ctcggcacgg cggtcggcgg caccacccgc ctggagcacg actacgtcct 2400
ggtcagcgag ggcggctcgc gctgggacgt ggaccaccgg cgggccgagc cgcacctgca 2460
ccgcgccttc gcccccagca cgctcgcctc caccgtcgcc gagaccttcg gcgcgcaggg 2520
cccggtgcag accgtctcca ccggctgcac gtccgggctg gacgcggtgg ggtacgccta 2580
ccacgccatc gccgagggcc gtgccgacgt gtgcctggcg ggcgcctcgg actcgccgat 2640
atcgccgatc accatggcgt gcttcgacgt catcaaggcg acctcgccca gcaacgacga 2700
cccggagcac gcctcccgcc ccttcgacgc ccgccgcaac gggttcgtga tgggcgaggg 2760
cggcgcggtg ctcgtgctgg aggagctgga gcacgcccgg gcccgcggcc ggacgtccta 2820
ctgcgagctc gccggctacg ccaccttcgg caacgcccac cacatgaccg ggctcacccg 2880
ggagggcctg gagatgcgcg gggcatcga caccgcgctg gacatggccc gcctggacgg 2940
cacgacatc gactacgtca acgcgcacgg ctccggcacc cagcagaacg accggcacga 3000
gaccgcggcg gtcaagcggt cgctgggcga gcacgcgtac cggaccccga tgagctcgat 3060
caagtcgatg gtgggccact cgctcggcgc gatcggctcg atcgaggtcg tcgcctgcgt 3120
cctcgccctg cgcaccagg tggtgccgcc cacggccaac tacgagacac cggaccccga 3180
gtgcgacctg gactacgtgc cgcgcgaggc acgcgagcgg gagctgcgca cgcgtgctgtc 3240
ggtgggcagc ggcttcggcg gcttccagtc cgcggtcgtg ctgaccggac cggagaggag 3300
gctgagatga gcgcaccccg gcgagccgtc gtcaccggac tcggagtggt ggcaccccac 3360
ggcatcggtg ccgagacgtt ctggaagacg gccgtggacg gcaccagcag cctggccgg 3420
atcgaccggg agggctgcgg ccacctgccc ctgaagatacg ccccgactc 3480
gacccggccg ccctgatcga ggacacctac ctcgtccaga ccgaccgctt cacccactc 3540
gcgatggcgg ccacccagct cgccctcgac gacgcccggc tctcccgcgc cgacatcgac 3600
tcgccgtact cggtgggcgt ggtgacggcc gcgggctccg gcggcggcga gttcggccag 3660
cgcgagctgc agaaactggt gggccagggc tcgaagtacg tcggccccta ccagtcgatc 3720
gcctggttct acgcggcgag caccggccag atctccatcc gcggcggctt caagggcccc 3780
tgcggcgtgg tggccgccga cgaggccggc ggcctggacg ccctcgcgca cgccgcgctg 3840
gcggtacggc gcggcaccgc caccgtcgtc gccggcgcga ccgaggcccc gctggccccg 3900
tactcgatgg tctgccagct gggttacccg gagctcagcc gcacgcgcca cccgggccgg 3960
gcctaccgtc ccttcacctc cgccgcctgc gggttcgtgc cgccgaggg cggggccgatg 4020
ttcgtcctgg aggaggaggg cgccggcacg cagcgcggcg ccgacgcgcg ggcgacggtg 4080
gccggccacg cggccacgtt caccggcgcc tcccgctggg aggagtccaa ggccggcctg 4140
gcgcacgcga tcggcacgggc gctggccggg gccggctgcc gtccgcagga cgtggacgtc 4200
gtgttcgccc acgccctcgg cgtgccggag gccgaccggg ccgaggcccc ggcctggcc 4260
gacgcgctcg gcccgcacgc gcggcgggtc cccgtcaccg ccccgaaggc gggcatcgc 4320
cgggcgttct gcgcggccgc ggtgctcgac gtggcgaccg cgctgctcgc catggagcac 4380
gagctgatcc gcccacccc ccatgtgctc gacgtctgcc acgacctgga cctggtgtc 4440
ggccgggcgc gtccgcccg gccgcgcacc gcgctggtgc tcagccgcgg actcatgggc 4500
aacaactcgg cgctcgtcct cgcgcagggc gccgcgccgt tcccgagta agtacccga 4560
acaggtgtct cacgtcccct tcgggcgcgg gcacccgagt caaggagctc aaccacatga 4620
ccgacatgac cgaacgcgtg gcacccagg tgaccttcga ggaactgtcc gccctgatga 4680
agcgcaccgc gggcgtgcac gtgaaccgc ctgacctgcg ggcgcgggcc gaggagggct 4740
tcgacggctt cggcctggac tccctgggcc tgctgggcat cgtggccgag ctgagaaga 4800
agcacggcgt gggactgccg gagcaggtgg agcgctgcaa gacgcccgcg gagttcctcg 4860
cgcaggtgaa cgccacccctc aggacgcgcg tgtgacatgg ccgggcacac cgagaacgag 4920
atcgtcatcg ccgcgccgct ggacctggtc tgggacatga ccaacgacgt cgagaactgg 4980
ccgcggctgt tcagcgagta cgcctccgcc gagatcctgg agcgcgaggg cgaccgcgtc 5040
cgcttccggc tcaccatgca cccggacgac gagggccggg tgtgagctg ggtctccgaa 5100
cgcgtcgccg accgcgcctc cctgacggtc cgcgcccacc gcgtggagac cggcccttc 5160
cagttcatgg acatccagtg gtgtacgag cagacgcccg agggcgtgct gatgcgctgg 5220
atcc                                                         5224
```

<210> SEQ ID NO 33
<211> LENGTH: 30601
<212> TYPE: DNA
<213> ORGANISM: Unknown
<220> FEATURE:
<223> OTHER INFORMATION: Description of Unknown Organism:Unknown

<400> SEQUENCE: 33

```
gatcttagac cttattcact tgatacgtgt aatagttatt acgatagtat gttttggcc 60
gattcctccg cgtcttcttt cgacgacgtg gaggtggagg caaaagcgaa gtagttgtgg 120
aagaataaga attatgatta tcatgattat tattcaaatt aactctattg ttacgtaccg 180
cgctccatgc agacgtttgc caggagacga cgggtggaag ataggaagc gaagaagcga 240
aagcggaaga cgtcgtattt gaattcgaag atgataatga tgtcattgat gctgatgatg 300
tttttgttgt ataatgagat cggcatggag gcatttcaca atctcttttgt tcgcgaggct 360
taatctctga gcactcgata tcgtcttgtt tacgaccgga aagcacgtct tcacaccaga 420
ttttgcggcg ttgaactccc ccgccacacg atacagaaca ctggaattat tattagaagc 480
ttcaatgatg ttctaagaac ttacgtgagt ccatggagat atctgccaag aattatttgt 540
gagtggtgga catagttctt cattgcattt atcaaacatc tttggttttc tggtttcatc 600
gcaagaagac gaagtgcaag atacactcg acgacgccat ccccaccac aagaagcaga 660
gcactgaaca atcgtacatt agtaaattct aaatctgaaa attatatatc ccacttttga 720
ccaatctcca ataatccagg ttcttctccc tttggacagg gttcaagtcg 780
gcaatttctt gcacttgttg gtctcttttg cacatcacaa tcaacatctt tcaaaatcgt 840
ccgaccaccg tcttccgcac tgacgcatgt aacatttcta ctttgttgaa catgagttcc 900
acaagtagct ggacactctt cccattccgc cattttccag tatgaacaat cacgaaggcg 960
acaatttctt gttgatactt ccttatccaa atgattgcaa tactcatcag gaagatcacg 1020
```

```
aacatgatct cggcacttga gaagacgacg ttgagtacca ttaccacaag ttgctgaaca 1080
ggctgtccat ggtccggttg cccatcggat tggtggtacg tcggcttgaa gttttttgaag 1140
tactctgggc ccatcacaag tatctttttc acaagtcttt tttaggcgtg gacgagtatt 1200
ctgaaatgat attttcgttc aagattaaaa gcaaactgaa acgtactcga tcacaaaaat 1260
attcatcaac aatagttcct tcagatccac gagtacacga aacacttcta gtctgaattc 1320
ctgatccaca agtgactgag caaggggacc aatgacttgg tttccaagat gtacatggca 1380
gaagatggca agtttgacta gtttctggca ttttggtatc tccacaaaaa gaagcatcaa 1440
cagattgttc gcggtatatg cattcggttg tacgttcccg atgaccgatt ccacaagata 1500
cagaacactg aaacgtattt atggtattga caacagcaat tctggagtat ttgaataaac 1560
ttacagcact ccaatcagta tttctccaaa atgggcaagt gcctaaatta catgtctgat 1620
gagaagcagg ccgatcagat gcagtaccac aaagtgacat atcgacttca gttccatttc 1680
cagaaacaca tgaaactctt cttgacgacc atccatcctc acaagaaaca ctacactgag 1740
accattctcc aagtttatat tttggacatg attctctatg acatggtttt gtaattatct 1800
tttccatttt aaggcaacga tgttccggta gtactgatct atgacgatcg gtacaattag 1860
cgtctcgata ctgtacacca tctccacact tagctgagca gtcagaccag actccgaact 1920
gccaccaagt acaagcatgt tcattacaat gttcttgtgt ctgtgctgga cccatctgg 1980
atgtatgtgt ttcccgatcg gctgcatcca aacattgagc atgacgcatt ttgactccac 2040
catcacaact tcgagagcac tctgaccaat gcccataaac ccatcttgga catggaattc 2100
tgttacattc ccgttctgtc gcctcttttct gttctctgcc gcacaatgac tcatcaactc 2160
gacgattcga atcatcaacg caatatgact tccgatgcat ttttccattc gatccgcaag 2220
tttcagaaca tgaagtccat tctccatagt tccattttct tccagagcag tcaatgtaac 2280
aactggcaat atcggatggt tttgaattac gatcacatag atgttcggat gctggagttt 2340
gacgatcacc ctccattttt acgcaagaaa ctcgttgacg tttctgtcca gatccacatt 2400
tggcactaca actagacaca tcttcagtga tccatctgta aatataaaaa tttattatag 2460
aaatctaatg aaaatatgta gtttaccttg tagaacaatc tatattgcac attcgtgttg 2520
cttgttttgg tttgagaaca ttttgacaat ttctatcatg actttgacga tgagtcgaca 2580
tgtccagaca cattaatttt tgcgattgct gtccacgaca ggctctatca cattctgtcc 2640
aagtatccgt aactctccac aaatacaatg cactggatat tggccgaatt acagcatttg 2700
gaacagccgc agtcatgtac tcatatgaga tgtcgggtgg atgactacca acagaaagaa 2760
catgaacata aatgtcactt ctaatcggac cagttccatt tatccgttca ataattgcat 2820
cagaaccaga atattcgaga acagtgtctt ggaatgcaat tgttggcga gccagtgata 2880
cttggaaatg accgttaagt aggaattcac cattggcggc acggagagct gaaggttaaa 2940
ataaagattt tcatgggtat tgataaacaca agggtgagtg atgaaaaaag taaatgttcc 3000
aaaaacactt tgtatagaaa ctcacaaaga taattgtcat cttctttcat attattatat 3060
ccttttctgcc ggatatcaat atttgcagaa ccagctggaa tcttcattac ttcgttataa 3120
ccaaaggttc cttgctcatt aaatgttcct ttgacaacct tacaggaaga atcatcccca 3180
ccgcaaacac cacatttgtc tcttcggaga gttgaatgaa gttgatgatc acagcctgaa 3240
aatccactta ttttcaattt tcttttgaaa tcagatcaat gttacctgct ggcatacaag 3300
ctccagctac acaaatatcg tctccatttc tatcacatgg tgttccatca acaactttat 3360
ctcgaagcag atagaacgct gcagatccac tgagccgaca atacagcttg caacgttcat 3420
ttggtgcaac attcgcatat tttggaaccc agtgagtagt cgttgaagcg acaccttgga 3480
ttccaatatc tttattgttg aattcagaac attgaacttc acggtatggt tgagtatccc 3540
atgggcattc ttgtgtatta catgaccgat aacgttctcg ttaccaaaca cagtactttc 3600
caccatttcg aggtctaaag taatatggga aaatgtcatt ttaatattga taggaaagct 3660
tagccagtgt ggcctaaaag ctggaagttt ttttaaagat gcgttttcta tcaatttaag 3720
ataaccggct acttcaggtg attctataaa ttttataaag cttggaagct aggtaaatct 3780
gaaaagcctt aaactatctc gaagcggccc gaaagcccag aaaagcagag acggacaaac 3840
atttaagagt gatcagaagc actccatacc ttgatgttac atttgatttt agtgtttcca 3900
cctcgttttc acttctgaac tcgccgattg aaaatatttt gattgaatat attatttgct 3960
ttcagactat ttgatatcat ttcgtttggc agtttaactc actttgggct gtcacaatct 4020
cttaatccttt tttgaacacc accaccacaa gtacgactgc attctcccca tgatcgccag 4080
tcaccccatt gtccgtcaat tttggtaagg gattcggggg ctagacgaac acaggctcca 4140
tgatgacaga actaaatatc caagttttta tgagtttctt ttgtgattaa tttctgagat 4200
actcaccatg cttcttgatt cgtcacaagg agttccgtcg gcccatggca tatgctgagt 4260
tcgacagccc atctggcttc cgtagaatgt tgcacaccaa agacggcggc atgtcggctg 4320
taaaatatca atgtttcatc ttaaagaata tatttaggca aactaaccat ataagggcac 4380
aactcagaag ctggtccaaa tacaaacttg cactgttgat gagcatcgta tttctttcct 4440
ggttcatcac gtacaaagac atcctcgtag taacgacctg cgaccggctg atcgaataga 4500
cattgagttt gacctcgatt atttctgaca aattgacaat taaatagaat caaaatttta 4560
atagctatct tactcgagga atcgttcgag cattccagct gaacatggcg accaactcca 4620
tggatgagtg ttatattcca acgttggtgc cattatgtgg aagttgttct gaaactgcgt 4680
tttatcaaat ttagtgcttt ggaacttgca aaccttatta accggcatgt aggtagagca 4740
ttttcgttcg tcatcatgag gaatcgaaaa cacatgaccc aattcatgag caattgtgaa 4800
tgcagcactc aatccattgt cttctatgat tgcacaactt ttttgcatat cacacattgt 4860
tccaagttca gcaagtccaa gtgtatcgca ttttccttgt gatcgacaaa tatctttacg 4920
cgtcaaaagg attgcaacgt catgatgttg gacactcgaa tcatctggat cattgtaata 4980
ctgctgccat ctacagaaat cttgaagtgt ttgttgagcg ttctgagtga ttcgtggtcc 5040
agcgttttcc gttttcaaaa cgatcaactt gacaacaacg acattgatag atgcacgaag 5100
ggattggtga cgatagatgg aagcaactgt ggagaagaga gtgagaacgt agtcttcaag 5160
agatcttccg tgtatattcgt acatttttgt atccgccacc acaaggactt caacatagtg 5220
atcccaagag ttggcagctc ttcgggatct tgcttttcgt tctataatta aatccttttg 5280
tttcataaaa ttatttaaac attttttttac tgtatccttc ctattaatct tgcaccccag 5340
agctccactt tgacctatct ttgttgtcat tgactctatc aaaaactgtt caactatgaa 5400
aatggggatg caagactaat aaaaggtatt ggtaactggt tccagtagag ctttttttac 5460
tatctgtttc attgattcaa ttttatataac catcttaacc gttcaaatct 5520
cataacatag aacagctggg cagcccgtga aaaggtgctg aaatcccagt aatttcaatg 5580
gcattcgacc acacacaagt gatccattat cctttgctct tttacttcgt taactaccat 5640
tagctatagg ggaccacga gcaaaattct atagtttctg tgtgtgttag ggtgttttaa 5700
tgggctatta cacaacaccc gatgggatca gcagaatctg agatcttttg ggaaccggaa 5760
```

-continued

```
aaaaatattg tgataacttc tcttttttct acattttta cagaactagc aggtaaactt 5820
tcagattgaa atctcgaaaa atgcatccgc ctactcaaaa agtcgttttt aaaatgattg 5880
tttctttgtg tttgtcctct tttcccgga cgtacgcaac acaaaaccgc ttgcgcgagg 5940
atgtacacaa aacgtacgtt ctgcgcaatc ttttccctgc agctctctct ctctcacttt 6000
ttctactcca taaatcagtt ctctgtctgt ctcccaccac ctaaatcatc atcagcatca 6060
tcacagtccc cccaccaagt tcttgtgtct tctctgacct ttacacgtcg actagggaaa 6120
agctctcaag cagacactcg agcgccagtt gaaaaaaata gtgtgtccaa atgagcagtt 6180
tcgaatttga accgtttgtt cttgttctga cataaaccca aaaaaacgaa ctaggcggca 6240
aaagagatct ggataatcta aagaatctag acaaatttca gaagttctta ccaataacat 6300
cttcccactg atcttgccac gtggcaaccg tcgtctccgt ctcgttgaca ctggtcgagt 6360
taagatggtc aaacgatttg aagtgcattg gatcgaactt tcggacgaga tgttgcctat 6420
ggcgacttgc tccgtcgtgc tctagatgtt taaagtgtca gagaaagtga ttacaaagtt 6480
tctacctgtt ccgtttccac taataattgg ctcaaccgta tggattccgc tgggtagtgc 6540
aagcattccg tactgaaaaa ggcttttatt caccaaaatt cgaacttata caaaccaatc 6600
cgtcttccga gtcgcataaa ttgacgatgc tgtgctgatg tacaccttta acgtgtgcac 6660
ggtagataca atcgggatct gttcgagaca ttcccacctct aacctcctcc tccgagtcca 6720
aatataagac catcggcgcg aaatttgaat tggaaaagtg gggaacactt ctggaattga 6780
aaattaatac gactgttata ataaaattga aatctcatac ttgttatgtg agtccggtat 6840
ttgattccat ctgtgcaaat gaacgatgta gacggcatca tctgatcgta atcgtaagtg 6900
acaagcatgt ccacagtctc tggcaactcc ttggagtcga cgtcgccgat ctgttgacgt 6960
gacatcacgt tttccacgac gtccataaga atctcttcgg acgatgtgat ggctgtcgat 7020
gacgtgtata ccggcgtctt gacgccatcg actgtgatgc actggcacac ctgaaactta 7080
gaacattatt tcacttcaaa acttttggga ttgttacctg agtacttggc cctggagaac 7140
agcacatctg atgagaattc tgagatcgtg ccactccctg ctgaaaggaa catttggtta 7200
aaaacaaaag ctgataaatt aaaataatta gataaaacg aacattgaca cgcataaacg 7260
aggcagacga cgaggagtat gagagcggcg acgacgggct gcagcagatg gaatgagccg 7320
ccgatggagc gcataccaac agctccgtga tgatgattat gattgtgtgg agagcagcaa 7380
agaaaaaaga gatggaaaga agcagaagct ccgataaagt tcgtccgtct cttctgaaac 7440
cttccaaaaa ctacctgctc gaggtgaagg gaagtcgtct gattgaactg ctactgcttc 7500
tgatcttttg ataatctccc gagtttgtgt tttcgtttag tcgaattaaa attgtagatt 7560
gtggaatgag cacttgcaat agggaacaga gcatcacaga ctgaaaaatt aaaaattatc 7620
tagaatgcaa gcaatttta aatttgtttt aaaatcactt attctgacgc catcttcttt 7680
tccgatttgc gcagaataaa taaaaacttg actgtaatat tgggaaaatt tcgaaaaaaa 7740
acaccgttaa gtctgagccc accttcgcc tttttttgtt gacgaaaaaa accaaacaag 7800
ctttaaattc ataaaattcc caattttaaa aacatctaaa gtcaattcct cccaataatg 7860
catttgtata tgaacaaaag tctgttgacc ataagtcgtt atattactac aagcaattgg 7920
tcatcaacaa acctcataaa aatcagtttt gaacgggagc aatttatata aactctgtgt 7980
gctcttttgc tctttttctt atttcttagt tgtcttctag ttccgccacc actttcgctg 8040
ctcttgacga aatctgtaaa ttgttcgtca tttttgattt ataagatttg tttggctctc 8100
ggtaggagct ctcaagctgc taatagtcct atagtaaagt actaaaaaca caaagaagca 8160
gatgaaggtg tcataaaaca ctgataagaa tcatcatgat taggttggtg cagagaaaag 8220
aagaagaaga aaaaggagat ttagagaaga gaaacaagaa taaaatgca aaaataaaaa 8280
aaatagtaat aacaatgaac gcagagtctt ccatgttgga gaggaacag gacccatgtt 8340
gatgtgtatc tgaggggatc caatgtgtag tgatggtagt aaacacttga gagggaactt 8400
ccacccccga ctagatgatt ggaagcaatt gatgatagat gtagagccaa agaattggga 8460
cctactaatg atctagtcaa gattcttctg ataagagaaa aagcaaggaa agaacatgaa 8520
aatgactggt gattgaaaaa taaaacggtt tatgaagtcg gggtgtacta aagatgcaag 8580
gtctcttgtg acgtatttt tcttccaggc acgttcgcgt tattcacgat tttatgcaaa 8640
caaggtaagg agtgttttga attttgaata taaaaattta aagaaatta agttagaca 8700
tttgaaaaat tagacaccct catgggaaaa attatagggc gaggagggc ggtgagagc 8760
gccctaattt ctgctcggtc gggtagaatg tctaatctaa atcctacctc atgtttggct 8820
ccttcttaaa tcaaaagctt aaggtcatct ctgaaacgtg cagttgacaa gttcaatggt 8880
aagaacaggg agcaagcatt tacaacaaaa agtaaacaa aaattgcatt tgtcgcagtt 8940
caaaatggaa caactcactc ccactcgaga acgttttgaa ggggagagga agaagaggaa 9000
aatcatcaca caggcacatg gaacttctgg gacacaaaac aatacaaact gggtgccgtg 9060
aatctcagta cacacacaca aaaatcaaaa aagacggaaa ttaggagcag atgtggtaaa 9120
gggtggttca atgctgatgg gagagagagg gagaaacttc aaaaaaagaa gtttagattt 9180
atgttggcta tttcaatcct aaatttatct aaacaattct aaaaatgctg gtttttggaag 9240
gttatctggt aatggtgaag ttttataaac aaaacaagac aaacaattct tgagatctta 9300
aaaatcttag cgactacaac aatatttagg tatttttaa tggaaaaaag tattgattgt 9360
tgacttggga aattgaacag caatttttg tacttttaaa tcagttatat tttaactttt 9420
tagagcacat ttcgtagaca aaagggaaa cgattggtcc aacatgtgga gatgatgatg 9480
tcaacaagtt ttggatcgga gccaaaaaag aaacaaaaca ttcataccat gatgggaaac 9540
aagaggtgca gcaacaactt ttatcaatat tttgtttatg ttttgattat ttttctggca 9600
cccagccagt aattcttttc cgtagagttg acctagaaaa tgttggaggc ggagtcttag 9660
gatcaagaga cgcagactat caaagtaaaa tgagtaagga gaagtgatat aaacttagga 9720
aacggaggaa aaaaggacga tgataagaga ttgaagactt ggaagagtgt gctctttgcg 9780
ggagagcata ttctttttgag aaaaatggga cctaggggca actgacgcaa ttgaaacatg 9840
gtcgagcggt cggcgggaag acaaaaagtg aagaaggatg ggcaagaaga agcaagagaa 9900
atggcacccca ccgtggaaca tgatcatgat gattgagagt gaaaattgga aatctcgaac 9960
tttttgcaa cggcgcgttt tggaaaacta acaaagttga ccaaaaaatt attttacatg 10020
tataccggga tgtctaagaa ttgtaaaatt gagtgatcct ttctgtgaca taatttaaag 10080
caatttattt tggttattc taagcgcctt tttatactag catgttatat tgttaattt 10140
attatcataaa ctgccgttct tcctatatt attattgcac ccccttttgtt cattctgaca 10200
gactatacct cgattaatca taaaatgtc acaaaagaat aaaaacaact attttacatg 10260
aaatacaaga aatttatcaa ttgccaaaaa ttcggccaat cggaaaaatg cttggttgcc 10320
aattgtcaa aaatttagtc aattggaatt tgtcgatttt ccgaaatgat atgaaagttt 10380
gaatgatgca gctaattttg cagtttaagt ttacatttc aagttttactg taattttttcc 10440
aaaatatgaa gaagagttttt acgaaattaa aagataataa aaaagcaatg caaacatagc 10500
```

```
tatgaaatct gatcccgact aagtttgatg gacataggat taataatatt agtctaactt 10560
tctatagaac actaaataaa tacattcact ctcgaaactc tcccttttct gccatcaact 10620
accgtactca cttttgactc aatgacccgc aactgtcaag atgagttagt ttcaagattc 10680
tctgaaacag caataatcta acaagagaaa ctgaaaaaat agagtaaaac taataataat 10740
accacataaa ttgacatgca tgatagatga ttttccggtt ttcaacaaga aaaacaacaa 10800
tttccgagaa atcctcatag tttttggtaa gaaaaaataa attgatagta atacggtatg 10860
actattactt ctaaagactt acctgattag aaacgtgtag taattgaaga agaaaagttg 10920
aatttgagaa gttgaatcga gtttacgatg tctgaaaaaa acatagatat tatggtaaga 10980
tcaagcatag aaaaaatgga aaaatacaag aaaatagaga ctagagattg cataggtttt 11040
gcggtggcga aaccgcacac attttttgtct gtgttatctc taattttacg ctctcggtgt 11100
tctctattta ctgtccagaa gaatgaagaa tatgggggaa aagtgcgcgg gaaaattgag 11160
agaccgagtg atgagagccg cagttttgca aaacttttttc gggcaataat ccgccggcga 11220
gtactacgag aagcacacac acatacgaaa actgttgagt taaaacctaa aaaattgttt 11280
cgacatattt aattttcgaa ctaaagttta gagggtctgt gcgtgcattt ttgaattttc 11340
caaacaactt tcagttttgc ggaagaaaat tacagcgatt ttttcgaata tttctgaaaa 11400
caacactatt gcgtatcaaa aattttttcga tttgccaaaa ttcagactaa gtttttggtgg 11460
ttttggtttg caaacattta aaagaactca aaaaacatttt ttagatgttc gaaaccgtac 11520
aattgtagga tacaaatagc tacagaacaa ttagaatata aaatagagtt gtcaaacatg 11580
tttaactaat acaaaaacac agaaactttg aaactcgaaa tttttatatc aaaattgaaa 11640
aagcttgtaa aatttaaata tggatacagt acaaacaata taatcataga tcaaaatagtt 11700
catttattta tatatcttgg caaatcaaat cgtatccctt acccactcat attcgatgag 11760
tctacaatta aatcagttgt tttttcatcc tcccggacta ttagttttaac ttccacttga 11820
acaagggcaa agagtacatt aggaagagtt tatgatgaca ggaaaaaagc tatgtaaaat 11880
gacctctttg gattgaaaaa gcgaacgaat tgaggtttag accccccgga aaatgaagaa 11940
ttcgtggcct cgagaatagc aaattggcgg aattaattat ccgtaagagt gtgaattgga 12000
aacaaccggg acgaatggat tactgaatca aaaatgaaag aaagaagaga tgaaaatacg 12060
tgtgaatcgg atgaaatgtg atgattttag aataacctaa atgcaacaaa acgacgtaaa 12120
gacgcggaag aacaggaatg atcaaggggt acatcttata ggggaaaaat gcactttttg 12180
tgctccaaat gtgagagata atcaggtagg aagagacgta gaataggaac aggaaacgt 12240
aacgatagtc cgcaggtgct tgatttctgt gcttttgcat gtgttccgat ggaattttttg 12300
gaacttttca aggggttttcg gaaagggttc gagatttcgc atgtgagctt tggaagaatt 12360
ttggaagaac tttcaggata acatcgctca agcttgtttg ttagatttca gacttcaaag 12420
tatataccga ttattgaaac attttaatcg tttcttacta ttagtaaagt ttaatcacag 12480
tttgaaaaaa aaatcacaat tttttcaatt atttagacca aactaattat ggtacagaaa 12540
ataacttgca acccgggtat ttcattctaa tttttttttcat ttggaaccac tagttttttga 12600
aatagaaact cgttaggatt cttcacatat tatcataact atcagtattt tgttgcacat 12660
cagatctaag ttcagtcaaa ttagaatcgc aaatttgacc atcacacttt aaaacaaatt 12720
tacttaggca cagggcatcc ttctaacttt tttgtccccg acaaaatgat gacaaaaatg 12780
acgtgaggaa tcaaggagaa aaaggaaaag aacaggaagc gaaaagtagg agaagctctt 12840
gattctctgtg ctcattcctt gttcggatga gctcactgtt tgcaacattg gcgttggtgc 12900
gcgggaatcg ccattgccga acttttttcaa gagacagaga gagagagaaa gagaaggaaa 12960
acgttccgat tttttaaaatg gaaaaaaatg aaagaggaag atgatgaaaa aatgaactct 13020
gcgtgacatt tgttaatatg gaaaaagcat gattacttca aaattgtaca ctaatcccca 13080
cagcacacat tttgaagact ttttttacaaa aacaatggtt taagcaagct ttaaaaaaatt 13140
gatagtatcc ttaatgctta atcatatcca agttagttt taagttttga tttcaaaaat 13200
ttctacacta aaaaatcata cttagtgatt atatgcaaaa caattttttaa attcaaggac 13260
atattttttga ttttttggaag gatgataact ttttttgtgat tccgaaaaag attaaagtag 13320
gtttaaaacc tctgaccttc tacagaaaaa acattacctc tatgaatttt ttttcatctc 13380
gttcagaact tgtctcgggt caagccatga agacatgaga tagggtgtaa aacgttccga 13440
agagaggttt atgactatta ttgtagttga agagaaaaat gatatctcaa tggatttcat 13500
acagatggtc ggatttcatt cataaaatat cataagaaaa ggtacgttta tgactgtcta 13560
ggtcaactgg ttttaggttt cttggaattg tttcaaacat ttttaggaaa tatttttcttg 13620
caaatatcta ctaaattgaa gtttgttatt gttttttgaca tattgtagat tttagagaag 13680
aatcactcag agcaaaaatg ttgggaaaac gtgagaaaaa tccaagaac aaaagaatgg 13740
tcttactatt agtagatcaa aaaaccagac caattattca tattcctact attcaatata 13800
tattcaaaaa tgagcaaacc aagaaattgc acctaattta tcatcccaca tatattccga 13860
cgaaacattc gctctacctt cttttttttct gtctaggaat tataaagggc cataattata 13920
atttcagtca aggttttggga aaattgttcg actaaccatt atgaaagtta aaaaccaatc 13980
agtcaaaaca cacaatagga atataaaatt cgtagaagaa aagcttttttt tttggtcgaa 14040
agcaaaatca aattctggaa ctgcgacttt tttagtgcaa ttatccattc aacgcaagtt 14100
gtctttcaaa atttaaattc cagaagagtt ataacaaaac agacaggtgt acaagtaaaa 14160
gaaaaataca agtttttatcg taaaaactga tacgaatcta gatacacctg ttaaaaaagg 14220
ctttctcgaa acccagatgc cgtacgaagt aagcagcagc caactaaaca ttttgagtaa 14280
acatatggca agtgttttgg cgcaaattgt aaagattttc cgtgtgggta actagaattt 14340
gaaactgtaa gtatgacgac ttaaccacac aaaatcaaat ttcaaagat cttaaaatgt 14400
tcgaacttttc aaaacttta agctctctcg catctaccgt agtcttctaa taacaacagt 14460
cgtaagagaa agctcaaaat ttttcaaact tttttctgaat gacagaatca gttgtataca 14520
aaaaaaaccc ccaaaatgcg agccccatga acctgacaac cagcaaagtc gaaattgtaa 14580
aatcgtatag atcttggttc acgacatgaa gagcaccgcg ggggcacacg agagcaacta 14640
ctgcaagcgc tcctgaagag aagaaacatc ttttttttccag gaccactggc cagtagtgct 14700
ccccccagatc actttctttt ttcttgcttc atctgatttg tgtctgcgtc gtctgatctc 14760
tttagaacct atccttcttc ttcttctttt tgatacttcg acatcagaac aacatcgaca 14820
tgtatcatct tttctctttt tttttttgtta tctattcatt cattcacttt tcatttagtt 14880
tgattaatag gtgacatgaa ctcctgtcac tttttcaattt caacttcttta aatcttaaac 14940
tcacagtgat tccagatatg agcaactcca atgaggtgtt gagtagaaac ctaaatataa 15000
catttttggat gttttgataa tgttggaaca aataaaattga aacaaacaag acttgaaata 15060
gagacaacgt gcagaataat gtctaccagc tggtttcagt ggcatatttgt accacgaacg 15120
tccgacagaa cgaataacat aaagatcaag aaaaactgtt tgggagcaga caaacaatca 15180
gaacacagtt ttgttgaggg gaccaaatca taattaatga ctaaatttta acgaagaaag 15240
```

```
tgctcgaaaa gaacagaatt tagaagttga tgaacaatat ttttactttt agattaacaa 15300
ttatgcttta caaatgacat ccaatctaaa gcatctggta atctgaaatt tgtcaaaaca 15360
gctttcaaga ctagtttcaa atttgtcgat tcaatggatc aagtgtgtaa ttgatccaat 15420
aaaaaagagt ataaagtgag aaggaagaaa gtgtgaaaaa agaagaacgt gaaacgtgca 15480
gaagatacga aatgagtttg aagactgcac ttttcgagcc tcgatggtca gtcacttggt 15540
cagttgcgaa aaagctgtga aaatgataca ttgtgtcggc tctcgtagag aagaaagcca 15600
catggtcagg atgactccaa ctgggatatt cagttgtaaa gaacacaatt gatattttg 15660
catcttttttt aactagtttt tacaatatga gaaattgttc tgtgcgaaaa atatgacttc 15720
ttccttgttg ccgaagtgta tttccctgga aattccagta aatacctaat gtaaaaaatc 15780
tcagcagaat gtgttcttac attttgttgt aataataatg tattaaaatt gcattaatta 15840
aaaatttctt caaatgttc ctacgtcttc tatgcacatt atttaggtca cagtttcatg 15900
gagcacaaaa cacctgccga cgcctctaaa atagttataa ctgcgcatga aatcaggtag 15960
aaaaaactac aaaataacca atacaaattg agtagggcga tggagaggtg ggcggttgga 16020
gaggcgggca acaagcgtcc tcatgacgcc ttgttcattt agaatgtgtt tgctttgaat 16080
tacatacaag tttctaaaat ttaacttaca aaatttaaaa aaagtcacaa caataataaa 16140
agttgtggca atgaaatgtt ttaaaaatct aaatattgag ttttaaataa atgattttg 16200
aaaattcaca aagaaatgtt acaatctgtg aatgaagacg aacaatgaaa aagtgaggaa 16260
cggacgcgga tattacacat tcagtcacac aataaacgtt cggacactac cacacatttc 16320
tctcatcatt tttttccaaa gtttattcta aagttcaata ttttagtttg attattttgg 16380
acactattct taaaattaat gtataaatagt ttagaaaata ttttgaaaca tgaaactttt 16440
ttgttgataa aatagtgcca aacatcctta tgttacgcag ttatccaacc acatttttct 16500
cattttttcca ccaaaaaaca ctgaaatggt ccataaaacc tattcaaatg gatatgagaa 16560
tattactttt ttgacatgaa attttcaatg atgtaatgta aaacaaagaa aaatattgcg 16620
ggaaaaattg aacggcgtat tgcaaaaatc ggtgtgcgga ggaggagaag gaaaaggaag 16680
agcaggagaa gcggaccgaa gaattcagaa gcttttaaaa taagaacggc gactttcaga 16740
caaacaatgg actgttgtat aaaaataaag cggaggcggt agagagtcaa agctttcaga 16800
aatgtattag aataggtttc actacctgtt gttgaactca aaaaggtgtg aaaaagtgaa 16860
agtttgtctg aagtttatga cgggaagtgt ccatcaaata actttcaaaa tttgacttat 16920
cagtgagaaa aacacgtcat tttggaacgt taaaatggt ggcaccgcaa aatgttcaca 16980
atgtgaagtg aattacgtaa taaaatcagt tttattaagc ttattaaact aacccttccg 17040
gactatttgt ggaatgaaac aattgggggg gtttttttttt ccaattttcg attttttttt 17100
gaatttataa ttaccggaac aaaaatatct ttaaattatt aagatttgag tgatgtttga 17160
aattttgaac ctgcaaaaca taagcacaaa aatatgagt ttttgttta aaatatcaat 17220
aggtgtttttt tcacagaact ttaaacaaca aatactcata atttgaatga aaacagtaga 17280
tcccacaata ttttgaaaac ttatctatat atatatat atatataa ttacgaaaaa 17340
aaaacaaaaa gaaaaaaaca aataatttgt cagttgataa ttttttagata tgagttgcca 17400
aaattgggca atatggtgaa gaaatacggt agttcgtcgc actgtcagac taattttcaa 17460
gtgttcctag tggaatgaaa ctaacagaag ctatacggta tataatatta ggaacacaat 17520
taaaacgaac agcggaagaa aagatcagt ggtcacttcc gatttctcag ctgacttttg 17580
aatgggcacc tatcatcatc tcacttgttt atttgaacag tctcgacttt ttccaattgt 17640
tggcttctag ttcaagaaac gaaaaaaaga gcaataacgg aacagaaaat tcagaaagtg 17700
gaagagaaat atgagaaaat gatgatgata ataataataa gttagaagag ggttatcgat 17760
gaggaacgga aacgttatct ctgatcgcca tctcattatt attatgagac acaaagatgt 17820
aagttatggt atctttgaaa gaaaagaaaa caggaaatta tacagaacac acacaatttc 17880
ggagatttca ttcgaagaac ctaacccaat ttgaactcac tcccacttcc tcttgtctat 17940
aaaacagtca atcacaggaa caggtgtctg tcttttcaaa atgtatacgt tttccgaata 18000
atgacacaca atatcacaga caaaatgatc aatgaggttg cagaaaagaa tgcaaaaaaa 18060
tatagaaaga gagggtgaac aggagataga gaatcaaaat ttgcatagat aaatatgcaa 18120
tagaaaataa caattttttga acaacaaaga aataatttag tggcatataa tatagcgatg 18180
gaacttgcaa attttttagaa ttatcatata aaaataacaa tgtttctata ttttatgccc 18240
tataagtctt gcagtatttc ttaaatttaa cagttcattt cttggtaatc tttatttttta 18300
tcaagaagtg ttcaggaaat tttaggacat caaattttta tttatttttct aaatctactt 18360
ttatcaaaat tttagaggtc tagtacacat ctacccaaaa agaagacttt ggagctctca 18420
aaaaccacct agtgtatgct aaagtacatg agaagtgacg tgtctttggg cagctggcca 18480
tctttgtcga tatgcgggtg atggtgtttc tgtgagcagt aacaggaaat tctggacacc 18540
tgctagggtg tcaaaccaaa tttatttcaa cccattcttg cttcaaaaaa cccccaacta 18600
aattattcaa attctcgtaa tttaatgaat cactcagtaa ctgtaacgtt ttttttttca 18660
gagacaatga tcgaaagtta acaaaaaaaa ctgaggatta aacgttaattt ggtatctaca 18720
gctgacattg gaacatatca aaaagtggta agtgaaagtg aaacgaaaag tgcaacattt 18780
gaaattgaga gtagaaaaga tcattgaagc agaaatatgg aagtgaattg aaagccgtgg 18840
cgccaaaacg acggtcaggc gccattgaga aaattaatga gagttcggaa ggttgaaaca 18900
acacaaagac aacgtgaaaa attagtttgg agaagataaa aatgtctgg agatggacga 18960
tttcttagtt agctgagaat agtttacatt gattttcggg aaaacgcaga atgttagaaa 19020
aatggaaaca tgtctagact tcagataaat ttgtagaatt tatatttgta gcaaaagcac 19080
actaacaaag gttacaaagc tattaggaaa aatacggaat gtattttga aaatttttga 19140
tttctctaaa ataataacac cattaatttg ctatatttgc tatatatgct atatagtatg 19200
ttcgcattac tgagcacaaa acttggaaaa agtttaaaaa aaaaggaaac ttgttttctg 19260
gagaaatcat taaaaacagt acaatttcag acagaaataa atctttcagt gaaagctttt 19320
ttttgagtaa gactaagtat gcactcacaa cttttctgag tgttccaaaa atgtttaaag 19380
aaaatactag taaaaatgag catttcgaaa agcaatatat catacaacta cacaaacatt 19440
tcaattaaag gaatcaattt tataatagtt ctaggcaatc ccacttttag attcaatttt 19500
ctagcacagg gagcattgga agatataaaa acataaagat aaaggtgata aagatccat 19560
taaacacatc atatctatca aaccatcact tccatcaaat ccacagattt atcacaaatc 19620
agtgtgtgac aaaatataccg taatattaag ttcaaatggt ggaaaagacg cagacaaagc 19680
tttgcataa atactaaata attgaaagaa acgcagagaa tgtaagagaa aaatatacaa 19740
tatgtgtatt atcaaccatc aacagttttt gattaaaacc atggagaagc gatatacagg 19800
agcaaattag gagacgcaga ttgagaaaaa atgagaaaat aatgaaagta cggaagggtt 19860
attgtacaat aagacaggta gcatctctca aagaacctat tgtcaagcag tttaaacatt 19920
caacaacgtt catttatttt ttagccttca ttatgatatc tcattggttc tataattgga 19980
```

-continued

```
tttttttaaat tcagatttct cattcatgta caagtaaagt tgttaattgg ttattatgcc  20040
caaagtttaa ttatttgagc gcagaaaatt tgaatggaaa tttcagaaaa ctgattcatg  20100
ctaacttcaa aaaatcctga ataaatacca attcttttcc aagtatgatt ctcgagcctg  20160
tttacgtgcc tgcctacggt ctattttcta attttttaa tgataaaatt ttagagtaga  20220
tcttcaaaaa tcttccttaa aaaatctcca aaaaaatcaa gttcaggaaa actaaagtac  20280
tccaataaaa tactcttatg caaaaacccc ccattcattt tgcagaaaaa gacaaacaag  20340
aattaaagat aaaaagttat gatagacagg aagctgattt attagatcaa tgaatcgact  20400
tttagtttttt cttgaactct aatttgaaat agtattcgaa tgagaaaatt gaaaatatac  20460
aaagatcaaa agttataatt gaaaatcaac aaattgatag tgtttgtata ggattaaatt  20520
aaaatgtgcg gtacatgaga cagtagtagt agtagccata gtacgtattg gtggctccac  20580
tcggctactg ataatttcct ttttttactga taatttgatg tcatttcgta attttatttg  20640
tgtttccaaa aattgtgggc gtggtttatg aattggtcaa gacatgaatt aaaggaattg  20700
taaagtaaag aagaaaatga cagaggagaa attattttcg tttgctttgg aaattgcaaa  20760
ataaattaga ttattaaaga taatagttac ggtttaaaat aaataggtga taaaaaaata  20820
tccaaaagtt caagtcctaa gaatcttgct attttgcaaa aaaaagcat gagcttttgg  20880
cctaaaaatg gcggacagct gtcgggacac tatccaagaa ttcgtgataa acgggtgaag  20940
caccgtctct tatcatcatg ccattttttcg aattttaaac tcagactttg ataaagaaaa  21000
ttaaaaagag agagtgtgag aaataagagt acacatggaa aatgcaagat ttgaatttgt  21060
ttccaatttt taaaatgtat ttaaagagt taccgttcca ttttttgatta gctttataag  21120
tggaaaaatc gttttttggat tatttttttga ggaatatttt tgaatgcgct ttcaattttc  21180
ctataaaaaa ctttgtgttc actttttttat cccgttttta tttttattttt tacaactttc  21240
aaattttttat gaatgtttta ttgtaaaatc ataaaaaggt gcgaaacatc taaattgcct  21300
ggattgcatt taaaagtgca ttagcagaaa tgtattccta tggaatgttt tttgtgcaac  21360
gagatccaga agctcgaaaa acatccaaat ttcttccaag aaagttgatg ttccaaaaat  21420
aaaaaagatt ttagcccaat caactaaaaa aaaactctcg ttttttttcat atttcacatt  21480
ttctggtcac tttgaaggaa acactaatcc caaactgaga accgaacatg gattaaacca  21540
tcccatttac tatttcttgt tgtcttcaaa aagtcttaga attgtgcaaa aaatagaatg  21600
tttcgaaata ttgcggtttt cgttaaaacc ttttttttgagt agattgaggg tccattagaa  21660
ttcccaagag aacttgatga ccttcatcat caaaattagt ggtcattgaa tgtttgatca  21720
gacaaaaatg gaaatgactg aatcggaaag agcaagaaaa tcgaaaaaaa aagtatttgg  21780
aaattctgga aaactttttta aaatttaaga agggcaacga taagaaacag gaaattaggg  21840
attttttttagt gatggagaag tacgtgataa ggttaaggtg gaacactagt gcacacgttt  21900
tgaatacact acgtgttttt atttatggta gaatatagca cttaaagaac gtttttaata  21960
caaactgaaa taaaaatacg gaaatgtaat ttttttttttt gaaagaatcc gcctgaaact  22020
gaattttcac atcaaacggt agtgattctc tttatgcgtt gggtgatatg tatttacgct  22080
gtcttaaagt tttcgactat aatttaagta atatgtttgt caaaaatcat catggtgctg  22140
tgtcctatgt agccttttct acacttgaaa aatgataatt tttatttgaa aatgtatttt  22200
aaattcaagt agaaagttat ttagtcttgt gtgccaagca ataaacacat agtctattag  22260
gcaataaaaa gtcagctact gttttgattta aaaacttaga ctactggtgt gcctgtgcaa  22320
gttactcccg tagtacggat acagagtgaa aactagtgat tgtactttag atcggctgat  22380
agtgaattta cagagaaata attataaaac ttaaaattttt tagcagctca gtcttcaggc  22440
tgcacagcca tattgttaca cttggagtta caaattctgc aaaccatcta ggattgaatg  22500
caaaaactct gaaagtcaca tcaagaaatt ccaacaaaaa acacattaga tgccaactca  22560
ttgaattgca ttgattccca agagaaatag tagtaaaagt gaccccctatc cattcctccg  22620
ttacatacaa atatacacac aaaaaagagt gtagacctct tccttctaac ccaaccaaca  22680
cacaacaata tcgttccctt ttatctctaa ttctctgcgt ctccataagc tttgagagct  22740
cttcggagca tcttgtgctt gctccttgta cggcggtaca gtttcctccc tctgctccct  22800
tatgtgtgtt taggtgttgt ttgaacaaat aagttttttgg ccatccacct ccttctcaaa  22860
acctttttttct tatgcttctt cttgttttttgt gcacattttg gctcttgctt gtctgctcga  22920
gccatagaca aggcggcgac attttttgaca aaattatatt agtactgtta tatagtactt  22980
aatacaacga tcacaacaac aacacaacga aatgaaaaca tgagatcaaa agacaaattg  23040
ttaggaggag ttggagtttttc tacaatcatg aaatgtttat ctagttatta taaaactgaa  23100
attgctcata aaattgtgat accatgaaga ccgaaaaact ctatgcaact gcatactgca  23160
catacttaca acctttattc tgacttgaat ttcagttttt ggtgttttgca gttattctat  23220
tttgtttaaa agaaaattca attaggaaat aagcaataaa ttttggcatg tatttcgata  23280
gaaggcacgt gtaaatgcca cccggaaatt agaaaaaata agatttctca aactgaaaat  23340
gattgtgaat tgaaaattta agagaatcat tgcaaaagta cacaaatgaa tcatttttca  23400
gattgaacag gaaagtcag aaatatcaga ttaccgtccc aacagaaacc ggaaataaca  23460
cttttcaggt aaagaattat acagaaatcg taataaattt aaaacaaaag agagttatga  23520
cacattgcag aacggtctct gtggaaaata ggaggaggtg ctgcaaaaac tccttagaca  23580
tggtcatact tacaaaaaaa acagagttta actaaaaatt aaattaagtg agaaaatgaa  23640
gaaaatggag gtctttcgcg gattcatttt acttcttctt ttttccactt ttcgttgcag  23700
gctttggttt aaaagttcg caaacaaata aacaatgaac attgtgttga gaagacaagc  23760
caagtgaaag gaaccattg agagcaaaaa caacaatcaa ttgaaataaa gagtaaagtt  23820
tattgaatat actgatatgt gaatactgga aaataatta gtctctataa ttggtaccgc  23880
ctggaagatt catttctgat tcccttgtgt ctttgaccaa aactttattt ttttcagttc  23940
aaaattacaa aaaataaata ctcatcttca tcgattcagt ggtgttttaa actcctacgt  24000
ttttctttta caataaaggt aatgtaaacg ttccgagcgt gtagttttct ctgaaaattt  24060
tttaaaaata acaactttat ggtattttttc ttaaagtctt aaactgaaac cgaaacattt  24120
ttgataggaa aactatttta acatttgggg aactcggcaa aagctctgca ggcttgccga  24180
acaactctca tttgaaagta ataaatatga aaatatttc ttttttttgat  24240
atttttatgaa tacgctcttt ggtagttttt gacgagaaaa ttacatgttg cataaatttc  24300
aagagttata actcatggag acccctaattt ctggtttcac tagaaaatca aaaaatcaag  24360
cgtttgagca gaagactgta ggaagagcaa acgtcataaa aattagggga tcaacgatcc  24420
gaaacgggga attgaaatac gatatcgcgat gagtttttggt tcgaaccggc tttgtcccaa  24480
aaaacaacag aacgatggtc tcaggctcac ttgactcatc tcggtgggaa caatttttat  24540
ttgtttttat tccgtacgca cagaaacttt ttttgaggta ttttttgatcg tgggtgggtg  24600
gaatggtagc acccaatttc aaatagtgtt tgatttgaag agacaatgaa agaaacaagt  24660
gggagataat ggaaatgacg tgatgaaatg gaacggagga aaactggtat aaatatcgtt  24720
```

```
gactatcaaa actacaataa tactaatgga gaaaagttca ggattcttga agattttaca 24780
ttatgatagt tgggatttac tggtttcaag ttcaaatgtc aaacatctgg aagaaaaacg 24840
tataagatta catcaaaata aaactaaaat ttgaaggata aagtaaaaca gcataatata 24900
gtgttttaca tctcatgtag gaaacgaaca aaatctttga acacctagat aacttcaaac 24960
ggaagttggg tgaagaaaag aataggggcc agaatagaag gtcattttga caaagtgaac 25020
agacaaagac attcctaact cggaggtatt ccaaaaactg ttccaatatt gaagaatgac 25080
actatttgat tttatatcat aacattatta atcacatggc ttttttctta ggaaatttat 25140
atcgcaaaat aaaaagtggc cttgatgagt cattcattca aaacatgcct aaaaaccttc 25200
ataattaatt ataaaaatgc tgatacttga ggacccgttt tttatatttt ataaacagtt 25260
gttttcttta ttccgttctc actttgagtt ttttttctga aatactaaaa aaattaacaa 25320
agttcggcgt ttttgtcga taattccatc tgattatttt cggttttttt acctaattat 25380
caaatatttt agccagagtg aaatttatta tcttattaat atgttttca atttgttttg 25440
gtattattct gttgaaggaa catgttgcat tttaaatctg ttgttaatac agcggccaca 25500
tgtttagaac tttataacct cgtttaaaca taaattgtat gccatattta ttgcaagtac 25560
tacatgagtt tgaaacagta tcagatacta tattttaaac aaaaatacac attttccccg 25620
ctatgagaga ttctgataca ttggttttca attttttttaa aaacttgaaa ttcctcaagt 25680
ctcccactga attacagatt tctgttctag atacctccaa agacacctag attcgacttc 25740
ggcatcttcc tcattttat cttcagtttc atcttttgtc taattttccg tacatttctt 25800
tgcatcctta ccatctctcc ctctctcact cactcttctt gttcactaaa tctcaattca 25860
aaatgtttc tgccacgtca tcatcatcat caatgccacc ttctcagagc ccattcgaaa 25920
aattaccacg gcatcaaaat attcgatatc acgaaaaatg cttctcaatt ccacttcata 25980
cacttaacta ttttctatgc gttattattt tttatttctt tgttttcact atatttatc 26040
acgaacgtta tggtggaaaa cctgaaaatg ttcaagttac atcagcaatt tatgattcaa 26100
attcaaacga actgtcatta atctttctat ttgattcttc aattcgtcga cgggaaatat 26160
tccttggatt tggtccaaat gactcaaaaa catcaagaaa tgaaactcaa attgagctta 26220
aaccaccacc cggatttgtt gataactcac aaatttcagt aagtttagga ttttttttca 26280
aaaaaacttg atatgaagtg ttgaaaaatt gataattggg ccgggcttac atcagagtat 26340
ctagttatct tgtatttcaa atattaatt tcaaacattg tagagattcg aaatgcgaca 26400
gtacttcagt aattaccacc cacattttga ctgtcaaaaa agttcccaaa aattgtcgaa 26460
aacttttatt aggatgtttt ctcattttgg cacgattgga gtgttttttt aacaaatccc 26520
ttttatgcat caaattaata tctaatttt aaatcaataa tttggattaa ttcaacttgt 26580
tttataagat tttctcgcta ttaaattagc aaaaaaaaac tatcttcaaa caattagcgt 26640
gcttttaaaac tactaggcct ttgttggcaa cgtcttttca cattttggca caaaactata 26700
aactatgctc agaatttggt aatgtttgaa aatgttttgg gcaagcatat agttattcca 26760
attctaaagt aagattagtc atctcattc cattccattt ttccattttt cacctattt 26820
ttccattatt taacaaccaa gactgagcaa acatttcct gttttaattt tcatatatga 26880
aaagacataa gcaaaagctg gatcaaagct tgggcaaatc ctattcaaag tattttccaa 26940
cgtttccatt ccctcgtttg taaagtacaa ttggtaatct taaggcttaa ttaattattg 27000
tgggagattc ataatgtgaa aactaaatgt taagatttgg tcatcaattg aaaaggaaaa 27060
accccagtct ttaactgtga atgcagaaca tccaaagtca ttgcttttac gagatcacac 27120
aggacatcca tatttagaag taagttcaaa tcagaaatcc ccaatccatt ttttcttgta 27180
gttaccactt caagaaccat actccgattt tcgcgacatt gttagttgtt tcagtccaat 27240
ttatggagat tttgagatgt ttttaacagg tttaacaaat taatttggtt tcttttttaa 27300
aacatttaat ttttatagct ttaacatcat ccatatcaat gggatcattt gttagtatac 27360
catatgaaga gcttactgga gagctttaca agtttctact tgtatttgaa aaaacgggac 27420
atgtcaggtt aactgcattt ccaatgatac gtcatcagcc tcgcttcgat tcggaaaatg 27480
aaaattatca tttgaaaatg atcaaactta aaacagattt aacgcatttg cattgttggc 27540
taatgcataa aaaccgggcc aaattcatga tcttccaaaa ctctgctgaa attgttttac 27600
cgatttcctc gacgctggaa aatcccaatt acgcctctga atttacacga atatttgaaa 27660
caccacgagt tgaaggatat gatattttag aatataatgt caaaatttca acggataaac 27720
gcttaggcga cttttcggat ttctccatca ggcagacaat tgaagcagca aaagcagaag 27780
aattaaccgg aaattctaaa acattaatca tgagaatggt atcacttttt ttcaaaataa 27840
tttactgttt ctattttggc atttatttca gcattctcca actccacaga atctcttaaa 27900
acgcggtaaa atgtatccat ttttcaaaaa tttcccatct ccaccacaag ttattccaaa 27960
gaaaacattg gacaaattgg atacaataac agaaataatt gaagaatctg atgcattctg 28020
gacacttatc aaagaatgtt cagaaaattc gaaatcttgg aaatgctcgt caagaaaatg 28080
tgtaagacca tcagttagac atcgatctct tcatggatgg tattcatatg atattcattt 28140
ttctaaattt ttgaatgttg aaagttttt ttgttcagat tttcaataaa cttttaagaa 28200
aagaataatt ttaaattcta taattcctga atttccaact atgtttatca tttcccaaag 28260
tacattcgaa aaagctcaat aagcaaaacg accacgaaat aacagtatta aaaaaaaga 28320
tgttgtcatt tgaagttctg gagtgcgatg aaaagtctct cacctcggac tttctgtaat 28380
ttatttagca tacaacatga atttgaccaa ctcgaaataa ggttaagact gaaaattttt 28440
cacaaaaatt ggaacacttg cgaagcgaat tcaagacttt tcgaagttat taaacaagct 28500
ttcaaattct cagtaaaact gaacgttttt tttatgctct ccaaatcatt ttaatatggc 28560
tgctcgcgtc gctgaagtat tttctagagt atgtttaata aaactaatat gtaaatgaaa 28620
aaccaaaaac tcagataaag agcataactt ttataacgca ttttcagaac tcttcaagct 28680
ttttcagatc acttctatca gcagtattct tcttttttcc aaagacacca agaactgaaa 28740
aggttgaagg agcatcaccg gaaatagagg atgactgctt attgttcttc ttttttctgaa 28800
taaaatcaaa ttaaacaccg aaaatatgaa acatattcac taacctgaac agctttcagg 28860
tttgatttat tctgattttc cgccgctgat ctgctctgac ttttgaaacc gggacttgga 28920
gagttaccat tgcgtatgcg agttcgaact ggacgccgat tcttctttct gaataaacga 28980
attatacaaa tttgtatttg aaaacggaca acatacactc cttcttccgc cgaattgctc 29040
atcgattttc tcatttcttg tgttttttcc tggcgttcag gttcaaaagg tggagcaact 29100
ggttttggaca tatacggaag aatgttcgag acttgaatct ttttggttg ctcaatattc 29160
tccattggaa tatgatcggg aagtcaaag tagctgttgg atcctggagc ttgatcaaat 29220
ccttcgagag ttaaagttc acgaactgct tcactcattg tgacccttc ctcttcggca 29280
ccagcacaga ttctatactg aaattgcttg ttgtgttgtt ttactcaaaa gaatagtgaa 29340
caaaatttc tcaccgtaat gaatctgaca atggctggtg ggacgttagc ttcaaatggc 29400
attcggtatc cgttctgaac acgtggtaaa acctcagcaa ctttcattcc cggataaggt 29460
```

-continued

```
                tcgattccat catggtacac ttcccaacac atgactccat aagcgaaaac atcagtcttt 29520
                ggagtataga acccagttct tggaacttct ggagccaacc atctaatagg aactctgaaa 29580
                aatttgaaaa ggttggaatt tttgacgttc tctaactttt tgtgaggatt catccgatag 29640
                ctatagcctt ctcgtgacag tccaaagtcg gatatcttta cttgtccatt cccgtagaga 29700
                caatttctgg acgcaatatc gcgatgaatt atttgaagtg aatgaagata ttcaagacca 29760
                agaccagctt gaagaaccat cgtatgtttc ttggaaattg gcaatgaacc aatgttcttc 29820
                tttagatatg aatccaaagc tccattgtca gcctaaaata atttacataa gacattttt 29880
                cttagtaaaa taaaattaat cagttaatta attaacatac caactccatt atgaccatca 29940
                aaggttcctg tcctgcagcc acaccataaa aagtgacgac attcggatgt ttgaacttc 30000
                tcatcaatct ggcttcgtgc atgatttctt tgatctgctc ttttgtcaaa gattccaact 30060
                ttgccagctt gattgcagct tttttgacgg tatttcctat gcgaattct cccaattgaa 30120
                cctctccaaa tgctccttct cctaattct tgattaatgt cacgtcagaa tgttgcttt 30180
                cccacggttc acgaccaatt ggacggatga ttacagtttc tgggccctaa aagcaaacaa 30240
                atgaaaataa gtttactcac ttaatttgta agatcacccc agcaacaggt tctttagaac 30300
                gatgatagta attgagaaga tctgcgatac tagaaaacca ttttttatca actgcaaact 30360
                tgttattgtg ctctcgaatt acataatgac gaatctgaaa taatattctt aaaaattatg 30420
                agcaatcgtt ttacgtacgt cctcaattac tccaacatag acagagagaa caaatttcct 30480
                tggctctccc acttttggat cagtaaatcg aactagaaaa tcgcctcgtt gagtgagcaa 30540
                ctgtttcata tcctcacgtg gcaataagcc atggtaccag ggttctttg caagtacttg 30600
                c                                                                  30601
```

<210> SEQ ID NO 34
<211> LENGTH: 8009
<212> TYPE: DNA
<213> ORGANISM: Unknown
<220> FEATURE:
<223> OTHER INFORMATION: Description of Unknown Organism:Unknown

<400> SEQUENCE: 34

```
                ggatccttgg ccacgccatg ggcgatgaaa ttgaccgcgt cgtaacgggt catgtcctgc 60
                tcctgcagga agaaggccgc gttcgattcc cgttccgcaa agatcgcgac aaggacattc 120
                gccccgtca cctcggtccg gcccgagctt tgcacatgga tcgcggcgcg ctggatcacc 180
                cgctggaagg cggcggtcgg cacggcttcc gagccttcga cttcggtgat cagcgtcgag 240
                agatcatcgt cgatgaactc ggtcaggtg gtgcgcaact cgccaagatc gacgccgcag 300
                gcgcgcatca cgcggctggc gtcgggctcg tcgatcagcg gacgagaag atgttcgagc 360
                gtcgccagtt catgtttgcg cgtgttggcc agcgccagtg cggcgtgaat tgcttgctcg 420
                agcgtggtcg aaaacgaagg catgcggcgc tcctttcctc gggtctcccg atactggcct 480
                catgtgatta gtttcggtg gatttcgccg cgcttcaagg cccggacgcg tgtttttcc 540
                acctctcgcc gctctgttgc aaaactgacc agcgcggcgg gctttcgcgc gatccgcagg 600
                cagcgcgcga aagtgctttc agaaccggtc cttgcgcgcc cgcgccgcgg tgaagacgcg 660
                gagcggcgcg gcatcccgg gcaggccgag cgcggcgcgc aacgcagcgt catcggcgcg 720
                caaaaaggga ttcgttgccc gttcctcgcc caaagtcacc ggcaaactgg ttccccggc 780
                cagccgcaag gccgtcaccc ggtccatccg gtcgtgcagc cgaccgttcc ccggttccag 840
                gctgagcgcg aaccggccgt tcgcggcggt gtattcatgc ccgaacaga cccgggtttc 900
                gggcggcagc gcggccgagc gggtcagcgt gtcgaacatc tgcgcggggg tcccctcgaa 960
                gagacgcccg cagccccagc tcatcaggct gtcgcggaa aagagcagcc ccgcccggg 1020
                cagataccag gcgatatggc cgagcgtatg gccgtcggcc gcgatcacct gcgcggcctc 1080
                catccccaga tgcagcacgt cgcccggggc caccggatga tcgacgcggg gcagccggtg 1140
                ggcatcggcc gcggcccccg ccaccttggc cccggtcgcc tgcgccagcg cctcgacccc 1200
                cgcgatgtga tcggcgtggt gatgggtgat caggatgtgg tgcagctgcc agcgccggtc 1260
                ggtcagcacc ttcagcaccg gggccgcctc ggggacatcg accaccacca cggtatcggt 1320
                ggcggtgtcg tgccagagcc aggcgtaatt gtcggtcagg cagggatcg gggtcagttc 1380
                gagggtcatg gccttttgcg catctttcgc tatcctgacc cagcttcgcg caaggaaggc 1440
                caacctgcaa tgcatctcga cgtgctcgac ctgcgtgatt tctactaccg cacccaattg 1500
                gggcgcacgg cgcaaaaggc gatccgcgac aaggtggtcg aactctggcc ggacacccag 1560
                tccggcatgg ccgggctgac ggtggcgggc tacggcttcc cggtgccgct gttgcgcccc 1620
                tatctgggcc gggcgcggcg ggtgatcggg ctgatgcccg cgcagcaggg cgtgatgccc 1680
                tggcccgccg gagagcccaa tgtctcggtg ctctgtgccg aaaccagctg gccgctggag 1740
                accgggatga tcgaccggct ggtggtgctg cacgggcttg aagtctccga cgaccccgat 1800
                gcgctgatgg aggaatgctg gcgcacgctg ggcccgggc ggcgggcgct gttcatcgtg 1860
                ccgaaccggg tcgggcttg ggcgccgcgc gaaaccacgc ccttcggctt tggccgcccc 1920
                tatacgatgg gccagctcga ggcgcaggca cgacgggtgg ggtttgccc cgaacgtcag 1980
                gcggcggcgc tgtacattcc gccctcgcag cggcggttct ggctgcgctc ctccgagatg 2040
                tgggaacggc tgggcacaag ggcggcgggc tatctggcg cggggtggt gatgcttgag 2100
                gtgatcaagc aggtgcattc ggtgcgccgc tcggggcttg gcgcggacgg gcgcaagccg 2160
                ctctcgatcc ttgaagggc gcccaagccg gtggtcgggc ggatgtgagc gcccgcggc 2220
                cgcaagaatc gcccggccgg aaaagcccgt ttccgcggca cttgccctg cggcggggaa 2280
                acgcagcggg gcgggcttcg acccttgcg ctaacactcc gtgccggtgc agaaaatgtg 2340
                ccagcctgat gcgattcct gccgccaaga tggttgcgga ggtcttgatg ctctgctaga 2400
                cgcaaccccg aatgcggcgt gcgagatcat tttgggcgcc gagggggcc tctgaatcgg 2460
                tgacgaacg attggttccg gtgtccgcgt gcggaggcaa aagcatcgga agggtggacg 2520
                tgtccgaacc agcttcgatt tccgcagcca ttgccgggcg ttatgccacg gccatcttcg 2580
                acctcgcgca ggaagccaag ggcatcgacg cgctctcggc cgacgtggac gcgctgacgg 2640
                ccgccttggc cggttcggcc gagctgcgtg acctgatttc ctcgccggtc tacacccgcg 2700
                aggagcaggg ggacgcgatc gccgcggtgg ctgcgaagat gggcctgtcg gcgccgcttg 2760
                ccaacggtct gaaactgatg gcgacgaagc gccgtctgtt cgcgctgccg cagctgctca 2820
                agggcctggc cgccgcgatc gccgaagcca aggcgagat gaccgcggat gtcacctcgg 2880
```

```
ccaccgcgct gagcgcggcg caggccgaga agctggcggc gacgctggcg aaacagacgg 2940
gcaagaccgt caaactgaac gtcgccgtcg atgaaagcct catcggtggc atgatcgtca 3000
agctgggttc gcgcatgatc gacaccacgg tcaaagccaa actcgcttcc cttcagaacg 3060
ccatgaaaga ggtcggataa atgggcatcc aagcagctga gatttctgcg atcctcaagg 3120
agcagatcaa gaacttcggg caggatgccc aggtcgccga agtgggccgc gtgctctcgg 3180
tcggtgacgg gatcgcgcgc gtgcacgggc tcgacaacgt ccaggcgggc gagatggtcg 3240
aattccccgg cggcatccgc gggatggcgc tgaaccttga agtcgacaac gtcgggatcg 3300
tgatcttcgg gtcggaccgc gacatcaagg aaggcgacac cgtcaagcgc accaacgcca 3360
tcgtggacgt tccggcgggc gaaggcctgc tgggccgcgt cgtcgacggc cttggcaacc 3420
cgatcgacgg caagggcccg atcgtggcga aagagcgtcg catcgccgac gtcaaagccc 3480
cgggcatcat tccgcggaaa tcggtgcatg agccgatggc gaccggcctc aagtcggtcg 3540
acgcgatgat cccgatcggc cgcggccagc gcgagctgat catcggcgac cgtcagaccg 3600
gcaagaccgc gatcgcgctc gacaccattc tgaaccagaa gtcgtacaac gacgccaacc 3660
cgggcaacaa gctgcactgc ttctatgtcg ccatcgggca gaagcgctcg accgtggcgc 3720
agctggtgaa gaagctcgaa gaagccggcg cgatggaata caccaccgtc gtcgccgcga 3780
ccgcttcgga cccggcgccg atgcagttcc ttgcccccta ttcggcgacc gcgatgcgg 3840
aatacttccg cgacaacgcg atgcacgcgc tgatcatcta tgatgacctc tcgaagcaag 3900
ccgtggccta tcgtcagatg tcgctgctgc tgcgccgtcc gccggggcgt gaagcctatc 3960
cgggcgacgt gttctatctg cactcgcgcc tgctgaaacg ttcggcgaaa ctgaacgagg 4020
atttcggttc gggctcgctg accgccgtgc cggtcatcga aacccagggc ggcgacgtgt 4080
cggccttcat cccgaccaac gtgatcctcg a tcaccgacgg tcagatcttc ctgaaaaccg 4140
aactgttcta ccagggcatc cgcccggccg tgaacaccgg tctctcggtg tcgcgcgtcg 4200
gttcgtcggc ccagaccaac tcgatgaagt cggttgccgg tccggtgaaa ctggagcttg 4260
cgcagtatcg cgaaatggcc gcctttgcgc agttcggttc cgaccttgac gccgcgacgc 4320
aaaagctgct gaaccgcggt gcccgtctga ccgagctgat gaaacagccg caatattcgc 4380
cgctgaccaa cgccgaaatc gtgcgcgtga tctttgcggg caccaacggc ttcctcgatg 4440
ccgttccggt gaaggaagtc ggccggttcg agaaaggcct gctgcctat ctgcgctcga 4500
cccgcaagga cgtgcttgag tggctcacca aggaagaccc caagatcaag ggcgacgccg 4560
agaagaagct caaagacgcg atcgccgagt tcgccaagac cttcgcttga cggcctgaaa 4620
ggacagggag atgcccagcc ttaaggacct caagaaccgg atcgtgagtg tcaagaacac 4680
tcgcaagatc acgaaagcga tgcagatggt cgcggcggcg aacattcgcc gcgcccagga 4740
aagcgccgaa gctgcccggc cctatgccga cggatgaac gccgtgatgt cgagccttgc 4800
cggtgcggtg ggctcgaccg acggtcgcc gcgcctactt gcgggcacgg gtcgacaa 4860
ggtccatctc ctcgtcatca tgacgggca gcgcgggctt tgcggcggct tcaacgccaa 4920
tatcgcgaaa ctcgcgaagg cgaaggcgat ggaactgctg cccagggca agacggtgaa 4980
gatcctcacc gtcggcaaga aggtcgcga cgcgctgcgt cgtgatctgg ccagtatta 5040
catcgatcac atcgacctga gcgacgtgaa gaaactgagc taccggtgg cgcagaagat 5100
ttcgcaaaac atcatcgacc gcttcgaggc gggcgaatac gatgtggcga cgatcttctt 5160
ctcggtcttc cagagcgtga tcagccaggt gccgaccgcc aagcaggta tcccggcgca 5220
gttcgaaacc gatgcggcct cggcctcggc ggtttacgac tacgaaccgg gcgatcagga 5280
aatcctgacc gcgctgctcc gcgtgccggt ggccacgcg atctttgcg cgctgctgga 5340
aaacaacgcg tccttcaacg gggcgcagat gtcggccatg gacaacgcca cccgcaacgc 5400
gggtgacatg atcgatcgct tgaccatcga gtataaccgc tcgcgtcagg ccgccatcac 5460
caaagagctc atcgaaatca tctcggcgc cgaggcgctc tgacggaacc ggagatagaa 5520
gagaatggca agcaaaggca aagtgaccca ggtcatcggc gccgtcgtcg acgtgcagtt 5580
cgaagacgcg ctccgcggca ttctgaacgc ccttgaaacc accaacaacg gcaagcgcct 5640
cgttctcgaa gtggcgcagc acctgggcga gaacaccgtc cgcaccatcg cgatggacgc 5700
gaccgaggat ctcgtgcgcg cgcggccgt gtccgacacc ggcggcccga tcaccgttcc 5760
ggtgggcaac gccacccctg gccgcatcct gaacgtcatc ggcgagccgg tggacgaacg 5820
cggtgacgtg tcgaaagccg aagcccgggc gatccaccag cccgcgccg atttcgcgcc 5880
gcagtcgacg gaaagccaga tcctcgtcac cggcatcaag gtgatcgacc tgctcgcccc 5940
ctattccaag gcggcaaga tcggtctctt cggcggcgcc ggtgtgggca gaccgttct 6000
gatcatggaa ctgatcaaca acatcgcgaa agtgcactcg ggcttctcgg tgttcgcggg 6060
cgttggcgaa cggacccgtg agggcaacga cctttaccac gagatgatcg aatcgggcgt 6120
tatcaacctc gagaagctcg aagaatcgaa agtggcgctg gtctacggcc agatgaacga 6180
acccccgggg gcccgtgccc gcgtggcgct gaccggcctg accctggcgg aacagttccg 6240
cgaccagtcg ggcaccgacg tgctgttctt cgtcgacaac atcttccgct tcacccaggc 6300
cggttcggaa gtgtcggcgc tccttggccg tatcccctcg gccgtcgag accagccgac 6360
gctggccacc gacatgggcg cgctgcaaga acgcatcacc tcgaccaaag ccggttcgat 6420
cacctcggtt caggccatct acgttccggc cgacgacctt accgaccgg cccggccac 6480
gtccttgtcc cacctcgacg ccacagaccg tctgtcgcgt gcgatctcgg aactcgggat 6540
ctaccccgcc gtcgacccgc tcgactccac ctcgcggtca cttgacccgc aagtcgtcgg 6600
cgaagagcac tatcaggtcg cccgtgacgt ccaaggatg ctgcaacgct acaagtcgct 6660
gcaggacatc atcgccatcc tcggcatgga cgaactgtcg gaagaagaca agctgacggt 6720
ggcccgcgcc cggaagatcc agcgcttcct gtcgcagccc ttcgacgtgg cgaaagtctt 6780
caccggctcg gacgcgtgc aggttccgct cgaagcacac atcaagtcgt tcaaggcgat 6840
ggttgcgggc gaatacgacc acctgccgga agcggcctc tacatggtgc gcgcatcga 6900
tgacgtgatc gcgaaagccc agcgcctcgc cgctgcggcg taaggggaa ccatggccga 6960
taccatgcag ttcgatctcg tgtcgccgga acggcggctt gcctccgttc ccgcgagcga 7020
ggtccgtctt cccggcgtgg aaggcgatct gacggcgatg ccgggccatg cgcccgtcat 7080
cctctcgctg cgtcccggca tcctgaccgt ggtcagcgcc ggggacgg ccgaatacgc 7140
cgtgaccggc ggcttcgccg aggttttcgg cgagaaggtg accgttctgg ccgagcgcgg 7200
tctgacccgg gcggaactga ccgccgcggt tcatgccgag atgctggccg aggccaagaa 7260
agtcgcggac gccgcgcatc cgtcggtggc cgatgccgcc gcgaagatgc tggccgacat 7320
ggaagcgctt ggctcgcaca tcaatctctg acgggacatc gccggata tctcgggccc 7380
cggtcatcgc gccggggccc ttgcttttg cttttgtctt gccgcgccgc atattagcgc 7440
gaagtgcag gcagccggag tgagcgacag gaacggatga agaagttttc ctcgacccgg 7500
atcggcgtgg cccagggatc gctggtgctg ttttcggatt atctggacgg cggcgtgatg 7560
tggacgggcg agggccccgcg cgaattcgcg aggctggtgg tgttcgacga agccttccgg 7620
```

-continued

```
       gagatcccgg cggtgcaggt gtcgctgtcg atgtgggaca tcgaccagaa gcacaatccg 7680
       cgcatggaca tttccgccga catggtgacg gccgagggct tcgtgatcgt ctttcgcacc 7740
       tggggcgaca cccgcgtcgc ccgcgtccgc gcggactggc tggcgatcgg cggctgcgcc 7800
       aatgacgacg actgggacgt ggcctgatcc cgcccggctt gactttccgc ccccccgcgc 7860
       cgatggtgcg cgcgactttc ccatccaacg aggcccgccc gtgcaacaag atgcccccg  7920
       ctggcagctc gtggtgatcc tgtgggggac gaaatatccg gtcgccgaac tcaacgccct 7980
       gatcgagacc gtgtggcccg ggcctcgag                                   8009
```

<210> SEQ ID NO 35
<211> LENGTH: 9810
<212> TYPE: DNA
<213> ORGANISM: Unknown
<220> FEATURE:
<223> OTHER INFORMATION: Description of Unknown Organism:Unknown

<400> SEQUENCE: 35

```
       gatatcgggc ttgtcatttt cgattgcgac ggggttctgg ttgattcgga agttctggcc   60
       gtggccgtcc tcatcgcaga actggaccgg gcgggcgtgc gggtcgacga ggccttcgtg  120
       catcggcatt ttctgggccg gagcttcccg gctgttcagg aggtcgtgca gcgccagttc  180
       ggcgtgaccc tgcccgagac cttccaggtc gaggaacgtg cccggctgct gtcagccttc  240
       gagaccggcc tgcgggccat gctcggggcc gcggagaccg tccgcgcgct gtcggtgccc  300
       tactgcctcg ccacgtcgag cacgccggcc cggctcacgc gctcgctgga gatcacgggc  360
       cttgcgggcc tcttcgaggg acgctgcttc accgcgagca aggtggcgcg cggcaagccc  420
       gcgcccgatc tgttcctgct cgccgcggcc gagatgggcg tcgcgcccga acgctgcctc  480
       gtgatcgagg ataccgagcc cggcgtgcgc gcaggcctcg cggccgggat gcaggtctgg  540
       cgcttcaccg gcggtagcca tttcgcgaac cgatccccg aggatgcgcc cgatgccctg  600
       ccgcaccggc ggttcgacag cttcgaccgt ttctacgaga ccctgcccgg cctgcgccgg  660
       gccaagtgcg agaccctgac atgatcgacc ggcccgagag cgagccgacg cccctcgacg  720
       atgccgcgcg cgcgggctgg ctctattatg tcgcaggcct gactcaggat cagatcgcgc  780
       gggagctcgg cacctcgcgt cagcgggcgc agcggctggt gagccggcc atctccgaac  840
       ggctgatcca cgtccggctc gagcaccggg tctcgggcg cctgcatctg gaagccgcgc  900
       tcctccggcg cttcgggttg aagctggccc gcgtggcgcc gagtctcggg tccgaggtgg  960
       atcccctgcc ctccatcgcc ccaccgccg ccgccgaggt ggagcggtg ctgcgctcgg  1020
       agcggccgat ggtggtggcc ttcggcaccg gccggtcgct gcgcgccacc gtcgaggaga 1080
       tgacctcgat ggtctgcgaa cagcacaaga tcgtcgcacg caacggaaat atttctgcgg 1140
       atggctcggc ctcctactac gatgtgatct tccgcatcgc cgaccgtgtg cgtgcgccgc 1200
       actatccgat gccgatgccg gtcatcgcgc aggatgcggc ggagcgggag ctgtttcatg 1260
       cgctaaagcc cgtgcagtcg gtgctgcggc ttgcgcgcaa tgccgatgtg accttcgtcg 1320
       ggctgggaca gatgggcgag gacgcgccgc tcctgaagga cgggttcatc acgcccgagg 1380
       agctgaccga gatgcaggat ctgggcgccg tcggagaggt ggcgggatgg gtcttcgact 1440
       cggagggtcg ctacctcgaa accagcatca atcagcgggt tgcgggcgtc cgtgtcgaac 1500
       tttccgagga tcggacggtg gtcgccatcg ccggtggcag gcgcaagctc gcggcgctgc 1560
       acgcaggctt aaggggccgt cttttcaacg gcctgatcac cgacgagttc acggcgcagg 1620
       cacttctgtc ctgaagccgc cgaaaggcgc ggcaaaaagt atttgacagg ctggcacccc 1680
       tcggtgagta attattcgcc gcacgaaata atgctcaccg tgcaggccag ggaggatact 1740
       gatgaccgca agatttgcgc ccctgatggg cgcgtgcgcc gtggctgcgc tctcgtccgc 1800
       cgccggcgcc gaaaccatca ccgtggcgac tgtcaacaac ggcgacatga tccgcatgca 1860
       ggggctcatg tccgagttca acgcgcagca cccccgcatc accgtcgact gggtgacgct 1920
       cgaggaaaac gtgctgcgcc agaaggtcac gaccgacatc gccaccaagg gcgggcagtt 1980
       cgacgtgctg accatcggca cctacgaggt tccgatctgg ggcaagcagg gctggctcgt 2040
       gagcctgaac gacctgccgc cggagtatga tgccgacgac atcctgcccg cgatccgcaa 2100
       cggcctgacc gtcgacgcg agctctatgc cgcgcccttc tacggcgaga gctcgatgat 2160
       catgtatcgc aaggacctga tggagaaggc ggggctgacc atgcccgacg cccccaccg 2220
       ggacttcgtg aaggaagcgg cgcagaagat gaccgacaag gatgccgagg tctacggcat 2280
       ctgcctgcgc ggcaaggccg gctggggcga gaacatgcc ttcctcagcg ccatggccaa 2340
       cagctacggc gcgcgctggt tcgacgagaa ctggccgcg cagttcgacg gcgaggcctg 2400
       gaaggccacg ctgaccgact atctcgacat gatgacgaac tacgcccgc ccgcgcctc 2460
       gaaaaacggc ttcaacgaga acctcgcgct gttccagcag ggcaagtgcg gcatgtggat 2520
       cgacgcgacg gtggccgcct ccttcgtgac caaccccgag gaatccacg tggccgacaa 2580
       ggtgggcttc gcgctcgccc ccgataccgg caagggcaag cggcgccaact ggctcgggcc 2640
       ctggaacctc gcgatccgg cgggctcgca gaaggtcgat gccgccaagc agttcatcgc 2700
       ctggcgacc tcgaaggact atgccgagct ggtggcctcg aaggaaggct gggccaacgt 2760
       gcctccgggg acgcggacgt cgctctacga gaacccggaa tatcagaagg tgccgttcgc 2820
       gaagatgacg ctcgacagca tcaacgcggc tgacccgacc caccggccgg tcgatccggt 2880
       gccttacgtc ggtgtgcagt tcgtggcaat ccccgagttc caggcgcatg gcaccgccgt 2940
       gggccagcag ttctcggcag ccctcgcggg ctcgatgtcg gccgagcagg cgcttcaggc 3000
       gggcccagcag ttcacgacgc gcgaaatgac ccgcgcgggc tacatccaagt gagcccttcc 3060
       gcgggccggc cctgagcggc cggcccgcac cgcttgccgc ttccggccgt atccgccgga 3120
       ggccttttcg ccccatcagc cccgaggcct ccatggcgca ccagcattca aagactgcgg 3180
       cgcgtctgat gatttcccg gccgtgatcc tcctgttcct gtggatgatc gtgccgctgt 3240
       cgatgacgct ctacttcagc ttcctgcgct acaacctcct catgccgggg atggagagct 3300
       tcaccggctg ggacaattac tattacttcc tgaccgatcc ggccttctcc gcggccctga 3360
       ccaacacgat cctcctcgtg gtcgggctcc ttctcatcac ccagcattca cgtggtcctgc 3420
       tcgcgctcct gctcgaccag cccttctggg ggcagggcat cgtgcgcgtg ctggtgatcg 3480
       ctcccttctt cgtcatgccc accgtctcgg cgctggtctg gaagaacatg ttcatgaacc 3540
       ccgtgaacgg gatgttcgcc catatcgccc gcgggctcgg ccttccgccg ttcgacttcc 3600
       tgtcgcaggc gccgctgcc tcgatcatcg gcatcgtggc ctggcagtgg ctgcccttgg 3660
```

-continued

```
ccacgctgat ccttctgacg gcgctccagt cgctcgaccg cgagcagatg gaggcggccg 3720
agatggacgg cgcctcggcg ctcgaccggt tcatccacat caccgtgccg cacctgacgc 3780
gtgccatcac cgtggtggtg ctgatccaga ccatcttcct tctgggcgtc ttcgccgaga 3840
tcctcgtcac gacgaacggt ggacccggca ccgcctcgac caacatcacc tacctcgtct 3900
atgcgcagtc gctcctgaat tacgacgtgg ggggcgggtc ggccggcggc atcgtcgccg 3960
tggtgctcgc caatatcgtg gcgatcttcc tgatgcgcat gatcggcaag aatctggacg 4020
cctgacatgt cacgccgcac ctcaacccgc cgcacgctga tcgtcacgct cgccgcctgg 4080
acgatagcct tcctcatctt cttcccgatc ctctggacgg tgctgatgag cttcaaatcg 4140
gaaggagacg ccatcaaggc gcccttcgcc atgctcttct cggactggac cctgcaatcc 4200
tacgccgatg tgcaggaacg gtcgaactac gcccgccact tcatgaattc ggtggtgatc 4260
tcgctgggct cgaccctcgt ggcgctcgcc atcgcgatcc ccgccgcctg ggccatggcc 4320
ttcgtgccgg gccggcggac gaaggacgtg ctgatgtgga tgctgtcgac caagatgatg 4380
ccggcggtgg cgtgctcat cccgctctat ctgatcttcc gcgacacggg ccttctcgac 4440
acgcggatcg gcctcgtgat cgtgctcacg ctcatcaacc tgccgatcgt ggtctggatg 4500
ctctacacct acttcaagga gatcccgggc gagatcctcg aggcggcgcg gatggacggg 4560
gcgacgctcg gctccggaga t cctctatatc ctcacgccga tggccgtgcc gggcatcgcc 4620
tcgacgctgc ttctgaacgt gatcctcgcc tggaacgagg ccttctggac gctgcagctg 4680
accacctcgc gggcggcccc gctcacgcag ttcatccgcga gctattccag ccccgagggc 4740
ctcttctacg ccaaactgtc ggcggcctcg accatggcca tcgcgccgat cctgatcctt 4800
ggctggttca gccagaaaca actcgtccgc ggcctgacct tcggcgcggt gaagtgagga 4860
ccacatgggc aagataaccc tgcgcaacgt ccagaagccg ttcggtgagg cggtcgtcat 4920
cccctcgctc gacctcgaca tcgaggatgg cgagttcgtc gtcttcgtcg gcccctcggg 4980
ctgcggcaaa tccacgctcc tgcgcctgat cgcgggcctc gaggatgtgt cggacggcca 5040
gatcatgatc gacgggcgcg acgccaccga gatgccgccc gcgaagcgcg gcctcgccat 5100
ggtgtttcag agctacgcg tctatccgca catgacggtg aagaagaaca tcgccttccc 5160
gctgcggatg gcgaagatgg agccacagga gatcgagccg cgcgtgtcga acgcggccaa 5220
gatcctgaac ctcaccaact atctcgaccg ccgccccggc cagctctcgg gcgggcaacg 5280
gcagcgggtg gccatcgggc gcgccatcgt gcgcgagccg gcggccttcc tgttcgacga 5340
gccgctctcg aacctcgatg cggcgctgcg ggtcaacatg cggctcgaga tcaccgagct 5400
gcaccagtcg ctcgagacca cgatgatcta tgtcacccac gatcaggtcg aggccatgac 5460
catggccgac aagatcgtgg tgctgaacgc gggccggatc gagcaggtgg gctcgcccct 5520
caccctctac cgcaatccgg cgaacctctt cgtggcgggc ttcatcggca gcccgaagat 5580
gaacctgatc gaggggcccg aggccgccaa gcacgcgccc accaccatcg ggatccgccc 5640
cgaacatatc gacctgtcgc gcgaggcggg ggcgtgggag ggcgaggtcg gcgtctcgga 5700
acatctcggc tcggacacgt tcctgcatgt gcatgtcgcg gggatgccca ccctcaccgt 5760
gcggacgggc ggagagttcg gcgtccatca cggcgaccgg gtctggctca cgccgcaggc 5820
cgacaagatc caccgcttcg gcgccgacgg aaaggcgctc tgacatgcgg ctcgacggca 5880
agaccgccct catcaccggc tcggcgcgcg gcataggccg cgccttcgcc gaggcctatg 5940
tgcgtgaagg cgcgcgcgtg gccatcgccg acatcaacct cgaggcagcc cgcgccaccg 6000
cggccgagat cggccccgcg gcctgcgcca tcgccctcga cgtgaccgat caggccagca 6060
tcgaccgctg cgtggccgag cttctcgacc gctggggaca gatcgacatc ctcgtgaaca 6120
atgcgggccct cttcgatctg gcgcccatcg tcgagatcac ccgcgagagc tacgaccggc 6180
tgttcgcgat caacgtctcg ggcacgctct tcatgatgca ggcggtggca cgggcgatga 6240
tcgcgggcgg ccggggcgga aagatcatca acatggcaag ccaggccggc cgccgcggcg 6300
aggcgctggt gggcgtctat tgcgcgacca aggccgccgt catctcgctc acccagagcg 6360
cggggctgaa cctcatccgc cacgggatca acgtcaatgc catcgccccg ggcgtggtgg 6420
acggcgagca ctgggacggg gtggatgcga agttcgccga ctacgagaac ctgccccgcg 6480
gcgagaagaa gcgtcaggtc ggcggcggcg tgcccttcgg ccgcatgggc cgcgccgagg 6540
acctgaccgg catggcgatc ttcctcgcca cgcccgaggc cgactacatc gtgcccagga 6600
cctacaacgt ggacggcggc aactggatga gctgaggccc aaggcccggc cctccccccg 6660
tcgaacgcgc ccctatccg aggtaatccc atgacccgct ccgtcacccg tccctcctat 6720
gaccgcaagg cgctcactcc cggcatcgtc catatcggcg tcggcaactt ccaccgggcg 6780
catcaggcgg tctatctcga cgatctcttc gcgctgggcg agggccacga ctgggccatc 6840
ctcggcgcgg gcgtccgccc gaccgatgcg cggatgcggc aggctctggc cgcgcaggac 6900
aatctctcga cggtgatcga gctcgatccg gcgggccacc gggcccggca ggtgggggcg 6960
atggtgggct tcctgccggt cgaggccgac aatgcggccc tgatcgagcc catgtcggat 7020
ccgcgcatcc gcatcgtctc gctgaccgtg accgagggcg gctattatgt cgatgcctcg 7080
ggcgccttcg atccgacgca tcccgatatc gtggccgatg cggccatcc tgcgcgggccc 7140
gcgaccgcct tcggcgcgat cctcgccgcc ctccgcgccc gccgcgacgc ggggttaca 7200
cccttcaccg tgatgtcctg cgacaacctc cccggcaacg gccatgtcac ccgcaacgcc 7260
gtggtgggcc tggccgagct ctacgacgcc gagcttgcgg gctgggtgaa ggcgcaggtg 7320
gccttcccga acggcatggt cgaccgcatc acccccgca cgagcgcgaa 7380
ctggcgcagg gcttcggcct cgccgatccg gtgcccgtca cctgcgagcc gttccggcag 7440
tgggtgatcg aggatcattt cccccgccgga cgccccgcgc tcgagaaggt gggcgtgacc 7500
ttcaccccgc atgtccatgc ctacgaggcg atgaagatcc gcatcctgaa cggggggccat 7560
gcggtgatcg cctatccgtc ggcgctcatg gacatccgac tcgtgcacgc ggccatgccc 7620
catccgctga tcgcggcctt cctgcacaag gtcgaggtcg aggagtcct gccccatgtc 7680
ccgcccgtgc ccgacaccag catccccgac tatcttaccc tgatcgagag ccgcttctcg 7740
aaccccgaga tcgccgacac gacgcgcagg ctctgcctcg acggttcgaa ccggcagccg 7800
aagttcatcg tgccgtcgct gcgcgacaat ctggcggcgg gcacggtgcc gaagggggctg 7860
gtgctgctct cggcgctctg gtgccgctac tgcttcgtgg cgacggactc gggcgtttgt 7920
gtcgagccga acgatccgaa ctggacggcg ctgcaggacc gggcgcggcg ggcgaaggag 7980
acgccggccg agtgctggcc gatgaccgaa gtctacggcg atctggcgca gaacgatctt 8040
ctggcggccg agttcggcg agccctcgag gcggtctggc gcgacggggc gaggcggtg 8100
ctgcggcgct tcctcgccgg ctgatccgca gggcgaccga ccgaagcgga 8160
gccctgccc cttgcggcgc accgtgaggc gaaacgaccg gccaccccgg gggccaccgc 8220
ctcggtaaca ccatggtatc gcgcaagaat gccggcgcct tgccgaacgg gcccggctg 8280
ccgggcgagg cgccggactt gtcaaggcgg cggccctcgg gtagagaggg cgggcgtggc 8340
cccgttagca cagtggtagt gcagcgctct tgtaaagcga aggtcgttcg ttcaaatcgg 8400
```

-continued

```
             acacggggca cgcgatcctc cctccgcatc ggcgctcgcc cccggtctgg actgcctctt  8460
             cggaaggcac ctgcccgctt gtgcgccgcg cccttcctc gcttcccaag cgtctgtcac    8520
             ggcttgcgga agccgtgcg cctcggttct ggacagccgc cccttgcggt gtaatctgcc    8580
             ctcagcgcga agccggcgga cagaagccgg cccgccacgt ccacaaggga ggaatgccat    8640
             ggatcgtcgt tcattcatca ccaaggccgc cgtgggaggg gccgccgcga gcgccctcgc    8700
             cgcgccggcg cttgcccagt ccgcgcccaa ggtcacctgg aggctcgcct cctccttccc    8760
             gaaatcgctc gacacgatct tcggcggcgc cgaagtgctg tcgaagatgc tctccgaggc    8820
             caccgacggc aacttccaga tccaggtctt ctcggcgggc gagctggtgc cggggcctgca   8880
             ggccgccgac gccgtgaccg agggcaccgt cgaatgctgc cacacggtcg gctactatta    8940
             ctggggcaag gatcccacat tcgcgctggc cgcggccgtg cccttctcgc tgtcggcgcg    9000
             cggcatcaac gcctggcact accatggcgg cggatcgac ctctacaacg atttcctcgc     9060
             gcagcacaac atcgtggcct tcccgggcgg caacaccggc gtgcagatgg gcggctggtt    9120
             ccggcgcgag atcaacaccg tggccgacat gcaggcctg aagatgcggg tcggcggctt     9180
             tgcggggaag gtgatggagc gtctgggcgt cgtgccgcag cagatcgcgg cggcgacat     9240
             ctatccggcg ctggagaagg ggacgatcga cgcgaccgaa tgggtcggcc cctatgacga    9300
             cgagaagctc ggcttcttca aggtggcgcc ctactactac tatcccggct ggtgggaagg    9360
             cggcccgacc gtccatttca tgttcaacaa gagcgcctac gaggggctga ccccggccta    9420
             tcagtcgctg ctgcgcaccg cctgccacgc ggccgatgcg aacatgctcc agctctacga    9480
             ctggaagaac ccgacggcga tcaagtcgct ggtggcgcag ggaacccagc tcaggcccttt   9540
             cagccccgag atcctgcagg cctgtttcga ggccgcgaac gaggtctatg ccgagatgga    9600
             agcctcgaac cccgccttca agaagatctg ggactcgatc aaggccttcc gctccgagca    9660
             ctacacctgg gcgcagatcc ccgaatacaa ctacgacacc ttcatgatgg tgcagcagaa    9720
             cgccggcaag ctctgagccc gagcgccgcg cgaaagagga ccccggagcc gcgttccggg    9780
             gtcttttcat gggcgacagg ggccggcgcg                                     9810
```

<210> SEQ ID NO 36
<211> LENGTH: 1886
<212> TYPE: DNA
<213> ORGANISM: Unknown
<220> FEATURE:
<223> OTHER INFORMATION: Description of Unknown Organism:Unknown

<400> SEQUENCE: 36

```
             tgagtgtcta ttttttttcg ggttttttta agtgtgaatc acatggttag gagcagttgt   60
             cttcaatgtg accaaccatc ccaaggctct aattcaacgt ttgggtgtgg gggcccgctg    120
             gcagctgtgt gtgccactgg gctgttggtg ttggtgcttt actccccctc atcgcaaacg    180
             gctaattggt cggcacaggg tatttccaca aaggcgctgt atccggcagt gcctgtgcct    240
             tccactctgc tgcctggaag cgcgcctgcc aaacaccagc tgcatgtttg gagggcacat    300
             gcgatgtcgg aggccacaac aaacaattca ttcaaacagt cattatttgg gtacaatgcc    360
             atctcctcca tttggcttca actggctggt gtggccgcca ctttctttgc atttggagct    420
             ttgatggcag ctgtaacgca acgcaaggag atcgccgtct tctccgcctc gggtcaggct    480
             gctgagccgg aggggcggga gcccctgaag cggccttttc cgtctcctgc tgccaaacct    540
             aagccgctct tctccacccc ggcaaattcc ttcagcaaca tcttccaggc gcctcatccg    600
             ctgcgcacgg actccaccta tggccgaggc ccgcgctcga ccagcttcac cgacatcagc    660
             aactggccct caacaacgc actccgcaac ccccagtcgg tgattgacat cggggggagga    720
             gtcgacttcc tgggggacag aagccctgga aacccgttca cgcggctgcg ggggtccccg    780
             agctccaccc tcagcaacct cggcatgggc ctaggcctgg ggctgggcaa gggcaagggc    840
             ttcggcaagg gcttcggcaa ggcggggg ttccccgtgg aggaggagg ggaggaggag        900
             caggaggtgc tgtcgtgggc cgaccgccgg cggcgctgg cggacccga cgccccgccg         960
             atgaacgagg acatcaagta cccgcagctg cggctggtgc gggcgtgcc gggcggccgg      1020
             gacgagaagc tcggtgtgat gtcgaggcag gaggcgctgg agctggcgga ggcggaagac    1080
             atcgacctcg tcctcgtcag catcgacacc gaccccccgg tggccaagct agtcaattac    1140
             tcgaagttga agtacgagtc cgagaagaag aagaaggaca gccacaagaa ggggaaggtg    1200
             aaggaggtga aggagctgaa ggtgtcccat aagatcggcc agcacgacta cgacgtccgc    1260
             gtgaagcagg cccgaaagtt cctggagggc ggccaccgca tcaaggtgtc gatggagttc    1320
             aaggggcgcg agaaccagtt cgtggagatc ggccgcgcgg tgatgaagcg cttccagaac    1380
             gacctggcgg acatgggcaa ggcggacgcc gtgcccaaga agctcggcac ccggctgatc    1440
             ctgaacctgg ccccggccgg ggaggcgctg aaggtgattg cggagcggag ggcagagcgc    1500
             gacaggaaag ccgcggctga ggaggagggg gagggcgacg acctcgactt cgtggacgag    1560
             aacgaggacg aggatgtgga gggggagggc gaggaggaag agccgagga gctggaggag     1620
             gagacagcgg aggggacgga ggtgccaacc cgcagctgat cgccgatccg cggggacag     1680
             ccacctcccc cccggccttc ctgccgggg ccgcaccat ccgtcgttgc ggtgcggcgc      1740
             tgccatcaac ggccgtcctt gagcttaatg ctcccgccct ccgttggccc gcggcggtcg    1800
             ccaggttgct ggcctggctg ccgcagctc ctcccctccc cgactgacac agtgtggatg     1860
             accgtgatgt gcgcctttttc gccttc                                        1886
```

<210> SEQ ID NO 37
<211> LENGTH: 3015
<212> TYPE: DNA
<213> ORGANISM: Unknown
<220> FEATURE:
<223> OTHER INFORMATION: Description of Unknown Organism:Unknown

<400> SEQUENCE: 37

```
             ccgctcatct ccaggcctcc ctgagtgcgt acccgagagc ggcaagtaga gaaaggaaca   60
```

```
cagatacagc accatggcct ctaggctcgt ccgtgtgctg gcggccgcca tgctggttgc   120
agcggccgtg tcggtcgacg cgcgcttcgt ggtgcgcatg gtgcaggtgg tacaccgcca   180
cggtgcgcgc agcgcactca tcgacgacaa cacgacgag atttgtggca ccctgtaccc   240
gtgcggtgag ctgaccggcg agggtgtcga gatggtccgt gctatcggcg agtttgcccg   300
cagccgctac aacaacctct cattggtgga gagccctctc ttcccgtcga cgcggtacaa   360
ctcctctgtc gtgcacacac gctccaccca cacccagcgc accatccaga gcgcgaccgc   420
cttttctgcgc ggcctcttcc aggacgacta cttctacccg gtggtgtact cgaccaacag   480
aacgaccgaa acgctgctca gcactgacgc ggtgccgtcc gtggtgggcc gtagctggct   540
cgacaacccg cgcctgcacg ccgccctcaa cccggtgatc gatgagcacc tcagctggga   600
cgccatccag agcgctgcca aggacgcatg ggtcgagggc ctgtgcgcgg actacaacgc   660
ccgcaccaac tgcgtcctcg acatgtacga cgtggccgcc gccttcgagg ccgccgggcg   720
tcttgacaat gccaccaatc tcaaggcggt gtatcccggc cttcaggagg tgaacgcccg   780
ctggttcaag tatgtcttca gctggaacca cacgagcaag ctcgatctca cgcagggctc   840
cgcctcgcag aaccttgcgc agacggtgct ggccaacatc aacgcccacc gcctctctcc   900
gtcgtacaac atgttccagt acagcgctca cgacacaacg gtgactccct ggctgtcac   960
gttcggtgac cagggcgaga cgacgatgcg tccgcccttc gcggttacca tcttcgtgga  1020
gctgctccag gacaccgcag atgccagtgg ctggtacgtg cgcctcatcc gcggcaaccc  1080
tgtgaaggca gccgacggca cctatgtctt ccaggagtct ggtatcaagg catactgcat  1140
cgatgaagcc gggaacaagt acctcgcaca caccggcatc tgcccgctga atagcttccg  1200
ccgcatggtc gactactcgc gccccgccgt ggctgacggt cactgcgcca tgacacagac  1260
tcagtacagc aacatggatt gcccgcgcac tatcgcggac aacaagccgg tgccgtccgcg  1320
ctgctggctc taccgccacg tttgccctag caaggcatgc ccggacagct acattctctc  1380
cgcggtcgac caccagtgct accccgggcc cgacgttacg aaccccacca gcagcagcag  1440
cagcgagggt accaccacca gcagcagcga gggtaccgcc accagcagca gcgacgttac  1500
caccaccagc agcagcgagg gtaccgccac cagcagcacg ccagcagcag  1560
cgagggtacc gccaccagca gcagcgacgc taccaccagc agcagcagcg acgctaccac  1620
caccagcagc agcgagggta ccaccagcag cagcagcgac gctaccacca gcagcagcga  1680
cgctaccacc accagtagca gcgagggtac cgccaccagc agcagcgacg ctaccaccac  1740
cagcagcgag ggtaccgcca ccagcagcga cgttacc accagcag gcgagggtac  1800
cgccaccagc agcagcgacg ctaccaccac cagcagcgag gagggtacca ccagcagcag  1860
cagcgacgct accaccagca gcagcgaggg taccgccacc accagcagcg acgctaccac  1920
cagcagcagc agcgagggta ccaccagcag cagcagcgac gctaccacca gcagcagcga  1980
cgttaccacc accagcagca gcgagggta ccgccaccaccacccagcagcg acgctaccacc  2040
cagcagcagc gagggtaccc caccaccag cagcgacgct accaccagca gcagcagca  2100
gggtaccacc agcagcagca gcgacgctac caccagcagc agcgagggta ccgccaccac  2160
cagcagcgac gctaccacca gcagcagcag cgagggtacc accagcagca gaagtgacgc  2220
taccaccagc agcagcgagg gtaccgccac caccagcgct acca ccagcagcag  2280
cagcgagggt accaccagca gcagcagcga cgctaccacc agcagcagcg agggtaccgc  2340
caccaccagc agcgacgcta ccaccagcag cagcagcgag ggtaccacca gcagcagcag  2400
cgacgctacc accaccagca gcgacgttac caccaccagc agcagcgc agggtaccgc  2460
caccagcag cgacgcta ccaccaccag cagcagcgt accaccacca gcagcagcag  2520
cgagggtacc accaccagca gcagcagca gcagcaaa agcacaagtt catcgcgatgt  2580
cccttccttc aaaaagcccg cgaactggag cccgcgcgtt ctctcgccgg aaagggggccg  2640
ccacattgcc ggggacatca tccgccgcgt gacgaacggt gttacgatcg gtgcgggtgt  2700
ccgaaagcac gatgagtaca gccggcaccg ccaacagtag cacaacggca tgtaactcta  2760
ttgtgcatgt ttgaatggag aggaggcttc tgtacagcga cattgtttc gagaaggtat  2820
cacaaccgct cgtttcaccc ccgtcatctt ttcatttga tctccgtcgt ctcatactgc  2880
ctttgtgggc tctctctggg tgtgggcgct tgtgcgtgtg tcgctgtaaa gtcgttgacg  2940
ccatcgctct tacctgtggg ctatttttt aattatggtt tattattact tccctctctg  3000
cgcgtccctc tgcag                                                   3015
```

<210> SEQ ID NO 38
<211> LENGTH: 38186
<212> TYPE: DNA
<213> ORGANISM: Unknown
<220> FEATURE:
<223> OTHER INFORMATION: Description of Unknown Organism:Unknown

<400> SEQUENCE: 38

```
gatccttcct gcctcttccg gcgtctgggg ctccaggcgc ccttggcttg cagattgatc     60
tccctgatct ctgcctccat ctgctcacag ccttctcccc tgtgtgtctc tgtctcttct    120
tgtaaattca tccgtcgttg gatcagggcc cacccggttc ctcgtggcct cgccttaact    180
gggccatgtc tgcagagacc ctatttccac ataaggtcct attcacagga accgggggtc    240
aggatgtcag cctgtctttc tgggagatgt agttcaaccc acaacacaca tcaaacagtt    300
attgagcgcc gactgcgtgc cctgccgtgt gcttgaaggt cccaccctca ggaagcgggg    360
cctagggatg gcggccgtga tcacgcaggc agcagagagc agctctggga agcggggagg    420
gacgaggacg gggaggcgac atcagcaagg ccgtgtgtga ccaggcagg gtgtccccgg    480
tgtagcacct ggctcgggca gaggccccga ggaggggctg gaggagctgg gcggaggagc    540
gggcaggacg ggcctgacac tagggacctc gggccccggg aatgcctctg ggggggcgtg    600
tacacccgtt gctcccagga ggcacacact gcggttcgct tcgccaagaa tgtttaattg    660
catttgatga ctacggtttc cattcattca tttgtagaga tataacactc agaccacaaa    720
atgcataaaa tgcggtggct tttagtatta acagagtgct gcacccgata ccacagcctc    780
actccagaac attctcatgg gcccaaaagg agacctgggg tgttagtcac cagctcactc    840
cccgtcccca gccctggca acccacgcta cttagtcatt atttaggtgt ttaggagttg    900
caaagtcaaa tcttttaaacc cacatatggc caggcgtggt ggctcacgcc tgtaatccca   960
gcactttcag aggccgagac gggcagatca cctgaggtca ggagttcgag accagcctgg  1020
ccaacatggt gaagccccgt ctccactaaa aatacaaaat tagccgggcg tggtggtggg  1080
```

-continued

```
cgcctgtaat cccagctact ctggaggctg agacaggaga atcgcttgaa cccaggaggc 1140
ggcggttgca gtgagccgag attgtgccac tgcactccag cctggacaac agagcgagac 1200
tccgtctcaa aaaaaaaaaa agtaccaaaa agtgcccccag gtcataaggg cacagctcga 1260
tagctggtcc ctaaaggaga cgtggtgtaa ccaccacaca gaacgaagct ggaacgttcc 1320
tgccgtcctt agaagctgcc tttgctaagg ggaattgccc tgacttccca caccattgat 1380
tcatctccag acccttggtt ttcatgttga ttttcaaaa atcacctgat agtctgaccg 1440
aatgtagctt tccactggtg tgtgtgtgtg tgtgtgtgtg tgtgtgtgtg tgagagagag 1500
atggagtctc gctctgtcac ccgggctcca gtgcagttgt gtgatcttgg ttcactgtaa 1560
cctcctcctc ccgggttcaa gagactcgtg cctcagcctc ccgagtagct gggattacag 1620
gcacccgcca ccacacccag ctaattttt gtattttag tagagatggg gtttcaccat 1680
gttggccagg ctggtctcga actcctgaca tcaggcgatc cacccacctt ggcctcccag 1740
agtgctggga ttacaggtgt gagccaccac gcccggcctt atttttcccc cattttcttt 1800
ttttttttt ttgagtcagg gtcttgttct gcgctcaggc tggagggcag tggtgtgggg 1860
atcacggctc actgcagcct cgacttcctg caccaccacg cctggctgtt tttttttt 1920
ccggtagaga cggggtcttt accgtgttgc ccaggctggt ctagaactcc tgggctcaag 1980
cgatcctccc gcctcggcct ccgcaaatgc tgagatcaca cgcgtgaggc cccgcacccg 2040
gcctccttc caccgctctt gtctacagcc gccctcctg gtccgattgt attggcagat 2100
gtcgccaata cggtgtcaaa cggcgaaggg gcactgagcg ttttttcttt ctcccgtcct 2160
tggcggcagc agctcggttc cggctacggg gctgagcccg tctctcagac gaggaaactg 2220
gggtccgaga ggtgagccgg tcccagaggc agggcgaggg ggaagcggga gtggggtccg 2280
cagcggaccc agccctgcct ccccctgca ggagatccca aacttcaact gccggaagct 2340
ggtggcctcc atgccgctgt tcgccaacgc cgaccccaac ttcgtcacgg ccatgctgac 2400
caagctcaag ttcgaggtct tccagccggg tgactacatc atccgcgaag gcaccatcgg 2460
gaagaagatg tacttcatcc agcacgcgt ggtcagcgtg ctcactaagg caacaagga 2520
gatgaagctg tccgatgcct cctacttcgg gggtgagctt gagggggggcg cgcctggagg 2580
gggagggggc acgcgacccc cgcggtgtgc agagccaggg ggccggggcc ggggccgggg 2640
ccggggatgg ggatgggat gggatgggg ccggggatgg ggatgggat ggggatgggg 2700
ccggggatgg ggatgggat ggggccgggg atgggatgg ggccgggat ggggccgggg 2760
atggggccgg ggatggggcc ggggccgca ccagggagg cctggtggg aagcgcccac 2820
gctggccaag gtgcagaggc cgggccgtgt gcctgggcgg ggagggccgc ggcgcccgcc 2880
tcgtccagca acccccccct gcgcgccacg tgcagagatc tgcctgctca cccgggccg 2940
ccgcacggcg agcgtgcggg ctgacaccta ctgccgcctc tattcgctga gcgtggacaa 3000
cttcaacgag gtgctggagg agtaccccag gatgcggccac gccttcgaga cggtggccat 3060
cgaccgcctg gaccgcatcg tgagcgggc cggggcgtg gccggggcgg gtgccctggc 3120
gggggagggg cgtggccaag gcatcaggag agtggcttgg acagtggcag ggggaagggc 3180
gtggctgtgg catcaggggc acggttgggg cagagacgtg gccaaggcat caggagtgtg 3240
gccatggcag caggggcgtg gctggggcag gggcagccgc tggccgctcc taggacccct 3300
ttgggtctag aggctgattt tctgacctat tgtcctactt cagccagagg cagcctgttt 3360
cccaagggag ggaatgcaca gggtgtttgc ggttgtgccg aatgctcggt gagcacctgc 3420
tgtgtgctgg gggtgcaggg gacagacccg gggccccact cagactccca gggaggctta 3480
tggactggtg atgaaatcac acacgactgg gctgtgtgcg agcagggcag gtgggccgg 3540
tgggcttccc tgagttggga atgcagagtg gagaccaggg taagggatgc catgtggaaa 3600
cggggaggaa gatgtgttcg tggagtggac acagcacatc ccaaggccct gaggtggaaa 3660
agaggcctag agtccagaga gccaggagg cctggaggag gttggggaag aaggggaggc 3720
cagacacaca gggcccagtg ggcggcaggg agagtttaga ctaaatcagg agcatcaggg 3780
agccatggag ggttctaggt gggcggagga cctggtcaga ttgtatccgc caaggcgggc 3840
cgtgtccagg agggagacgg tgacctggcc tctcaggggg gcagtctctg gggcagggag 3900
cggcagagcc ctgatgactg gatgtaggcg ccagagagat ggcggctcat gctgctgttc 3960
gtgggaatgg gaatgaagac catggctgaa acgcaggaca ggtgcgacgg agtggtgtca 4020
gggagctccc tggtgtacag taggaagctc tccacaactt gctctataca gtgagtatgc 4080
aacccgttcc tgagtatcag gtgcttaggt tataacttct gtatacagca ggtgctcagc 4140
acaggctgtg tacaggcagg tgttttcggt atgcctgtgg cacactggag gcagtcatta 4200
cataatcagc gtatacaggt ggtacacatg catacttggt gcacagtgat acctgctcca 4260
tgtacacagc aggcattaaa tacctgttta ctgccaggcg cggtggctca cgcctgtagt 4320
cccagcactt tcggaggcca aggtgggtgg atcacgaggt caggagattg agaccatcct 4380
ggctaacatg gtgaaacccc gtctctacta aaaaaaaaat acaaaaaatt agccgggtgt 4440
ggtggcgggc gcctgtagtc ccagctactc gggaggatga ggcaggagaa tggtgtgaac 4500
ccgggaggtg gaccttgcag tgggccgaga tcgcgccact cgactccagc ccgggcgaca 4560
gagcaagact ccgtctcaga aacaaagcaa aacaaaagcc ctgctttctg tatgcaggtg 4620
cttcatgcat gctgctgtg catagcaggt gctcagcctg tatatggcag gtactcaata 4680
tccatactat aggccagaga tgctacatat gtgcttattg tatacagtag gtggtaaatg 4740
catgcttgct ctacacggca agcactgtgt gcgcacccgc ggtgcagagt aggtgctcgg 4800
tgcccgctgt acgcagcagg cgctccctgt gcacacgcta acgcccctc tcccgcaggc 4860
aagaagaatt ccatcctcct gcacaaggtg cagcatgacc tcaactcggg cgtattcaac 4920
aaccaggaga acgccatcat ccaggagatc gtcaagtacg accgcgagat ggtgcagcag 4980
gccgagctgg gtcagcgcgt gggcctcttc ccgccgccgc cgccgcgccc gcaggtcacc 5040
tcggccatcg ccacgctgca gcaggcggcg gccatgagct tctgcccgca ggtggcgggt 5100
ccgctcgtgg ggccgctggc gctcggctcg ccgcgcctcg tgcgccgccc gccccggggg 5160
cccgcacctg ccgccgcctc accgggcccc cgcccccg ccagcccccc gggcgcgccc 5220
gccagcccc gggcaccgcg gacctcgccc tacggcggcc tgcccgcgc cccccttgct 5280
gggcccgccc tgcccgccc cgcctgagc cgcgcgtgag cgcctcgcag 5340
ccctcgctgc ctcacggcgc cccggccc gcggcctcca cagccggc cagcagctcc 5400
acaccgcgct tggggcccac gccgctgcc cggccgccg cgccagccc ggaccgcagg 5460
gactcggcct cacccggcgc cgcggcggcg ctggacccc aggactccg gcgctcgcgc 5520
ctctcgtcca acttgtgacc ctcgccgacc gcccgcagg gccgggaggg ccggggcgct 5580
ggccgtcatc cagaccaaag ccatgccatt gcgctgcccc ggccgccagt ccgcccagaa 5640
gccatagacg agacgtaggt agccgtagtt ggacggacgg caggccgg cggggcagcc 5700
ccctccgcgc ccccggccgt ccccctcat cgccccgcgc ccaccccat cgccctgcc 5760
ccggcggcg gcctcgcgtg cgagggggct cccttcacct cggtgcctca gttcccccag 5820
```

```
ctgtaagaca gggacggggc ggcccagtgg ctgagaggag ccggctgtgg agccccgccc 5880
gccccccacc ctctaggtgg cccccgtccg aggaggatcg ttttctaagt gcaatacttg 5940
gcccgccggc ttcccgctgc ccccatcgcg ctcacgcaat aaccggcccg gcccccgtcc 6000
gcgcgcgtcc cccggtgacc tcggggagca gcaccccgcc tccctccagc actggcaccg 6060
agaggcaggc ctggctgcgc agggcgcggg ggggaggctg gggtcccgcc gccgtgatga 6120
atgtactgac gagccgaggc agcagtgccc ccaccgtggc cccccacgcc ccattaaccc 6180
ccacaccccc attccgcgca ataaacgaca gcattggcgc caagcctggc cgcgtgtgat 6240
tgcccgagac ccgcagggcg tgcacccttc ctgaagacag tggctcctgg gggtggcaaa 6300
agagctttat ttacacactg acaaggctca cggggtgtca gctgaagaag taggtggaac 6360
gcttcacctg ctccaggtcg aaggcccctg cggaggaagc agagcggacg gcgtgggtgg 6420
cgggaaagcc ccgccctggc ccgcagttcg agccacccct gcgaggctgc ccacccgcct 6480
acctggcttg ggcaccgcct gcagtgtctc cttcagctgt ctggcctcca agatcttctg 6540
gggcctgggg ttggaagcag ggtggggtga ggctgaggcc aggttttggg gtggggggtg 6600
aatccaggta gttggggtca gggagcgcct tactcagagc agaaccgctt gaccaggaat 6660
ctggacaggt cctgcaggat gggctcgctg tgcaagcgga caaactgctc ccggcacacc 6720
tgggcaggag tcagaggatc cccaggggtg atcaggcagg tctgggcac cacccctacc 6780
caacgcccca gtgtgggggc cccaccccatg ggtggactga ggctcagact acggggggcac 6840
ctggttcatg acggagacat cagctgcgtg agtccagtaa cagtcgtgca cagagacgaa 6900
ggtcaggccc ttcctgtggc agagcggagg actcctgaag ggaggggagc tcacagggcc 6960
acccagtgac cagcatcctg gccctgcgct cagcccccgc cacttgaggt ccagggaagc 7020
ccaccctcct gcaggcctcg cccccaccct cgccccgccc ctccccaaac atcctggggtt 7080
aggtatcagt acaggggggag gaaatgttcc cagaagcctc ctcgccccac ccctgccgcc 7140
ccccacgctg ctgtgggagc ctcagctccg agggcggcta cgaggtcccc tcctgccagg 7200
gccaccaccc cgcatcctga gcattcccag ctcccgtggc cggtagattc tgctggaacg 7260
acctccacgt gctccagatc taaccacaca tcgcggtgcc aagaaatgcc cagcaggaag 7320
gggcagcgcc catgctcggc tctccctgtc gggccacagg aggggagctg ccaggaccac 7380
ctacattcgg ggcacacagc ctcagggcct ctacacaggc cccacagaca cagcagatcc 7440
actctgccca gtccctgccc ccagctagac ccagccttgc cagctgtgcc ctgctagcca 7500
gaagacgccc ctgggaggcg agcggcaccc acgccgtccg gagacgccca cctgtagcag 7560
tgcagggcgg tgagcatcat gtgggaggag tccagcgagt ggatgaagtt gggcgggaag 7620
ccgttcttct gcttacgtgt gttgggcttt ctgaggacgg aacaggtgcc ggtgggggcg 7680
gcccagggac accctaact ggccgctgtc tccaccgtgg ctgctctcca gaccccggc 7740
caggcccag cccgggcccc ccactcaccg gctgatgtct ccgttgtggg tgtaggtgat 7800
gctctgaatt ccacctccta tttgctaaaa aggggaaggg gccggtgagt cccacccgag 7860
gcccagcacg gtggtggtac attgaggtgg tggtacactg gggtagtggc acgctaggat 7920
ggtggcacac tggcgcggga tggggtggca cactgggggcg gtggtacact ggggtggtgg 7980
tacgctgggg cactggtaca ctggggacgct gttacactgg gatgtgcca cactggggag 8040
ggatggggtg gtacactgac cttgaccttg gagtccaggc gatagggctg gatgacgggg 8100
acgcccaggg gtgtgaccca ctccaccaca gagcccatgt gggagatgag gcgggcactc 8160
tcggtcagcc agtgctgtgg gacacaggcc gtctcagggc aggggctca ggccggggat 8220
cccgtccact tgcttaggga gtcctggccg agcggggaca ggacaggaag tacctggatg 8280
gcccgggtcc ccgagaacat ctcctgtaga ctcttgaaga cctggcgtac gagatagtga 8340
gaggcctccc acacgaactc ctgcagaggg cgggcagcag gtgcaggtcc tcaggggctg 8400
gcccgttcac gccctactcc cccctatttc agagccactg aggcccaagg cctagggcct 8460
agcaggggg cagggggatg gggcctggcg cccacgcagt cagcaagaaa cgcccaagcc 8520
ctaacaggca gccagtggtc tgggggagca gccagggctc ctgctgggag gctgggtcgg 8580
gggcacaccc gtctgagttt taaatggcag tgaaaccaac gtgttcgcag cgcgacatgc 8640
ctggcgcacc tggggaaagt cgctcagctc ccggaggcgc ttctcaatct gcaggcgccc 8700
gccatagcgc gtgaccccgt acaccaccgt catcaccgtc tgcttcacca cctttgcgggt 8760
gatgaaacct tccagcacct gtgccaccga catgccccgc tgggcgtcct gcctacggaa 8820
cacctccacc tgcacggcgg gtgggccggg ggcgcgggtc agccccgcta gcagcccagg 8880
ggccaccaag cacccatgaa gcccccgccc cagccccacc acatcctcag gacaggccaa 8940
ggtgagggca cctggggccg agactcaggg ctcacattgc ccccacgccg agatgccccc 9000
gggcagcagg gcacaccta cctgcgcggc cacgccgtcg tacacgtcct gcggcacatc 9060
cgagggctcc aggttgacgg aggcggcgcc cacgctgtcg cggcccagag cagcataatg 9120
ctgcaggccg ttgcaagagc cgtcctgagg aaggggcggc aaacgggaga tggaagctag 9180
agaggcagag acgtgtggga ccccaaacca ccccccaggt cgagccgttc ctagggccgt 9240
gcaccccca gccaagtgca ccggagcccc cgcacgcct cggagagac caggagccat 9300
ggctccccgca cactctagga ccacctccag agaataccac gagcgaaggt gaaatctcac 9360
accctcaagt cgagccccag gcccagtgca cactgacgg cctcggggc cagcccagc 9420
tggctcacct gatgacggg gaggtgggag acataggcgg cagggtcgga ggcgcgcaca 9480
gcgttcgcca cctccataca gcaggccagc gtctgccagg gttcctccgc gcccatccac 9540
cactttcggc cctgcgggga cagcggatgg gggcagtga ggccgggcc cgatccctga 9600
gcccgctggg aggctgtgtt gcggggaggt gggaaatggg gaggagacgc acacccgtga 9660
tagtgaacac gggacgcatg tgggcgagag acgggcggt ggctggatga gttctccata 9720
gccacggatg gaggatggga gctgcgggtg gaccgggctg aaacaagcgt gtccggagct 9780
gccggggag gagggtggac agaggacctg ggggcgccgg gggaggaagc agctcggcgg 9840
atgcagggga ggggggaacg tggggaacgc gggggccctg gggcagggga gaagggagaa 9900
gcaggacggg cagggggcgc ggggaggag agcgggcggg ggacgtgggg gcgccagggg 9960
aggggagg gaggaggaag acggcaggg ggcgccaggg gaggggagg ggaggaggaa 10020
gacgggcagg gggcgcgggg gcgccggggg aggcgcggg ggcgccgggg ggcgcgcagg 10080
gggtgccggg agggcgggga atgcgggggc cccgccccta ccgtcaaggg ttggtccgcg 10140
gagtccagga tgtcatccat cacctcctcc gcaaaggcca ggcgcttccg cagcggctcc 10200
cgcttcttca accccgtgag attgaccagg tggatcttga gccaatccag gccgtgcggg 10260
ccgagcgggc ggcctgggc gaactccaga agggccccgg ccacgtcgct gcccaggtgg 10320
ttgaagtgcg gcgggcaggg gtaggtgcgg ccgcggaagt ccatgttgtg cggcagccag 10380
aagacgcggt cccgcaggtg ctgcgccagc gagaggcggt acagcgcctc cgcccgcagg 10440
ctgtgcatct cccggggccac cttctgcgcag tgcgccagct cacggcgcag ctcggcctg 10500
cgggcgggcg cggcgctgtg cggcaggtgg gcctcgggcg gctgggcgc ctcggagggc 10560
```

```
ggggccggca cgcctagctg ggggcagccc ttggcctgga agagctgcag caccaggtcc 10620
agcacgcgcc cgttgacgcg ccaggcgcag ttgcccagtt gggtgagggc gtccagtgcg 10680
ccatgcagcg cggtgggcgg gcaggtttcc agcagctcct ggtgctgcgt ggcgccttcc 10740
accgtgcgca tcagcttggt ggggctgagc aggaaagcac cagagtgcgg cgatgtccag 10800
ggcagcgggg ggcaaagcat gggtacatcc accgcctcga aggtcagcgt gggctccgcg 10860
gccttctcca gcagctgcac gtaggccggg tgcggcttca ggatgccgat ctggggtgcg 10920
acaggcagac gggtcagggc cccggtgctg gggctttcct gttcccaccc cttaaacttg 10980
ggtgagaggg gccggctccc cggccaacaa gaaaccagtg tggcctccca cgaacagaaa 11040
ccacctccag aaacggccgg acacctgcat ggacaccat ggtgtgtccc gagtcctggg 11100
aggtactgac ggctgcgctg agatcaaggc tccgcccaaa ggcgccaacc ccatgggtc 11160
cctggtcctc ccagcgggat gcccccagc tcaggagggc actgcctggc acctgctgga 11220
cgttgcggaa ggaatacacg tggtagagca cggggacaag ccgagaggaa cgatgcgggct 11280
tgtccaggct gcatggcatc tgcgtagcct gcaccagcat ctccgccagc agcttgccca 11340
gctccatctg cactggcagg gccagggct gctcccgcag ggcctccggc gcccccagct 11400
cctcccagta ctgccgcggc aggcagggct cgggcacctg taggacaggg cggtcagggc 11460
gctgggcacc gggcccctg agctagatgc cccaccgcc gtgcgtgacg cccggtgggg 11520
catctgtcag cccaagcata cagatgaaca gactgaagct tgggtgcaaa cccggctgct 11580
ccagggaggg agagcgccca cccaccactg gccccagcca ggaggagagg gggtgcgagc 11640
ctcacctcgg cgtcggaggc cagcaagcag aggtacttcc tgtagtggtt ctgcagcgcc 11700
tgcacctggc cactgacccg ctgcctctgc accacgtgcc ggctgaaagt gcgcgcactc 11760
agctcccggg ccagggtggt gaaggactca ccttgggcgg gcagcgcctg caggacctgc 11820
ggaaggcagc cgtgagtgcc tgcccgcccc gcccggggac ccggccgcgc ggaggaagac 11880
gcacctgcag gagcatccgc accacctcgc gctcgtccag caggcacagg aaggggtaaa 11940
gtgagaaccg gccctcgtac acctcgcgct ctaggcggtt cttggtctcc cgcagcgccc 12000
ggcacagtgc ttctcccat tggtcccgca gggtcttcag ggtcttctcc tgcggggat 12060
gaacgggccc ggtgagcccc gtgcagctg gtgggaccca ggctcacagg acggggtca 12120
ccgcagctcc ctgcagagac ctcatggccc tcaaggtcc tgctgtgtgt tccgggtagc 12180
tcctcacccc ggcctgccct ctgcggctt cagcgtgcct gacgcagcca agagcaaaag 12240
cccagctgca gtgtgcgcag aagcacaggc caagacccaa cctcgggacc ccacaagttt 12300
tccctgagcg gcagccaggc tgagttccta ggcccctgcat gaccagacca gggcatgagc 12360
aattcaaccg catacacgga gctcagcccc tgcggcggac acgcgacccc ggctcagccc 12420
ctgcggcgga cacgggaccc cggctcagcc cgtgcggtgg acacgcgacc ccggctcagc 12480
ccctgcgcgcg gacacgggac cccggctcag cccctaccgc tgcttgacc tccttgcttg 12540
gcaacgtggg cttctccacg gacaccacgc acaccctgct ggccagctcc atgtggagct 12600
gcttctcaaa gaggcactgc agggtcttca agggcaggtg cagcttcggg taggacacac 12660
gcccatcctg cagggatggg ggtagtgagg ttgggggctt gccagagggc gacctgccct 12720
cccaggaccc cgagacagca tgggtgcacg cgtttctgcg tctcctgcaa gttgctggtg 12780
gctatcgctg acgcggggaa aggcgggctg cgggtaaagt cagtgccagc agtgcaaacc 12840
aaaggccttg accctcctgg cctcgacccc tctagaaggg acactgggca ccgtgcaggg 12900
ggtggcaggg gcggtgatgc tgggagctgg cagagcctgg ggagaccgtt cactgcaccc 12960
ccagatgttg gctgtttct cctcaaactc agaactgtat gaatgtgacc catccagaaa 13020
tagatgaatt aaaaataaca actaaagcct agcgctttga gaatcaaaga cgcacgtcca 13080
cataaaagct tgtacacaaa cgttcacagc tgcatgactc gcagtcgata agtagaaaca 13140
gcccaacgtc ccataaacgg acgaacagac gggcacgcg cggccatcca cgcaccggag 13200
catgactcag ccctgaccca ggtcgcctcc cggaggacgt atgaggacgt cacgctcagt 13260
gggagatgcc aaacacaaaa ggtctcgcag tgtgtggtcc catttctatg gaatgtccag 13320
agcagactca tccacagatg ggaggggat ggggagtgac ggggatgggg acgaggcttc 13380
ctttttagggt gatggaacat tctagaatta gacaaccgtg actacactaa aatcgctgaa 13440
ttacaccttt aagagggttt tatggcaggt gaattacacc tcagtaacag acgagcccac 13500
tgcgtgcacc tggcagcccc actcaaacgc actgctctc tgtcacccca ccctctctct 13560
gcggccccg accacctcgt ccccctgagc ccacaccctc agggccaaga ccctcccagc 13620
tctgggtcct cccatcttct cagaggagga agggaggaat tcagggccca gcccaggtga 13680
gccctgggca ccggggaggc ccattggtct gagctgaggc tccaggaacc cccaaaggc 13740
agctataagg actgaagtct gccggggccc acgtgggctc accttggcat acacgtcct 13800
gagcagcttg gaggtgttga ccggggggcg cagctgcggc gggaggctga aggtgggctt 13860
caccttgtgc acggccttca gaacagtggc ccgatcctcc tcagacagca gaacggcggt 13920
gaagagtgcc tgcagcttca gcccctcctg gctcatctgt tccagacacc tgtggtgcag 13980
gcggcctgct cgagggacgg gccagccca cgctgggctt ccacagaccc caggggaacc 14040
tcgtgaccac ctcctgctag cctgcaggtc tcggtgtggc tgtcaggccc tctgggggtc 14100
cccagcccc agcccaggca ccgtcccaga tcttaaaacc ctgggaggga catggtgggg 14160
ggtgggggcc ctcccgacac cacctacctt tcgatggtcc cggcgtcctg gtcctgcctc 14220
cccatgcact ggagggcagc cgcataggac agcaggtccg gagtcaagcc ggcatccttc 14280
accatgaata acacatatac cagctccttg aaggcaccct gggagaccaa gccaggtgta 14340
gggtctgggg ggatggccca acctccacat cctccctgct ccctggagac cccttctctg 14400
tagccaccag ctcagcaggg gacagggtca ccaggcagga gtggccagct gggcagaccg 14460
atgcatcccc ctgaggttct gacacacaag ctccacctgc agaggcagcc gcatggccgg 14520
ccaggtggga ctgtgggagg ttcacgttcc tctgggaggc agcttgttaa acctccagat 14580
ttgtcaattg tgtggatctt tcaaaggac tgacttggct tgactgttct ctgctgtttc 14640
tgccttccat ttcatcgatt tgttttaatc tttgtaactt cctctcatct acttgcttta 14700
ggttttagtga cagcttcttc ttctagtttc ctaaggtgaa aggtgacgta tttggtctga 14760
gatgtttcac ttttttttccc cccaaagtg agtcttgctc tgttgcccag gctggagtgc 14820
agtggcacaa tctcagctgg gccgggttct ctgcctccca ggttccagca cttctcctgc 14880
ctcagcctcc tgagtagctg ggattacagg cacacgccac cacaccagct aattttttgt 14940
attcttagca gatacggggt ttcaccatgt tggccaggct ggtctcgaac tcctgacatc 15000
gtgatccgcc agcctcagcc tcccaaagtg ctgggatgac aggtgtgcac caccgcccc 15060
ggccatcacc tttccgaata taggcatttt tgtgactataa attacccgtc gagcactgtg 15120
tcagctgcat ccaggacttt ctgacaggtg gtgttttcat ttcattatc tccaagtgtt 15180
ttcgaacttc atagtttact tcttcttttg aaattttatt taattatttt tttagataga 15240
gtctcgctct gtcgcccagg ctggagtgca gtggcgcaat ctcagctcac tgtcaacctc 15300
```

```
cgcctcccgg gttcaaccga ttctcctgcc tcagcctcct gagtagctgg gactacaggc 15360
acatgccacc acacccagct aattatttg tatttttagt agagatgggg tttcgccctg 15420
ttggccaggc tggtctccaa ctcctgacct caggggatcc acccgcctcg gcctcccaaa 15480
gtgctgggat tacaggtgtg agccaccacg cccagccatg tatagcttaa atatccccctg 15540
caattttttt tttttttcatt taatttttgg ccaggcacag tggctcatgc ctgtaacccc 15600
agcactttgg gaggccaaga caggaggatc acaaggtcag gagtttaaga ccagcctggc 15660
caacatagtg aaaccccatc tccactaaaa atacaaaaaa aaaaaaaaaa aattagctgg 15720
gcgtggtggc tcatgcctgt gctccctcca ctaaaaatac aaaaaaaaaa aaaattagc 15780
tgggcgtggt ggcacatgcc tgtaatctca gctactggga gcctggggca ggagaatcac 15840
ttgaacgcag aaagcggaaa ttgcggtaag ccgggatctc accactgcac tccagcctgg 15900
gagacagaaa ctttgctgtc gacagacttg gagactctgt cttaaaatat acacacacac 15960
acatatatat atatatataa aataacatat atatataatt tttttcttgt attcattttt 16020
cctgacatcc ctgttctgag caatttctcc tttgacccag tggctgctta agagtggcct 16080
gtaactgtaa cagactattc caaaggaaa aaaattccct tacatcctcc caccccatag 16140
tcctgcagct gaagacatgc tgtgacatga ggtggccaca caccagagac cagagacatg 16200
agttttgggg catttttttt tttttttttt tttgagacgg agtctcgctc tgtcgcccag 16260
gctggagtgc agtggctcga tctcggctca ctgcaagctc tgcctcccag gttcactcca 16320
tcctcctgcc tcagcctccc aagtagctgg gactcaggc gcccgccacc acacccggct 16380
aattttttgt atattttag tagagacggg gtttcactgt gttagccagg atggtctcat 16440
ctcctgacct cgtgatccgc ccgcctcagc ctcccaaagt gctgggatta caggcgtgag 16500
ccactgtgcc cggccggttt tggggcagtt tctaaacaac ctctgtatgg tagacctcac 16560
tggccacaca tagtccttaa attgaaatat tcagttcttc cctttcacca gcttcaagtg 16620
ttcagtagca cacacagctg ttggcagatg cggaaaattc ccaacatcat agaaagttct 16680
actggatggt gctggttaga atacgtggcc gggcgcggtc gctcacgcct gtaatcccag 16740
cacttaggga ggctgaggcg ggcggattac ctgaggtcag gagtttgaga ccagcccggc 16800
caacatggca aaagcccgtc tctactaaaa atacaaaaat tggccgggcg tggtggtgtgg 16860
tccctgtaat cccagccact caggaggctg cggcagggag aattattgaa cccaggaggc 16920
ggaggctgta gtgagccgag atcatgcac tgcaccctag cctgggcaac agacagagag 16980
tctatctcaa aaaaaaaaaa aaaaaaaaga tagaagcaat gccttagcct ggctaacatg 17040
ctgaaaccc acctctacta aaaataaaaa ttaaaacaat tatccggggg tggtggcaca 17100
cgcctgtaat cccagctgct cgggaggctg agctcgcagt ccagcgacat ccaggactgc 17160
tggccacccc ggaacgctgg gagaggcagg aggggcccct gctagagcct ctggagagac 17220
ttcgggtctg cagacatctt gattccagac ttctgattca tgcgttttctg 17280
ctgtgcaagc cgccaggttt gggacacttt cgtaggggcc gatcccaaaa gcgccctgtt 17340
acagtgtggg ctctctgccc agggaatcca ggggggcttgt gaccttgag gggaaaatac 17400
acgaccctca tcctcagtcc tcccggagtc tggcgccccc tgcagcaagg aggaaccagg 17460
cagcacgccg cctccacctc gcggtaagag cactgcggac ttcaccgcaa gactggcccc 17520
acctgatcct gaatttcgct gtttgatgcg ttaataaaga agcacatcaa gttctctacc 17580
acgaattggt cttaatattg cgatatctgt attttaatat aatagtatcc catgtttacc 17640
caaatattaa gagaagcttt tactgttgtt tctcaaatta gggctgaagg atcatggggg 17700
gggagaaagc tgggaacgtt tgctgctttg aaagggtgtg taaacaacac cctccaaaac 17760
aaccaagagt tccgaggaga aactttggcc ggatacggtg gctcacgcct gtaatctcag 17820
ctcctcggga ggctcagggg gcagatcac gaggtcagga gtttgagacc agcttggcca 17880
acacgtgaa acccccgtct ctactcaaaa tacaaaaatt aatcgggggt ggtggcgggc 17940
acctgtaact ccagctactt aggaggctga ggcaggataa tcacttgaac ctgggaggtg 18000
gaggtggcca tgagccgaga tcgcaccacc gcactccaac ctagtaacag ggagagtatg 18060
tcccagaaaa caaataaata aacaaacaaa agaaaacg caagggaaat tggaaaatac 18120
tccagatgaa ccacaacgaa gatgggtggg atacatctaa agctgtgctc agagggaatg 18180
cggcgccagt gaacacccac atttcacaca gaaggatctc agcacagcag cccgaccttc 18240
cacctcagga aaccagaaaa aggagcaaag tcaaccccaa caccaaagcc tcatcctgac 18300
gagggctctg caggctgccc cccgacgagg ccaaaagcac ccctgcccag acagattcac 18360
gagccccgag aaagaacgga aggaaatgct caaggcatta gcagaatttc tccctacttt 18420
tttggtcatt ttcaaaattt gagagtcaca cgtgatttgt atttgaaaag cctaaaagaa 18480
ttattaaaat aaaaaacaaa ggacttgaac ctgggggcta agagagaaaa gtccagtcta 18540
aatgagggca agttcctgtc tccaacgacc agggcaggtg gcccggctcc cggctgcact 18600
cacctgccgc gcccagccaa gcatacggc gttgtacatg tccagcgtga gcagcttccg 18660
cttctgccgc tggccgtggt ggacgaccag caggtggtgg gcgagggggca gctggtcagt 18720
gagcaggcag cacttgaaga aggccaggag cctctgctgc tgacctgaga gctgggcctg 18780
cgagtgctgc cccgacgggg cctgctccac atcgaggctc agcttcccag gggcctcctg 18840
cagcagccgg gccagctgct cctcccaggg gctctcgggg gcctggcgcg tgcagtcctc 18900
caggcacccg gccatctgct tgctcaggag ccggggctcc acctgcaggc gcctggtcag 18960
cgccttgaac tcccgctct ggaatggcat ctgcagctc gccttcaacc gctgcatacg 19020
catctgctgg gtccgcttat ccttctccag tatctttgcc cagcggccac agggcaccgg 19080
ggtggcatcc ttggccccca tctggacctt cctgggtggc tggaggctac catctccact 19140
gccacattct gggagccgcg ccacatccac cctgttcacc accacctccg cacgctctc 19200
agcctgcagc tgccgcaccc gcgcctgggg cactgtgagg ggcagaaggc gaggagtgga 19260
gagggacccc ctccccattc gagcacccgt ctctctggac cctgagccgg gccaggaggt 19320
gcaggtggct gagctcgctg gacccaagg cgtgaattcc tcatacttgc caacaacgtt 19380
gtaaggtctg cccgctgctt tccagacaca cgcacccac cacctccgca cctcccacc 19440
cgagcctcac agaactcagc agccctaaca agctgccacc gaaacctgca gcaccacgtg 19500
tccccggtca ctggccgctc agaccctca ggtgcacagg ccagaaaccc ggggtctgtg 19560
acaactccct ccgtccacct tcagtacct cctctgggct tgcctccaga atctatccag 19620
gtgcccccg cctcccctgc ccctctcact gtctagctca gggcctctgc acagactccc 19680
aggaccctga accgccacct ccctggctca accatggcct gcaagttcgc acccgcctc 19740
agcaagaccc cccagctgg tggagctgca acacacacac tcctaggctc ccagtgtcta 19800
caccggtgga cgctgagcca ctagctcgca gggaaaacgc ggctcctgct cgtgccgcct 19860
caggttgcat ttttgccaac caatcaatgc ctaagtgttc tgtatctctt taaagaagcc 19920
ttgttggaaa tctattgctg gccgggcatg gcggctcacg tcggtcatcc cagcactttg 19980
ggaggccgag gcaggaagat cacctaaggt caggagttcg agaccagcct ggcaacatg 20040
```

```
gtgaaacccc gtctctatta gaaatccaaa aaattagctg ggcgtggtgg catgtgtcta 20100
tagtaccagc tacttgggag gctgaggcag gagaattgct tgagcctggg aggcagaggt 20160
tgcagtgact caagatagcg ccattgaact ccagcctggg caacagaaca ataatccatc 20220
taaaaaaaaa agactgttga aataagccgg gtacaggcgt gcgcacctgt ggtcccagct 20280
actccggtgg ctgaggtgaa agaatcacct aagcctagga gttcctggct gctgtgagcc 20340
gtgatcaggc caccgtgctg cagcctgaga gacagagcag gaccctgtct caaaaaaaaa 20400
aagggggggg gggacccagg tgtccagatg tggtggctca cgcctgtaat cccagcactt 20460
taggaggccg aggcaggcgg atcacgaggt caggagatca agaccatcct ggctaacacg 20520
gtgaaacccc gtccctacta aaaatacgaa aaattaaccg ggcgtggtgg tgcgcgcctg 20580
tagttccagc tactcggag gttgaggcag gagaattgct tgaactcggg aggcggaggc 20640
tgcagtgagc caagatcgca ccattgcact ccagcctagc aacagattga gaatccgtct 20700
caagaaaaaa aaaattgctg aaataaaaag acaagcgtga tgtccgcctt cagagtgctc 20760
caaaactcag gagatactttt taggattaac agttgagagc tttgtttttgt tttgttttgt 20820
ttttgagatg gaatttccct cgttgcccag gctagagtgc aatggcatga tctcggctca 20880
ccgcaacctc caccttccgg gttcaagcga ttctcctgtc tcagtctccc cgggttcaag 20940
cgattttcct gcctcagcct cctgagtagc tggcactgca ggcgttcacc accatgccca 21000
gctaattttt gtatttttag tagagacagt gttttcaccat gttggccagg ctgtcttga 21060
actcatgacc tcttgatccg cccgcctcgg cctcccaaag tgctgggatt acaggcgtga 21120
gccaccgcac caggcctcgg acccttgacc tcttgatccg cccaccttgg ccacccaaaa 21180
gtgctgggag tacaggcgtg agccaccgca caggcctcg aacccccgac ctcttgatcc 21240
gcccacctcg gccaccaaa agtgctggga ttacaggcgt gagccaccgc acctggccag 21300
gttttttccc tttataaagg ttctcccgcc tctcccttcc cggctgccta atggacgcag 21360
acaggatgtg ggacagaagc accggcggga agcaagcaca gggaagctcc cacctccctc 21420
ccacaccacc agccaggcca ggacgagggc ctgccaccgc tggagcctgg gctgtccctc 21480
ccaagtttcg cagtcatcca gtctccatta ggccgcctaa cccagagcc aagccaggac 21540
agctgagtca gttcaggtt cacatcctgg ctctgcacat gtggccttgg cggcggggcc 21600
gggggggggg tctctccaga cataatcttg ggcctcacct atgtccctgg aaagtgggag 21660
cacctggtgg ggttctgggg aggggggaatt acgagagctc caggaaggag cctgctcagc 21720
aaggacaggg cccatgagcg gtgcaagaga tgtttcagca acgccgtctg ggcgtgtcct 21780
gggacccgag aggtggagac cgccctcagc ctgtctcaga atctgagcct ttgccttttc 21840
tcccggcagc agggagcgga ctctcctctc ccgggccgcc gtgggggtcg cgctcaccct 21900
ccagcagctc cacgtggccc cagtccttcc tgcggtcttg gtcttgctcc tgggggctgg 21960
cggacgagct cctcctgggg ccgcagacgc caccggccgt ccctgcggga aagacgagag 22020
cggctgagcg gggccgggcg tgtgggcggg ggcctccata aggcagaag ccgaagggtc 22080
gaagggcaaa ggagccctaa acgcagcgga aactctcgga gcacgggctt aagttggaaa 22140
gaaactaaga cagcgaaggt ggaagggccc cgccgcggcg aacacgggcg cggaaccgcc 22200
gagagagggt tcctcgcact cgaggtgcag caggtcaaag gttaagagcc ctaaacacca 22260
cacctgggt caggaggctg cataagaaac cacgagtcaa aggtcagact gcacggagga 22320
gcctcagtcg aaaagcgggc aagggcgagt ggaaagcggg gccggtcgg tgggctgcgc 22380
acgcccaggt gcaaagaggc aaaggtcaaa gcgccaaagg ccccggccgc gcggggagga 22440
gcccacgccg tggccccgg gctgcctggc cgtctccctt tgtgttacct tcttttgccgg 22500
ggagtcccgg gcggccgcaa ggccgtaggg ctcgtttgag ccccgcgct ccgcggccc 22560
agcaaagtgc cgacattacg cacgccgctc caggccaccc caccgcccg cgcctgcgca 22620
tgcgccccgcg ccgcctgccg ggagttgtgg tttcatggtc gacggaggct gcgaagggaa 22680
accccagccg gaagtagact cccaggatgc agcggaggcg cgaaggcatg cgccggtgga 22740
cgctctgatt ggttcctcct gctgttttta aagggagggg gcgggacaga gctgttgccg 22800
tggcaactgg gaggcactct caggctgttt tcccgaggac ctcaaatccg gactttttt 22860
ctgttttttct ttcttttttg gttttgtttt ggacgcgttg tgcccaggc tggagtgcag 22920
tggcgtgatc atagctcagt gcagcttcga actgctgggg taaagagatc ctcgcccctc 22980
ggcttcccaa agcgctggga ttgcagacgc cgccaccgtg cccggctttt tttttttttt 23040
tttcaaggca tactcatcta ataacgagga cagcatctgc aatttagaga ttcctgtccg 23100
caaccttcat tgctccaacg acaactttttg ggtaagagtc attaggatgc cgtctatcat 23160
ggaggaagct gaggctcaga gagggccacc aagttgctgg aagacacagc acgtgcgacc 23220
tcagggaggc tgcaaggaga gaaagcccca gtccgcgaga ctcccagcct ccagcttcag 23280
tttaccctcc aatccccaag ccctcagggg caggagccga atggagcggc aggcttggat 23340
tcacctgcta agtggggtga ggtcaaggga atgaaataaa cctcggagcc tagagcctgc 23400
cctggtctcc gcgtgatcct gcctaggagg agcagggcgg gagctttaga atggaacctg 23460
gaaggtgc ccacctgtgt cgttcagccg gggcagcagg ccagaggcgg gagcgcctgc 23520
tgtggggcag taggcttggg aagggtgaga ataggaatat ctgggggtaa ctgtgttcca 23580
ggctaatatc ccagttgcaa agggagctg gtttggtggc tcaggcctgt catcccagca 23640
ctttgggagg ctgaggcggg cggatcacct aaggtcagag ttcgagacca gcttggcaaa 23700
tacgcaagca tgcctggcaa catggcaaaa ccccgtctct agtaaaaata caaaaattat 23760
ccgggggtgg tggcgggcac ctgtaatccc agctactcgg gaggctgagg caggagaatc 23820
gcttgaaccc gggaggcgga ggttgcagtg agccaagatc tcgcactgc actccagcct 23880
gggtgacaga gcgagaacct gtctcaaaaa aaaaagtg caaagggagg tcagttcagt 23940
gcctcaggcc tgtaatccca gcactttggg aggccgcggc gggaggatcg cttgagccca 24000
ggagttccag acaagccttg ggcaacgag atactgagac ccagtctcca ccaagggaaa 24060
aaaagaaatt agccaggcat ggtggtgcac acctgtggtc ccagatactc gggaggctga 24120
ggcaggagga ctgcttgagc ccaggaggtt tagactgcag tgagctgaga tggcgccact 24180
gtactccagc ctgggttgac agaacaggac cctgtctcaa aacaaaacaa gtgcaaaggc 24240
cctgaggcag gaacaagcgt ggacagagga gcaattggga caagtgggg ctggggagag 24300
ggagcaaaga tgtagctggg gctcagttag ggggcctgac cacacggggg ctcgggggcc 24360
tcagctcaag ctatcctcca tccccaaacc ctggcacttc agtttcccca tcagcccaga 24420
acgaggactc gacctcactc tggaagggc tggcagcctc cttcagcac attccagacg 24480
ctgctgccga cgcctgcgtg agcgcactga tgcacgagac ttcgacagac 24540
ggcagcaccc tccctcacct gcctcagtcc acctcaggt gcccagcgg gctgtgacct 24600
cagacctcac ccactactgg ggtcacctgc ctggccctga atcagccagg cctggtgtgc 24660
caagacctac agacacccc tgcaccctg caggctggca gagccagaaa cttgggtgga 24720
aaccgacttc tgaactattt caccattcct tatgcgttag tcttttcttt tatttgatga 24780
```

-continued

```
gatcccagca ctttgggagg ccgaggcggg cggatcacgt gaggtcagga gtttgagacc 24840
agcctggcca acatggtgaa accccgtctc tactaaaaat acgaaaatta gccgggcatg 24900
gtggcctgtg cctgtaatcc cagctactca ggaggccaag ggaggaaaat cacttgaacc 24960
tgagaggtgg aggttacagt gagccaagat cgcaccactg cactccagcc ttgggcaatg 25020
tagccaaacc ccatcactac aaataataca aaaaaatttt gttggctgtg atggtgcctg 25080
cctgtggccc catctacttg ggaggctgag gtgggaagat gtagaattgc ttgagccagg 25140
aggcagaggc tgcagtgagc tgtgattgag ccactgcact ccagcctggg cgacagagcg 25200
agaccctgtc tcaaaaaaaa aagaacataa tctgggtttt ggaataagac agcagtttct 25260
gaaacagctc attgcccaaa ttccagcctc gcaactctgt agccgccacc accccccagc 25320
cccaccattt attttaacta catctgtctc caccactcct gtattaagta aatgcaatat 25380
tggctggtca tggtggctca tgcctgtaat ccagcacttt gggaggctg aggcaggcag 25440
atcccctgag gtcaggagtt cgagactggc ctggccaacg tggtgaaacc ctgtctccac 25500
taaaaattca aaaattagcc ggacgtggta gtgggtggtg cctgtaatcc cagctacttg 25560
ggaggctgag gtaagagaaa tgcttgaatc caagagactg aggttgcagt gagctgagat 25620
ctcgccgctg cactccagcc tgaacgacag agcgagactc cgtctcaaaa ataaattaat 25680
aaatacaaca ttaattattt ttcttgctta agttttacga agagacttaa tatcaccatc 25740
aaaagtggga aaccatatat ctggccgggc gtggtggctc ccgcctgtca tcccagcact 25800
acgggaggcc gaggcgggcg gatcccctga ggccgggagc tggagaccag cctggctaac 25860
atggtgaaac cctcatctcc aataaaaata acaaaaatta gccgggcatg gtggtgcct 25920
gtaatcccag ctattcagga ggctgaggca gaagaatcac ttgaacccgg gaggcggagg 25980
ttgcagggag ccgagatcac accactgccc tccggcctgg gcgacagago gagactctgt 26040
ctaaaaacaa aacaaaacaa aacccaacca agcaaacccc acagagtcga gaatcgctag 26100
atggaagggg atggcccagg tccctggagc ccctgtgaca aattaccaca aactcggtgc 26160
cttaaagcaa cgttcatttt cttacatttc tggaaatgaa aagtccaaaa tcaggactgc 26220
ggggctgaag tcaaggtgtg tggaggcctc gctccctcca gaggccctgg ggctccttcc 26280
tgcctctccc agcttttgaa ggctccaggt gtgcttggcc tgcggccaca tcactcccgt 26340
ctcggtctct gtggtcgcac tgcagcctcc tcgtctgcct gtgtgaaatc tcctcctgtc 26400
tccgtattgt gaccgcgttt aggatgcccc aggacaatct tctccatatc gttcagatct 26460
tcatggtgtc aatatattga gactcttttt ccaaataagg caaatgtcac attctaggga 26520
tcagggtggg gacttaccctt tgggccaacc acagaggcta caaagaggaa gacaccactc 26580
aatacaaagc gtgcgccagc ccagccctga tcggtgtttg ttgttgttgt ttttgtttga 26640
gacagagtct cgctctgtcg cccaggctgg agggcagtgg catgatctca gctcattgca 26700
acctccgcct cctgggttgt atagattctc ctgcctcagc ctcctgagta gctggatta 26760
caggcgtgaa aaggagcaag gctctgcccc agccacagcg cggatgcacc ttgaggatgt 26820
catgctcagt gaaagacgcc agacacagaa ggacacacag tgtgtgatcc cctttatatg 26880
aaatgtccac aacaggccca tccacagagg caggaagggg atgtgtgggt gccgggggct 26940
ggcagagggg atgagtgaca gctgatgggg cttcttcttg cggtgatgga atcttctgga 27000
actagacagt cgtggtggtt gcacaactct acgaggtact aaaatcactg aactggctgg 27060
gtgcagtggc tcatgcctgt aatcccagca ctttgggagg cagaagcagg tagatcacga 27120
ggtcaggagt ttgagaccag cctggccaac atggtaaaac tctgtctcta ctaaaaatac 27180
aaaaattagc tgggtgtggt ggcaggtgcc tgtaatccca gctactcagg aggctgaggc 27240
aggagaatcg cttgaaccag ggaggcagag tttgcagtga gccgagatcg caccactgca 27300
ctccagtctg ggtgacagag ccagactccg tctcaaagaa ataataataa aataaaatca 27360
ctgaactgta cagtgtaagt gggtgaattg tgtggtatat gagtgatgtt tccgaggtgt 27420
cattaaagaa actcagacgc ctggggtggg gccagtctca ccgctgtggg tcccatcccc 27480
atcatttctc acaaggtcct cagatcaccc ttccgcggtg ggggcggac actctaagaa 27540
gggaagacct gggctcctgc tggcgagaag gcggtggaca tttcttcagt gtctggtgcc 27600
gcgccctctg cccagctgtc tccgtggagg gtctcattgt cttcctccag acgtctcttt 27660
actggcccat tttacagagg cggaaccgaa gcttgggtg ttggccacag ggctctagtg 27720
tgggaagcca ggccaggctg gacctcagcc atggggaccc ctgtccctga gactgtggca 27780
cctgccacac cctctgtgtg acccgcctaa gccaggaaga gaggtgtcagg agatgcctga 27840
gccaccaaga aggcatccca gcgtccagcc agaccggtta tccctccaga gggctccccg 27900
gcaggacagg ctggtcgcca tgtcttcagc ctggtgctat ttaaaggtgg gtgccacctg 27960
gggctgtggc cgcagggcca ggactgggct gctgggagct gtgtccccac agccgaggtc 28020
gccgccctc tcaggcctcg gtttccccag ttgtcaatgc ctccacttgg ctgtgagtct 28080
gtgagggtca ctgtgctcac cttttgggggc ccagcgcatg gggcaggcag aggaagggtg 28140
ggggccagcc gccttgctgg gtggttcccc gtggggcctg gggtatggct ctaagggagg 28200
agcaagtgtg ggtgcgaatg ggccgcccc attcctgccg cctccgactg gccccgccag 28260
ccggccaccg acaggtctac gtgctatcc tccctcctgc ccacctacct gcccaaacac 28320
acgtccccag tcgtcacctg cccaccacc cgcgcattcc cacacccttg tgggcctggc 28380
tttcgggaaa ctacaatttg cgggagaga agtcccacga gggcatgccc cggagcctgg 28440
ctggtcccac ggctgacgca cgcggcagga cctcccgtgt ccatctctgt ccccaagcat 28500
ctccgcctct gcccctctct gtctctgtgt ctctctcgtc tctcccggtc atcttccttg 28560
tgtctcttga ctgccgccgt ctttctgtct ctgtctccct ccgggtctct gtctccctcc 28620
aggtctctgc ggcccgcgtc tcacactccc gccccgcaa cccgaggtcc tagcccgccc 28680
gggactcgg ctgactcacg gacacgcccc gcgagacaaa ccgcgaggccg 28740
agcgcggagt cccgcacgcg cgcgccccctg tgcacctggc ccccgccccc gagacgtccg 28800
attggccggc gccctagcct ggtccgccc aagtggaccc cgccccgcc ccgaggcacc 28860
ccattggccg gcgtccccgc cccagcgaac ccggccccgc ccccgaggcg ccccattggc 28920
cccgccgcgc gaaggcagag ccgcggacgc ccgggagcga cgagcgcgca gcgaaccggg 28980
tgccgggtca tgcgccgccg cctgtggctg ggcctgctgct ggctgcgggcg 29040
ccggacgccg cgggaacccc gagcgcgtcg cggggacccct gcagctaccc gcacctggag 29100
ggcgacgtgc gctgcggcg cctcttctcc tccactcact tcttcctgcg cgtggatccc 29160
ggcggccgcg tgcagggcac ccgctgcgcg cacggccagg acagtgagtg cggggcggcg 29220
ggggcctggg gtggggaggc ggcgggtgag gcaaacgcg gtccgtctt cacggtgacc 29280
tgcgcccgcg gggagtccc ggaggctcct ctgtgcagcc tcggcctcag tttccgtggt 29340
ctgtgagatg ggtgcagcct gctggtggg aggttgcac tgttaaagcg aaggctgcag 29400
cggcggaccc ggctcagggg cagagaagcg tccgtgtggt acaacccgtg gggtggggcc 29460
acccatctgc aggtgggaaa ctgaggctcc agaggggctg gggcaggccc agctgcatgg 29520
```

```
cggaagcggc ggggggctga cctccggact cctgacatca cagaatccag tcagggctgc 29580
ctgagtcggg gcccctctg cttcttccca gacaccccat ctggcaggtg aggacaagga 29640
ggcacacaga agggatggga cctgcccagg gtcacactga cagggtggc ggagctgggt 29700
ccccacaggg cccaggacgt cacggagcgg gcgtctctgt ccccagggtc tgccgagcac 29760
actgaggtag gccctcagtg tttgtggaat gtcaggagca agaggagagg ctgggcacag 29820
caggggatgt gggtacctgg aggccagggg agtcggtgtc cccgccgggc gggggggcact 29880
gggaagggg cccgggcccg ctggctgccg cctgaatcac caccatcagg gcaggtaatc 29940
accccctgtc cttcccaccg ctttcatctg ggcgccaagg ccctcattag gccgcacgtg 30000
acgagggcgg acaggggact ggctgggccg gtccatccat ggcgggcatg gccaggcggg 30060
gtggcctcgg gccggggcag aggcctggct ccgctgcctg acctggaaca gtctctgcct 30120
ctctccaagc ctcggttccc ccagctggac ggtgatgggg gtgagggcta gctgagggct 30180
ctcctgccct tcgtgcattc gctggtcact aatcgggcac cttgtgggtg ctgtgctccg 30240
catggggac ccagtggtga cagagacgcc caccctcctg ggctcccag agcagaggcg 30300
cgcagcagtt agacacgtga acaagggcgc aggtgggtgc acagaacagt gaacggttgg 30360
ccgggtgcag tggctcacgt cggtaatccc agcactttgg gaggccgagg cgggcagatc 30420
acgaggtcag gagatcgaga ccatcccggc taacacggtg aaaccccgtc tctaccaaaa 30480
atacaaaaat tagccgggtg tggtggcggg cgcctgtagt cccagctact cggaggctg 30540
aggcaggaga atgacgtgaa gccgggaggt ggagcttgca gtgagctgag atcgcgccac 30600
tgccctccac cctgggcgac agagcgagac tccgtctcaa aaaaaaaaaa aaaaaagaa 30660
cagtgaatga cgtgaacaag ggtgcaggtg ggtgcgcaga acagtgaacg gcggtgttgg 30720
gaggcacctt gccagggag gggaggtgca gggcgaggaa gggccaggg gagatcgtga 30780
cacagacgcc ccagaacaac caccctcaaag acgttcctgt gtgtcctgga aggtcgggct 30840
gggaggctgc cccgaggagc tttcactttg acaggagct ggccgggcac gcagggaact 30900
gtacacccag ctgacaaagc ggcagacacc caggccgggg tgagcgagtg tgggtgagga 30960
gtggcggctg gccccagggt ccttgctgga caagacactt cagctcaggg tggggcaggg 31020
ctcacccagg gctacccaca gacgatggcg tccaaatctg gctctgccac tccaggcct 31080
caactggccc ctctgcaacg tgggctgctg agcgggcttg gtaggacagc tggcatacag 31140
tcggcgctca agcatgtctg tggtgtccca taaaccaccg gtgtcccact ctaggccact 31200
gccagcccgg cctccagtcc agagtcccag tccggagtcc cagtgactgt gcgtgggccg 31260
ggcagctgag ctgtgagggc cgggctgggg gctccatatg gggtggtgtg agctgtgagg 31320
gccgggctgg gggctccata tgggtggtg tgagctgtga gggccggggct gggggctcca 31380
tatgggtgg tgtgagctgt gagggccggg ctgggggctc catatgggt ggtgtgagct 31440
gtgagggccg ggctgggggg tccctgggt ggtgtgagct gtgagggccg gctggggg 31500
tctctggggt ggtgtgagct gtgagggccg ggctggggc tccatatggg gtggtgtgag 31560
ctgtgagggc cgggctgggg gctccatatg gggtggtgtg agctgtgagg gccgggctgg 31620
gggtccctg ggtggtgtg agctgtgagg gccgggctgg gggctccctg gggtggtgtg 31680
agctctgagg gccgggctgg ggggtctctg gggtggtgtg agctgtgagg gccgggctgg 31740
gggctccata tgggtggtg tgagctctga gggccgggct ggggctccc tggggtgctg 31800
ctggtcgctg gctcattgac agttatcagt ggtctgggtg ggccctgccc cttctgactc 31860
ccacatccca ggaaccctt cccaaccttc ctcgtggtgt tgctgccccc ctgacgtccg 31920
tccctctggg tgtgtgggag cccccccgcc atacacacac acagatgctg ctcttgggct 31980
gagctgcagg gacagcgctg acctggccct cccacggggt cctcatcgat ctctgcactc 32040
ccccagctcg tggggccgt cctgcttccc gttccctctg cctgctcctt gctcctcccc 32100
cacatgctgg ggggggctcc tggtgtcagt cacggctctg ggggatcctg agtgtccgtc 32160
gtggtcggga ggggactcgt ggtcccgggg gtctcctggt atctgtcgtg gtcctgaggg 32220
ccctgcacga agcacagcgg acagcagcgg tgctgggggt gagcagcaa ggccctcccc 32280
gaccccgcc tcccccaggc atcctggaga tccgctctgt acacgtgggc gtcgtggtca 32340
tcaaagcagt gtcctcaggc ttctacgtgg ccatgaaccg ccgggggccgc ctctacgggt 32400
cggtgagtgc cgggcagggc tgggcggcgc gggcagggtg gggagggtgg gccggcctca 32460
ccccccgccg cagcgactct acaccgtgga ctgcaggttc gggagcgaa tcgaagagaa 32520
cggccacaac acctacgcct cacagcgctg gcgccgccgc ggccagccca tgttcctggc 32580
gctggacagg aggggggggc cccggccagg cggccggacg cggcggtacc acctgtccgc 32640
ccacttcctg cccgtcctgg tctcctgagg ccctgagagg ccggcggctc ccaaggtgc 32700
ctgggctggt ggcgagggga ccggccacgc ttgttcttcc ccctgccggg tctgtaagcg 32760
ctgagtgccc accgtgtgcg ggcgctgtgg acacagccca ggagccctcc aggggggtcc 32820
cagcctgagg gggtggtggc caccaagcag gttcaatcct gagttgggga cctcgaggac 32880
ccaacagggc gcctctcggg ctgaaggacg cagacgtcga aaggtcgagg gacgtccc 32940
aggcagggcc cggcagaggc aggggctcgg ggtgggagc acgttgggag tggggggcagg 33000
agcggagggg agggaggg gccgggagac cggtgacaga cgccgcagaa caccagcctc 33060
gaagccggtc ccgtcccggg aatctgcaaa tacaacgcct tgcgaggaca aaggcacctg 33120
caggtgggac ggagatggag gagcatccag ggtggggggt ccagggcccc agtgtcctca 33180
cagggtcctc acgacaggag gcgggacagt gagagccaga gagagatggg gatggccgc 33240
gctgtggccg tgaagggag gaagggccct aagctgaggg acgtgggtgc ctccagatgc 33300
tggggaaggc gggaacggtt ccgcactgga gccccggga gggaccggcc tgctcctgcc 33360
ttgatatgag cccagtggga cccagtttgg actctggcct ccagaaccgc cagaaaataa 33420
acgtagtaag ccatcaactt tgtggtcttt tgttacagca gacgtcggaa atatgcacac 33480
ggtgtctgaa actgttctca tgacaaaata agcctcagat cccccgggga agggcggagg 33540
ccaacgcctc ggtgttcctc cgatcccccg ggaagggcgg aggccgacgc ctcggtgttc 33600
ctcggatccc ccgggaaggg cagaggccga cgcctcggtg tcctcagat ccccgggaa 33660
gggcagaggc tgagggcagg agccgtgctg ggtgcaggc aggcctggg gcttcatgcc 33720
gctgtcctgc gggacgacaga gagggctggc cgtcggttgg caccctgtgc 33780
cagcgccctc ctgacatcct gactccgctg ggacttctgc ctacagccct gggagtcaaa 33840
ctccagcctc tcagagaaaa ggtcagagcc aagagcccca cagcctggag ccaggcagtg 33900
acaccctggg cctgtctccc cttctgtgtg tggggcgaca gcagcatcgc cctggtgaag 33960
tcccccggga cggccagggc tccatcccca gccgccgcct tccacataaa tacaggaaga 34020
ctgggccgag gcacttgctg ggaggtgctg agcagcctga cacggaaaac ccttctggga 34080
agggagggtc gtgccggcc cgagagcttc tgctcaccct gcagacagaa gcgagcccca 34140
cccccagggga caccaggcgg cctctgggga catctttggc tggcatggag tgggtggagg 34200
acagggctgc acccaggatg tccccaggtt ggcagtgtga gggagatcg gcccacgttg 34260
```

```
gccagtcgga gggcgtcgcc acttgagttg tcactgggag ctgcacaggt caccacagct  34320
gaaataaaac ttgctggcac cccacgcagg aacgtaacat gtgcctcgaa gaaacgggtc  34380
agcaggccgg gcgcggggc tcacgcctgt catcccagca ctttgggagg ccgaggcggg  34440
tggatcacga ggtcaggaga tcaaggccat cttggtcaac atggtgaaac cccgtgtcta  34500
ctaaaaatac aaaaaattag ccgggcgtgg tggcgggcgc ctgtaattcc agctacttga  34560
gaggctgagg cggggaatcg cttgaatccg ggaggcggag gttgcagtga gctgagatcg  34620
cgccactgca ctccagcctg gcgacagag cgagactccg tctcaaaaaa aaaaaaaaaa  34680
aagaaacagg tcagcagttg tttctttgtt tctaaaacag agcgtggaat gggcgtacag  34740
ctccgcacat cccagggcag tgaaatcccg gttcacacag agccctcagc agcttattcg  34800
caagcccaaa cctggggacc ccgttgtcc tcaggcagtg aggtgggggc ccccaacag  34860
agaggagcgg cctggggca cagaaccagc ggctcccag gaaatcgcca gcagtgaaaa  34920
taagacaacc ccaaactgtt gcaaactgtg cttccgctta cgaagcactc ctgagcggca  34980
gggcggatgg ggagagggcg gctgcaggcg cgaggggccc ggggacgcag gggtgcgggc  35040
cttaccaggg ccctgtcctg tcgtgcagca ggctcctggg cagggaaga caccagggc  35100
ggccacttct tactgctgtc tgacctcgag caatgcggcc tcacagcccc caccagggtg  35160
ccggtgtcct ctgggcccag cgccccgagg gctcatgcct gggtggggcg aaccaatcgg  35220
tcctgctcct ctggccactc cacgcgaggg aagtcccagc ctcacaggca ggcgcacacc  35280
ccggcagcat ctctgacaaa ggccctccag ttccgagtct ccaggtcccg ccgctgcaag  35340
cctcacctgc ccagcccctcc tctccagctc caactccaac tccaagaac caccacggac  35400
acacagaacc cgagccttgt ctccctcaac gcctcctgac tcaaaactcc atcttccaac  35460
aggaaaacgg ctcggccggg ggactgtgac ccggagcagg cggcccagcc tgtcgcgcag  35520
actcggggcc taaaacactt gttctctcag tccggagatc aaggacgatc cgaggtaacc  35580
tccctacctc ggtgtcctcc atgcaacctc gtcttagggc accgggtacg ttacctcgtg  35640
aggagccgag tccgcgggtc ctggggttga gatgtggacg ccctcagggc tggcactctg  35700
ccctggccgg cacagtcatg gaagtcccaa cgcttctctc cgctccgcaa cccagaggg  35760
cggccacgag gagggccgc cacgcacgac cccagagggc ggccaccagg agggccccgcc  35820
acgcgcgacc ccagagggcg gccaccagga gggcccgcca cggcgttgcg gcagcagccc  35880
agaaggtgcc ctgcgcacg tccgacagg tgggatccga gttacctggc caagggggct  35940
gacgcagaca cgtcgcggga cacagtgaag agtgtggtgc agagcggagg gcgggagtct  36000
ttggagaaca ggtaggggcg tggggcacgc gcctccacg cgcaggagcc gtctaccgtg  36060
gagggacacg ggtggtcctg ctggaggctc ctctccgtta gctgtctcca tcgtctgatt  36120
cttggatccc aggatggtgg gatcatcagc aactgagatg aacccactgc cccggcccccc  36180
tgagcccgca ggtccccacg ccttgccagc tgtgcccgag ctggctgcac cccgggccag  36240
gcatccagca accttgagca gtggggtccg gcttttcaga aggggccagg aacccggcgtg  36300
gctgaggtgt gaccgaagcg tggggcagag gcgctgggcc ctggcgcttt aacgctggtg  36360
tttctggttt taaatttcac gacccagtga cactgccacc ctgctacctc gccagcagcc  36420
ctcctgggct taacttcggg agagcagttt tgctagccgg ccctgggtgc caagccctgc  36480
aggaggcgca gaccctggg gacaggaccg gactctgcag agcccgacca gcctcccagc  36540
ttggcctttt cctgacgcac gggcgcagaa ggaaagccac agcaccggct tctcttttgta  36600
agtagtgtat tttaaatagc tttcaagata cacatatttt ttccttttaaa aaagtctgtt  36660
ggagcagttt tgttcttgaa ttttgctggt catcctcatg gtcccgagcc ccctactcc  36720
gggtcgtgga ggcggccgag ggggaggctg ggggcccacg tggcccgtcc tggcggcacc  36780
tgcagcactg ggggagccgc tgaaccccgt gcttcagcgc tggggagcc gctgggcccc  36840
gtcttccgcc acaaaccatg catggccgcc acgtgagctc aaacgtccgt ttatttcaaa  36900
gcagtaataa tttaaaatta taaaaatctt tccaccgctg aacgtttaga gggtgaggtt  36960
agacagagga cggggaggct ggggacgacc cagaggggac catgtggccc acgccttccc  37020
aagccagggg gccggtgggc cgggcccggg tcctgccctg aacaggcgg gacctgcagc  37080
gctgaccagc caagcgtggc gccgccgggg cacccagtct gtgggtgccg tgtggcgctg  37140
gctgaggtg ggtgggaaag gccccgtgct ttcccgacgg ccgacgtggg ctcacgagtt  37200
gcttgtggcg ttctcgttgc tgggcgagct ggaggaggac gatgacgacg aggaggagaa  37260
gctcacccca gtgaggccag ggggttcgt ggccgtgttc tgtcccgtga ggctttttcg  37320
gcagacgggg cagctgtcgt gcttttgtgg gacagaggca gggacggag aaggggcagg  37380
ttagaggcgg gagggccgcg tcgggtgg gggggcgggt gggcgggca ctcacctgct  37440
ccagccaggg cacgatgcag ccgtcgtgga acaggtggtt gcagggcagc tgccgcacac  37500
gctcacccag cgcgtagtcg tccttgcaca cagggcactc gagcccggag cctgcgggag  37560
tgtgcagctg cggtcacagc gggcgtgggg ggcctgccga gccttcaagg gcaggctact  37620
ccacagcctc agccggaggc cgccctgag cccagcgagg ggagaaaagc cgtgtgtgtg  37680
tcccccggc tgccagaggg gacctggaca gaaccctctc ctcccagccc accttcaggg  37740
aaatgctcga ggccgggtgc ggtggctcac gcctgtcatc ccagcacttt ggggaggccag  37800
ggcaggagga tcacctgagg tcaggagttc gagacctgcc tgaccaacat ggtgaaaccc  37860
tgtctctact gaaaatacaa gtatgagcca ggcgtggcgg cgggtgcctg taattcccac  37920
tactcggag gctgagctct catcctacg tgctcctcag tgacggggac ggtggggagg  37980
gcctggattt tctctttatc tgccgtgggg gggcctgtgt tttcaaactg attgaggagc  38040
tgaaagacaa gaggcagag tgccgggagc tcctcggggg ccgccccgg ggctctgaaa  38100
cgcgaggctg caggacctgc aaaagcaccg aggccgcgtt tgtcctgggc cctgggcccc  38160
ttggagcccg cccggggtcg gagatc                                       38186
```

<210> SEQ ID NO 39
<211> LENGTH: 720
<212> TYPE: DNA
<213> ORGANISM: Unknown
<220> FEATURE:
<223> OTHER INFORMATION: Description of Unknown Organism:Unknown

<400> SEQUENCE: 39

```
cgccggcgct tgacctgact ttcatgaatc gaaaggaaa tcctctatga acgcactgca   60
tcgcatcggc gccggaacgc tactggccgt gttgctcgct tttggcctga ccggctgcgg  120
```

-continued

```
     ggagaaggag gaggttcagc agtcgctcga gccggtggct tttcacgact ctgacgagtg    180
     tcacgtgtgc ggcatgatca tcactgactt ccccggcccc aagggccagg cggtcgaaaa    240
     gcggggagtg aagaaatttt gttccaccgc cgaaatgctt ggttggtggc tgcagccgga    300
     aaaccgtctg ctcgatgcca agctctacgt ccacgacatg gggcgcagcg tttgggaaaa    360
     gccggatgac ggtcatctga tcgacgcaac cagcgcctac tatgtggtcg gtacgtcact    420
     caaaggcgcc atgggcgcgt cgcttgcaag ctttgccgag gagcaggacg ccaaggcgct    480
     tgccggcatg cacgcggtc gtgtgctgcg cttcgaggaa atcgatcagg cgctgctgca     540
     ggaggctgca agcatgcagc acggcggcat gcacgaccat cgcgccaaacg tgcacataa    600
     cgcacacgca ggccactgag cagcagtggt ctgaacagca cacacaagaa atcgaggtaa    660
     gcacaatgat gggtatcagc gtctggcaac tcctgatcat tcttctgatc gtcgtcatgc    720
```

<210> SEQ ID NO 40
<211> LENGTH: 127
<212> TYPE: DNA
<213> ORGANISM: Unknown
<220> FEATURE:
<223> OTHER INFORMATION: Description of Unknown Organism:Unknown
<221> NAME/KEY: UNSURE
<222> LOCATION: (9)
<223> OTHER INFORMATION: May be any nucleic acid
<221> NAME/KEY: UNSURE
<222> LOCATION: (101)
<223> OTHER INFORMATION: May be any nucleic acid
<221> NAME/KEY: UNSURE
<222> LOCATION: (119)
<223> OTHER INFORMATION: May be any nucleic acid

<400> SEQUENCE: 40

```
     gcggccgcnc ggcgctggct gctgtgcgga ggccacggcg ggccgcgagc cgcctcgtcc     60
     tcgccctcct gccctgggtg cggcccccg gtcccggcg nccactcgc cccggcgtnc       120
     ccgcgct                                                             127
```

<210> SEQ ID NO 41
<211> LENGTH: 6858
<212> TYPE: DNA
<213> ORGANISM: Unknown
<220> FEATURE:
<223> OTHER INFORMATION: Description of Unknown Organism:Unknown

<400> SEQUENCE: 41

```
     actcgccaag tgatcgaccg gcccctgagg gccgcgacgc agagggcgcc ccgtgcactg     60
     gcacaggcgg ccttgtgcgt tagactctga tattcgtgcg ccctctcgtt ggcaggacca    120
     tccatcctgt gtgccggggg ccgcgcacac cgatcccgga tccgcctcgg ccctgccctg    180
     cgcgcccctc cgttctcgac ctccccgacg ctgtctgaac acgcgtcgcc gggggacgac    240
     ggcgggcggc ccgcctcggg ggaggggtaa gcgtcccggg atgcccgttc aaccgttccg    300
     caaggctcgc ccatcgtggg ggagaaccgg cgcgacgcta ggagagacaa gtgatccagc    360
     aggagtcgcg gctcaaggtc gccgacaaca ccggtgcgaa ggaaatcctg accatccgtg    420
     tgctcggcgg ttccggacgc cgctacgcag gcatcggcga ccatcgtc gccaccgtga      480
     aggacgccat ccccggcggc aacgtcaaga aggcgcacgt cgtcaaggcc gtggtggtcc    540
     gcacccgcaa gcagtcccgc cgtcccgacg gctcgtacat caagttcgac gagaacgcgg    600
     cggtcatcct gaagaccgac ggcgagcccc gtggcacgca catcttcggc cccgtgggtc    660
     gcgagctgcg tgacaagaag ttcatgaaga tcgtgtcgct cgccccggag gtgatctgac    720
     ctcatggcca agatcaagaa ggacgacctc gtgcaggtca tcagtggcaa ggacaagggc    780
     aagcagggca aggtcctgcg cgtgttcccg acggatgagc gcgtgctcgt cgagggcgtg    840
     aaccgcgtga ccaagcacct gcgcgccggc caggacaaca acggttccac cgagggcgcg    900
     ctgcaggtcg tcgaggcccc gatccacatc tcgaacgtgg ccgtggtgga cccggagacc    960
     aagaagccga cccgtgtggg ctaccgcttc gagaccgtcg agaaggacgg cgtgacgaag   1020
     accgtgaagg tccgcttcgc caaggcctcg gggaaggagc tgtgatgacc gaggtgcagc   1080
     agaccgagaa ggtcaccccg cgtctgaaga ccaagtaccg cgaggagatc cgcggacgcc   1140
     tgcaggagca gttccagtac gggaacgtca tgcaggtgcc gggcctcgtg aaggtcgtcg   1200
     tcaacatggg cgtcggcgag gccgccaagg actccaagat catcgacgac gccgtcaccg   1260
     acctcaccgc catcaccggc cagaagccga tgatcaccaa ggccgcaag tccatcgcgc    1320
     agttcaagct cgtgagggc atgcccatcg gcacgcacgc caccctccgt ggcgatcgca   1380
     tgtgggagtt cctgaccgc ctggtcacgc tgccgctgcc gcgcatccgt gacttccgcg   1440
     gcctgtccga ccgccagttc gacggcaacg gcaactacac cttcggcctg tccgagcaga   1500
     ccgtgttcca cgagatcgat caggacaaga tcgaccgcgt gcgcggcatg gacatcaccg   1560
     tggtgacgac cgccaagaac gacgacgagg gccgcgcgt gctcaaggcg ctggcttcc    1620
     cgttcaagac cgaccagtaa gacctccacg ccacaggtcc tccaccggtg aaccggtggc   1680
     ggaaaccacg gcgagaaagg gcgtgaagca catgaccatg accgatcccg tcgcagacat   1740
     gctgacccgt ctgcgcaacg caaactcggc ctaccacgac accgtgtcca tgccgtcctc   1800
     gaagctgaag actcgcgtcg ccgagatcct caaggccgag ggctacatcc aggactggcg   1860
     cgaggaggag gccgaggtcg gcaagaagct gaccatcgac ctgaagttcg gcccgcagcg   1920
     tgagcgtgcg atcgccggcc tgcgccgcat ctcaagccg ggcctgcgcg tgtacgcgaa    1980
     gtccacgaac ctgccccacg tgctgggcgg cctcggcatc gccatcctgt ccacctcctc   2040
     tggtctcctc acgaaccagc aggccgccaa gaaggctggc gtgggcggag aagtcctcgc   2100
```

```
ctacgtctgg tgacgggcaa gacggaagaa aggctgaact gacatgtctc gaatcggacg 2160
tctcccgatc accatccccg ccggcgtcga tgtgaccatc gacggcgacc gcgtctccgt 2220
gaagggcccc aagggcccca agggtcagct cgagcactcg ctgcccacgc ccatcacggc 2280
caccctcgag gaggggcagg tcaccgtggc ccgccccgac gacgagcgtg agtcccgctc 2340
cctgcacggt ctgacccgta ccctcatcag caacatggtc gagggcgtga ccaacggctt 2400
ctccaagcag ctcgaggtcg tcggcaccgg ctaccgcgtg caggccaagg gccaggacct 2460
cgagttcgac ctgggctact cccaccccgt cccggtgaag gtgtcccagg gcatcacctt 2520
cacggtggag ggtaacaggg tcaccgtcgc cggtatcgac aagcagcagc aggtcggcga 2580
gaccgccgcc aacatccgca agctgcgccg ccccgacccg tacaagggca agggcgtcta 2640
cgcgggcgag cagatccgcc gcaaggccgg aaagaagtga tgtctactct gaaggtgaag 2700
ggcaagggca agttcaacgc ccgcacccgc cgccacctcc gggtgcgcaa gcggatctcc 2760
ggcaccacgt ccgtccccg cctcgtcgtc aaccgctctg cacggcacat gttcgtgcag 2820
gtcgtggacg acacgcagag ccgcacgatc gcgtacgcct ccaccatgga ggccgacgtg 2880
cgtgcgctcg agggtgacaa gacggccaag gccaagcgcg tgggcgagct cgtcgccgag 2940
cgtgccaagg cggccggcat cgaggccgcg gtcttcgacc gggcgggcaa caagtaccac 3000
gggcgcgtcg cggccgtggc cgacggtgcg cgagagggtg ggctgcagct gtgaccgaga 3060
acatcaacca gaaggacact caggtgaccg agagcaccga gaccaccgtc tccgagaccg 3120
ggtcgggctc gcgagccaga ccaccgagcg cgccaccggt ggccgcggcg gtcgcgacgg 3180
cggccgcggt ggccggacgg cgatcgtcgt ggcggccgtc ggacgaccga accgtcgtgg 3240
cgcccaggac gacgaggaag gaccagttcc tcgagcgcgt cgtgggcatc aaccgcgtct 3300
ccaaggtcgg ccgccgcttc tccttcaccg ccctcgtggt ggtgggtgac ggcgacggca 3360
ccgtcggcgt cggctacggc aaggcgaagg aggtccccgc tgcgatccag aaggccgtgg 3420
aggaggccaa gaagtccttc ttccgcgtcc cccgcgtcgg ctccaccatc ccgcacctgg 3480
tgcagggtga ggacgccgcc ggcgtcgtgc tgctccgccc ggcctccccg ggtaccgcgg 3540
tgatcgccgg cggtccggtg cgcgccgtgc tcgagtgcga cggcatccac gacgtgctct 3600
ccaagtccat gggctccgtg aacgcgatca acatcgtgcg cggcacggtg gagggcctca 3660
agaagctgaa gagccccag gccgtcgccg cccgccgcgg caaggccctg gacgagatcg 3720
cccccccatgc gatgctgcgc accatggaga acgatcgcgc ccagaagagc gcgaaggcag 3780
gtgcgtgacg cgtgtttgag tccactcgca agaacatcca gccctcggac gccaccctgg 3840
tcatcaccca gacccgcggc gtcacgggct ccaagcagaa ccatcgggac accctgcgct 3900
cgctgggcct gaagcggatc ggccaccagg tcacccgcaa ggccgacgcg gtgacggtcg 3960
gcatggtcaa caccgtgccg cacctggtgt ccgtgaggga ggtcaacaat ggctgacaac 4020
gacgccatca aggtccacga cctgcgtccg gccccggtg ccaagaccgc caagacccgc 4080
gtgggtcgcg gtgaggcgtc gaagggcaag accgccggtc gcggcaccaa gggcaccaag 4140
gcccgttacc aggtccgtgc gggcttcgag ggcggtcagc tgccctgca gatgcgtctg 4200
ccgaagctcc gcggcttcaa gaacccgttc cgcacggagt accaggtcgt gaacctggac 4260
aagctctccg cgcacttccc cgagggcggt gaggtcaccg tggacgtgct cgtctccaag 4320
ggcctcgtcc gtcgtggcca gccgtgaag gtgctgggca cggggagat caccgcggcc 4380
gtgcaggtga aggcgaacgc cttctctgcg tccgccgtgg agaagatcca ggccgccggc 4440
gggtccaccg agaccctctg acacgccgac ccatcgaccg agggccctgg ccggagcagc 4500
cgctcgggcc aggccctggt ccgtccgtgt agactcgcac agccgccccg gtgtggccga 4560
cgtctcgtgc ccccgccccg cggaaccgcg cacgcccac aggaccagcc gcaggaggac 4620
tcgtgctcaa ggccatcgcc cggatcgtcc ggacgcctga cctgttgcgg aagatcgcct 4680
tcacgctcgg gctcatcgcc gtctatcgga tgggcgactt cgtgccggcc accggcgtgg 4740
actacccggc ggtgcagcag tgcctggcag cgggcaacgc ccagggcggc ctgtactcct 4800
tcgtgaacat gttctcgggc ggggcgctcc tgcaggtgtc tgtcttcgcg ctgggcatca 4860
tgccgtacat cacgcgctcg atcatcgtgc agctgctgcg cgtcgtgatc ccgcgcttcg 4920
agcagctcca ccaggagcgc gcaggggcc aggcgacgct gacgcagtac acccgctacc 4980
tgaccctcgc cctcgccctg ctgcaggcga ccacgatggc ctcgctggcc cgcaccgggg 5040
ccctgctcgg atgcagcctg ccgctgctgc gcgacggctc catcctcacg gtgctgctcg 5100
tggtcatcgc cctgaccacc ggctgtctca tcgtcatgtg gttcggggag cggatcaccg 5160
agaacggcgt gggcaacggc atgtccctgc tcatcttcac ctccatcgcg gcaggcttcc 5220
cggccggtct cggccaggtg gtccagacgc agggctggcg cgtgttcgcg atcgtcatgg 5280
ggatcggcct gctcaccatg ctggccatcg tcttcgtgga gagtcgcag cgccggatcc 5340
cggtccagta cgccaagcgg cagatcggct cacgaccgt gggcgggtcg agcacctaca 5400
tcccggtcaa ggtgaacatg gccaacgtca tccggtcat cttcgcctcc tccgtgctga 5460
tgctcccggg catcctcatc cagttcaaca cgccgcagga cggcagtgcg ccggccccgt 5520
ggatcacgtg gctgagccgg tacttcggct ccggtgacca cccggtgtac atggccctgt 5580
acttcctgct catcatcggc ttcacgtact tctacgtgtc catcacgttc aacccggtgg 5640
agatctcgga caacatgaag cgctacggcg gcttcatccc ggcgtccgcg ccggccggcc 5700
ccaccgagcg ttacctgcag tacgtcatca gccgcatcac gttcgtggtg ggggccctct 5760
acctcggtat cgtggccatg atcccgctga tcgccttcgc ggtgatcggc accagccaga 5820
acttcccgct cggcggcacg tccatcctca tcatggtggg cgtcggcctc cagaccgtga 5880
agcaggtcag cgcacagatg gagcagcgcc actacgaggg cctgctgcgc tgagccccga 5940
cccgatcccg caacgccgtc cgtatcgaca gtgaggaaca cacgatgacc cgcatgctgc 6000
tcatgggccc tcccggttcc ggcaagggca ccaggccac gacatcctgg gacaagctgg 6060
ggatcgtccc gatctccacc ggtgacatct tccgccacaa cgtgaagtcg atgaccgccc 6120
tcggcgtcga ggccaagagg tacatcgaca acggcgactt cgtccccgat gaggtcacga 6180
accgcatggt cgccgaccgc atcgcccagg ccgacgcgga gcacggcttc ctgctggacg 6240
gctacccgcg cacgaagggc caggtcgagg cgctgacgc catgctcgcc gaggccggcc 6300
agtcgctgtc cgccgtcgtc gagctggagg tgcccgacga aggtcgtg gagcgcctgc 6360
tcaagcgtgc cgagatcgag ggccgcgcgg acgacccca ggaggtcatc gagcaccgcc 6420
tggacctgta ccaccgcgag accgagtccg tcatccagga gtacgtggag cgcggcatcg 6480
tcgcccgcgt ggacggcacc ggccagatcg acgacgtcac cgagcgcctg ctgcaggccg 6540
tgtactccgt gcgctccgcc acgggctccc tgcccatcga tggcgaggtc gcgagtcctg 6600
gaccccgtga tcggccgccc ctcgctcgag ctcaagaccc cccccagct gctgacccatg 6660
cagcgcgcgg gggtggtcct gtccgaggca ctgacgccg cctgccgg cgcgccgggc 6720
ttcaccaccg cggagctgga cgccgtgttc gcggtggtgc tggccgaacg cggtgcgacc 6780
tccaacttcc tgggctacta cgacttcccg gcctcgatct gcacctcggt caacgaggag 6840
```

```
                        gtcgtgcacg gcatcccc                                          6858
```

<210> SEQ ID NO 42
<211> LENGTH: 578
<212> TYPE: DNA
<213> ORGANISM: Homo sapiens
<220> FEATURE:
<221> NAME/KEY: UNSURE
<222> LOCATION: (5)
<223> OTHER INFORMATION: May be any nucleic acid
<221> NAME/KEY: UNSURE
<222> LOCATION: (23)
<223> OTHER INFORMATION: May be any nucleic acid
<221> NAME/KEY: UNSURE
<222> LOCATION: (31)
<223> OTHER INFORMATION: May be any nucleic acid
<221> NAME/KEY: UNSURE
<222> LOCATION: (48)
<223> OTHER INFORMATION: May be any nucleic acid
<221> NAME/KEY: UNSURE
<222> LOCATION: (211)
<223> OTHER INFORMATION: May be any nucleic acid
<221> NAME/KEY: UNSURE
<222> LOCATION: (292)
<223> OTHER INFORMATION: May be any nucleic acid
<221> NAME/KEY: UNSURE
<222> LOCATION: (308)
<223> OTHER INFORMATION: May be any nucleic acid
<221> NAME/KEY: UNSURE
<222> LOCATION: (350)
<223> OTHER INFORMATION: May be any nucleic acid
<221> NAME/KEY: UNSURE
<222> LOCATION: (384)
<223> OTHER INFORMATION: May be any nucleic acid
<221> NAME/KEY: UNSURE
<222> LOCATION: (477)
<223> OTHER INFORMATION: May be any nucleic acid
<221> NAME/KEY: UNSURE
<222> LOCATION: (507)
<223> OTHER INFORMATION: May be any nucleic acid
<221> NAME/KEY: UNSURE
<222> LOCATION: (529)
<223> OTHER INFORMATION: May be any nucleic acid
<221> NAME/KEY: UNSURE
<222> LOCATION: (549)
<223> OTHER INFORMATION: May be any nucleic acid
<221> NAME/KEY: UNSURE
<222> LOCATION: (551)
<223> OTHER INFORMATION: May be any nucleic acid
<221> NAME/KEY: UNSURE
<222> LOCATION: (558)
<223> OTHER INFORMATION: May be any nucleic acid

<400> SEQUENCE: 42

```
      ttctngtcta tggcagagat ggncaggttg ncgttgagca ggtactgncc atcagccgtc   60
      ttcagcgcca ggtagttccc atcgttctgc acacccgggt ggctccgctg cttcacgtca  120
      atattagtgg caccagctgg gatggtgaca atgtcattgt agccataatt ggtgggggtg  180
      agggacccgg agaccttcct gcaggagttg nctttgcccc cacacacccc gcatttgtcc  240
      agcttccgag gcgagtccac cacatggtca cagccggcct tgacacactg gncacggaca  300
      cagatggnca gtgtttctgg cccacacagg gtgccatcaa tcaccttggn ctcgaacact  360
      ttggaactcg ctcctccccc gggntcggga ggaacaactt gcagggggtcc cggggggggac  420
      aacccagcat tcttggggga cccactgcag gaggattccc cgtccatgtc aagtgtnatt  480
      ggtgggcatt attcttctca caattgntgc tccctgaagg ttttcccgnc aagggggggat  540
      tcccccccng ntggaatnat tggtacttgg gtctccga                           578
```

<210> SEQ ID NO 43
<211> LENGTH: 305
<212> TYPE: DNA
<213> ORGANISM: Homo sapiens
<220> FEATURE:
<221> NAME/KEY: UNSURE
<222> LOCATION: (128)
<223> OTHER INFORMATION: May be any nucleic acid
<221> NAME/KEY: UNSURE
<222> LOCATION: (146)
<223> OTHER INFORMATION: May be any nucleic acid

```
<400> SEQUENCE: 43
catttaagtt tgctagtcct ttgcaaacag actgacgctg agtgtcctgt ctgagtcaat    60
    aagtgcactt ttaccttta acctatgccc tctacttgaa cccgagcaag gtccagtcca    120
    ctggacangt tgatgatagg gtctgncgcc ccatacccto tcctcttccc ccttaggaat    180
    ttgtgcagta ctggagggt tgcggcaatg ggaggcctgg gtgggccgtg ctgccttgat    240
    atggccaagg gacccagtca ccacagtgga gacccttgtc tgcacctcag taccgcatgt    300
    ccagg                                                                305

<210> SEQ ID NO 44
<211> LENGTH: 333
<212> TYPE: DNA
<213> ORGANISM: Homo sapiens
<220> FEATURE:
<221> NAME/KEY: UNSURE
<222> LOCATION: (82)
<223> OTHER INFORMATION: May be any nucleic acid
<221> NAME/KEY: UNSURE
<222> LOCATION: (255)
<223> OTHER INFORMATION: May be any nucleic acid
<221> NAME/KEY: UNSURE
<222> LOCATION: (275)
<223> OTHER INFORMATION: May be any nucleic acid
<221> NAME/KEY: UNSURE
<222> LOCATION: (299)
<223> OTHER INFORMATION: May be any nucleic acid
<221> NAME/KEY: UNSURE
<222> LOCATION: (313)
<223> OTHER INFORMATION: May be any nucleic acid
<221> NAME/KEY: UNSURE
<222> LOCATION: (324)
<223> OTHER INFORMATION: May be any nucleic acid

<400> SEQUENCE: 44
ggcacaggtg actttagcat gcagagcagc aaagagagag caaccaccaa catcatccag    60
    ccgctgctcc acgcacagtg gntgctgggg gactggtctg agtgctctag cactgcgggg    120
    ccggctggca gaggcgaact gtagagtgca gggacccctc cggtgcaggc ctctgccacc    180
    tgcaacaagg ctctggaaac ccgaggatgc caagccctgg cagaaccagc tgtgcccct     240
    gtgatttcag ggggncaggg gccattttgt gctcnggac atgcggtaat ggaggttgnc    300
    agacaaggtc ttncattgtg gtgnatgggt tcc                                 333

<210> SEQ ID NO 45
<211> LENGTH: 102
<212> TYPE: DNA
<213> ORGANISM: Unknown
<220> FEATURE:
<223> OTHER INFORMATION: Description of Unknown Organism:Unknown

<400> SEQUENCE: 45

<220> FEATURE:
<221> NAME/KEY: UNSURE
<222> LOCATION: (64)
<223> OTHER INFORMATION: May be any nucleic acid
<221> NAME/KEY: UNSURE
<222> LOCATION: (69)
<223> OTHER INFORMATION: May be any nucleic acid
<221> NAME/KEY: UNSURE
<222> LOCATION: (71)
<223> OTHER INFORMATION: May be any nucleic acid
<221> NAME/KEY: UNSURE
<222> LOCATION: (72)
<223> OTHER INFORMATION: May be any nucleic acid

<400> SEQUENCE:

gcagcagcag cgcagcgcag agagagcagc agcagcagca gcagcagcag cagagcagat    60
    cntnctggna nnaaaaaatc gcggcagcag ctgctctagc ag                       102

<210> SEQ ID NO 46
<211> LENGTH: 123
<212> TYPE: DNA
<213> ORGANISM: Unknown
<220> FEATURE:
```

```
<223> OTHER INFORMATION: Description of Unknown Organism:Unknown
<221> NAME/KEY: UNSURE
<222> LOCATION: (9)
<223> OTHER INFORMATION: May be any nucleic acid
<221> NAME/KEY: UNSURE
<222> LOCATION: (51)
<223> OTHER INFORMATION: May be any nucleic acid
<221> NAME/KEY: UNSURE
<222> LOCATION: (52)
<223> OTHER INFORMATION: May be any nucleic acid
<221> NAME/KEY: UNSURE
<222> LOCATION: (57)
<223> OTHER INFORMATION: May be any nucleic acid
<221> NAME/KEY: UNSURE
<222> LOCATION: (67)
<223> OTHER INFORMATION: May be any nucleic acid
<221> NAME/KEY: UNSURE
<222> LOCATION: (123)
<223> OTHER INFORMATION: May be any nucleic acid

<400> SEQUENCE: 46
caggcaagnc ggcacgtagg agcagcagca gcagcagcag cagcagtaac nnagtcnacg    60
aggggngcc cgggacccaa ggcgcccgaa cagagaggcg gagcacaatc cactggtcgg    120
cgn                                                                 123

<210> SEQ ID NO 47
<211> LENGTH: 109
<212> TYPE: DNA
<213> ORGANISM: Unknown
<220> FEATURE:
<223> OTHER INFORMATION: Description of Unknown Organism:Unknown
<221> NAME/KEY: UNSURE
<222> LOCATION: (87)
<223> OTHER INFORMATION: May be any nucleic acid
<221> NAME/KEY: UNSURE
<222> LOCATION: (95)
<223> OTHER INFORMATION: May be any nucleic acid
<221> NAME/KEY: UNSURE
<222> LOCATION: (102)
<223> OTHER INFORMATION: May be any nucleic acid
<221> NAME/KEY: UNSURE
<222> LOCATION: (106)
<223> OTHER INFORMATION: May be any nucleic acid
<221> NAME/KEY: UNSURE
<222> LOCATION: (107)
<223> OTHER INFORMATION: May be any nucleic acid

<400> SEQUENCE: 47
ggcacgcagg agcagcagca gcagcagcag cagcagcagc agagagagag cagcagagag    60
agagagcagc agagcagagc agagcanagt agagnagagc anagcnnac               109

<210> SEQ ID NO 48
<211> LENGTH: 293
<212> TYPE: DNA
<213> ORGANISM: Homo sapiens
<220> FEATURE:
<221> NAME/KEY: UNSURE
<222> LOCATION: (86)
<223> OTHER INFORMATION: May be any nucleic acid
<221> NAME/KEY: UNSURE
<222> LOCATION: (166)
<223> OTHER INFORMATION: May be any nucleic acid
<221> NAME/KEY: UNSURE
<222> LOCATION: (185)
<223> OTHER INFORMATION: May be any nucleic acid
<221> NAME/KEY: UNSURE
<222> LOCATION: (209)
<223> OTHER INFORMATION: May be any nucleic acid
<221> NAME/KEY: UNSURE
<222> LOCATION: (214)
<223> OTHER INFORMATION: May be any nucleic acid
<221> NAME/KEY: UNSURE
<222> LOCATION: (219)
<223> OTHER INFORMATION: May be any nucleic acid
<221> NAME/KEY: UNSURE
```

<222> LOCATION: (234)
<223> OTHER INFORMATION: May be any nucleic acid
<221> NAME/KEY: UNSURE
<222> LOCATION: (290)
<223> OTHER INFORMATION: May be any nucleic acid

<400> SEQUENCE: 48

```
ggcacgaggg ggaaactgct ccgcgcgcgc cggggaggag gaaccgcccg gtcctttagg   60
gtccgggccc ggccgggcat ggattnaatg cctgagcccg ggtcccgctg tcttctgctt  120
cttcccttgc tgctgctgct gctgctgctg ctgccggccc cggagntggg cccgagccag  180
gccgnagctg aggagaacga cttgggttng cctncccana aaatggaaag gganttgggg  240
ttaatcgaag tcattgggac cattttaaaa ggggcttcct ggattatagn ctt         293
```

<210> SEQ ID NO 49
<211> LENGTH: 506
<212> TYPE: DNA
<213> ORGANISM: Homo sapiens
<220> FEATURE:
<221> NAME/KEY: UNSURE
<222> LOCATION: (283)
<223> OTHER INFORMATION: May be any nucleic acid
<221> NAME/KEY: UNSURE
<222> LOCATION: (342)
<223> OTHER INFORMATION: May be any nucleic acid
<221> NAME/KEY: UNSURE
<222> LOCATION: (356)
<223> OTHER INFORMATION: May be any nucleic acid
<221> NAME/KEY: UNSURE
<222> LOCATION: (362)
<223> OTHER INFORMATION: May be any nucleic acid
<221> NAME/KEY: UNSURE
<222> LOCATION: (364)
<223> OTHER INFORMATION: May be any nucleic acid
<221> NAME/KEY: UNSURE
<222> LOCATION: (368)
<223> OTHER INFORMATION: May be any nucleic acid
<221> NAME/KEY: UNSURE
<222> LOCATION: (429)
<223> OTHER INFORMATION: May be any nucleic acid
<221> NAME/KEY: UNSURE
<222> LOCATION: (454)
<223> OTHER INFORMATION: May be any nucleic acid
<221> NAME/KEY: UNSURE
<222> LOCATION: (461)
<223> OTHER INFORMATION: May be any nucleic acid

<400> SEQUENCE: 49

```
aattcggcac gagcacccgg ccactgcagt cttctgccct gctggacagc agcagcagca   60
gcagcagcag cagcagcagc agcagcaaca gtaacagcag cagttcgtcc ggacccaacc  120
cttctacctc ctttgagccc atcaaggcag accccacagg tgttttggaa ctccccaaag  180
agctgtcaga aatctttgat cccacacgag agtgcatgag ctcggagctg ctggaggagt  240
tgatgtcctc agaagtgttt gcccctctgc tttcgtcttt ctncacccccc gggagaccac  300
gattatatct acaacctgga cgagagtgaa ggtgttttgtg anctcttttg atgtgnctgt  360
tntnaacntt tgactgacag ggacatgcct tttttggttg ggacccagat tttttgactt  420
ggggtttnc ttgggacttt tcaaccgacc ctanagagtt nagagcaaan aggttggttt  480
ttcggcttcc ttaacgaaag ttttgg                                       506
```

<210> SEQ ID NO 50
<211> LENGTH: 419
<212> TYPE: DNA
<213> ORGANISM: Homo sapiens
<220> FEATURE:
<221> NAME/KEY: UNSURE
<222> LOCATION: (137)
<223> OTHER INFORMATION: May be any nucleic acid
<221> NAME/KEY: UNSURE
<222> LOCATION: (221)
<223> OTHER INFORMATION: May be any nucleic acid
<221> NAME/KEY: UNSURE
<222> LOCATION: (259)
<223> OTHER INFORMATION: May be any nucleic acid
<221> NAME/KEY: UNSURE
<222> LOCATION: (327)
<223> OTHER INFORMATION: May be any nucleic acid
<221> NAME/KEY: UNSURE -continued

```
<222> LOCATION: (385)
<223> OTHER INFORMATION: May be any nucleic acid
<221> NAME/KEY: UNSURE
<222> LOCATION: (389)
<223> OTHER INFORMATION: May be any nucleic acid
<221> NAME/KEY: UNSURE
<222> LOCATION: (416)
<223> OTHER INFORMATION: May be any nucleic acid
<221> NAME/KEY: UNSURE
<222> LOCATION: (418)
<223> OTHER INFORMATION: May be any nucleic acid

<400> SEQUENCE: 50
tttaagcacc aaaacttgtg ttttaatgat gttggatgga aatctttcct aaatgtgtca    60
     tgcatgctct tgtctccctt aatggagaga gtgtgacact gcttagcact tggatggctt   120
     ggggtggtgg ttatgancag cagtctgtca cagctcagcg aggtgaagcc tgtgggcgtt   180
     ttgctctgtg ctgaatggct cagtggccct acaaagcgga ntcagctctt ggtggctttc   240
     tgttgtggtg ggctgctgnt gctgctgctg ctgctgctgc tgctgccctt gcctctaaaa   300
     gaactcactt cctcttcctc ctgctgncac ctgtcttttg gcttgtggga ttggagtcat   360
     ggggcccaga tggagccttg ctccntgant tatgataggc ccctcggtct cttttntnc    419

<210> SEQ ID NO 51
<211> LENGTH: 495
<212> TYPE: DNA
<213> ORGANISM: Saccharomyces cerevisiae
<220> FEATURE:
<221> NAME/KEY: UNSURE
<222> LOCATION: (177)
<223> OTHER INFORMATION: May be any nucleic acid
<221> NAME/KEY: UNSURE
<222> LOCATION: (322)
<223> OTHER INFORMATION: May be any nucleic acid
<221> NAME/KEY: UNSURE
<222> LOCATION: (328)
<223> OTHER INFORMATION: May be any nucleic acid
<221> NAME/KEY: UNSURE
<222> LOCATION: (342)
<223> OTHER INFORMATION: May be any nucleic acid
<221> NAME/KEY: UNSURE
<222> LOCATION: (368)
<223> OTHER INFORMATION: May be any nucleic acid
<221> NAME/KEY: UNSURE
<222> LOCATION: (371)
<223> OTHER INFORMATION: May be any nucleic acid
<221> NAME/KEY: UNSURE
<222> LOCATION: (375)
<223> OTHER INFORMATION: May be any nucleic acid
<221> NAME/KEY: UNSURE
<222> LOCATION: (380)
<223> OTHER INFORMATION: May be any nucleic acid
<221> NAME/KEY: UNSURE
<222> LOCATION: (386)
<223> OTHER INFORMATION: May be any nucleic acid
<221> NAME/KEY: UNSURE
<222> LOCATION: (396)
<223> OTHER INFORMATION: May be any nucleic acid
<221> NAME/KEY: UNSURE
<222> LOCATION: (404)
<223> OTHER INFORMATION: May be any nucleic acid
<221> NAME/KEY: UNSURE
<222> LOCATION: (423)
<223> OTHER INFORMATION: May be any nucleic acid
<221> NAME/KEY: UNSURE
<222> LOCATION: (426)
<223> OTHER INFORMATION: May be any nucleic acid
<221> NAME/KEY: UNSURE
<222> LOCATION: (436)
<223> OTHER INFORMATION: May be any nucleic acid
<221> NAME/KEY: UNSURE
<222> LOCATION: (443)
<223> OTHER INFORMATION: May be any nucleic acid
<221> NAME/KEY: UNSURE
<222> LOCATION: (456)
<223> OTHER INFORMATION: May be any nucleic acid
<221> NAME/KEY: UNSURE
<222> LOCATION: (460)
<223> OTHER INFORMATION: May be any nucleic acid
```

```
<221> NAME/KEY: UNSURE
<222> LOCATION: (467)
<223> OTHER INFORMATION: May be any nucleic acid
<221> NAME/KEY: UNSURE
<222> LOCATION: (468)
<223> OTHER INFORMATION: May be any nucleic acid
<221> NAME/KEY: UNSURE
<222> LOCATION: (471)
<223> OTHER INFORMATION: May be any nucleic acid
<221> NAME/KEY: UNSURE
<222> LOCATION: (474)
<223> OTHER INFORMATION: May be any nucleic acid

<400> SEQUENCE: 51
aattcggcac gagcaaagtt ctgcgctcca ttgtgggcat caaacgacac gtcaaagccc    60
     tccatctggg ggacacagtg gactctgatc agttcaagcg ggaggaggat ttctactaca   120
     cagaggtgca gctgaaggag aatctgctg ctgctgctgc tgctgctgcc gcagacnccc    180
     agtccctggg actcccacct ccgagccagc tcccacccc agcatgactg gcctgcctct    240
     gtctgctctt ccaccacctc ttgcacaaag cccagtcctc cggcccagaa catcctgggc   300
     ccggagttcc ttccttgcct tnagggntt ttcagcaagt tnagttcctt gggtccttt    360
     tgggaaantt naggnagttn aaggantacc aggttnttgc catncttt cc agatccaagt  420
     ttnacnaaaa attttnaaca gtntaaattg ggtttnttgn ccctttnngg nggntgttt    480
     ttttttcggg tccgg                                                     495

<210> SEQ ID NO 52
<211> LENGTH: 81
<212> TYPE: DNA
<213> ORGANISM: Unknown
<220> FEATURE:
<223> OTHER INFORMATION: Description of Unknown Organism:Unknown
<221> NAME/KEY: UNSURE
<222> LOCATION: (65)
<223> OTHER INFORMATION: May be any nucleic acid
<221> NAME/KEY: UNSURE
<222> LOCATION: (67)
<223> OTHER INFORMATION: May be any nucleic acid
<221> NAME/KEY: UNSURE
<222> LOCATION: (71)
<223> OTHER INFORMATION: May be any nucleic acid
<221> NAME/KEY: UNSURE
<222> LOCATION: (75)
<223> OTHER INFORMATION: May be any nucleic acid

<400> SEQUENCE: 52
ggcacgcagg agcagagcag cagcagcaga gagagcagca gcagcagcag cagcagcaga    60
     gagananata natanatata t                                              81

<210> SEQ ID NO 53
<211> LENGTH: 305
<212> TYPE: DNA
<213> ORGANISM: Homo sapiens
<220> FEATURE:
<221> NAME/KEY: UNSURE
<222> LOCATION: (11)
<223> OTHER INFORMATION: May be any nucleic acid
<221> NAME/KEY: UNSURE
<222> LOCATION: (62)
<223> OTHER INFORMATION: May be any nucleic acid
<221> NAME/KEY: UNSURE
<222> LOCATION: (81)
<223> OTHER INFORMATION: May be any nucleic acid
<221> NAME/KEY: UNSURE
<222> LOCATION: (256)
<223> OTHER INFORMATION: May be any nucleic acid
<221> NAME/KEY: UNSURE
<222> LOCATION: (289)
<223> OTHER INFORMATION: May be any nucleic acid

<400> SEQUENCE: 53
aggcacttga nttgaaaatg gaaaccctta ctgctggtgg tgctgcggtg atgaggccta    60
     tnatgcagcc ccagggtttt nttaatgctc aaatggtcgc ccaacgcagc agagagctgc   120
     taagtcatca cttccgacaa cagagggtgg ctataatgat gcagcagcag cagcagcagc   180
     aacagcagca gcagcagcag cagcagcagc aacagcaaca gcaacagcaa cagcagcaac   240
     agcagcaaac ccaggncttc agcccacctc ctaatgtgac tgcttcccnc agcatggatg   300
```

```
                                                ggctt                                              305
```

<210> SEQ ID NO 54
<211> LENGTH: 307
<212> TYPE: DNA
<213> ORGANISM: Hepatitis C virus
<220> FEATURE:
<221> NAME/KEY: UNSURE
<222> LOCATION: (212)
<223> OTHER INFORMATION: May be any nucleic acid

<400> SEQUENCE: 54

```
tggggtgtga agctccggtg ctggtgcggc gggggactgc ggggccagcc tcagtttaaa    60
cccccctcagc agtctttctg tcgttgccct ccacactgcg agactctgga gggcgatctg   120
gaggtctgga agataaccga ttcctgggag atttgggggt agtctccaat ctgtccctgg   180
ctcatcttgt gacccgaagc cggcggcctt gncaggagta ttctagaatg agtgcacata   240
aaaatacctt caaacggtag cagcagcagc agcagcagca gcagcaagca gcagcagcag   300
cagcagc                                                              307
```

<210> SEQ ID NO 55
<211> LENGTH: 88
<212> TYPE: DNA
<213> ORGANISM: Unknown
<220> FEATURE:
<221> NAME/KEY: UNSURE
<222> LOCATION: (6)
<223> OTHER INFORMATION: May be any nucleic acid
<221> NAME/KEY: UNSURE
<222> LOCATION: (7)
<223> OTHER INFORMATION: May be any nucleic acid
<221> NAME/KEY: UNSURE
<222> LOCATION: (78)
<223> OTHER INFORMATION: May be any nucleic acid
<221> NAME/KEY: UNSURE
<222> LOCATION: (83)
<223> OTHER INFORMATION: May be any nucleic acid
<221> NAME/KEY: UNSURE
<222> LOCATION: (87)
<223> OTHER INFORMATION: May be any nucleic acid
<223> OTHER INFORMATION: Description of Unknown Organism:Unknown

<400> SEQUENCE: 55

```
ggacanngac tactctctct ctctctctct ctctctctgc tgctgctgct gtgctgctgc    60
tgctgctgct gctgccgntg tgngcana                                       88
```

<210> SEQ ID NO 56
<211> LENGTH: 346
<212> TYPE: DNA
<213> ORGANISM: Unknown
<220> FEATURE:
<221> NAME/KEY: UNSURE
<222> LOCATION: (278)
<223> OTHER INFORMATION: May be any nucleic acid
<221> NAME/KEY: UNSURE
<222> LOCATION: (288)
<223> OTHER INFORMATION: May be any nucleic acid
<221> NAME/KEY: UNSURE
<222> LOCATION: (299)
<223> OTHER INFORMATION: May be any nucleic acid
<221> NAME/KEY: UNSURE
<222> LOCATION: (313)
<223> OTHER INFORMATION: May be any nucleic acid
<221> NAME/KEY: UNSURE
<222> LOCATION: (342)
<223> OTHER INFORMATION: May be any nucleic acid
<223> OTHER INFORMATION: Description of Unknown Organism:Unknown

<400> SEQUENCE: 56

```
ggcacagccc aactggtgat gctgctgctg ctgctgctgc tgccgccgcc gcctctattg    60
ctgatactct agtgggctg gaagggtggt tcctattcgc accatcgcca accagagaca   120
gagggaaaaa aaaaaccggc agccactgct gaatgttggg ttcggaggct gcatccgact   180
cggtcacaag gaaaatggat tcagtttgca tctctccctc ctttaaacag cttctccggg   240
tctcagcatg ggcttccagg gcagcgattg aggagacnttt accaaggngc accacacant   300
```
agatgctgag acntcgtgac tccaggataa gaaacattaa cngggg 346

<210> SEQ ID NO 57
<211> LENGTH: 496
<212> TYPE: DNA
<213> ORGANISM: Unknown
<220> FEATURE:
<223> OTHER INFORMATION: Description of Unknown Organism:Unknown
<221> NAME/KEY: UNSURE
<222> LOCATION: (11)
<223> OTHER INFORMATION: May be any nucleic acid
<221> NAME/KEY: UNSURE
<222> LOCATION: (78)
<223> OTHER INFORMATION: May be any nucleic acid
<221> NAME/KEY: UNSURE
<222> LOCATION: (195)
<223> OTHER INFORMATION: May be any nucleic acid
<221> NAME/KEY: UNSURE
<222> LOCATION: (197)
<223> OTHER INFORMATION: May be any nucleic acid
<221> NAME/KEY: UNSURE
<222> LOCATION: (286)
<223> OTHER INFORMATION: May be any nucleic acid
<221> NAME/KEY: UNSURE
<222> LOCATION: (291)
<223> OTHER INFORMATION: May be any nucleic acid
<221> NAME/KEY: UNSURE
<222> LOCATION: (293)
<223> OTHER INFORMATION: May be any nucleic acid
<221> NAME/KEY: UNSURE
<222> LOCATION: (315)
<223> OTHER INFORMATION: May be any nucleic acid
<221> NAME/KEY: UNSURE
<222> LOCATION: (328)
<223> OTHER INFORMATION: May be any nucleic acid
<221> NAME/KEY: UNSURE
<222> LOCATION: (329)
<223> OTHER INFORMATION: May be any nucleic acid
<221> NAME/KEY: UNSURE
<222> LOCATION: (344)
<223> OTHER INFORMATION: May be any nucleic acid
<221> NAME/KEY: UNSURE
<222> LOCATION: (346)
<223> OTHER INFORMATION: May be any nucleic acid
<221> NAME/KEY: UNSURE
<222> LOCATION: (352)
<223> OTHER INFORMATION: May be any nucleic acid
<221> NAME/KEY: UNSURE
<222> LOCATION: (354)
<223> OTHER INFORMATION: May be any nucleic acid
<221> NAME/KEY: UNSURE
<222> LOCATION: (358)
<223> OTHER INFORMATION: May be any nucleic acid
<221> NAME/KEY: UNSURE
<222> LOCATION: (366)
<223> OTHER INFORMATION: May be any nucleic acid
<221> NAME/KEY: UNSURE
<222> LOCATION: (399)
<223> OTHER INFORMATION: May be any nucleic acid
<221> NAME/KEY: UNSURE
<222> LOCATION: (406)
<223> OTHER INFORMATION: May be any nucleic acid
<221> NAME/KEY: UNSURE
<222> LOCATION: (410)
<223> OTHER INFORMATION: May be any nucleic acid
<221> NAME/KEY: UNSURE
<222> LOCATION: (418)
<223> OTHER INFORMATION: May be any nucleic acid
<221> NAME/KEY: UNSURE
<222> LOCATION: (420)
<223> OTHER INFORMATION: May be any nucleic acid
<221> NAME/KEY: UNSURE
<222> LOCATION: (435)
<223> OTHER INFORMATION: May be any nucleic acid
<221> NAME/KEY: UNSURE
<222> LOCATION: (443)
<223> OTHER INFORMATION: May be any nucleic acid
<221> NAME/KEY: UNSURE

```
<222> LOCATION: (453)
<223> OTHER INFORMATION: May be any nucleic acid
<221> NAME/KEY: UNSURE
<222> LOCATION: (454)
<223> OTHER INFORMATION: May be any nucleic acid
<221> NAME/KEY: UNSURE
<222> LOCATION: (459)
<223> OTHER INFORMATION: May be any nucleic acid
<221> NAME/KEY: UNSURE
<222> LOCATION: (471)
<223> OTHER INFORMATION: May be any nucleic acid
<221> NAME/KEY: UNSURE
<222> LOCATION: (473)
<223> OTHER INFORMATION: May be any nucleic acid
<221> NAME/KEY: UNSURE
<222> LOCATION: (474)
<223> OTHER INFORMATION: May be any nucleic acid
<221> NAME/KEY: UNSURE
<222> LOCATION: (481)
<223> OTHER INFORMATION: May be any nucleic acid

<400> SEQUENCE: 57
gaattcggca naggtgcaca gatgtggtgg atggggaggg ccgcacggga cagaagttct    60
ccctgtgtat tctgacgnct gagaaaggag catttcatcc gggcggagac caaggagatc   120
gtcaatgggt ggctggagat gctcatggtc tatccccgga ccaacaagca gaatcagaag   180
aagaaacgga aagtngnagc cccccacacc acaggagcct gggactgcca agttgggctg   240
ttaccagcag cagcagcagc agcagcagca gcagcagcat ccccantgct ntnggaaagt   300
tcccaccacc aagtnccaca atttgggnna aaaccaaggt tgtngnagac gngntttngg   360
gatttnggca ttgtgggttg cttgcatgga aggacattng gttgtnggtn ccttggangn   420
tacaattacc atttncggtt gtnaaggtta aanntccgnc attcagaagg ntnnaaggtg   480
ntttgaagtc catttg                                                   496

<210> SEQ ID NO 58
<211> LENGTH: 268
<212> TYPE: DNA
<213> ORGANISM: Drosophila sp.
<220> FEATURE:
<221> NAME/KEY: UNSURE
<222> LOCATION: (16)
<223> OTHER INFORMATION: May be any nucleic acid
<221> NAME/KEY: UNSURE
<222> LOCATION: (51)
<223> OTHER INFORMATION: May be any nucleic acid
<221> NAME/KEY: UNSURE
<222> LOCATION: (60)
<223> OTHER INFORMATION: May be any nucleic acid
<221> NAME/KEY: UNSURE
<222> LOCATION: (202)
<223> OTHER INFORMATION: May be any nucleic acid

<400> SEQUENCE: 58
aacacttatc cttganagct ctgtttggga agcaggacaa agctacatgt naggaaactn    60
tggagcctcc gcagactctc caccagcagc agcagcagca gcagcagcag caagagaagc   120
ttccaattag cagggggtt gtacgctccc tgtcctatga ggaacccaga agacactcac    180
ccccccattga gaagcagctc tntccagcca ttcagaaact catggtcagg agcgcagacc   240
tccacccatt gtcagagctg cctgaaaa                                      268

<210> SEQ ID NO 59
<211> LENGTH: 471
<212> TYPE: DNA
<213> ORGANISM: Homo sapiens
<220> FEATURE:
<221> NAME/KEY: UNSURE
<222> LOCATION: (249)
<223> OTHER INFORMATION: May be any nucleic acid
<221> NAME/KEY: UNSURE
<222> LOCATION: (386)
<223> OTHER INFORMATION: May be any nucleic acid
<221> NAME/KEY: UNSURE
<222> LOCATION: (449)
<223> OTHER INFORMATION: May be any nucleic acid

<400> SEQUENCE: 59
tcgacccacg cgtccgctga ggaacagacg ttccctggcg gccctggcgc cttcaaaccc    60
```

```
agacatgctg ctgctgctgc tgctgctgcc cctgctctgg gggacaaagg ggatggaggg    120
agacagacaa tatggggatg gttacttgct gcaagtgcag gagctggtga cggtgcagga    180
gggcctgtgt gtccatgtgc cctgctcctt ctcctacccc caggatggct ggactgactc    240
tgacccagnt catggctact ggttccgggc aggagacaga ccataccaag acgctccagt    300
ggccacaaac aacccagaca gagaagtgca ggcagagacc cagggccgat tccaactcct    360
tggggacatt tggagcaacg actgcnccct gagcatcaga gacgccagga gagggataa    420
ggggtcatat ttctttcggc tagagagang aagcatgaaa tggagttaca a             471
```

<210> SEQ ID NO 60
<211> LENGTH: 379
<212> TYPE: DNA
<213> ORGANISM: Unknown
<220> FEATURE:
<223> OTHER INFORMATION: Description of Unknown Organism:Unknown
<221> NAME/KEY: UNSURE
<222> LOCATION: (2)
<223> OTHER INFORMATION: May be any nucleic acid
<221> NAME/KEY: UNSURE
<222> LOCATION: (14)
<223> OTHER INFORMATION: May be any nucleic acid
<221> NAME/KEY: UNSURE
<222> LOCATION: (31)
<223> OTHER INFORMATION: May be any nucleic acid
<221> NAME/KEY: UNSURE
<222> LOCATION: (135)
<223> OTHER INFORMATION: May be any nucleic acid
<221> NAME/KEY: UNSURE
<222> LOCATION: (315)
<223> OTHER INFORMATION: May be any nucleic acid
<221> NAME/KEY: UNSURE
<222> LOCATION: (332)
<223> OTHER INFORMATION: May be any nucleic acid
<221> NAME/KEY: UNSURE
<222> LOCATION: (349)
<223> OTHER INFORMATION: May be any nucleic acid
<221> NAME/KEY: UNSURE
<222> LOCATION: (357)
<223> OTHER INFORMATION: May be any nucleic acid
<221> NAME/KEY: UNSURE
<222> LOCATION: (374)
<223> OTHER INFORMATION: May be any nucleic acid

<400> SEQUENCE: 60

```
anttcggcan aggnaaggga gagggtgacc ngcatcccaa ctagatttca gtggagtgaa    60
gttcaggagg catggagctg acaaccatga ggcctcggca gccaccgcca ccaccgccgc   120
cgccaccacc gtagncagca gcagcagcag cagcagcagc aagagttaac tctgacttag   180
ggaatagaga cagccagaga gaaatgtgat caatgaagga gacatctgga gtgtgcgtgc   240
ttcttcagag gggacgggtg atgggcagat ttggaaaaag caccgcagat tgggaaccct   300
atcttttctt tttcntaaaa ttgttgttat gnaaatttgg gttttttccng taacttntta   360
aaaacttaaa agtnggttt                                                379
```

<210> SEQ ID NO 61
<211> LENGTH: 255
<212> TYPE: DNA
<213> ORGANISM: Unknown
<220> FEATURE:
<223> OTHER INFORMATION: Description of Unknown Organism:Unknown
<221> NAME/KEY: UNSURE
<222> LOCATION: (121)
<223> OTHER INFORMATION: May be any nucleic acid
<221> NAME/KEY: UNSURE
<222> LOCATION: (183)
<223> OTHER INFORMATION: May be any nucleic acid
<221> NAME/KEY: UNSURE
<222> LOCATION: (254)
<223> OTHER INFORMATION: May be any nucleic acid
<221> NAME/KEY: UNSURE
<222> LOCATION: (255)
<223> OTHER INFORMATION: May be any nucleic acid

<400> SEQUENCE: 61

```
aattccgaca atggaaagca ctcttagcct tgcagtggtc tacattttta aggaaccaat    60
atttcagcat tctttattac ccggcacgct gtgtcctttg tcagagttca agtttatggt   120
nactgccagg gtcagacagt ccatttgctg ctgctgctgc tgctgctgct ttctcgaact   180
ggnatggcat tagggaagct gctgtctgag tgttagggaa tgtcttggct aagtaaagcc   240
```

-continued aatgttcttt cctnn 255

<210> SEQ ID NO 62
<211> LENGTH: 5289
<212> TYPE: DNA
<213> ORGANISM: Unknown
<220> FEATURE:
<223> OTHER INFORMATION: Description of Unknown Organism:Unknown

<400> SEQUENCE: 62

```
cgagctctcc cagccgcagc ctccgaatcc acggcctcca ccccgcgcct ctccagcgct   60
ctatcccgtc gctgcgccct tgtcgccggc cccggccgct gcatccgcgt ccgcacaggc  120
tccttgctgg gcacaaatag ctccaccatg gggctggcct ggggactcgg tgtcctgctc  180
ctgttgcatg cctgcggctc caaccgcatt ccagagtcca gtgtgtttt                240
gacatctttg aactcaccgg agctgcccgc aagcggtctg ggcgccgact ggtgaaggga  300
cctgacccttctagcccagc tttccgcatc gaggatgcca acctgatccc ccctgtgcct  360
gacaagaagt tccaagacct agtggatgct gtgcgggcgg agaaaggttt cctcctcctg  420
gcctccctga ggcaaatgaa gaagacccgg ggtaccctgc tggctgtgga gcggaaagac  480
cactctggcc aggtcttcag cgtgatctcc aatggcaagg cgggcaccct ggacctgagc  540
ctgaccgtgc agggggaagca gcatgtggtg tcggtggaag aagcactcct ggcgactggc  600
cagtggaaga gcatcaccct gtttgtgcag gaggacaggg cccagctgta catcgactgt  660
gagaagatgg agaatgcgga gctggatgtc cccatccaga gcatcttcac caggggacctg  720
gccagcatcg ccaggctccg cattgccaaa ggaggtgtca acgacaattt ccaggggtg   780
ctgcagaatg taaggttttgt ctttggaacc acaccagaag acatcctcag gaacaaaggc  840
tgctccagct ctaccagtgt cttttgtcacc cttgacaaca acgtggtgaa tgggtccagc  900
cctgccatcc gcaccgacta cattggccac aagacaaagg acctgcaagc catctgtgcc  960
atctcatgtg acgagctgtc cagcatggtc ctggagctca gggtctacg caccatcgtg 1020
accacgctgc aggacagtat ccgcaaagtg accgaagaga acaaagagct ggccaacgag 1080
ctgaggaggc ccccactctg ctaccacaac ggagtgcagt acaggactgg cgacgagtgg 1140
acggtggaca gctgcactga gtgtcgctgc cagaactcag ttaccatctg caaaaaagtg 1200
tcctgtccca tcatgccctg ctccaatgcc acagttccgg atggagaatg ctgcccacgg 1260
tgctggccca gcgactctcg agacgatggc tggtccccgt ggtctgagtg gacctcttgc 1320
tctgtgacct gtggcaatgg aatccagcag cgtggccgct cctgcgacag cctcaacaac 1380
agatgcgagg gctcctctgt gcagacgcgg acctgccaca tccaggagtg tgacaagaga 1440
tttaaacagg atggcggctg gagccactgg tccccatgtt catcttgctc cgtaacatgt 1500
ggagacggtg tgatcacaag gatccggctc tgcaactccc ccagccccca gatgaatggg 1560
aagccatgtg agggcaaagc ccgggagacc aaagcctgcc agaaagactc ctgccccatc 1620
aatggaggct ggggaccttg gtcaccatgg gacatctgtt ctgtcacctg tggaggaggg 1680
gtacagaaac gtagccggct ctgcaacaac cccaaacccc agtttggagg caaggactgc 1740
gttggtgatg tgacagaaaa ccagatctgc aacaagcagg actgtcccat tgacggatgc 1800
ctgtccaatc cctgctttgc tggtgtccag tgtaccagct accctgatgg cagctggaag 1860
tgtggtgcct gtcccccagg ctatagtgga gatggagtcg agtgcaaaga cgttgatgag 1920
tgcaaagaag tccctgatgc ctgcttcaac cacaacaggag agcacaggtg tgagaacaca 1980
gaccccggct acaactgcct gcccctgccca ccgcgcttca ctggctcgca gcccttttggc 2040
cggggcgtgg aacatgccac cgcaacaag caggtatgca agccccgaaa ccctgcacca 2100
gacgggacac acgactgcaa caagaacgcc aagtgcaact acctgggcca ctacagcgac 2160
cccatgtacc gctgcgagtg caagcctggc tacgccggca acggcatcat ctgcggggag 2220
gacacagacc tggacgggctg gcccaatgag gaacctgctgt gcgtggccaa cgcaacttac 2280
cactcagaa aggataattg ccccaacctt cccaactcag ggcgaggaaga ctatgacaag 2340
gatggaatcg gcgatgcctg cgatgatgac gatgacaatg ataagattcc agatgacagg 2400
gacaactgtc cattccatta caacccagcc cagtacgact atgacagaga tgacgtggga 2460
gaccgctgtg acaactgccc ctacaaccac aaccccagaa aggctgacac agataacaat 2520
ggggaaggag acgcctgtgc agctgacatt gatggggaca gtatcctcaa tgaacgggac 2580
aactgccagt atgtctacaa tgtggaccag aaagacactg acatggacgg ggttggtgat 2640
cagtgtgaca actgcccccct ggaacacaat ccagaccagc tcgactctga ctcggaccgc 2700
attggagaca cctgtgacaa caatcaggat attgatgaac acggccacca gaacaatctg 2760
gacaactgtc cctacgtgcc caacgccaac caggctgacc atgacaagga tggcaaaggc 2820
gatgcctgtg accatgatga cgacaatgat ggcattcctg atgacgggaa caactgcagg 2880
ctggtgccca tcctgaccaa gaaggactct gatggtgatg tcgaggtga tgcttgcaaa 2940
gatgattttg accaggacaa ggtgccagac attgatgaa tctgtcccga aaatgttgat 3000
atcagtgaga ctgatttccg ccgattccag atgattcctc tagatcccaa agggacatcc 3060
cagaatgacc ctaactgggt tgtacgccat cagggtaaag aactcgtcca gactgtcaac 3120
tgtgaccctg gacttgctgt aggttatgac gaatttaacg ccgtggactt cagtggcacc 3180
ttcttcatca acaccgagag ggatgacgac tatgccggct ttgtgttgg ctaccagttc 3240
agcagccgct tctatgttgt gatgtggaag caagtcactc agtcctactg ggacaccaac 3300
cccacgaggg ctcagggta tctctggact tccgtgaagg ttgtaaactc caccacgggg 3360
cctgcgagc acctgcggaa tgccctgtgg cacacaggaa acacctctgg ccaggtgcgc 3420
acactgtggc atgaccctcg tcacattggc tggaaagatt tcactgccta cagatggcat 3480
ctgagccaca ggccaaagac aggtttcatc agagtgtgaa tgtatgaagg aagaaaatc 3540
atggctgact caggacccat ctatgacaaa acctatgctg gtgggaggct aggcttgttc 3600
gtcttctctc aagaaatggt gttcttctcc gacctgaaat atgaatgcag agactcctaa 3660
tcatcaaact gttgatcaaa agactgatca taaccaatg ctggtattgc accttctgga 3720
accatgggct tagaaaaccc ccaggatcgc gcctcgctgc tcctgctgca tctctgcttg 3780
catgagtgtg gactcctaga acatgtgact tgcctgcaaga aaatgcaatt ttccaaatca 3840
gaccctgcat tcagcctctg actgagaaga atcttccaag gagacaaaca atgactttgg 3900
ttggcttttg caaaagcaaa agcatccaca tgctttggtt ggaaggtgcc tgtcccactc 3960
tgcttttgtc agagcagaat gcgactgtga ggccagctct gagcagtgga ctccaaaatg 4020
```

-continued

```
ttttcaggca tgtgagagaa gggaggactc actagaattg acaaacaaaa ccagccctga 4080
cctactccct ctggaatggg ggcgggtggg ggggccaaag cccaaagggg aggatgcata 4140
cccaagagat gattgtatga agaaaatatg gaggaactgt tacatttttg gtactaaatc 4200
attttcaggg gattgaaaga ctattgctgg atttcatgat cgtgaccggt gttagctgat 4260
taacccacat aaataggcac ttaaatagga gcaggaaagg aaggaaaaga ctggcttctg 4320
gacttcctcc cagatttcca ccccttaaca catccacctgt agtgaccaga acagggagtc 4380
ggagttaaac cgacacaagg cagggccagc tgctgcagct tggttctatt gaaattgtca 4440
gttgtattcc agatgtagct tctgcagatg tagcagcaaa ataagaatac ccaccatctc 4500
agcgagcacc aggctgtctc ccaaggacg gcagccatgc ttgtatttt atggttagaa 4560
aggcacaaaa ttatcaacta agacattcct tctttctctt tttttcctga acatcatgga 4620
gttttccagt tgtctctttt ggactgtagt ttttagtgtt ttaaacaaac actttacaat 4680
gtaaactatt tattttttac ttattctggg ggatctgtct gaaagactat tcatggaaca 4740
ggaagaagcg taaggactat ccatatcatc tttgctacaa gtcattatga ctgtaagatt 4800
gtaaatacag attatttatt aactctgttc tacctggaat ctagtttcat atggaaagtg 4860
tttgagagca ggtagttgag atcgatcagc aaatctttca caggaatggc acaaggaaac 4920
cagcatagca agctgctctt caccttgtgc ttagactgga tgatttggaa ttcttttttc 4980
cttttttttc ccaagtggaa ttacttggtt gtccattgc aagtgttttt agtttgcaaa 5040
gaaagccaag aggccattaa tactgtctta tcccatccct tgtgcctatt tccagggaga 5100
tgaaaagcat ctacatttat tattttgcc ttttttccaa agaaaaaaat gacaaaggtg 5160
aaacttgtat acaaatatta cctcattgt tgtgtgactg agtaaagaat tgggatca 5220
aacagaaaga gtttaagtgt ctaacaaact taaagctact gtagtaccta aaaaaaaaaa 5280
aaaaaaaa                                                          5289
```

<210> SEQ ID NO 63
<211> LENGTH: 2053
<212> TYPE: DNA
<213> ORGANISM: Unknown
<220> FEATURE:
<223> OTHER INFORMATION: Description of Unknown Organism:Unknown

<400> SEQUENCE: 63

```
gaattccggc ggccgctgag agcccaccct ggcgagctct cccagccgca gcctccgaat 60
ccacggcctc caccccgcgc ctctccagcg ctctatcccg tcgctgcgcc cttgtcgccg 120
gccccggcgc tgcatccgcg tccgcacagg ctccttgact gggcacaaat agctccacca 180
tggggctggc ctggggactc ggtgtcctgc tcctgttgca tgcctgccga tccaaccgca 240
ttccagagtc tgggggagac aacagtgtgt ttgacatctt tgaactcacc ggagctgccc 300
gcaacggtac tgggcgccga ctggtgaagg gccctgaccc ttctagccca gcttccgca 360
tcgaggatgc caacctgatc cccctgtgc ctgacaagaa gttccaagac ctagtggatg 420
ctgtgcgggc ggagaaggt ttcctcctcc tggcctccct gaggcaaatg aagaagaccc 480
ggggtaccct gctggctgtg gagcggaaag accactctgg ccaggtcttc agccgtgatct 540
ccaatggcaa ggcgggcacc ctggacctga gcctgaccgt gcaggggaag cagcatgtgg 600
tgtcggtgga agaagcactc ctggcgactg gccagtggaa gagcatcacc ctgtttgtgc 660
aggaggacag ggcccagctg tacatcgact gtgagaagat ggagaatgcg gagctggatg 720
tccccatcca gagcatcttc accagggacc tggccagcat cgccaggctc cgcattgcca 780
aaggaggtgt caacgacaat ttccaggggg tcctgcagaa tgtaaggttt gtcttttggaa 840
ccacaccaga agacatcctc aggaacaaag gctgctccag ctctaccagt gtctttgtca 900
cccttgacaa caacgtgtg aatgggtcca gccctgccat ccgcaccgac tacattggcc 960
acaagacaaa ggacctgcaa gccatctgtg gcatctcatg tgacgagctg tccagcatgg 1020
tcctggagct cagggggctctga cgcaccatcg tgaccacgct gcaggacagt atccgcaaag 1080
tgaccgaaga gaacaaagag ctggccaacg agctgaggag gccccactg tgctaccaca 1140
acggagtgca gtacaggact ggcgacgagt ggacgtgga cagctgcact gagtgtcgct 1200
gccagaactc agttaccatc tgcaaaaag tgtcctgtcc catcatgccc tgctccaatg 1260
ccacagttcc ggatggaaa tgctgcccac ggtgctgcc cagcgactct gcagacgacg 1320
gctggtcccc gtggtctgag tggacctctt gctctgtgac ctgtggcaat ggaatccagc 1380
agctggccgc tcctgcgaca gcctcaacaa cagatgcgag ggctcctctg tgcagacgcg 1440
gacctgccac atccaggagt gtgacaagga atttaaacag gatgcggct ggagccactg 1500
gtccccatgg tcatcttgct ccgtaacatg tggagacggt gtgatcacaa ggatccggct 1560
ctgcaactcc cccagccccc agatgaatgg gaagccatgt gagggcaaag cccgggagac 1620
caaagcctgc cagaaagact cctgccccat caatggaggc tggggacctt ggtcaccatg 1680
ggacatctgt tctgtcacct gtggaggagg ggtacagaaa cgtagccggc tctgcaacaa 1740
ccccacaccc cagtttggag gcaaggactg cattggtgat gtgacagaaa accagatctg 1800
caacaagcag gactgtccca ttgacgatg cctgtccaat ccctgctttg ctggtgtcca 1860
gtgtaccagc taccctgatg gcagctggaa gtgtggtgcc tgtccccag gctatagtgg 1920
agatggagtc gagtgcaaag acgttgatga gtgcaagaa gtccctgatg cctgcttcaa 1980
ccacaatgga gagcacaggt gtgagaacac agaccccggc tacaactgcc tgccctgccc 2040
accgccgga att                                                     2053
```

<210> SEQ ID NO 64
<211> LENGTH: 4339
<212> TYPE: DNA
<213> ORGANISM: Unknown
<220> FEATURE:
<223> OTHER INFORMATION: Description of Unknown Organism:Unknown

<400> SEQUENCE: 64

-continued

```
agccactgcc tggagtcagc cagcctcatc ggacttctgc aggcaatcgc gaagctgcta   60
tccagttctg ccacggtctc tcccggcgca ccggcagtct cagcgtcttc accggactca  120
gcgtccttgt ccttcacttc acctttgcca cctctccggg ttactgagcc ccggtgcaca  180
caggctccgt gttgggcaca aaggctccac catggagctc ctgcggggac taggtgtcct  240
gttcctgttg catatgtgtg gaagcaaccg cattccagag tctgggggag ataacggtgt  300
gtttgacatc tttgaactca ttggaggtgc acgaaggggc cccggtcgcc gactggtgaa  360
gggccaagat ctatccagcc ccgccttccg cattgagaat gccaacctga tccccgctgt  420
gccggatgac aagttccaag acctactgga cgctgtgtgg gccgacaaag gcttcatctt  480
cttggcttcc ttgaggcaga tgaagaagac ccggggcaca ctcctggctg tggaacggaa  540
agacaacact ggccagatct tcagtgtggt ctccaacggc aaagctggca ccctggacct  600
gagcctgagc ctgccaggga agcaacaagt ggtgtcagtg gaggaagctc tcctggccac  660
tggccagtgg aagagcatca cgctgttttgt tcaagaggac cgggctcaac tctacataga  720
ctgtgataag atggagagcg cggagctgga tgtacccatc cagagcatct tcaccaggga  780
tctggccagc gttgccaggc tccgagttgc aaaggagat gtcaatgaca attttcaggg  840
ggtgctgcag aatgtgaggt tgtctttgg aaccacccca gaagacattc tcaggaacaa  900
aggctgctcc agctctacca acgtccttct tacccttgac aacaacgtgg tgaacggttc  960
cagccctgct atccgcacca actacatcgg ccacaaaaca aaggacctcc aagctatctg 1020
tggcctctcc tgtgatgaac tatccagcat ggtcctggaa ctgaagggcc tgcgcaccat 1080
cgtgaccact ctgcaggaca gcatccgaaa agtgacggaa gagaacagag agctggtcag 1140
tgagctgaag cggcctcccc tctgctttca caatgagtc cagtacaaga caacgagga 1200
gtggactgta gacagttgca cagagtgtca ctgccagaac tcgttacca tctgcaaaaa 1260
ggtgtcctgt cccatcatgc cctgctccaa cgccacagtt cctgatggtg aatgctgccc 1320
acggtgctgg cccagcgact ctgctgacga tggctggtct ccctggtctg agtggacctc 1380
ctgctctgcc acatgtggca atggaattca gcaacgtggt cgttcctgtg acagcctcaa 1440
caacagatgc gagggctctt cggtacagac gaggacctgc cacattcagg agtgtgacaa 1500
aagatttaaa caggatggtg gctggagtca ctggtctcca tggtcgtcct gttctgtgac 1560
ctgtggtgac ggtgtgatca caaggatccg tctctgcaac tcccccagcc cccagatgaa 1620
cgggaagccc tgtgaaggtg aagcccggga gaccaaagcc tgcaagaaag acgcctgccc 1680
aattaatgga ggctgggtc cctggtcacc atgggacatc tgtctctgtca cctgtggagg 1740
aggagtgcag agacgcagcc gactctgtaa caacccccaca ccccagtttg gaggcaaaga 1800
ctgtgttggc gatgtgacag aaaatcaagt ttgcaacaag caggactgcc caattgatgg 1860
atgcctgtcc aatccctgct ttgctggtgc caagtgtact agctaccctg atggtagctg 1920
gaaatgtggt gcgtgtcctc ctggctacag tggaaatggc atccagtgca agacgtcga 1980
tgagtgcaaa gaagtgcctg atgcttgctt caatcacaac ggagaacatc ggtgcaagaa 2040
cacagatcct ggctacaact gcctgccctg cccaccacga ttcactggct cacagccctt 2100
cggccgaggt gtcgaacatg ccatggccaa caaacaggtg tgcaaaccgc gaaacccctg 2160
cacggacggg acgcatgact gcaacaagaa cgctaagtgc aactacctgg gtcactacag 2220
cgaccccatg taccgctgtg agtgcaagcc cggctatgca ggcaatggca tcatctgcgg 2280
agaggacaca gacctggacg gctggcctaa tgaaaacctg gtgtgtgtgg ccaacgcaac 2340
ctaccactgc aaaaaggaca actgccccaa ccttcccaac tcggggcagg aagactatga 2400
caaggacgga attggcgatg cctgcgatga tgacgatgaa gacacagatc ccctgatga 2460
cagggacaac tgtccattcc attacaaccc agcccagtat gactatgaca gagatgatgt 2520
gggagaccgc tgtgacaact gccctacaa ccacaaccct gaccaagcag acacagacaa 2580
aaacggggag ggcgatgcct gtgctgtgga catcgatgga gatgaatcc tcaatgaacg 2640
agacaactgc cagtacgttt acaacgtgga ccagagggac acggacatgg atgggtttgg 2700
agatcagtgt gacaactgcc ccctggaaca caatccagac cagtcggaact ctgactcaga 2760
cctcataggg gacacttgtg acaacaatca ggacatcgat gaggatggcc atcagaacaa 2820
cctggacaac tgtccctatg tgcctaacgc caaccaggcc gaccatgata aagatggcaa 2880
aggagatgcc tgtgaccatg acgatgacaa tgacggcatc cctgatgaca gagacaactg 2940
caggctggtg cccaatcctg accagaagga ctctgatgggt gatggccgag gtgacgcctg 3000
caaagacgac tttgaccatg acaatgtgcc agatattgat gacatctgtc ctgagaattt 3060
tgacatcagt gaaaccgatt tccgacgatt ccagatgatt cctctagatc ccaaaggaac 3120
ctcccaaat gaccctaact gggttgtccg ccatcaggc aaagaactcg tccagactgt 3180
aaactgtgac cctggacttg ctgtaggtta tgatgatgtt aatgctgtgg acttcagcgg 3240
taccttcttc atcaacaccg agagagatga tgactacgtt ggcttggtat tcggctacca 3300
gtccagcagc cgcttctacg ttgtgatgtg gaaacaagtc acccagtcct actgggacac 3360
caacccaca agggctcagg gatactcagg cctgtctgta aaggttgtga actccaccac 3420
cgcccctggc gagcacctgc ggaatgcact gtggcacaca ggaaacaccc ctggccagtt 3480
gcgcacctg tggcatgacc ctcgccacat cggctggaaa gatttcactg cgtacagatg 3540
gcgtctcagc cacaggccaa agaccggtta tcagagtg gtgatgtatg aaggaaagaa 3600
aatcatggct gactcgggac ccatctatga caaacctac gccggcgta gactaggcct 3660
gttcgtcttc tctcaggaaa tggtgttctt ctcagacatg aaatacgagt gtcgagattc 3720
ctaatcatca gctgccaatc ataaccagcg ctggcaatgc accttctaaa aacaagggct 3780
agagaaaccc cccaccccctg ccgggatcgc ctttcctcgc cttccttgcc tctcttcttg 3840
catagtgtgg acttgtaag cctgagacct gcctcaagaa aatgcagttt tcgaacccag 3900
agtcagcact cggccttaa cgaatgagaa tgcatcttcc aagaccatga agagttcctt 3960
gggtttgctt ttgggaaagc caaagcgcct attttacttcc cactaggaag gtgcccgctc 4020
cactctgcct tactcacaga gccagaactt cttcgaggcc acctctgagc agcacacaca 4080
gaagcatttt caggcatgtc aagaaagga aaaatgactc actagaactc accgccaaac 4140
aacctctgac ataggtcctg agatgtgggg aggcaggagc caaagctcta ggggggcat 4200
gtacccaaga tgactgta tgaagaaaat gtggaggagc tgttcggtac taaatcattt 4260
tcaggggaca gacagacttg ctgcatttcc gcatgctgct ggtgagagct gattgaccca 4320
atcttccaca caggcactt                                              4339
```

<210> SEQ ID NO 65
<211> LENGTH: 186
<212> TYPE: DNA
<213> ORGANISM: Unknown

```
<220> FEATURE:
<223> OTHER INFORMATION: Description of Unknown Organism:Unknown

<400> SEQUENCE: 65
gcacagttaa tggaggctgg ggtccctggt caccatggga catctgctct gtcacctgtg    60
     gaggaggagt gcagagacgc agccgactct gtaacaaccc cacacccag tttggaggca    120
     aagactgtgt tggcgatgtg acagaaaatc aagtttgcaa caagcaggac tgcccaattg    180
     gtaagc                                                               186

<210> SEQ ID NO 66
<211> LENGTH: 5774
<212> TYPE: DNA
<213> ORGANISM: Unknown
<220> FEATURE:
<223> OTHER INFORMATION: Description of Unknown Organism:Unknown

<400> SEQUENCE: 66
gtcactttgg ttgatagcag ccgctctggt agaggttagg acttcagctg atggacaagc    60
     tggtaatgaa gaaatggtgc aaatagattt accaataaag agatatagag agtatgagct   120
     ggtgactcca gtcagcacaa atctagaagg acgctatctc tcccatactc tttctgcgag   180
     tcacaaaaag aggtcagcga gggacgtgtc ttccaaccct gagcagttgt tctttaacat   240
     cacggcattt ggaaaagatt ttcatctgcg actaaagccc aacactcaac tagtagctcc   300
     tggggctgtt gtggagtggc atgagacatc tctggtgcct gggaatataa ccgatcccat   360
     taacaaccat caaccaggaa gtgctacgta tagaatccgg aaaacagagc ctttgcagac   420
     taactgtgct tatgttggtg acatcgtgga cattccagga acctctgttg ccatcagcaa   480
     ctgtgatggt ctggctgaaa tgataaaaag tgataatgaa gagtatttca ttgaaccctt   540
     ggaaagaggt aaacagatgg aggaagaaaa aggaaggatt catgttgtct acaagagatc   600
     agctgtagaa caggctccca tagacatgtc caaagacttc cactacagag agtcggacct   660
     ggaaggcctt gatgatctag gtactgttta tggcaacatc caccagcagc tgaatgaaac   720
     aatgagacgc cgcagacacg cgggagaaaa cgattacaat atcgaggtac tgctgggagt   780
     ggatgactct gtggtccgtt tccatggcaa agagcacgtc caaaactacc tcctgaccct   840
     aatgaacatt gtgaatgaaa tttaccatga tgagtccctc ggagtgcata taaatgtggt   900
     cctggtgcgc atgataatgc tgggatatgc aaagtccatc agcctactag aaagggggaaa   960
     cccatccaga agcttggaga atgtgtgtcg ctgggcgtcc caacagcaaa gatctgatct  1020
     caaccactct gaacaccatg accatgcaat tttttttaacc aggcaagact ttggacctgc  1080
     tggaatgcaa ggatatgctc cagtcaccgg catgtgtcat ccagtgagaa gttgtaccct  1140
     gaatcatgag gatggttttt catctgcttt tgtagtagcc catgaaacgg gccatgtgtt  1200
     gggaatggag catgatggac aaggcaacag gtgtggtgat gagactgcta tgggaagtgt  1260
     catggctccc ttggtacaag cagcattcca tcgttaccac tggtcccgat gcagtggtca  1320
     agaactgaaa agatatatcc attcctatga ctgtctcctt gatgacccctt ttgatcatga  1380
     ttggcctaaa ctcccagaac ttcctggaat caattattct atggatgagc aatgtcgttt  1440
     tgattttggt gttggctata aatgtgcac cgcgttccga acctttgacc catgtaaaca  1500
     gctgtggtgt agccatcctg ataatcccta cttttgtaag actaaaaagg gacctccact  1560
     tgatgggact gaatgtgctg ctggaaaatg gtgctataag ggtcattgca tgtggaagaa  1620
     tgctaatcag caaaaacaag atggcaattg ggggtcatgg actaaatttg gctcctgttc  1680
     tcggacatgt ggaactggtg ttcgtttcag aacacgccag tgcaataatc ccatgcccat  1740
     caatggtggt caggattgtc ctggtgttaa ttttgagtac cagctttgta acacagaaga  1800
     atgccaaaaa cactttgagg acttcagagc acagcagtgt cagcagcgaa actcccactt  1860
     tgaataccag aataccaaac accactggtt gccatatgaa catcctgacc caagaaaaag  1920
     atgccacctt tactgtcagt ccaaggagac tggagatgtt gcttacatga acaactggt  1980
     gcatgatgga acgcactgtt cttacaaaga tccatatagc atatgtgtgc gaggagagtg  2040
     tgtgaaagtg ggctgtgata agaaaattgg ttctaataag gttgaggata agtgtggtgt  2100
     ctgtggagga gataattccc actgccgaac cgtgaagggg acatttacca gaactcccag  2160
     gaagcttggg taccttaaga tgtttgatat accccctggg gctagacatg tgttaatcca  2220
     agaagacgag gcttctcctc atattcttgc tattaagaa caggctacag gccattatat  2280
     tttaaatggc aaaggggagg aagccaagtc gcggaccttc atagatcttg gtgtggagtg  2340
     ggattataac attgaagatg acattgaaag tcttcacacc gatgggccctt tacatgatcc  2400
     tgttattgtt ttgattatac ctcaagaaaa tgataccgc tctagcctga catataagta  2460
     catcatccat gaagactctg tacctacaat caacagcaac aatgtcatcc aggaagaatt  2520
     agatactttt gagtgggctt tgaagagctg gtctcaggtt tccaaaccct gtggtggagg  2580
     tttccagtac actaaatatg gatgccgtag gaaaagtgat aataaaatgg tccatcgcag  2640
     cttctgtgag gccaacaaaa agccgaaacc tattagcga atgtgcaata ttcaagagtg  2700
     tacacatcca ctctgggtag cagaagaatg ggaacactgc accaaaacct gtggaagttc  2760
     tggctatcag cttcgcactg tacgctgcct tcagccactc cttgatggca ccaaccgctc  2820
     tgtgcacagc aaatactgca tgggtgaccg tcccgagagc cgccggcct gtaacagagt  2880
     gccctgccct gcacagtgga aaacaggacc ctggagtgag tgttcagtga cctgcggtga  2940
     aggaacggag gtgaggcagg tcctctgcag ggctggggac cactgtgatg gtgaaaagcc  3000
     tgagtcggtc agagcctgtc aactgcctcc ttgtaatgat gaaccatgtt tgggagacaa  3060
     gtccatattc tgtcaaatgg aagtgttggc acgatactgc tccataccag gttataacaa  3120
     gttatgttgt gagtcctgca gcaagcgcag tagcaccctg ccaccaccat accttctaga  3180
     agctgctgaa actcatgatg atgtcatctc taaccctagt gacctcccta gatcctctagt  3240
     gatgcctaca tctttggttc cttatcattc agagacccct gcaaagaaga tgtctttgag  3300
     tagcatctct tcagtgggag gtccaaatgc atatgctgct tcaggccaa acagtaaacc  3360
     tgatggtgct aatttacgcc agaggagtgc tcagcaagca ggaagtaaga ctgtgagact  3420
     ggtcaccgta ccatcctccc cacccaccaa gagggtccac ctcagttcag cttcacaaat  3480
     ggctgctgct tccttctttg cagccagtga ttcaataggt gcttcttctc aggcaagaac  3540
```

```
ctcaaagaaa gatggaaaga tcattgacaa cagacgtccg acaagatcat ccaccttaga 3600
aagatgagaa agtgaaccaa aaaggctaga aaccagagga aaacctggac aacctctctc 3660
ttcccatggt gcatatgctt gtttaaagtg gaaatctcta tagatcgtca gctcatttta 3720
tctgtaattg gaagaacaga aagtgctggc tcactttcta gttgctttca tcctccttt 3780
gttctgcatt gactcattta ccagaattca ttggaagaaa tcaccaaaga ttattacaaa 3840
agaaaaatat gttgctaaga ttgtgttggt cgctctctga agcagaaaag ggactggaac 3900
caattgtgca tatcagctga cttttgtt gttttagaaa agttacagta aaaattaaaa 3960
agagatacca atggtttaca ctttaacaag aaatttttgga tatggaacaa agaattctta 4020
gacttgtatt cctatttatc tatattagaa atattgtatg agcaaatttg cagctgttgt 4080
gtaaatactg tatattgcaa aaatcagtat tatttaaga gatgtgttct caaatgattg 4140
tttactatat tacatttctg gatgttctag gtgcctgtcg ttgagtattg ccttgtttga 4200
cattctatag gttaattttc aaagcagagt attacaaaag agaagttaga attacagcta 4260
ctgacaatat aaagggtttt gttgaatcaa caatgtgata cgtaaattat agaaaaagaa 4320
aagaaacaca aaagctatag atatacagat atcagcttac ctattgcctt ctatacttat 4380
aatttaaagg attggtgtct tagtacactt gtggtcacag ggatcaacga atagtaaata 4440
atgaactcgt gcaagacaaa actgaaaccc tctttccagg acctcagtag gcaccgttga 4500
ggtgtccttt gtttttgtgt gtgtgtgttc ttttttaatt ttcgcattgt tgacagatac 4560
aaacagttat actcaatgta ctgtaataat cgcaaaggaa aaagttttgg gataacttat 4620
ttgtatgttg gtagctgaga aaaatcat cagtctagaa ttgatatttg agtatagtag 4680
agctttgggg cttgaaggc aggttcaaga aagcatatgt cgatcggttga gatatttatt 4740
ttccatatgg ttcatgttca aatgttcaca accacaatgt atctgactgc aataatgtgc 4800
taataattta tgtcagtagt caccttgctc acagcaaagc cagaaatgct ctctccaggg 4860
agtagatgta aagtacttgt acatagaatt cagaactgaa gatatttatt aaaagttgat 4920
tttttttct tgatagtatt tttatgtact aaatatttac actaatatca attacatatt 4980
ttggtaaact agagagacat aattagagat gcatgctttt ttctgtgcat agagaccttt 5040
aagcaaacta ctacagccaa ctcaaaagct aaaactgaac aaatttgatg ttatgcaaac 5100
atcttgcatt tttagtagtt gatattaagt tgatgacttg tttccttca aggaaacatt 5160
aaattgtatg gactcagcta gctgttcaat gaaattgtga attagaaaca ttttaaaag 5220
tttttgaaag agataagtgc atcatgaatt acatgtacat gagaggagat agtgatatca 5280
gcataatgat tttgaggtca gtacctgagc tgtctaaaaa tatattatac aaactaaaat 5340
gtagatgaat taacctctca aagcacagaa tgtgcaagaa cttttgcatt ttaatcgttg 5400
taaactaaca gcttaaacta ttgactctat acctctaaag aattgctgct actttgtgca 5460
agaacttgaa aggtcaaatt aggcaaattc cagatagtaa aacaatccct aagccttaag 5520
tctttttttt ttcctaaaaa ttcccataga ataaaattct ctctagttta cttgtgtgtg 5580
catacatctc atccacaggg gaagataaag atggtcacac aaacagtttc cataaagatg 5640
tacatattca ttatacttct gacctttggg cttctttc tactaagcta aaaattcctt 5700
tttatcaaag tgtacactac tgatgctgtt tgttgtactg agagcacgta ccaataaaaa 5760
tgttaacaaa atat                                                   5774
```

<210> SEQ ID NO 67
<211> LENGTH: 5535
<212> TYPE: DNA
<213> ORGANISM: Unknown
<220> FEATURE:
<223> OTHER INFORMATION: Description of Unknown Organism:Unknown

<400> SEQUENCE: 67

```
ggactttaga agccgttgct gccctctctg tcacctgaag cggggccctc tcccatccca   60
cccttgcccc gcctccctgc ccccaccggg ccggccctgc ccgccgccgg accctggcat  120
gtcaagacct ggtccgcgcc tgcctgccca gcccgcgaa ccccggcggc cccgcgagct  180
aggatgaggg gccaggccgc cgcccccgggc cccgtctgga tcctcgcccc gctgctactg  240
ctgctgctgc tgctgggacg ccgcgcgcgg gcggccgcc gagcagacgc ggggcccggg  300
cccgagccgt gcgccacgct ggtgcaggga aagttcttcg gctacttctc cgcggccgcc  360
gtgttcccgg ccaacgcctc gcgctgctcc tggacgctac gcaacccgga cccgcggcgc  420
tacactctct acatgaaggt ggccaaggcg cccgtgccct gcagcggccc cggccgcgtg  480
cgcacctacc agttcgactc cttcctcgag tccacgcgca cctacctggg cgtggagagc  540
ttcgacgagg tgctgcggct ctgcgacccc tccgcacccc tggccttcct gcaggccagc  600
aagcagttcc tgcagatgcg cgccagcag ccgccccagc acgacgggct ccggccccgg  660
gccgggccgc cgggccccac cgacgacttc tccgtggagt acctggtggt gggggaaccgc  720
aaccccagcc gtgccgcctg ccagatgctg tgccgctggc tgggcccggt tctggccggt  780
agtcgcagct cgcaccctg cgggatcatg cagaccccct gcgcctgcct gggcggcgag  840
gcggcggcc ctgccgcggg acccctggcc ccccgcgggg atgtctgctt gagagatgcg  900
gtggctggtg gccctgaaaa ctgcctcacc agcctgaccc aggaccgggg cgggcacggc  960
gccacaggcg gctggaagct gtggtcctg tgggcgcaat gcacggga ctgcgggga  1020
ggcctccaga cgcggacgcg cacctgcctg ccgcggccgg gcgtggaggg cggcggctgc  1080
gagggggtgc tggaggaggg tcgccagtgc aaccgcgagg cctgcggccc cgctgggcgc  1140
accagctccc ggagccagtc cctgcggtcc acagatgccc ggcggcgcga ggagctgggg  1200
gacgagctgc agcagtttgg gttcccagcc cccagaccg gtgacccagc agccgaggag  1260
tggtccccgt ggagcgtgtg ctccagcacc tgcggcagac ccgcacgcgt  1320
ttctgcgtgt cctcctccta cagcacgcag tgcagcggac ccctgcgcga gcagcggctg  1380
tgcaacaact ctgccgtgtg cccagtgcat ggtgcctggg atgagtggtc gccctggagc  1440
ctctgctcca gcacctgtgg ccgtggcttt cgggatcgca gcgcacctg caggccccc  1500
cagttgggg caacccctg tgaggcccct gagaagcaaa ccaagttctg caacattgcc  1560
ctgtgccctg gccggcagt ggatggaac tggaatgagt ggtcgagctg gagcgcctcc  1620
tccgcagct gctccaggg ccgacagcag cgcacgcgtg aatgcaacgg gccttcctac  1680
ggggtgcgg agtgccaggg ccactgggtg gagacccgag actgcttcct gcagcagtgt  1740
ccagtggatg gcaagtggca ggcctgggcg tcatgggca gttgcagcgt cacgtgtggg  1800
```

-continued

```
gctggcagcc agcgacggga gcgtgtctgc tctgggccct tcttcggggg agcagcctgc 1860
cagggccccc aggatgagta ccggcagtgc ggcacccagc ggtgtcccga gccccatgag 1920
atctgtgatg aggacaactt tggtgctgtg atctggaagg agaccccagc gggagaggtg 1980
gctgctgtcc ggtgtccccg caacgccaca ggactcatcc tgcgacggtg tgagctggac 2040
gaggaaggca tcgcctactg ggagccccccc acctacatcc gctgtgtttc cattgactac 2100
agaaacatcc agatgatgac ccggggagcac ctggccaagg ctcagcgagg gctgcctggg 2160
gaggggggtct cggaggtcat ccagacactg gtgagatct ctcaggacgg gaccagctac 2220
agtggggacc tgctgtccac catcgatgtc ctgaggaaca tgacagagat tttccggaga 2280
gcgtactaca gccccacccc tggggacgta cagaactttg tccagatcct tagcaacctg 2340
ttggcagagg agaatcggga caagtgggag gaggcccagc tggcgggccc caacgccaag 2400
gagctgttcc ggctggtgga ggactttgtg gacgtcatcg gcttccgcat gaaggacctg 2460
agggatgcat accaggtgac agacaacctg gttctcagca tccataagct cccagccagc 2520
ggagccactg acatcagctt ccccatgaag ggctggcggg ccacgggtga ctgggccaag 2580
gtgccagagg acagggtcac tgtgtccaag agtgtcttct ccacggggct gacagaggcc 2640
gatgaagcat ccgtgtttgt ggtgggcacc gtgctctaca ggaacctggg cagcttcctg 2700
gccctgcaga ggaacacgac cgtcctgaat tctaaggtga tctccgtgac tgtgaaaccc 2760
ccgcctcgct ccctgcgcac acccttggga atcgagtttg cccacatgta taatggcacc 2820
accaaccaga cctgtatcct gtgggatgag acggatgtac cctcctcctc cgcccccccg 2880
cagctcgggc cctggtcgtg gcgcggctgc cgcacggtgc ccctcgacgc cctccggacg 2940
cgctgcctct gtgaccggct ctccaccttc gccatcttag cccagctcag cgccgacgcg 3000
aacatggaga aggcgactct gccgtcggtg acgctcatcg tgggctgtgg cgtgtcctcc 3060
ctcaccctgc tcatgctggt catcatctac gtgtccgtgt ggaggtacat tcgctcagag 3120
cgttctgtca tcctcatcaa ctttctgcctg tccatcatct cctcaatgc cctcatcctc 3180
atcgggcaga cccagacccg caacaaggtg atgtgcacgc tggtggccgc cttcctgcac 3240
ttcttcttcc tgtcctcctt ctgctgggtg ctcaccgagg acgctgcagtc ctacatggcc 3300
gtgacgggcc acctccggaa ccgcctcatc cgcaagcgct tcctctgcct gggctggggg 3360
ctccctgcac tggttgtggc catttctgtg ggattcacca aggcaaaagg gtacagcacc 3420
atgaactact gctggctctc cctggagggg ggactgctct atgccttcgt gggacctgcc 3480
gctgccgttg tgctggtgaa catggtcatt gggatccttg tgttcaacaa gctcgtgtcc 3540
aaagacggca tcacggacaa gaagctgaag gagcgggcag gggcctccct gtggagctcc 3600
tgcgtggtgc tgcccgctgct ggcgctgacc tggatgtcgg ctgtgctcgc cgtcaccgac 3660
cgccgctccg ccctcttcca gatcctcttc gctgtcttcg actgctggga gggcttcgtc 3720
atcgtcatgg tgcactgtat cctccgtaga gaggtccagg acgctgtgaa atgccgtggt 3780
gttgaccggc aggaggaggg caacgggggac tcaggggggct ccttccagaa cggccacgcc 3840
cagctcatga ccgacttcga aaggacgtg gatctggcct gtagatcagt gctgaacaag 3900
gacatcgcgg cctgccgcac tgccaccatc acgggcacac tgaagcggcc gtctctgccc 3960
gaggaggaga agctgaagct ggcccatgcc aagggggccgc ccaccaattt caacagcctg 4020
ccggccaacg tgtccaagct gcacctgcac ggctcacccc gctatcccgg cgggccccctg 4080
cccgacttcc ccaaccactc actgaccctc aagagggaca aggcgcccaa gtcctccttc 4140
gtcggtgacg gggacatctt caagaagctg gactcggagc tgagccgggc caggagaag 4200
gctctgacca cgagctacgt gatcctgccc acggccacgg ccacgctgcg gcccaagcc 4260
aaggaggagc ccaagtacag catccacatt gaccagatgc cgcagaccccg cctcatccac 4320
ctcagcacgg ccccccgagggc cagcctcccc gcccgcagcc cgccctcccg ccagccccccc 4380
agcggcgggc cccccgaggc acccccctgcc cagccccccac cgcctccgcc cccaccgcca 4440
ccacctcccc agcagcccct gccccccaccg cccaatctgg agccggccac cccgagcctg 4500
ggggatcccg gggagcctgc cgcccatccg ggacccagca cggggcccag caccaagaac 4560
gagaatgtcg ccaccttgtc tgtgagctcc ctggagcggc ggaagtcgcg gtatgcagaa 4620
ctggactttg agaagatcat gcacacccgg aagcggcacc aagacatgtt ccaggacctg 4680
aaccggaagc tgcagcacgc agcggagaag gacaaggagg tgctgggggcc ggacagcaag 4740
ccggaaaagc agcagacgcc caacaagagc ccctgggaga gcctccaggg agcccagggg 4800
acgcccacgt gggtgaagaa ggagctggag ccgctgcagc cgtcgccgct ggagcttcgc 4860
agcgtggagt gggagaggtc gggcgccacg atcccgctgg tggccaggga catcatcgac 4920
ctccagaccg aggtctgagc gggtgggcgg cggccacgca ctgggccacg gaggagggat 4980
gctgctccgc ccgctcctgc cgcagacggg cacagacacg acgctgggca gcgggccagg 5040
cccgcacccc ggcctcaggg cgctcagacg gcggccaggc acagggcccg cagtgctggg 5100
accagagcca gatgcaggac aggaggcggc ccggcagcg ggcacagggc accagaggcc 5160
gaaggtgcct cagactccgc cctcctcggg ccgaggccca gcgggcagat gggcggacgg 5220
ctgtggaccg tggacaggcc cagcgcggcc agcgtcccag ggtacccgcc tgagctccctg 5280
ctgcgaggga gctgcctgct tggcccggcc ggcctggcac cgtttttttaa acaccccccat 5340
ccctcgggaa gcagccagct ccccacacct tccagggccc taggccccctc ctagacccag 5400
gtggagggca cagccctccg accctcatgg cccccagggg caggactgag tcccctccag 5460
gaagaagcag gggggaatct attttttctc tccttttcctt ttcttcaata aaagaattaa 5520
aaaacccaaa aaaaa                                                 5535
```

<210> SEQ ID NO 68
<211> LENGTH: 398
<212> TYPE: DNA
<213> ORGANISM: Unknown
<220> FEATURE:
<223> OTHER INFORMATION: Description of Unknown Organism:Unknown

<400> SEQUENCE: 68

```
cggggcaacc cgctggagtg gacgggccag gtgacggtgc gcaagaagcg caagccctac   60
tccaagttcc agacgctcga gctcgagaag gagttcctct tcaacgcgta cgtcagcaag  120
cagaagcgct gggagctggc gcgcaacctc aacctcaccg agcgccaggt caagatctgg  180
ttccagaacc ggcgcatgaa gaacaagaag aacagccagc gccaggcggc cagcagcagc  240
agcagcaaca gcagcagcag cagcagcagc aacagcagca gcggccgcc ggcggggcgt  300
```

-continued

```
            cggccgccgc caacggccac cagggccacc aagcgcacca ccacgcgccc cccaacggcg  360
            ccgtcgcagc cctcaagcac caccagtgac ccgtagcg                           398

<210> SEQ ID NO 69
<211> LENGTH: 8670
<212> TYPE: DNA
<213> ORGANISM: Unknown
<220> FEATURE:
<223> OTHER INFORMATION: Description of Unknown Organism:Unknown

<400> SEQUENCE: 69
cccgggtgcg gtgtcgtgtg tggggctggg cgccatgttc ctggacatgc tgagggccaa   60
            gcgcgacacg gcgcccgacc gccgccagct ggacgaccgg atgatggggg cggacccggg  120
            ggacatagcg gccaaggtga gggcagggtt ttgcgtgcgt gcttgattgt gcgtgtgcgt  180
            gcgtgcgtgc gtgcgtgcgg tgttgcgtgt gtatttgaac tgtgttttgt gtatgtactt  240
            agggtaaga gtgcatacac atgcatgcga ccggtggcct tacaaatcaa caacacgtac  300
            gcctgcatgt atccaggtgg cagcgtggcg acgagcacgt ggcttcgagg gcccaggcac  360
            ggcgggcccc agcggcagcg ccgccagtgg cagcggcgcc agcggctcgg caccgcaggc  420
            gcgctcgccc cgacctcagc caccgcgggc gcgctcacct tcacgcgggt gaaccccggc  480
            gaggagccgc ccgtgtacgc gtgcgagcaa acaggtgcgt aagcgacgtg tgggcagcgc  540
            gaagaggcgt gggggcgaga gagcaaaggg actagggaaa cgcacagcca aatacggtat  600
            gcgggcaacg aggcgatggc cctggaaatc gcagggccct tttgaaatcg tgtaaggcgc  660
            aattgctggg cgactaccgt agtctactga tgcattgcac tactttgtatt actgtatcct  720
            actgcagtag tgccgttgcc agccgcgctg ctgcccttg gctcccttcc caatccaaat  780
            ggcccatgcc tcgcgcactc cgagcaccca gagcacccag aagcgttgc gtgcgctccg  840
            ccgccgccct ctccccgcc ttcacttctt aattaatcgt gaatgtaatc cccccccccc  900
            ccgcttcctc aggctgggtg cacgtgtcg cgacgcctgc acggagggtg tggtggatgc  960
            ccgcagcgaa ctgctggtgt gcccggtgag tcgacgagga ggaggtgcaa gggggatacc 1020
            agcgcgtgtt tctcagggcc tgtgtgggac accgaaacgt ggtaaaagag acccgcccgc 1080
            gaactgtgta tgtggagtag cgtggcgtgt gcgccggac cgacaaggca gcttgtggac 1140
            tgccccacgt tgcagagtca gctgacaacg acacgtgcgc cttcctgtca ttgcccgtgc 1200
            gcacgcacgt cctccgcact cccaacaaat tgacagcgac acgtgcgcct tcctataagc 1260
            ctatgcccgc acacgctccc gcgccctcag gtgtcgggcc agaccacaga ccggttggtc 1320
            cacgagtgcg aggaggatga ggcgggcggc tgcggcggcg ccggcggggc gccgcggcga 1380
            ggaggacggc ctgggactgg gcatcacagg tgggtgcagg gctggcaggg actcacgcat 1440
            gggccttgta cgtgactgcg gttctgcatg gctagtggct cacgcgctgc gcacgttcac 1500
            gtacgcttg tgggcatgca gtgccttgac gtgaggctgc gctgccttgc tgctgccgcc 1560
            ttgccccgct ccctgcacac actgcagccg gcttcgggcg ctacttcacc gcgggctacg 1620
            agtgcgagaa cgcgcagcag ctcaacaggc tgctggggta caagcgcgtg tgagagcgcg 1680
            ccgcagggg agtgtgttca tattgtggtt gtttgggccg tgggcgcggg ctgcatgtgc 1740
            gtattgcacg cgtacagcat tggtgactgg tcaggtgtaa gcggccggca gtgcgccgcg 1800
            aggcgctgca gcgagttgtg gggcatgcgt catgcgcaga cggccctg acgacaaggc 1860
            gttgagttgg cgtttggagg tgtgggacga cgtgggggttt gtgccgtcaa agcacagaac 1920
            agaaggcgtg accgttttac gagctcgtat gatgtagcat ggattgaata atgacatgtg 1980
            attttttgtta caagcgacga atgcgtgggg ttttggatgg caggggtttc agtcgcccga 2040
            ttgcgcatgc acacgtgacc aaatttatgc tcaacgacgt gaccattgct ttatacatac 2100
            ttgtgtatcg gttggcactt ataacaattg gctcgtcaaa ttgacgcgag gctgcacttc 2160
            gatcctgaaa gccccagttc aacaagtcgg atagccaaat gccccgctc gctctccagc 2220
            atcaagggc ctctaagtgc ctcgcggcaa cccagcgcaa gtgtgctcgc gttgcggtga 2280
            gctggactcg tgcacttgtc gacgccgtcg gcaccgcaat cgaaagacgc gtgcgtcgag 2340
            caattgtgga agccgctgac gaattgtccg catgtgacat tgcaggctcg cgtcccccgct 2400
            cgtctcagcg tcatggccca ggtgcggacg ttgggactgc acttgcagga atgtgatggg 2460
            gccgcaccga gtctgcgcgg acgtctcgct gacgtttcgc gttgaatgca tctcgcaata 2520
            ggcagctgct gcgcctgctg acaaacactaa gaagctgtgg ggcggtcgct tcacgggcaa 2580
            gacggacccg ctcatggaga agttcaacga gtcgctgccc tttgacaagc gcctgtgggc 2640
            tgaggacatc aaggtgcggc acagggaggg gggcgagtgg tggggtgggg ctgggggga 2700
            cgcgggtttg gtggccaggg cagggaggga agacgtgcgg ggctaggcaa gaggctgcga 2760
            gggcccaggg taacaccaga ccgtgccgtg tcgcgtgccc ggcttgctgc ccaccttgcc 2820
            cggccatccc caccgccctc cccaccagca atgacacgta cacattcaca cactccccca 2880
            cacccacata cccacacacc cacgcattcc ccaacaggc agccaggcgt acgccaaggc 2940
            tcttgccaag gccggcattc tggcacatga cgaggccgtg accattgtgg aggggctggc 3000
            caaggtgcgc acacccggca gcagggcggg tggtgggtg gtgggggtgg ggggcagag 3060
            agaggcgcgg gctgagaggg ggctgagagg ggggtcagcg aggcgcaggc tcaggggag 3120
            gcgtctgagg ggggcgggga tggtggtggg ggagctgcgg gtgctgggc tgctgcggtg 3180
            gcgggcggc gggcggcgg gcgacgtgta cgtgagtagc cgctgaccgg gcgctgggcc 3240
            tttgcgcacg ccacagccca catgacaccg ccgcaaggcc cgccgcgccc cacccacgtt 3300
            cacacactcc ccacacccac gcgtgcgcgc gcctccttcc cctcaataca cgcgcctcct 3360
            tcccctggcc cccgcctgct cccccccatcc ggccgcccg cctgcaggtg gctgaggagt 3420
            ggaaggcggg tgccttttgt atcaaggcgg gtgacaggca catccacacg gccaacgagc 3480
            ggcgcctcac ggagctggtg ggggcggtgg gcggcaagct gcacaccggc cgctcgcgca 3540
            acgaccaggt gagggtgggt gggtgggggt gggtgggtg ggtggtgggg tgggtgggtg 3600
            ggtgggtggg tgggtgggtg ggtgggtggg ggtttgagat accggtacca ggccaaacta 3660
            aaccgaaccc aagggggttg cgtaggggcg tgggagggg ggagtgcgga agccgggagg 3720
            caggagtaag ggcgggagga ggggccggga ggagaagcag gacgaagtc gatgacaggg 3780
            gcagtcggtg gcggcggtgg cgggtgtgcc gttgtgcagt ggctgtggag gccatgtgca 3840
            gggcggcggc ggggccgggc cggggtggg agcttgtcc agaccccgtg gccctcttcc 3900
            agccccgtcc gccactgccg ccaccaccac cgccgccgcc gtagccacca cccctcacgt 3960
```

-continued

```
cgaggcactt cacagatgcg aagcaaccac accgttctcc acatgaacag ctaccctccc 4020
aaacccaact ttcccttccc gccttaccta accatgaccc gctaccccc ccccctttat 4080
ttcttaacta accatgaatg cccccccccg gctgtacctg gctacgactt cacttcgtaa 4140
acttaatgtg tgtaaccccc cttacacaca cacacacacc cctccccgcc cctccaaagg 4200
ttgccaccga ctaccggctg tggctggtgg gtcaggtgga ggtgatgcgg tccgaggtgg 4260
gcgagctgat gcgcgtggcg gcggaccgct ccgaggcaga ggtggaggtg ctcatgccgg 4320
gtgaggggc aggaggggg ggaggggag ggggaggtgc tcatgccggt gagggtaggg 4380
aggggagggg cagaggaggg agggggagga ggggggcggct gagtgcggga gaggcaggga 4440
tgagggcgat agaaagttgc gtattgtcgg taaactcaaa ggactagacg aagagaacaa 4500
acctaaacaa gggagctgga gcgaggccaa atctgaacgt gacatcgccc gcctcctccc 4560
gctgcctgct cccccacctc ctcccccatc tcgccccccc cccacacac acacaggctt 4620
cacgcacctt cagaatgcca tgactgtgcg ctggagccac tggctgatga gccacgccgc 4680
ggcctggcag cgcgacgaca tgcggctgcg ggacctgctg ccgcgggtgg ccacactgcc 4740
gctgggctcg ggtggtgag ggaggggagg ggaggggagg ggggggaggg gagggagagg 4800
agggagaag ggggggggag acgaggaggg tggaagggtg ggggcggggc ggtggaggct 4860
agagggtggg gctgggtggg tggacggagt gcactggtag aggagggata gggtacattg 4920
agacgggagg agggatgcag gggcgaaggt ggggaggagg ggaggggagg aggcgtggga 4980
ctggagtggg ccgacgagtg tgcggacggg gcaggcggca acggggatta acggcggggg 5040
ggccggggcg tgtgcacgac aggggcttgc gcgtctgcga ttgtgggggc acacagggac 5100
aggagcacga cgtgggacac gcatagatac gccgcattga caacacacac acacacacac 5160
acacacacac acacacacac acacacacaa acacaaacac acacaaacac aaacacacac 5220
acgcccccc cctacacac acgcccctc cccaggcgcc ctggccggca acccctttct 5280
ggtggaccgc cagttcatcg ccaaggagtt gggtttcggc ggcggcgtgt gccccaactc 5340
catggacgcg gtgagggag gaggaggggg aggagggcgg ggggggcag gagggggag 5400
gaggaggggg ggagggggtt aactttgaag cgtaaggaaa cagtcgggag gagggggga 5460
aggaggggc ctggaggagg ggggaggag gagggtggct ggagggggct ggggaggag 5520
gagggggagg attgggaggg ggctggggga gggtgcccgc agctggggga ggtggggagg 5580
gaggggggttg ctgctggtgt aaagggcctg taggcactga gagcactgtg gggagccggg 5640
gtactgcctg gggccccgcg ctgcagaggt gtcgcggcag gtggcggcgc atcccccgca 5700
tccccacacg cggggccgctg ccgctgcccg ccacacccctt gccactttgt gtgctttcct 5760
aggatataca cacacacaca cacacacaca cacacacaca cacacacaaa cacaaacaca 5820
cacgggcgcg ggctttcgtt tcgttttttta acacaaacac acactccccc tgtgctcctc 5880
aacacactcc atctttctca cacaaacaca cacgcacaca cacatgcgca ggtgtctgac 5940
cgcgactttg tgatcgagac ggtgtttgcg gccagcctgc tgtgcgtgca cctgtcgcgc 6000
tgggcggagg acctcatcat ctacagctcc ggcccccttcg gctacgtgca gtgcagcgac 6060
gcctacgcca ccggctcctc gctcatgccg cagaagaaga accccgacgc cctggagctc 6120
atcaggtgcg ggaggatgg ggtggggtg ggggggttac attcatggt agttaagaag 6180
tgaaggcgta ggggggtggat ggggtgggtt acattcatga acatttaaga agtgaaggcg 6240
tagccaggaa cagtagtaga gcagacgcgt tgtagtgtgt gggtttgggt gggagggatg 6300
gttgggtaaa gcggtacagg atgtactgag gactgcagac cgaaggagcg ggggagggg 6360
agcaggcagg cgggcgaggg ggcgtggggg cgggggttac tggcaccgtg ccgggtaagc 6420
aacacgtgac acggagatgc accacacaaa gagggacgtg gggagtggca ggcggggggcc 6480
agggctgaga ggcgcgtgtg gagggtgcg gggttgggcg gggggctgtt tcatgatacc 6540
gctgcctcca cctcctccac cgcctcctgc cacctccacc tcccccactg ccccctcccg 6600
cctcctcctg ctgcaggggc aaggggcggtc gtgtgcaggg caacctgatg gcgtcatgg 6660
cggtgctcaa gggcacgccc accacataca acaaggactt ccaggcgaga gagcgagagc 6720
gagggaggga gggagagcga gggagagga gggagaggga gggagaggga gacagaggga 6780
cagggacagg gacagggaca gggacaggga cagggacagg ggcaggggca ggggcagggg 6840
caggggcagg ggcaggggag gcccccggg ggcggcgggc ccggggcatg aggtcagaca 6900
tagggggcgct gcactgagcc cgcgagggcgg gcgggaggca ggggggagga ggcgggggc 6960
gggagcggac atgcgccgca aacacagacg ggttgagaaa gcacaacgac tggaacgcag 7020
tgggcttact gacaattcat cattgtgcgc atatgtgtgt atgtgtatgt gtgtgtttgt 7080
ttgtgcagga gtgttgggag ctgctgttg acacggtgga cacggtgcac gacgtggtgc 7140
gcatcgccac cggcgtgctg tccaccctgc ggatcaagcc cgaccgcatg aaggccggtg 7200
agcgtagccg agcagggctg gagcagcagc cgggcagcag tagcagcagg gcaggggagc 7260
agcgggagcg ggagcagcag gagggtggt tggaagcgg tggggagtg gtgggagcgg 7320
aggaagggaa ggaggagcag gagcaggagg aagaggagga ggaaggcgg tggggggtgg 7380
ggggtcgtgt ccttggccgc atgggcgagg gcggggaggc gggggaggggc cggggaagca 7440
gagcctgcac ccacgctccg cgggtcccta ccgtcttgcg cctaaccccg tgcgcctagc 7500
ctcttgcgcc caccccctta gtgcatcctg taccctctct tccaaacatc cttgcaactc 7560
cctgacctcc tcgccaaacc tccccgccc caggcctgtt ccgccgacat gctcgccacg 7620
gacttggccg agtacctggt gcgcaagggc gtgccgttcc gggagacaca ccaccacagg 7680
tgcggccggg cgggaggggcg tgagggcgtg ggtgggcat gcccggggtt gtgagagcta 7740
tcgaacgttg tgccgcgcct gtttcacaat gtcgggccac agggtatgca gtttcctctc 7800
catatgtata acaaactgac caccaatcat gcacgctcac acgctctccc acacacacgc 7860
gcaccacgcc accacagcgg cgccgccgtg aagatggcgg aggaccgcgg ctgcacgctg 7920
ttcgacctca ccgtggacga cctcaagacc atccaccgc tcttcaccga cgacgtggcg 7980
gcggtgagcg gcggcgcgga cagcagcagc agcagcagca gcagcagca gcagcagcag 8040
tagcctgggg gggagcgtgt gggaggaacg gcgggggagg ggaggcgggg ggtgtcgttt 8100
gcagccgagc gcacgtggtg ctttgccccca ttccatgcca gcagggtgac acacctgacc 8160
atgctggtgt gctgctaggt ggttcacacc tacgtgtgaa tttgtgctgg cgtgcgcaca 8220
ccttactgtg gccatgtgaa cggcatcctc atgtcctcgt gattgcgccc ggcacattgc 8280
ccacaacccc gcaccaccca gctcctcaat ccagtgcaag gaaggaaat gcacgcccgc 8340
cgcaccaaca acacgacgca tgtgtttgcc acgtgcgcgc acacacgcgc aggtgtggga 8400
cttcaaccgc agcgccgaga tgcgcacac accagcaaage gctcggtgct 8460
ggagcaggtg cagaagatgc gcacctacct ggcggcgag ggacagcact gagcgggtcg 8520
ggggaggggg ggccggtgtg tatgtgtgtg tgtgtgcgtg tgtaagtctc ggtggagggg 8580
tggtcctcta tatggcgcg gggcacagg gggacgggtg tgacagagtt acggccggag 8640
ccagcggagt cccgggatgg attaaggatc                                 8670
```

<210> SEQ ID NO 70
<211> LENGTH: 745
<212> TYPE: DNA
<213> ORGANISM: Unknown
<220> FEATURE:
<223> OTHER INFORMATION: Description of Unknown Organism:Unknown

<400> SEQUENCE: 70

```
atgagatggc gacgcgcccc gcgccgctcc gggcgtcccg gccccgggc ccagcgcccc    60
ggctccgccg cccgctcgtc gccgccgctg ccgctgctgc cactactgct gctgctgggg   120
accgcggccc tggcgccggg ggcggcggcc ggcaacgagg cggctcccgc gggggcctcg   180
gtgtgctact cgtccccgcc cagcgtggga tcggtgcagg agctagctca gcgcgccgcg   240
gtggtgatcg agggaaaggt gcacccgcag cggcggcagc aggggcact cgacaggaag    300
gcggcggcgg cggcgggcga ggcaggggcg tggggcggcg atcgcgagcc gccagccgcc   360
ggcccacggg cgctgggcc gcccgccgag gagccgctgc tcgccgccaa cgggaccgtg    420
ccctcttggc ccaccgcccc ggtgcccagc gccggcgagc ccggggagga ggcgccctat   480
ctggtgaagg tgcaccaggt gtgggcggtg aaagccgggg gcttgaagaa ggactcgctg   540
ctcaccgtgc gcctggggac ctgggggccac cccgccttcc cctcctgcgg gaggctcaag   600
gaggacagca ggtacatctt cttcatggag cccgacgcca acagcaccag ccgcgcgccg   660
gccgccttcc gagcctcttt ccccccctctg gagacgggcc ggaacctcaa gaaggaggtc   720
agccgggtgc tgtgcaagcg gtgcg                                         745
```

<210> SEQ ID NO 71
<211> LENGTH: 1986
<212> TYPE: DNA
<213> ORGANISM: Unknown
<220> FEATURE:
<223> OTHER INFORMATION: Description of Unknown Organism:Unknown

<400> SEQUENCE: 71

```
gaattccttt tttttttttt tttttcttt tttttttgc ccttatacct cttcgccttt     60
ctgtggttcc atccacttct tcccccctcct cctcccataa acaactctcc taccctgca   120
cccccaataa ataaataaaa ggaggagggc aagggggag gaggaggagt ggtgctgcga    180
ggggaaggaa aagggaggca gcgcgagaag agccgggcag agtccgaacc gacagccaga   240
agcccgcacg cacctcgcac catgagatgg cgacgcgccc cgcgccgctc cgggcgtccc   300
ggccccgggg cccagcgccc cggctccgcc gcccgctcgt cgccgccgct gccgctgctg   360
ccactactgc tgctgctggg gaccgcggcc ctggcgccgg gggcggcggc cggcaacgag   420
gcggctcccg cgggggcctc ggtgtgctac tcgtccccgc ccagcgtggg atcggtgcag   480
gagctagctc agcgcgccgc ggtggtgatc gagggaaagg tgcacccgca gcgcgcggag   540
caggggcac tcgacaggaa ggcggcggcg gcgggcgggcg aggcaggggc gtggggcggc   600
gatcgcgagc cgccagccgc gggcccacgg gcgctgggcc gcccgccga ggagccgctg    660
ctcgccgcca acgggaccgt gccctcttgg cccaccgccc cggtgcccag cgccggcgag   720
cccggggagg aggcgcccta tctggtgaag gtgcaccagg tgtgggcggt gaaagccggg   780
ggcttgaaga aggactcgct gctcaccgtg cgcctgggga cctgggccca ccccgccttc   840
ccctcctgcg ggaggctcaa ggaggacagc aggtacatct tcttcatgga gcccgacgcc   900
aacagcacca gccgcgcgcc ggccgccttc cgagcctctt tcccccctct ggagacgggc   960
cggaacctca gaaggaggt cagccgggtg ctgtgcaagc ggtgcgcctt gcctccccaa   1020
ttgaaagaga tgaaaagcca ggaatcggct gcaggttcca aactagtcct tcggtgtgaa   1080
accagttctg aatactcctc tctcagattc aagtggttca agaatggaa tgaattgaat   1140
cgaaaaaaca aaccacaaaa tatcaagata caaaaaaagc caggggagtc agaacttcgc   1200
attaacaaag catcactgcc tgattctgga gagtatatgt gcaaagtgat cagcaaatta   1260
ggaaatgaca gtgcctctgc caatatcacc atcgtggaat caaacgctac atctacatcc   1320
accactggga caagccatct tgtaaaatgt gcggaaaagg agaaaactt ctgtgtgaat    1380
ggaggggagt gcttcatggt gaaagacctt tcaaaccct cgagatactt gtgcaagtgc   1440
ccaaatgagt ttactggtga tcgctgccaa aactacgtaa tggcagctt ctacagtacg    1500
tccactccct ttctgtctct gcctgaatag gagcatgctc agttggtgct gctttcttgt   1560
tgctgcatct cccctcagat tccacctaga gctagatgtg tcttaccaga tctaatattg   1620
actgcctctg cctgtcgcat gagaacatta acaaaagcaa ttgtattact tcctctgttc   1680
gcgactagtt ggctctgaga tactaatagg tgtgtgaggc tccggatgtt tctgaattg    1740
atattgaatg atgtgataca aattgatagt caatatcaag cagtgaaata tgataataaa   1800
ggcatttcaa agtctcactt ttattgataa aataaaaatc attctactga acagtccatc   1860
ttcttttatac aatgaccaca tcctgaaaag ggtgttgcta agctgtaacc gatatgcact   1920
tgaaatgatg gtaagttaat tttgattcag aatgtgttat ttgtcacaaa taaacataat   1980
aaaagg                                                              1986
```

<210> SEQ ID NO 72
<211> LENGTH: 2003
<212> TYPE: DNA
<213> ORGANISM: Unknown
<220> FEATURE:
<223> OTHER INFORMATION: Description of Unknown Organism:Unknown
<221> NAME/KEY: UNSURE
<222> LOCATION: (31)

```
<223> OTHER INFORMATION: May be any nucleic acid
<221> NAME/KEY: UNSURE
<222> LOCATION: (32)
<223> OTHER INFORMATION: May be any nucleic acid

<400> SEQUENCE: 72
ggaattcctt ttttttttt tttttttctt nntttttttt tgcccttata cctcttcgcc    60
tttctgtggt tccatccact tcttccccct cctcctccca taaacaactc tcctacccct   120
gcaccccaa taaataaata aaaggaggag ggcaaggggg gaggaggagg agtggtgctg    180
cgaggggaag gaaaagggag gcagcgcgag aagagccggg cagagtccga accgacagcc   240
agaagcccgc acgcacctcg caccatgaga tggcgacgcg ccccgcgccg ctccgggcgt   300
cccggccccc gggcccagcg ccccggctcc gccgcccgct cgtcgccgcc gctgccgctg   360
ctgccactac tgctgctgct ggggaccgcg gccctggcgc cggggcggc ggccggcaac    420
gaggcggctc ccgcgggggc ctcggtgtgc tactcgtccc cgcccagcgt gggatcggtg   480
caggagctag ctcagcgcgc cgcggtggtg atcgagggaa aggtgcaccc gcacggcgg    540
cagcaggggg cactcgacag gaaggcggcg gcggcggcgg gcgaggcagg ggcgtggggc   600
ggcgatcgcg agccgccagc cgcgggccca cgggcgctgg ggccgcccgc cgaggagccg   660
ctgctcgccg ccaacgggac cgtgccctct tggcccaccg ccccggtgcc cagcgccggc   720
gagcccgggg aggaggcgcc ctatctggtg aaggtgcacc aggtgtgggc ggtgaaagcc   780
gggggcttga agaaggactc gctgctcacc gtgcgcctgg ggacctgggg ccaccccgcc   840
ttcccctcct gcgggaggct caaggaggac agcaggtaca tcttcttcat ggagcccgac   900
gccaacagca ccagccgcgc gccggccgcc ttcgagcct cttttccccc tctggagacg    960
ggccggaacc tcaagaagga ggtcagccgg gtgctgtgca agcggtgcgc cttgcctccc  1020
caattgaaag agatgaaaag ccaggaatcg gctgcaggtt ccaaactagt ccttcggtgt  1080
gaaaccagtt ctgaatactc ctctctcaga ttcaagtggt tcaagaatgg gaatgaattg  1140
aatcgaaaaa acaaaccaca aaatatcaag atacaaaaaa agccagggaa gtcagaactt  1200
cgcattaaca aagcatcact ggctgattct ggagagtata tgtgcaaagt gatcagcaaa  1260
ttaggaaatg acagtgcctc tgccaatatc accatcgtga aatcaaacgc tacatctaca  1320
tccaccactg ggacaagcca tcttgtaaaa tgtcgggaga aggagaaaac tttctgtgtg  1380
aatggagggg agtgcttcat ggtgaaagac ctttcaaacc cctcgagata cttgtgcaag  1440
tgcccaaatg agtttactgg tgatcgctgc caaaactacg taatggccag cttctacagt  1500
acgtccactc cctttctgtc tctgcctgca taggagcatg ctcagttggt gctgctttct  1560
tgttgctgca tctcccctca gattccacct agagctagat gtgtcttacc agatctaata  1620
ttgactgcct ctgcctgtcg catgagaaca ttaacaaaag caattgtatt acttcctctg  1680
ttcgcgacta gttggctctg agatactaat aggtgtgtga ggctccggat gtttctggaa  1740
ttgatattga atgatgtgat acaaattgat agtcaatatc aagcagtgaa atatgataat  1800
aaaggcattt caaagtctca cttttattga taaaataaaa atcattctac tgaacagtcc  1860
atcttcttta tacaatgacc acatcctgaa aagggtgttg ctaagctgta accgatatgc  1920
acttgaaatg atggtaagtt aattttgatt cagaatgtgt tatttgtcac aaataaacat  1980
aataaaagga aaaaaaaaaa aaa                                          2003

<210> SEQ ID NO 73
<211> LENGTH: 957
<212> TYPE: DNA
<213> ORGANISM: Unknown
<220> FEATURE:
<223> OTHER INFORMATION: Description of Unknown Organism:Unknown
<221> NAME/KEY: UNSURE
<222> LOCATION: (809)
<223> OTHER INFORMATION: May be any nucleic acid
<221> NAME/KEY: UNSURE
<222> LOCATION: (810)
<223> OTHER INFORMATION: May be any nucleic acid
<221> NAME/KEY: UNSURE
<222> LOCATION: (811)
<223> OTHER INFORMATION: May be any nucleic acid

<400> SEQUENCE: 73
tctcgcccca acttttttccc ccgcgctccg cagcagcagc agcagcagca gcagcagcag    60
caaaatggca gacctcttca gcggactcgt gggcggcgtc gtcggcgctg ttgctgcagc   120
agatttgcct gcggagggc agagggcccc ccgccccgcc ccggcactg cctggacttg     180
ctgctgcagc aaactgcaag aaggggcccg cgagctggag ggttttgtgc agcagctgag   240
ttttgttgca gggaagctgg cctgctgcct gcggtggggg gcggagcagc tggcgcgctg   300
cgctgcggag gggcggctgc ccagcagcag cagcagcagc agctgctgcg cgctgctgca   360
gctcgagaag caggacctcg agcagagcct cgaggccggc aagcagggcg cggagtgcct   420
cttgagagc agcaaactgg ccctcgaggc cctcctcgag ggggcccgcg ttgcagcaac   480
gcggggtttg ctgctggtcg agagcagcaa agacacgtg ctgcgcagca ttccccacac    540
ccaggagaag ctgcccagg cctacagttc tttcctgcgg ggtaccagg gggcagcagc     600
ggggaggtct ctgggctacg ggcccctgc tgctgcttac ggccagcagc agcagcccag    660
cagctacggg gcgcccccg cctccagcca gcagccctcc ggcttcttct ggtagccctg    720
cagcagcagc agcagcagca gcagcagcag cagcgcgggc ggcagccgcg cgggggccgg   780
ggccgccgctg cagcaacagc agcagccgnn ncggctacgcg ccgggacag ctcgcaggga    840
actccacagg cagcggggaga gcagcgggga cgagaagcag gtcatgtagc gcaggcagca   900
gcgccagctg cagcagcagc agcagcagca gcagcagcag cagcagctcc tgcaccg      957
```

-continued

```
<210> SEQ ID NO 74
<211> LENGTH: 957
<212> TYPE: DNA
<213> ORGANISM: Unknown
<220> FEATURE:
<223> OTHER INFORMATION: Description of Unknown Organism:Unknown
<221> NAME/KEY: UNSURE
<222> LOCATION: (809)
<223> OTHER INFORMATION: May be any nucleic acid
<221> NAME/KEY: UNSURE
<222> LOCATION: (810)
<223> OTHER INFORMATION: May be any nucleic acid
<221> NAME/KEY: UNSURE
<222> LOCATION: (811)
<223> OTHER INFORMATION: May be any nucleic acid

<400> SEQUENCE: 74
tctcgcccca actttttccc ccgcgctccg cagcagcagc agcagcagca gcagcagcag    60
    caaaatggca gacctcttca gcggactcgt gggcggcgtc gtcggcgctg ttgctgcagc   120
    agatttgcct gcggagggcg agagggcccc ccgccccgcc cccggcactg cctggacttg   180
    ctgctgcagc aaactgcaag aaggggcccg cgagctggag ggttttgtgc agcagctgag   240
    ttttgttgca gggaagctgg cctgctgcct gcggtggggg gcggagcagc tggcgcgctg   300
    cgctgcggag gggcggctgc ccagcagcag cagcagcagc agctgctgcg cgctgctgca   360
    gctcgagaag caggacctcg agcagagcct cgaggccggc aagcagggcg cggagtgcct   420
    cttgaggagc agcaaactgc cctcgaggc cctcctcgag ggggcccgcg ttgcagcaac   480
    gcggggtttg ctgctggtcg agagcagcaa agacacggtg ctgcgcagca ttccccacac   540
    ccaggagaag ctggcccagg cctacagttc tttcctccgg ggctaccagg gggcagcagc   600
    ggggaggtct ctgggctacg ggcccctgc tgctgcttac ggcagcagc agcagcccag   660
    cagctacggg gcgccccccg cctccagcca gcagccctcc ggcttcttct ggtagccctg   720
    cagcagcagc agcagcagca gcagcagcag cagcgcgggc ggcagccgcg cgggggccgg   780
    ggcgccgctg cagcaacagc agcagccgnn ncggctagcg ccgcggagca ctcgcaggga   840
    actccacagg cagcgggaga gcagcaggga cgagaagcag gtcatgtagc gcaggcagca   900
    gcgccagctg cagcagcagc agcagcagca gcagcagcag cagcagctcc tgcaccg     957
```

```
<210> SEQ ID NO 75
<211> LENGTH: 1089
<212> TYPE: DNA
<213> ORGANISM: Unknown
<220> FEATURE:
<223> OTHER INFORMATION: Description of Unknown Organism:Unknown
<221> NAME/KEY: UNSURE
<222> LOCATION: (376)
<223> OTHER INFORMATION: May be any nucleic acid
<221> NAME/KEY: UNSURE
<222> LOCATION: (377)
<223> OTHER INFORMATION: May be any nucleic acid
<221> NAME/KEY: UNSURE
<222> LOCATION: (847)
<223> OTHER INFORMATION: May be any nucleic acid
<221> NAME/KEY: UNSURE
<222> LOCATION: (848)
<223> OTHER INFORMATION: May be any nucleic acid
<221> NAME/KEY: UNSURE
<222> LOCATION: (849)
<223> OTHER INFORMATION: May be any nucleic acid
<221> NAME/KEY: UNSURE
<222> LOCATION: (850)
<223> OTHER INFORMATION: May be any nucleic acid

<400> SEQUENCE: 75
gaattccctc caactcttcg cgactctctc tctctcgccc caacttttc ccccgcgccc     60
    cgcagcagca gcagcagcag cagcagcaaa atggcagacc tcttcagcgg actcgtgggc    120
    ggcgtcgtcg gcgctgttgc tgcagcagat ttgcctgcgg agggcgagag ggcccccgc    180
    cccgccccg gcactgcctg gacttgctgc tgcagcaaac tgcaagaagg ggcccgcgag    240
    ctggagggtt ttctgcagca gctgagtttt gttgcaggga agctggcctg ctgcctgcgg    300
    gtgggggcgg agcagctggc gcgctgcgct gcggagggc ggctgcccag cagcagcagc    360
    agcagcagct gctgcnngct gctgcagctc gagaagcagg acctcgagca gagcctcgag    420
    gccggcaagc agggcgcgga gtgcctcttg aggagcagca aactggccct cgaggccctc    480
    ctcgaggggg cccgcgttgc agcaacgcgg ggtttgctgc tggtcgagag cagcaaagac    540
    acggtgctgc gcagcattcc ccacacccag gagaagctgg ctcaggccta cagttctttc    600
    ctgcggggct accagggggc agcagcgggg aggtctctgg gctacggggc ccctgctgct    660
    gcttacggcc agcagcagca gcccagctac ggggccccct cagcagcag cagcagcag    720
    ccctccggct tcttctggta gccctgcagc agcagcagca gcagcagcag cagcagcag    780
    ggcggcggca gccgcggcgg ggcggggcgg ccgctgcagc aacagcagca gccgcggcgg    840
    ctagcgnnnn gagcactcgc agggaactcc acaggcagcg ggagagcagc agggacgaga    900
    agcaggtcta tgtagcgcag gcagcagcgc cagctgcagc agcagcagca gcagcagcag    960
```

```
              cagcagcagc agctcctgca ccgcagcgtt gtgtcattta ttacgttggc agctctgagg 1020
              cctcggcgca gccaacgcgc ctcaggtatc tttcagactc ttttctctaa ggtcttccag 1080
              acggaattc                                                          1089
```

<210> SEQ ID NO 76
<211> LENGTH: 1985
<212> TYPE: DNA
<213> ORGANISM: Unknown
<220> FEATURE:
<223> OTHER INFORMATION: Description of Unknown Organism:Unknown

<400> SEQUENCE: 76

```
              cgccgagctt tcggcacctc tgccgggtgg taccgagcct tcccggcgcc ccctcctctc 60
              ctcccaccgg cctgcccttc cccgcgggac tatcgccctc acgtttccct cagcccttt  120
              ctctcccggc cgagccgcgg cggcagcagc agcagcagca gcagcaggag gaggagcccg 180
              gtggcggcgg tggccgggga gcccatggcg tacagtcaag gaggcggcaa aaaaaaagtc 240
              tgctactact acgacggtga tattggaaat tattattatg acagggtca tcccatgaag  300
              cctcatagaa tccgcatgac ccataacttg ctgttaaatt atggcttata cagaaaaatg 360
              gaaatatata ggcccataa agccactgcc gaagaaatga caaaatatca cagtgatgag 420
              tatatcaaat ttctacggtc aataagacca gataacatgt ctgagtatag taagcagatg 480
              catatattta atgttggaga agattgtcca cgctttgatg gactctttga gttttgtcag 540
              ctctcaactg gcggttcagt tgctggagct gtgaagttaa accgacaaca gactgatatg 600
              gctgttaatt gggctggagg attacatcat gctaagaaat acgaagcatc aggattctgt 660
              tacgttaatg atattgtgct tgccatcctt gaattactaa agtatcatca gagagtctta 720
              tatattgata tagatattca tcatggtgat ggtgttgaag aagctttta tacaacagat 780
              cgtgtaatga cggtatcatt ccataaaaat ggggaatact ttcctggcac aggagacttg 840
              agggatattg gtgctggaaa aggcaaatac tatgctgtca tccgtaatgt gtgtgatggt 900
              atagatgatg agtcatatgg gcagatattt aagcctatta tctcaaaggt gatggagatg 960
              tatcaaccta gtgctgtggt attacagtgt ggtgcagact cattatctgg tgatagactg 1020
              ggttgtttca atctaacagt caaaggtcat gctaaatgtg tagaagttgt aaaaactttt 1080
              aacttaccat tactgatgct tggaggaggt ggctacacaa tccgtaatgt tgctcgatgt 1140
              tggacatatg agactgcagt tgcccttgat tgtgagattc ccaatgagtt gccatataat 1200
              gattactttg agtatttggg accagcttcc aaactgcata ttagtccttc aaacatgaca 1260
              aaccagaaca ctccagaata tatgaaaaag ataaaacagc gtttgtttga aaatttgcgc 1320
              atgttacctc atgcacctag tgtccagatg caagctattc cagaagatgc tgttcatgaa 1380
              gacagtggag atgaagatgg agaagatcca gacaagagaa tttctattcg agcatcagac 1440
              aagcggatag cttgtgatga agaattctca gattctgagg atgaaggaga aggaggtcga 1500
              agaaatgtgg ctgatcataa gaaaggagca agaaagcta gaattgaaga agataagaaa 1560
              gaaacagagg acaaaaaaac agacgttaag gaagaagata aatccaagga caacagtggt 1620
              gaaaaaacag ataccaaagg aaccaaatca gaacagctca gcaaccctg aatttgacag 1680
              tctcaccaat ttcagaaaat cattaaaaag aaaatattga aaggaaaatg ttttctttt  1740
              gaagacttct ggcttcattt tatactactt tggcatggac tgtattatt tcaaatggg   1800
              actttttcgt ttttgttttt ctgggcaagt tttattgtga gattttctaa ttatgaagca 1860
              aaatttcttt tctccaccat gctttatgtg atagtattta aaattgatgt gagttattat 1920
              gtcaaaaaaa ctgatctatt aagaagtaa ttggcctttc tgagctgaaa aaaaaaaaa  1980
              aaaag                                                              1985
```

<210> SEQ ID NO 77
<211> LENGTH: 476
<212> TYPE: DNA
<213> ORGANISM: Unknown
<220> FEATURE:
<223> OTHER INFORMATION: Description of Unknown Organism:Unknown

<400> SEQUENCE: 77

```
              ccaccctcct cccctcccc cggccacttc gctaacttgg tggctgttgt gatgcgtatt  60
              cctgtagatc cgagcaccag ccggcgcttc agcccccct ccagcagcct gcagcccggc  120
              aaaatgagcg acgtgagccc ggtggtggct gcgcaacagc agcagcaaca gcagcagcag 180
              caacagcagc agcagcagca gcaacagcag cagcagcagc aggaggcggc ggcggcggct 240
              gcggcggcag cggcggctgc ggcggcggca gctgcagtgc cccggttgcg gccgccccac 300
              gacaaccgca ccatggtgga gatcatcgcc gaccacccgg ccgaactcgt ccgcaccgac 360
              agccccaact tcctgtgctc ggtgctgccc tcgcactggc gctgcaacaa gaccctgccc 420
              gtggccttca aggtaagagg ctaccccgcc ccccgccccc ggccgggagc ggcgga     476
```

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence:DNA Primer

<400> SEQUENCE: 78

```
              gcattttgga tccgcctttt catg                                          24
```

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence:DNA Primer

<400> SEQUENCE: 79
gttgtgtgct gcagattgtt cc                                           22

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence:DNA Primer

<400> SEQUENCE: 80
gaaaaatggg gatccgaggt g                                            21

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence:DNA Primer

<400> SEQUENCE: 81
gcaggagaat tccgtccatg                                              20

<210> SEQ ID NO 82
<211> LENGTH: 5
<212> TYPE: PRT
<213> ORGANISM: Homo sapiens
<220> FEATURE:
<221> NAME/KEY: UNSURE
<222> LOCATION: (3)
<223> OTHER INFORMATION: Can be any amino acid

<400> SEQUENCE: 82

Trp Ser Xaa Trp Ser
     1               5

<210> SEQ ID NO 83
<211> LENGTH: 6
<212> TYPE: PRT
<213> ORGANISM: Homo sapiens

<400> SEQUENCE: 83

Cys Ser Val Thr Cys Gly
     1               5

<210> SEQ ID NO 84
<211> LENGTH: 5
<212> TYPE: PRT
<213> ORGANISM: Homo sapiens
<220> FEATURE:
<221> NAME/KEY: UNSURE
<222> LOCATION: (4)
<223> OTHER INFORMATION: Can be any amino acid

<400> SEQUENCE: 84

Gly Cys Gln Xaa Arg
     1               5

<210> SEQ ID NO 85
<211> LENGTH: 733
<212> TYPE: DNA
<213> ORGANISM: Homo sapiens

<400> SEQUENCE: 85

```
gggatccgga gcccaaatct tctgacaaaa ctcacacatg cccaccgtgc ccagcacctg    60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300
ggctgaatgg caaggagtac aagtgcaagg tctccaacaa agccctccca acccccatcg   360
agaaaaccat ctccaaagcc aaagggcagc cccgagaacc acaggtgtac accctgcccc   420
catcccggga tgagctgacc aagaaccagg tcagcctgac ctgcctggtc aaaggcttct   480
atcccagcga catcgccgtg gagtgggaga gcaatgggca gccggagaac aactacaaga   540
ccacgcctcc cgtgctggac tccgacggct ccttcttcct ctacagcaag ctcaccgtgg   600
acaagagcag gtggcagcag gggaacgtct tctcatgctc cgtgatgcat gaggctctgc   660
acaaccacta cacgcagaag agcctctccc tgtctccggg taaatgagtg cgacggccgc   720
gactctagag gat                                                      733
```

<210> SEQ ID NO 86
<211> LENGTH: 86
<212> TYPE: DNA
<213> ORGANISM: Artificial Sequence
<220> FEATURE:
<223> OTHER INFORMATION: Description of Artificial Sequence:DNA Primer

<400> SEQUENCE: 86

```
gcgcctcgag atttccccga aatctagatt tccccgaaat gatttccccg aaatgatttc    60
cccgaaatat ctgccatctc aattag                                         86
```

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence:DNA Primer

<400> SEQUENCE: 87

```
gcggcaagct ttttgcaaag cctaggc                                        27
```

<210> SEQ ID NO 88
<211> LENGTH: 271
<212> TYPE: DNA
<213> ORGANISM: Artificial Sequence
<220> FEATURE:
<223> OTHER INFORMATION: Description of Artificial Sequence:PCR Fragment

<400> SEQUENCE: 88

```
ctcgagattt ccccgaaatc tagatttccc cgaaatgatt tccccgaaat gatttccccg    60
aaatatctgc catctcaatt agtcagcaac catagtcccg ccctaactc cgcccatcc    120
gccctaact ccgcccagtt ccgcccattc tccgcccat ggctgactaa ttttttttat    180
ttatgcagag gccgaggccg cctcggcctc tgagctattc cagaagtagt gaggaggctt   240
ttttggaggc ctaggctttt gcaaaaagct t                                   271
```

<210> SEQ ID NO 89
<211> LENGTH: 32
<212> TYPE: DNA
<213> ORGANISM: Homo sapiens

<400> SEQUENCE: 89

```
gcgctcgagg gatgacagcg atagaacccc gg                                  32
```

<210> SEQ ID NO 90
<211> LENGTH: 31
<212> TYPE: DNA
<213> ORGANISM: Homo sapiens

<400> SEQUENCE: 90

```
                    gcgaagcttc gcgactcccc ggatccgcct c                           31
```

<210> SEQ ID NO 91
<211> LENGTH: 12
<212> TYPE: DNA
<213> ORGANISM: Homo sapiens

<400> SEQUENCE: 91

```
                    ggggactttc cc                                                12
```

<210> SEQ ID NO 92
<211> LENGTH: 73
<212> TYPE: DNA
<213> ORGANISM: Homo sapiens

<400> SEQUENCE: 92

```
                    gcggcctcga ggggactttc ccggggactt tccggggact ttccgggact ttccatcctg 60
                    ccatctcaat tag                                               73
```

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence:PCR Fragment

<400> SEQUENCE: 93

```
                    gcggcaagct ttttgcaaag cctaggc                                 27
```

<210> SEQ ID NO 94
<211> LENGTH: 652
<212> TYPE: DNA
<213> ORGANISM: Homo sapiens

<400> SEQUENCE: 94

```
                    ggcataagat cacactttag ttcagagaca catttgcata aatacttgaa atggatccac 60
                    ccctgcaggt ggcagcctga gaacatggcg ctgcagggggg accagggcag cgtctggttc 120
                    aggtggacga acagcggtgc catcacgtgg tgcttgccca tgggcccgaa gagccgtgtg 180
                    cagggcttgg agtcgtcgtg gggcatgctg aggacgtgcc ctagttcatg ggccagggtg 240
                    tgggccgcct ggagcccctc atcctcgatc acggagcagc ttttgttggg gtcacaaatg 300
                    gtcccgatgt ctgccacacc cagggtgtca cacagcccct cctgcccaca gaagttctgt 360
                    ctggtgagca ggatggccgt gtcgtagtgc tctgggtggc ggtcgctggg ctggttgaaa 420
                    cgccgctgcc agttgcagaa gttacgcagt gtaagccccc cattgtcgga cacctctggg 480
                    ccccattttt catcttctac gatcagcact tttaccacca tcangttgat ggaattcttg 540
                    atgctggggt gcttgtagaa tcggcttgc cacgaaaatt aacctcagga tgtggttctg 600
                    caggtcggcc cgtaaagggc gccatggacg catcggccac caacagcgtt tc            652
```

<210> SEQ ID NO 95
<211> LENGTH: 716
<212> TYPE: CDNA
<213> ORGANISM: Homo sapiens

<400> SEQUENCE: 95

```
                    taagtttgct agtcctttgc aaacagactg acgctgagtg tcctgtctga gtcaataagt 60
                    gcacttttac cttttaacct atgccctcta cttgaacccg agcaaggtcc agtccactgg 120
                    acagttgatg atagggtctg ccgccccata ccctctcctc ttccccctta ggaatttgtg 180
                    cagtactgga ggggttgcgg caatgggagg cctgggtggg ccgtgctgcc ttgatatggc 240
                    caagggaccc agtcaccaca gtggagaccc ttgtctgcac ctcagtaccg catgtccagg 300
                    agcacaagac tggccctgc cccctgaat cacaggggc acagctggct ttcgcagggc 360
                    ttggcatcct cgggtttcag agccttgttg caggtggcag aggcctggcc ggagggtcc 420
                    ctgcactcta cagttcgcct ctgccagccg gccccaggg tgctagagca ctcagaccag 480
                    tcccccagca cccactgtgc gtggagcagc ggctgatga tgttggtggt tgctctctct 540
                    ttgctgctct gcatgctaaa agtcacgtca ttaggaanca aagaaggtgt atttgacttt 600
                    tggggggaa gaacctcgcc caggactgtg aggagctgca ctgtcagaag gctctgcnaa 660
                    ggcccngaag ctctgcangc gctccagggt ggcgatggag ccgtgtactt caggat       716
```

<210> SEQ ID NO 96

<211> LENGTH: 543
<212> TYPE: DNA
<213> ORGANISM: Homo sapiens

<400> SEQUENCE: 96

```
ggcataagat cacactttag ttcagagaca catttgcata aatacttgaa atggatccac   60
ccctgcaggt ggcagcctga gaacatggcg ctgcaggggg accagggcag cgtctggttc  120
aggtggacga acagcggtgc catcacgtgg tgcttgccca tggcctcgaa gagccgtgtg  180
cagggcttgg agtcgtcgtg gggcatgctg aggacgtgcc ctagttcatg ggccagggtg  240
tgggccgctg gagccctcat cctcgatcac ggagcagctt tgttggggt cacaaatggt   300
cccgatgtct gccacaccca gggtgtcaca cagcccctcc tgcccacaga agttctgtct  360
ggtgagcagg atggccgtgt cgtagtgctc tgggtggcgg tcgctgggct ggttgaaacg  420
ccgctgccag ttgcagaagt tacgcagtgt aaggcccca ttgtcggaca gctctgggc   480
ccattttca tcttctacga tcagcacttt taaccacatc aggttgatgg aattcttgat   540
gcc                                                                543
```

<210> SEQ ID NO 97
<211> LENGTH: 377
<212> TYPE: DNA
<213> ORGANISM: Mus musculus

<400> SEQUENCE: 97

```
gcaaagtgcc accaccttc ggatccaaaa ctagaagcaa gaggtttgtg tccgaggctc    60
gcttcgtgga aacacttctg gtggctgatg cgtccatggc tgccttctat gggaccgacc  120
tgcagaacca catcctcacg gtgatgtcaa tggcagcccg aatctacaag caccccgagca 180
tcaagaactc cgtcaacctt gtggtggtga aagtgctaat agtggaagag aaggatgggg  240
gcccggaggt gtcggacaac ggggggctca cactgcgcaa cttctgcagc tggcaacggc  300
gtttcaacaa gcccagtgac cgccacccgg agcactatga cactgccatc ttgttcacca  360
gacagaactt ctgtggg                                                  377
```

<210> SEQ ID NO 98
<211> LENGTH: 432
<212> TYPE: DNA
<213> ORGANISM: Rattus norvegicus

<400> SEQUENCE: 98

```
ctaaagtaca gtggttccat ggccaccctg gagcggctgc anagcttcca gccctccct    60
gagcctctta cagtacagct cctgactgtg tctggtgagg tcttccctcc aaaagtcaaa  120
tatacccttct tcgtccccaa tgacacggac ttcaacgtgc agagtagcaa agaaagagca 180
agcaccaaca tcattcagtc cttgccctat gcanagtggg tgctggggga ctggtctgaa  240
tgtccaagca catgtggagg tggctggcag cggcggactg tggaatgcag ggacccctca  300
ggtcaggcct ctgacacctg tgatgaggcg ctgaaacctg aggatgccaa gccctgtgga  360
agccagccat gtctcctctg atccccttgg tggacatgtc taaggcttat ggatttgggc  420
tactggcgtt tt                                                      432
```

<210> SEQ ID NO 99
<211> LENGTH: 354
<212> TYPE: DNA
<213> ORGANISM: Mus musculus

<400> SEQUENCE: 99

```
caaagtgcac caccttcgg atccaaaact agaagcaaga ggtttgtgtc cgaggctcgc    60
ttcgtggaaa cacttctggt ggctgatgcg tccatggctg ccttctatgg gaccgacctg  120
cagaaccaca tcctcacggt gatgtcaatg gcagccacga atctacaagc acccgagcat  180
caggaactcc gtcaaccttg tggtggtgaa agtgctaata gtggaagagg aaggatgggg  240
cccggagtgt cggacaacgg ggggctcaca ctgcgcaact tctgcagctg gcaacggcgt  300
ttcaacaagc ccagtgaccg ccacccggag cactatgaca ctgccatctt gttc         354
```

<210> SEQ ID NO 100
<211> LENGTH: 389
<212> TYPE: DNA
<213> ORGANISM: Homo sapiens

<400> SEQUENCE: 100

```
ttgtgcccag aagacactgg ccctgggcc tgggttgagt tcaaaaccaa agaaagaag    60
aaaagtgctg taaattcggg atttctccac cggatgctcc tgcttccgca tgggtgtcac  120
ctccatgccg ttcctncctc tttctaggga aaagcttcag ggagcagcag tgtgagaagt  180
ataatgccta caattacact gacatggacg ggaatctcct gcagtgggtc cccaagtatg  240
ctggggtgtc cccccgggac cgcctgcaa gttgttctgc cgagcccggg ggagagcga   300
gttcaaagtg ttcgaggcca aggtgagaat caccctgggg gacttcagat ccagagatgg  360
```

```
                ggggagggaa ggtcggcctg ttccccaca                           389
```

<210> SEQ ID NO 101
<211> LENGTH: 305
<212> TYPE: DNA
<213> ORGANISM: Homo sapiens

<400> SEQUENCE: 101

```
catttaagtt tgctagtcct ttgcaaacag actgacgctg agtgtcctgt ctgagtcaat  60
aagtgcactt ttaccttta acctatgccc tctacttgaa cccgagcaag gtccagtcca   120
ctggacangt tgatgatagg gtctgncgcc ccatacctc tcctcttccc ccttaggaat   180
ttgtcagta ctggaggggt tgcggcaatg ggaggcctgg gtgggccgtg ctgccttgat   240
atggccaagg gacccagtca ccacagtgga gacccttgtc tgcacctcag taccgcatgt   300
ccagg                                                              305
```

<210> SEQ ID NO 102
<211> LENGTH: 152
<212> TYPE: DNA
<213> ORGANISM: Homo sapiens

<400> SEQUENCE: 102

```
atcgtagaag atgaaaaatg gggcccagag gtgtccgaca atgggggct tacactgcgt   60
aacttctgca actggcagcg gcgtttcaac cagcccagcg accgncaccc agagcactac   120
gncacggcca tcctnctcac cagacagaac tt                                152
```

<210> SEQ ID NO 103
<211> LENGTH: 632
<212> TYPE: DNA
<213> ORGANISM: Homo sapiens

<400> SEQUENCE: 103

```
tttaataata ataatgcccg gggctttatt atgctgtatc actgctcaga ggttaataat   60
cctcactaac tatcctatca aatttgcaac tggcagttta ctctgatgat tcaactcctt   120
ttctatctac ccccataatc ccacttact gatacacctc actggttact ggcaagatac    180
gctggatccc tccagccttc ttgctttccc tgcaccagcc cttcctcact ttgccttgcc   240
ctcaaagcta acaccactta aaccacttaa ctgcattctg ccattgtgca aaagtctatg    300
aaatgtttag gtttcttaa aggatcacag ctctcatgag ataacacccc tccatcatgg     360
gacagacact tcaagcttct tttttgtaa ccttccccac aagtcttaga acatgatgac      420
cactccccca gctgccactg ggggcaggga tggtctgcac aaggtctggt gctggctggc    480
ttcacttcct ttgcacactc ggaagcaggc tgtccattaa tgtctcggca ttctaccagt    540
cttctctgcc aacccaattc acatgactta gaacattcgc cccactcttc aatgacccat    600
gctgaaaaag tggggatagc attgaaagaa tc                                 632
```

<210> SEQ ID NO 104
<211> LENGTH: 519
<212> TYPE: DNA
<213> ORGANISM: Homo sapiens

<400> SEQUENCE: 104

```
ttttttctc aacttgtaat agatgtaaca aaagaaataa taataataat gcccggggct    60
ttattatgct atatcactgc tcagaggtta ataatcctca ctaactatcc tatcaaattt    120
gcaactggca gtttactctg atgattcaac tccttttcta tctaccccca taatcccacc    180
ttactgatac acctcactgg ttactggcaa gatacgctgg atccctccag ccttcttgct    240
ttccctgcac cagcccttcc tcactttgcc ttgccctcaa agctaacacc acttaaacca    300
cttaactgca ttctgccatt gtgcaaaagt ctatgaaatg tttaggtttc tttaaaggat    360
cacagctctc atgataac ccctccat catgggacag acacttcaag cttctttttt       420
tgtaaccctt cccacaggtc ttagaacatg atgaccactc cccagctgc cactggggc    480
agggatgtct gcacaagggc tggtgctggc tgcccggac                          519
```

<210> SEQ ID NO 105
<211> LENGTH: 475
<212> TYPE: DNA
<213> ORGANISM: Homo sapiens

<400> SEQUENCE: 105

```
gagtcatgat gcgatcacaa ccagctttta cacactgtcc ttgcacacag acagaggtgg   60
aatctgggct acatggagta ccatctacaa ccttgggctg caaaacgaag aagtagccaa    120
tgcctttggc ttggcagatg agcttgcacc tgtcctttgg tgagacgcca gcgtacttgg    180
gaatccattc caccgcaggc ccactcccaa aggaagcttt tgaaaactcg ttgtgtgctt    240
```

```
          cacattgttc ctctctaaag gttttttccat tattgtctgg acagtcctca aggttacagg   300
          atctgtagcg cactcgtttg ccttcacagt acttccctcc attctttggg actgggttgt   360
          cacattccct catcgtgtac tggactcctc caccgcacgt tctcgaacag tctccccaag   420
          gcccccacat tccccagctt ccatgaaaag gcgtatcaaa atgctttctg tcggt         475

<210> SEQ ID NO 106
<211> LENGTH: 455
<212> TYPE: DNA
<213> ORGANISM: Homo sapiens

<400> SEQUENCE: 106
aataataata atgcccgggg ctttattatg ctgtatcact gctcagaggt taataatcct   60
          cactaactat cctatcaaat ttgcaactgg cagtttactc tgatgattca actccttttc  120
          tatctacccc cataatccca ccttactgat acacctcact ggttactggc aagatacgct  180
          ggatccctcc agccttcttg ctttccctgc accagccctt cctcactttg ccttgccctc  240
          aaagctaaca ccacttaaac cacttaactg cattctgcca ttgtgcaaaa gtctatgaaa  300
          tgtttaggtt tctttaaagg atcacagctc tcatgagata cacccctcc atcatgggac   360
          agacacttca agcttctttt tttgtaaccc ttcccacagg tcttagaaca tgatgaccac  420
          tcccccagct gccactgggg cagggatgg tctgg                              455

<210> SEQ ID NO 107
<211> LENGTH: 515
<212> TYPE: DNA
<213> ORGANISM: Homo sapiens

<400> SEQUENCE: 107
aacccttccc acaggtctta gaacatgatg accactcccc cagctgccac tgcggggcag   60
          ggatggtctg cacaaggtct ggtgctggct ggcttcactt cctttgcaca ctcggaagca  120
          ggctgtccat taatgtctcg gcattcttcc agtcttctct gccaacccaa ttcacatgac  180
          ttagaacatt cgccccactc ttcaatgacc catgctgaaa agtgggggat agcattgaaa  240
          gattccttct tcttctttac gaagtaggtg tatttaattt taggtcgaag ggcattgcca  300
          cagtaagaac ctggatggtc aagggctctt tggagcaggc taaagctgcg aattctttcc  360
          aatgccgcag aggagccgct gtacctcaag acaacacctt gtacataat gtcttgctct   420
          aaggtggaca aagtgtagtc accataaaga atatatgtgc catcagcagc ttttgatggc  480
          aggaagctgt cattgttctt ggatccctct gttcc                             515

<210> SEQ ID NO 108
<211> LENGTH: 359
<212> TYPE: DNA
<213> ORGANISM: Homo sapiens

<400> SEQUENCE: 108
acttcgtaaa gaagaagaag gaatcttttca atgctatccc cactttttca gcatgggtca   60
          ttgaagagtg gggcgaatgt tctaagtcat gtgaattggg ttggcagaga agactggtag  120
          aatgccgaga cattaatgga cagcctgctt ccgagtgtgc aaaggaagtg aagccagcca  180
          gcaccagacc ttgtgcagac catccctgcc cccagtggca gctggggga gtggtcatca   240
          tgttctaaga cctgcgggaa gggttacaaa aaagaagct tgaagtgtc ttgtcccatg    300
          atggaggggt gttatctcat tgagagctgt gatcctttaa agaaacctaa acatttcat   359

<210> SEQ ID NO 109
<211> LENGTH: 320
<212> TYPE: DNA
<213> ORGANISM: Homo sapiens

<400> SEQUENCE: 109
cagagaacat tcgccccact cttcaatgac ccatgctgaa aaagtgggga tagcattgaa   60
          agattccttc ttcttcttta cgaagtaggt gtatttaatt ttaggtcgaa gggcattgcc  120
          cacagtaaga acctggatgg tcaagggctc tttgagaggg ctaaagctgc gaattctttc  180
          caatgccgca gaggagccgc tgtacctcaa gacaacacct tgtacataa tgtcttgctc   240
          taaggtggac aaagtgtagt caccattaag atatatgtg ccatcagcag ctttgatggc   300
          aagaaagctg cccttgttcc                                              320

<210> SEQ ID NO 110
<211> LENGTH: 316
<212> TYPE: DNA
<213> ORGANISM: Homo sapiens

<400> SEQUENCE: 110
aatgccgaga cattaatgga cagcctgctt ccgagtgtgc aaaggaagtg aagccagcca   60
```

```
                gcaccagacc ttgtgcagac catccctgcc cccagtggca gctgggggag tggtcatcat     120
                gttctaagac ctgtgggaag ggttacaaaa aaagaagctt gaagtgtctg tcccatgatg     180
                gagggtgtt atctcatgag agctgtgatc ctttaaagaa acctaaacat ttcatagact       240
                tttgcacaat ggcagaatgc agttaagtgg tttaagtggt gttagctttg agggcaaggc      300
                aaagtgagga agggct                                                      316

<210> SEQ ID NO 111
<211> LENGTH: 318
<212> TYPE: DNA
<213> ORGANISM: Homo sapiens

<400> SEQUENCE: 111
agantnccga dacattaatg gacagcctgc ttccgagtgt gcaaaggaag tgaagccagc      60
                cagcaccaga ccttgtgcag accatccctg cccccagtgg cagctggggg agtggtcatc     120
                atgttctaag acctgtggga aggttacaa aaaaagaagc ttgaagtgtc tgtcccatga      180
                tggaggggtg ttatctcatg agagctgtga tccttaaag aaacctaaac atttcataga       240
                cttttgcaca atggcagaat ncagttaagt ggtttaagtg gtgttagctt tgagggcaag      300
                gcaaagtgag gaagggct                                                    318

<210> SEQ ID NO 112
<211> LENGTH: 314
<212> TYPE: DNA
<213> ORGANISM: Homo sapiens

<400> SEQUENCE: 112
ttttttttct aaacttgtaa tagatgtaac aaaagaaata ataataataa tgcccggggc      60
                tttattatgc tatatcactg ctcagaggtt aataatcctc actaactatc ctatcaaatt     120
                tgcaactggc agtttactct gatgattcaa ctccttttct atctacccc ataatcccac       180
                cttactgata cacctcactg gttactgcaa agatacgctg gatccctcca gccttcttgc     240
                tttccctgca ccagcccttc ctcactttgc cttgccctca aagctaacac cacttaaacc     300
                acttaactgc attc                                                        314

<210> SEQ ID NO 113
<211> LENGTH: 316
<212> TYPE: DNA
<213> ORGANISM: Homo sapiens

<400> SEQUENCE: 113
aaggaatcct tcaatgctat cccactgtt tcagcatggg tcattgaaga gtggggcgaa       60
                tgttctaagt catgtgaatt gggttggcag aaaagacttg tagaatgccg agacattaat      120
                ggacagcctg cgtccgagtg tgcaaaggaa gtgaagccag ccagcaccag accttgtgca     180
                gaccatccct gcccccagtg gcagctgggg ggagtggtca tcatgttcta agacctgtgg     240
                gaagggggtac aaaaaaagag gcgtgaagtg tctgtcccat gatggagggg tttatctcat    300
                gagaactgtg atcctt                                                      316

<210> SEQ ID NO 114
<211> LENGTH: 265
<212> TYPE: DNA
<213> ORGANISM: Homo sapiens

<400> SEQUENCE: 114
agcagtttan ncctntcaaa gagcccttga ccatccaggt tcttactgtg ggcaatgccc      60
                ttcgacctaa aattaaatac acctacttcg taaagangaa gaaggaatct ttcaatgcta     120
                tcccccacttt ttcagcatgg gtcattgaag agtggggcga atgttctaag tcatgtgaat    180
                tgggttggca gagaagactg gtagaatgcc gagacattaa tggacagcct ncttccgagt    240
                gtgcaaagna agtgaagcca gccag                                            265

<210> SEQ ID NO 115
<211> LENGTH: 334
<212> TYPE: DNA
<213> ORGANISM: Mus musculus

<400> SEQUENCE: 115
cgtttgtgga ggaaacggtt ccacatgcaa gaagatgtca ggaatagtca ctagtacaag      60
                acctgggtat catgacattg tcacaattcc tgctgagcc accaacattg aagtgaaaca      120
                tcggaatcaa aggggtcca gaaacaatgg cagctttctg gctattagag ccgctgatgg      180
                tacctatatt ctgaatggaa acttcactct gtccacacta gagcaagacc tcacctacaa     240
                aggtactgtc ttaaggtaca gtggttcctc ggctgcgctg gagagaatcc gcagctttag     300
                tccactcaaa gaacccttaa ccatccaggt tctt                                  334
```

<210> SEQ ID NO 116
<211> LENGTH: 528
<212> TYPE: DNA
<213> ORGANISM: Mus musculus

<400> SEQUENCE: 116

```
agaattcctg gatgatggtc atggtaattg cttccgtggt aggtctagca acaattacc   60
atgaccatca tccaggaatt ctgtgatggt ggctgacgtg catttggacc agggcttgga  120
tgcatcgatg ctggtaagga ttgaagacat taaacgcttg tcttctgtag taccgaagtt  180
ctcttcacag aatttggaat cgtcatgaga aaggccaagt agatgcccaa tttcatgagc  240
cacagtgaag gctgcatgga ggccatcatc ttcaatcact gcacagctgc gctccggaga  300
acatatggtc ccaacgtctg ccattcccag ggtgtcacat gaatgatgcc cacataaatc  360
ctctcgggtg aacaggatgg ctgcatcgta gtgctcttcg tgatcatccc ctagctggtt  420
atgttggtgc tgccatttgc aaaagttctt gagggtcgtg gccgcattct tgctcacctc  480
cagactcgtg tccttgtccg tcagcaccac caccttcacc accgccag              528
```

<210> SEQ ID NO 117
<211> LENGTH: 438
<212> TYPE: DNA
<213> ORGANISM: Homo sapiens

<400> SEQUENCE: 117

```
atttgatagg atagttagtg aggattatta acctctgagc agtgatatag cataataaag   60
ccccgggcat tattattatt atttcttttg ttacatctat tacaagtttta gaaaaaacaa  120
agcaattgtc aaaaaaagt agaactatta caacccctgt ttcctggtac ttatcaaata   180
cttagtatca tgggggttgg gaaatgaaaa gtaggagaaa agtgagattt tactaagacc  240
tgttttactt tacctcacta acaatggggg gagaaaggag tacaaatagg atctttgacc  300
agcactgttt atgggctgct atgggtttca gaggaatgtt tatacattat ttctacccga  360
ggatttaaaa cttcagattg ttccaaccng gaggggaagg gcttccggcc aacgtggaat  420
taaccggcaa tnggcctt                                                438
```

<210> SEQ ID NO 118
<211> LENGTH: 455
<212> TYPE: DNA
<213> ORGANISM: Homo sapiens

<400> SEQUENCE: 118

```
atttgatagg atagttagtg aggattatta acctctgagc agtgatatag cataataaag   60
ccccgggcat tattattatt atttcttttg ttacatctat tacaagtttta gaaaaaacaa  120
agcaattgtc aaaaaaagt agaactatta caacccctgt ttcctggtac ttatcaaata   180
cttagtatca tgggggttgg gaaatgaaaa gtaggagaaa agtgagattt tactaagacc  240
tgttttactt tacctcacta acaatggggg gagaaaggag tacaaatagg atctttgacc  300
agcactgttt atggctgcta tggtttcaga gaatgtttat acattatttc taccgaggat  360
taaaacttcc agattgtttc aacatggaga ggaaaggctc aggcaacgtg gaaataacgc  420
aaatgggctt cctcttttcc ttttttgggac cntct                            455
```

<210> SEQ ID NO 119
<211> LENGTH: 380
<212> TYPE: DNA
<213> ORGANISM: Homo sapiens

<400> SEQUENCE: 119

```
aatttgatag gatagttagt gaggnttatt aacctctgag cagtgatata gcataataaa   60
gccccgggca ttattattat tattncttttt gttacatcta ttacaagttta gaaaaaaca  120
aagcaattgt caaaaaaagt tagaactatt acaaccctg tttcctggta cttatcaaat   180
acttagtatn atgggggttg ggaaatgaaa agtaggagaa aagtgagatt ttactaagac  240
ctgttttact ttacctcact aacaatgggg ggagaaagga gtacanatag gatctttgac  300
cagcactgtt tatggctgct atggtttcag aggaatgttt atacattatt tctaccgaga  360
nttaaaactt cagattgttc                                              380
```

<210> SEQ ID NO 120
<211> LENGTH: 199
<212> TYPE: DNA
<213> ORGANISM: Mus musculus

<400> SEQUENCE: 120

```
caatggcagc ttgctggcta atatagccgc tgatggtacc tatatactga atgaaaactt   60
cactctgtcc acactagagc aagacctcac ctacgaatgt actgtcttaa ggtacagtgg  120
```

```
                ttcctcggct gcgcaggaaa gagtccgcag ctttagtcca ctcaaataac ccttaaccat    180
                ccaggttctt atggtagga                                                199

<210> SEQ ID NO 121
<211> LENGTH: 439
<212> TYPE: DNA
<213> ORGANISM: Homo sapiens

<400> SEQUENCE: 121
atttaacctc tgagcagtga tatagcataa taaagccccg ggcattatta ttattatttc     60
                ttttgttaca tctattacaa gtttagaaaa aacaaagcaa ttgtcaaaaa aagttagaac    120
                tattacaacc cctgtttcct ggtacttatc aaatacttag tatcatgggg gttgggaaat    180
                gaaaagtagg aggaaagnng agnttttact aagacctgtt ttacctttac ctcactaaca    240
                atgggggggag aaaggagtac aaataggatc tttgaccagc actgtttatg gctgctatgg    300
                tttcagagaa tgtttataca ttatttctac cgagaattaa aacttcagat tgttcaacat    360
                ggagagaaag gctcagcaac gtggaaataa cgcaaatggg cttccccctt tccctttttt    420
                gggaccatct caggtcctt                                                439

<210> SEQ ID NO 122
<211> LENGTH: 471
<212> TYPE: DNA
<213> ORGANISM: Homo sapiens

<400> SEQUENCE: 122
cagagtaaac tgccagttgc aaatttgata ggatagttag tgaggattat taacctctga     60
                gcagtgatat agcataataa agccccgggc attattatta ttattatttc ttttgttaca    120
                tctattacaa gtttagaaaa aacaaagcaa ttgtcaaaaa aagttagaac tattacaacc    180
                cctgtttcct ggtacttatc aaatacttag tatcatgggg gttgggaaat gaaaagtagg    240
                agaaagtgaa gattttacta agacctgttt tactttttcct cactaacaa gggggggagaa    300
                aggagtacaa ataggatctt tgaccagcac tgtttatggc tgctatggtt tcagagaatg    360
                tttatacatt atttctaccc gagaattaaa acttcagatt ggttcaacat gagagaaagg    420
                ctccagcaac gtgaaattaa cgccaatggc ttcctccttc cctttttttgg a             471

<210> SEQ ID NO 123
<211> LENGTH: 424
<212> TYPE: DNA
<213> ORGANISM: Homo sapiens

<400> SEQUENCE: 123
cgtgaggatt attaacctct gagcagtgat atagcatant aaagccccgg nattattatt     60
                attatttctt ttgttacatc tattacaagt ttagaaaaaa caaagcaatt gtcaaaaaaa    120
                gttagaacta ttacaacccc tgtttcctgg tacttatcaa atacttagta tcatgggggt    180
                tgggaaatga aaagtaggag aaaagtgaga ttttactaag acctgtttta ctttacctca    240
                ctaacaatgg ggggagaaag gagtacaaat aggatccagc accactgttt tatggcctg    300
                ctaatggttt cagagaatgt ttatacatta tttctacccg agaattaaaa cttcagattg    360
                ttcaacctga gagaaaggct cagcaacgtg aaatnacgcc aatggcttcc tcttttccctt    420
                tttg                                                                424

<210> SEQ ID NO 124
<211> LENGTH: 458
<212> TYPE: DNA
<213> ORGANISM: Homo sapiens

<400> SEQUENCE: 124
tacatctatt acaagtttag aaaaaacaaa gcaattgtca aaaaagtta gaactattac     60
                aacccctgtt tcctggtact tatcaaatac ttagtatcat ggggggttggg aaatgaaaag    120
                taggagaaaa gtgagatttt actaagacct gttttacttt acctcactaa caatgggggg    180
                agaaaggagt acaaatagga tctttgacca gcactgttta tggctgctat ggtttcagag    240
                aatgtttata cattatttct accgagaatt aaaacttcag attgttcaac atgagagaaa    300
                ggctcagcaa cgtgaaataa cgcaaatggc ttcctctttc ctttttggaa ccacagccag    360
                ccttggtctc cttgcagtgg ctacatgatt acatcatttc tggataatag tcatggggaa    420
                tgtttgatgg acaagctcag aatcccatac agntccca                            458

<210> SEQ ID NO 125
<211> LENGTH: 968
<212> TYPE: PRT
<213> ORGANISM: Homo sapiens

<400> SEQUENCE: 125
```

```
Met Gln Arg Ala Val Pro Glu Gly Phe Gly Arg Lys Leu Gly Ser
  1               5                  10                  15
Asp Met Met Gly Asn Ala Glu Arg Ala Pro Gly Ser Arg Ser Phe Gly
             20                  25                  30
Pro Val Pro Thr Leu Leu Leu Ala Ala Ala Leu Leu Ala Val Ser
             35                  40                  45
Asp Ala Leu Gly Arg Pro Ser Glu Glu Asp Glu Glu Leu Val Val Pro
 50                  55                  60
Glu Leu Glu Arg Ala Pro Gly His Gly Thr Thr Arg Leu Arg Leu His
 65                  70                  75                  80
Ala Phe Asp Gln Gln Leu Asp Leu Glu Leu Arg Pro Asp Ser Ser Phe
                 85                  90                  95
Leu Ala Pro Gly Phe Thr Leu Gln Asn Val Gly Arg Lys Ser Gly Ser
                100                 105                 110
Glu Thr Pro Leu Pro Glu Thr Asp Leu Ala His Cys Phe Tyr Ser Gly
            115                 120                 125
Thr Val Asn Gly Asp Pro Ser Ser Ala Ala Leu Ser Leu Cys Glu
    130                 135                 140
Gly Val Arg Gly Ala Phe Tyr Leu Leu Gly Glu Ala Tyr Phe Ile Gln
145                 150                 155                 160
Pro Leu Pro Ala Ala Ser Glu Arg Leu Ala Thr Ala Ala Pro Gly Glu
                165                 170                 175
Lys Pro Pro Ala Pro Leu Gln Phe His Leu Leu Arg Arg Asn Arg Gln
            180                 185                 190
Gly Asp Val Gly Gly Thr Cys Gly Val Val Asp Asp Glu Pro Arg Pro
        195                 200                 205
Thr Gly Lys Ala Glu Thr Glu Asp Glu Asp Glu Gly Thr Glu Gly Glu
210                 215                 220
Asp Glu Gly Pro Gln Trp Ser Pro Gln Asp Pro Ala Leu Gln Gly Val
225                 230                 235                 240
Gly Gln Pro Thr Gly Thr Gly Ser Ile Arg Lys Lys Arg Phe Val Ser
                245                 250                 255
Ser His Arg Tyr Val Glu Thr Met Leu Val Ala Asp Gln Ser Met Ala
            260                 265                 270
Glu Phe His Gly Ser Gly Leu Lys His Tyr Leu Leu Thr Leu Phe Ser
        275                 280                 285
Val Ala Ala Arg Leu Tyr Lys His Pro Ser Ile Arg Asn Ser Val Ser
290                 295                 300
Leu Val Val Val Lys Ile Leu Val Ile His Asp Glu Gln Lys Gly Pro
305                 310                 315                 320
Glu Val Thr Ser Asn Ala Ala Leu Thr Leu Arg Asn Phe Cys Asn Trp
                325                 330                 335
Gln Lys Gln His Asn Pro Pro Ser Asp Arg Asp Ala Glu His Tyr Asp
            340                 345                 350
Thr Ala Ile Leu Phe Thr Arg Gln Asp Leu Cys Gly Ser Gln Thr Cys
        355                 360                 365
Asp Thr Leu Gly Met Ala Asp Val Gly Thr Val Cys Asp Pro Ser Arg
370                 375                 380
Ser Cys Ser Val Ile Glu Asp Asp Gly Leu Gln Ala Ala Phe Thr Thr
385                 390                 395                 400
Ala His Glu Leu Gly His Val Phe Asn Met Pro His Asp Ala Lys
                405                 410                 415
Gln Cys Ala Ser Leu Asn Gly Val Asn Gln Asp Ser His Met Met Ala
            420                 425                 430
Ser Met Leu Ser Asn Leu Asp His Ser Gln Pro Trp Ser Pro Cys Ser
        435                 440                 445
Ala Tyr Met Ile Thr Ser Phe Leu Asp Asn Gly His Gly Glu Cys Leu
450                 455                 460
Met Asp Lys Pro Gln Asn Pro Ile Gln Leu Pro Gly Asp Leu Pro Gly
465                 470                 475                 480
Thr Ser Tyr Asp Ala Asn Arg Gln Cys Gln Phe Thr Phe Gly Glu Asp
                485                 490                 495
Ser Lys His Cys Pro Asp Ala Ala Ser Thr Cys Ser Thr Leu Trp Cys
            500                 505                 510
Thr Gly Thr Ser Gly Gly Val Leu Val Cys Gln Thr Lys His Phe Pro
        515                 520                 525
Trp Ala Asp Gly Thr Ser Cys Gly Glu Gly Lys Trp Cys Ile Asn Gly
530                 535                 540
Lys Cys Val Asn Lys Thr Asp Arg Lys His Phe Asp Thr Pro Phe His
545                 550                 555                 560
Gly Ser Trp Gly Met Trp Gly Pro Trp Gly Asp Cys Ser Arg Thr Cys
                565                 570                 575
Gly Gly Gly Val Gln Tyr Thr Met Arg Glu Cys Asp Asn Pro Val Pro
            580                 585                 590
Lys Asn Gly Gly Lys Tyr Cys Glu Gly Lys Arg Val Arg Tyr Arg Ser
        595                 600                 605
Cys Asn Leu Glu Asp Cys Pro Asp Asn Asn Gly Lys Thr Phe Arg Glu
610                 615                 620
Glu Gln Cys Glu Ala His Asn Glu Phe Ser Lys Ala Ser Phe Gly Ser
```

```
        625                 630                 635                 640
    Gly Pro Ala Val Glu Trp Ile Pro Lys Tyr Ala Gly Val Ser Pro Lys
                    645                 650                 655
    Asp Arg Cys Lys Leu Ile Cys Gln Ala Lys Gly Ile Gly Tyr Phe Phe
                660                 665                 670
    Val Leu Gln Pro Lys Val Val Asp Gly Thr Pro Cys Ser Pro Asp Ser
            675                 680                 685
    Thr Ser Val Cys Val Gln Gly Gln Cys Val Lys Ala Gly Cys Asp Arg
        690                 695                 700
    Ile Ile Asp Ser Lys Lys Lys Phe Asp Lys Cys Gly Val Cys Gly Gly
    705                 710                 715                 720
    Asn Gly Ser Thr Cys Lys Lys Ile Ser Gly Ser Val Thr Ser Ala Lys
                    725                 730                 735
    Pro Gly Tyr His Asp Ile Ile Thr Ile Pro Thr Gly Ala Thr Asn Ile
                    740                 745                 750
    Glu Val Lys Gln Arg Asn Gln Arg Gly Ser Arg Asn Asn Gly Ser Phe
                755                 760                 765
    Leu Ala Ile Lys Ala Ala Asp Gly Thr Tyr Ile Leu Asn Gly Asp Tyr
            770                 775                 780
    Thr Leu Ser Thr Leu Glu Gln Asp Ile Met Tyr Lys Gly Val Val Leu
    785                 790                 795                 800
    Arg Tyr Ser Gly Ser Ser Ala Ala Leu Glu Arg Ile Arg Ser Phe Ser
                    805                 810                 815
    Pro Leu Lys Glu Pro Leu Thr Ile Gln Val Leu Thr Val Gly Asn Ala
                820                 825                 830
    Leu Arg Pro Lys Ile Lys Tyr Thr Tyr Phe Val Lys Lys Lys Lys Glu
            835                 840                 845
    Ser Phe Asn Ala Ile Pro Thr Phe Ser Ala Trp Val Ile Glu Glu Trp
    850                 855                 860
    Gly Glu Cys Ser Lys Ser Cys Glu Leu Gly Trp Gln Arg Arg Leu Val
    865                 870                 875                 880
    Glu Cys Arg Asp Ile Asn Gly Gln Pro Ala Ser Glu Cys Ala Lys Glu
                    885                 890                 895
    Val Lys Pro Ala Ser Thr Arg Pro Cys Ala Asp His Pro Cys Pro Gln
                900                 905                 910
    Trp Gln Leu Gly Glu Trp Ser Ser Cys Ser Lys Thr Cys Gly Lys Gly
            915                 920                 925
    Tyr Lys Lys Arg Ser Leu Lys Cys Leu Ser His Asp Gly Gly Val Leu
        930                 935                 940
    Ser His Glu Ser Cys Asp Pro Leu Lys Lys Pro Lys His Phe Ile Asp
    945                 950                 955                 960
    Phe Cys Thr Met Ala Glu Cys Ser
                    965
-297-
```